(12) United States Patent
Szalay et al.

(10) Patent No.: US 7,662,398 B2
(45) Date of Patent: Feb. 16, 2010

(54) MICROORGANISMS FOR THERAPY

(75) Inventors: Aladar A. Szalay, Highland, CA (US); Tatyana Timiryasova, Scotrun, PA (US); Yong A. Yu, San Diego, CA (US); Qian Zhang, San Diego, CA (US)

(73) Assignee: Genelux Corporation, San Diego, CA (US)

( * ) Notice: Subject to any disclaimer, the term of this patent is extended or adjusted under 35 U.S.C. 154(b) by 0 days.

(21) Appl. No.: 11/529,662

(22) Filed: Sep. 27, 2006

(65) Prior Publication Data

US 2007/0025981 A1     Feb. 1, 2007

Related U.S. Application Data

(60) Division of application No. 11/238,025, filed on Sep. 27, 2005, which is a continuation of application No. 10/872,156, filed on Jun. 18, 2004.

(30) Foreign Application Priority Data

Jun. 18, 2003 (EP) ................. 03013826
Aug. 14, 2003 (EP) ................. 03018478
Oct. 22, 2003 (EP) ................. 03024283

(51) Int. Cl.
*A61K 39/285* (2006.01)
*A61K 39/385* (2006.01)
*A61K 39/12* (2006.01)
*A01N 65/00* (2006.01)
*A61K 39/20* (2006.01)

(52) U.S. Cl. ............... 424/232.1; 424/196.11; 424/199.1; 424/93.1

(58) Field of Classification Search ............ None
See application file for complete search history.

(56) References Cited

U.S. PATENT DOCUMENTS

| | | | |
|---|---|---|---|
| 4,442,203 A | 4/1984 | Varshavsky | 435/6 |
| 4,603,112 A | 7/1986 | Paoletti et al. | 435/235.1 |
| 4,722,848 A | 2/1988 | Paoletti et al. | 424/199.1 |
| 4,769,330 A | 9/1988 | Paoletti et al. | 435/436 |
| 4,778,759 A | 10/1988 | Szalay et al. | 435/477 |
| 5,110,587 A | 5/1992 | Paoletti et al. | 435/235.1 |
| 5,155,020 A | 10/1992 | Paoletti | 435/69.1 |
| 5,221,623 A | 6/1993 | Legocki et al. | 435/252.3 |
| 5,300,436 A | 4/1994 | Goldstein et al. | 435/190 |
| 5,364,773 A | 11/1994 | Paoletti et al. | 435/69.1 |
| 5,368,855 A | 11/1994 | Boyle et al. | 435/320.1 |
| 5,378,457 A | 1/1995 | Paoletti et al. | 424/205.1 |
| 5,550,050 A | 8/1996 | Holland et al. | 435/382 |
| 5,639,275 A | 6/1997 | Baetge et al. | 604/891.1 |
| 5,646,298 A | 7/1997 | Powell et al. | 548/427 |
| 5,650,135 A | 7/1997 | Contag et al. | 424/9.1 |
| 5,650,148 A | 7/1997 | Gage et al. | 424/93.2 |
| 5,653,975 A | 8/1997 | Baetge et al. | 424/93.1 |
| 5,656,481 A | 8/1997 | Baetge et al. | 435/325 |
| 5,676,943 A | 10/1997 | Baetge et al. | 424/93.21 |
| 5,693,533 A | 12/1997 | Raney et al. | 435/366 |
| 5,704,910 A | 1/1998 | Humes | 604/502 |
| 5,710,137 A | 1/1998 | Fisher | 514/44 |
| 5,718,902 A | 2/1998 | Yilma et al. | 424/211.1 |
| 5,750,103 A | 5/1998 | Cherksey | 424/93.21 |
| 5,756,455 A | 5/1998 | Kinzler et al. | 514/12 |
| 5,762,959 A | 6/1998 | Soon-Shiong et al. | 424/451 |
| 5,795,790 A | 8/1998 | Schinstine et al. | 435/382 |
| 5,798,113 A | 8/1998 | Dionne et al. | 424/422 |
| 5,800,828 A | 9/1998 | Dionne et al. | 424/422 |
| 5,800,829 A | 9/1998 | Dionne et al. | 424/422 |
| 5,830,702 A | 11/1998 | Portnoy et al. | 435/69.3 |
| 5,833,975 A | 11/1998 | Paoletti et al. | 424/93.2 |
| 5,833,979 A | 11/1998 | Schinstine et al. | 424/93.21 |
| 5,834,001 A | 11/1998 | Dionne et al. | 424/422 |
| 5,837,234 A | 11/1998 | Gentile et al. | 424/93.7 |

(Continued)

FOREIGN PATENT DOCUMENTS

AU         709336         4/1995

(Continued)

OTHER PUBLICATIONS

Perkus et al., Deletion of 55 Open Reading Frames from the Termini of Vaccinia Virus, 1991, Virology, vol. 180, pp. 406-410.*
Li et al., Mini Review:Oncolytic virotherapy as a personalized cancer vaccine, 2008, Int. Journal of Cancer, vol. 123, pp. 493-499.*
"A New Way to Kill Cancer: SLU Research Shows Viruses can destroy lung, colon tumors," Science Daily: Your link to the latest research news http://www.sciencedaily.com/releases/2004/05/040517071951.htm (accessed on May 17, 2004).
"Generation of Recombinant Vaccinia Viruses," Unit 16.17 in *Short Protocols in Molecular Biology 2nd edition: a compendium of Methods from Current Protocols in Molecular Biology*, Green Publishing and Wiley-Interscience Supplement 15:16.71-16.82 (1992).

(Continued)

*Primary Examiner*—Gary B Nickol
*Assistant Examiner*—Benjamin P Blumel
(74) *Attorney, Agent, or Firm*—K & L Gates LLP; Stephanie Seidman

(57) ABSTRACT

Therapeutic methods and microorganisms therefor are provided. The microorganisms are designed to accumulate in immunoprivileged tissues and cells, such as in tumors and other proliferating tissue and in inflamed tissues, compared to other tissues, cells and organs, so that they exhibit relatively low toxicity to host organisms. The microorganisms also are designed or modified to result in leaky cell membranes of cells in which they accumulate, resulting in production of antibodies reactive against proteins and other cellular products and also permitting exploitation of proliferating tissues, particularly tumors, to produce selected proteins and other products. Vaccines containing the microorganisms are provided. Combinations of the microorganisms and anti-cancer agents and uses thereof for treating cancer also are provided.

22 Claims, 2 Drawing Sheets

U.S. PATENT DOCUMENTS

| | | | |
|---|---|---|---|
| 5,840,576 A | 11/1998 | Schinstine et al. | 435/325 |
| 5,853,385 A | 12/1998 | Emerich et al. | 604/500 |
| 5,853,717 A | 12/1998 | Schinstine et al. | 424/93.21 |
| 5,861,290 A | 1/1999 | Goldsmith et al. | 435/456 |
| 5,866,131 A | 2/1999 | Ramshaw et al. | 424/186.1 |
| 5,976,796 A | 11/1999 | Szalay et al. | 435/6 |
| 6,007,806 A | 12/1999 | Lathe et al. | 424/93.2 |
| 6,025,155 A | 2/2000 | Hadlaczky et al. | 435/69.1 |
| 6,045,802 A | 4/2000 | Schlom et al. | 424/199.1 |
| 6,077,697 A | 6/2000 | Hadlaczky et al. | 435/172.3 |
| 6,080,849 A | 6/2000 | Bermudes et al. | 536/23.7 |
| 6,093,700 A | 7/2000 | Mastrangelo et al. | 514/44 |
| 6,099,848 A | 8/2000 | Frankel et al. | 424/246.1 |
| 6,106,826 A | 8/2000 | Brandt et al. | 424/93.2 |
| 6,190,657 B1 | 2/2001 | Pawelek et al. | 424/93.1 |
| 6,217,847 B1 | 4/2001 | Contag et al. | 424/9.1 |
| 6,232,523 B1 | 5/2001 | Tan et al. | 800/10 |
| 6,235,967 B1 | 5/2001 | Tan et al. | 800/10 |
| 6,235,968 B1 | 5/2001 | Tan et al. | 800/10 |
| 6,251,384 B1 | 6/2001 | Tan et al. | 424/93.2 |
| 6,265,189 B1 | 7/2001 | Paoletti et al. | 435/70.1 |
| 6,416,754 B1 | 7/2002 | Brown et al. | 424/93.21 |
| 6,428,968 B1 | 8/2002 | Molnar-Kimber et al. | 435/7.23 |
| 6,455,673 B1 | 9/2002 | Collier | 530/350 |
| 6,491,905 B1 | 12/2002 | Sorscher et al. | 435/325 |
| 6,503,703 B1 | 1/2003 | Palese et al. | 435/5 |
| 6,511,967 B1 | 1/2003 | Weissleder et al. | 514/44 |
| 6,537,594 B1 | 3/2003 | Paoletti et al. | 424/93.2 |
| 6,548,068 B1 | 4/2003 | Schlom et al. | 424/199.1 |
| 6,589,531 B1 | 7/2003 | Andino-Pavlovsky et al. | 424/199.1 |
| 6,596,279 B1 | 7/2003 | Paoletti et al. | 424/199.1 |
| 6,627,190 B2 | 9/2003 | Wold et al. | 424/93.2 |
| 6,649,143 B1 | 11/2003 | Contag et al. | 424/9.1 |
| 6,649,159 B2 | 11/2003 | Yang et al. | 424/93.21 |
| 6,652,849 B2 | 11/2003 | Brown et al. | 424/93.2 |
| 6,685,935 B1 | 2/2004 | Pawelek et al. | 424/93.2 |
| 6,713,293 B1 | 3/2004 | Grummt et al. | 435/182 |
| 6,743,967 B2 | 6/2004 | Hadlaczky et al. | 800/25 |
| 6,759,038 B2 | 7/2004 | Tan et al. | 424/93.21 |
| 6,884,414 B1 | 4/2005 | Palese et al. | 424/93.2 |
| 6,984,374 B2 | 1/2006 | Szalay et al. | 424/9.1 |
| 7,045,313 B1 | 5/2006 | Moss et al. | 435/69.1 |
| 2001/0008025 A1 | 7/2001 | Hadlaczky et al. | 800/8 |
| 2001/0029023 A1 | 10/2001 | Szalay et al. | 435/7.1 |
| 2002/0054865 A1 | 5/2002 | Fujimori et al. | 424/93.21 |
| 2002/0160410 A1 | 10/2002 | Hadlaczky et al. | 435/6 |
| 2002/0160970 A1 | 10/2002 | Hadlaczky et al. | 514/44 |
| 2003/0009015 A1 | 1/2003 | Ulrich et al. | 536/23.1 |
| 2003/0031628 A1 | 2/2003 | Zhao et al. | 424/9.6 |
| 2003/0031681 A1 | 2/2003 | McCart et al. | 424/186.1 |
| 2003/0033617 A1 | 2/2003 | Hadlaczky et al. | 800/6 |
| 2003/0044384 A1 | 3/2003 | Roberts et al. | 424/93.2 |
| 2003/0059400 A1 | 3/2003 | Szalay | 424/93.2 |
| 2003/0083293 A1 | 5/2003 | Hadlaczky et al. | 514/44 |
| 2003/0086906 A1 | 5/2003 | Mastrangelo et al. | 424/93.2 |
| 2003/0101480 A1 | 5/2003 | Hadlaczky et al. | 800/278 |
| 2003/0133949 A1 | 7/2003 | Szalay et al. | 424/200.1 |
| 2003/0161788 A1 | 8/2003 | Zhao et al. | 424/9.6 |
| 2003/0165465 A1 | 9/2003 | Roberts et al. | 424/93.2 |
| 2003/0165477 A1 | 9/2003 | Balloul et al. | 424/93.21 |
| 2003/0198627 A1 | 10/2003 | Arts et al. | 424/93.21 |
| 2003/0213007 A1 | 11/2003 | Slattery et al. | 800/15 |
| 2003/0228261 A1 | 12/2003 | Szalay et al. | 424/9.34 |
| 2003/0228330 A1 | 12/2003 | Falkner et al. | 424/232.1 |
| 2004/0076622 A1 | 4/2004 | Studeny et al. | 424/93.21 |
| 2004/0091995 A1 | 5/2004 | Schlom et al. | 435/235.1 |
| 2004/0143861 A1 | 7/2004 | Hadlaczky et al. | 800/14 |
| 2004/0213741 A1 | 10/2004 | Szalay et al. | 424/9.6 |
| 2004/0234455 A1 | 11/2004 | Szalay et al. | 424/9.6 |
| 2005/0025745 A1 | 2/2005 | Fujimori et al. | 424/93.2 |
| 2005/0025747 A1 | 2/2005 | Laidlaw et al. | 424/93.2 |
| 2005/0031643 A1 | 2/2005 | Szalay et al. | 424/199.1 |
| 2005/0063993 A1 | 3/2005 | Schlom et al. | 424/199.1 |
| 2005/0069491 A1 | 3/2005 | Yu et al. | 424/1.11 |
| 2005/0249670 A1 | 11/2005 | Szalay et al. | 424/9.32 |
| 2006/0051370 A1 | 3/2006 | Szalay et al. | 424/199.1 |
| 2006/0099224 A1 | 5/2006 | Kirn | 424/199.1 |
| 2006/0134801 A1 | 6/2006 | Chada et al. | 436/177 |
| 2007/0202572 A1 | 8/2007 | Szalay et al. | 435/69.1 |
| 2007/0212727 A1 | 9/2007 | Szalay et al. | 435/6 |
| 2008/0193373 A1 | 8/2008 | Stritzker et al. | 424/1.17 |
| 2009/0053244 A1 | 2/2009 | Chen et al. | 424/174.1 |
| 2009/0081639 A1 | 3/2009 | Hill et al. | 435/5 |
| 2009/0098529 A1 | 4/2009 | Chen et al. | 435/5 |
| 2009/0117034 A1 | 5/2009 | Chen et al. | 424/1.17 |
| 2009/0117047 A1 | 5/2009 | Szalay et al. | 424/9.3 |
| 2009/0117048 A1 | 5/2009 | Szalay et al. | 424/9.3 |
| 2009/0117049 A1 | 5/2009 | Szalay et al. | 424/9.3 |
| 2009/0123382 A1 | 5/2009 | Szalay et al. | 424/9.6 |
| 2009/0136917 A1 | 5/2009 | Szalay et al. | 435/5 |
| 2009/0155287 A1 | 6/2009 | Chen et al. | 424/158.1 |

FOREIGN PATENT DOCUMENTS

| | | |
|---|---|---|
| CA | 2105277 | 12/2006 |
| EP | 0 037 441 A1 | 10/1981 |
| EP | 0 037 441 B1 | 5/1984 |
| EP | 0 861 093 | 9/1998 |
| EP | 1 146 125 | 10/2001 |
| EP | 1 281 772 A1 | 2/2003 |
| EP | 1 281 777 A1 | 2/2003 |
| EP | 1 281 767 | 5/2003 |
| EP | 1 369 491 | 12/2003 |
| EP | 1489164 | 12/2004 |
| EP | 1 254 250 | 3/2005 |
| EP | 1 512 746 | 3/2005 |
| EP | 1 526 185 | 4/2005 |
| JP | 55035004 | 3/1980 |
| JP | 09-502993 | 3/1997 |
| JP | 2002097144 | 4/2002 |
| WO | 88/00617 | 1/1988 |
| WO | 90/13658 | 11/1990 |
| WO | 91/07989 | 6/1991 |
| WO | WO 91/19810 | 12/1991 |
| WO | 92/22327 | 12/1992 |
| WO | 94/10302 | 5/1994 |
| WO | 95/31105 | 11/1995 |
| WO | 96/11279 | 4/1996 |
| WO | 96/40238 | 12/1996 |
| WO | 97/18841 | 5/1997 |
| WO | 97/40183 | 10/1997 |
| WO | 98/14605 | 4/1998 |
| WO | WO 99/18799 | 4/1999 |
| WO | 99/32646 | 7/1999 |
| WO | 00/47237 | 8/2000 |
| WO | WO 00/62735 | 10/2000 |
| WO | 00/73479 | 12/2000 |
| WO | 01/05229 | 1/2001 |
| WO | 01/12234 | 2/2001 |
| WO | 01/14579 | 3/2001 |
| WO | 01/18195 | 3/2001 |
| WO | 01/20989 | 3/2001 |
| WO | 01/24637 | 4/2001 |
| WO | 01/25399 | 4/2001 |
| WO | 01/55444 | 8/2001 |
| WO | 03/006069 | 1/2003 |
| WO | 03/014380 | 2/2003 |
| WO | 03/045153 A1 | 6/2003 |
| WO | WO 03/049117 | 6/2003 |
| WO | 03/057007 | 7/2003 |
| WO | 03/063593 | 8/2003 |
| WO | 03/092600 | 11/2003 |
| WO | 03/102168 A1 | 12/2003 |

| | | |
|---|---|---|
| WO | 03/102169 | 12/2003 |
| WO | 03/104485 A2 | 12/2003 |
| WO | WO 2004/014314 | 2/2004 |
| WO | WO 2004/030631 | 4/2004 |
| WO | 2004/044175 | 5/2004 |
| WO | WO 2004/098534 | 11/2004 |
| WO | 2005/047458 | 5/2005 |
| WO | 2005/057488 | 6/2005 |
| WO | 2005/072622 | 8/2005 |
| WO | WO 2006/050274 | 5/2006 |
| WO | 2008/100292 | 5/2009 |

OTHER PUBLICATIONS

"WHO Collaborating Centre for Orthopoxvirus Diagnosis and Repository for Variola Virus Strains and DNA," Vector: Ministry of Public Health and Social Development of Russian Federation, State Research Center of Virology and Biotechnology http://wvvw.vector.nsc.ru/DesktopDefault.aspx?Icid=9&tabid=294&tabindex=1 (accessed on Sep. 12, 2005).

Aboody et al., "Neural stem cells display extensive tropism for pathology in adult brain: evidence from intracranial gliomas," Proc Natl Acad Sci U S A. 97(23):12846-51 (2000).

Adonai et al., "Ex vivo cell labeling with $^{64}$Cu-pyruvaldehyde-bis($N^4$-methylthiosemicarbazone) for imaging cell trafficking in mice with positron-emission tomography," Proc. Natl. Acad. Sci. USA 99: 3030-3035 (2002).

Advani et al., "Replication-competent, Nonneuroinvasive Genetically Engineered Herpes Virus Is Highly Effective in the Treatment of Therapy-resistant Experimental Human Tumors," Cancer Research 59: 2055-2058 (1999).

Bergsland, E.K. and A.P. Venook, "Shedding Old Paradigms: Developing Viruses to Treat Cancer," J. Clin. Oncol., 20(9): 2220-2222 (2002).

Bermudes et al., "Live bacteria as anticancer agents and tumor-selective protein delivery vectors," Current Opinion in Drug Discovery & Development 5(2):194-199 (2002).

Bermudes et al., "Tumor-targeted Salmonella: Highly selective delivery vectors," Adv Exp Med Biol. 465:57-63 (2000).

Bernards et al., "Effective tumor immunotherapy directed against an oncogene-encoded produt using a vaccinia virus vector," Proc. Natl. Acad. Sci. USA 84: 6854-6858 (1987).

Beshara et al., "Kinetic analysis of $^{52}$Fe-labelled iron(III) hydroxide-sucrose complex following blous administration using positron emission tomography," Br. J. Haematol. 104: 288-295 (1999).

Beshara et al., "Pharmacokinetics and red cell utilization of iron(III) hydroxide-sucrose complex in anaemic patients: a study using positron emission tomography," Br. J. Haematol. 104: 296-302 (1999).

Beyer et al., "Oncoretrovirus and lentivirus vectors pseudotyped with lymphocytic choriomeningitis virus glycoprotein: generation concentration, and broad host range," J Virol. 76(3):1488-95 (2002).

Bickels, J. et al., "Coley's toxin: historical perspective", Isr. Med. Assoc. J., 4(6): 471-472 (2002).

Biffi et al., "Antiproliferative effect of fermented milk on the growth of a human breast cancer cell line," Nutr Cancer. 28(1):93-9 (1997).

Bisno et al., "*Streptococcal* infections of skin and soft tissues," N. Engl. J. Med. 334(4): 240-245 (1996).

Blanchard, T.J. et al., "Modified vaccinia virus Ankara undergoes limited replication in human cells and lacks several immunomodulatory proteins: implications for use as a human vaccine," Journal of General Virology, 79: 1159-1167(1998).

Blasberg, R.G. and J.G. Tjuvajev, "Herpes simplex virus thymidine kinase as a marker/reporter gene for PET imaging of gene therapy," Q J Nucl Med 43(2): 163-169 (1999).

Blasco, R. and B. Moss, "Selection of recombinant vaccinia viruses on the basis of plaque formation," Gene, 158: 157-162 (1995).

Block et al., "Gene therapy of metastatic colon carcinoma: regression of multiple hepatic metastases by adenoviral expression of bacterial cytosine deaminase," Cancer Gene Ther. 7(3):438-45 (2000).

Bodey et al., "Clostridial bacteremia in cancer patients. A 12-year experience," Cancer 67(7):1928-42 (1991).

Bogdahn et al., "Autocrine Tumor Cell Growth-inhibiting Activities from Human Malignant Melanoma", Cancer Research 49:5358-5363 (1989).

Bogdanov et al., "Antitumor action of glycopeptides from the cell wall of *Lactobacillus bulgaricus*," Bulletin of Experimental Biology and Medicine. 84(12): 1750-1753 (1977); translated from the original Russian article: Byulleten' Éksperimental'noi Biologii I Meditsiny 84(12):709-12 (1977).

Bogdanov et al., "Antitumour glycopeptides from *Lactobacillus bulgaricus* cell wall," FEBS Lett. 57(3):259-61 (1975).

Boland et al., "Adenovirus-mediated Transfer of the Thyroid Sodium/Iodide Symporter Gene into Tumors for a Targeted Radiotherapy," Cancer Research 60: 3484-3492 (2000).

Bonnekoh et al., "Adenoviral-Mediated Herpes Simplex Virus-Thymidine Kinase Gene Transfer in Vivo for Treatment of Experimental Human Melanoma," J .Invest. Dermatol. 106(6): 1163-1168 (1996).

Borellini, F. and J.M. Ostrove, "The Transfer of Technology from the Laboratory to the Clinic: In Process Controls and Final Product Testing", Chapter 18 in *Gene Therapy Technologies, Applications and Regulations*, A. Meager (Ed.), John Wiley & Sons Ltd., pp. 359-373 (1999).

Boulanger, D. et al., "Morphogenesis and release of fowlpox virusm," Journal of General Virology, 81: 675-687 (2000).

Bouvier et al., "Functional characterization of the human dopamine D-4.2 receptor using vaccinia virus as an expression system," European Journal of Pharmacology 290(1):11-17 (1995).

Boyd, J.E., "Facilities for Large-Scale Production of Vectors under GMP Conditions", Chapter 20 in *Gene Therapy Technologies, Applications and Regulations*, A. Meager (Ed.), pp. 383-400 (1999).

Brain, J.D. et al., "Pulmonary intravascular macrophages: their contribution to the mononuclear phagocyte system in 13 species", Am. J. Physiol., 276(1 pt 1): L146-L154 (1999).

Breman, J.G. And D.A. Henderson, "Diagnosis and Management of Smallpox", N. Engl. J. Med., 346(17): 1300-1308 (2002).

Brockstedt et al., "Development of Anti-tumor Immunity against a Non-immunogenic Mammary Carcinoma through in Vivo Somatic GM-CSF, IL-2, and HSVtk Combination Gene Therapy," Mol. Ther. 6(5): 627-636 (2002).

Broder, C.C. and P.L. Earl, "Recombinant Vaccinia Viruses," Mol. Biotechnol. 13: 223-245 (1999).

Broder, C.C. et al., "Expression of foreign genes in cultured human primary macrophages using recombinant vaccinia virus vectors", Gene, 142: 167-174 (1994).

Broyles, S.S., "Vaccinia virus transcription", Journal of General Virology, 84: 2293-2303 (2003).

Brunke M et al., "Luciferase assembly after transport into mammalian microsomes involves molecular chaperones and peptidyl-prolyl cis/trans-isomerases," J Biol Chem. 271(38):23487-94 (1996).

Calonder et al., "Kinetic modeling of $^{52}$Fe/$^{52m}$Mn-Citrate at the Blood-Brain Barrier by Positron Emission Tomography," J. Neurochem. 73: 2047-2055 (1999).

Carrillo and Lipman et al., "The Multiple Sequence Alignment Problem in Biology," SIAM J Applied Math 48:1073-1082 (1988).

Carroll, S.F. and R.J. Collier, "Active Site of *Pseudomonas aeruginosa* Exotoxin A," J. Biol. Chem. 262:8707-8711(1987).

Carter, G.C. et al., "Vaccinia virus cores are transported on microtubules", Journal of General Virology, 84: 2443-2458 (2003).

Cavanagh, L.L. and U.H. von Andrian, "Travellers in many guises: The origins and destinations of dendritic cells", Immunology and Cell Biology, 80: 448-462 (2002).

Certified English translation of abstract for Aksac S., "[Antibody formation against *Agrobacterium tumefaciens* in patients with various cancers]," Turk Hij Tecr Biyol Derg. 34(1-2):48-51 (1974) [Article in Italian].

Certified English translation of journal article for Al'tshtein [Altshteyn] et al., "[Isolation of a recombinant vaccinia virus based on the LIVP strain inducing the surface antigen of the hepatitis B virus]," Dokl Akad Nauk SSSR. 285(3):696-9 (1985) [Article in Russian].

Certified English translation of Timiryasova et al., "Analysis of Reporter Gene Expression in Various Regions of the Genome of the Vaccinia Virus," Molecular Biology 27(2): 2-11 (1993).

Chakrabarti et al., "Compact, Synthetic, Vaccinia Virus Early/Late Promoter for Protein Expression," BioTechniques 23(6): 1094-1097 (1997).

Chakrabarti et al., "Vaccinia virus expression vector: coexpression of β-galactosidase provides visual screening of recombinant virus plaques," Mol. Cell Biol. 5:3403-3409 (1985).

Chalfie et al., "Green Fluorescent Protein as a Marker for Gene Expression," Science 263: 802-805 (1994).

Chaloupka et al., "Comparative Analysis of Six European Influenza Vaccines" European J. Microbiology Infectious Disease, 15(2):121-127, (1996).

Chamberlain et al., "Costimulation enhances the active immunotherapy effect of recombinant anticancer vaccines," Cancer Res. 56: 2832-2836 (1996).

Chambers, A.F. et al., "Dissemination and Growth of Cancer Cells in Metastatic Sites," Nat. Rev. Cancer, 2: 563-572 (2002).

Chambers, A.F. et al., "Molecular biology of breast cancer metastasis Clinical implications of experimental studies on metastatic inefficiency," Breast Cancer Res., 2: 400-407 (2000).

Chang et al., "Differential apoptotic susceptibility to anti-Fas IgM and anticancer drugs in a human endometrial adenocarcinoma cell line HHUA on laminin and type I collagen," Osaka City Med J. 44(2):173-80 (1998).

Chaudhuri et al., "Light-based imaging of green fluorescent protein-positive ovarian cancer xenografts during therapy," Gynecol. Oncol. 82(3): 581-589 (2001).

Cheadle, E.J. And A.M. Jackson, "Bugs as Drugs for Cancer", Immunol., 107: 10-19 (2002).

Chen et al. "Cancer gene therapy by direct tumor injections of a nonviral T7 vector encoding a thymidine kinase gene," Hum Gene Ther. 9(5):729-36 (1998).

Chen et al. "Evaluation of combined vaccinia virus-mediated antitumor gene therapy with p53, IL-2, and IL-12 in a glioma model." Cancer Gene Ther. 7(11):1437-47 (2000).

Chen et al., "Evaluation of Cytokine Toxicity Induced by Vaccinia Virus-mediated IL-2 and IL-2 Antitumor Immunotherapy," Cytokine (2001) 15(61):305-314.

Chen et al., "Low-dose vaccinia virus-mediated cytokine gene therapy of glioma," J Immunother. 24(1):46-57 (2001).

Chernajovsky et al., "Fighting cancer with oncolytic viruses," BMJ, 332(7534):170-172, (2006).

Child et al., "Insertional inactivation of the large subunit of ribonucleotide reductase encoded by vaccinia virus is associated with reduced virulence in vivo," Virology 174:625-629 (1990).

Chiocca, E.A., "Oncolytic Viruses", Nat. Rev. Cancer, 2(12): 938-950 (2002).

Cichutek, K., "Development and Regulation of Gene Therapy Drugs in Germany", Chapter 17 in Gene Therapy Technologies, Applications and Regulations, A. Meager (Ed.), John Wiley & Sons Ltd. pp. 347-358 (c1999).

Clairmont et al., "Biodistribution and genetic stability of the novel antitumor agent VNP20009, a genetically modified strain of *Salmonella typhimurium*," J Infect Dis. 181(6):1996-2002 (2000).

Clairmont, C. et al., "Enhanced antitumor activity from tumor-targeting *Salmonella* expressing endostatin," American Association for Cancer Research: 91st Annual Meeting of the AACR, Apr. 1-5, 2000, 41:732 Abstract #4653 (2000).

Cole, A.M. and T. Ganz, "Human antimicrobial peptides: analysis and application," Biotechniques. 29(4):822-6, 828, 830-1 (2000).

Colinas et al., "A DNA ligase gene in the copenhagen strain of vaccinia virus is nonessential for viral replication and recombination," Virology 179: 267-275 (1990).

Collins, J.L. and C.J. Wust, "Suppression of SV40 tumors after immunization with group A *Streptococcus pyogenes* and *Bordetella pertussis*," Cancer Res. 34(5):932-7 (1974).

Compton, J.L. and A.A. Szalay, "Insertion of nonhomologous DNA into the yeast genome mediated by homologous recombination with a cotransforming plasmid," Mol Gen Genet. 188(1):44-50 (1982).

Condeelis, J. and J.E. Segall, "Intravital imaging of cell movement in tumours", Nat. Rev. Cancer, 3: 921-930 (2003).

Contag et al., "Photonic detection of bacterial pathogens in living hosts," Mol. Microbiol. 18: 593-603 (1995).

Coupar, B.E.H. et al., "A general method for the construction of recombinant vaccinia viruses expressing multiple foreign genes", Gene, 68: 1-10 (1988).

Coussens, L.M. and Z. Werb, "Inflammation and cancer", Nature, 420: 860-867 (2002).

Craperi et al. "Increased bax expression is associated with cell death induced by ganciclovir in a herpes thymidine kinase gene-expressing glioma cell line." Hum Gene Ther. 10(4):679-688 (1999).

Crystal, "Transfer of Genes to Humans: Early Lessons and Obstacles to Success," Science, 270:404-410, (1995).

Culver et al., "In vivo gene transfer with retroviral vector-producer cells for treatment of experimental brain tumors." Science. 256(5063):1550-2 (1992).

Dang et al., "Combination bacteriolytic therapy for the treatment of experimental tumors," Proc Natl Acad Sci U S A. 98(26):15155-60 (2001).

Davis, "The Many Faces of Epidermal Growth Factor Repeats," The New Biologist, 2(5):410-419, (1990).

Davison et al., "New vaccinia virus recombination plasmids incorporating a synthetic late promoter for high level expression of foreign proteins," Nucleic Acids Research 18: 4285-4286 (1990).

Davison, A. J. and B. Moss, "Structure of Vaccinia Virus Early Promoters," J. Mol. Biol. 210: 749-769 (1989).

De Clercq, E., "Cidofovir in the therapy and short-term prophylaxis of poxvirus infections", Trends in Pharmacological Sciences, 23(10): 456-458 (2002).

de Wet et al., "Firefly Luciferase Gene: Structure and Expression in Mammalian Cells," Mol. Cell. Biol. 7: 725-737 (1987).

Demers, G.W. et al., "Pharmacologic Indicators of Antitumor Efficacy for Oncolytic Virotherapy", Cancer Res., 63: 4003-4008 (2003).

Derwent English abstract for Japanese Patent Publication JP 55035004, published Feb. 3, 1987, entitled, "Cellular immunopotentiator—contg. Vaccinia attenuated virus showing no infectivity to man or rabbit and has lost humoral immunity," Derwent Accession No. 2512008.

Derwent English abstract for WO 94/10302, published May 11, 1994 entitled: "Vectors inhibiting HIV replication in potential host cells—contg. DNA encoding Pol, Gag, Env, Rev, and/or Tat in antisense direction and further DNA causing spontaneous amplification," Accession Nbr. 1994-152544 [19].

Devereux, J., et al., "A comprehensive set of sequence analysis programs for the VAX," Nucleic Acids Research 12(1): 387-95 (1984).

Dietrich, G. et al., "Delivery of antigen-encoding plasmid DNA into the cytosol of macrophages by attenuated suicide *Listeria monocytogenes*," Nat Biotechnol. 16(2):181-5 (1998).

Ding et al., "Zinc-dependent dimers observed in crystals of human endostatin," Proc. Natl. Acad. Sci. USA 95:10443-10448 (1998).

Djeha et al., Combined adenovirus-mediated nitroreductase gene delivery and CB1954 treatment: a well-tolerated therapy for established solid tumors. Mol Ther. Feb 2001;3(2):233-40.

Djeha et al., "Expression of *Escherichia coli* B nitroreductase in established human tumor xenografts in mice results in potent antitumoral and bystander effects upon systemic administration of the prodrug CB1954," Cancer Gene Ther. 7(5):721-31 (2000).

Dobbelstein, M., "Viruses in therapy—royal road or dead end?", Virus Research, 92: 219-221 (2003).

Domi, A. and B. Moss, "Cloning the vaccinia virus genome as a bacterial artificial chromosome in *Escherichia coli* and recovery of infectious virus in mammalian cells", Proc. Natl. Acad. Sci. U.S.A., 99(19): 12415-12420 (2002).

Dunn et al., "Cancer immunoediting: from immunosurveillance to tumor escape.," Nat Immunol. 3(11):991-8 (2002).

Earl et al., "T-Lymphocyte Priming and Protection Against Friend Leukemoa by Vaccinia-Retrovirus env Gene Recombinant," Science 234: 728-731 (1986).

Eastham et al. "Prostate cancer gene therapy: herpes simplex virus thymidine kinase gene transduction followed by ganciclovir in mouse and human prostate cancer models." Hum Gene Ther. 7(4):515-23 (1996).

Ebert et al., "Oncolytic vesicular stomatitis virus for treatment of orthotopic hepatocellular carcinoma in immune-competent rats," Cancer Research 63: 3605-3611(2003).

Ebert et al., "Syncytia induction enhances the oncolytic potential of vesicular stomatitis virus in virotherapy for cancer," Cancer Research 64: 3265-3270 (2004).

Eck et al., "Gene-Based Therapy," Goodman & Gilman's The Pharmacological Basis of Therapeutics, McGraw-Hill, New York, p. 77-101, (1996).

Ehrengruber, M.U., "Alphaviral gene transfer in neurobiology", Brain Research Bulletin, 59(1): 13-22 (2002).

Eliopoulos et al., "CD40 induces apoptosis in carcinoma cells through activation of cytotoxic ligands of the tumor necrosis factor superfamily," Mol Cell Biol. 20(15):5503-15 (2000).

Engebrecht et al., "Measuring Gene Expression with Light," Science 227: 1345-1347 (1985).

Escher, A et al., "The β subunit polypeptide of Vibrio harveyi luciferase determines light emission at 42° C," Mol Gen Genet. 230(3):385-93 (1991).

Escher, A. and A.A. Szalay, "GroE-mediated folding of bacterial luciferases in vivo," Mol Gen Genet. 238(1-2):65-73 (1993).

Escher, A. et al., "Bacterial luciferase αβ fusion protein is fully active as a monomer and highly sensitive in vivo to elevated temperature," Proc Natl Acad Sci U S A. 86(17):6528-32 (1989).

Esposito, J.J. and F. Fenner, "Poxviruses", Chapter 85 in Field's Virology, 4th Edn., vol. 2, pp. 2885-2921. Edited by D. M. Knipe and P. M. Howley, Philadelphia: Lippincott Williams & Wilkins, (2001).

Essbauer, S. and W. Ahne, "Viruses of lower vertebrates," J Vet Med B Infect Dis Vet Public Health. 48(6):403-75 (2001).

Estin et al, "Recombinant vaccinia virus vaccine against the human melanoma antigen p97 for use in immunotherapy," Proc. Natl. Acad. Sci. USA 85: 1052-1056 (1988).

Fabricius et al., "Quantitative investigations into the elimination of in vitro-obtained spores of the non-pathogenic *Clostridium butyricum* strain CNRZ 528, and their persistence in organs of different species following intravenous spore administration," Res. Microbiol. 144: 741-753 (1993).
Farkas-Himsley et al., "The bacterial colicin active against tumor cells in vitro and in vivo is verotoxin 1," Proc Natl Acad Sci U S A. 92(15):6996-7000 (1995).
Fatyol, K and A.A. Szalay, "The p14$^{ARF}$ tumor suppressor protein facilitates nucleolar sequestration of hypoxia-inducible factor-1β (HIF-1β) and inhibits HIF-1-mediated transcription," J Biol Chem. 276(30):28421-28429 (2001).
Feng et al, "The antitumor activity of a mixed bacterial vaccine against mouse hepatoma," Chinese Pharmaceutical Journal 30(7): 405-407 (1995) [Article in Chinese].
Fernández-Piñas, F. and C.P. Wolk, "Expresssion of *luxCD-E* in *Anabaena sp.* can replace the use of exogenous aldehyde for in vivo localization of transcription by *luxAB*,"Gene 150:169-174 (1994).
Ferretti et al., "Complete genome sequence of an M1 strain of *Streptococcus pyogenes*," Proc. Natl. Acad. Sci. USA 98(8): 4658-4663 (2001).
Fidler, I.J., "The pathogenesis of cancer metastasis: the 'seed and soil' hypothesis revisited", Nature Cancer Research, 3: 1-6 (2003).
Flexner et al., "Characterization of Human Immunodeficiency Virus *gag/pol* Gene Products Expressed by Recombinant Vaccinia Viruses," Virology 166: 339-349 (1988).
Flexner et al., "Successful vaccination with a polyvalent live vector despite existing immunity to an expressed antigen," Nature 355:259-262 (1988).
Fodor et al., "Vaccinia virus mediated p53 gene therapy for bladder cancer in an orthotopic murine model," J. Urol. 173(2):604-9 (2005).
Foran, D.R. and W.M. Brown, "Nucleotide sequence of the LuxA and LuxB genes of the bioluminescent marine bacterium *Vibrio fischeri*," Nucleic Acids Res. 16: 777 (1988).
Forbes, N.S. et al., "Sparse Initial Entrapment of Systematically Injected *Salmonella typhimurium* Leads to Heterogenous Accumulation within Tumors," Cancer Res., 63: 5188-5193 (2003).
Fox, A.W., "Emergency and Compassionate-use INDs and Accelerated NDS or ANDA Approvals—Procedures, Benefits and Pitfalls", Chapter 26 in Principles and Practice of Pharmaceutical Medicine, A.J. Fletcher, et al.(Eds.), John Wiley & Sons, pp. 299-305, (2002).
Francis et al., "Monitoring bioluminescent *staphyloccus aureus* infections in living mice using a novel *lux*ABCDE construct," Infection and Immunity 68(6): 3594-3600 (2000).
Freitag, N. E. and K.E. Jacobs, "Examination of *Listeria monocytogenes* Intracellular Gene Expression by Using Green Fluorescent Protein of *Aequorea victoria*," Infect.Immun. 67:1844-1852 (1999).
Friberg, S. and S. Mattson, "On the Growth Rates of Human Malignant Tumors: Implications for Medical Decision Making," Journal of Surgical Oncology, 65: 284-297 (1997).
Friedlos et al., "Three new prodrugs for suicide gene therapy using carboxypeptidase G2 elicit bystander efficacy in two xenograft models," Cancer Res. 62(6):1724-1729 (2002).
Gallagher, R., "Vaccination Undermined", The Scientist, 17(22): 1-3 (2003).
Gambhir et al., "Imaging transgene expression with radionuclide imaging technologies," Neoplasia 2(1-2): 118-138 (2000).
Gautam et al., "Delivery Systems for Pulmonary Gene Therapy," Am. J. Respir. Med., 1(1):35-46, (2002).
Giacomin, L.T. and A.A. Szalay, "Expression of a PALI promoter luciferase gene function in *Arabidopsis thaliana* in response to infection by phytopathogenic bacteria," Plant Sci. 116: 59-72 (1996).
Giedlin et al., "Vesicular stomatitis virus: an exciting new therapeutic oncolytic virus candidate for cancer or just another chapter from *Field's Virology*?" Cancer Cell 4: 241-243 (2003).
Gnant et al., "Regional *Versus* Systemic Delivery of Recombinant Vaccinia Virus as Suicide Gene Therapy for Murine Liver Metastases," Annals of Surgery 230(3): 352-361 (1999).
Gnant et al., "Sensitization of tumor necrosis factor β-resistant human melanoma by tumor-specific in vivo transfer of the gene encoding endothelial monocyte-activating polypeptide II using recombinant vaccinia virus," Cancer Research 59: 4668-4674 (1999).
Gnant et al., "Systemic administration of a recombinant vaccinia virus expressing the cytosine deaminase gene and subsequent treatment with 5-fluorocytosine leads to tumor-specific gene expression and prolongation of survival in mice," Cancer Res. 59(14):3396-3403 (1999).
Gnant, M.F.X. et al, "Tumor-Specific Gene Delivery Using Recombinant Vaccinia Virus in a Rabbit Model of Liver Metastases", Journal of the National Cancer Institute, 91(20): 1744-1750 (1999).
Goebel et al., "Appendix to 'The complete DNA Sequence of Vaccinia Virus,'" Virology 179: 517-563 (1990).
Goebel et al., "The complete DNA sequence of vaccinia virus," Virology 179:247-266 (1990).
Gomella, L.G. et al., "Phase I Study Of Intravesical Vaccinia Virus As A Vector For Gene Therapy Of Bladder Cancer", J. Urology, 166: 1291-1295 (2001).
Gómez, C.E. and M. Esteban, "Recombinant proteins produced by vaccinia virus vectors can be incorporated within the virion (IMV form) into different compartments," Arch. Virol., 146: 875-892 (2001).
Gorecki, "Prospects and problems of gene therapy: an update," Expert Opin. Emerging Drugs, 6(2):187-198, (2001).
Gray, J.W., "Evidence emerges for early metastasis and parallel evolution of primary and metastatic tumors", Cancer Cell, 4(1): 4-6 (2003).
Greco et al., "Development of a novel enzyme/prodrug combination for gene therapy of cancer: horseradish peroxidase/indole-3-acetic acid," Cancer Gene Ther. 7(11):1414-20 (2000).
Green, D.R. and G.I. Evan, "A matter of life and death", Cancer Cell, 1: 19-30 (2002).
Greer III, L.F. and A.A. Szalay, "Imaging of light emission from the expression of luciferases in living cells and organisms: a review," Luminescence. 17(1):43-74 (2002).
Greinwald et al., "Treatment of lymphangiomas in children: an update of Picibanil (Ok-432) sclerotherapy," Otolaryngol Head Neck Surg 121(4): 381-387 (1999).
Gribskov et al., "Sigma factors from *E. coli, B. subtilis*, phage SP01, and phage T4 are homologous proteins," Nucl. Acids Res. 14:6745-6763 (1986).
Gridley et al., "Evaluation of radiation effects against C6 glioma in combination with vaccinia virus-p53 gene therapy," Int J Oncol. 13(5):1093-8 (1998).
Gridley et al., "Proton radiation and TNF-β/Bax gene therapy for orthotopic C6 brain tumor in Wistar rats," Technol Cancer Res Treat. 3(2):217-27 (2004).

Griffin, D.E., "A Review of Alphavirus Replication in Neurons", Neuroscience and Biobehavioral Reviews, 22(6): 721-723 (1998).

Grote et al., "Live attenuated measles virus induces regression of human lymphoma xenografts in immunodeficient mice," Blood 97(12):3746-54 (2001).

Grove et al. "Virus-directed enzyme prodrug therapy using CB1954" Anti-Cancer Drug Design 14(6) 461-472 (1999).

Gura, "Systems for identifying new drugs are often faulty," Science, 278:1041-1042, (1997).

Guy et al., "Expression of the neu protooncogene in the mammary epithelium of transgenic mice induces metastatic disease," Proc. Natl. Acad. Sci.USA 89: 10578-10582 (1992).

Hacein-Bey-Abina, S. et al., "A Serious Adverse Event after Successful Gene Therapy for X-Linked Severe Combined Immunodeficiency", N. Engl. J. Med., 348(3): 255-256 (2003).

Haghighat et al. "Antitumor effect of IL-2, p53, and bax gene transfer in C6 glioma cells," Anticancer Res. 20(3A):1337-42 (2000).

Hall et al., "Adenovirus-mediated herpes simplex virus thymidine kinase gene and ganciclovir therapy leads to systemic activity against spontaneous and induced metastasis in an orthotopic mouse model of prostate cancer," Int J Cancer. 70(2):183-7 (1997).

Hall et al., "In vitro efficacy of transferrin-toxin conjugates against glioblastoma multiforme," J Neurosurg. 76(5):838-44 (1992).

Hall et al., "In vivo efficacy of intrathecal transferrin-*Pseudomonas* exotoxin A immunotoxin against LOX melanoma," Neurosurgery 34(4):649-55; discussion 655-6 (1994).

Halsell, J.S. et al., "Myopericarditis Following Smallpox Vaccination Among Vaccinia-Naïve US Military Personnel", J. Am. Med. Assoc., 289(24): 3283-3289 (2003).

Hamblin et al., "Rapid control of wound infections by targeted photodynamic therapy monitored by in vivo bioluminescence imaging," Photochemistry and Photobiology 75(1): 51-57 (2002).

Hanahan, D. and R.A. Weinberg, "The Hallmarks of Cancer", Cell, 100: 57-70 (2000).

Hansen et al., "Assessment of GFP fluorescence in cells of *Streptococcus gordonii* under conditions of low pH and low oxygen concentration," Microbiology 147: 1383-1391 (2001).

Hansen, R.M. and J.A. Libnoch, "Remission of Chronic Lymphocytic Leukemia After Smallpox Vaccination", Arch. Intern. Med., 138: 1137-1138 (1978).

Hansen, R.M. and J.A. Libnoch, "Remission of chronic lymphocytic leukemia after smallpox vaccination," Arch Intern Med. 138(7):1137-8 (1978).

Harrison et al., "Gene-modified PA1-STK cells home to tumor sites in patients with malignant pleural mesothelioma," Ann Thorac Surg. 70(2):407-11 (2000).

Hasegawa et al., "Avoidance of bone marrow suppression using A-5021 as a nucleoside analog for retrovirus-mediated herpes simplex virus type I thymidine kinase gene therapy,." Cancer Gene Ther. 7(4):557-62 (2000).

Hasegawa et al., "In vivo tumor delivery of the green fluorescent protein gene to report future occurrence of metastasis," Cancer Gene Therapy 7: 1336-1340 (2000).

Hatta, "Antitumor Mechanisms of *Eubacterium lentum* and its Components," Asian Pacific Journal of Allergy and Immunology 13: 129-137 (1995).

Hawkins, L.K. et al., "Oncolytic biotherapy: a novel therapeutic platform", The Lancet Oncology, 3: 17-26 (2002).

Hemann et al., "High-Copy Expression Vector Based on Amplification-Promoting Sequences", DNA and Cell Biology 13:437-445 (1994).

Hermiston, T.W. and I. Kuhn, "Armed therapeutic viruses: Strategies and challenges to arming oncolytic viruses with therapeutic genes", Cancer Gene Therapy, 9: 1022-1035 (2002).

Herrlinger et al., "Neural precursor cells for delivery of replication-conditional HSV-1 vectors to intracerebral gliomas," Mol Ther. 1(4):347-57 (2000).

Hershey, P. et al., "Adjuvant Immunotherapy of Patients With High-Risk Melanoma Using Vaccinia Viral Lysates of Melanoma: Results of a Randomized Trial", Journal of Clinical Oncology, 20(20): 4181-4190(2002).

Hess et al., "*Listeria monocytogenes* p60 supports host cell invasion by and in vivo survival of attenuated *Salmonella typhimurium*," Infect Immun. 63(5):2047-53 (1995).

Hetz et al., "Microcin E492, a channel-forming bacteriocin from *Klebsiella pneumoniae*, induces apoptosis in some human cell lines," Proc Natl Acad Sci U S A. 99(5):2696-701 (2002).

Hiller et al., "Characterization of Intracellular and Extracellular Vaccinia Virus Variants: $N_1$-Isonicotinoyl-$N_2$-3-Methyl-4-Chlorobenzoylhydrazine Interferes with Cytoplasmic Virus Dissemination and Release," Journal of Virology 39(3): 903-913 (1981).

Hollinshead, M. et al., "Vaccinia virus utilizes microtubules for movement to the cell surface," Journal of Cell Biology, 154: 389-402 (2001).

Hostanska et al., "Aqueous ethanolic extract of St. John's wort (Hypericum perforatum L.) induces growth inhibition and apoptosis in human malignant cells in vitro," Pharmazie 57(5):323-31 (2002).

Hsueh et al., "Outbreak of Pseudomonas fluorescens bacteremia among oncology patients," J Clin Microbiol. 36(10):2914-7 (1998).

Huang et al., "Impact of liver P450 reductase suppression on cyclophosphamide activation, pharmacokinetics and antitumoral activity in a cytochrome P450-based cancer gene therapy model," Cancer Gene Ther. 7(7):1034-42 (2000).

Huang et al., "Oncolysis of hepatic metastasis of colorectal cancer by recombinant vesticular stomatitis virus in immune-competent mice," Mol. Ther. 8(3): 434-440 (2003).

Hughes, R.G. and N. Turner, "Financial Aspects of Clinical Trials", Chapter 42 in *Principles and Practice of Pharmaceutical Medicine*, A.J. Fletcher, et al.(eds.), pp. 501-512, John Wiley & Sons, Ltd. (2002).

Humlova, Z. et al., "Vaccinia virus induces apoptosis of infected macrophages," J. General Virol., 83: 2821-2832 (2002).

Hurst et al., "A novel model of a metastatic human breast tumour xenograft line," Br. J. Cancer 68: 274-276 (1993).

Ianaro et al., "Expression of TGF-β in attenuated *Salmonella typhimurium*: oral administration leads to the reduction of inflammation, II-2 and IFN-γ, but enhancement of IL-10, in carrageein-induced oedema in mice," Immunology 84:8-15 (1995).

Isaacs et al., "Vaccinia virus complement-control protein prevents antibody-dependent complement-enhanced neutralization of infectivity and contributes to virulence," Proc Natl Acad Sci U S A. 89:628-632 (1992).

Jacobs et al., "Positron Emission Tomography-based Imaging of Transgene Expression Mediated by Replication-conditional, Oncolytic Herpes Simplex Virus Type I Mutant Vectors in Vivo," Cancer Research 61: 2983-2995 (2001).

Jain, R.K. And B.T. Fenton, "Intratumoral Lymphatic Vessels: A Case of Mistaken Identity or Malfunction?", Journal of the National Cancer Institute, 94(6): 417-421 (2002).

Jain, R.K. and N.S. Forbes, "Can engineered bacteria help control cancer," Proc. Natl. Acad. Sci. USA 98(26): 14748-14750 (2001).

Jain, R.K., "Molecular regulation of vessel maturation", Nat. Med., 9(6): 685-693 (2003).

Jemal, A. et al., "Cancer Statistics, 2003", CA Cancer J Clin, 53(1): 5-26 (2003).

Jiang et al. "Apoptosis in human hepatoma cell lines by chemotherapeutic drugs via Fas-dependent and Fas-independent pathways," Hepatology. 29(1):101-10 (1999).

Johnson et al., "An update on the vaccinia virus genome," Virology 196: 381-401 (1993).

Johnson et al., "Improved tumor-specific immunotoxins in the treatment of CNS and leptomeningeal neoplasia," J Neurosurg. 70(2):240-8 (1989).

Joklik, W.K., "The Purification of Four Strains of Poxviruses," Virology 18:9-18 (1962).

Jordan et al., "Melanocyte-Directed enzyme prodrug therapy (MDEPT): development of second generation prodrugs for targeted treatment of malignant melanoma," Bioorg Med Chem. 9(6):1549-58 (2001).

Kaklij et al., "Antitumor activity of *Streptococcus thermophilus* against fibrosarcoma: role of T-cells,"Cancer Lett. 56(1):37-43 (1991).

Kaklij, G.S. and S.M. Kelkar, "Tumor-specific transplantation resistance in mice after treatment of initial tumors with *Streptococcus thermophilus*," Microbiol Immunol. 40(1):55-8 (1996).

Kammertoens et al., "Combined chemotherapy of murine mammary tumors by local activation of the prodrugs ifosfamide and 5-fluorocytosine," Cancer Gene Ther. 7(4):629-36 (2000).

Kan et al., "Direct retroviral delivery of human cytochrome P450 2B6 for gene-directed enzyme prodrug therapy of cancer," Cancer Gene Ther. 8(7):473-82 (2001).

Kantor et al., "Antitumor Activity and Immune Responses Induced by a Recombinant Carcinoembryonic Antigen-Vaccinia Virus Vaccine," J. Natl. Cancer Inst. 84: 1084-1091 (1992).

Kaplitt et al., "Mutant herpes simplex virus induced regression of tumors growing in immunocompetent rats," J. Neurooncol 19(2): 137-147 (1994).

Kato et al., "Antitumor activity of *Lactobacillus casei* in mice," Gann. 72(4):517-23 (1981).

Kato et al., "Correlation between increase in Ia-bearing macrophages and induction of T cell-dependent antitumor activity by *Lactobacillus casei* in mice," Cancer Immunol Immunother. 26(3):215-21 (1988).

Katz et al., "Mutations in the vaccinia virus A33R and B5R envelope proteins that enhance release of extracellular virions and eliminate formation of actin-containing microvilli without preventing tyrosine phosphorylation of the A36R protein," J. Virology 77:12266-12275 (2003).

Kaufman et al., "A recombinant vaccinia virus expressing human carcinoembryonic antigen CEA," Int. J. Cancer, 48(6):900-907, (1991).

Kaufman et al., "Insertion of interleukin-2 (IL-2) and interleukin-12 (IL-12) genes into vaccinia virus results in effective anti-tumor responses without toxicity," *Vaccine* 20:1862-1869 (2002).

Kawa, A. and S. Arakawa, "The Effect of Attenuated Vaccinia Virus AS Strain on Multiple Myeloma; A Case Report", Japan. J. Exp. Med. 58(1): 79-81 (1987).

Kawamura et al., "Expression of *Escherichia coli* uracil phosphoribosyltransferase gene in murine colon carcinoma cells augments the antitumoral effect of 5-fluorouracil and induces protective immunity," Cancer Gene Ther. 7(4):637-43 (2000).

Kaye et al., "A single amino acid substitution results in a retinoblastoma protein defective in phosphorylation and oncoprotein binding," Proc. Natl. Acad. Sci. USA, 87:6922-6926, (1990).

Keith, K.A. et al., "Evaluation of Nucleoside Phosphonates and Their Analogs and Prodrugs for Inhibition of Orthopoxvirus Replication," Antimicr. Agents Chemothera., 47(7): 2193-2198 (2003).

Kelkar et al., "Antitumor activity of lactic acid bacteria on a solid fibrosarcoma, sarcoma-180 and Ehrlich ascites carcinoma," Cancer Lett. 42(1-2):73-7 (1988).

Kelland et al., "Of mice and men: values and liabilities of the athymic nude mouse model in anticancer drug development," European J. Cancer, 40:827-836, (2004).

Kerbel et al., "Human Tumor Xenografts as Predictive Preclinical Models for Anticancer Drug Activity in Humans," Cancer Biology & Therapy, 2:4 suppl. 1, S134-S139, (2003).

Kern, E.R., "In vitro activity of potential anti-poxvirus agents", Antiviral Research 57: 35-40 (2003).

Ketlinsky et al., "[Mechanism of the anti-tumoral effect of the blastolysin fraction isolated from *Lactobacillus bulgaricus*]," Vopr Onkol. 33(3):51-6 (1987) [Article in Russian].

Kihara, A. and I. Pastan, "Analysis of Sequences Required for the Cytotoxic Action of a Chimeric Toxin Composed of Pseudomonas Exotoxin and Transforming Growth Factor α," Bioconj.Chem. 5: 532-538 (1994).

Kim, E.M. et al., "Overview analysis of adjuvant therapies for melanomaFa special reference to results from vaccinia melanoma oncolysate adjuvant therapy trials", Surgical Oncology, 10: 53-59 (2001).

Kim et al., "A tale of two trials: selectively replicating herpesviruses for brain tumors," Gene Therapy, 7(10):815-816, (2000).

Kimura et al., "Selective localization and growth of Bifidobacterium bifidum in mouse tumors following intravenous administration," Cancer Res. 40(6):2061-8 (1980).

Kirn, D.H. and F. McCormick, "Replicating viruses as selective cancer therapeutics," Mol Med Today 2(12): 519-527 (1996).

Kleer, C.G. et al., "Molecular biology of breast cancer metastasis Inflammatory breast cancer: clinical syndrome and molecular determinants," Breast Cancer Res. 2: 423-429 (2000).

Kohler et al., "Continuous cultures of fused cells secreting antibody of predefined specificity," Nature, 256:495, (1975).

Kohwi et al., "Antitumor effect of Bifidobacterium infantis in mice," Gann. 69(5)613-8 (1978).

Kokkinakis et al., "Effect of long-term depletion of plasma methionine on the growth and survival of human brain tumor xenografts in athymic mice," Nutr Cancer. 29(3):195-204 (1997).

Kondo et al., "Activity of Immunotoxins Constructed with Modified Pseudomonas Exotoxin A Lacking the Cell Recognition Domain," J.Biol.Chem. 263: 9470-9475 (1988).

Kopylova-Sviridova et al., "Transient expression assay in a baculovirus system using firefly luciferase gene as a reporter," Virus Genes. 6(4):379-86 (1992).

Kotwal et al., "Mapping and Insertional Mutagenesis of a Vaccinia Virus Gene Encoding a 13, 800-Da Secreted Protein," Virology 171:579-587 (1989).

Koyama et al., "Combined suicide gene therapy for human colon cancer cells using adenovirus-mediated transfer of *escherichia coli* cytosine deaminase gene and *Escherichia coli* uracil phosphoribosyltransferase gene with 5-fluorocytosine," Cancer Gene Ther. 7(7):1015-22 (2000).

Kozak, M., "Structural features in Eukaryotic mRNAs that modulate the Initiation of Translation," J. Biol. Chem. 266:19867-19870 (1991).

Krauss, O. et al., "An investigation of incorporation of cellular antigens into vaccinia virus particles", Journal of General Virology, 83: 2347-2359 (2002).

Kutinova et al., "Hepatitis B virus proteins expressed by recombinant vaccinia viruses: influence of preS2 sequence on expression surface and nucleocapsid proteins in human diploid cells," *Archives of Virology* 134:1-15 (1994).

Kutinova et al., "Search for optimal parent for recombinant vaccinia virus vaccines. Study of three vaccinia virus vaccinal strains and several virus lines derived from them," Vaccine 13(5): 487-493 (1995).

Kwak, H. et al., "Poxviruses as vectors for cancer immunotherapy", Curr. Opin. Drug Disc. Develop., 6(2): 161-168 (2003).

Lachmann, R.H. and S. Efstathiou, "Gene transfer with herpes simplex vectors," Curr Opin Mol Ther. 1(5):622-32 (1999).

Lamberton et al., "Construction and characterization of a bioluminescent *Streptococcus pyogene*," Proceedings of the 12th International Symposium on Bioluminescence and Chemiluminescence Progress & Current Appications, Stanley, P.E. and L.J. Kricka et al (Eds). World Scientific Publishing Co. Pte. Ltd., pp. 85-88 (2002).

Lamberton et al., "Generation and characterization of a bioluminescent *Streptococcus pyogenes*," Proceedings of the 12th International Symposium on Bioluminescence & Chemiluminescence: Apr. 5-9, 2002, Robinson College, University of Cambridge, UK, p. 3.22 (2002).

Lamensans et al., "Enhancement of immunity against murine syngeneic tumors by a fraction extracted from non-pathogenic mycobacteria," Proc Natl Acad Sci U S A. 72(9):3656-60 (1975).

Lammertyn et al., "Evaluation of a novel subtilisin inhibitor gene and mutant derivatives for the expression and secretion of mouse tumor necrosis factor alpha by *Streptomyces lividans*," Appl Environ Microbiol. 63(5):1808-13 (1997).

Langridge W.H. et al, "Detection of baculovirus gene expression in insect cells and larvae by low light video image analysis," J Virol Methods. 61(1-2):151-6 (1996).

Langridge W.H. et al., "Uptake of DNA and RNA into cells mediated by electroporation," Methods Enzymol. 153:336-50. (1987).

Langridge, W.H. and, A.A.Szalay, "Bacterial and coelenterate luciferases as reporter genes in plant cells," Chapter 37 in Methods Mol Biol. 82:385-96.(1998).

Larson et al. "Triumph over mischance: a role for nuclear medicine in gene therapy," J Nucl Med. 38(8):1230-3 (1997).

Lathe et al., "Tumour prevention and rejection with recombinant vaccinia," Nature (London) 326: 878-880 (1987).

Lattime et al., "In Situ Cytokine Gene Transfection Using Vaccinia Virus Vectors," Semin Oncol 23(1): 88-100 (1996).

Lawrence J.C., "The bacteriology of burns", J. of Hospital Infection 6: 3-17 (1985).

Lee et al. "Prodrug and antedrug: two diametrical approaches in designing safer drugs," Arch. Pharm. Res. 25(2): 111-136 (2002).

Lee et al., "Molecular attenuation of vaccinia virus: mutant generation and animal characterization," Journal of Virology 66:2617-2630 (1992).

Lee et al., "The lux genes of the luminous bacterial symbiont *Photobacterium leiognathi*, of the ponyfish," Eur. J. Biochem. 201: 161-167 (1991).

Legocki et al., "Bioluminescence in soybean root nodules: Demonstration of a general approach to assay gene expression in vivo by using bacterial luciferase," Proc. Natl. Acad. Sci 83: 9080-9084 (1986).

Lemmon et al., "Anaerobic bacteria as a gene delivery system that is controlled by the tumor microenvironment," Gene Therapy 4: 791-796 (1997).

Lemmon et al., "Anaerobic bacteria as a gene delivery system to tumors," Proceedings of the 85th Annual Meeting of the American Association for Cancer Research, San Francisco, CA Apr. 10-13, 1994, published in: Proc. Am. Cancer Research Assn 35: 374 (1994).

Ley, K., "The role of selectins in inflammation and disease", Trends in Molec. Med., 9(6): 263-268 (2003).

Li et al "An engineered and assembled fusion protein of antitumor antibiotic lidamycin and scFV antibody directed against type IV collagenase" Yaoxue Xuebao 35(7) 488-91 (Jul. 2000) [English abstract on last page of article].

Li et al., "*Bifidobacterium adolescentis* as a delivery system of endostatin for cancer gene therapy: Selective Inhibitor of angiogenesis and hypoxic tumor growth," Cancer Gene Therapy 10: 105-111 (2003).

Li et al., "Enzyme/prodrug gene therapy approach for breast cancer using a recombinant adenovirus expressing *Escherichia coli* cytosine deaminase," Cancer Gene Ther. 4(2):113-7 (1997).

Liau et al., "Treatment of intracranial gliomas with bone marrow-derived dendritic cells pulsed with tumor antigens," J. Neurosurg. 90(6): 1115-1124 (1999).

Lindsey et al., "Modified cold virus kills colon cancer," Lancet Oncol., 3(5):264, (2002).

Liu et al., "An E I B-19 kDa gene deletion mutant adenovirus demonstrates tumor necrosis factor-enhanced cancer selectivity and enhanced oncolytic potency," Molecular Therapy 9(6): 786-803 (2004).

Liu et al., "Anticancer efficacy of systemically delivered anaerobic bacteria as gene therapy vectors targeting tumor hypoxia/necrosis," Gene Ther. 9(4):291-6 (2002).

Liu, H et al., "Detection of GDNF secretion in glial cell culture and from transformed cell implants in the brains of live animals," Mol Genet Genomics. 266(4):614-23. (2001).

Liu, J. et al., "Visualizing and quantifying protein secretion using a *Renilla luciferase*-GFP fusion protein," Luminescence. 15(1):45-49 (2000).

Lopez et al., "Infections in children with malignant disease in Argentina," Cancer 47(5): 1023-1030 (1981).

Lorenz et al., "Expression of the *Renilla reniformis* luciferase gene in mammalian cells," J Biolumin Chemilumin. 11(1):31-7 (1996).

Lorenz et al., "Isolation and expression of a cDNA encoding *Renilla reniformis* luciferase," PNAS USA 88: 4438-4442 (1991).

Louie, A.Y. et al., "In vivo visualization of gene expression using magnetic resonance imaging", Nature Biotechnology, 18: 321-325 (2000).

Lusso, P., "Chemokines and Viruses: The Dearest Enemies", Virology, 273: 228-240 (2000).

Lyford, J., "Gene therapy 'cause T-cell leukemia': Insertional mutagenesis pinpointed as cause of T-cell Leukemia in X-SCID gene therapy trial", The Scientist, (Daily News, Oct. 20, 2003) pp. 1-4 (2003).

MacDonald, I.C. et al., "Cancer spread and micrometastasis development: quantitative approaches for in vivo models", BioEssays, 24: 885-893 (2002).

Mackenzie et al., "Human mesenchymal stem cells persist, demonstrate site-specific multipotential differentiation, and are present in sites of wound healing and tissue regeneration after transplantation into fetal sheep," Blood Cells, Molecules, and Diseases 27(3): 601-604 (2001).

MacLaren et al. "Receptive non-invasive imaging of the dopamine D2 recepter gene in living animals" Gene Therapy (MacMillan Press)v.6 pp. 785-791, (May 1995).

MacLeod R.A .et al., "Expression of genes from the marine bacterium *Alteromonas haloplanktis* 214 in *Escherichia coli* K-12," Arch Microbiol. 142(3):248-52 (1985).

Maeda, H. et al., "Tumor vascular permeability and the EPR effect in macromolecular therapeutics: a review", J. Controlled Release, 65: 271-284 (2000).

Mahy, B.W.J., "An overview on the use of a viral pathogen as a bioterrorism agent: why smallpox?", Antivir. Res., 57: 1-5 (2003).

Maina C.V. et al., "Molecular weight determination program," Nucleic Acids Res. 12(1 Pt 2):695-702 (1984).

Makower, D. et al., "Phase II Clinical Trial of Intralesional Administration of the Oncolytic Adenovirus ONYX-015 in Patients with Hepatobiliary Tumors with Correlative p53 Studies," Clin. Cancer Res., 9: 693-702 (2003).

Martino et al., "Bacteremia due to glucose non-fermenting gram-negative bacilli in patients with hematological neoplasias and solid tumors," Eur J Clin Microbiol Infect Dis. 15(7):610-5 (1996).

Mastrangelo, M.J. et al., "Poxvirus vectors: orphaned and underappreciated", J. Clin. Invest., 105(8): 1031-1034 (2000).

Matz et al., "Fluorescent proteins from nonbioluminescent Anthozoa species," Nat.Biotech. 17: 969-973 (1999).

Mayerhofer, R et al., "Monitoring of spatial expression of firefly luciferase in transformed zebrafish," J Biolumin Chemilumin. 10(5):271-5 (1995).

Mayford et al., "CaMKII Regulates the Frequency-Response Function of Hippocampal Synapses for the Production of Both LTD and LTP," Cell 81: 891-904 (1995).

Mayr et al., "The Smallpox Vaccination Strain MVA: Marker, Genetic Structure, Experience Gained with the Parenteral Vaccination and Behavior in Organisms with a Debilitated Defense Mechanism," Zentbl. Bakteriol. Hyg. Abt 1 Orig. B 167: 375-390 (1978) [In German, English abstract on first page of article].

McAllister et al., "Recombinant yellow fever viruses are effective therapeutic vaccines for treatment of murine experimental solid tumors and pulmonary metastases," J. Virol. 74:9197-9205 (2000).

McAneny et al., "Results of a Phase I trial of a recombinant vaccinia virus that expresses carcinoembryonic antigen in patients with advanced colorectal cancer,"Ann. Surg. Oncol. 3(5): 495-500 (1996).

McCart, J.A. et al., "Complex interaction between the replicating oncolytic effect and the enzyme/prodrug effect of vaccinia-mediated tumor regression", Gene Therapy, 7: 1217-1223 (2000).

McCart, J.A. et al., "Systemic Cancer Therapy with a Tumor-selective Vaccinia Virus Mutant Lacking Thymidine Kinase and Vaccinia Growth Factor Genes", Cancer Research, 61: 8751-8757 (2001).

McCluskie et al., "Route and Method of Delivery of DNA Vaccine Influence Immune Responses in Mice and Non-Human Primates," Mol. Med., 5:287-300, (1999).

McDonald, D.M. and P.L. Choyke, "Imaging of angiogenesis: from microscope to clinic", Nature Medicine, 9(6): 713-725 (2003).

McIntosh et al., "A probiotic strain of *L. acidophilus* reduces DMH-induced large intestinal tumors in male Sprague-Dawley rats," Nutr Cancer. 35(2):153-9 (1999).

Meadows et al., "Some biological properties and an in vivo evaluation of tyrosine phenol-lyase on growth of B-16 melanoma," Cancer Res. 36(1):167-7 (1976).

Meager, A. et al., "The Development of the Regulatory Process in Europe for Biological Medicines: How it Affects Gene Therapy Products", Chapter 16 in *Gene Therapy Technologies, Applications and Regulations*, A. Meager (Ed.), John Wiley & Sons Ltd., pp. 319-346 (1999).

Meck et al., "A virus-directed enzyme prodrug therapy approach to purging neuroblastoma cells from hematopoietic cells using adenovirus encoding rabbit carboxylesterase and CPT-11," Cancer Res. 61(13):5083-9 (2001).

Meighen, E.A. and R.B. Szittner, "Multiple Repetitive Elements and Organization of the *lux* Operons of Luminescent Terrestrial Bacteria," J. Bacteriol. 174(16):5371-5381 (1992).

Mengaud et al., "Expression in *Escherichia coli* and Sequence Analysis of the Listeriolysin O Determinant of *Listeria monocytogenes*," Infect.Immun. 56(4): 766-772 (1988).

Meyer et al., "Mapping of deletions in the genome of the highly attenuated vaccinia virus MVA and their influence on virulence," Journal of General Virology 72(Pt 5): 1031-1038 (1991).

Micheau et al., "Sensitization of cancer cells treated with cytotoxic drugs to fas-mediated cytotoxicity," J Natl Cancer Inst. 89(11):783-9 (1997).

Michl et al., "Claudin-4: a new target for pancreatic cancer treatment using *Clostridium perfringens* enterotoxin," Gastroenterology 121(3):678-84 (2001).

Middleton, J. et al., "Leukocyte extravasation: chemokine transport and presentation by the endothelium", Blood, 100(12): 3853-3860 (2002).

Miki et al., "Methioninase gene therapy of human cancer cells is synergistic with recombinant methioninase treatment," Cancer Res. 60(10):2696-702 (2000).

Mikryukov et al., "Structural-functional organization of segment of vaccinia virus genome," Soviet Biotechnology (Biotekhnologiya) 4: 19-25 (1988) [corresponds to pp. 442-449 in the Russian language edition].

Minton et al., "Chemotherapeutic tumour targeting using clostridial spores," FEMS Microbiol Rev. 17(3):357-64 (1995).

Mirzadeh et al., "Radiometal labeling of immunoproteins: covalent linkage of 2-(4-isothiocyanatobenzy)diethylenetriaminepentaacetic acid ligands to immunoglobulin," Bioconjug Chem. 1(1):59-65 (1990).

Mizutani et al., "Doxorubicin sensitizes human bladder carcinoma cells to Fas-mediated cytotoxicity," Cancer. 79(6):1180-9 (1997).

Mizutani et al., "Sensitization of human bladder cancer cells to Fas-mediated cytotoxicity by cis-diamminedichloroplatinum (II)," J Urol. 160(2):561-70 (1998).

Mizutani, T and T. Mitsuoka, "Inhibitory effect of some intestinal bacteria on liver tumorigenesis in gnotobiotic C3H/He male mice," Cancer Lett. 11(2):89-95 (1980).

Mohr et al., "Rabbit cytochrome P450 4B1: A novel prodrug activating gene for pharmacogene therapy of hepatocellular carcinoma," Cancer Gene Ther. 7(7):1008-14 (2000).

Moolten, F.L., "Tumor chemosensitivity conferred by inserted herpes thymidine kinase genes: paradigm for a prospective cancer control strategy," Cancer Res. 46(10):5276-81 (1986).

Moore et al. , "Measuring transferrin receptor gene expression by NMR imaging," Biochimica et Biophysica Acta 1402(3):239-249 (1998).

Moore et al., "Steroid hormone synthesis by a vaccinia enzyme: a new type of virus virulence factor," EMBO J. 1992 11:1973-1980, corrigendum in The EMBO Journal 11(9): 3490 (1992).

Moore, A.E., "Effects of Viruses on Tumors", Annu. Rev. Microbiol., 8: 393-402 (1954).

Moretta, A., "Natural Killer Cells and Dendritic Cells: Rendezvous in Abused Tissues", Nat. Rev. Immunol., 2: 957-964 (2002).

Morinaga et al., "Antitumor Activity and its Properties of *Eubacterium lentum*," Jpn. J. Cancer Res. (Gann) 79: 117-124(1988).

Morris, D.W. et al., "Plasmid vectors capable of transferring large DNA fragments to yeast," DNA. 1(1):27-36 (1981).

Moss, B., "Poxviridae: the viruses and their replication," Chapter 84 in Field's Virology, 4th Edn., vol. 2, pp. 2849-2883. Edited by D. M. Knipe and P. M. Howley, Philadelphia: Lippincott Williams & Wilkins, (2001).

Moss, B., "Poxviridae: the viruses and their replication," Chapter 83 in Fields Virology, 3rd Edn, pp. 2637-2671. Edited by B. N. Fields, D. M. Knipe & P.M. Howley. Philadelphia: Lippincott-Raven (1996).

Moss, B., "Genetically engineered poxviruses for recombinant gene expression, vaccination, and safety," Proc. Natl. Acad. Sci. USA 93: 11341-11348 (1996).

Moss, B., "Poxvirus vectors: cytoplasmic expression of transferred genes," Curr. Opin. Genet. Dev. 3: 86-90 (1993).

Mountz et al. "Technetium-99m NeoTect imaging in vivo of T cells from hCAR transgenic mice," FASEB J. 16(5):A1211 March Meeting abstract (2002).

Mukherjee et al., "Replication-restricted vaccinia as a cytokine gene therapy vector in cancer: persistent transgene expression despite antibody generation," Cancer Gene Ther. 7(5):663-70 (2000).

Mullen et al., "Viral Oncolysis," The Oncologist 7: 106-119 (2002).

Mulryan et al., "Attenuated recombinant vaccinia virus expressing oncofetal antigen (tumor-associated antigen) 5T4 induces active therapy of established tumors," Mol Cancer Ther 1(12): 1129-1137 (2002).

Muravlev et al., "Protective activity of vaccinia virus envelope proteins isolated with the use of nonionic detergents," Voprosy Virusologii 40(4): 154-8 (1995) ) [article in Russian, English summary on last page of article].

Newton et al. "Expression and characterization of recombinant human eosinophil-derived neurotoxin and eosinophil-derived neurotoxin-anti-transferrin receptor sFv," J. Biol. Chem. 269(43):26739-45, (1994).

Neyts et al., "Therapy and short-term prophylaxis of poxvirus infections: historical background and perspectives", Antivir. Res. 57: 25-33 (2003).

Nibbering et al. "Radiolabelled antimicrobial peptides for imaging of infections: a review," Nucl Med Commun. 19(12):1117-21 (1998).

Nichterlein et al., "Clinafloxacin (CI 960) is Superior to Standard Therapeutics in the Treatment of Murine Listeriosis and *Salmonellosis*," Zentralbl.Bakteriol. 286: 401-412 (1997).

Nisato, R.E. et al., "Lymphangiogenesis and tumor metastasis", Thromb. Haemost., 90: 591-597 (2003).

Nogrady, T., *Medicinal Chemistry A Biochemical Approach*, New York: Oxford University Press, pp. 388-392 (1985).

Nolan G.P., et al., "Plasmid mapping computer program," Nucleic Acids Res. 12(1 Pt 2):717-29 (1984).

Norton et al., "Expression of Secreted Platelet-Derived Growth Factor-B by Recombinant Nonreplicating and Noncytopathic Vaccinia Virus," Annals of Surgery 224(4):555-562 (1996).

Nuyts et al., "Clostridium spores for tumor-specific drug delivery," Anticancer Drugs. 13(2):115-25 (2002).

Ober, B.T. et al., "Immunogenicity and Safety of Defective Vaccinia Virus Lister:Comparison with Modified Vaccinia Virus Ankara", J. Virol., 76(15): 7713-7723 (2002).

O'Brien et al., "Shiga toxin: biochemistry, genetics, mode of action, and role in pathogenesis," Curr Top Microbiol Immunol. 180:65-94 (1992).

Oertli et al., "Non-replicating recombinant vaccinia virus encoding murine B-7 molecules effective costimulation of naive CD4+splenocytes in vitro," J. Gen. Virol. 77: 3121-3125 (1996).

Okamoto et al., "Severe impairment of anti-cancer effect of lipoteichoic acid-relatedmolecule isolated from a penicillin-killed *Streptococcus pyogenes* in toll-like receptor 4-deficient mice," International Immunopharmacology 1(9-10): 1789-1795 (2001).

O'Kane et al., "Visualization of Bioluminescence as a Marker of Gene Expression in Rhizobium-Infected Soybean Root Nodules," J. Plant Mol. Biol. 10: 387-399 (1988).

Olsson et al., "Engineering of monomeric bacterial luciferases by fusion of luxA and luxB genes in Vibrio harveyi," Gene 81(2):335-47 (1989).

Olsson, O. et al., "The use of the *luxA* gene of the bacterial luciferase operon as a reporter gene,"Mol Gen Genet. 215(1):1-9 (1988).

O'Mahony et al., "Probiotic impact on microbial flora, inflammation and tumour development in IL-10 knockout mice," Aliment Pharmacol Ther. 15(8):1219-25 (2001).

Overholser et al., "Experimental Bacterial Endocarditis after Dental Extractions in Rats with Periodontitis," J. Infect. Dis. 155(1) (1987), 107-112.

Overwijk et al., "Vaccination with a recombinant vaccinia virus enclding a 'self' antigen induces autoimmune vitiligo and tumor cell destruction in mice: Requirement for CD4+T lymphocytes," Proc. Natl. Acad. Sci. USA 96: 2982-2987 (1999).

Pace, "Strep Throat," JAMA, 284(22):2964 (2000).

Padera, T.P. et al., "Lymphatic Metastasis in the Absence of Functional Intratumor Lymphatics", 296: 1883-1886(2002).
Pak et al., "Cloning of the growth factor gene from vaccinia virus LIVP strain in *Escherichia coli* cells," Mol Gen Mikrobiol Virusol Sep.-Oct.; (9-10):19-21 (1992) ) [article in Russian, English summary on last page of article].
Pan et al., "Regression of Established B16F10 Melanoma with a Recombinant *Listeria monocytogenes* Vaccine," Cancer Research 59:5264-5269 (1999).
Paniacli, D. et al., "Vaccinia virus vectors utilizing the /?-galactosidase assay for rapid selection of recombinant viruses and measurement of gene expression", Gene, 47: 193-199 (1986).
Pardal, R. et al., "Applying the principles of stem-cell biology to cancer," Nature Reviews Cancer, 3: 895-902 (2003).
Parish, C.R., "Cancer immunotherapy: The past, the present and the future", Immunology and Cell Biology, 81: 106-113 (2003).
Patel et al., "A poxvirus-derived vector that directs high levels of expression of cloned genes in mammalian cells," Proc. Natl. Acad. Sci. USA 85: 9431-9435 (1988).
Paul et al., "Redirected cellular cytotoxicity by infection of effector cells with a recombinant vaccinia virus encoding a tumor-specific monoclonal antibody," Cancer Gene Ther. 7(4):615-23 (2000).
Pawelek et al., "Tumor-targeted *Salmonella* as a Novel Anticancer Vector," Cancer Therapy 57: 4537-4544 (1997).
Pawelek et al., "Tumor-targeted *Salmonella* as a novel anticancer vector," Cancer Res. 57(20):4537-4544 (1997).
Pawelek, J.M. et al., "Bacteria as tumour-targeting vectors," The Lancet Oncology, 4: 548-556 (2003).
Pearson et al., "Improved tools for biological sequence comparison," Proc. Natl. Acad. Sci. USA 85:2444-2448 (1988).
Pecora, A.L. et al., "Phase I Trial of Intravenous Administration of PV701, an Oncolytic Virus, in Patients With Advanced Solid Cancers", Journal of Clinical Oncology, 20(9): 2251-2266 (2002).
Pekhov AA, Zhukova OS, Ivanova TP, Zanin VA, Dobrynin IaV. [Cytotoxic effect of methionine-gamma-lyase on neoplastic cells in culture] Biull Eksp Biol Med. 95(5):87-8 (1983) [Article in Russian].
Peplinski et al., "In vivo gene therapy of a murine pancreas tumor with recombinant vaccinia virus encoding human interleukin-1beta," Surgery 118:185-191(1995).
Peplinski, G.R. et al., "Vaccinia Virus For Human Gene Therapy", Surgical Oncology Clinics of North America, 7(3): 575-588 (1998).
Perkus et al. "Recombinant Vaccinia Virus: Immunization Against Multiple Pathogens," Science 229(4717):981-984 (1985).
Pfleiderer et al., "A novel vaccinia virus expression system allowing construction of recombinants without the need for selection markers, plasmids and bacterial hosts," *J. General Virology* 76:2957-2962 (1995).
Pfeifer et al., "Gene Therapy: Promises and Problems," Annu. Rev. Genomics Hum. Genet., 2:177-211, (2001).
Phillips-Jones, M.K., "Bioluminescence (*lux*) expression in the anaerobe *Clostridium perfringens*," FEMS Microbiology Letters 106: 265-270 (1993).
Phillips-Jones, M.K., "Use of *lux* reporter system for monitoring rapid changes in α-toxin gene expression in *Clostridium perfringens* during growth," FEMS Microbiology Letters 188: 29-33 (2000).
Picot et al., "*Pseudomonas fluorescens* as a potential pathogen: adherence to nerve cells," Microbes Infect. 3(12):985-95 (2001).
Pilcher, H., "GM Bug activates cancer drug: Bacteria targets medicine to shrivel mouse tumours," news @ nature.com, Published online: Apr. 22, 2004; http://www.nature.com/news/2004/040419/full/040419-9.html, (accessed on Nov. 18, 2004).
Pinkert et al., "An albumin enhancer located 10 kb upstream functions along with its promoter to direct efficient, liver-specific expression in transgenic mice," Genes & Dev. 1: 268-76 (1987).
Plucienniczak et al., "Nucelotide sequence of a cluster and late genes in a conserved segment of the vaccinia virus genome," Nucleic Acids Research 13(3): 993-998 (1985).
Pluen, A. et al., "Role of tumor—host interactions in interstitial diffusion of macromolecules: Cranial vs. subcutaneous tumors", Proc. Natl. Acad. Sci. U.S.A., 98(8): 4628-4633 (2001).
Polverini et al., "Assay and Purification of Naturally Occuring Inhibitor of Angiogenesis," Methods in Enzymology 198:440-450 (1991).
Pongor S. and A.A. Szalay, "Prediction of homology and divergence in the secondary structure of Polypeptides," Proc Natl Acad Sci U S A. 82(2):366-70 (1985).
Pongor S. et al., "Microcomputer programs for prediction and comparative evaluation of protein secondary structure from nucleotide sequence data: application to ribulose-1,5-bisphosphate carboxylase sequences," DNA. 4(4):319-26 (1985).
Poptani et al., "Monitoring thymidine kinase and ganciclovir-induced changes in rat malignant glioma in vivo by nuclear magnetic resonance imaging," Cancer Gene Ther 5(2): 101-109 (1998).
Prasher et al., "Primary structure of the Aequorea victoris greenfluorescent protein," Gene 111: 229-233 (1992).
Prasher et al., "Sequence Comparison of Complementary DNAs Encoding Aequorin Isotypes," Biochemistry 26: 1326-1332 (1987).
Prikhod'ko, G. G. and IV Babkin, "5'-variable genome sequence of vaccinia virus LIVP. Possible role of short direct repeats in formation of DNA deletions," Genetika 27(1): 13-26 (1991) [article in Russian, English summary on last page of article].
Prikhod'ko, G. G. et al., "Cloning, Sequencing and Translation Analysis of the Vaccinia Virus LIVP HindIII N Fragment," Genetika 27(6): 955-963 (1991) ) [article in Russian, English summary on last page of article].
Proudfoot, A.E.I. et al., "Strategies for Chemokine Antagonists as Therapeutics", Seminars in Immunology, 15: 57-65 (2003).
Puhlmann et al. "Thymidine kinase-deleted vaccinia virus expressing purine nucleoside phosphorylase as a vector for tumor-directed gene therapy." Hum Gene Ther. 10(4):649-57 (1999).
Puhlmann et al., "Vaccinia virus as a vector for tumor-directed gene therapy: biodistribution of a thymidine kinase-deleted mutant," Cancer Gene Therapy 7(1): 66-73 (2000).
Qazi et al, "Real-time monitoring of intracellular *Staphylococcus aureus* replication," J Bacteriol. 186(4): 1065-1077 (2004).
Qin, H. and S.K. Chatterjee, "Cancer gene therapy using tumor cells infected with recombinant vaccinia virus expressing GM-CSF," Human Gene Ther. 7: 1853-1860 (1996).
Quenelle, D.C. et al., "Efficacy of Multiple- or Single-Dose Cidofovir against Vaccinia and Cowpox Virus Infections in Mice", Antimicrobial Agents and Chemotherapy, 47(10): 3275-3280 (2003).
Ramirez, J.C. et al., "Tissue distribution of the Ankara strain of vaccinia virus (MVA) after mucosal or systemic administration", Arch. Virol., 148: 827-839 (2003).
Rangarajan, A. and R.A. Weinberg, "Comparative biology of mouse versus human cells: modeling human cancer in mice", Nature Reviews Cancer, 3: 952-959 (2003).
Ransohoff, R.M. et al., "Three or more routes for leukocyte migration into the central nervous system", Nat. Rev. Immunol., 3: 569-581 (2003).
Rao et al., "Il-12 is an effective adjuvant to recombinant vaccinia virus-based tumor vaccines," J. Immunol. 156: 3357-3365 (1996).
Reddy et al. "Folate-mediated targeting of therapeutic and imaging agents to cancers," Crit Rev Ther Drug Carrier Syst. 15(6):587-627 (1998).
Rehemtulla et al., "Rapid and quantitative assessment of cancer treatment response using in vivo bioluminescence imaging," Neoplasia, 2(6):491-495 (2000).
Reno, F., "Non-clinical Toxicology", Principles and Practice of Pharmaceutical Medicine, A.J. Fletcher et al.(eds.), ch.6: 55-64 (c2002) John Wiley & Sons Ltd.
Rezmer et al., "Identification and localization of transformed cells in *Agrobacterium tumefaciens*-induced plant tumors," Planta. 209(4):399-405 (1999).
Ribas, A. et al., "Current Developments in Cancer Vaccines and Cellular Immunotherapy", Journal of Clinical Oncology, 21(12): 2415-2432 (2003).
Ring, C.J.A., "Cytolytic viruses as potential anti-cancer agents", J. Gen. Virol., 83: 491-502 (2002).
Rocchetta et al., "Validation of a Noninvasive, Real-Time Imaging Technology Using Bioluminescent *Escherichia coli* in the Neutropenic Mouse Thigh Model of Infection," Antimicrobial Agents and Chemotherapy 45(1): 129-137 (2001).
Rodriguez et al., "Highly attenuated vaccinia virus mutants for the generation of safe recombinant viruses," Proc. Natl. Acad. Sci. USA 86: 1287-1291 (1989).

Rodriguez, J.F. et al., "Expression of the firefly luciferase gene in vaccinia virus: A highly sensitive gene marker to follow virus dissemination in tissues of infected animals," Proc. Natl. Acad. Sci. U.S.A., 85: 1667-1671 (1988).

Rolston et al., "In vitro activity of LY264826, a new glycopeptide antibiotic, against gram-positive bacteria isolated from patients in cancer," Antimicrob. Agents Chemother. 34(11):2137-2141 (1990).

Roseman et al., "The vaccinia virus HindIII fragment: nucleotide sequence of the left 6.2kb," Virology 178: 410-418 (1990).

Roth et al "p53 as a target for cancer vaccines: recombinant canarypox virus vectors expressing p53 protect mice against lethal tumor cell challenge," Proc. Natl. Acad. Sci. USA 93: 4781-4786 (1996).

Rothenberg, M.L. et al., "Improving the evaluation of new cancer treatments: challenges and opportunities," Nat. Rev. Cancer, 3: 303-309 (2003).

Rubanyi et al., "The future of human gene therapy," Molecular Aspects of Medicine, 22:113-142, (2001).

Rudinger, "Characteristics of the amino acids as components of a peptide hormone sequence," Peptide Hormones, Parsons, University Park Press, Baltimore, p. 1-7, (1976).

Ruef et al. "Sternal wound infection after heart operations in pediatric patients associated with nasal carriage of Staphylococcus aureus" J. of Thoracic and Cardiovascular Surgery 112(3): 681-686 (1996).

Saito, H. and T. Watanabe T., "Effects of a bacteriocin from Mycobacterium smegmatis on BALB/3T3 and simian virus 40-transformed BALB/c mouse cells," Microbiol Immunol. 25(1):13-22 (1981).

Sakamoto et al., "Antitumor Effect of Normal Intestinal Microflora on Ehrlich Ascites Tumor," Jpn. J. Cancer Res. (Gann) 79: 109-116 (1988).

Santoro, J. and M.E. Levison, "Rat Model of Experimental Endocarditis," Infect. Immun. 19(3): 915-918(1978).

Schempp et al., "Inhibition of tumour cell growth by hyperforin, a novel anticancer drug from St. John's wort that acts by induction of apoptosis," Oncogene 21(8):1242-50 (2002).

Schirrmacher et al., "Antitumor effects of Newcastle Disease Virus in vivo: local versus systemic effects," Int J Oncol. 18(5):945-52 (2001).

Schlör et al., "In vivo and in vitro studies on interactions between the components of the hemolysin (HlyA) secretion machinery of Escherichia coli," Mol.Gen.Genet. 256: 306-319 (1997).

Schmidt et al. "Generation of effective cancer vaccines genetically engineered to secrete cytokines using adenovirus-enhanced transferrinfection (AVET)," Gene. 190(1):211-6 (1997).

Schoen et al., "Bacterial delivery of functional messenger RNA to mammalian cells," Cell Microbiol. 7(5):709-24 (2005).

Scholl et al., "Recombinant Vaccinia Virus Encoding Human MUC1 and IL2 as Immunotherapy in Patients with Breast Cancer," J. Immunother 23(5): 570-580 (2000).

Schroder, J.M., "Epithelial antimicrobial peptides: innate local host response elements," Cell Mol Life Sci. 56(1-2):32-46 (1999).

Schuller et al., "Investigation and management of Clostridium difficile colonisation in a paediatric oncology unit.," Arch Dis Child. 72(3):219-222 (1995).

Schwartz and Dayhoff, eds., Atlas of Protein Sequence and Structure, National Biomedical Research Foundation, pp. 353-358 (1979).

Sekine et al., "A new morphologically characterized cell wall preparation (whole peptidoglycan) from Bifidobacterium infantis with a higher efficacy on the regression of an established tumor in mice," Cancer Res. 45(3):1300-7 (1985).

Sekine et al., "Analysis of antitumor properties of effector cells stimulated with a cell wall preparation (WPG) of Bifidobacterium infantis," Biol Pharm Bull. 18(1):148-53 (1995).

Shapiro, D. and A.W. Fox, "Biotechnology Products and Their Development", Principles and Practice of Pharmaceutical Medicine, A.J. Fletcher, et al.(eds.), ch.17: 191-201, c2002 John Wiley & Sons.

Shariatmadari et al., "Improved technique for detection of enhanced green fluorescent protein in transgenic mice," Biotechniques 30:1282-1285 (2001).

Sharma et al., "Death the Fas way: regulation and pathophysiology of CD95 and its ligand," Pharmacol Ther. 88(3):333-47 (2000).

Shata, M.T. et al., "Optimization of recombinant vaccinia-based ELISPOT assay," J. Immunological Methods, 283: 281-289 (2003).

Shchelkunov et al., "The gene encoding the late nonstructural 36K protein of vaccinia virus is essential for virus reproduction," Virus Research 28: 273-283 (1993).

Shenk, T., "Delivery systems for gene therapy: the adenovirus," Stem Cell Biology and Gene Therapy, Quesenberry, P.J. et al. (Eds.), ch.6: pp. 161-178, c1998 Wiley-Liss, Inc.

Shepherd, A.J., "Good Laboratory Practice in the Research and Development Laboratory," Gene Therapy Technologies, Applications and Regulations, A. Meager (Ed.), ch.19: 375-381 (c1999) John Wiley & Sons Ltd.

Shilo, B. and R.A. Weinberg, "DNA sequences homologous to vertebrate oncogenes are conserved in Drosophila melanogaster," Proc. Natl. Acad. Sci. USA 78:6789-6792 (1981).

Shimizu et al, "Significance of priming of hosts with virus in the tumor-specific immunotherapy model utilizing virus-reactive helper T cell activity," Nippon Gan Chiryo Gakkai Shi. May 20, 1989;24(5):1007-14. [Article in Japanese].

Shimizu et al., "Antitumor activity of 2-keto-3-deoxyoctonate-free lipopolysaccharide of Vibrio anguillarum in mice," Gann 74(2): 279-284 (1983).

Shimizu et al., "Antitumor activity of marine bacteria, Vibrio anguillarum, in mice," Gann 70: 429-433 (1979).

Shimizu et al., "Immunotherapy of tumor-bearing mice utilizing virus help," Cancer Immunol Immunother. 27(3):223-7 (1988).

Shimizu, Y. et al., "Immunotherapy of tumor-bearing mice utilizing virus help," Cancer Immunol. Immunother., 27: 223-227 (1988).

Shinozaki et al., "Oncolysis of multifocal hepatocellular carcinoma in the rat liver by hepatic artery infusion of vesicular stomatitis virus," Mol. Ther. 9(3): 368-376 (2004).

Silva et al., "Cloning, overexpression, and purification of functional human purine nucleoside phosphorylase," Protein Expr. Purif. 27(1): 158-164 (2003).

Simon et al., "Surveillance for nosocomial and central line-related infections among pediatric hematology-oncology patients," Infect Control Hosp Epidemiol. 21(9):592-6 (2000).

Simonds et al., "Deoxyribonucleic acid hybridization among strains of lactobacilli," J Bacteriol. 107(1):382-4 (1971).

Sinkovics, J. and J. Horvath, "New Developments in the Virus Therapy of Cancer: A Historical Review," Intervirology, 36: 193-214 (1993).

Sinkovics, J.G. and J.C. Horvath, "Newcastle disease virus (NDV): brief history of its oncolytic strains," J. Clin. Virol., 16: 1-15 (2000).

Sinkovics, J.G. and J.C. Horvath, "Virus therapy of human cancers," Melanoma Research, 13: 431-432 (2003).

Sivanandham et al., "Colon cancer cell vaccine prepared with replication-deficient vaccinia viruses encoding B7.1 and interleukin-2 induce antitumor response in syngeneic mice," Cancer Immunol Immunother 46(5):261-7 (1998).

Sivanandham et al., "Therapeutic effect of a vaccinia colon oncolysate prepared with interleukin-2-gene encoded vaccinia virus studied in a syngeneic CC-36 murine colon hepatic metastasis model," Cancer Immunological Immunotherapy, 38:259-264, (1994).

Skolnick et al., "From genes to protein structure and function: novel applications of computational approaches in the genomic era," Trends in Biotech., 18:34-39, (2000).

Smee, D.F. and R.W. Sidwell, "A review of compounds exhibiting anti-orthopoxvirus activity in animal models," Antiviral Research, 57: 41-52 (2003).

Smee, D.F. et al., "Effects of cidofovir on the pathogenesis of a lethal vaccinia virus respiratory infection in mice", Antivir. Res., 52: 55-62 (2001).

Smith, G.L. and B. Moss, "Infectious poxvirus vectors have capacity for at least 25000 base pairs of foreign DNA", Gene, 25: 21-28 (1983).

Smith, G.L. et al., "The formation and function of extracellular enveloped vaccinia virus," J. Gen. Virol., 83: 2915-2931 (2002).

Smith, T.F. and M.S.Waterman, "Comparison of biosequences," Adv. Appl. Math. 2:482-489 (1981).

Smyth et al., "Bovine enterovirus as an oncolytic virus: foetal calf serum facilitates its infection of human cells," Int J Mol Med. 10(1):49-53 (2002).

Soby et al., "Catabolite-repressor-like protein regulates the expression of a gene under the control of the *Escherichia coli* lac promoter in the plant pathogen *Xanthomonas campestris* pv. *Campestris*," Appl Microbiol Biotechnol. 46(5-6):559-61 (1996).

Somia, N. and I.M. Verma, "Gene Therapy: Trial and Tribulations," Nat. Rev. Genet., 1(2): 91-99 (2000).

Sorscher et al., "Tumor cell bystander killing in colonic carcinoma utilizing the *Escherichia coli DeoD* gene to generate toxic purines," Gene Therapy 1(4): 233-238 (1994).

Spencer et al., "Unilateral Transplantation of Human Fetal Mesencephalic Tissue Into The Caudate Nucleus Of Patients with Parkinson's Disease", New England Journal of Medicine 327: 1541-1548 (1992).

Spooner et al., "In suicide gene therapy, the site of subcellular localization of the activating enzyme is more important than the rate at which it activates prodrug," Cancer Gene Ther. 7(10):1348-56 (2000).

Steffens et al., "Enhanced green fluorescent protein fusion proteins of herpes simplex virus type 1 thymidine kinase and cytochrome P450 4B1: applications for prodrug-activating gene therapy," Cancer Gene Ther. 7(5):806-12 (2000).

Stehle, G. et al., "Plasma protein (albumin) catabolism by the tumor itself—implications for tumor metabolism and the genesis of cachexia", Critical Reviews in Oncology/Hematology, 26: 77-100 (1997).

Stevens, D.L., "*Stretococcal* toxic-shock syndrome: spectrum of disease, pathogenesis, and new concepts in treatment," Emerg. Infect. Dis. 1(3): 69-78 (1995).

Stojdl, D.F. et al., "VSV strains with defects in their ability to shut-down innate immunity are potent systemic anti-cancer agents", Cancer Cell, 4:263-275 (2003).

Studeny et al., "Bone Marrow-derived Mesenchymal Stem Cells as Vehicles for Interferon-β Delivery into Tumors," Cancer Research 62: 3603-3608 (2002).

Sudimack et al. "Targeted drug delivery via the folate receptor." Adv Drug Deliv Rev. 41(2):147-62 (2000).

Sugimoto et al., "Gene structures of low-neurovirulent vaccinia virus LC16m0, LC16m8, and their Lister Original (LO) strains," Microbial. Immuol. 29: 421-428 (1985).

Sugimoto, M. and K. Yamanouchi., "Characteristics of an attenuated vaccinia virus strain, LC16m0, and its recombinant virus vaccines," Vaccine 12(8): 675-681 (1994).

Sutton et al. "In vivo adenovirus-mediated suicide gene therapy of orthotopic bladder cancer." Mol Ther. 2(3):211-7 (2000).

Suvorov et al., "Physical and genetic chromosomal map of an M type 1 strain of *Streptococcus pyogenes*," J. Bacteriol. 178(18): 5546-5549 (1996).

Suzuki et al., "Management of orbital lymphangioma using intralesional injection of OK-432," Br. J. Opthalmol. 84(6): 614-617 (2000).

Suzuki M., Szalay A.A., "Bacterial transformation using temperature-sensitive mutants deficient in peptidoglycan synthesis," Methods Enzymol. 68:331-342 (1979).

Suzuki, S. et al. "Coexpression of the partial androgen receptor enhances the efficacy of prostate-specific antigen promoter-driven suicide gene therapy for prostate cancer cells at low testosterone concentrations," Cancer Research 61(4):1276-1279 (2001).

Symons, J.A. et al., "A study of the vaccinia virus interferon-y receptor and its contribution to virus virulence", Journal of General Virology, 83: 1953-1964 (2002).

Szalay A.A .et al, "Genetic engineering of halotolerance in microorganisms: a summary," Basic Life Sci. 14:321-32 (1979).

Szalay A.A. et al., "Separation of the complementary strands of DNA fragments on polyacrylamide gels," Nucleic Acids Res. 4(5):1569-78 (1977).

Sze et al., "Dr. Gary J. Becker Young Investigator Award: intraarterial adenovirus for metastatic gastrointestinal cancer: activity, radiographic response, and survival," J. Vasc. Interv. Radiol. 14(3): 279-290 (2003).

Takahashi-Nishimaki et al., "Genetic analysis of vaccinia virus Lister strain and its attenuated mutant LC16m8: production of intermediate variants by homologous recombination," J. Gen. Virol. 68: 2705-2710 (1987).

Tanaka et al, "Preliminary evaluation of intratumoral injection of a *Streptococcus pyrogenes* preparation in patients with malignant brain tumors," Cancer 46(7):1688-94 (1980).

Tartaglia et al., "NYVAC: a highly attenuated strain of vaccinia virus," Virology 188(1):217-32 (1992).

Technology Evaluation Center, "Special Report: Vaccines for the Treatment of Malignant Melanoma", TEC Assessment Program, 16(4): 1-46 (2001).

t'Hart, B.A. et al., "Gene thereapy in nonhuman primate models of human autoimmune disease", Gene Therapy, 10: 890-901 (2003).

Thatcher et al., "The potential of acetaminophen as a prodrug in gene-directed enzyme prodrug therapy," Cancer Gene Ther. 7(4):521-5 (2000).

Theuer et al., "A recombinant form of pseudomonas exotoxin directed at the epidermal growth factor receptor that is cytotoxic without requiring proteolytic processing," J.Biol.Chem. 267(24): 16872-16877 (1992).

Theys et al., "Specific targeting of cytosine deaminase to solid tumors by engineered *Clostridium acetobutylicum*," Cancer Gene Ther. 8(4):294-7 (2001).

Theys et al., "Stable *Escherichia coli-Clostridium acetobutylicum* shuttle vector for secretion of murine tumor necrosis factor alpha," Appl Environ Microbiol. 65(10):4295-4300 (1999).

Theys et al., "Tumor-specific gene delivery using genetically engineered bacteria," Curr Gene Ther 3(3): 207-221 (2003).

Tietze et al., "Highly selective glycosylated prodrugs of cytostatic CC-1065 analogues for antibody-directed enzyme tumor therapy," Chembiochem. 2(10):758-65 (2001).

Timiriasova et al., "[Analysis of reporter gene expression at different segments of the vaccinia virus genome]," Mol. Biol. (Mosk.) 27(2): 392-401 (1993) [article in Russian, English abstract on last page of article].

Timiryasova et al., "Construction of recombinant vaccinia viruses using PUV-inactivated virus as a helper," BioTechniques 31: 534-540 (2001).

Timiryasova et al., "Radiation enhances the anti-tumor effects of vaccinia-p53 gene therapy in glioma," Technol Cancer Res Treat. 2(3):223-35 (2003).

Timiryasova, T.M. et al., "Antitumor Effect of Vaccinia Virus in Glioma Model", Oncology Research, 11(3): 133-144 (1999).

Timiryasova, T.M. et al., "Visualization of Vaccinia Virus Infection Using the Renilla-Luciferase-GFP Fusion Protein", Bioluminescence & chemiluminescence: Proceedings of the 11th International Symposium on Bioluminescence Chemiluminescence: Asilomar Conference Grounds, Pacific Grove, Monterey, California: Sep. 6-10, 2000 / (eds.): Case, J.F. et al., World Scientific Publishing Co. (c2001), pp. 457-460.

Timiryasova, T.M. et al., "Replication-deficient vaccinia virus gene therapy vector: evalution of exogenous gene expression mediated by PUV-inactivated virus in glioma cells," Journal of Gene Medicine, 3: 468-477 (2001).

Timiryasova, T.M. et al., "Vaccinia virus-mediated expression of wild-type p53 suppresses glioma cell growth and induces apoptosis." Int J Oncol. 14(5):845-54 (1999).

Tjuvajev et al., "Imaging Adenoviral-mediated Herpes Virus Thymidine Kinase Gene Transfer and Expression In Vivo," Cancer Research 59: 5186-5193 (1999).

Tjuvajev et al., "Imaging Herpes Virus Thymidine Kinase Gene Transfer and Expression by Positron Emission Tomography,"Cancer Res. 58(19): 4333-4341 (1998).

Tjuvajev et al., "Imaging the Expression of Transfected Genes in Vivo," Cancer Res. 55(24): 6126-6132 (1995).

Tjuvajev et al., "Noninvasive Imaging of Herpes Virus Thymidine Kinase Gene Therapy and Expression: A Potential Method for Monitoring Clinical Gene Therapy," Cancer Res 56(18): 4087-4095 (1996).

Tjuvajev, J. et al., "*Salmonella*-based tumor-targeted cancer therapy: tumor amplified protein expression therapy (TAPET™) for diagnostic imaging," J. Controlled Release, 74: 313-315 (2001).

Toguchi et al., "Suicide Gene Therapy of C6 Glioma Cells Mediated by Replication-Deficient and Replication Competent Vaccinia Viruses," Cancer Gene Therapy 10: S32 (2003) presented at the Eleventh International Conference on Gene Therapy of Cancer, Dec. 12-14, 2002, San Diego California.

Tokugawa et al., "A model system for the continuous production of a heterologous protein using a novel secretion promoting factor which operates in *Escherichia coli*," J.Biotechnol. 37:33-37 (1994).

Tokugawa et al., "A novel protein secretion factor from a *Vibrio* species which operates in *Escherichia coli*," J.Biotechnol. 35: 69-76 (1994).

Tonetti DA et al "Stable transfection of an estrogen receptor beta cDNA isoform into MDA-MB-231 breast cancer cells," J Steroid Biochem Mol Biol. 87(1):47-55 (2003).

Toso et al, "Phase I study of the intravenous administration of attenuated *Salmonella typhimurium* to patients with metastatic melanoma," J Clin Oncol. 20(1):142-52 (2002).

Toth et al., "An oncolytic adenovirus vector combining enhanced cell-to-cell spreading, mediated by the ADP cytolytic protein, with selective replication in cancer cells with deregulated *Wnt* signaling," Cancer Research 64: 3638-3644 (2004).

Tresco et al., "Polymer-encapsulated PC12 Cells: Long-Term Survival and Associated Reduction in Lesion-Induced Rotational Behavior," Cell Transplantation 1:255-264 (1992).

Tscharke, D.C. et al., "A model for vaccinia virus pathogenesis and immunity based on intradermal injection of mouse ear pinnae," J. Gen. Virol., 80: 2751-2755 (1999).

Tscharke, D.C. et al., "Dermal infection with vaccinia virus reveals roles for virus proteins not seen using other inoculation routes," Journal of General Virology, 83: 1977-1986 (2002).

Tseng, J.C. et al., "In Vivo Antitumor Activity of Sindbis Viral Vectors," Journal of the National Cancer Institute, 94(23): 1790-1802 (2002).

Tseng, J.C. et al., "Systemic tumor targeting and killing by Sindbis viral vectors," Nat. Biotechnol., 22(1): 70-77 (2004).

Tsung et al. "Gene expression and cytopathic effect of vaccinia virus inactivated by psoralen and long-wave UV light," J. Virol. 70: 165-171 (1996).

Tsung, K. et al., "Immune Response Against Large Tumors Eradicated by Treatment with Cyclophosphamide and IL-12," J. Immunol., 160: 1369-1377 (1998).

Ullrich C.I. and R. Aloni, "Vascularization is a general requirement for growth of plant and animal tumours," Journal of Experimental Botany 51(353):1951-60 (2000).

Umphress et al., "Vaccinia virus mediated expression of human APC induces apoptosis in colon cancer cells," Transgenics 4:19-33 (2003).

Vanderplasschen, A. et al., "Antibodies against vaccinia virus do not neutralize extracellular enveloped virus but prevent virus release from infected cells and comet formation," Journal of General Virology, 78: 2041-2048 (1997).

Vanderplasschen, A. et al., "Intracellular and extracellular vaccinia virions enter cells by different mechanisms," Journal of General Virology, 79: 877-887 (1998).

Varghese, S. and S.D. Rabkin, "Oncolytic herpes simplex virus vectors for cancer virotherapy," Cancer Gene Therapy, 9: 967-978 (2002).

Veijola et al., "Cloning, Baculovirus Expression, and Characterization of the α Subunit of Prolyl 4-Hydroxylase from the nematode *Caenorhabditis elegans*," J. Biol. Chem. 269: 26746-26753 (1994).

Vento, S. and F. Cainelli, "Infections in patients with cancer undergoing chemotherapy: aetiology, prevention, and treatment," Lancet, 4: 595-604 (2003).

Verma et al., "Gene therapy- promises, problems and prospects," Nature, 389:239-242, (1997).

Vestweber, D., "Regulation of endothelial cell contacts during leukocyte extravasation," Curr. Opin. Cell Biol., 14: 587-593 (2002).

Vidal et al., "Tissue-specific control elements of the Thy-1 gene," EMBO J. 9(3): 833-840(1990).

Vile, R. et al., "The oncolytic virotherapy treatment platform for cancer: Unique biological and biosafety points to consider," Cancer Gene Therapy, 9:1062-1067 (2002).

Vogel, J.R., "Outsourcing Clinical Drug Development Activities to Contract Reseach Organizations (CROs): Critical Success Factors," Principles and Practice of Pharmaceutical Medicine, A.J. Fletcher et al.(eds.), ch.40: 461-482 (e2002) John Wiley & Sons Ltd.

Vogt et al., "Untersuchungen über die Möglichkeit der Tumorlokalisation in vivo auf ser Basis eines szintigrafischer Klostridienstäbchen-Nachweises mit $^{131}$J-markierten Antikörpern und F(ab$^3$)$_2$-Antikörperfragmenten," Zeitschrift für Experimentelle Chirurgie 12(4): 209-215 (1979) [article in German, English summary on the last page of the article].

Voisey et al., "Elimination of internal restriction enzyme sites from a bacterial luminescence (luxCDABE) operon," Biotechniques 24(I):56, 58 (1998).

Volm et al., "Enhancement of Incorporation of $^{131}$Iododeoxyuridine into Tumors after Application of *Clostridium oncolyticum s. butyricum* (M 55)," Eur. J. Nucl. Med. 2(2): 117-120(1977).

Wahl et al., "Improved Radioimaging and Tumor localization with Monoclonal F(ab$^1$)$_2$," J. Nucl. Med., 24:316-325, (1983).

Wallack, M.K. et al., "A Phase III Randomized, Double-Blind, Multiinstitutional Trial of Vaccinia Melanoma Oncolysate-Active Specific Immunotherapy for Patients with Stage II Melanoma," Cancer, 75(1): 34-42 (1995).

Wallack, M.K. et al., "Increased Survival of Patients Treated With a Vaccinia Melanoma Oncolysate Vaccine," Annals of Surgery, 226(2): 198-206 (1997).

Wallack, M.K. et al., "Surgical Adjuvant Active Specific Immunotherapy for Patients with Stage III Melanoma: The Final Analysis of Data From a Phase III, Randomized, Double-Blind, Multicenter Vaccinia Melanoma Oncolysate Trial," J. Am. Coll. Surg., 187(1): 69-79 (1998).

Wang Y. et al., "A study of protein-protein interactions in living cells using luminescence resonance energy transfer (LRET) from *Renilla* luciferase to *Aequorea* GFP," Mol Gen Genet. 264(5):578-87 (2001).

Wang Y. et al., "*Renilla* luciferase- Aequorea GFP (Ruc-GFP) fusion protein, a novel dual reporter for real-time imaging of gene expression in cell cultures and in live animals," Mol Genet Genomics. 268(2):160-8 (2002).

Wang, Y. et al., "The *Renilla* Luciferase-Modified GFP Fusion Protein is Functional in Transformed Cells," Bioluminescence & chemiluminescence: Proceedings of the 9th International Symposium on Bioluminescence Chemiluminescence: Woods Hole, Massachusetts, Oct. 1996 / (eds.) Hastings, J.W. et al., John Wiley & Sons Ltd. (c1997), pp. 419-422.

Warrington et al. "Developing VDEPT for DT-diaphorase (NQO1) using an AAV vector plasmid," Int J Radiat Oncol Biol Phys. 42(4):909-12 (1998).

Watson et al. Molecular Biology of the Gene, 4th Edition, 1987, The Benjamin/Cummings Pub. co., p. 224.

Webley et al., "Measurement of the critical DNA lesions produced by antibody-directed enzyme prodrug therapy (ADEPT) in vitro, in vivo and in clinical material," Br J Cancer. 84(12):1671-6 (2001).

Weedon et al., "Sensitisation of human carcinoma cells to the prodrug CB1954 by adenovirus vector-mediated expression of *E. coli* nitroreductase," Int J Cancer. 86(6):848-54 (2000).

Wegner et al., "Cis-acting suquences from mouse rDNA promote plasmid DNA amplification and persistence in mouse cells: implication of HMG-I in their function", Nucleic Acids Research 17:9909-9932 (1989).

Wehl et al., "Trends in infection morbidity in a pediatric oncology ward, 1986-1995," Med Pediatr Oncol. 32(5):336-43 (1999).

Weissleder et al. "Drug targeting in magnetic resonance imaging," Magnetic Resonance Quarterly. 8(1):55-63 (1992).

Weissleder, T. et al., "In vivo magnetic resonance imaging of transgene expression," Nat. Med. 6(3): 351-354 (2000).

Welling et al "Radiochemical and biological characteristics of $^{99m}$Tc-UBI 29-41 for imaging of bacterial infections." Nucl Med Biol. 29(4):413-22 (2002).

Welling et al "Technetium-99m labelled antimicrobial peptides discriminate between bacterial infections and sterile inflammations." Eur J Nucl Med. 27(3):292-301 (2000).

West et al. "Identification of a somatodendritic targeting signal in the cytoplasmic domain of the transferrin receptor." J Neurosci. 17(16):6038-47 (1997).

Westphal et al., "The nitroreductase/CB1954 combination in Epstein-Barr virus-positive B-cell lines: induction of bystander killing in vitro and in vivo," Cancer Gene Ther. 7(1):97-106 (2000).

Wharton, M. et al., "Recommendations for Using Smallpox Vaccine in a Pre-Event Vaccination Program", MMWR, 52(RR-7): 1-16 (2003).

Whitley, R.J., "Smallpox: a potential agent of bioterrorism", Antiviral Research 57: 7-12 (2003).

Williams J.G. and Szalay A.A., "Stable integration of foreign DNA into the chromosome of the cyanobacterium Synechococcus R2," Gene. 24(1):37-51 (1983).

Williams, W Sanders, "Southwestern Internal Medicine Conference: Prospects for Gene Therapy of Ischemic Heart Disease," The American Journal of the Medical Sciences, 306(2):129-136, (1993).

Winn et al., "Behavioral Recovery following Intrastriatal Implantation of Microencapsulated PC12 Cells," Experimental Neurology 113:322-329 (1991).

Winn, S.R. et al., "Polymer-encapsulated cells genetically modified to secrete human nerve growth factor promote the survival of axotomized septal cholinergic neurons," Proceedings of the National Academy of Sciences U.S.A. , 91:2324-2328 (1994).

Wisher, M., "Biosafety and product release testing issues relevant to replication-competent oncolytic viruses," Cancer Gene Therapy, 9: 1056-1061 (2002).

Wittrup, D., "Tumor Targeting Theory", IBC's 15th Annual International Antibody Engineering Conference entitled Antibody Engineering: Forging the Future of Antibody Therapeutics, Nov. 30-Dec. 3, 2003—The Paradise Point Resort—San Diego, CA, pp. 1-17.

Wlodaver, C.G. et al., "Laboratory-acquired vaccinia infection," Journal of Clinical Virology, xxx: 1-5 (2003).

Wolfe et al., "Deletion of the vaccinia virus B5R gene encoding a 42-kilodalton membrane glycoprotein inhibits extracellular virus envelope formation and dissemination," Journal of Virology 67(8): 4732-4741(1993) and erratum in Journal of Virology, vol. 67, pp. 5709-5711 (1993).

Wollowski et al., "Protective role of probiotics and prebiotics in colon cancer," Am J Clin Nutr. 73 (2 Suppl):451S-455S (2001).

Wong, M.M. and E.N. Fish, Chemokines: attractive mediators of the immune response, Semin. Immunol. 15: 5-14 (2003).

Wu et al., "Biological purging of breast cancer cells using an attenuated replication-competent herpes simplex virus in human hematopoietic stem cell transplantation," Cancer Res. 61(7):3009-15 (2001).

Wu et al., "High resolution microPET imaging of carcino-embryonic antigen-positive xenografts by using a copper-64-labeled engineered antibody fragment," PNAS USA 97(15): 8495-8500 (2000).

Xie et al., "Adenovirus-mediated Tissue-targeted Expression of a Caspase-9-based Artificial Death Switch for the Treatment of Prostate Cancer," Cancer Research 61: 6795-6804 (2001).

Yadav, R. et al., "Migration of leukocytes through the vessel wall and beyond," Thromb. Haemost., 90: 598-606 (2003).

Yamamoto et al., "Production of L-forms of Streptococcus pyogenes and their antitumor effects," Jpn J Exp Med. 50(5):383-8 (1980).

Yang et al., "Effects of growth medium composition, iron sources and atmospheric oxygen concentrations on production of luciferase-bacterial magnetic particle complex by a recombinant Magnetospirillum magneticum AMB-1," Enzyme Microb. Technol. 29: 13-19 (2001).

Yang et al., "Visualizing gene expression by whole-body fluorescence imaging," PNAS 97(22): 12278-12282 (2000).

Yang et al., "Whole-body optical imaging of green fluorescent protein-expressing tumors and metastases," Proc. Natl. Acad. Sci. USA 97(3):1206-1211 (2000).

Yansura, D.G. and D.J. Henner, "Use of the Escherichia coli lac repressor and operator to control gene expression in Bacillus subtilis," Proc. Natl. Acad. Sci USA 81: 439-443 (1984).

Yazawa et al., "Bifidobacterium longum as a delivery system for cancer gene therapy: Selective localization and growth in hypoxic tumors," Cancer Gene Ther. 7(2):269-74 (2000).

Yazawa et al., Bifidobacterium longum as a delivery system for gene therapy of chemically induced rat mammary tumors. Breast Cancer Res Treat. 66(2):165-70 (2001).

Yazawa et al., "Current progress in suicide gene therapy for cancer," World J. Surg 26(7): 783-789 (2002).

Yong et al., . Visualization of tumors and metastases in live animals with bacteria and vaccinia virus encoding light-emitting proteins, Nature Biotechnology 22(3):313-320 (2004).

Yoshida et al., "Cell growth-inhibitory action of SAGP, an antitumor glycoprotein from Streptococcus pyogenes (Su strain)," Jpn. J. Pharmacol. 45(2): 143-147 (1987).

Yoshida et al., "Characterization of a streptococcal antitumor glycoprotein (SAGP)," Life Sciences 62(12): 1043-1053 (1998).

Yoshida et al., "Growth-inhibitory effect of streptococcal antitumor glycoprotein on human epidermoid carcinoma A431 cells: involvement of dephosphorylation of epidermal growth factor receptor," Cancer Research 61(16): 6151-6157 (2001).

Yu Y.A. et al., "A Renilla luciferase-Aequorea GFP (ruc-gfp) fusion gene construct permits real-time detection of promoter activation by exogenously administered mifepristone in vivo," Mol Genet Genomics. 268(2):169-78 (2002).

Yu Y.A. et al., "Optical imaging: bacteria, viruses, and mammalian cells encoding light-emitting proteins reveal the locations of primary tumors and metastases in animals," Anal Bioanal Chem. 377(6):964-72 (2003).

Yu Y.A., "Visualization of molecular and cellular events with green fluorescent proteins in developing embryos: a review," Luminescence. 18(1):1-18 (2003) Erratum in: Luminescence. Jul.-Aug. 2003;18(4):243.

Yu, Y.A. et al. "Visualization of tumors and metastases in live animals with bacteria and vaccinia virus encoding light-emitting proteins," Nat Biotech. 22(3): 313-320 (2004).

Yun A.C. et al. "Nitrogenase promoter-lacZ fusion studies of essential nitrogen fixation genes in Bradyrhizobium japonicum I110," J Bacteriol. 167(3):784-91 (1986).

Zambryski et al., "Tumor induction by Agrobacterium tumefaciens: analysis of the boundaries of T-DNA," J Mol Appl Genet. 1(4):361-70 (1982).

Zaucha, G.M. et al., "The Pathology of Experimental Aerosolized Monkeypox Virus Infection in Cynomolgus Monkeys (Macaca fascicularis)," Lab. Invest., 81: 1581-1600 (2001).

Zeh, H.J. and D.L. Bartlett, "Development of a replication-selective, oncolytic poxvirus for the treatment of human cancers," Cancer Gene Therapy, 9: 1001-1012 (2002).

Zhang et al., "Urothelium-specific Expression of an Oncogene in Transgenic Mice Induced the Formation of Carcinoma in Situ and Invasive Transitional Cell Carcinoma," Cancer Res.59: 3512-3517 (1999).

Zhao et al., "Spatial-temporal imaging of bacterial infection and antibiotic response in intact animals," Proceeding of the National Academy of Sciences 98(17): 9814-9818 (2001).

Zheng et al., "Tumor amplified protein expression therapy: Salmonella as a tumor-selective protein delivery vector," Oncology Research 12(3):127-135 (2000).

Zhu et al., "Smad3 MutantMice Develop Metastatic Colorectal Cancer," Cell 94: 703-714 (1998).

Zimmermann et al., "Independent regulatory elements in the nestin gene direct transgene expression to neural stem cells," Neuron 12: 11-24 (1994).

Zinkernagel, R.M., "Uncertainties—discrepancies in immunology", Immunological Reviews, 185: 103-125 (2002).

Zinn et al. "Noninvasive monitoring of gene transfer using a reporter receptor imaged with a high-affinity peptide radiolabeled with 99mTc or 188Re," J Nucl Med. May 2000;41(5):887-95.

Zinn et al., "Simulataneous evaluation of dual gene transfer to adherent cells by gamma-ray imaging," Nuclear Medicine and Biology 28(2):135-144 (2001).

Zinoviev et al., "Identification of the gene encoding vaccinia virus immunodominant protein p35," Gene 147: 209-214 (1994).

Zolotukhin et al., "A "Humanized" Green Fluorescent Protein cDNA adapted for high-level expression in mammalian cells," J. Virol. 70:4646-4654 (1996).

zur Hausen, H., Papillomaviruses and cancer: from basic studies to clinical application. Nature Reviews Cancer 2(5):342-50 (2002).

Buller et al., "Decreased virulence of recombinant vaccinia virus expression vectors is associated with a thymidine kinase-negative phenotype," Nature 317:813-815 (1985).

Chkheidze et al., "Identification of DNA binding proteins in vaccinia virus by DNA-protein crosslinking," FEBS 336(2):340-342 (1993).

Contag et al., "Visualizing Gene Expression in Living Mammals Using a Bioluminescent Reporter," Photochemistry and Photobiology 66(4):523-531 (1997).

Demkowicz et al., "Human Cytotoxic T-Cell Memory: Long-Lived Responses to Vaccinia Virus," J. Virol. 70(4):2627-2631 (1996).

Giavedoni et al., "Vaccinia virus recombinants expressing chimeric proteins of human immunodeficiency virus and gamma-interferon are attenuated for nude mice," Proc. Natl. Acad. Sci. 89:3409-3413 (1992).

Hauser et al., "Poxvirus as a vector to transduce human dendritic cells for immunotherapy: abortive infection but reduced APC function," Gene Ther. 7(18):1575-1583 (2000).

Huang et al., "Bacterial penetration across the blood-brain barrier during the development of neonatal meningitis," Microbes and Infection 2(10):1237-1244 (2000).

Huebner et al. "Production of type-specific antigen in virus-free hamster tumor cells induced by adenovirus type 12," Proc. Natl. Acad. Sci. 51:432-439 (1964).

Kass et al, "Induction of Protective Host Immunity to Carcinoembryonic Antigen (CEA), a Self-Antigen in CEA Transgenic Mice, by Immunizing with a Recombinant Vaccinia-CEA Virus," Cancer Research 59:676-683 (1999).

Lu et al., "Delivery of adenoviral vectors to the prostate for gene therapy," Cancer Gene Therapy 6(1):64-72 (1999).

Martinez et al., "Specific Antibody to *Cryptococcus neoformans* Glucurunoxylomannan Antagonizes Antifungal Drug Action against *Cryptococcal* Biofilms in Vitro," J. Infect. Diseases 194:261-266 (2006).

Mastrangelo et al., "Virotherapy clinical trials for regional disease: In situ immune modulation using recombinant poxvirus vectors," Cancer Gene Therapy 9:1013-1021 (2002).

Okuse et al., "Enhancement of antiviral activity against hepatitis C virus in vitro by interferon combination therapy," Antiviral Research 65:23-34 (2005).

Orkin et al., "Report and Recommendations of the Panel to Assess the NIH Investment in Research on Gene Therapy," (1995).

Paoletti et al., "Applications of pox virus vectors to vaccination: An update," Proc. Natl. Acad. Sci. 93:11349-11353 (1996).

Peplinski et al., "Prevention of murine breast cancer by vaccination with tumor cells modified by cytokine-producing recombinant vaccinia viruses," Annals Surg. Oncol. 3(1):15-23 (1996).

Qin et al., "Construction of recombinant vaccinia virus expressing GM-CSF and its use as a tumor vaccine," Gene Ther. 3(1):59-66 (1996).

Ramirez et al., "Biology of attenuated modified vaccinia virus Ankara recombinant vector in mice: Virus fate and activation of B- and T-Cell immune responses in comparsion with the Western Reserve Strain and advantages as a vaccine," J. Virol. 74(2):923-933 (2000).

Shen et al., "Fighting cancer with vaccinia virus: Teaching new tricks to an old dog," Mol. Therapy 11(2):180-195 (2005).

Shida et al., "Effects and virulences of recombinant vaccinia viruses derived from attenuated strains that express the human T-cell leukemia virus type I envelope gene," J. Virol. 62(12):4474-4480 (1988).

Sroller et al., "Effect of 3-beta-hydroxysteroid dehydrogenase gene deletion on virulence and immunogenicity of different vaccinia viruses and their recombinants," Arch. Virol. 143:1311-1320 (1998).

Steele et al., "Recent developments in the Virus therapy of Cancer," P.S.E.B.M. 223:118-127 (2000).

Stienlauf et al., "Kinetics of formation of neutralizing antibodies against vaccinia virus following re-vaccination," Vaccine 17:201-204 (1999).

Sui et al., "Cell Cycle-Dependent Antagonistic Interactions between Paclitaxel and gamma-Radiation in Combination Therapy," Clin. Canc. Res. 10:4848-4857 (2004).

Taylor et al., "Comparison of the virulence of wild-type thymidine kinase (tk)-deficient and tk+ phenotypes of vaccinia virus recombinants after intranasal inoculation of mice," J. Gen. Virol. 72 (Pt 1):125-130 (1991).

Upton et al., "Poxvirus orthologous clusters: toward defining the minimum essential poxvirus genome," J. Virol. 77(13):7590-7600 (2003).

Xiong et al., "Cell cycle dependent antagonistic interactions between Paclitaxel and Carboplatin in combination therapy," Cancer Biology Therapy 6(7):1067-1073 (2007).

ATCC Accession No. 37253 (accessed Jun. 30, 2005) (2 pages).

ATCC Accession No. VR-1549 (accessed Dec. 10, 2004) (2 pages).

Drexler et al., "Modified vaccinia virus Ankara as antigen delivery system: how can we best use its potential," Curr. Opin. Biotechnol. 15(6):506-512 (2004).

Emens, L., "Cancer vaccines:on the threshold of success," Expert Opinion of Emerging Drugs 13(2):295-308 (2008).

Genbank Accession No. M57977 (accessed Oct. 15, 2008) (11 pages).

Guo et al., "Vaccinia as a vector for gene delivery" Expert Opin Biol Ther 4(6):901-17 (2004).

Heise et al., "Efficacy of a replication-competent adenovirus (ONYX-015) following intratumoral injection: intratumoral spread and distribution effects," Cancer Gene Ther. 6(6):499-504 (1999).

Ikeda et al., "Oncolytic virus therapy of multiple tumors in the brain requires suppression of innate and elicited antiviral responses," Nat Med. 5(8):881-887 (1999).

Kim et al., "Replication-selective virotherapy for cancer: biological principles, risk management and future directions," Nat. Med. 7:781-787 (2001).

Kutinova et al., "Hepatitis B virus proteins expressed by recombinant vaccinia viruses: influence of preS2 sequence on expression surface and nucleocapsid proteins in human diploid cells," Archives of Virology 134:1-15 (1994).

Larocca et al., "Gene Transfer to Mammalian Cells Using Genetically Targeted Filamentous Bacteriophage," FASEB Journal, 13:727-734, (1999).

NCBI Nucleotide AF012825 (date of last modification Aug. 6, 2002) (96 pages).

NCBI Nucleotide AF380138 (date of last modification Dec. 13, 2001) (99 pages).

NCBI Nucleotide AX003206 (date of last modification Aug. 24, 2000) (3 pages).

NCBI Nucleotide AY243312 (date of last modification Apr. 10, 2003) (102 pages).

NCBI Nucleotide AY484669 (date of last modification Mar. 30, 2004) (92 pages).

NCBI Nucleotide AY603355 (date of last modification May 15, 2004) (92 pages).

NCBI Nucleotide M35027 (date of last modification Aug. 3, 1993) (92 pages).

NCBI Nucleotide M57977 (date of last modification Apr. 14, 2000) (9 pages).

NCBI Nucleotide U94848 (date of last modification Apr. 14, 2003) (85 pages).

NCBI Nucleotide X69198 (date of last modification Sep. 10, 2004) (93 pages).

NCBI Nucleotide X94355 (date of last modification May 9, 2003) (108 pages).

NCBI Nucleotide. AF095689 (date of last modification Feb. 14, 2000) (89 pages).

NCBI Nucleotide. AY009089 (date of last modification Jul. 30, 2002) (114 pages).

NCBI Protein AAA48282 (date of last modification Apr. 14, 2000) (1 page).

Okada et al., "Sensitization of human tumor cells to homologous complement by vaccinia virus treatment" Cancer Immunol Immunother 25(1):7-9 (1987).

Pfleiderer et al., "A novel vaccinia virus expression system allowing construction of recombinants without the need for selection markers, plasmids and bacterial hosts," J. General Virology 76:2957-2962 (1995).

Pfleiderer et al., "Requirements for optimal expression of secreted and nonsecreted recombinant proteins in vaccinia virus systems," Protein Expr Purif. 6(5):559-69 (1995).

Smith et al., "Host range selection of vaccinia recombinants containing insertions of foreign genes into non-coding sequences," Vaccine. 11(1):43-53 (1993).

Sutter et al., "Vaccinia vectors as candidate vaccines: The development of modified vaccinia virus Ankara for antigen delivery," Current Drug Targets—Infectious Disorders 3(3):263-271 (2003).

Buller et al., In:Quinnan, G., ed. Vaccinia Viruses as Vectors for Vaccine Antigens, New York:Elsevier 37-46 (1985).

Certified English Translation of Chernos et al., "Tests for safety, 'Take'—Rate, Reactogenicity and Antigenic Properties of a Live Recombinant Smallpox-Hepatitis B Vaccine in Volunteers," Vopr. Virusol. (Moscow) 35:132-135 (1990).

Chernos et al., "Tests for safety, 'Take' —Rate, Reactogenicity and Antigenic Properties of a Live Recombinant Smallpox-Hepatitis B Vaccine in Volunteers", Vopr. Virusol. (Moscow) 35:132-135 (1990). [article in the Russian language].

Conry et al., Phase I trial of a recombinant vaccinia virus encoding carcinoembryonic antigen in metastatic adenocarcinoma: comparison of intradermal versus subcutaneous administration. Clin Cancer Res 5:2330-2337 (1999).

DiStefano, A. and A. Buzdar, "Viral-induced remission in chronic lymphocytic leukemia?" Arch Intern Med. 139(8):946 (1979).

Enserink M., "Public health. Treating vaccine reactions: two lifelines, but no guarantees," Science 298(5602):2313 (2002).

Guo et al., "The enhanced tumor selectivity of an oncolytic vaccinia lacking the host range and antiapoptosis genes SPI-1 and SPI-2," Cancer Res. 65(21):9991-9998 (2005).

Kaufman et al., "Phase II randomized study of vaccine treatment of advanced prostate cancer (E7897): a trial of the Eastern Cooperative Oncology Group," J Clin Oncol 22:2122-2132 (2004).

Lane et al., "Complications of smallpox vaccination, 1968: results of ten statewide surveys," J Infect Dis 122:303-309 (1970).

Lane et al., "Complications of smallpox vaccinations, 1968: national surveillance in the United States," New Engl J Med 281:1201-1208 (1969).

Roenigk et al., "Immunotherapy of malignant melanoma with vaccinia virus," Arch Dermatol 109:668-673 (1977).

Yettra M., "Remission of chronic lymphocytic leukemia after smallpox vaccination," Arch Intern Med. 139(5):603 (1979).

Casado et al, "Strategies to accomplish targeted expression of transgenes in ovarian cancer for molecular therapeutic applications", Clinical Cancer Research 7(8):2496-2504 (2001).

Galmiche et al., "Expression of a functional single chain antibody on the surface of extracellular enveloped vaccinia virus as a step towards selective tumour cell targeting", J. Gen. Virol. 78:3019-3027 (1997).

Hughes et al., "Vaccinia virus encodes an active thymidylate kinase that complements a cdc8 mutant of *Saccharomyces cerevisiae*," J. Biol. Chem. 266(30):20103-20109 (1991).

Advisory Committee on Immunization Practices (ACIP), "Smallpox vaccination and adverse reactions: guidance for clinicians", Morbidity and Mortality Weekly Report 52(RR-4): 1-29 (Feb. 21, 2003).

Advisory Committee on Immunization Practices (ACIP), Vaccinia (smallpox) vaccine: recommendations of the Advisory Committee on Immunization Practices (ACIP), MMWR, 50(RR-10): 1-26 & ce1-ce7 (Jun. 22, 2001).

Aksac S., "[Antibody formation against Agrobacterium tumefaciens in patients with various cancers]," Turk Hij Tecr Biyol Derg. 34(1-2):48-51 (1974) [Article in Italian].

Alcamí, A. et al., "Vaccinia virus strains Lister, USSR and Evans express soluble and cell-surface tumour necrosis factor receptors", J. Gen. Virol., 80: 949-959 (1999).

Altenbrunn et al., "Scintographic Tumor Localization in Mice with Radioiodinated Anti-*Clostridium* Antibodies," Int. J. Nucl. Med. Biol. 8(1): 90-93 (1981).

Altschul et al., "Basic local alignment search tool," J Molec Biol 215:403-410 (1990).

Al'tshtein et al., "[Isolation of a recombinant vaccinia virus based on the LIVP strain inducing the surface antigen of the hepatitis B virus]," Dokl Akad Nauk SSSR. 285(3):696-9 (1985) [Article in Russian].

Anaissie et al., "Pseudomonas putida. Newly recognized pathogen in patients with cancer," Am J Med. 82(6):1191-4 (1987).

Anand, A and A.E. Glatt, "Clostridium difficile infection associated with antineoplastic chemotherapy: a review," Clin Infect Dis. 17(1):109-13 (1993).

Ando, N. and M. Matumoto, "Unmasking of growth of dermovaccinia strain dairen I in L cells by acid treatment of cells after virus adsorption," Japan. J. Microbiol. 14(3): 181-186 (1979).

Antoine et al., "The complete genomic sequence of the modified vaccinia Ankara strain: comparison with other orthopoxviruses," Virology 244: 365-396 (1998).

Antoine, G. et al., "Characterization of the vaccinia MVA hemagglutinin gene locus and its evaluation as an insertion site for foreign genes", Gene, 177: 43-46 (1996).

Arab et al., "Verotoxin induces apoptosis and the complete, rapid, long-term elimination of human astrocytoma xenografts in nude mice," Oncol Res. 11(1):33-9 (1999).

Arakawa et al., "Clinical trial of attenuated vaccinia virus AS strain in the treatment of advanced adenocarcinoma. Report on two cases," J Cancer Res Clin Oncol. 113(1):95-8 (1987).

Arakawa, S. et al., "Clinical trial of attenuated vaccinia virus AS strain in the treatment of advanced adeocarcinoma", J. Cancer Res. Clin. Oncol., 113: 95-98 (1987).

ATCC Accession No. 11842, (2005).
ATCC Accession No. 11863, (2005).
ATCC Accession No. 13124, (2005).
ATCC Accession No. 15696, (2005).
ATCC Accession No. 15697, (2005).
ATCC Accession No. 15707, (2005).
ATCC Accession No. 15955, (2005).
ATCC Accession No. 17583, (2005).
ATCC Accession No. 17836, (2005).
ATCC Accession No. 19401, (2005).
ATCC Accession No. 19402, (2005).
ATCC Accession No. 19404, (2005).
ATCC Accession No. 25527, (2005).
ATCC Accession No. 25752, (2005).
ATCC Accession No. 25923, (2005).
ATCC Accession No. 27337, (2005).
ATCC Accession No. 27555, (2005).
ATCC Accession No. 29212, (2005).
ATCC Accession No. 35782, (2005).
ATCC Accession No. 3624, (2005).
ATCC Accession No. 37253, (2005).
ATCC Accession No. 393, (2005).
ATCC Accession No. 43142, (2005).
ATCC Accession No. 47054, (2005).
ATCC Accession No. 51299, (2005).
ATCC Accession No. 59324, (2005).
ATCC Accession No. 59325, (2005).
ATCC Accession No. 700057, (2005).
ATCC Accession No. 824, (2005).
ATCC Accession No. 9338, (2005).
ATCC Accession No. 9714, (2005).
ATCC Accession No. BAA-250D, (2005).
ATCC Accession No. CCL-70, (2005).
ATCC Accession Nos. CCL-121, (2004).
ATCC Accession Nos. CRL-12011, (2004).
ATCC Accession Nos. CRL-12012, (2004).
ATCC catalog No. 700294, (2004).
ATCC No. CCL-107, (2004).
ATCC No. CRL-6475, (2004).
ATCC under Accession No. VR-1549, (2004).

Azmi et al., "In situ localization of endogenous cytokinins during shooty tumor development on *Eucalyptus globulus* Labill," Planta 213(1):29-36 (2001).

Baeksgaard, L. and J.B. Sorensen, "Acute tumor lyssi syndrome in solid tumors—a case report and review of the literature", Cancer Chemother. Pharmacol., 51: 187-192 (2003).

Baker, R.O. et al., "Potential antiviral tehrapeutics for smallpox, monkeypox, and other orthopoxvirus infections", Antiviral Research, 57: 13-23 (2003).

Baker, S.J. and E.P. Reddy, "Transducers of life and death: TNF receptor superfamily and associated proteins," Oncogene 12(1):1-9 (1996).

Balkwill, F., "Chemokine biology in cancer", Seminars in Immunol., 15: 49-55 (2003).

Banerjee et al., "*Bacillus* infections in patients with cancer," Arch Intern Med. 148(8):1769-74 (1988).
Barrett et al., "Yellow Fever Vaccines," Biologicals 25:17-25 (1997).
Bauerschnitz et al., "Treatment of Ovarian Cancer with a Tropism Modified Oncolytic Adenovirus," Cancer Research 62: 1266-1270 (2002).
Baxby, D., "Poxviruses", Chapter 15 in *Principles and Practice of Clinical Virology*, Zuckerman, A.J. et al.(eds.), John Wiley & Sons Ltd., pp. 451-465 (2000).
Beebe, J.L. and E.W. Koneman, "Recovery of Uncommon Bacteria from Blood: Association with Neoplastic Disease," Clin. Microbiol. Rev., 8(3): 336-356 (1995).
Belas et al., "Bacterial Bioluminescence: Isolation and Expression of the Luciferase Genes from *Vibrio harveyi*," Science, 218: 791-793 (1982).
Bell, J.C. et al., "Getting oncolytic virus therapies off the ground," Cancer Cell, 4: 7-11(2003).
Bendig, M.M., "The production of foreign proteins in mammalian cells," Genetic Engineering 7:91-127 (1988).
Benes et al., "M13 and pUC vectors with new unique restriction sites for cloning," Gene 130: 151-152 (1993).
Bennett et al., "Positron emission tomography imaging for herpes virus infection: Implications for oncolytic viral treatments of cancer," Nature Med 7(7): 859-863 (2001).
Bentires-Alj et al., "Cytosine deaminase suicide gene therapy for peritoneal carcinomatosis," Cancer Gene Ther. 7(1):20-6 (2000).
Berger, F. and S.S. Gambhir, "Recent advances in imaging endogenous or transferred gene expression utilizing radionuclide technologies in living subjects," Breast Cancer Research 3: 28-35 (2001).
Murosaki et al., "Antitumor effect of heat-killed *Lactobacillus plantarum* L-137 through restoration of impaired interleukin-12 production in tumor-bearing mice," Cancer Immunol Immunother. 49(3):157-64 (2000).
Mutschler et al., "10. Chemotherapy of Malignant Tumors" in: Drug Actions: Basic Principles and Therapeutic Aspects (medpharm (CRC Press), Suttgart, pp. 595-612, (1995).
Myklebust et al., "Eradication of small cell lung cancer cells from human bone marrow with immunotoxins," Cancer Res. 53(16):3784-8 (1993).
Nagahari et al. "Secretion into the culture medium of a foreign gene product from *Escherichia coli*: use of the *ompF* gene for secretion of human β-endorphin." EMBO J. 4(13A):3589-92 (1985).
Nakamura et al., "Induction of apoptosis in HL60 leukemic cells by anticancer drugs in combination with anti-Fas monoclonal antibody," Anticancer Res. 17(1A):173-9 (1997).
Nakao, H. and T. Takeda, "*Escherichia coli* Shiga toxin," J Nat Toxins. 9(3):299-313 (2000).
Nauciel, C. and A.F. Goguel, "Inhibition of tumor growth by the peptidoglycan from *Bacillus megaterium*," J Natl Cancer Inst. 59(6):1723-6 (1977).
NCBI Nucleotide AF012825, (2002).
NCBI Nucleotide AF380138, (2009).
NCBI Nucleotide AX003206, (2000).
NCBI Nucleotide AY243312, (2006).
NCBI Nucleotide AY484669, (2005).
NCBI Nucleotide AY603355, (2004).
NCBI Nucleotide M35027, (2006).
NCBI Nucleotide M57977, (2000).
NCBI Nucleotide U94848, (2003).
NCBI Nucleotide X69198, (2005).
NCBI Nucleotide X94355, (2005).
NCBI Nucleotide. AF095689, (2000).
NCBI Nucleotide. AY009089, (2002).
NCBI Protein AAA48282, (2000).
Needleman et al., "A general method applicable to the search for similarities in the amino acid sequences of two proteins," J. Mol. Biol. 48:443-453 (1970).
Netesova et al., "Structural and functional studies of the *Hind*III-I-Genome Fragment of Vaccinia virus Strain L-IVP," Mol Biol (Mosk.) Nov.-Dec. 25(6): 1526-32 (1991) ) [article in Russian, English summary on last page of article].

Nettleton, P.F. et al., "Parapoxviruses are strongly inhibited in vitro by cidofovir," Antivir. Res., 48: 205-208 (2000).
First complaint, tiled in the Superior Court for the State of California, County of Los Angeles, dated Dec. 21, 2005 (Case No. BC344912) *Genelux Corporation. A Delaware corporation (Plaintiff) vs. Dr. Bernard Huber, an individual; Patentanwäte Huber & Schiissler: a partnership under the Code Gesellschaft des Burgerlichen Rechts; Dr. Gerd Ste/tie. An indivichtal; and Does 1 through 10, inclusive (Defindants)*.
*Stipulation and Order of Dismissal.* Case No. CV06-1462 AG(FM0x).
Petition for Retroactive Grant of Foreign Filing License, tiled on May 9, 2008, in connection with U.S. Appl. No. 10/872,156.
*Joint Stipulation Regarding Defendants' Motion to Compel: (I) Deposition Testimony on Identified Subjects. Pursuant to Rule 30(13)(6), and (2) the Production of Documents [Local Rule 37-2.1 ]*. Case No. CV06-1462 AG (FM0x).
*Notice of Removal of Acaon Under 28 U.S.C. 1441 (Diversity) Case No, CV06-1462 AG (FM0x), Genelux Corporation. A Delaware corporation (Plaintiff. vs. Dr. Bernard Huber, an individual; Patentanwiihe Huber &Schüssler. A partnership under the Code Gesellschaft des Btu-get-lichen Rechts; Dr. Gerd Stehle, an individual; and Does 1 through 10, inclusive (Defendants)*.
*Answer and Counterclaims for Fraud, Negligent Misrepresentation, Breach of Fiduciaty Duty; Breach of Contract: and Indemnity. Case No. CV06-1462 AG (FM0x), Genelux Corporation, a Delaware corporation (Plaintiff) vs. Dr. Bernard Huber, an individual; Patentanwillte Huber & Schüssler, a partnership under the Code Gesellschaft des Burgerlichen Rechts: Dr. Gerd Ste/the. An individual; and Does I through 10, inclusive (Defendants); Dr. Bernard Huber. On individual; Patentanwiilte Huber & Schüssler, a partnership under the Code Gesellschaft des Burgerliehen Reclas; Dr. Gerd Stehle. An individual (Counterclaimants) vs. Genelux Corporation. a Delaware corporation, Ronald Simus, an individual, David Wood, an individual, and Aladar A. Szalay, an individual (Counterdefendants).*
*Report of Parties' Planning Meeting for Scheduling Conference.* Case No. CV06-1462 Ag (FM0x).
*Notice of Motion and Motion to Compel Further Responses by Defendant/Counterclaimant Dr. Bernard Huber to Interrogatories; Joint Stipulation of the Parties; Declaration of Howard M. Loeb.* Case No. CV06-1462 AG(FM0x).
*Order Regarding Discovery Motions.* Case No. CV06-1462 AG (FM0x).
Declaration of Paula K. Schoeneck.
*Notice of Motion and Motion to Dismiss Counterclaimants Huber and Stehle's Fourth Cause of Action far Failure to State a Claim upon which Relief can be Granted; Memorandum of Points and Authorities; Declaration Pursuant to Local Rule 7-3.* Case No. CV06-1462 GHK (FM0x).
*Counterclaimants' Opposition to Counterdefendant Genelux's Motion to Dismiss.* Case No. CV06-1462 GHK (FM0x).
*Reply to Opposition to Motion to Dismiss Counterclaimants Huber and Stehle's Fourth Cause of Action for Failure to State a Claim upon which Relief can he Granted.* Case No. CV06-1462 GHK (FM0x).
*Court Order granting Genelux's motion to dismiss.* Case No. CV06-1462 GHK (FM0x).
*First Amended Counterclaims for Fraud: Negligent Misrepresentation. Breach of Fiduciary Duty; Breach of Contract; Breach of the Implied Covenant of Good Faith and Fair Dealing; and Indemnity.* Case No. CV06-1462 GHK (FM0x).
*Notice of Motion and Motion to Dismiss Counterclaimants Huber and Stehle 's Seventh Cause of Action for Failure to State a Claim Upon Which Relief Can he Granted; Memorandum of Points and Authorities; Declaration Pursuant to Local Rule 7-3.* Case No. CV06-1462 GHK (FM0x).
*Counterclaimants' Opposition to Motion to Dismiss Seventh Cause of Action.* Case No. CV06-1462 GHK (FM0x).
*Reply to Opposition to Motion to Dismiss Counterclaimants Huber and Stehle's Seventh Cause of Action for Failure to State a Claim Upon Which Relief can be Granted.* Case No. CV06-1462 AG(FM0x).
*(In Chambers) Order Denying Motion to Dismiss Counterclaimants' Seventh Cause of Action.* Case No. CV06-1462 AG(FM0x).

*Reply to First Amended Counterclaims.* Case No. CV06-1462 AG(FMOx).

Office Action, issued May 12, 2008, in connection with U.S. Appl. No. 10/872,156.

Office Action, issued Dec. 6, 2007, in connection with U.S. Appl. No. 11/238,025.

Office Action, issued Apr. 3, 2008, in connection with U.S. Appl. No. 11/796,027.

Office Action, issued Apr. 1, 2008, in connection with U.S. Appl. No. 11/796,028.

Office Action, issued Dec. 21, 2007, in connection with Canadian Patent Application No. 2,527,225.

Office Action, issued Nov. 19, 2007, in connection with U.S. Appl. No. 10/485,179.

Office Action, issued Aug. 1, 2007, in connection with U.S. Appl. No. 10/866,606.

Office Action, issued Mar. 18, 2008, in connection with U.S. Appl. No. 10/866,606.

WO 2007/075879, Published Jul. 5, 2007.

Amato et al., "Luminous with Promise" Chem, Eng. News. 84(49):69-73 (2006).

Chen et al. "Real-dine monitoring of vaccinia virus infection in cultured cells and in living mice using light-emitting proteins" *Proceedings of the 14th International Symposium on Bioluminescence & Chemiluminescence: Chemistry, Biology and Applications*, World Scientific: Singapore: 181-184 (2007).

Davis et al., "Oncolytic virotherapy for cancer treatment: challenges and solutions" *J. Gene Med.* 7(11):1380-1389 (2005).

Gherardi et al., "Recombinant poxviruses as mucosal vaccine vectors" *J Gen Virol* 86:2925-2936 (2005).

Jia et al., "Viral vectors for cancer gene therapy: Viral dissemination and tumor targeting" Curr. Gene Ther. 5:133-142 (2005).

Kelly et al. Novel oncolytic agent Glv-1h68 is effective against malignant pleural mesothelioma. *Hum Gene Ther.* 19(8):774-82 (2008).

Kelly et al., "Real-time intraoperative detection of melanoma lymph node metastases using recombinant vaccinia virus GLV-1h68 in an immunocompetent animal model" Int. J. Cancer (accessed on 10.21.08) (30 pp.) (2008).

Lin et al., Oncolytic Vaccinia Virotherapy of Anaplastic Thyroid Cancer in Vivo. J Clin Endocrinol Metab (accessed on 10.21.08) (16 pages) (2008).

Lin S-F, Yu Z, Riedl C, et al. Treatment of anaplastie thyroid carcinoma in vitro with a mutant vaccinia virus. Surgery 2007;142(6):976-83.

Parato et al., "Recent progress in the battle between oncolytic viruses and tumours" Nature Rev. 5:965-976 (2005).

Raab et al., "Four-color labeling of cell culture and tumors of live mice upon infection with: GFP-Ruc and RFP-CBG99 expressing Vaccinia virus strains" *Proceedings of the 14th International Symposium on Bioluminescence & Chemiluminescence: Chemistry, Biology and Applications*, World Scientific: Singapore, 197-200 (2007).

Zhang et al., "Eradication of solid human tumors in nude mice with an intravenously injected light emitting oncolytic vaccinia virus", Cancer Res. 67(20):10038-10046 (2007).

"Safety Study of Gl-Onc I, an Oncolytic Virus, in Patients with Advanced Solid Tumors", www.clinicaltrials.gov/ct2/show/NCT00794131?term=genelux&rank=1 (accessed on Dec. 2, 2008, 5 pages).

Office Action, issued Dec. 18, 2008, in connection with U.S. Appl. No. 10/866,606.

Brown M. "Killer into cure — oncolytic viruses". Microbiology Today. 2005;56:128-31.

Everts Bet al. "Replication-selective oncolytic viruses in the treatment of cancer". Cancer Gene Ther. 2005;12:141-61.

Gentschev et al., "Use of an oncolytic vaccinia virus for treatment of canine breast cancer in nude mice: preclinical development of a therapeutic agent", Cancer Gene Therapy (2008) Published online: Oct. 24, 2008; www.nature.com/cgt/jounial/vaop/ncurrent/abs/cgt200887a.html, (accessed on Dec. 05, 2008).

Hermiston T et al.. "Genetically based therapeutics for cancer: similarities and contrasts with traditional drug discovery and development". Mol. Ther. 2005;11(4):496-507.

Liu Ta-Chiang, Galanis E, Kim D. "Clinical trial results with oncolytic virotherapy: a century of promise, a decade of progress". Nat Clin Pract Oncol; 4:101-116 (2006).

Naik AM et al. "Intravenous and isolated limb perfusion delivery of wild type and a tumor-selective replicating mutant vaccinia virus in nonhuman primates". Hum Gene Ther. 2006;17:1-15.

Thorne SH et al. "Vaccinia virus and oncolytic virotherapy of cancer". Curr Opin Mol Ther. 2005;7(4):359-65.

Woo et al., "Advances in oncolytic viral therapy. Curr. Opin. Investig. Drugs 7, 549-559 (2006).

Office Action, issued Sep. 2, 2008 in connection with U.S. Appl. No. 11/238,025.

Office Action, Jan. 30, 2009, in connection with U.S. Appl. No. 11/796,028.

Office Action, issued Feb. 2, 2009, in connection with U.S. Appl. No. 11/796,027.

Yu et al., "Regression of human pancreatic tumor xenografts in mice after a single systemic injection of recombinant vaccinia virus Glv-1h68," *Molecular Cancer Therapeutics* 8:141-151 (2009).

Office Action, issued Dec. 6, 2007, in connection with U.S. Appl. No. 11/238,025.

Office Action, issued Apr. 1, 2008, in connection with U.S. Appl. No. 11/796,028.

Office Action, issued Dec. 21, 2007, in connection with Canadian Patent Application Serial No. 2,527,225.

Office Action, issued Nov. 19, 2007, in connection with U.S. Appl. No. 10/485,179.

Office Action, issued Aug. 1, 2007, in connection with U.S. Appl. No. 10/866,606.

Office Action, issued Mar. 18, 2008, in connection with U.S. Appl. No. 10/866,606.

Davis et al., "Oncolytic virotherapy for cancer treatment: challenges and solutions" *J. Gene Med.* 7(11):1380-1389 (2005).

Gherardi et al., "Recombinant poxviruses as mucosal vaccine vectors" *J Gen Virol* 86:2925-2936 (2005).

Parato et al., "Recent progress in the battle between oncolytic viruses and tumours" *Nature Rev.* 5:965-976 (2005).

Office Action, issued Apr. 9, 2009 in connection with U.S. Appl. No.10/485,179.

Brader et al, "Imaging genetically engineered oncolytic vaccinia virus (GLV-1h99) using a human norepinephrine transporter reporter gene", Clin. Cancer Res. 15(11):3791-3801 (2009).

Chen et al. "A novel recombinant vaccinia virus expressing the human norepinephrine transporter retains oncolytic potential and facilitates deep tissue imaging", Mol. Med. (2009) (Epub ahead of print).

Worschech et al., "The immunologic aspects of poxvirus oncolytic therapy", Cancer Immunol. Immunother. (2009) (Epub ahead of print).

European Examination Report, issued Oct. 31, 2006, in connection with European Patent Application No. 03024283.8.

European Examination Report, issued Dec. 13, 2006, in connection with European Patent Application No. 03018478.2.

An International Preliminary Report on Patentability, issued Feb. 9, 2006, in connection with corresponding PCT Patent Application No. US2004/019866.

Copy of a Canadian Office Action, issued Sep. 25, 2006, in connection with corresponding Canadian Patent Application No. 2,527,225.

Office Action, issued Oct. 25, 2006, in connection with U.S. Appl. No. 10/872,156.

Office Action, issued Jul. 31, 2007, in connection with U.S. Appl. No. 10/872,156.

Office Action, issued Dec. 18, 2006, in connection with U.S. Appl. No. 11/238,025.

MedicineNet.com, definition of Tumor www.medterms.com/script/main/art.asp?articlekey=5863 (Accessed on May 30, 2007).

* cited by examiner ced with a WR strain of
MICROORGANISMS FOR THERAPY

RELATED APPLICATIONS

This application is a divisional of U.S. application Ser. No. 11/238,025, to Aladar A. Szalay, Tatyana Timiryasova, Yong A. Yu and Qian Zhang, filed on Sep. 27, 2005, entitled "MICROORGANISMS FOR THERAPY," which is a continuation of U.S. application Ser. No. 10/872,156, to Aladar A. Szalay, Tatyana Timiryasova, Yong A. Yu and Qian Zhang, filed on Jun. 18, 2004, entitled "MICROORGANISMS FOR THERAPY." The subject matter of each of these applications is incorporated by reference in its entirety.

This application also is related to International Application Serial No. PCT/US04/19866, filed on Jun. 18, 2004, entitled "MICROORGANISMS FOR THERAPY". This application also is related to U.S. application Ser. No. 10/866,606, filed Jun. 10, 2004, entitled "Light emitting microorganisms and cells for diagnosis and therapy of tumors," which is a continuation of U.S. application Ser. No. 10/189,918, filed Jul. 3, 2002, entitled "Light emitting microorganisms and cells for diagnosis and therapy of tumors"; U.S. application Ser. No. 10/849,664, filed May 19, 2004, entitled, "Light emitting microorganisms and cells for diagnosis and therapy of diseases associated with wounded or inflamed tissue" which is a continuation of U.S. application Ser. No. 10/163,763, filed Jun. 5, 2002, entitled "Light emitting microorganisms and cells for diagnosis and therapy of diseases associated with wounded or inflamed tissue"; International PCT Application WO 03/014380, filed Jul. 31, 2002, entitled "Microorganisms and Cells for Diagnosis and Therapy of Tumors"; PCT Application WO 03/104485, filed Jun. 5, 2003, entitled, "Light Emitting Microorganisms and Cells for Diagnosis and Therapy of Diseases Associated with Wounded or Inflamed tissue"; EP Application No. 01 118 417.3, filed Jul. 31, 2001, entitled "Light-emitting microorganisms and cells for tumour diagnosis/therapy"; EP Application No. 01 125 911.6, filed Oct. 30, 2001, entitled "Light emitting microorganisms and cells for diagnosis and therapy of tumors"; EP Application No. 02 794 632.6, filed Jan. 28, 2004, entitled "Microorganisms and Cells for Diagnosis and Therapy of Tumors"; and EP Application No. 02 012 552.2, filed Jun. 5, 2002, entitled "Light Emitting Microorganisms and Cells for Diagnosis and Therapy of Diseases associated with wounded or inflamed tissue." The subject matter of each of these applications is incorporated by reference in its entirety.

FIELD OF THE INVENTION

Vaccines that contain attenuated or modified microorganisms, including microbes and cells, and methods for preparing the microorganisms and vaccines are provided. In particular, modified bacteria, eukaryotic cells and viruses are provided and methods of use thereof for treatment of proliferative and inflammatory disorders and for production of products in tumors are provided.

BACKGROUND

In the late 19th century, a variety of attempts were made to treat cancer patients with microorganisms. One surgeon, William Coley, administered live *Streptococcus pyogenes* to patients with tumors with limited success. In the early 20th century, scientists documented vaccinia viral oncolysis in mice, which led to administration of several live viruses to patients with tumors from the 1940s through the 1960s. These forays into this avenue of cancer treatment were not successful.

Since that time, a variety of genetically engineered viruses have been tested for treatment of cancers. In one study, for example, nude mice bearing nonmetastatic colon adenocarcinoma cells were systemically injected with a WR strain of vaccinia virus modified by having a vaccinia growth factor deletion and an enhanced green fluorescence protein inserted into the thymidine kinase locus. The virus was observed to have antitumor effect, including one complete response, despite a lack of exogenous therapeutic genes in the modified virus (McCart et al. (2001) *Cancer Res* 1:8751-8757). In another study, vaccinia melanoma oncolysate (VMO) was injected into sites near melanoma positive lymph nodes in a Phase III clinical trial of melanoma patients. As a control, New York City Board of Health strain vaccinia virus (VV) was administered to melanoma patients. The melanoma patients treated with VMO had a survival rate better than that for untreated patients, but similar to patients treated with the VV control (Kim et al. (2001) *Surgical Oncol* 10:53-59).

Other studies have demonstrated limited success with this approach. This therapy is not completely effective, particularly for systemically delivered viruses or bacteria. Limitations on the control of microbial vehicle function in vivo result in ineffective therapeutic results as well as raising safety concerns. It would be desirable to improve this type of therapy or to develop more effective approaches for treatments of neoplastic disease. Therefore, among the objects herein, it is an object to provide therapeutic methods and microorganisms for the treatment of neoplastic and other diseases.

SUMMARY

Provided herein are therapeutic methods and microorganisms, including viruses, bacteria and eukaryotic cells, for uses in the methods for the treatment of neoplastic diseases and other diseases. Diseases for treatment are those in which the targeted tissues and/or cells are immunoprivileged in that they, and often the local environment thereof, somehow escape or are inaccessible to the immune system. Such tissues include tumors and other tissues and cells involved in other proliferative disorders, wounds and other tissues involved in inflammatory responses. The microorganisms, which include bacterial cells, viruses and mammalian cells, are selected or are designed to be non-pathogenic and to preferentially accumulate in the immunoprivileged tissues. The microorganisms, once in the tissues or cells or vicinity thereof, affect the cell membranes of the cells in such tissues so that they become leaky or lyse, but sufficiently slowly so that the targeted cells and tumors leak enough antigen or other proteins for a time sufficient to elicit an immune response.

The microorganisms are administered by any route, including systemic administration, such as i.v. or using oral or nasal or other delivery systems that direct agents to the lymphatics. In exemplary methods, the microorganisms are used to treat tumors and to prevent recurrence and metastatic spread. Exemplary microorganisms include highly attenuated viruses and bacteria, as well as mammalian cells. The microorganisms are optionally modified to deliver other products, including other therapeutic products to the targeted tissues.

When the microorganisms are administered to a host that contains tumors, the tumors in the host essentially become antigen and protein factories. This can be exploited so that the tumors can be used to produce proteins or other cellular products encoded by or produced by the microorganisms. In addition, the host sera can be harvested to isolate antibodies to products produced by the microorganisms as well as the tumor cells. Hence also provided are methods for producing gene products by administering the microorganisms to an animal, generally a non-human animal, and harvesting the tumors to isolate the product. Also provided are methods for producing antibodies to selected proteins or cell products, such as metabolites or intermediates, by administering a microorganism that expresses or produces the protein or other product to a host, typically a non-human host; and harvesting serum from the host and isolating antibodies that specifically bind to the protein or other product.

Thus provided are methods and microorganisms for elimination of immunoprivileged cells or tissues, particularly tumors. The methods include administration, typically systemic administration, with a microorganism that preferentially accumulates in immunoprivileged cells, such as tumor cells, resulting in leakage proteins and other compounds, such as tumor antigens, resulting in vaccination of the host against non-host proteins and, such as the tumor antigens, providing for elimination of the immunoprivileged cells, such as tumor cells, by the host's immune system. The microorganisms are selected not for their ability to rapidly lyse cells, but rather for the ability to accumulate in immunoprivileged cells, such as tumors, resulting in a leakage of antigens in a sufficient amount and for a sufficient time to elicit an immune response.

Hence provided are uses of microorganisms or cells containing heterologous DNA, polypeptides or RNA to induce autoimmunization of an organism against a tumor. In particular, the microorganisms are selected or designed to accumulate in tumors and to accumulate very little, if at all (to be non-toxic to the host) in non-tumorous cells, tissues or organs, and to in some manner result in the tumor cell lyses or cell membrane disruption such that tumor antigens leak. Exemplary of such microorganisms are the LIVP-derived vaccinia virus and the bacteria described herein and also mammalian cells modified to target the tumors and to disrupt the cells membrane. The microorganisms can be modified to express heterologous products that mediate or increase the leakage of the tumor cell antigens and/or that are therapeutic, such as anti-tumor compounds.

Also provided are methods for production of antibodies against a tumor by (a) injecting a microorganism or cell containing a DNA sequence encoding a desired polypeptide or RNA into an organism bearing a tumor and (b) isolating antibodies against the tumor.

Provided are attenuated microorganisms that accumulate in immunoprivileged tissues and cells, such as tumor cells, but do not accumulate to toxic levels in non-targeted organs and tissues, and that upon administration to an animal bearing the immunoprivileged tissues and cells, result in autoimmunity, such as by production of anti-tumor (or anti-tumor antigen) antibodies against the immunoprivileged cells or products thereof. The microorganisms are selected or produced to render the immunoprivileged cells leaky, such as by a slow lysis or apoptotic process. The goal is to achieve such leakiness, but to not lyse the cells so rapidly that the host cannot mount an immune response.

Uses of and methods of use of the microorganisms for eliminating immunoprivileged tissues and cells are provided. The microorganisms optionally include reporter genes and/or other heterologous nucleic acids that disrupt genes in the microorganism and can also encode and provide therapeutic products or products, such as RNA, including RNAi, that alter gene and/or protein expression in the cells or tissues where the microorganism accumulates. Among the viruses provided are attenuated pox viruses that contain a modified TK and HA gene and a modified F3 gene or locus that corresponds to the F3 gene in vaccinia. In particular, provided are recombinant vaccinia viruses that contain a modified TK and HA gene and optionally a modified F3 gene or locus, wherein the resulting virus does not accumulate to toxic levels in non-targeted organs. Vaccinia viruses where the TK gene and F3 gene are modified and vaccinia viruses where the HA and F3 gene are modified, and viruses where all three genes are modified are provided. Modification includes inactivation by insertion, deletion or replacement of one or more nucleotide bases whereby an activity or product of the virus is altered. Included among the alterations is insertion of heterologous nucleic acid, such as therapeutic protein-encoding nucleic acids.

In exemplary embodiments, the vaccinia viruses are Lister strain viruses, particularly LIVP strain viruses (LIVP refers to the Lister virus from the Institute of Viral Preparations, Moscow, Russia, the original source for this now widely disseminated virus strain). Modifications include modification of the virus at the unique NotI site in the locus designed F3. In particular, the modification can be at position 35 of the F3 locus (gene) or at position 1475 inside of the HindIII-F fragment of vaccinia virus DNA strain LIVP.

The heterologous nucleic acid can include regulatory sequences operatively linked to the nucleic acid encoding the protein. Regulatory sequences include promoters, such as the vaccinia virus early/late promoter p7.5 and an early/late vaccinia pE/L promoter. The heterologous nucleic acid in the microorganism can encode a detectable protein or a product capable of inducing a detectable signal. Inclusion of detectable protein or a product that can generate a detectable signal permits monitoring of the distribution of the administered microorganism as well as monitoring therapeutic efficacy, since the microorganism will be eliminated when the immunoprivileged cells are eliminated.

Host cells containing the recombinant viruses, such as the triple mutant vaccinia virus exemplified herein are provided. Also contemplated are tumor cells that contain any of the microorganisms provided herein or used in the methods.

Pharmaceutical compositions containing the microorganisms in a pharmaceutically acceptable vehicle for use in the methods herein are provided. The pharmaceutical compositions can be formulated for any mode of administration, including, but not limited to systemic administration, such as for intravenous administration or is formulated. The compositions can contain a delivery vehicle, such as a lipid-based carrier, including liposomes and micelles associated with the microorganism.

Also provided are methods (and uses of the microorganisms) for eliminating immunoprivileged cells, such as tumor cells in an animal, by administering the pharmaceutical compositions to an animal, whereby the virus accumulates in the immunoprivileged cells, thereby mediating autoimmunization resulting in elimination of the cells or a reduction in their number.

Therapeutic methods for eliminating immunoprivileged cells or tissues, in an animal, by administering a microorganism to an animal, where the microorganism accumulates in the immunoprivileged cells; the microorganism does not accumulate in unaffected organs and tissues and has low toxicity in the animal; and the microorganism results in leakage of the cell membranes in the immunoprivileged cells, whereby the animal produces autoantibodies against the cells or products of the cells are provided. These methods include tumor treatment, treatment for inflammatory conditions, including wounds, and proliferative disorders, including psoriasis, cancers, diabetic retinopathies, restenosis and other such disorders. It is desirable for the microorganisms to not accumulate in unaffected organs, particularly the ovaries or testes.

The microorganisms attenuated include attenuated viruses, such as pox viruses and other cytoplasmic viruses, bacteria such as *vibrio, E. coli, salmonella, streptococcus* and *listeria*, and mammalian cells, such as immune cells, including B cells and lymphocytes, such as T cells, and stem cells.

Also provided are methods for production of a polypeptide or RNA or compound, such as a cellular product, and uses of the microorganism therefore are provided. Such methods can include the steps of: (a) administering a microorganism containing nucleic acid encoding the polypeptide or RNA or producing the product compound to tumor-bearing animal, where the microorganism accumulates in the immunoprivileged cells; and the microorganism does not accumulate to toxic levels in organs and tissues that do not comprise immunoprivileged cells or tissues; (b) harvesting the tumor tissue from the animal; and (c) isolating the polypeptide or RNA or compound from the tumor.

As noted, the microorganisms include eukaryotic cells, prokaryotic cells and viruses, such as a cytoplasmic virus or an attenuated bacterium or a stem cell or an immune cell. The bacterium can be selected from among attenuated *vibrio, E. coli, listeria, salmonella* and *streptococcus* strains. The microorganism can express or produce detectable products, such as a fluorescent protein (i.e., green, red and blue fluorescent proteins and modified variants thereof), and/or luciferase which, when contacted with a luciferin produces light, and also can encode additional products, such as therapeutic products. In the methods and uses provided herein, the animals can be non-human animals or can include humans.

Also provided are methods for simultaneously producing a polypeptide, RNA molecule or cellular compound and an antibody that specifically reacts with the polypeptide, RNA molecule or compound, by: a) administering a microorganism to a tumor-bearing animal, wherein the microorganism expresses or produces the compound, polypeptide or RNA molecule; and b) isolating the antibody from serum in the animal. The method optionally includes, after step a) harvesting the tumor tissue from the animal; and isolating the polypeptide, RNA molecule or cellular compound from the tumor tissue.

Also provided are methods for eliminating immunoprivileged cells or tissues in an animal, such as tumor cells, and uses of the microorganisms therefore by administering at least two microorganisms, wherein the microorganisms are administered simultaneously, sequentially or intermittently, wherein the microorganisms accumulate in the immunoprivileged cells, whereby the animal is autoimmunized against the immunoprivileged cells or tissues.

Uses of at least two microorganisms for formulation of a medicament for elimination of immunoprivileged cells or tissues, wherein they accumulate in the immunoprivileged cells, whereby the animal is autoimmunized against the immunoprivileged cells or tissues are provided. Combinations containing at least two microorganisms formulated for administration to an animal for elimination of immunoprivileged cells or tissues are provided. Kits containing packaged combination optionally with instructions for administration and other reagents are provided.

Uses of a microorganism encoding heterologous nucleic acid for inducing autoimmunization against products produced in immunoprivileged cells, wherein, when administered, the microorganism accumulates in immunoprivileged tissues and does not accumulate or accumulates at a sufficiently low level in other tissues or organs to be non-toxic to an animal containing the immunoprivileged tissues are provided.

Methods for the production of antibodies against products produced in immunoprivileged tissues or cells by: (a) administering a microorganism containing nucleic acid encoding a selected protein or RNA into an animal containing the immunoprivileged tissues or cells; and (b) isolating antibodies against the protein or RNA from the blood or serum of the animal are provided.

Also provided are methods for inhibiting growth of immunoprivileged cells or tissue in a subject by: (a) administering to a subject a modified microorganism, wherein the modified microorganism encodes a detectable gene product; (b) monitoring the presence of the detectable gene product in the subject until the detectable gene product is substantially present only in immunoprivileged tissue or cells of a subject; and (c) administering to a subject a therapeutic compound that works in conjunction with the microorganism to inhibit growth of immunoprivileged cells or tissue or by: (a) administering to a subject a modified microorganism that encodes a detectable gene product; (b) administering to a subject a therapeutic substance that reduces the pathogenicity of the microorganism; (c) monitoring the presence of the detectable gene product in the subject until the detectable gene product is substantially present only in immunoprivileged tissue or cells of a subject; and (d) terminating or suspending administration of the therapeutic compound, whereby the microorganism increases in pathogenicity and the growth of the immunoprivileged cells or tissue is inhibited.

DETAILED DESCRIPTION

Figure 1:
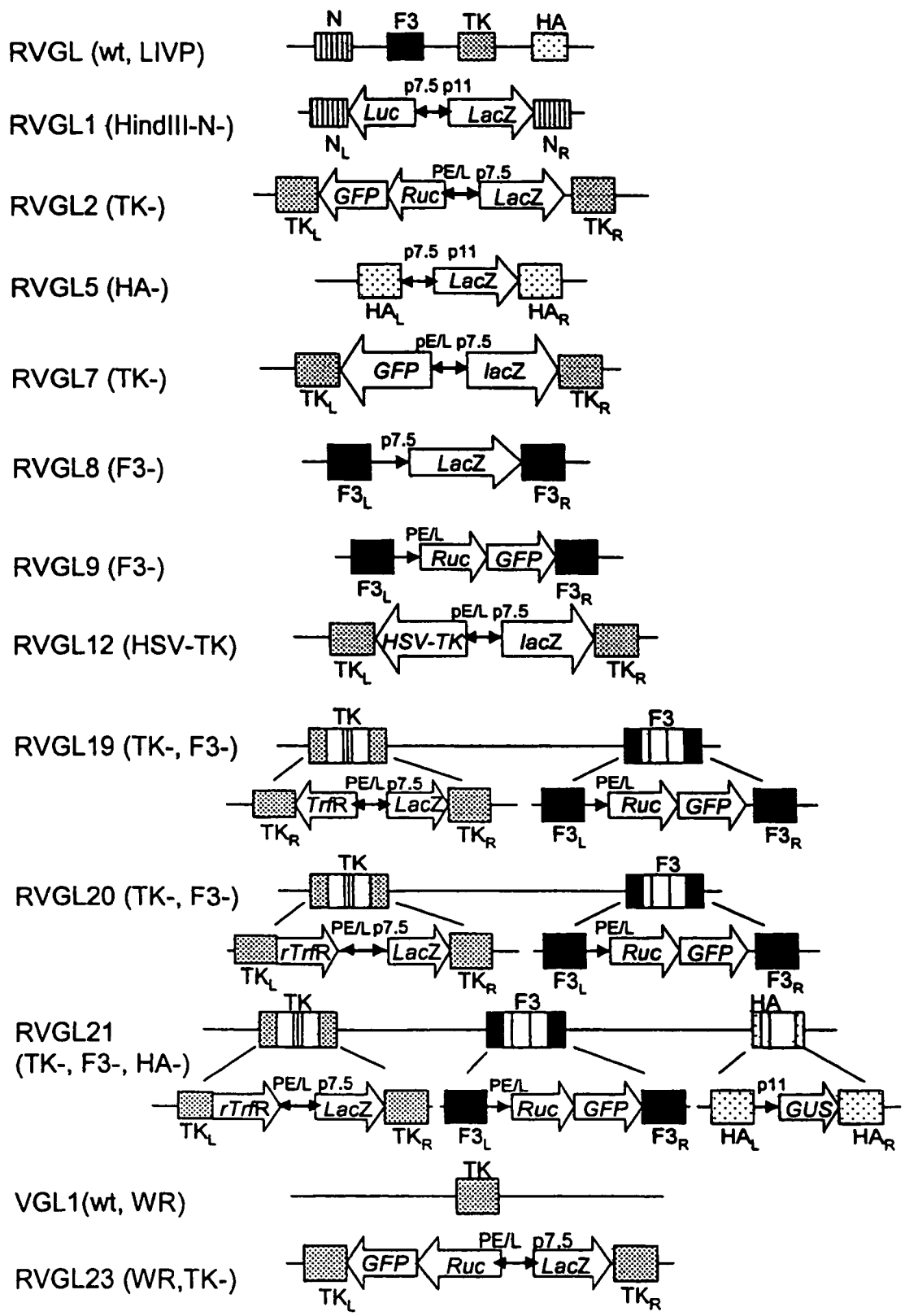
FIG. 1: Schematic of the various vaccinia strains described in the Examples. Results achieved with the viruses are described in the Examples.

A. Definitions
B. Microorganisms for Tumor-Specific Therapy
   1. Characteristics
      a. Attenuated
         i. Reduced toxicity
         ii. Accumulate in immunoprivileged cells and tissues, such as tumor, not substantially in other organs
         iii. Ability to Elicit or Enhance Immune Response to Tumor Cells
         iv. Balance of Pathogenicity and Release of Tumor Antigens
      b. Immunogenicity
      c. Replication Competent
      d. Genetic Variants
         i. Modified Characteristics
         ii. Exogenous Gene Expression
         iii. Detectable gene product
         iv. Therapeutic gene product
         v. Expressing a superantigen
         vi. Expressing a gene product to be harvested
   2. Viruses
      a. Cytoplasmic viruses
         i. Poxviruses
            a. Vaccinia Virus
            b. Modified Vaccinia Viruses c. The F3 Gene
            d. Multiple Modifications
            e. The Lister Strain
         ii. Other cytoplasmic viruses
      b. Adenovirus, Herpes, Retroviruses
   3. Bacteria
      a. Aerobic bacteria
      b. Anaerobic bacteria
   4. Eukaryotic cells
C. Methods for Making a Modified Microorganism
   1. Genetic Modifications
   2. Screening for above characteristics
D. Therapeutic Methods
   1. Administration
      a. Steps prior to administering the microorganism
      b. Mode of administration
      c. Dosage
      d. Number of administrations
      e. Co-administrations
         i. Administering a plurality of microorganisms
         ii. Therapeutic compounds
      f. State of subject
   2. Monitoring
      a. Monitoring microorganismal gene expression
      b. Monitoring tumor size
      c. Monitoring antibody titer
      d. Monitoring general health diagnostics
      e. Monitoring coordinated with treatment
E. Methods of Producing Gene Products and Antibodies
   1. Production of Recombinant Proteins and RNA molecules
   2. Production of Antibodies
F. Pharmaceutical Compositions, combinations and kits
   1. Pharmaceutical Compositions
   2. Host Cells
   3. Combinations
   4. Kits
G. Examples

A. DEFINITIONS

Unless defined otherwise, all technical and scientific terms used herein have the same meaning as is commonly understood by one of skill in the art to which the invention(s) belong. All patents, patent applications, published applications and publications, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information.

As used herein, microorganisms refers to isolated cells or viruses, including eukaryotic cells, such as mammalian cells, viruses and bacteria. The microorganisms are modified or selected for their ability to accumulate in tumors and other immunoprivileged cells and tissues, and to minimize accumulation in other tissues or organs. Accumulation occurs by virtue of selection or modification of the microorganisms for particular traits or by proper selection of cells. The microorganism can be further modified to alter a trait thereof and/or to deliver a gene product. The microorganisms provided herein are typically modified relative to wild type to exhibit one or more characteristics such as reduced pathogenicity, reduced toxicity, preferential accumulation in tumors relative to normal organs or tissues, increased immunogenicity, increased ability to elicit or enhance an immune response to tumor cells, increased lytic or tumor cell killing capacity, decreased lytic or tumor cell killing capacity.

As used herein, immunoprivileged cells and tissues refer to cells and tissues, such as solid tumors and wounded tissues, which are sequestered from the immune system. Generally administration of a microorganism elicits an immune response that clears the microorganism; immunoprivileged sites, however, are shielded or sequestered from the immune response, permitting the microorganisms to survive and generally to replicate. Immunoprivileged tissues include inflamed tissues, such as wounded tissues, and proliferating tissues, such as tumor tissues.

As used herein, "modified" with reference to a gene refers to a deleted gene, or a gene encoding a gene product having one or more truncations, mutations, insertions or deletions, typically accompanied by at least a change, generally a partial loss of function.

As used herein F3 gene refers to a gene or locus in a virus, such as a vaccinia virus, that corresponds to the F3 gene of vaccinia virus strain LIVP. This includes the F3 gene of any vaccinia virus strain or poxvirus encoding a gene product having substantially the same or at least a related biological function or locus in the genome. F3 genes encompassed herein typically have at least about 40%, at least about 50%, at least about 60%, at least about 70%, at least about 80%, at least about 85%, at least about 90%, at least about 93%, at least about 95%, at least about 96%, at least about 97%, at least about 98%, or at least about 99% identity along the full length of the sequence of nucleotides set forth in SEQ ID NO:1. The proteins encoded by F3 genes encompassed herein typically have at least about 50%, at least about 60%, at least about 65%, at least about 70%, at least about 75%, at least about 85%, at least about 90%, at least about 93%, at least about 95%, at least about 96%, at least about 97%, at least about 98%, or at least about 99% identity to the sequence of amino acids set forth SEQ ID NO:2 along the full-length sequence thereof. Also included are corresponding loci in other viruses that when modified or eliminated result in reduced toxicity and/or enhanced accumulation in tumors (compared to non-tumorous cells, tissues and organs). The corresponding loci in other viruses equivalent to the F3 gene in LIVP can be determined by the structural location of the gene in the viral genome: the LIVP F3 gene is located on the HindIII-F fragment of vaccinia virus between open reading frames F14L and F15L as defined by Goebel et al., Virology (1990) 179:247-266, and in the opposite orientation of ORFs F14L and F15L; thus corresponding loci in other viruses such as poxviruses including orthopoxviruses are included.

As used herein, attenuate toxicity of a microorganism means to reduce or eliminate deleterious or toxic effects to a host upon administration of the microorganism compared to the unattenuated microorganism.

As use herein, a microorganism with low toxicity means that upon administration a microorganism does not accumulate in organs and tissues in the host to an extent that results in damage or harm to organs or that impact on survival of the host to a greater extent than the disease being treated does.

As used herein, subject (or organism) refers to an animal, including a human being.

As used herein, animal includes any animal, such as, but are not limited to primates including humans, gorillas and monkeys; rodents, such as mice and rats; fowl, such as chickens; ruminants, such as goats, cows, deer, sheep; ovine, and other animals including pigs, horses, cats, dogs, and rabbits. Non-human animals exclude humans as the contemplated animal.

As used herein, accumulation of a microorganism in a targeted tissue refers to the distribution of the microorganism throughout the organism after a time period long enough for the microbes to infect the host's organs or tissues. As one skilled in the art will recognize, the time period for infection of a microbe will vary depending on the microbe, the targeted organ(s) or tissue(s), the immunocompetence of the host, and dosage. Generally, accumulation can be determined at timepoints from about 1 day to about 1 week after infection with the microbes. For purposes herein, the microorganisms preferentially accumulate in the target tissue, such as a tumor, but are cleared from other tissues and organs in the host to the extent that toxicity of the microorganism is mild or tolerable and at most not fatal.

As used herein, preferential accumulation refers to accumulation of a microorganism at a first location at a higher level than accumulation at a second location. Thus, a microorganism that preferentially accumulates in immunoprivileged tissue such as tumor relative to normal tissues or organs refers to a microorganism that accumulates in immunoprivileged tissue such as tumor at a higher level than the microorganism accumulates in normal tissues or organs.

As used herein, a "compound" produced in a tumor or other immunoprivileged site refers to any compound that is produced in the tumor by virtue of the presence of an introduced microorganism, generally a recombinant microorganism, expressing one or more genes. For example, a compound produced in a tumor can be, for example, a metabolite, an encoded polypeptide or RNA, or compound that is generated by a recombinant polypeptide (e.g., enzyme) and the cellular machinery of the tumor or immunoprivileged tissue or cells.

As used herein, a delivery vehicle for administration refers to a lipid-based or other polymer-based composition, such as liposome, micelle or reverse micelle, that associates with an agent, such as a microorganism provided herein, for delivery into a host animal.

As used herein, the term "viral vector" is used according to its art-recognized meaning. It refers to a nucleic acid vector construct that includes at least one element of viral origin and can be packaged into a viral vector particle. The viral vector particles can be used for the purpose of transferring DNA, RNA or other nucleic acids into cells either in vitro or in vivo. Viral vectors include, but are not limited to, retroviral vectors, vaccinia vectors, lentiviral vectors, herpes virus vectors (e.g., HSV), baculoviral vectors, cytomegalovirus (CMV) vectors, papillomavirus vectors, simian virus (SV40) vectors, semliki forest virus vectors, phage vectors, adenoviral vectors, and adeno-associated viral (AAV) vectors.

As used herein, oncolytic viruses refer to viruses that replicate selectively in tumor cells.

As used herein, "disease or disorder" refers to a pathological condition in an organism resulting from, e.g., infection or genetic defect, and characterized by identifiable symptoms.

As used herein, neoplasm (neoplasia) refers to abnormal new growth, and thus means the same as tumor, which can be benign or malignant. Unlike hyperplasia, neoplastic proliferation persists even in the absence of the original stimulus.

As used herein, neoplastic disease refers to any disorder involving cancer, including tumor development, growth, metastasis and progression.

As used herein, cancer is a general term for diseases caused by or characterized by any type of malignant tumor.

As used herein, malignant, as applies to tumors, refers to primary tumors that have the capacity of metastasis with loss of growth control and positional control.

As used herein, metastasis refers to a growth of abnormal or neoplastic cells distant from the site primarily involved by the morbid process.

As used herein, an anti-cancer agent or compound (used interchangeably with "anti-tumor or anti-neoplastic agent") refers to any agents or compounds used in anti-cancer treatment. These include any agents, when used alone or in combination with other compounds, that can alleviate, reduce, ameliorate, prevent, or place or maintain in a state of remission of clinical symptoms or diagnostic markers associated with neoplastic disease, tumors and cancer, and can be used in methods, combinations and compositions provided herein. Exemplary anti-neoplastic agents include the microorganism provided herein used singly or in combination and/or in combination with other agents, such as alkylating agents, antimetabolite, certain natural products, platinum coordination complexes, anthracenediones, substituted ureas, methylhydrazine derivatives, adrenocortical suppressants, certain hormones, antagonists and anti-cancer polysaccharides.

In general, for practice of the methods herein and when using the microorganisms provided herein, the original tumor is not excised, but is employed to accumulate the administered microorganism and as the cells become leaky or lyse to become an antigen or other product factor. The antigens can serve to elicit an immune response in the host. The antigens and products can be isolated from the tumor.

As used herein, angiogenesis is intended to encompass the totality of processes directly or indirectly involved in the establishment and maintenance of new vasculature (neovascularization), including, but not limited to, neovascularization associated with tumors and neovascularization associated with wounds.

As used herein, by homologous means about greater than 25% nucleic acid sequence identity, such as 25%, 40%, 60%, 70%, 80%, 90% or 95%. If necessary the percentage homology will be specified. The terms "homology" and "identity" are often used interchangeably but homology for proteins can include conservative amino acid changes. In general, sequences (protein or nucleic acid) are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carillo et al. (1988) SIAM J Applied Math 48:1073). By sequence identity, the number of identical amino acids is determined by standard alignment algorithm programs, and used with default gap penalties established by each supplier. Substantially homologous nucleic acid molecules would hybridize typically at moderate stringency or at high stringency all along the length of the nucleic acid or along at least about 70%, 80% or 90% of the full length nucleic acid molecule of interest. Also provided are nucleic acid molecules that contain degenerate codons in place of codons in the hybridizing nucleic acid molecule. (For proteins, for determination of homology conservative amino acids can be aligned as well as identical amino acids; in this case percentage of identity and percentage homology vary). Whether any two nucleic acid molecules have nucleotide sequences that are at least 80%, 85%, 90%, 95%, 96%, 97%, 98% or 99% "identical" can be determined using known computer algorithms such as the "FASTA" program, using for example, the default parameters as in Pearson et al. (1988)

Proc. Natl. Acad. Sci. USA 85:2444 (other programs include the GCG program package (Devereux, J., et al., Nucleic Acids Research 12(I):387 (1984)), BLASTP, BLASTN, FASTA Atschul, S. F., et al., J Molec Biol 215:403 (1990); Guide to Huge Computers, Mrtin J. Bishop, ed., Academic Press, San Diego, 1994, and Carillo et al. (1988) SIAM J Applied Math 48:1073). For example, the BLAST function of the National Center for Biotechnology Information database can be used to determine identity. Other commercially or publicly available programs include, DNAStar "MegAlign" program (Madison, Wis.) and the University of Wisconsin Genetics Computer Group (UWG) "Gap" program (Madison Wis.)). Percent homology or identity of proteins and/or nucleic acid molecules can be determined, for example, by comparing sequence information using a GAP computer program (e.g., Needleman et al. (1970) J. Mol. Biol. 48:443, as revised by Smith and Waterman ((1981) Adv. Appl. Math. 2:482).

Briefly, a GAP program defines similarity as the number of aligned symbols (i.e., nucleotides or amino acids) that are similar, divided by the total number of symbols in the shorter of the two sequences. Default parameters for the GAP program can include: (1) a unary comparison matrix (containing a value of 1 for identities and 0 for non-identities) and the weighted comparison matrix of Gribskov et al. (1986) Nucl. Acids Res. 14:6745, as described by Schwartz and Dayhoff, eds., ATLAS OF PROTEIN SEQUENCE AND STRUCTURE, National Biomedical Research Foundation, pp. 353-358 (1979); (2) a penalty of 3.0 for each gap and an additional 0.10 penalty for each symbol in each gap; and (3) no penalty for end gaps. Therefore, as used herein, the term "identity" represents a comparison between a test and a reference polypeptide or polynucleotide.

As used herein, recitation that amino acids of a polypeptide correspond to amino acids in a disclosed sequence, such as amino acids set forth in the Sequence listing, refers to amino acids identified upon alignment of the polypeptide with the disclosed sequence to maximize identity or homology (where conserved amino acids are aligned) using a standard alignment algorithm, such as the GAP algorithm.

As used herein, the term "at least 90% identical to" refers to percent identities from 90 to 100% relative to the reference polypeptides. Identity at a level of 90% or more is indicative of the fact that, assuming for exemplification purposes a test and reference polynucleotide length of 100 amino acids are compared, no more than 10% (i.e., 10 out of 100) of amino acids in the test polypeptide differs from that of the reference polypeptides. Similar comparisons can be made between a test and reference polynucleotides. Such differences can be represented as point mutations randomly distributed over the entire length of an amino acid sequence or they can be clustered in one or more locations of varying length up to the maximum allowable, e.g., 10/100 amino acid difference (approximately 90% identity). Differences are defined as nucleic acid or amino acid substitutions, insertions or deletions. At the level of homologies or identities above about 85-90%, the result should be independent of the program and gap parameters set; such high levels of identity can be assessed readily, often without relying on software.

As used herein, primer refers to an oligonucleotide containing two or more deoxyribonucleotides or ribonucleotides, typically more than three, from which synthesis of a primer extension product can be initiated. Experimental conditions conducive to synthesis include the presence of nucleoside triphosphates and an agent for polymerization and extension, such as DNA polymerase, and a suitable buffer, temperature and pH.

As used herein, chemiluminescence refers to a chemical reaction in which energy is specifically channeled to a molecule causing it to become electronically excited and subsequently to release a photon thereby emitting visible light. Temperature does not contribute to this channeled energy. Thus, chemiluminescence involves the direct conversion of chemical energy to light energy.

As used herein, luminescence refers to the detectable EM radiation, generally, UV, IR or visible EM radiation that is produced when the excited product of an exergic chemical process reverts to its ground state with the emission of light. Chemiluminescence is luminescence that results from a chemical reaction. Bioluminescence is chemiluminescence that results from a chemical reaction using biological molecules (or synthetic versions or analogs thereof) as substrates and/or enzymes.

As used herein, bioluminescence, which is a type of chemiluminescence, refers to the emission of light by biological molecules, particularly proteins. The essential condition for bioluminescence is molecular oxygen, either bound or free in the presence of an oxygenase, a luciferase, which acts on a substrate, a luciferin. Bioluminescence is generated by an enzyme or other protein (luciferase) that is an oxygenase that acts on a substrate luciferin (a bioluminescence substrate) in the presence of molecular oxygen, and transforms the substrate to an excited state, which, upon return to a lower energy level releases the energy in the form of light.

As used herein, the substrates and enzymes for producing bioluminescence are generically referred to as luciferin and luciferase, respectively. When reference is made to a particular species thereof, for clarity, each generic term is used with the name of the organism from which it derives, for example, bacterial luciferin or firefly luciferase.

As used herein, luciferase refers to oxygenases that catalyze a light emitting reaction. For instance, bacterial luciferases catalyze the oxidation of flavin mononucleotide (FMN) and aliphatic aldehydes, which reaction produces light. Another class of luciferases, found among marine arthropods, catalyzes the oxidation of Cypridina (Vargula) luciferin, and another class of luciferases catalyzes the oxidation of Coleoptera luciferin.

Thus, luciferase refers to an enzyme or photoprotein that catalyzes a bioluminescent reaction (a reaction that produces bioluminescence). The luciferases, such as firefly and Gaussia and *Renilla* luciferases, are enzymes which act catalytically and are unchanged during the bioluminescence generating reaction. The luciferase photoproteins, such as the aequorin photoprotein to which luciferin is non-covalently bound, are changed, such as by release of the luciferin, during bioluminescence generating reaction. The luciferase is a protein that occurs naturally in an organism or a variant or mutant thereof, such as a variant produced by mutagenesis that has one or more properties, such as thermal stability, that differ from the naturally-occurring protein. Luciferases and modified mutant or variant forms thereof are well known. For purposes herein, reference to luciferase refers to either the photoproteins or luciferases.

Thus, reference, for example, to "*Renilla* luciferase" means an enzyme isolated from member of the genus *Renilla* or an equivalent molecule obtained from any other source, such as from another related copepod, or that has been prepared synthetically. It is intended to encompass *Renilla* luciferases with conservative amino acid substitutions that do not substantially alter activity. Suitable conservative substitutions of amino acids are known to those of skill in this art and can be made generally without altering the biological activity of the resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. co., p. 224).

As used herein, "*Aequorea* GFP" refers to GFPs from the genus *Aequorea* and to mutants or variants thereof. Such variants and GFPs from other species are well known and are available and known to those of skill in the art. This nomenclature encompass GFPs with conservative amino acid substitutions that do not substantially alter activity and physical properties, such as the emission spectra and ability to shift the spectral output of bioluminescence generating systems. The luciferases and luciferin and activators thereof are referred to as bioluminescence generating reagents or components. Typically, a subset of these reagents will be provided or combined with an article of manufacture. Bioluminescence will be produced upon contacting the combination with the remaining reagents. Thus, as used herein, the component luciferases, luciferins, and other factors, such as $O_2$, $Mg^{2+}$, $Ca^{2+}$ also are referred to as bioluminescence generating reagents (or agents or components).

As used herein, bioluminescence substrate refers to the compound that is oxidized in the presence of a luciferase, and any necessary activators, and generates light. These substrates are referred to as luciferins herein, are substrates that undergo oxidation in a bioluminescence reaction. These bioluminescence substrates include any luciferin or analog thereof or any synthetic compound with which a luciferase interacts to generate light. Typical substrates include those that are oxidized in the presence of a luciferase or protein in a light-generating reaction. Bioluminescence substrates, thus, include those compounds that those of skill in the art recognize as luciferins. Luciferins, for example, include firefly luciferin, Cypridina (also known as Vargula) luciferin (coelenterazine), bacterial luciferin, as well as synthetic analogs of these substrates or other compounds that are oxidized in the presence of a luciferase in a reaction the produces bioluminescence.

As used herein, capable of conversion into a bioluminescence substrate means susceptible to chemical reaction, such as oxidation or reduction, that yields a bioluminescence substrate. For example, the luminescence producing reaction of bioluminescent bacteria involves the reduction of a flavin mononucleotide group (FMN) to reduced flavin mononucleotide (FMNH2) by a flavin reductase enzyme. The reduced flavin mononucleotide (substrate) then reacts with oxygen (an activator) and bacterial luciferase to form an intermediate peroxy flavin that undergoes further reaction, in the presence of a long-chain aldehyde, to generate light. With respect to this reaction, the reduced flavin and the long chain aldehyde are substrates.

As used herein, a bioluminescence generating system refers to the set of reagents required to conduct a bioluminescent reaction. Thus, the specific luciferase, luciferin and other substrates, solvents and other reagents that can be required to complete a bioluminescent reaction from a bioluminescence system. Thus a bioluminescence generating system refers to any set of reagents that, under appropriate reaction conditions, yield bioluminescence. Appropriate reaction conditions refers to the conditions necessary for a bioluminescence reaction to occur, such as pH, salt concentrations and temperature. In general, bioluminescence systems include a bioluminescence substrate, luciferin, a luciferase, which includes enzymes, luciferases and photoproteins, and one or more activators. A specific bioluminescence system may be identified by reference to the specific organism from which the luciferase derives; for example, the *Renilla* bioluminescence system includes a *Renilla* luciferase, such as a luciferase isolated from the *Renilla* or produced using recombinant means or modifications of these luciferases. This system also includes the particular activators necessary to complete the bioluminescence reaction, such as oxygen and a substrate with which the luciferase reacts in the presence of the oxygen to produce light.

As used herein, a fluorescent protein refers to a protein that possesses the ability to fluoresce (i.e., to absorb energy at one wavelength and emit it at another wavelength). For example, a green fluorescent protein refers to a polypeptide that has a peak in the emission spectrum at about 510 nm.

As used herein, genetic therapy or gene therapy involves the transfer of heterologous nucleic acid, such as DNA, into certain cells, target cells, of a mammal, particularly a human, with a disorder or conditions for which such therapy is sought. The nucleic acid, such as DNA, is introduced into the selected target cells, such as directly or in a vector or other delivery vehicle, in a manner such that the heterologous nucleic acid, such as DNA, is expressed and a therapeutic product encoded thereby is produced. Alternatively, the heterologous nucleic acid, such as DNA, can in some manner mediate expression of DNA that encodes the therapeutic product, or it can encode a product, such as a peptide or RNA that in some manner mediates, directly or indirectly, expression of a therapeutic product. Genetic therapy also can be used to deliver nucleic acid encoding a gene product that replaces a defective gene or supplements a gene product produced by the mammal or the cell in which it is introduced. The introduced nucleic acid can encode a therapeutic compound, such as a growth factor inhibitor thereof, or a tumor necrosis factor or inhibitor thereof, such as a receptor therefor, that is not normally produced in the mammalian host or that is not produced in therapeutically effective amounts or at a therapeutically useful time. The heterologous nucleic acid, such as DNA, encoding the therapeutic product can be modified prior to introduction into the cells of the afflicted host in order to enhance or otherwise alter the product or expression thereof. Genetic therapy also can involve delivery of an inhibitor or repressor or other modulator of gene expression.

As used herein, heterologous nucleic acid is nucleic acid that is not normally produced in vivo by the microorganism from which it is expressed or that is produced by a microorganism but is at a different locus or expressed differently or that mediates or encodes mediators that alter expression of endogenous nucleic acid, such as DNA, by affecting transcription, translation, or other regulatable biochemical processes. Heterologous nucleic acid is often not endogenous to the cell into which it is introduced, but has been obtained from another cell or prepared synthetically. Heterologous nucleic acid, however, can be endogenous, but is nucleic acid that is expressed from a different locus or altered in its expression or sequence. Generally, although not necessarily, such nucleic acid encodes RNA and proteins that are not normally produced by the cell or in the same way in the cell in which it is expressed. Heterologous nucleic acid, such as DNA, also can be referred to as foreign nucleic acid, such as DNA. Thus, heterologous nucleic acid or foreign nucleic acid includes a nucleic acid molecule not present in the exact orientation or position as the counterpart nucleic acid molecule, such as DNA, is found in a genome. It also can refer to a nucleic acid molecule from another organism or species (i.e., exogenous). Any nucleic acid, such as DNA, that one of skill in the art would recognize or consider as heterologous or foreign to the cell in which the nucleic acid is expressed is herein encompassed by heterologous nucleic acid; heterologous nucleic acid includes exogenously added nucleic acid that also is expressed endogenously. Examples of heterologous nucleic acid include, but are not limited to, nucleic acid that encodes traceable marker proteins, such as a protein that confers drug resistance, nucleic acid that encodes therapeutically effective substances, such as anti-cancer agents, enzymes and hormones, and nucleic acid, such as DNA, that encodes other types of proteins, such as antibodies. Antibodies that are encoded by heterologous nucleic acid can be secreted or expressed on the surface of the cell in which the heterologous nucleic acid has been introduced.

As used herein, a therapeutically effective product for gene therapy is a product that is encoded by heterologous nucleic acid, typically DNA, (or an RNA product such as dsRNA, RNAi, including siRNA, that, upon introduction of the nucleic acid into a host, a product is expressed that ameliorates or eliminates the symptoms, manifestations of an inherited or acquired disease or that cures the disease. Also included are biologically active nucleic acid molecules, such as RNAi and antisense.

As used herein, cancer or tumor treatment or agent refers to any therapeutic regimen and/or compound that, when used alone or in combination with other treatments or compounds, can alleviate, reduce, ameliorate, prevent, or place or maintain in a state of remission of clinical symptoms or diagnostic markers associated with deficient angiogenesis.

As used herein, nucleic acids include DNA, RNA and analogs thereof, including peptide nucleic acids (PNA) and mixtures thereof. Nucleic acids can be single or double-stranded. When referring to probes or primers, which are optionally labeled, such as with a detectable label, such as a fluorescent or radiolabel, single-stranded molecules are provided. Such molecules are typically of a length such that their target is statistically unique or of low copy number (typically less than 5, generally less than 3) for probing or priming a library. Generally a probe or primer contains at least 14, 16 or 30 contiguous nucleotides of sequence complementary to or identical to a gene of interest. Probes and primers can be 10, 20, 30, 50, 100 or more nucleic acids long.

As used herein, operative linkage of heterologous nucleic acids to regulatory and effector sequences of nucleotides, such as promoters, enhancers, transcriptional and translational stop sites, and other signal sequences refers to the relationship between such nucleic acid, such as DNA, and such sequences of nucleotides. For example, operative linkage of heterologous DNA to a promoter refers to the physical relationship between the DNA and the promoter such that the transcription of such DNA is initiated from the promoter by an RNA polymerase that specifically recognizes, binds to and transcribes the DNA. Thus, operatively linked or operationally associated refers to the functional relationship of nucleic acid, such as DNA, with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it can be necessary to remove, add or alter 5' untranslated portions of the clones to eliminate extra, potentially inappropriate alternative translation initiation (i.e., start) codons or other sequences that can interfere with or reduce expression, either at the level of transcription or translation. Alternatively, consensus ribosome binding sites (see, e.g., Kozak J. Biol. Chem. 266:19867-19870 (1991)) can be inserted immediately 5' of the start codon and can enhance expression. The desirability of (or need for) such modification can be empirically determined.

As used herein, a sequence complementary to at least a portion of an RNA, with reference to antisense oligonucleotides, means a sequence of nucleotides having sufficient complementarity to be able to hybridize with the RNA, generally under moderate or high stringency conditions, forming a stable duplex; in the case of double-stranded antisense nucleic acids, a single strand of the duplex DNA (or dsRNA) can thus be tested, or triplex formation can be assayed. The ability to hybridize depends on the degree of complementarity and the length of the antisense nucleic acid. Generally, the longer the hybridizing nucleic acid, the more base mismatches with an encoding RNA it can contain and still form a stable duplex (or triplex, as the case can be). One skilled in the art can ascertain a tolerable degree of mismatch by use of standard procedures to determine the melting point of the hybridized complex.

As used herein, amelioration of the symptoms of a particular disorder such as by administration of a particular pharmaceutical composition, refers to any lessening, whether permanent or temporary, lasting or transient that can be attributed to or associated with administration of the composition.

As used herein, antisense polynucleotides refer to synthetic sequences of nucleotide bases complementary to mRNA or the sense strand of double-stranded DNA. A mixture of sense and antisense polynucleotides under appropriate conditions leads to the binding of the two molecules, or hybridization. When these polynucleotides bind to (hybridize with) mRNA, inhibition of protein synthesis (translation) occurs. When these polynucleotides bind to double-stranded DNA, inhibition of RNA synthesis (transcription) occurs. The resulting inhibition of translation and/or transcription leads to an inhibition of the synthesis of the protein encoded by the sense strand. Antisense nucleic acid molecules typically contain a sufficient number of nucleotides to specifically bind to a target nucleic acid, generally at least 5 contiguous nucleotides, often at least 14 or 16 or 30 contiguous nucleotides or modified nucleotides complementary to the coding portion of a nucleic acid molecule that encodes a gene of interest.

As used herein, antibody refers to an immunoglobulin, whether natural or partially or wholly synthetically produced, including any derivative thereof that retains the specific binding ability of the antibody. Hence antibody includes any protein having a binding domain that is homologous or substantially homologous to an immunoglobulin binding domain. Antibodies include members of any immunoglobulin class, including IgG, IgM, IgA, IgD and IgE.

As used herein, antibody fragment refers to any derivative of an antibody that is less then full length, retaining at least a portion of the full-length antibody's specific binding ability. Examples of antibody fragments include, but are not limited to, Fab, Fab', F(ab)$_2$, single-chain Fvs (scFV), FV, dsFV diabody and Fd fragments. The fragment can include multiple chains linked together, such as by disulfide bridges. An antibody fragment generally contains at least about 50 amino acids and typically at least 200 amino acids.

As used herein, a Fv antibody fragment is composed of one variable heavy chain domain ($V_H$) and one variable light chain domain linked by noncovalent interactions.

As used herein, a dsFV refers to an Fv with an engineered intermolecular disulfide bond, which stabilizes the $V_H$-$V_L$ pair.

As used herein, a F(ab)2 fragment is an antibody fragment that results from digestion of an immunoglobulin with pepsin at pH 4.0-4.5; it can be recombinantly produced to produce the equivalent fragment.

As used herein, Fab fragments are antibody fragments that result from digestion of an immunoglobulin with papain; it can be recombinantly produced to produce the equivalent fragment.

As used herein, scFVs refer to antibody fragments that contain a variable light chain ($V_L$) and variable heavy chain ($V_H$) covalently connected by a polypeptide linker in any order. The linker is of a length such that the two variable domains are bridged without substantial interference. Included linkers are (Gly-Ser)n residues with some Glu or Lys residues dispersed throughout to increase solubility.

As used herein, humanized antibodies refer to antibodies that are modified to include human sequences of amino acids so that administration to a human does not provoke an immune response. Methods for preparation of such antibodies are known. For example, to produce such antibodies, the encoding nucleic acid in the hybridoma or other prokaryotic or eukaryotic cell, such as an E. coli or a CHO cell, that expresses the monoclonal antibody is altered by recombinant nucleic acid techniques to express an antibody in which the amino acid composition of the non-variable region is based on human antibodies. Computer programs have been designed to identify such non-variable regions.

As used herein, diabodies are dimeric scFV; diabodies typically have shorter peptide linkers than scFvs, and they generally dimerize.

As used herein, production by recombinant means by using recombinant DNA methods means the use of the well known methods of molecular biology for expressing proteins encoded by cloned DNA.

As used herein the term assessing or determining is intended to include quantitative and qualitative determination in the sense of obtaining an absolute value for the activity of a product, and also of obtaining an index, ratio, percentage, visual or other value indicative of the level of the activity. Assessment can be direct or indirect.

As used herein, biological activity refers to the in vivo activities of a compound or microorganisms or physiological responses that result upon in vivo administration thereof or of composition or other mixture. Biological activity, thus, encompasses therapeutic effects and pharmaceutical activity of such compounds, compositions and mixtures. Biological activities can be observed in in vitro systems designed to test or use such activities.

As used herein, an effective amount of a microorganism or compound for treating a particular disease is an amount that is sufficient to ameliorate, or in some manner reduce the symptoms associated with the disease. Such an amount can be administered as a single dosage or can be administered according to a regimen, whereby it is effective. The amount can cure the disease but, typically, is administered in order to ameliorate the symptoms of the disease. Repeated administration can be required to achieve the desired amelioration of symptoms.

As used herein equivalent, when referring to two sequences of nucleic acids, means that the two sequences in question encode the same sequence of amino acids or equivalent proteins. When equivalent is used in referring to two proteins or peptides or other molecules, it means that the two proteins or peptides have substantially the same amino acid sequence with only amino acid substitutions (such as, but not limited to, conservative changes) or structure and the any changes do not substantially alter the activity or function of the protein or peptide. When equivalent refers to a property, the property does not need to be present to the same extent (e.g., two peptides can exhibit different rates of the same type of enzymatic activity), but the activities are usually substantially the same. Complementary, when referring to two nucleotide sequences, means that the two sequences of nucleotides are capable of hybridizing, typically with less than 25%, 15% or 5% mismatches between opposed nucleotides. If necessary, the percentage of complementarity will be specified. Typically the two molecules are selected such that they will hybridize under conditions of high stringency.

As used herein, an agent or compound that modulates the activity of a protein or expression of a gene or nucleic acid either decreases or increases or otherwise alters the activity of the protein or, in some manner, up- or down-regulates or otherwise alters expression of the nucleic acid in a cell.

As used herein, a method for treating or preventing neoplastic disease means that any of the symptoms, such as the tumor, metastasis thereof, the vascularization of the tumors or other parameters by which the disease is characterized are reduced, ameliorated, prevented, placed in a state of remission, or maintained in a state of remission. It also means that the hallmarks of neoplastic disease and metastasis can be eliminated, reduced or prevented by the treatment. Non-limiting examples of the hallmarks include uncontrolled degradation of the basement membrane and proximal extracellular matrix, migration, division, and organization of the endothelial cells into new functioning capillaries, and the persistence of such functioning capillaries.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound is regenerated by metabolic processes. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

As used herein, a promoter region or promoter element or regulatory region refers to a segment of DNA or RNA that controls transcription of the DNA or RNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences can be cis acting or can be responsive to trans acting factors. Promoters, depending upon the nature of the regulation, can be constitutive or regulated. Exemplary promoters contemplated for use in prokaryotes include the bacteriophage T7 and T3 promoters.

As used herein, a receptor refers to a molecule that has an affinity for a ligand. Receptors can be naturally-occurring or synthetic molecules. Receptors also can be referred to in the art as anti-ligands. As used herein, the receptor and anti-ligand are interchangeable. Receptors can be used in their unaltered state or bound to other polypeptides, including as homodimers. Receptors can be attached to, covalently or noncovalently, or in physical contact with, a binding member, either directly or indirectly via a specific binding substance or linker. Examples of receptors, include, but are not limited to: antibodies, cell membrane receptors surface receptors and internalizing receptors, monoclonal antibodies and antisera reactive with specific antigenic determinants (such as on viruses, cells, or other materials), drugs, polynucleotides, nucleic acids, peptides, cofactors, lectins, sugars, polysaccharides, cells, cellular membranes, and organelles.

As used herein, sample refers to anything that can contain an analyte for which an analyte assay is desired. The sample can be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein: stringency of hybridization in determining percentage mismatch is as follows:

1) high stringency: 0.1×SSPE, 0.1% SDS, 65° C.
2) medium stringency: 0.2×SSPE, 0.1% SDS, 50° C.
3) low stringency: 1.0×SSPE, 0.1% SDS, 50° C.

Those of skill in this art know that the washing step selects for stable hybrids and also know the ingredients of SSPE (see, e.g., Sambrook, E. F. Fritsch, T. Maniatis, in: Molecular Cloning, A Laboratory Manual, Cold Spring Harbor Laboratory Press (1989), vol. 3, p. B.13, see, also, numerous catalogs that describe commonly used laboratory solutions). SSPE is pH 7.4 phosphate-buffered 0.18 M NaCl. Further, those of skill in the art recognize that the stability of hybrids is determined by Tm, which is a function of the sodium ion concentration and temperature: (Tm=81.5° C.−16.6(log 10[Na+])+0.41(% G+C)−600/1)), so that the only parameters in the wash conditions critical to hybrid stability are sodium ion concentration in the SSPE (or SSC) and temperature. Any nucleic acid molecules provided herein can also include those that hybridize under conditions of at least low stringency, generally moderate or high stringency, along at least 70, 80, 90% of the full length of the disclosed molecule. It is understood that equivalent stringencies can be achieved using alternative buffers, salts and temperatures. By way of example and not limitation, procedures using conditions of low stringency are as follows (see also Shilo and Weinberg, Proc. Natl. Acad. Sci. USA 78:6789-6792 (1981)):

Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA (10×SSC is 1.5 M sodium chloride, and 0.15 M sodium citrate, adjusted to a pH of 7). Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$ cpm $^{32}$P-labeled probe is used. Filters are incubated in hybridization mixture for 18-20 hours at 40° C., and then washed for 1.5 hours at 55° C. in a solution containing 2×SSC, 25 mM Tris-HCl (pH 7.4), 5 mM EDTA, and 0.1% SDS. The wash solution is replaced with fresh solution and incubated an additional 1.5 hours at 60° C. Filters are blotted dry and exposed for autoradiography. If necessary, filters are washed for a third time at 65-68° C. and reexposed to film. Other conditions of low stringency which can be used are well known in the art (e.g., as employed for cross-species hybridizations).

By way of example and not way of limitation, procedures using conditions of moderate stringency include, for example, but are not limited to, procedures using such conditions of moderate stringency are as follows: Filters containing DNA are pretreated for 6 hours at 55° C. in a solution containing 6×SSC, 5× Denhart's solution, 0.5% SDS and 100 µg/ml denatured salmon sperm DNA. Hybridizations are carried out in the same solution and 5-20×10$^6$ cpm $^{32}$P-labeled probe is used. Filters are incubated in hybridization mixture for 18-20 hours at 55° C., and then washed twice for 30 minutes at 60° C. in a solution containing 1×SSC and 0.1% SDS. Filters are blotted dry and exposed for autoradiography. Other conditions of moderate stringency which can be used are well-known in the art. Washing of filters is done at 37° C. for 1 hour in a solution containing 2×SSC, 0.1% SDS. By way of example and not way of limitation, procedures using conditions of high stringency are as follows: Prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 hours at 65° C. in prehybridization mixture containing 100 µg/ml denatured salmon sperm DNA and 5-20×10$^6$ cpm of $^{32}$P-labeled probe. Washing of filters is done at 37° C. for 1 hour in a solution containing 2×SSC, 0.01% PVP, 0.01% Ficoll, and 0.01% BSA. This is followed by a wash in 0.1×SSC at 50° C. for 45 minutes before autoradiography. Other conditions of high stringency which can be used are well known in the art.

The term substantially identical or homologous or similar varies with the context as understood by those skilled in the relevant art and generally means at least 60% or 70%, preferably means at least 80%, more preferably at least 90%, and most preferably at least 95%, 96%, 97%, 98%, 99% or greater identity.

As used herein, substantially identical to a product means sufficiently similar so that the property of interest is sufficiently unchanged so that the substantially identical product can be used in place of the product.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound can, however, be a mixture of stereoisomers or isomers. In such instances, further purification might increase the specific activity of the compound.

As used herein, a molecule, such as an antibody, that specifically binds to a polypeptide typically has a binding affinity (Ka) of at least about 10$^6$ l/mol, 10$^7$ l/mol, 10$^8$ l/mol, 10$^9$ l/mol, 10$^{10}$ l/mol or greater and binds to a protein of interest generally with at least 2-fold, 5-fold, generally 10-fold or even 100-fold or greater, affinity than to other proteins. For example, an antibody that specifically binds to the protease domain compared to the full-length molecule, such as the zymogen form, binds with at least about 2-fold, typically 5-fold or 10-fold higher affinity, to a polypeptide that contains only the protease domain than to the zymogen form of the full-length. Such specific binding also is referred to as selective binding. Thus, specific or selective binding refers to greater binding affinity (generally at least 2-fold, 5-fold, 10-fold or more) to a targeted site or locus compared to a non-targeted site or locus.

As used herein, the terms a therapeutic agent, therapeutic compound, therapeutic regimen, or chemotherapeutic include conventional drugs and drug therapies, including vaccines, which are known to those skilled in the art.

As used herein, treatment means any manner in which the symptoms of a condition, disorder or disease are ameliorated or otherwise beneficially altered. Treatment also encompasses any pharmaceutical use of the microorganisms described and provided herein.

As used herein, proliferative disorders include any disorders involving abnormal proliferation of cells. Such disorders include, but are not limited to, neoplastic diseases, psoriasis, restenosis, macular degeneration, diabetic retinopathies, inflammatory responses and disorders, including wound healing responses.

As used herein, vector (or plasmid) refers to discrete elements that are used to introduce heterologous nucleic acid into cells for either expression or replication thereof. The vectors typically remain episomal, but can be designed to effect integration of a gene or portion thereof into a chromosome of the genome. Also contemplated are vectors that are artificial chromosomes, such as yeast artificial chromosomes and mammalian artificial chromosomes. Selection and use of such vectors are well known to those of skill in the art. An expression vector includes vectors capable of expressing DNA that is operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, a combination refers to any association between two or among more items.

As used herein, a composition refers to any mixture. It can be a solution, a suspension, an emulsion, liquid, powder, a paste, aqueous, non-aqueous or any combination thereof.

As used herein, fluid refers to any composition that can flow. Fluids thus encompass compositions that are in the form of semi-solids, pastes, solutions, aqueous mixtures, gels, lotions, creams and other such compositions.

As used herein, a kit is a packaged combination optionally including instructions for use of the combination and/or other reactions and components for such use.

For clarity of disclosure, and not by way of limitation, the detailed description is divided into the subsections that follow.

B. MICROORGANISMS FOR TUMOR-SPECIFIC THERAPY

Provided herein are microorganisms, and methods for making and using such microorganisms for therapy of neoplastic disease and other proliferative disorders and inflammatory disorders. The microbe (or microorganism)-mediated treatment methods provided herein involve administration of microorganisms to hosts, accumulation of the microorganism in the targeted cell or tissue, such as in a tumor, resulting in leaking or lysing of the cells, whereby an immune response against leaked or released antigens is mounted, thereby resulting in an inhibition of the tissues or cells in which the microorganism accumulates.

In addition to the gene therapeutic methods of cancer treatment, live attenuated microorganisms can be used for vaccination, such as in cancer vaccination or antitumor immunity. Immunization, for example, against a tumor can include a tumor-specific T-cell-mediated response through microbe-delivered antigens or cytokines. To do so, the microbes can be specifically targeted to the tumor tissues, with minimal infection to any other key organs and also can be modified or provided to produce the antigens and/or cytokines.

The microorganisms provided herein and the use of such microorganisms herein can accumulate in immunoprivileged cells or immunoprivileged tissues, including tumors and/or metastases, and also including wounded tissues and cells. While the microorganisms provided herein can typically be cleared from the subject to whom the microorganisms are administered by activity of the subject's immune system, microorganisms can nevertheless accumulate, survive and proliferate in immunoprivileged cells and tissues such as tumors because such immunoprivileged areas are sequestered from the host's immune system. Accordingly, the methods provided herein, as applied to tumors and/or metastases, and therapeutic methods relating thereto, can readily be applied to other immunoprivileged cells and tissues, including wounded cells and tissues.

1. Characteristics

The microorganisms provided herein and used in the methods herein are attenuated, immunogenic, and replication competent.

a. Attenuated

The microbes used in the methods provided herein are typically attenuated. Attenuated microbes have a decreased capacity to cause disease in a host. The decreased capacity can result from any of a variety of different modifications to the ability of a microbe to be pathogenic. For example, a microbe can have reduced toxicity, reduced ability to accumulate in non-tumorous organs or tissue, reduced ability to cause cell lysis or cell death, or reduced ability to replicate compared to the non-attenuated form thereof. The attenuated microbes provided herein, however, retain at least some capacity to replicate and to cause immunoprivileged cells and tissues, such as tumor cells to leak or lyse, undergo cell death, or otherwise cause or enhance an immune response to immunoprivileged cells and tissues, such as tumor cells.

i. Reduced Toxicity

Microbes can be toxic to their hosts by manufacturing one or more compounds that worsen the health condition of the host. Toxicity to the host can be manifested in any of a variety of manners, including septic shock, neurological effects, or muscular effects. The microbes provided herein can have a reduced toxicity to the host. The reduced toxicity of a microbe of the present methods and compositions can range from a toxicity in which the host experiences no toxic effects, to a toxicity in which the host does not typically die from the toxic effects of the microbes. In some embodiments, the microbes are of a reduced toxicity such that a host typically has no significant long-term effect from the presence of the microbes in the host, beyond any effect on tumorous, metastatic or necrotic organs or tissues. For example, the reduced toxicity can be a minor fever or minor infection, which lasts for less than about a month, and following the fever or infection, the host experiences no adverse effects resultant from the fever or infection. In another example, the reduced toxicity can be measured as an unintentional decline in body weight of about 5% or less for the host after administration of the microbes. In other examples, the microbe has no toxicity to the host.

Exemplary vaccinia viruses of the LIVP strain (a widely available attenuated Lister strain) that have reduced toxicity compared to other vaccinia viruses employed and are further modified. Modified LIVP were prepared. These modified LIVP include insertions in the TK and/or HA genes and in the locus designed F3. As an example of reduced toxicity, recombinant vaccinia viruses were tested for their toxicity to mice with impaired immune systems (nude mice) relative to the corresponding wild type vaccinia virus. Intravenous (i.v.) injection of wild type vaccinia virus VGL (strain LIVP) at $1 \times 10^7$ PFU/mouse causes toxicity in nude mice: three mice out of seven lost the weight and died (one mouse died in one week after virus injection, one mouse died ten days after virus injection. Similar modifications can be made to other pox viruses and other viruses to reduce toxicity thereof. Such modifications can be empirically identified, if necessary.

ii. Accumulate in Immunoprivileged Cells and Tissues, such as Tumor, not Substantially in Other Organs Microbes can accumulate in any of a variety of tissues and organs of the host. Accumulation can be evenly distributed over the entire host organism, or can be concentrated in one or a few organs or tissues, The microbes provided herein can accumulate in targeted tissues, such as immunoprivileged cells and tissues, such as tumors and also metastases. In some embodiments, the microbes provided herein exhibit accumulation in immunoprivileged cells and tissues, such as tumor cells relative to normal organs or tissues that is equal to or greater than the accumulation that occurs with wild type microbes. In other embodiments the microbes provided herein exhibit accumulation in immunoprivileged cells and tissues, such as tumor cells that is equal to or greater than the accumulation in any other particular organ or tissue. For example, the microbes provided herein can demonstrate an accumulation in immunoprivileged cells and tissues, such as tumor cells that is at least about 2-fold greater, at least about 5-fold greater, at least about 10-fold greater, at least about 100-fold greater, at least about 1,000-fold greater, at least about 10,000-fold greater, at least about 100,000-fold greater, or at least about 1,000,000-fold greater, than the accumulation in any other particular organ or tissue.

In some embodiments, a microbe can accumulate in targeted tissues and cells, such as immunoprivileged cells and tissues, such as tumor cells, without accumulating in one or more selected tissues or organs. For example, a microbe can accumulate in tumor cells without accumulating in the brain. In another example, a microbe can accumulate in tumor cells without accumulating in neural cells. In another example, a microbe can accumulate in tumor cells without accumulating in ovaries. In another example, a microbe can accumulate in tumor cells without accumulating in the blood. In another example, a microbe can accumulate in tumor cells without accumulating in the heart. In another example, a microbe can accumulate in tumor cells without accumulating in the bladder. In another example, a microbe can accumulate in tumor cells without accumulating in testes. In another example, a microbe can accumulate in tumor cells without accumulating in the spleen. In another example, a microbe can accumulate in tumor cells without accumulating in the lungs.

One skilled in the art can determine the desired capability for the microbes to selectively accumulate in targeted tissue or cells, such as in an immunoprivileged cells and tissues, such as tumor rather than non-target organs or tissues, according to a variety of factors known in the art, including, but not limited to, toxicity of the microbes, dosage, tumor to be treated, immunocompetence of host, and disease state of the host.

Provided herein as an example of selective accumulation in immunoprivileged cells and tissues, such as tumors relative to normal organs or tissues, presence of various vaccinia viruses was assayed in tumor samples and different organs. Wild type VGL virus (LIVP) was recovered from tumor, testes, bladder, and liver and as well as from brain. Recombinant virus RVGL9 was found mostly in tumors, and no virus was recovered from brain tissue in six tested animals. Therefore, this finding demonstrates the tumor accumulation properties of a recombinant vaccinia virus of the LIVP strain with an insertion in the F3 gene for tumor therapy purposes.

iii. Ability to Elicit or Enhance Immune Response to Tumor Cells

The microorganisms herein cause or enhance an immune response to antigens in the targeted tissues or cells, such as immunoprivileged cells and tissues, such as tumor cells. The immune response can be triggered by any of a variety of mechanisms, including the presence of immunostimulatory cytokines and the release of antigenic compounds that can cause an immune response.

Cells, in response to an infection such as a microorganismal infection, can send out signals to stimulate an immune response against the cells. Exemplary signals sent from such cells include antigens, cytokines and chemokines such as interferon-gamma and interleukin-15. The microorganism provided herein can cause targeted cells to send out such signals in response to infection by the microbes, resulting in a stimulation of the host's immune system against the targeted cells or tissues, such as tumor cells.

In another embodiment, targeted cells or tissues, such as tumor cells, can contain one or more compounds that can be recognized by the host's immune system in mounting an immune response against a tumor. Such antigenic compounds can be compounds on the cell surface or the tumor cell, and can be protein, carbohydrate, lipid, nucleic acid, or combinations thereof. Microbe-mediated release of antigenic compounds can result in triggering the host's immune system to mount an immune response against the tumor. The amount of antigenic compound released by the tumor cells is any amount sufficient to trigger an immune response in a subject; for example, the antigenic compounds released from one or more tumor cells can trigger a host immune response in the organism that is known to be accessible to leukocytes.

The time duration of antigen release is an amount of time sufficient for the host to establish an immune response to one or more tumor antigens. In some embodiments, the duration is an amount of time sufficient for the host to establish a sustained immune response to one or more tumor antigens. One skilled in the art can determine such a time duration based on a variety of factors affecting the time duration for a subject to develop an immune response, including the level of the tumor antigen in the subject, the number of different tumor antigens, the antigenicity of the antigen, the immunocompetence of the host, and the access of the antigenic material to the vasculature of the host. Typically, the duration of antigen release can be at least about a week, at least about 10 days, at least about two weeks, or at least about a month.

The microorganism provided herein can have any of a variety of properties that can cause target cells and tissues, such as tumor cells, to release antigenic compounds. Exemplary properties are the ability to lyse cells and the ability to elicit apoptosis in tumor cells. Microbes that are unable to lyse tumor cells or cause tumor cell death can nevertheless be used in the methods provided herein when such microbes can cause some release or display of antigenic compounds from tumor cells. A variety of mechanisms for antigen release or display without lysis or cell death are known in the art, and any such mechanism can be used by the microbes provided herein, including, but not limited to, secretion of antigenic compounds, enhanced cell membrane permeability, or altered cell surface expression or altered MHC presentation in tumor cells when the tumor cells can be accessed by the host's immune system. Regardless of the mechanism by which the host's immune system is activated, the net result of the presence of the microbes in the tumor is a stimulation of the host's immune system, at least in part, against the tumor cells. In one example, the microbes can cause an immune response against tumor cells not infected by the microbes.

In one embodiment, the microbes provided herein can cause tumor cells to release an antigen that is not present on the tumor cell surface. Tumor cells can produce compounds such as proteins that can cause an immune response; however, in circumstances in which the antigenic compound is not on the tumor cell surface, the tumor can proliferate, and even metastasize, without the antigenic compound causing an immune response. Within the scope of the present methods, the microbes provided herein can cause antigenic compounds within the cell to release away from the cell and away from the tumor, which can result in triggering an immune response to such an antigen. Even if not all cells of a tumor are releasing antigens, the immune response can initially be targeted toward the "leaky" tumor cells, and the bystander effect of the immune response can result in further tumor cell death around the "leaky" tumor cells.

iv. Balance of Pathogenicity and Release of Tumor Antigens

Typical methods of involving treatment of targeted cells and tissues, such as immunoprivileged cells and tissues, such as tumors, are designed to cause rapid and complete removal thereof. For example, many viruses, bacterial or eukaryotic cells can cause lysis and/or apoptosis in a variety of cells, including tumor cells. Microorganisms that can vigorously lyse or cause cell death can be highly pathogenic, and can even kill the host. Furthermore, therapeutic methods based upon such rapid and complete lysis are typically therapeutically ineffective.

In contrast, the microorganisms provided herein are not aggressive in causing cell death or lysis. They can have only a limited or no ability to cause cell death as long as they accumulate in the target cells or tissues and result in alteration of cell membranes to cause leakage of antigens against which an immune response is mounted. It is desirable that their apoptotic or lytic effect is sufficiently slow or ineffective to permit sufficient antigenic leakage for a sufficient time for the host to mount an effective immune response against the target tissues. Such immune response alone or in combination with the lytic/apoptotic effect of the microorganism results in elimination of the target tissue and also elimination of future development, such as metastases and reoccurrence, of such tissues or cells. While the microbes provided herein can have a limited ability to cause cell death, the microbes provided herein can nevertheless stimulate the host's immune system to attack tumor cells. As a result, such microorganisms also are typically unlikely to have substantial toxicity to the host.

In one embodiment, the microbes have a limited, or no, ability to cause tumor cell death, while still causing or enhancing an immune response against tumor cells. In one example, the rate of microorganism-mediated tumor cell death is less than the rate of tumor cell growth or replication. In another example, the rate of microorganism-mediated tumor cell death is slow enough for the host to establish a sustained immune response to one or more tumor antigens. Typically, the time for of cell death is sufficient to establish an anti-tumor immune response and can be at least about a week, at least about 10 days, at least about two weeks, or at least about a month, depending upon the host and the targeted cells or tissues.

In another embodiment, the microbes provided herein can cause cell death in tumor cells, without causing substantial cell death in non-tumor tissues. In such an embodiment, the microbes can aggressively kill tumor cells, as long as no substantial cell death occurs in non-tumor cells, and optionally, so long as the host has sufficient capability to mount an immune response against the tumor cells.

In one embodiment, the ability of the microbes to cause cell death is slower than the host's immune response against the microbes. The ability for the host to control infection by the microbes can be determined by the immune response (e.g., antibody titer) against microorganismal antigens. Typically, after the host has mounted immune response against the microbes, the microbes can have reduced pathogenicity in the host. Thus, when the ability of the microbes to cause cell death is slower than the host's immune response against the microbes, microbe-mediated cell death can occur without risk of serious disease or death to the host. In one example, the ability of the microbes to cause tumor cell death is slower than the host's immune response against the microbes.

b. Immunogenicity

The microorganisms provided herein also can be immunogenic. An immunogenic microorganism can create a host immune response against the microorganism. In one embodiment, the microorganisms can be sufficiently immunogenic to result in a large anti-(microorganism) antibody titer. The microorganisms provided herein can have the ability to elicit an immune response. The immune response can be activated in response to viral antigens or can be activated as a result of microorganismal-infection induced cytokine or chemokine production. Immune response against the microorganism can decrease the likelihood of pathogenicity toward the host organism.

Immune response against the microorganism also can result in target tissue or cell, such as tumor cell, killing. In one embodiment, the immune response against microorganismal infection can result in an immune response against tumor cells, including developing antibodies against tumor antigens. In one example, an immune response mounted against the microorganism can result in tumor cell killing by the "bystander effect," where uninfected tumor cells nearby infected tumor cells are killed at the same time as infected cells, or alternatively, where uninfected tumor cells nearby extracellular microorganisms are killed at the same time as the microorganisms. As a result of bystander effect tumor cell death, tumor cell antigens can be released from cells, and the host organism's immune system can mount an immune response against tumor cell antigens, resulting in an immune response against the tumor itself.

In one embodiment, the microorganism can be selected or modified to express one or more antigenic compounds, including superantigenic compounds. The antigenic compounds such as superantigens can be endogenous gene products or can be exogenous gene products. Superantigens, including toxoids, are known in the art and described elsewhere herein.

c. Replication Competent

The microorganisms provided herein can be replication competent. In a variety of viral or bacterial systems, the administered microorganism is rendered replication incompetent to limit pathogenicity risk to the host. While replication incompetence can protect the host from the microorganism, that also limits the ability of the microorganism to infect and kill tumor cells, and typically results in only a short-lived effect. In contrast, the microorganisms provided herein can be attenuated but replication competent, resulting in low toxicity to the host and accumulation mainly or solely in tumors. Thus, the microorganisms provided herein can be replication competent without creating a pathogenicity risk to the host.

Attenuation of the microorganisms provided herein can include, but is not limited to, reducing the replication competence of the microorganism. For example, a microorganism can be modified to decrease or eliminate an activity related to replication, such as a transcriptional activator that regulates replication in the microorganism. In an example, a microorganism, such as a virus, can have the viral thymidine kinase gene modified.

d. Genetic Variants

The microorganisms provided herein can be modified from their wild type form. Modifications can include any of a variety of changes, and typically include changes to the genome or nucleic acid molecules of the microorganisms. Exemplary nucleic acid molecular modifications include truncations, insertions, deletions and mutations. In an exemplary modification, a microorganismal gene can be modified by truncation, insertion, deletion or mutation. In an exemplary insertion, an exogenous gene can be inserted into the genome of the microorganism.

i. Modified Characteristics

Modifications of the microorganisms provided herein can result in a modification of microorganismal characteristics, including those provided herein such as pathogenicity, toxicity, ability to preferentially accumulate in tumor, ability to lyse cells or cause cell death, ability to elicit an immune response against tumor cells, immunogenicity, replication competence. Variants can be obtained by general methods such as mutagenesis and passage in cell or tissue culture and selection of desired properties, as is known in the art, as exemplified for respiratory syncytial virus in Murphy et al., Virus Res. 1994, 32:13-26.

Variants also can be obtained by mutagenic methods in which nucleic acid residues of the microorganism are added, removed or modified relative to the wild type. Any of a variety of known mutagenic methods can be used, including recombination-based methods, restriction endonuclease-based methods, and PCR-based methods. Mutagenic methods can be directed against particular nucleotide sequences such as genes, or can be random, where selection methods based on desired characteristics can be used to select mutated microorganisms. Any of a variety of microorganismal modifications can be made, according to the selected microorganism and the particular known modifications of the selected microorganism.

ii. Exogenous Gene Expression

The microorganisms provided herein also can have the ability to express one or more exogenous genes. Gene expression can include expression of a protein encoded by a gene and/or expression of an RNA molecule encoded by a gene. In some embodiments, the microorganisms can express exogenous genes at levels high enough that permit harvesting products of the exogenous genes from the tumor. Expression of endogenous genes can be controlled by a constitutive promoter, or by an inducible promoter. Expression can also be influenced by one or more proteins or RNA molecules expressed by the microorganism. An exemplary inducible promoter system can include a chimeric transcription factor containing a progesterone receptor fused to the yeast GAL4 DNA-binding domain and to the activation domain of the herpes simplex virus protein VP16, and a synthetic promoter containing a series of GAL4 recognition sequences upstream of the adenovirus major late E1B TATA box, linked to one or more exogenous genes; in this exemplary system, administration of RU486 to a subject can result in induction of the exogenous genes. Exogenous genes expressed can include genes encoding a therapeutic gene product, genes encoding a detectable gene product such as a gene product that can be used for imaging, genes encoding a gene product to be harvested, genes encoding an antigen of an antibody to be harvested. The microorganisms provided herein can be used for expressing genes in vivo and in vitro. Exemplary proteins include reporter proteins (*E. coli* β-galactosidase, β-glucuronidase, xanthineguanine phosphoribosyltransferase), proteins facilitating detection, i.e., a detectable protein or a protein capable of inducing a detectable signal, (e.g., luciferase, green and red fluorescent proteins, transferrin receptor), proteins useful for tumor therapy (pseudomonas A endotoxin, diphtheria toxin, p53, Arf, Bax, tumor necrosis factor-alpha, HSV TK, *E. coli* purine nucleoside phosphorylase, angiostatin, endostatin, different cytokines) and many other proteins.

iii. Detectable Gene Product

The microorganisms provided herein can express one or more genes whose products are detectable or whose products can provide a detectable signal. A variety of detectable gene products, such as detectable proteins are known in the art, and can be used with the microorganisms provided herein. Detectable proteins include receptors or other proteins that can specifically bind a detectable compound, proteins that can emit a detectable signal such as a fluorescence signal, enzymes that can catalyze a detectable reaction or catalyze formation of a detectable product.

In some embodiments, the microorganism expresses a gene encoding a protein that can emit a detectable signal or that can catalyze a detectable reaction. A variety of DNA sequences encoding proteins that can emit a detectable signal or that can catalyze a detectable reaction, such as luminescent or fluorescent proteins, are known and can be used in the microorganisms and methods provided herein. Exemplary genes encoding light-emitting proteins include genes from bacterial luciferase from *Vibrio harveyi* (Belas et al., Science 218 (1982), 791-793), bacterial luciferase from *Vibrio fischeri* (Foran and Brown, Nucleic acids Res. 16 (1988), 177), firefly luciferase (de Wet et al., Mol. Cell. Biol. 7 (1987), 725-737), aequorin from *Aequorea victoria* (Prasher et al., Biochem. 26 (1987), 1326-1332), *Renilla* luciferase from *Renilla reniformis* (Lorenz et al., PNAS USA 88 (1991), 4438-4442) and green fluorescent protein from *Aequorea victoria* (Prasher et al., Gene 111 (1987), 229-233). Transformation and expression of these genes in microorganisms can permit detection of microorganismal colonies, for example, using a low light imaging camera. Fusion of the lux A and lux B genes can result in a fully functional luciferase protein (Escher et al., PNAS 86 (1989), 6528-6532). This fusion gene (Fab2) has introduced into a variety of microorganisms followed by microorganismal infection and imaging based on luciferase expression. In some embodiments, luciferases expressed in bacteria can require exogenously added substrates such as decanal or coelenterazine for light emission. In other embodiments, microorganisms can express a complete lux operon, which can include proteins that can provide luciferase substrates such as decanal. For example, bacteria containing the complete lux operon sequence, when injected intraperitoneally, intramuscularly, or intravenously, allowed the visualization and localization of bacteria in live mice indicating that the luciferase light emission can penetrate the tissues and can be detected externally (Contag et al., Mol. Microbiol. 18 (1995), 593-603).

In other embodiments, the microorganism can express a gene that can bind a detectable compound or that can form a product that can bind a detectable compound. A variety of gene products, such as proteins, that can specifically bind a detectable compound are known in the art, including receptors, metal binding proteins, ligand binding proteins, and antibodies. Any of a variety of detectable compounds can be used, and can be imaged by any of a variety of known imaging methods. Exemplary compounds include receptor ligands and antigens for antibodies. The ligand can be labeled according to the imaging method to be used. Exemplary imaging methods include any of a variety magnetic resonance methods such as magnetic resonance imaging (MRI) and magnetic resonance spectroscopy (MRS), and also include any of a variety of tomographic methods including computed tomography (CT), computed axial tomography (CAT), electron beam computed tomography (EBCT), high resolution computed tomography (HRCT), hypocycloidal tomography, positron emission tomography (PET), single-photon emission computed tomography (SPECT), spiral computed tomography and ultrasonic tomography.

Labels appropriate for magnetic resonance imaging are known in the art, and include, for example, gadolinium chelates and iron oxides. Use of chelates in contrast agents is known in the art. Labels appropriate for tomographic imaging methods are known in the art, and include, for example, β-emitters such as $^{11}C$, $^{13}N$, $^{15}O$ or $^{64}Cu$ or (b) γ-emitters such as $^{123}I$. Other exemplary radionuclides that can be used, for example, as tracers for PET include $^{55}Co$, $^{67}Ga$, $^{68}Ga$, $^{67}Cu$ (II), $^{67}Cu(II)$, $^{57}Ni$, $^{52}Fe$ and $^{18}F$. Examples of useful radionuclide-labeled agents are $^{64}Cu$-labeled engineered antibody fragment (Wu et al., PNAS USA 97 (2002), 8495-8500), $^{64}Cu$-labeled somatostatin (Lewis et al., J. Med. Chem. 42 (1999), 1341-1347), $^{64}Cu$-pyruvaldehyde-bis (N4methylthiosemicarbazone)-($^{64}Cu$-PTSM) (Adonai et al., PNAS USA 99 (2002), 3030-3035), $^{52}Fe$-citrate (Leenders et al., J. Neural. Transm. Suppl. 43 (1994), 123-132), $^{52}Fe/^{52m}Mn$-citrate (Calonder et al., J. Neurochem. 73 (1999), 2047-2055) and $^{52}Fe$-labeled iron (III) hydroxide-sucrose complex (Beshara et al., Br. J. Haematol. 104 (1999), 288-295, 296-302).

iv. Therapeutic Gene Product

The microorganisms provided herein can express one or more genes whose products cause cell death or whose products cause an anti-tumor immune response, such genes can be considered therapeutic genes. A variety of therapeutic gene products, such as toxic or apoptotic proteins, or siRNA, are known in the art, and can be used with the microorganisms provided herein. The therapeutic genes can act by directly killing the host cell, for example, as a channel-forming or other lytic protein, or by triggering apoptosis, or by inhibiting essential cellular processes, or by triggering an immune response against the cell, or by interacting with a compound that has a similar effect, for example, by converting a less active compound to a cytotoxic compound.

In some embodiments, the microorganism can express a therapeutic protein. A large number of therapeutic proteins that can be expressed for tumor treatment are known in the art, including, but not limited to tumor suppressors, toxins, cytostatic proteins, and cytokines. An exemplary, non-limiting list of such proteins includes WT1, p53, p16, Rb, BRCA1, cystic fibrosis transmembrane regulator (CFTR), Factor VIII, low density lipoprotein receptor, beta-galactosidase, alpha-galactosidase, beta-glucocerebrosidase, insulin, parathyroid hormone, alpha-1-antitrypsin, rsCD40L, Fas-ligand, TRAIL, TNF, antibodies, microcin E492, diphtheria toxin, *Pseudomonas* exotoxin, *Escherichia coli* Shig toxin, *Escherichia coli* Verotoxin 1, and hyperforin.

In other embodiments, the microorganism can express a protein that converts a less active compound into a compound that causes tumor cell death. Exemplary methods of conversion of such a prodrug compound include enzymatic conversion and photolytic conversion. A large variety of protein/compound pairs are known in the art, and include, but are not limited to Herpes simplex virus thymidine kinase/gancyclovir, varicella zoster thymidine kinase/gancyclovir, cytosine deaminase/5-fluorouracil, purine nucleoside phosphorylase/6-methylpurine deoxyriboside, beta lactamase/cephalosporin-doxorubicin, carboxypeptidase G2/4-[(2-chloroethyl)(2-mesuloxyethyl)amino]benzoyl-L-glutamic acid, cytochrome P450/acetominophen, horseradish peroxidase/indole-3-acetic acid, nitroreductase/CB 1954, rabbit carboxylesterase/7-ethyl-10-[4-(1-piperidino)-1-piperidino] carbonyloxycamptothecin, mushroom tyrosinase/bis-(2-chloroethyl)amino-4-hydroxyphenylaminomethanone 28, beta galactosidase/1-chloromethyl-5-hydroxy-1,2-dihyro-3H-benz[e]indole, beta glucuronidase/epirubicin glucuronide, thymidine phosphorylase/5'-deoxy5-fluorouridine, deoxycytidine kinase/cytosine arabinoside, and linamerase/linamarin.

In another embodiment, the therapeutic gene product can be an siRNA molecule. The siRNA molecule can be directed against expression of a tumor-promoting gene, such as, but not limited to, an oncogene, growth factor, angiogenesis promoting gene, or a receptor. The siRNA molecule also can be directed against expression of any gene essential for cell growth, cell replication or cell survival. The siRNA molecule also can be directed against expression of any gene that stabilizes the cell membrane or otherwise limits the number of tumor cell antigens released from the tumor cell. Design of an siRNA can be readily determined according to the selected target of the siRNA; methods of siRNA design and down-regulation of genes are known in the art, as exemplified in U.S. Pat. Pub. No. 20030198627.

In one embodiment, the therapeutic compound can be controlled by a regulatory sequence. Suitable regulatory sequences which, for example, are functional in a mammalian host cell are well known in the art. In one example, the regulatory sequence can contain a natural or synthetic vaccinia virus promoter. In another embodiment, the regulatory sequence contains a poxvirus promoter. When viral microorganisms are used, strong late promoters can be used to achieve high levels of expression of the foreign genes. Early and intermediate-stage promoters, however, can also be used. In one embodiment, the promoters contain early and late promoter elements, for example, the vaccinia virus early/late promoter p7.5, vaccinia late promoter p11, a synthetic early/late vaccinia pE/L promoter (Patel et al., (1988), Proc. Natl. Acad. Sci. USA 85, 9431-9435; Davison and Moss, (1989), J Mol Biol 210, 749-769; Davison et al., (1990), Nucleic Acids Res. 18, 4285-4286; Chakrabarti et al., (1997), BioTechniques 23, 1094-1097).

v. Expressing a Superantigen

The microorganisms provided herein can be modified to express one or more superantigens. Superantigens are antigens that can activate a large immune response, often brought about by a large response of T cells. A variety of superantigens are known in the art including, but not limited to, diphtheria toxin, staphylococcal enterotoxins (SEA, SEB, SEC1, SEC2, SED, SEE and SEH), Toxic Shock Syndrome Toxin 1, Exfoliating Toxins (EXft), Streptococcal Pyrogenic Exotoxin A, B and C (SPE A, B and C), Mouse Mammary Tumor Virus proteins (MMTV), Streptococcal M proteins, Clostridial Perfringens Enterotoxin (CPET), mycoplasma arthritis superantigens.

Since many superantigens also are toxins, if expression of a microorganism of reduced toxicity is desired, the superantigen can be modified to retain at least some of its superantigenicity while reducing its toxicity, resulting in a compound such as a toxoid. A variety of recombinant superantigens and toxoids of superantigens are known in the art, and can readily be expressed in the microorganisms provided herein. Exemplary toxoids include toxoids of diphtheria toxin, as exemplified in U.S. Pat. No. 6,455,673 and toxoids of Staphylococcal enterotoxins, as exemplified in U.S. Pat. Pub. No. 20030009015.

vi. Expressing a Gene Product to be Harvested

Exemplary genes expressible by a microorganism for the purpose of harvesting include human genes. An exemplary list of genes includes the list of human genes and genetic disorders authored and edited by Dr. Victor A. McKusick and his colleagues at Johns Hopkins University and elsewhere, and developed for the World Wide Web by NCBI, the National Center for Biotechnology Information. Online Mendelian Inheritance in Man, OMIM™. Center for Medical Genetics, Johns Hopkins University (Baltimore, Md.) and National Center for Biotechnology Information, National Library of Medicine (Bethesda, Md.), 1999. and those available in public databases, such as PubMed and GenBank (see, e.g., (ncbi.nlm.nih.gov/entrez/query.fcgi?db=OMIM) These genes include, but are not limited to: 239f2h9, 3pk, 4ebp1, 4ebp2, al1, al2 ml, al2 m2, al2 m3, al2m4, al5, alb, albg, alst, a2m, a2mr, a2mrap, aa, aaa, aaa, aabt, aac1, aac2, aact, aadac, aanat, aars, aas, aat, aavs1, abc1, abc2, abc3, abc7, abc8, abcr, abi1, abl1, abl2, abl1, abo, abp, abp1, abpa, abpx, abr, acaa, acac, acaca, acacb, acad1, acadm, acads, acadsb, acadv1, acat, acat1, acat2, acc, accb, accn1, accn2, accpn, ace1, ach, ache, achm1, achm2, achrb, achrd, achrg, acls, acly, aco1, aco2, acox, acox1, acox2, acox3, acp1, acp2, acp5, acpp, acr, acrv1, acs3, acs3, acs4, act2, act35, acta1, acta2, acta3, actb, actc, actg1, actg2, act11, actn1, actn2, actn3, actsa, acug, acvr1, acvr2b, acvrl1, acvrlk1, acvrlk2, acvrlk3, acy1, ad1, ad2, ad3, ad4, ad5, ada, adam10, adam11, adam12, adam3, adam3a, adam3b, adam8, adar, adarb1, adarb2, adcp1, adcp2, adcy1, adcy2, adcy3, adcy3, adcy4, adcy5, adcy6, adcy7, adcy8, adcy9, adcyap1, adcyaplr1, add1, add2, add3, add1, adfn, adh1, adh2, adh3, adh4, adh5, adh7, adhaps, adhc1, adhr, adhr, adk, adl, adm, adm1x, adora1, adora2a, adora2b, adora21, adora21, adora3, adprt, adra1a, adra1b, adra1c, adra1d, adra2a, adra2b, adra2c, adra211, adra212, adra2r, adrb1, adrb1r, adrb2, adrb2r11, adrb3, adrbk1, adrbk2, ads1, adss, adtb1, adx, adxr, ae1, ae2, ae3, aegl1, aemk, aes, af10, af17, af4, af6, af8t, af9, afd1, afdn, afg3, afg311, afm, afp, afx1, aga, agc1, ager, ag1, agmx1, agmx2, agp1, agp7, agps, agrn, agrp, agrt, ags, agt, agti1, agtr1, agtr1a, agtr2, agtrl1, agxt, ahc, ahcy, ahd, ahds, ahnak, aho2, ahr, ahsg, ahx, aib1, aic, aic1, aied, aih1, aih2, aih3, aim1, air, airc, aire, ak1, ak2, ak3, akap149, akt1, akt2, aku, alad, alas1, alas2, alb, alb2, alba, alcam, ald, aldh1, aldh10, aldh2, aldh3, aldh4, aldh5, aldh6, aldh9, ald11, aldoa, aldob, aldoc, aldr1, alds, alk, alk1, alk2, alk3, alk6, alms1, alox12, alox15, alox5, alp, alpi, alpl, alpp, alpp12, alr, alr, als1, als2, als4, als5, alss, ambn, ambp, amcd1, amcd2b, amcn, amcn1, amcx1, amd1, amdm, amelx, amely, amfr, amg, amg1, amgx, amh, amhr, amhr2, aml1, aml1t1, aml2, aml3, amog, ampd1, ampd2, ampd3, amph, amph1, ampk, amt, amy1a, amy1b, amy1c, amy2a, amy2b, an 2, anc, ancr, ang, ang1, anh1, ank1, ank2, ank3, anop1, anova, anp, anpep, anpra, anprb, anprc, ans, ant1, ant2, ant3, ant3y, anx 1, anx 11, anx 13, anx2, anx214, anx3, anx4, anx5, anx6, anx7, anx8, aoah, aoc2, aox1, ap2tf, apah1, apba1, apba2, apbb1, apbb2, apc, apcs, ape, apeced, apeh, apex, api1, api2, api3, apj, aplp, aplp1, aplp2, apnh, apo31, apoa1, apoa2, apoa4, apob, apobec1, apoc1, apoc2, apoc3, apoc4, apod, apoe, apoer2, apoh, apolmt, apolp1, apolp2, app, appbp1, appl1, aprf, aprt, aps, apt1, aptl1g1, apx1, apy, aqdq, aqp0, aqp1, aqp2, aqp21, aqp3, aqp4, aqp5, aqp6, aqp7, ar, ar1, ara, araf1, araf2, arcn1, ard1, ard1, areg, arf1, arf2, arf3, arf41, arf5, arg, arg1, args, arh12, arh6, arh9, arha, arhb, arhc, arhg, arhgap2, arhgap3, arhgap6, arhgdia, arhgdib, arhh, arix, arl2, armd1, arnt, arnt1, aro, arp, arp1, arpkd, arr3, arrb1, arrb2, arsa, arsacs, arsb, arsc1, arsc2, arsd, arse, arsf, art, art1, art3, art4, art5, arvd1, arvd2, arvd3, arvd4, as, asat, asb, ascl1, ascl2, asct1, asd1, asd2, asgr1, asgr2, ash1, asip, as1, asln, asm1, asma, asmd, asmt, asmt1x, asmty, asnrs, asns, aspa, ass, astm1, astn, asv, at, at1, at2r1, at3, ata, atbf1, atcay, atf1, ath1, aths, atm, atoh1, atox1, atp1a1, atp1a2, atp1a3, atp1a11, atp1b1, atp1b2, atp1b3, atp1b11, atp1g1, atp2a1, atp2a2, atp2a3, atp2b, atp2b1, atp2b2, atp2b2, atp2b3, atp2b4, atp4a, atp4b, atp5, atp5a, atp5b, atp5g1, atp5g2, atp5g3, atp5o, atp6a, atp6b1, atp6c, atp6e, atp6n1, atp7a, atp7b, atpm, atpsb, atpsk1, atpsk2, atq1, atr, atr, atr1, atr1, atr2, atrc1, atrc2, atrx, ats, atsv, atx1, atx2, au, auf1, auf1a, aut, avcd, aved, avp, avpr1a, avpr1b, avpr2, avpr3, avrp, avsd, awa1, ax1, axl1g, axsf, azf1, azf2, azgp1, azu1, b120, b144, b1g1, b29, b2m, b2mr, b3galt4, b4galt1, ba2r, bab1, bag1, bai1, bai2, bai3, bak1, bam22, bap1, bap135, bapx1, bard1, bark2, bas, bat1, bat2, bat3, bat4, bat5, bax, bb1, bbbg1, bbbg2, bbs1, bbs2, bbs3, bbs4, bbs5, bcas1, bcat1, bcat2, bcate2, bcd1, bcei, bche, bckdha, bckdhb, bcl1, bcl10, bcl2, bcl2a1, bcl212, bcl3, bcl5, bcl6, bcl7, bcl7a, bcl8, bcl9, bclw, bcm, bcm1, bcma, bcns, bcns, bcp, bcpm, bcpr, bcr, bcr12, bcr13, bcr14, bcsg1, bct1, bct2, bdb, bdb1, bdc, bde, bdkrb1, bdkrb2, bdmf, bdmr, bdnf, bed, bedp, bek, bene, bevi, bf, bf1, bf2, bfhd, bfic, bfls, bffic2, bfp, bfsp1, bft, bglap, bgmr, bgn, bgp, bhd, bhpcdh, bhr1, bicd1, bid, bigh3, bin1, bir, bjs, bkma1, blast1, blau, blk, blm, blmh, bltr, blvra, blvrb, blym, bmal1, bmd, bmh, bmi1, bmp1, bmp2, bmp2a, bmp2b1, bmp3, bmp4, bmp5, bmp6, bmp7, bmp8, bmpr1a, bmpr1b, bmx, bmyb, bn51t, bnc, bnc1, bnp, bor, bpad, bpag1, bpag2, bpes, bpes1, bpes2, bpgm, bph1, bpi, br, br140, braf, brca1, brca2, brca3, brcacox, brcd1, brcd2, brdt, brf1, brhc, bric, brks, bm3a, bm3b, bm3c, brm1, brw1c, bs, bsap, bsep, bsf2, bsg, bsnd, bss1, bst1, bst2, btak, btc, btd, bteb, bteb1, btg1, btg2, bths, btk, btk1, btn, bts, bub1b, bubr1, bwr1a, bwr1b, bws, bwscr1a, bwscr1b, bzrp, bzx, c11orf13, c1nh, c1qa, c1qb, c1qbp, c1qg, c1r, c1s, c2, c21orf1, c21orf2, c21orf3, c2ta, c3, c3br, c3dr, c3g, c4a, c4b, c4 bpa, c4 bpb, c4f, c4s, c5, c5ar, c5r1, c6, c7, c8a, c8b, c8g, c9, ca1, ca12, ca125, ca2, ca21 h, ca3, ca4, ca5, ca6, ca7, ca8, ca9, caaf1, cabp9k, cac, cac, caca, cacd, cacna1a, cacna1b, cacna1c, cacna1d, cacna1e, cacna1f, cacna1s, cacna2, cacnb1, cacnb2, cacnb3, cacnb4, cacng, cacnl1a1, cacnl1a2, cacnl1a3, cacnl1a4, cacnl1a5, cacnl1a6, cacnl2a, cacnlb1, cacnlg, cacp, cact, cacy, cad, cad11, cadasi1, cae1, cae3, caf, caf1a, caga, cagb, cain, cak, cak1, cal11, calb1, calb2, calb3, calc1, calc2, calca, calcb, calcr, cald1, calla, calm1, calm2, calm3, calm11, calm13, calna, calna3, calnb, calnb1, calr, cals, calt, calu, cam, camk4, camkg, caml1, camlg, camp, can, canp3, canx, cap2, cap3, cap37, capb, capg, capl, capn1, capn2, capn3, capn4, cappa2, cappb, capr, caps, capza2, capzb, car, carp, cars, cart1, cas, cas2, casi1, casp1, casp10, casp2, casp3, casp3, casp4, casp5, casp6, casp7, casp8, casq1, casq2, casr cast, cat, cat1, cat4, catf1, catm, cav1, cav2, cav3, cbbm, cbd, cbfa1, cbfa2, cbfa2t1, cbfa3, cbfb, cbg, cb1, cbl2, cbln2, cbp, cbp, cbp2, cbp68, cbr1, cbs, cbt, cbt1, cc10, cca, cca1, ccal 1, cca12, ccb11, ccckr5, ccg1, ccg2, cchl1a1, cchl1a2, cchl1a3, cch1b1, cck, cckar, cckbr, cc1, ccm1, ccm2, ccm3, ccn1, ccna, ccnb1, ccnc, ccnd1, ccnd2, ccnd3, ccne, ccnf, ccng1, ccnh, ccnt, ccnt1, cco, ccr10, ccr2, ccr3, ccr9, ccsp, cct, ccv, cczs, cd, cd10, cd11a, cd11b, cd11c, cd13, cd137, cd14, cd15, cd151, cd156, cd16, cd164, cd18, cd19, cd1a, cd1b, cd1c, cd1d, cd1e, cd2, cd20, cd22, cd23, cd24, cd26, cd27, cd271, cd28, cd281g, cd281g2, cd30, cd32, cd33, cd34, cd36, cd3611, cd3612, cd37, cd38, cd39, cd3911, cd3d, cd3e, cd3g, cd3z, cd4, cd40, cd401g, cd41b, cd43, cd44, cd45, cd46, cd47, cd48, cd49b, cd49d, cd5, cd53, cd57, cd58, cd59, cd51, cd6, cd63, cd64, cd68, cd69, cd7, cd70, cd71, cd72, cd74, cd79a, cd79b, cd80, cd81, cd82, cd82, cd86, cd8a, cd8b, cd8b1, cd9, cd94, cd95, cd97, cd99, cda, cda1, cda3, cdan1, cdan2, cdan3, cdb2, cdc2, cdc20, cdc25a, cdc25b, cdc25c, cdc27, cdc211, cdc212, cdc214, cdc34, cdc42, cdc51, cdc7, cdc711, cdcd1, cdcd2, cdcd3, cdc11, cdcre1, cdg1, cdgd1, cdgg1, cdgs2, cdh1, cdh11, cdh12, cdh13, cdh14, cdh15, cdh16, cdh16, cdh17, cd2, cdh3, cdh3, cdh5, cdh7, cdh8, cdhb, cdhh, cdhp, cdhs, cdk2, cdk3, cdk4, cdk5, cdk7, cdk8, cdk9, cdkn1, cdkn1a, cdkn1b, cdkn1c, cdkn2a, cdkn2b, cdkn2d, cdkn3, cdkn4, cdl1, cdm, cdmp1, cdmt, cdpx1, cdpx2, cdpxr, cdr1, cdr2, cdr3, cdr62a, cdsn, cdsp, cdtb, cdw50, cdx1, cdx2, cdx3, cdx4, cea, cebp, cebpa, cebpb, cebpd, cebpe, cecr, cel, cel1, cen1, cenpa, cenpb, cenpc, cenpc1, cenpe, cenpf, cerd4, ces, ces1, cetn1, cetp, cf, cf2r, cfag, cfag, cfc, cfd1, cfeom1, cfeom2, cfh, cfl1, cfl2, cfnd, cfns, cftr, cg1, cga, cgat, cgb, cgd, cgfl, cgh, cgrp, cgs23, cgt, cgthba, chac, chat, chc1, chd1, chd2, chd3, chd4, chd5, chdr, che1, che2, ched, chek1, chga, chgb, chgc, chh, chi311, chip28, chit, chk1, chlr1, chlr2, chm, chm1, chn, chn1, chn2, chop10, chr, chr39a, chr39b, chr39c, chrm1, chrm2, chrm3, chrm4, chrm5, chrna1, chrna2, chrna3, chrna4, chrna5, chrna7, chrnb1, chrnb2, chrnb3, chrnb4, chrnd, chrne, chrng, chrs, chs1, chx10, ciipx, cip1, cirbp, cish, ck2a1, ckap1, ckb, ckbb, ckbe, ckm, ckmm, ckmt1, ckmt2, ckn1, ckn2, ckr3, ckr11, ckr13, cl, cl100, cla1, cla1, clac, clapb1, clapm1, claps3, clc, clc7, clck2, clcn1, clcn2, clcn3, clcn4, clcn5, clcn6, clcn7, clcnka, clcnkb, cld, cldn3, cldn5, clg, clg1, clg3, clg4a, clg4b, cli, clim1, clim2, clk2, clk3, cln1, cln2, cln3, cln5, cln6, cln80, clns1a, clns1b, clp, clpp, clps, clta, cltb, cltc, cltc11, cltd, clth, clu, cma1, cmah, cmar, cmd1, cmd1a, cmd1b, cmd1c, cmd1d, cmd1e, cmd1f, cmd3a, cmdj, cmh1, cmh2, cmh3, cmh4, cmh6, cmkbr1, cmkbr2, cmkbr3, cmkbr5, cmkbr6, cmkbr7, cmkbr8, cmkbr9, cmkbr12, cmklr1, cmkr11, cmkr12, cml, cmm, cmm2, cmoat, cmp, cmpd1, cmpd2, cmpd3, cmpx1, cmt1a, cmt1b, cmt2a, cmt2b, cmt2d, cmt2d, cmt4a, cmt4b, cmtnd, cmtx1, cmtx2, cna1, cna2, cnbp1, cnc, cncg1, cncg2, cncg31, cnd, cng3, cnga1, cnga3, cngb1, cnn1, cnn2, cnn3, cnp, cnr1, cnsn, cntf, cntfr, cntn1, co, cocal, coca2, coch, cod1, cod2, coh1, coi1, col10a1, col11a1, col1a2, col12a11, col13a1, col15a1, col16a1, col17a1, col18a1, col19a1, col1a1, col1a2, col1ar, col2a1, col3a1, col4a1, col4a2, col4a3, col4a4, col4a5, col4a6, col5a1, col5a2, col6a1, col6a2, col6a3, col7a1, col8a1, col8a2, col9a1, col9a1, col9a2, col9a3, colq, comp, comt, copeb, copt1, copt2, cord1, cord2, cord5, cord6, cort, cot, cox10, cox4, cox5b, cox6a1, cox6b, cox7a1, cox7a2, cox7a3, cox7am, cox8, cp, cp107, cp115, cp20, cp47, cp49, cpa1, cpa3, cpb2, cpb2, cpd, cpe, cpetr2, cpm, cpn, cpn1, cpn2, cpo, cpp, cpp32, cpp32, cppi, cpsl, cpsb, cpsd, cpt1a, cpt1b, cpt2, cpu, cpx, cpx, cpxd, cr1, cr2, cr3a, crabp1, crabp2, crapb, crarf, crat, crbp1, crbp2, crd, crd1, creb1, creb2, crebbp, creb11, crem, crfb4, crfr2, crh, crhbp, crhr, crhr1, crhr2, crip, crk, crk1, crm1, crmp1, crmp2, crp, crp1, crs, crs1c, crs2, crs3, crsa, crt, crtl1, crtm, crx, cry1, cry2, crya1, crya2, cryaa, cryab, cryb1, cryb2, cryb3, cryba1, cryba2, cryba4, crybb1, crybb2, crybb3, cryg1, cryg2, cryg3, cryg4, cryg8, cryg, cryga, crygb, crygc, crygd, crygs, crym, cryz, cs, csa, csb, csbp1, csci, csd, csd2, csda, cse, cse11, csf1, csf1r, csf2, csf2ra, csf2rb, csf2ry, cs3, csf3r, csh1, csh2, csk, csmf, csn1, csn10, csn2, csn3, csnb1, csnb2, csnb3, csnk1a1, csnk1d, csnk1e, csnk1g2, csnk2a1, csnk2a2, csnk2b, csnu3, cso, cspb, cspg1, cspg2, cspg3, csr, csrb, csrp1, csrp2, cst1, cst1, cst2, cst3, cst4, cst4, cst5, cst6, csta, cstb, csx, ct2, ctaa1, ctaa2, ctag, ctb, ctbp1, ctbp2, ctgf, cth, cthm, ctk, ctla1, ctla3, ctla4, ctla8, ctm, ctnna1, ctnna2, ctnnb1, ctnnd, ctnnd1, ctnr, ctns, ctp, ctpct, ctps, ctr1, ctr2, ctrb1, ctrl, ctsa, ctsb, ctsc, ctsd, ctse, ctsg, ctsg12, ctsh, ctsk, ctsl, ctss, ctsw, ctsz, ctx, cubn, cul3, cul4b, cul5, cutl1, cvap, cvd1, cv1, cx26, cx31, cx32, cx37, cx40, cx43, cx46, cx50, cxb3s, cxcr4, cxorf4, cyb5, cyb561, cyba, cybb, cyc1, cyk4, cyld1, cymp, cyp1, cyp11a, cyp11b1, cyp11b2, cyp17, cyp19, cyp1a1, cyp1a2, cyp1b1, cyp21, cyp24, cyp27, cyp27a1, cyp27b1, cyp2a, cyp2a3, cyp2a6, cyp2b, cyp2c, cyp2c19, cyp2c9, cyp2d, cyp2d, cyp2e, cyp2e1, cyp2f1, cyp2j2, cyp3a4, cyp4a11, cyp4b1, cyp51, cyp7, cyp7a1, cyr61, cyrn1, cyrn2, czp3, d10s105e, d10s170, d10s170, d11s302e, d11s636, d11s813e, d11s833e, d12s2489e, d12s53e, d13s1056e, d13s25, d14s46e, d15s12, d15s226e, d15s227e, d16s2531e, d16s469e, d17s136e, d17s811e, d18s892e, d19s204, d19s381e, d1s111, d1s155e, d1s166e, d1s1733e, d1s2223e, d1s61, d2h, d2s201e, d2s448, d2s488e, d2s69e, d3s1231e, d3s1319e, d3s48e, d4, d4s90, d5s1708, d5s346, d6, d6s1101, d6s207e, d6s2245e, d6s228e, d6s229e, d6s230e, d6s231e, d6s51e, d6s52e, d6s54e, d6s81e, d6s82e, d7s437, d8s2298e, d9s46e, da1, da2b, dab2, dac, dad1, daf, dag, dag1, dag2, dagk1, dagk4, dam10, dam6, damox, dan, dao, dap, dap3, dap5, dapk1, dar, dat1, dax1, daxx, daz, dazh, dazl, dba, dbccr1, dbcn, dbh, dbi, dbi, dbl, dbm, dbn1, dbp, dbp, dbp1, dbp2, dbpa, dbt, dbx, dby, dcc, dce, dci, dck, dcn, dcoh, dcp1, dcr, dcr3, dct, dctn1, dcx, ddb1, ddb2, ddc, ddh1, ddh2, ddit1, ddit3, ddost, ddp, ddpac, ddr, ddx1, ddx10, ddx11, ddx12, ddx15, ddx16, ddx2a, ddx3, ddx5, ddx6, ddx9, dec, decr, def1, def4, def5, def6, defa1, defa4, defa5, defa6, defb1, defb2, dek, denn, dents, dep1, der12, des, dff1, dffa, dffrx, dffry, dfn1, dfn2, dfn3, dfn4, dfn6, dfna1, dfna10, dfna11, dfna12, dfna13, dfna2, dfna2, dfna4, dfna5, dfna6, dfna7, dfna8, dfna9, dfnb1, dfnb12, dfnb13, dfnb14, dfnb16, dfnb17, dfnb18, dfnb2, dfnb3, dfnb4, dfnb5, dfnb6, dfnb7, dfnb8, dfnb9, dgcr, dgcr2, dgcr2, dgcr6, dgi1, dgka, dgkq, dgpt, dgpt, dgs, dgs2, dgsi, dgu, dhc2, dhcr7, dhfr, dhlag, dhp, dhpr, dhps, dhrd, dhtr, di, di1, dia, dia1, dia2, dia4, diaph1, diaph2, dif2, diff6, dipi, dir, dkc, dkc1, dlc1, dld, dlg1, dlg2, dlg3, dlg4, dlst, dlx1, dlx2, dlx2, dl3, dlx4, dlx5, dlx6, dlx7, dlx8, dm, dm2, dmahp, dmbt1, dmd, dmda1, dmd1, dmh, dmk, dmpl, dmpk, dmsfh, dmt, dmt1, dmtn, dna21, dnah, dnah1, dnah 11, dnah12, dnah2, dnahc1, dnahc11, dnahc2, dnahc3, dnase1, dnase111, dnase 113, dnase2, dnch2, dnc1, dncm, dnec1, dne11, dn1, dn11, dn111, dnm1, dnmt1, dnmt2, dnpk1, dns, dntt, do, doc1, doc2, dock1, dock180, dod, dok1, dom, dp1, dp1, dp2, dp3, dpagt2, dpc4, dpd, dpde1, dpde2, dpde3, dpde4, dpep1, dph212, dpp, dpp4, dpp6, dpt, dpyd, dpys, dpys11, dpys12, dr1, dr3, dr31g, dr5, dra, drad, drada, dra1, drd1, drd1b, drd1b, drd112, drd2, drd3, drd4, drd5, dri11, drp1, drp1, drp2, drp2, drp3, drp1a, drt, dsc1, dsc2, dsc3, dsc3, dsc4, dscam, dscr, dsg1, dsg2, dsg3, dsp, dspg3, dspp, dss, dss1, dtd, dtdp2, dtdst, dtna, dtr, dts, dus, dusp1, dusp11, dusp2, dusp3, dusp4, dusp5, dusp6, dusp7, dusp8, dut, dv1, dv11, dv11, dv13, dxf68sle, dxs1272e, dxs128, dxs1283e, dxs423e, dxs435e, dxs522e, dxs648, dxs707, dxs8237e, dxys155e, dylx2, dyrk, dys, dysf, dyt1, dyt3, dyt5, dyt6, dyt7, dyt8, dyt9, dyx1, dyx2, e11s, e14, e1b, e2a, e2f1, e2f2, e2f3, e2f4, e3, e4f, e4f1, e4tf1a, e4tf1b, ea1, eaac1, eaat1, eaat2, eac, ead, eag, eap, ear1, ear2, ear3, ebaf, ebf, ebi1, ebm, ebn1, ebn1, ebn2, ebr2a, ebs1, ebvm1, ebvs1, ec1, eca1, ecb2, ece1, ecgf1, ech1, echs1, eck, ecm1, ecp, ecs1, ect2, ed1, ed2, ed3, ed4, eda, eda3, eddr1, edg3, edg6, edh, edh17b2, edh17b2, edh17b3, edm1, edm2, edm3, edmd, edmd2, edn, edn1, edn2, edn3, ednra, ednrb, eec1, eec2, eef1a1, eef1a2, eef1b1, eef1b2, eef1b3, eef1b4, eef2, eeg1, eegv1, eek, een, ef1a, ef2, efe2, efemp1, efl6, efmr, efna1, efna3, efna4, efnb1, efnb2, efnb3, efp, eftu, egf, egfr, egi, egr1, egr2, egr3, egr4, ehhadh, ehoc1, ei, eif1a, eif2gA, eif2s3 A, eif3s10, eif3s6, eif4a1, eif4a2, eif4c, eif4e, eif4ebp1, eif4e2, eif4e11, eif4e12, eif4g, eif4g1, eif4g2, eif5a, ejm1, el1, ela1, ela2, elam1, elanh2, elav11, elav12, elav14, elc, ele1, elf3, elk1, elk2, elk3, elk4, el1, eln, em9, emap, emap1, emd, emd2, emk 1, emp1, emp55, emr1, ems1, emt, emtb, emx1, emx2, en1, en2, ena78, end, endog, enfl2, eng, en1, eno1, eno2, eno3, enpep, ent1, entk, enur1, enur2, enx2, eos, ep3, ep300, epa, epb3, epb311, epb41, epb4112, epb42, epb49, epb72, epha1, epha2, epha3, epha8, ephb1, ephb2, ephb3, ephb4, ephb6, epht1, epht2, epht3, ephx1, ephx2, epim, eplg1, eplg2, eplg3, eplg4, eplg5, eplg8, epm1, epm2, epm2a, epmr, epo, epor, eppk, eprs, eps15, eps8, ept, erba1, erba2, erba12, erba13, erbb2, erbb3, erbb4, erc55, ercc1, ercc2, ercc3, ercc4, ercc5, ercc6, ercm1, erda1, erf1, erg, erg3, ergic53, erh, erk, erk1, erk2, erk3, erm, erp11, erv1, erv1, erv3, ervr, ervt1ervt2, ervt3, ervt4, ervt5, eryf1, es1, es130, esa, esa1, esa4, esat, esb3, esd, esg, esr, esr1, esr2, esr11, esr12, esrra, esrrb, esrrg, ess1, est, est1, est2, est25263, esx, etfa, etfb, etfdh, etk1, etk2, etm1, etm2, eto, ets1, ets2, ety1, etv3, etv4, etv5, etv6, evc, evc1, evda, evdb, evi1, evi2, evi2a, evi2b, evp1, evr1, evx1, evx2, ews, ewsr1, exlm1, ext1, ext2, ext3, ext11, ext12, eya1, eya2, eya3, eyc11, eyc13, ezh1, ezh1, ezh2, f10, f11, f12, f13a, f13a1, f13b, f2, f2r, f2r12, f2r13, f3, f5, f5f8d, f7, f7e, f7r, f8a, f8b, f8c, f8vwf, f9, fa, fa1, faa, fabp1, fabp2fabp3, fabp4, fabp6, facd, faca, facc, facd, face, fac11, fac12, fac13, fac14, facv11, fad, fadd, fadk, fah, fak2, faldh, fal139, falz, fanca, fancc, fancd, fance, fancg, fap, fapa, farr, fas, fasl, fasn, fast1, fat, fau, fbln1, fbln2, fbn1, fbn2, fbn1, fbp1, fcar, fcc1, fce, fce2, fcer1a, fcer1b, fcer1g, fcer2, fcgr1a, fcgr1b, fcgr1c, fcgr2a, fcgr3a, fcgrt, fcmd, fcn1, fcn2, fcp, fcp1, fcpx, fct3a, fdc, fdft1, fdh, fdps11, fdps12, fdps13, fdps14, fdps15, fdx1, fdxr, fe65, fe6511, fea, feb1, feb2, fecb, fech, fen1, feo, feom, feom1, feom2, fer, fes, fet1, fevr, ffin, fga, fgarat, fgb, fgc, fgd1, fgdy, fgf1, fgf10, fgf11, fgf12, fgf3, fgf14, fgf2, fgf2, fgf3, fgf4, fgf5, fgf6, fgf7, fgf8, faf9, fgfa, fgfb, fgfr1, fgfr2, fgfr3, fgfr4, fgg, fgr, fgs1, fh, fh, fh3, fhc, fnf1, fhf3, fhf4, fhh2, fhit, fh11, fh12, fhr2, fic1, figf, fih, fim, fim1, fim3, fimg, fkbp12, fkbp1a, fkbp2, fkh2, fkh11, fkh1110, fkh112, fkh115, fkh116, fkh117, fkh12, fkh15, fkh16, fkh17, fkh18, fkh19, fkhr, fkhr11, flg, fli1, flii, fln1, fln2, flna, flnb, flnms, flot2, flt1, flt2, flt3, flt4, fmf, fmn, fmo1, fmo2, fmo3, fmod, finr1, finr2, fms, fl1, fn12, fnra, fnrb, fnrb1, fnta, fntb, folh, folh1, folr1, folr2, folt, fos, fosb, fos11, fos12, fpah, fpc, fpd1, fpdmm, fpf, fpgs, fpl, fpp, fpr1, fprh1, fprh2, fpr11, fpr12, fprp, fps12, fps13, fps14, fps15, fr, frap1, fraxa, fraxe, fraxf, frda, freac2, freac6, freac9, frg1, frp1, frv1, frv2, frv3, fsg1, fsgs, fshb, fshd1a, fshmd1a, fshprh1, fshr, fssv, fth1, fth16, ft1, ftz1, ftzf1, fuca1, fuca2, fur, fus, fuse, fut1, fut2, fut3, fut4, fut5, fut6, fut7, fut8, fvt1, fxr1, fxy, fy, fyn, fzd1, fzd2, fzd3, fzd5, fzd6, fzd7, fzr, g0s8, g10p1, g10p2, g17, g17 p1, g19p1, g1p1, g1p2, g1p3, g22p1, g6 pc, g6pd, g6pd1, g6pd1, g6pt, g6pt1, g6s, g7p1, ga2, gaa, gabatr, gabpa, gabpb1, gabra1, gabra2, gabra3, gabra4, gabra5, gabra6, gabrb1, gabrb2, gabrb3, gabrd, gabre, gabrg1, gabrg2, gabrg3, gabrr1, gabrr2, gad1, gad2, gad3, gadd153, gadd45, gak, gal, galbp, galc, gale, galgt, galk1, galk2, galn, galnact, galnr, galnr1, galns, galnt1, galnt2, galnt3, galr1, galt, gan, gan1, ganab, ganc, gap, gap1m, gap43, gapd, gar22, garp, gars, gart, gas, gas1, gas2, gas41, gas6, gas7, gasr, gast, gata1, gata2, gata3, gata4, gata6, gay1, gba, gbas, gbbb1, gbbb2, gbe1, gbp1, gbx2, gc, gcap, gcap2, gcdh, gcf1, gcf2, gcfx, gcg, gcgr, gch1, gck, gckr, gcn511, gcn512, gcnf, gcnt1, gcnt2, gcp, gcp2, gcs, gcs1, gcsf, gcsfr, gcsp, gctg, gcy, gda, gde, gdf5, gdf8, gdh, gdi1, gdi2, gdid4, gdld, gdnf, gdnfr, gdnfra, gdnfrb, gdx, gdxy, ge, gem, geney, gey, gf1, gfl, gfap, gfer, gfer, gfi1, gfpt, gfra1, gfra2, ggcx, ggt1, ggt2, ggta1, ggtb1, ggtb2, gh1, gh2, Ghc®, ghdx, ghn, ghr, ghrf, ghrh, ghrhr, ghs, ghv, gif, gifb, gip, gip, gipr, girk1, girk2, girk3, girk4, gja1, gja3, gja4, gjaS, gja8, gjb1, gjb2, gjb3, gk, gk2, gla, glat, glb1, glb2, glc1a, glc1b, glc1c, glc1d, glc1f, glc3a, glc3b, glc1c, glc1r, glct2, glct3, gldc, glepp1, glg1, gli, gli2, gli3, gli4, glnn, glns, glo1, glo2, glp1r, glra1, glra2, glra3, glrb, glrx, gls, glud1, glud2, glu1, glur1, glur2, glur3, glur4, glur5, glur6, glur7, glut1, glut2, glut3, glut4, glut5, glvr1, glvr2, gly96, glya, glyb, glys1, glyt1, glyt1, glyt2, gm2a, gma, gmcsf, gmds, gm1, gmpr, gmps, gna11, gna15, gna16, gnai1, gnai2, gnai2a, gnai2b, gnai21, gnai3, gna1, gnao1, gnaq, gnas, gnas1, gnat1, gnat2, gnaz, gnb1, gnb2, gnb3, gng5, gnl1, gnpta, gnrh1, gnrh2, gnrhr, gns, gnt1, golga4, got1, got2, gp130, gp1ba, gp1bb, gp2, gp2b, gp39, gp3a, gp75, gp78, gp9, gpa, gpam, gpat, gpb, gpc, gpc1, gpc3, gpc4, gpd, gpd1, gpd2, gpds1, gpe, gpi, gpi2, gpm6a, gpm6b, gpoa, gpr1, gpr10, gpr11, gpr12, gpr13, gpr15, gpr17, gpr18, gpr19, gpr2, gpr20, gpr21, gpr22, gpr23, gpr25, gpr29, gpr3, gpr30, gpr31, gpr32, gpr35, gpr37, gpr39, gpr4, gpr5, gpr6, gpr7, gpr8, gpr9, grcy4, gprk21, gprk4, gprk5, gprk6, gprv28, gpsa, gpsc, gpt, gpx1, gpx2, gpx3, gpx4, gr2, grb1, grb10, grb2, grf2, gria1, gria2, gria3, gria4, grid2, grik1, grik2, grik3, grik4, grik5, grin1, grin2a, grin2b, grin2c, grin2d, grina, grk1, grk5, grk6, gr1, gr111, grm3, grm8, grmp, grn, gro1, gro2, gro3, grp, grp58, grp78, grpr, grx, gs, gs1, gsas, gsc, gsc1, gse, gshs, gs1, gsm1, gsn, gsp, gspt1, gsr, gss, gst12, gst11, gst2, gst2, gst3, gst4, gst5, gsta1, gsta2, gstm1, gstm11, gstm2, gstm3, gstm4, gstm5, gstp1, gstt2, gt1, gt335, gta, gtb, gtbp, gtd, gtf2e2, gtf2f1, gtf2h1, gtf2h2, gtf2h4, gtf21, gtf2s, gtf3a, gtg, guc1a2, guc1a3, guc1b3, guc2c, guc2d, guc2f, guca1a, guca1b, guca2, guca2, guca2a, guca2b, gucsa3, gucsb3, gucy1a2, gucy1a3, gucy1b3, gucy2c, gucy2d, gucy2f, guk1, guk2, gulo, gulop, gusb, gusm, gust, gxp1, gypa, gypb, gypc, gype, gys, gys1, gys2, gzma, gzmb, gzmh, gzmm, h, h142t, h19, h1f0, h1f1, h1f2, h1f3, h1f4, h1f5, h1fv, h2a, h2ax, h2az, h2b, h2b, h3f2, h3f3b, h3 ft, h3t, h4, h4f2, h4f5, h4fa, h4fb, h4fe, h4fg, h4fh, h4fi, h4fj, h4fk, h4fl, h4m, h4m, h6, ha2, habp1, hadha, hadhb, hadhsc, haf, hagh, hah1, haip1, hal, hap, hap1, hap2, hars, has2, hat1, hausp, hb1, hb1, hb6, hba1, hba2, hbac, hbb, hbbc, hbd, hbe1, hbegf, hbf2, hbg1, hbg2, hbgr, hbhr, hbm, hbp, hbq1, hbz, hc2, hc3, hca, hcat2, hccs, hcdh, hcf2, hcfc1, hcg, hck, h11, hc12, hc13, hcls1, hcp, hcp1, hcs, hcvs, hd, hdac1, hdc, hdgf, hdhc7, hdlbp, hdld, hdldt1, hdr, hed, hed, hegf1, hek, hek3, heln1, hem1, hema, hemb, hemc, hempas, hen1, hen2, hep, hep10, her2, her4, herg, herv1, hes1, hesx1, het, hexa, hexb, hf1, hf10, hfc1, hfe, hfe2, hfh11, hfsp, hgd, hgf, hgf1, hg1, hh, hh72, hhc1, hhc2, hhd, hhh, hhmjg, hhr23a, hht1, hht2, hiap2, higm1, hilda, hint, hiomt, hip, hip1, hip116, hip2, hir, hira, his1, his2, hive1, hivep1, hivep2, hjcd, hk1, hk2, hk3, hk33, hke4, hke6, hkr1, hkr2, hkr3, hkr4, hl 11, hl19, hla-a, hla-b, hla-c, hla-cda12, hla-dma, hla-dmb, hla-dna, hla-dob, hla-dpa1hla-dpb1, hla-dqa1, hla-drlb, hla-dra, hla-e, hla-f, hla-g, hla-ha2, hladp, hlaf, hlals, hlcs, hlm2, hlp, hlp3, hlr1, hlr2, hlt, hlx1, hlxb9, hmaa, hmab, hmat1, hmbs, hmcs, hmg1, hmg14, hmg17, hmg2, hmgc1, hmgcr, hmgcs1, hmgcs2, hmgic, hmgiy, hmgx, hmmr, hmn2, hmox1, hmox2, hmr, hms1, hmsn1, hmx1, hmx2, hnd, hnf1a, hnf2, hnf3a, hnf3b, hnf4a, hnp36, hnpcc6, hnrpa1, hnrpa2b1, hnrpd, hnrpf, hnrpg, hnrph1, hnrph2, hnrph3, hnrpk, homg, hops, hox10, hox11, hox12, hox1, hox1a, hox1b, hox1c, hox1d, hox1e, hox1f, hox1g, hox1h, hox1i, hox1j, hox2, hox2a, hox2b, hox2c, hox2d, hox2e, hox2f, hox2g, hox2h, hox2i, hox3, hox3a, hox3b, hox3c, hox3d, hox3e, hox3f, hox3g, hox4, hox4a, hox4b, hox4c, hox4d, hox4e, hox4f, hox4g, hox4h, hox4i, hox7, hox8, hoxa1, hoxa10, hoxa11, hoxa13, hoxa3, hoxa4, hoxa5, hoxa6, hoxa7, hoxa9, hoxa, hoxb1, hoxb2, hoxb3, hoxb4, hoxb5, hoxb6, hoxb7, hoxb8, hoxb9, hoxb, hoxc12, hoxc13, hoxc4, hoxc5, hoxc6, hoxc8, hoxc9, hoxc, hoxd1, hoxd10, hoxd11, hoxd12, hoxd13, hoxd3, hoxd4, hoxd8, hoxd9, hoxd, hoxhb9, hp, hp4, hpafp, hpc1, hpc2, hpca, hpca11, hpcx, hpd, hpdr1, hpdr2, hpe1, hpe2, hpe3, hpe4, hpe5, hpect1, hpfh, hpfh2, hpgd, hplh1, hplh2, hpn, hpr, hprt, hprt1, hps, hpt, hpt1, hptp, hptx, hpv18i1, hpv18i2, hpx, hr, hras, hrb, hrc, hrc1, hrca1, hrd, hres1, hrf, hrg, hrga, hrh1, hrh2, hrmt1l1, hrpt2, hrx, hrx, hry, hsa11, hsa12, hsan1, hsas1, hscr2, hsd11, hsd11b1, hsd11b2, hsd11k, hsd11l, hsd17b1, hsd17b2, hsd17b3, hsd17b4, hsd3b1, hsd3b2, hsh, hsn1, hsorc1, hsp27, hsp73, hspa1a, hspa1b, hspa11, hspa2, hspa3, hspa4, hspa5, hspa6, hspa7, hspa8, hspa9, hspb 1, hspb2, hspc2, hspca11, hspca12, hspca13, hspca14, hspcb, hspg1, hspg2, hsr1, hsst, hstd, hstf1, htc2, htf4, htk, htk1, ht1, htlf, htlvr, htn1, htn2, htn3, htnb, htor, htr1a, htr1b, htr1d, htr1e, htr1e1, htr1f, htr2a, htr2b, htr2c, htr3, htr4, htr5a, htr6, htr7, htrx1, hts1, htt, htx, htx1, hub, hud, hup2, hur, hus, hvls, hvbs1, hvbs6, hvbs7, hvem, hvh2, hvh3, hvh8, hxb, hxb1, hy, hya, hya11, hyd2, hygn1, hy1, hyp, hyplip1, hypp, hypx, hyr, hyrc1, hys, ia1, ia2, iap, iapp, iar, iars, ibd1, ibd2, ibm2, ibsp, ica1, icam1, icam2, icam3, icca, ich1, icr2, icr2b, ics1, id1, id2, id3, id4, ida, idd, iddm1, iddm10, iddm11, iddm12, iddm13, iddm15, iddm17, iddm2, iddm3, iddm4, iddm5, iddm6, iddm7, iddm8, iddmx, ide, idg2, idh1, idh2, idh3a, idh3g, ido, ids, idua, ier1, ier3, iex1, if, ifcr, ifgr2, ifi16, ifi27, ifi35, ifi4, ifi5111, ifi54, ifi56, ifi616, ifi78, ifna1, ifna10, ifna13, ifna14, ifna16, iffia17, iffia21, ifna6, ifna7, ifna8, ifna, ifnai1, ifnar1, ifnar2, ifnb1, ifnb2, ifnb3, ifng, ifngr1, ifngr2, ifngt1, ifnr, ifnw1, ifrd2, iga, igat, igb, igbp1, igd1, igda1, igdc1, igds2, iger, iges, igf1, igf1r, igf2, igf2r, igfbp1, igfbp10, igfbp2, igfbp3, igfbp4, igfbp6, igfbp7, igfr1, igfr2, igfr3, igh, igha1, igha2, ighd, ighdy2, ighe, ighg1, ighg2, ighg3, ighg4, ighj, ighm, ighmbp2, ighr, ighv, igi, igj, igk, igkc, igkde1, igkj, igkjrb1, igkv, iglc, iglc1, iglj, iglp1, iglp2, iglv, igm, igo1, igsf1, ihh, ik1, ikba, il10, il10r, il11a, il11ra, il12a, il12b, il12rb1, il12rb2, il13, il13ra1, il13ra2, il15, il15ra, il17, il1a, il1b, il1bc, il1r1, il1r2, il1ra, il1rap, il1rb, il1rn, il2, il2r, il2ra, il2rb, il2rg, il3, il3ra, il3ray, il4, il4r, il4ra, il5, il5ra, il6, il6r, il6st, il7, il7r, il8, il8ra, il8rb, il9, il9r, ila, ilf1, illbp, imd1, imd2, imd4, imd5, imd6, impa1, impdh1, impdh2, impdh11, impg1, impt1, indx, infa2, infa4, infa5, ing1, inha, inhba, inhbb, inhbc, ini1, ink4b, inlu, inp10, inpp1, inpp5a, inpp5b, inpp5d, inpp11, ins, insig1, ins1, ins13, ins14, insr, insrr, int1, int111, int2, int3, int4, int6, iosca, ip2, ipf1, ip1, ipm150, ipox, ipp, ipp2, ipw, iqgap1, ir10, ir20, ireb1, ireb2, irf1, irf2, irf4, irf4, irr, irs1, isa, iscw, is11, islr, isot, issx, it15, itba1, itba2, itf, itf2, itga1, itga2, itga2b, itga4, itga5, itga6, itga7, itgad, itga1, itgam, itgav, itgax, itgb1, itgb2, itgb3, itgb4, itgb6, itgb7, iti, itih1, itih2, itih3, itih4, itih11, iti1, itk, itm1, itpa, itpka, itpkb, itpr1, itpr2, itpr3, itsn, ivd, iv1, jag1, jak1, jak2, jak3, jbs, jcap, jh8, jip, jk, jme, jmj, joag, jpd, jrk, jrk1, jtk14, jty1, jun, junb, jund, jup, jv18, jws, k12t, kai1, kal1, kar, kars, katp1, kcna1, kcna10, kcna1b, kcna2b, kcna3, kcna4, kcna5, kcna6, kcna7, kcna8, kcna9, kcnab1, kcnab2, kcnb1, kcnc1, kcnc2, kcnc3, kcnc4, kcne1, kcnh1, kcnh2, kcnj1, kcnj10, kcnj11, kcnj12, kcnj15, kcnj3, kcnj4, kcnj5, kcnj6, kcnj7, kcnj8, kcnjn1, kcnk1, kcnk2, kcnk3, kcnma1, kcnq1, kcnq2, kcnq3, kcnq4, kcns2, kd, kdr, ke1, kera, kf1, kfs, kfsd, kfs1, khk, kiaa0122, kid, kid1, kif2, kif3c, kif5b, kip1, kip2, kiss1, kit, klc2, klk1, klk2, klk3, klk3, klkb1, klkr, klrb1, klrc1, klrc2, klrc3, klrc4, klrd1, klst, kms, kms, kng, kno, kns1, kns2, kns11, kns14, kox1, kox11, kox12, kox13, kox15, kox16, kox18, kox19, kox2, kox2, kox22, kox25, kox30, kox32, kox4, kox5, kox6, kox7, kox9, kpna3, kpps1, kpps2, krag, kras1p, kras2, krev1, krg2, krn1, krn11, krox20, krt1, krt10, krt12, krt13, krt14, krt15, krt16, krt17, krt18, krt19, krt2a, krt2e, krt3, krt4, krt5, krt6a, krt6b, krt7, krt8, krt9, krtha2, krtha5, krthb1, krthb6, ks, ktn1, ku70, kup, kylqt1, kwe, 11.2, 11 cam, 123mrp, lab7, lab72, lac, laci, lacs, lad, lad, lad1, laf4, lag3, lag5, lair1, lak1, lalba, lal1, lam1, lama1, lama2, lama3, lama3, lama4, lama5, lamb1, lamb2, lamb2, lamb2t, lamb3, lambr, lamc1, lamc2, lamm, lamnb2, lamp, lamp1, lamp2, lamr1, lams, lap, lap18, laptm5, lar, lar1, lard, large, lars, lbp, lbr, lca, lca1, lcad, lcamb, lcat, lccs, lcfs2, lch, lck, lcn1, lcn2, lco, lcp1, lcp2, lct, ld, ld78, ldb1, ldb2, ldc, ldh1, ldh3, ldha, ldhb, ldhc, ldlr, le, lect2, lef1, lefty1, lefty2, lep, lepr, lerk5, lerk8, leu1, leu7, leut, lfala, lfa3, lfh11, lfp, igals1, lgals3, lgals3 bp, lgals7, lgcr, lgmd1, lgmd1a, lgmd1b, lgmd1c, lgmd1d, lgmd2b, lgmd2c, lgmd2d, lgmd2e, lgmd2f, lgmd2g, lgmd2h, lgs, lgtn, lhb, lhcgr, lhs, lhx1, lhx3, li, li2, lif, lifr, lig1, lig3, lig4, lim1, lim2, limab1, limk1, limpii, lip2, lipa, lipb, lipc, lipd, lipe, lipo, lis1, lis2, lisx, litaf, lkb1, lkn1, llg11, lman1, lmn1, lmn2, lmna, lmnb1, lmnb2, lmo1, lmo2, lmo3, lmo4, lmo5, lmp10, lmp2, lmp7, lmpx, lms, lmx1, lmx1a, lmx1b, lmyc, lnhr, lnrh, locr, loh11cr2a, lor, lot1, lox, lox1, lox11, lpa, lpaab, lpaata, lpap lpc1, lpc2d, lpd1, lph, lpi, lp1, lpna3, lpp, lps, lpsa, lqt1, lqt2, lqt3, lqt4, lr3, lre1, lre2, lrp, lrp1, lrp2, lrp5, lrp7, lrp8, lrpap1, lrpr1, lrs1, lsamp, lsirf, ls1, lsn, lsp1, lss, lst1, lta, lta4h, ltb, ltb4r, ltbp1, ltbp2, ltbp2, ltbp3, ltbp3, ltbr, ltc4s, ltf, ltk, ltn, lu, lum, luxs, luzp, lw, ly64, ly6e, ly9, lyam1, lyb2, lyf1, ly11, lyn, lyp, lyst, lyt10, lyz, lztr1, m11s1, m130, m17s1, m17s2, m195, m1s1, m3s1, m4s1, m6a, m6b, m6p2, m6pr, m6s1, m7v1, m7vs1, mab211, mac1a, mac2, mac25, macam1, macs, mad, mad211, madd, madh1, madh2, madh3, madh4, madh5, madh6, madh6, madh7, madh9, madm, madr1, maf, mafd1, mafd2, mag, mage1, mageb3, mageb4, mage11, magoh, magp, magp1, magp2, mak, ma1, ma11, man2a2, mana1, mana2, mana2x, manb, manb1, manba, maoa, maob, map1a, map1a1c3, map1b, map1b1c3, map2, map4, map80, map97, mapk1, mapkap3, mapkkk4, mapt, mar, mark3, mars, mas1, masp1, mat1a, mat2a, mata1, mata2, matk, matn1, matn3, max, maz, mb, mbd1, mb1, mb2, mbp, mbp1, mbs, mbs2, mc1r, mc2r, mc3r, mc4r, mc5r, mcad, mcc, mcdc1, mcdr1, mcf2, mcf3, mcfd1, mch2, mch3, mch4, mch5, mckd, mc1, mc11, mcm, mcm2, mcm2, mcm3, mcm6, mcm7, mcmt, mcop, mcor, mcp, mcp1, mcp3, mcph1, mcr, mcs, mcsf, mcsp, mct1, md1, mdb, mdc, mdcr, mddc, mdeg, mdf1, mdg, mdg1, mdh1, mdh2, mdk, mdk, mdm2, mdm4, mdr1, mdr3, mdrs1, mdrv, mds, mds1, mdu1, mdu2, mdu3, mdx, me1, me2, mea, mea6, mec11, mecp2, med, mef, mef2a, mef2b, mef2c, mef2d, mefv, mehmo, meis1, meis2, mekk, mekk1, mekk4, me1, mel18, melf, memo1, men1, men2a, meox1, meox2, mep1a, mep1b, mer2, mer6, mest, met, metrs, mfap1, mfap2, mfap3, mfap4, mfd1, mfi2, mfs1, mfs2, mft, mfts, mg50, mga, mga1, mga3, mgat1, mgat2, mgat5, mgc1, mgcn, mgcr, mgct, mgdf, mgea, mgf, mgi, mgmt, mgp, mgsa, mgst1, mgst2, mhc, mhc2ta, mhp2, mhs, mhs2, mhs3, mhs4, mhs6, mia, mic10, mic11, mic12, mic17, mic18, mic2, mic2x, mic2y, mic3, mic4, mic7, mica, micb, mid1, midas, mif, mif, mig, mip, mip2a, mip2b, mip3b, mipep, mitf, miwc, mjd, mk, mki67, mkks, mkp2, mkp3, mkpx, mks, mks, mks1, mks2, m1a1, m1ck, m1f1, m1f2, m1h1, m1k1, m1k3, m11, m112, m11t1, m11t2, m11t3, m11t4, m11t6, m11t7, mlm, mlm, mln, mlp, mlr, mlrg, mlrw, mls, mltn, mlvar, mlvi2, mlvt, mmac1, mme, mmp1, mmp10, mmp11, mmp12, mmp13, mmp14, mmp15, mmp16, mmp17, mmp19, mmp2, mmp21, mmp22, mmp3, mmp7, mmp8, mmp9, mn, mn, mnb, mnbh, mnda, mng1, mnk, mns, mnt, mocod, mocs1, mocs2, mody1, mody3, mog, mok2, mom1, mos, mot2, mov34, mox1, mox2, mox44, moz, mp19, mpb1, mpd1, mpdz, mpe, mpe16, mpg, mpi, mpif2, mp1, mp11g, mpo, mpp 1, mpp2, mpp3, mppb, mpri, mpm, mps2, mps3a, mps3c, mps4a, mpsh, mpts, mpvl7, mpz, mr1, mr77, mrbc, mrc1, mre11, mre11a, mrg1, mrgh, mros, mrp, mrp, mrp1, mrp123, mrs, mrsd, mrsr, mrst, mrx1, mrx14, mrx2, mrx20, mrx21, mrx23, mrx29, mrx41, mrx48, mrx49, mrx9, mrxa, mrxs1, mrxs2, mrxs3, mrxs4, mrxs5, mrxs6, mrxs8, ms3315, ms336, msg1, msh2, msh3, msh4, msh6, msi1, msk16, msk39, msk41, mslr1, msmb, msn, msr1, mss1, mss4, mss4, msse, mst, mst1, mstr, mstd, mstn, msud1, msx1, msx2, mt1a, mt1b, mt1e, mt1f, mt1g, mt1h, mt1i, mt1j, mt1k, mt1l, mt1x, mt2, mt2a, mt3, mtacr1, mtap, mtbt1, mtcp1, mterf, mtf1, mthy1, mthfc, mthfd, mthfr, mtk1, mtm1, mtmr1, mtmx, mtnr1a, mtnr1b, mtp, mtpa, mtr, mtms, mtrr, mts, mts, mts1, mts1, mts2, mttf1, mtx, mtxn, mu, muc1, muc2, muc3, muc4, muc5, muc5ac, muc5b, muc6, muc8, mu1, mum1, muppl, musk, mut, mvk, mvlk, mvwf, mwfe, mx, mx1, mx2, mxi1, mxs1, myb, myb11, myb12, mybpc1, mybpc2, mybpc3, mybpcf, mybph, myc, myc11, myc12, myclk1, mycn, myd88, myf3, myf4, myf5, myf6, myh1, myh10, myh11, myh12, myh2, myh3, myh4, myh6, myh7, myh8, myh9, myk1, my1, my11, my12, my13, my14, my15, mylk, mymy, myo10, myo15, myo1a, myo1c, myo1d, myo1e, myo5a, myo6, myo7a, myo9b, myoc, myod1, myog, myp1, myp2, myp3, myr5, mzf1, n33, nab1, nab2, nabc1, nac1a, naca, nacae, nacp, nadmr, naga, nagc, naglu, nagr1, naip, namsd, nanta3, nap114, nap2, nap21, napb, naptb, nars, nat1, nat1, nat2, nb, nb4s, nbat, nbc3, nbccs, nbccs, nbia1, nbs, nbs, nbs1, nca, ncad, ncam1, ncan, ncbp, ncc1, ncc2, ncc3, ncc4, ncct, ncf1, ncf2, ncf4, nck, ncl, ncst2, ncx1, ncx2, nd, ndhii, ndn, ndp, ndst1, ndufa1, ndufa2, ndufa5, ndufa6, ndufa7, ndufb8, ndufb9, ndufs1, ndufs2, ndufs4, ndufs7, ndufs8, ndufv1, ndufv2, ndufv3, neb, nec1, nec2, nedd1, nedd2, nedd4, nefh, nef1, negf1, negf2, ne111, neb112, nem1, neo1, nep, net, net1, neu, neu, neud4, neurod, neurod2, neurod3, nf1, nf1a, nf2, nfatc1, nfatc2, nfatp, nfe1, nfe2, nfe211, nfe212, nfe2u, nfia, nfib, nfic, nfix, nfkb1, nfkb2, nfkb3, nfkbia, nfkbi11, nfrkb, nfya, nfyb, nga1, ngbe, ngfb, ngfg, ngfic, ngfr, ngl, ngn, nhbp, nhcp1, nhcp2, nhe1, nhe3, nhe4, nhe5, nhlh1, nhlh2, nhp211, nhs, nid, niddm1, ninj1, nipp1, nipsnap1, nipsnap2, nis, nklr, nkcc1, nkcc2, nkg2, nkg2a, nkg2c, nkg2e, nkg2f, nkhc, nkna, nknar, nknb, nkrpla, nksl, nksf2, nktr, nkx2a, nkx3.2, nkx3a, nkx6a, nli, nm, nm1, nm23, nmb, nmbr, mndar1, nmdar2a, nmdar2b, nmdar2c, nmdar2d, mndara1, nme1, nme2, nme4, nmor1, nmor2, nms1, nmyc, nnat, nmnt, nno1, nog, no11, nos1, nos2a, nos2b, nos2c, nos3, not, notch1, notch2, notch3, notch4, nov, nov, nov2, nova1, nova3, novp, np, np10, npat, npc, npc1, npd, nph1, nph2, nphl2, nphn, nphp1, nphp2, nphs1, npm1, nppa, nppb, nppc, npps, npr1, npr2, npr3, nps1, npt1, npt2, nptx2, npy, npy1r, npy2r, npy3r, npy5r, npy6r, nqo2, nramp, nramp1, nramp2, nrap, nras, nrb54, nrcam, nrd1, nrf1, nrf1, nrf2, nrgn, nrip1, nrk2, nr1, nrtn, nru, ns1, nsf, nsp, nsp11, nsrd9, nt4, nt5, nt5, ntcp1, ntcp2, ntf3, ntf4, ntf5, nth11, ntn, ntn, ntn21, ntrk1, ntrk2, ntrk3, ntrk4, ntrkr1, ntrkr3, nts, ntt, ntt, nuc1, nucb1, numa1, nup214, nup98, nurr1, ny1, nys1, nys2, nysa, oa1, oa2, oa3, oar, oasd, oat, oat11, oat22, oat23, oatp, oaz, ob, ob10, obf1, obp, obr, oca2, ocm, ocp2, ocr1, ocr11, oct, oct1, oct1, oct2, oct2, oct3, oct7, octn2, octs3, odc1, oddd, odf1, odg1, odod, ofc1, ofc2, ofc3, ofd1, ofe og22, ogdh, ogg1, ogr1, ogs1, ogs2, ohds, ohs, oias, oip1, ok, olfi, olfinf, olfr1, olfr2, omg, omgp, omp, on, op2, opa1, opa2, opa3, opca3, opcm1, opd1, opg1, ophn1, op11, opn, oppg, oprd1, oprk1, oprm1, oprt, opta2, optb1, oqt1, orld2, orlf1, orc11, orc21, orc41, orc51, orfx, orm1, orm2, orw, osbp, osm, osp, ost, ost48, osx, otc, otf1, otf2, otf3, otm, otof, ots, otx1, otx2, ovc, ovcs, ovo11, ox40, oxa11, oxct, oxt, oxtr, ozf, p, p, p1, p15, p16, p167, p28, p2rx3, p2rx4, p2ry1, p2ry2, p2ry4, p2ry7, p2u, p2x3, p2x4, p2y1, p2y2, p2y2, p2y4, p3p40phox, p450c11, p450c17, p450c2a, p450c2d, p450c2e, p450scc, p4ha, p4ha1, p4ha1, p4hb, p5cdh, p79r, pa2g4, pab1, pab2, pabp2, pabp1 1, pac1, pac1, pacapr, pace, pace4, paep, paf1, paf2, pafah, pafah1b1, pafah1b2, pafah1b3, paga, pah, pahx, pai1, pai2, paics, pak1, pak3, palb, pals, pam, pang, pap, papa, papa2, pappa, par1, par1, par2, par3, par4, par4, par5, park1, park2, park3, pawr, pax1, pax2, pax3, pax4, pax5, pax6, pax7, pax8, pax9, pbca, pbcra, pbfe, pbg pbt, pbx1, pbx2, pbx3, pc, pc1, pc2, pc3, pc3, pca1, pcad, pcap, pcar1, pcbc, pcbd, pcbp1, pcbp2, pcca, pccb, pcdh7, pcdx, pchc, pchc1, pci, pck1, pcl, pclp, pcm1, pcm1, pcmt1, pcna, pcnt, pcolce, pcp, pcp4, pcs, pcsk1, pcsk2, pcsk3, pcsk4, pcsk5, pcsk6, pctk1, pctk3, pcyt1, pdb, pdb2, pdc, pdc, pdcd1, pdcd2, pddr, pde1a, pde1b, pde1b1, pde3b, pde4a, pde4b, pde4c, pde4d, pde5a, pde6a, pde6b, pde6c, pde6d, pde6g, pde6h, pde7a, pdea, pdea2, pdeb pdeb, pdeg, pdeslb, pdgb, pdgfa, pdgfb, pdgfr, pdgfra, pdgfrb, pdha1, pdha2, pdhb, pdj, pdk4, pdnp1, pdnp2, pdnp3, pdr, pds, pds1, pdx1, pdyn, pe1, pea15, pebp2a1, pebp2a3, pecam1, ped, ped, pedf, pee, peg1, peg3, pemp, penk, pent, peo, peo1, peo2, pepa, pepb, pepc, pepd, pepe, pepn, peps, per, per2, peta3, pets1, pex1, pex5, pex6, pex7, pf4, pf4v1, pfas, pfbi, pfc, pfd, pfhb1, pfic1, pfic2, pfkfb1, pfkfb2, pfkl, pfk-mn, pfkp, pfkx, pfl, pfm, pfn1, pfn2, pfrx, pga3, pga4, pga5, pgam1, pgam2, pgamm, pgc, pgd, pgf, pgft, pgk1, pgk2, pgka, pgl, pgl1, pgl2, pgm1, pgm2, pgm3, pgm5, pgn, pgp, pgp1, pgr, pgs, pgt, pgy1, pgy3, pha1, pha2, pha2a, pha2b, phap1, phb, phc, phe1a, phe3, phex, phf1, phhi, phhi, phk, phka1, phka2, phkb, phkd, phkg1, phkg2, ph1, ph111, phog, phox1, phox2a, php, php1b, phpx, phyh, pi, pi10, pi3, pi4, pi5, pi6, pi7, pi8, pi9, piga, pigc, pigf, pigh, pigr, pik3c2b, pik3ca, pik3r1, pik4cb, pi1, pim1, pin, pin1, pin11, pip, pip5k1b, pir1, pir51, pit, pitl, pitpn, pitx1, pitx2, pitx3, pjs, pk1, pk120, pk3, pk428, pkca, pkcb, pkcc, pkcg, pkcs1, pkd1, pkd2, pkd4, pkdts, pkhdl, pklr, pkm2, pkp1, pks1, pks1, pks2, pku1, pl, pla2, pla2a, pla2b, pla2g1b, pla2g2a, pla2g4, pla2g4a, pla2g5, pla21, pla21, plag1, plag11, planh1, planh2, planh3, plat, plau, plaur, plb, plc, plc1, plcb3, plcb4, plcd1, plce, plcg1, plcg2, plc1, pld1, plec1, plg, plgf, plg1, pli, pln, plod, plod2, plos1, plp, pls, pls1, plt1, pltn, pltp, plzf, pmca1, pmca2, pmca3, pmca4, pmch, pmch11, pmch12, pmd, pme117, pmi1, pm1, pmm1, pmm2, pmp2, pmp22, pmp35, pmp69, pmp70, pms1, pms2, pms11, pms12, pmx1, pn1, pnd, pnem, pnkd, pnlip, pnmt, pnoc, pod1, podx1, pof, pof1, pol2rb, pola, polb, pold1, pold2, pole, polg, polr2a, polr2c, pol2re, polr2g, polr2i, polrmt, polz, pomc, pon, pon1, pon2, pon3, por, porc, potx, poulf1, pou2af1, pou3f1, pou3f2, pou3f3, pou3f4, pou4f1, pou4f3, pou5f1, pp, pp14, pp 2, pp 4, pp 5, ppac, ppard, pparg, ppargl, pparg2, ppat, pbbp, ppcd, ppd, ppef1, ppef2, ppfia3, ppgb, pph, pph1, ppia, ppid, ppi11, ppkb, ppks1, ppks2, ppl, ppla2, ppmx, ppnd, ppnoc, ppo1, ppox, ppp1a, ppp1ca, ppp1cb, ppp1cc, ppp1r2, ppp1r5, ppp1r7, pppd1r8, ppp2b, ppp2ca, ppp2cb, ppp2r1b, ppp2r4, ppp2r5a, ppp2r5b, ppp2r5c, ppp2r5d, ppp2r5e, ppp3ca, ppp3cb, ppp3 cc, pp 3r1, ppp4c, ppp5c, ppt, ppt2, ppx, ppy, ppyr1, pr, prad1, prb1, prb2, prb3, prb4, prca1, prca2, prcc, prcp, prelp, prep, prf1, prg, prg1, prg1, prgs, prh1, prh2, prim1, prim2a, prim2b, prip, prk1, prkaa1, prkaa2, prkab1, prkaca, prkacb, prkacg, prkag1, prkag2, prkar1a, prkar1b, prkar2b, prkca, prkcb1, prkcd, prkcg, prkci, prkcl1, prkcnh1, prkcq, prkcsh, prkdc, prkg1, prkg1b, prkg2, prkgr1b, prkgr2, prkm1, prkm3, prkm4, prkm9, prkn, prkr, prkx, prky, prl, prlr, prm1, prm2, prmt2, prnp, proa, proc, prodh, prohb, prop1, pros1, pros30, prox1, prp8, prph, prps1, prps2, pipsap1, prr1, prr2, prs, prsc1, prss1, prss1l, prss2, prss7, prss8, prss11, prtn3, prts, psa, psa, psach, psap, psbg1, psbg2, psc2, psc5, psca, psd, psen1, psen2, psf1, psf2, psg1, psg11, psg12, psg13, psg2, psg3, psg4, psg5, psg6, psg7, psg8, psg11, pskh1, psm, psma1, psma2, psma3, psma5, psmb1, psmb10, psmb2, psmb3, psmb4, psmb5, psmb8, psmb9, psmc1, psmc2, psmc3, psmc5, psmd7, psmd9, psme1, psme2, psors1, psors2, psors3, psp, psps1, psps2, pss1, psst, pst, pst, pst1, psti, ptafr, ptc, ptc, ptc, ptch, ptd, pten, ptgds, ptger1, ptger2, ptger3, ptgfr, ptgfrn, ptgir, ptgs1, ptgs2, pth, pthlh, pthr, pthr1, pthr2, ptk1, ptk2, ptk2b, ptk3, ptk7, ptlah, ptma, ptms, ptn, ptos1, ptp18, ptp1b, ptp4a1, ptp4a2, ptpa, ptpa, ptpd, ptpg, ptpg1, ptpgmc1, ptpn1, ptpn10, ptpn11, ptpn12, ptpn13, ptpn14, ptpn2, ptpn5, ptpn6, ptpn7, ptpra, ptprb, ptprc, ptprcap, ptprd, ptpre, ptprf, ptprg, ptprh, ptprj, ptprk, ptprl1, ptprl2, ptprm, ptpm, ptpro, ptprs, ptprz1, ptpt, pts, pts1r, ptx1, ptx3, pujo, pum, pur1, pur1, pura, pva1b, pvr, pvr11, pvr12, pvrr1, pvrr2, pvs, pvt1, pwcr, pwp2, pwp2h, pws, pxaaa1, pxe, pxe1, pxf, pxmp1, pxmp11, pxmp3, pxr1, pycr1, pycs, pygb, pygl, pygm, pyk2, pyst1, pyst2, pzp, qars, qdpr, qin, qm, qpc, qprs, rab, rab1, rab13, rab1a, rab21, rab3a, rab3b, rab4, rab5, rab5a, rab6, rab7, rabgd1a, rabgdib, rabggta, rabggtb, rabif, rac2, rac3, rad1, rad17, rad23a, rad23b, rad51a, rad51c, rad51d, rad5311, rad52, rad54, rad6a, rad6b, raf1, rafa1, rag1, rag2, rage, rala, ralb, ralgds, ramp, ranbp211, ranbp3, rao, rap1a, rap1b, rap1ga1, rap1gds1, rap2a, rap74, rapsn, rara, rarb, rarg, rars, rasa1, rasa2, rasgfr3, rask2, rb1, rbbp2, rbbp5, rbbp6, rb11, rb12, rbm1, rbm2, rbm3, rbmy1a1, rbp1, rbp2, rbp3, rbp4, rbp5, rbp56, rbp6, rbq3, rbtn1, rbtn11, rbtn12, rca1, rcac, rcc1, rccp1, rccp2, rcd1, rcd2, rcdp1, rcn1, rcn2, rcp, rcv1, rd, rdbp, rdc7, rdp, rdpa, rdrc, rds, rdt, rdx, reca, recc1, recq1, red1, red2, reg, reg1a, reg1, rel, rela, reln, ren, renbp, rens1, rent1, rep8, req, ret, rev3, rev31, rfc1, rfc2, rfc3, rfc4, rfc5, rfp, rfx1, rfx2, rfx5, rfxank, rfxap, rgc1, rgr, rgs, rgs1, rgs14, rgs16, rgs2, rgs2, rgs3, rgs5, rh50a, rhag, rhbd1, rhc, rhce, rhd, rheb2, rho, rho7, rhogap2, rhogap3, rhohl2, rhoh6, rhoh9, rhok, rhom1, rhom2, rhom3, rieg1, rieg2, rige, rigui, ring1, ring10, ring11, ring12, ring3, ring31, ring4, ring5, ring6, ring7, rip, rip140, riz, rk, rl, rlbp1, rlf, rln1, rln2, rmch1, rmd1, rmrp, rmrpr, rn5s1, rnase1, rnase2, rnase3, rnase4, rnase5, rnase6, rnase1, rnaseli, rne1, rnf1, rnf3, rnf4, rnf5, rnh, rnpep, rnpulz, rnr1, rnr2, rnr3, rnr4, rnr5, rns1, rns2, rns3, rns4, rns4i, rntmi, rnu1, rnu15a, rnu17a, rnu17b, rnu1a, mu2, rnu3, ro52, rom1, romk1, ron, ror1, rora, rorb, rorc, rorg, ros1, rosp1, rox, rp1, rp10, rp105, rp11, rp12, rp13, rp14, rp15, rp17, rp18, rp19, rp2, rp22, rp24, rp25, rp3, rp4, rp6, rp7, rp9, rpa1, rpa2, rpa3, rpd311, rpe, rpe65, rpe119rp122, rp123a, rpl231, rp129, rp130, rp135a, rp136a, rp17a, rpms12, rpn1, rpn2, rpo12, rps1, rps14, rps17, rps17a, rps17b, rps1711, rps1712, rps18, rps20a, rps20b, rps24, rps25, rps3, rps4x, rps4y, rps6, rps6ka1, rps6ka2, rps6ka3, rps8, rpsm12, rptpm, rpul, rpx, rrad, rras, rrbp1, rreb1, rrm1, rrm2, rrp, rrp22, rs1, rs1, rscla1, rsk1, rsk2, rsk3, rsn, rss, rsts, rsu1, rt6, rtefl, rtkn, rtn1, rtn2, rts, rts, rtt, rws, rxra, rxrb, rxrg, ryr1, ryr2, ryr3, rzrb, rzrg, s100a1, s100a10, s100a11, s100a12, s100a13, s100a2, s100a3, s100a4, s100a5, s100a6, s100a7, s100a8, s100a9, s100b, s100d, s100e, s100, s100p, s152, s4, s7, saa1, saa2, saa4, sacs, safb, sag, sah, sahh, sai1, sakap84, sall1, sall2, sams1, sams2, sap, sap 1, sap1, sap2, sap62, sar, sar1, sar2, sard, sas, sat, satb1, satt, sbma, sc, sc1, sc5d1, sca1, sca10, sca2, sca2, sca3, sca4, sca5, sca6, sca7, sca8, sca8, scar, scca1, scca2, sccd, scd, sceh, scg1, scg2, scg3, schad, scida, scidx, scidx1, scl, sclc1, scl1, scn, scn1a, scn1b, scn2a, scn2a1, scn2a2, scn2b, scn3a, scn4a, scn5a, scn6a, scn8a, scnn1a, scnn1b, scnn1d, scnn1g, scot, scp, scp1, scp2, scpn, scra1, scra1, scs, sctr, scya1, scya11, scya13, scya14, scya15, scya16, scya19, scya2, scya21, scya22, scya24, scya25, scya3, scya311, scya4, scya5, scya7, scya8, scyb5, scyb6, scyd1, sczd1, sczd2, sczd3, sczd4, sczd5, sczd6, sczd7, sczd8, sdc1, sdc2, sdc4, sdf1, sdf2, sdh1, sdh2, sdha, sdhb, sdhc, sdhd, sdhf, sds22, sdty3, sdys, se, sea, sec1311, sec13r, sec141, sec7, sed1, sedt, sef2, sell1, sele, sel1, selp, selp1g, sema3f, sema4, sema5, semg, semg1, semg2, sen1, sep, sepp1, serca1, serca3, serk1, ses1, set, sex, sf, sf1, sfa1, sfd, sfmd, sfrs1, sfrs2, sfrs7, sftb3, sftp1, sftp2, sftp4, sftpa1, sftpa2, sftpb, sftpc, sftpd, sgb, sgca, sgcb, sgcd, sgcg, sgd, sgk, sglt1, sglt2, sgm1, sgne1, sgp2, sgpa, sgsh, sh2d1a, sh3 bp2, sh3d1a, sh3gbr, sh3p17, shb, shbg, shc1, shc11, shfd1, shfd2, shfin1, shfin2, shfin3, shh, ship, shmt1, shmt2, shoc2, shot, shox, shox2, shps1, shs, shsf1, si, siah1, siah2, siasd, siat1, siat4, siat4c, siat8, sids, sil, silv, sim1, sim2, sipa1, sis, siv, six1, six5, sja, sjs, ski, ski2, ski2w, skiv21, skp1a, skp1b, skp2, sla, slap, slbp, slc, slc10a1, slc10a2, slc12a1, slc12a2, slc12a3, slc14a1, slc14a2, slc15a1, slc16a1, slc16a2, slc17a1, slc17a2, slc18a1, slc18a2, slc18a3, slc19a1, slc1a1, slc1a2, slc1a3, slc1a4, slc1a5, slc20a1, slc20a2, slc20a3, slc21a2, slc21a3, slc22a1, slc22a2, slc22a5, slc2a1, slc2a2, slc2a3, slc2a4, slc2a5, slc2c, slc3a1, slc4a1, slc4a2, slc4a6, slc5a1, slc5a2, slc5a3, slc5a5, slc6a1, slc6a10, slc6a12, slc6a2, slc6a3, slc6a4, slc6a6, slc6a8, slc6a9, slc7a1, slc7a2, slc7a4, slc7a5, slc7a7, slc8a1, slc8a2, slc9a1, slc9a2, slc9a3, slc9a4, slc9a5, sld, sle1, sleb1, slim1, sln, slo, slos, slp76, sls, slug, sm1, sm22, sma4, smad1, smad1, smad2, smad3, smad4, smad5, smad6, smad7, smad9, sma1, smam1, smarca1, smarca2, smarca3, smarca5, smarcb1, smax2, smc1, smcc, smcr, smcx, smcy, sml1, smn, smn1, smn2, smnr, smo, smoh, smpd1, sms, smt3, smt3h1, smtn, smubp2, sn, snap25, snat, snca, sncb, sncg, snf2h, snf211, snf212, snf213, snf5, snl, snn, snrp70, snrpa, snrpe, snrpn, snt1, snt2b1, snt2b2, sntb1, snt1, snx, soat, sod1, sod2, sod3, solh, son, sord, sor11, sos1, sos2, sox1, sox10, sox11, sox2, sox20, sox22, sox3, sox4, sox9, sp1, sp1, sp3, sp3, sp4, spa1, spag1, spag4, spam1, sparc, spat, spbp, spch1, spd, spf30, spg3a, spg4, spg5a, spg6, spg7, spg8, spg9, spgp, spgy1a, sph2, spi1, spink1, spk, spmd, spn, spp1, spp2, sppm, spr, sprk, sprr1a, sprr1b, sprr2a, sprr2b, sprr2c, sprr3, sps1, spsma, spta1, sptan1, sptb, sptbn1, sra1, sra2, src, src1, src1, src2, srd5a1, srd5a2, srebf1, srebf2, sri, srk, srm, srn1, srp14, srp19, srp46, srpr, srpx, srs, srvx, sry, ss, ss, ssa, ssa1, ssa2, ssadh, ssav1, ssbp, ssdd, ssr2, ssrc, sst, sstr1, sstr2, sstr3, sstr4, sstr5, ssx1, ssxt, st2, st3, st4, st5, st6, st8, sta, stac, stam, star, stat, stat1, stat3, stat4, stat5, ssx1, stc1, stch, std, std, step, step, stf1, stfa, stfb, stgd1, stgd2, stgd3, stgd4, sthe, stk1, stk11, stk15, stk2, stk6, st1, stm, stm2, stm7, stmy1, stmy2, stmy3, stp, stp1, stp2, sts, sts1, stx, stx1b, stx7, stxbp1, stxbp2, sultlc1, supt6h, sur, sur1, surf1, surf2, surf3, surf4, surf5, surf6, svct2, svmt, sw, sxi2, syb1, syb2, syb11, sycp1, syk, sym1, syn1, syn2, syn3, syngap, syns1, syp, syt, syt1, syt2, syt3, syt4, syt5, t, t3d, taa16, tac1r, tac2, tac2r, tac3, tacr1, tacr2, taf2, taf2a, taf2a, taf2d, taf2h, taf2n, tafii100, tagln, tak1, tall, tal2, taldo1, tam, tan1, tap1, tap2, tapa1, tapbp, tapvr1, tars, tas, task, tat, taut, tax, tax1, m/z, tbg, tbp, tbp1, tbs, tbx1, tbx2, tbx3, tbx5, tbxa2r, tbxas1, tc1, tc2, tcbp, tcd, tcea1, tceb11, tceb3, tcf1, tcf12, tcf13, tcf1311, tcf14, tcf15, tcf17, tcf19, tcf2, tcf20, tcf21, tcf3, tcf4, tcf5, tcf611, tcf612, tcf7, tcf8, tcf9, tcfeb, tcf11, tcf14, tcl1, tcl1a, tcl2, tcl3, tcl4, tcl5, tcn1, tcn2, tco, tcof1, tcp1, tcp10, tcp11, tcp228, tcpt, tcra, tcrb, tcrd, tcrg, tcra, tcs1, tcta, tcte1, tcte3, tcte11, tdf, tdfa, tdfx, tdg, tdgf1, tdn, tdo, tdo2, tdt, tead4, tec, teck, tecta, tef, tegt, tek, tel, tem, tep1, terc, terf1, tert, tes1, teskl, tex28, tf, tf2s, tf6, tfa, tfam, tfap2a, tfap2b, tfap2c, tfap4, tfcoup1, tfcoup2, tfcp2, tfdp1, tfdp2, tfe3, tff1, tff2, tff3, tfiiia, tfn, tfpi, tfpi2, tfr, tfrc, tfs1, tft, tg, tg737, tgb1, tgb2, tgd, tgfa, tgfb1, tgfb2, tgfb3, tgfb4, tgfbi, tgfbr1, tgfbr2, tgfbr3, tgfbre, tgfr, tgm1, tgm2, tgm3, tgm4, tgn38, tgn46, th, thas, thbd, thbp1, thbs1, thbs2, thbs3, thc, thh, th1, thop1, thpo, thr1, thra, thra1, thra1, thrb, thrm, thrsp, thy1, tia11, tiam1, tiar, tic, tie, tie1, tie2, tigr, til, til3, til4, tim, timp, timrp1, timp2, timp3, tinur, titf1, titf2, tjp1, tk1, tk2, tkc, tkcr, tkr, tkt, tkt2, tkt11, tla519, tlcn, tle1, tle2, tle3, tlh1, tln, tlr1, tlr2, tlr3, tlr4, tlr5, tm4sf1, tm4sf2, tm7sf2, tmc, tmd, tmdci, tmem1, tm1, tmip, tmod, tmp, tmpo, tmprss2, tms, tmsa, tmsb, tmvcf, tna, tndm, tnf, tnfa, tnfaip1, tnfaip2, tnfaip4, tnfaip6, tnfar, tnfb, tnfbr, tnfc, tnfcr, tnfr1, tnfr2, tnfrsf10b, tnfrsf12, tnfrsf14, tnfrsf16, tnfrsf17, tnfrsf1a, tnfrsf1b, tnfrsf4, tnfrsf5, tnfrsf6, tnfrsf6b, tnfrsf7, tnfrsf8, tnfrsf9, tnfsf11, tnfsf12, tnfsf5, tnfsf6, tnfsf7, tnnc1, tnnc2, tnni1, tnni2, tnni3, tnnt1, tnnt2, tnnt3, tnp1, tnp2, tnr, tns, tnx, tnxa, toc, top1, top2, top2a, top2b, top3, tp1, tp120, tp250, tp53, tp53 bp2, tp63, tp73, tpa, tpbg, tpc, tpc, tph, tph2, tpi1, tpl2, tpm1, tpm2, tpm3, tpm4, tpmt, tpo, tpo, tpp2, tpr, tpr1, tprd, tps1, tps2, tpsn, tpst1, tpst2, tpt, tpt1, tptps, tpx, tpx1, tr, tr2, tr4, tra1, trafl, traf5, trailr2, tran, trance, trap170, trc3, trc8, tre, treb36, trek, trf1, trg1, trh, trhr, tric5, trio, trip1, trip14, trip6, trk, trk1, trka, trkb, trkc, trke, trl1, trl2, trm1, trm1, trm2, trma, trmi1, trmi2, trn, trn1, tro, trp1, trp1, trp2, trp3, trpc1, trpm2, trpo, trps1, trps2, trq1, trr, trr3, trrap, trsp, trt1, trt2, trv1, trv2, trv3, trv4, trv5, try1, try2, ts, ts13, ts546, tsbn51, tsc tsc1, tsc2, tsd, tse1, tsg101, tsg7, tshb, tshr, tsix, tsp3, tspy, tssc3, tst1, tst1, tsta3, tsy, ttc1, ttc3, ttf, ttf1, ttf2, ttg2, ttim1, ttn, ttp, ttp1, ttpa, ttr, tuba3, tuba11, tubb, tufm, tuft1, tulp1, tuple1, tw, tweak, twik1, twist, txgp11, txk, txn, txnr, txnrd1, tyh, tyk1, tyk2, tyk3, tyms, tyr, tyr1, tyro3, tyrp1, tyrp2, tys, u17hg, u1rnp, u22hg, u2af1, u2aflrs1, u2aflrs2, u2aflrs3, uba52, ubb, ubc, ubc4, ubc7, ubc8, ubch2, ubc1, ube1, ube2, ube2a, ube2b, ube2e2, ube2g, ube2g2, ube2h, ube2i, ube211, ube2v1, ube3a, ubh1, ubid4, ub11, uch11, ucn, ucp1, ucp2, ucp3, udpgdh, uev1, ufd11, ufs, ugalt, ugb, ugcg, ugdh, ugn, ugp1, ugp2, ugpp2, ugt1, ugt1a1, ugt2b11, ugt2b15, ugt2b17, ugt2b4, ugt2b7, ugt2b8, ugt2b9, ugt1, uhg, uhx1, ukhc, umod, umph2, umpk, umps, unc18, unc18b, und, ung, unr, unr, uox, up, upk1b, ups, uqbp, uqcrb, uqcrc1, uqcrc2, uqcrfs1, uqor1, uqor13, uqor22, urk, urkr, uroc, urod, uros, usf1, usf2, ush1, ush1a, ush1b, ush1c, ush1d, ush1e, ush1f, ush2a, ush3, usp11, usp5, usp7, usp9x, usp9y, ut1, ut2, ute, utr, utm, utx, uty, uv20, uv24, uvo, vacht, vacm1, vamp1, vamp2, vars1, vasp, vat1, vat2, vav, vav1, vav2, vbch, vbp1, vcam1, vcf, vcl, vcp, vdac1, vdac2, vdd1, vdi, vdr, vegf, vegfb, vegfd, vegfr3, vgf, vg1, vgr1, vh1, vhr, vil1, vil2, vim, vip, vipr1, vipr2, vis1, vla1, vla5a, vlacs, vlcad, vldlr, vmat1, vmcm, vmd1, vmd2, vnra, vnt, vp, vpp1, vpp3, vpreb1, vpreb2, vrf, vrk1, vrk2, vrnf, vmi, vsn11, vtn, vwf, vws, wafl, wars, was, wbs, wd1, wdr2, wee1, wfrs, wfs, wfs1, wgn1, wher, wi, wisp1, wisp2, wisp3, wnd, wnt1, wnt10b, wnt13, wnt14, wnt15, wnt2, wnt3, wnt5a, wnt7a, wnt7b, wnt8b, wrb, wm, ws1, ws2a, ws2b, ws4, wsn, wss, wss, wt1, wt2, wt3, wt4, wt5, wts, wts1, wws, x11, xbp1, xbp2, xce, xdh, xe169, xe7, xe7y, xg, xgr, xh2, xiap, xic, xist, xk, xla, xla2, xlp, xlpd, xlrs1, xm, xpa, xpb, xpc, xpcc, xpct, xpf, xpf, xpg, xpmc2h, xpnpep2, xpo1, xrcc1, xrcc2, xrcc3, xrcc4, xrcc5, xrcc9, xrs, xs, xwnt2, yb1, yes1, yk140, y11, yrrm1, yt, ywha1, ywhab, ywhah, ywhaz, yy1, zac, zag, zan, zap70, zf87, zfin1, zfp3, zfp36, zfp37, zfx, zfy, zic1, zic2, zic3, zipk, znf1, znf10, znf117, znf11a, znf11b, znf12, znf121, znf123, znf124, znf125, znf126, znf13, znf14, znf141, znf144, znf146, znf147, znf157, znf16, znf160, znf162, znf163, znf165, znf169, znf173, znf179, znf189, znf19, znf192, znf193, znf195, znf198, znf2, znf20, znf200, znf204, znf217, znf22, znf23, znf24, znf25, znf26, znf27, znf29, znf3, znf32, znf34, zn35, znf36, znf38, znf4, znf40, znf41, znf42, znf44, znf45, znf46, znf5, znf6, znf69, znf7, znf70, znf71, znf72, znf73, znf74, znf75, znf75a, znf75c, znf76, znf77, znf79, znf8, zn80, znf81, znf83, znf9, znfc150, znfc25, znfxy, znt3, znt4, zp3a, zp3b, zpk, zws1, and zyx.

Furthermore, genes from bacteria, plants, yeast, and mammals (e.g., mice) can be used with the microorganisms provided herein. Non-limiting examples of *E. coli* genes include: aarF, aas, aat, abpS, abs, accA, accB, accC, accD, acd, aceA, aceB, aceE, aceF, aceK, ackA, ackB, acnA, acnB, acpD, acpP, acpS, acpX, acrA, acrB, acrC, acrD, acrE, acrF, acrR, acs, ada, add, adhB, adhC, adhE, adhR, adiA, adiY, adk, aegA, aer, aes, agaA, agaB, agaC, agaD, agaI, agaR, agaS, agaV, agaW, agaZ, agp, ahpC, ahpF, aidB, ais, alaS, alaT, alaU, alaV, alaW, alaX, aldA, aldB, aldH, alkA, alkB, alpA, alr, alsA, alsB, alsC, alsE, alsK, alx, amiA, amiB, amn, ampC, ampD, ampE, ampG, ampH, amtB, amyA, ansA, ansB, apaG, apaH, aphA, appA, appB, appC, appY, apt, aqpZ, araA, araB, araC, araD, araE, araF, araG, araH, araJ, arcA, arcB, argA, argB, argC, argD, argE, argF, argG, argH, argI, argM, argP, argQ, argR, argS, argT, argU, argV, argW, argX, argY, argZ, aroA, aroB, aroC, aroD, aroE, aroF, aroG, aroH, aroI, aroK, aroL, aroM, aroP, aroT, arsB, arsC, arsR, artI, artJ, artM, artP, artQ, ascB, ascF, ascG, asd, aslA, aslB, asmA, asnA, asnB, asnC, asnS, asnT, asnU, asnV, asnW, aspA, aspC, aspS, aspT, aspU, aspV, asr, asu, atoA, atoB, atoC, atoD, atoS, atpA, atpB, atpC, atpD, atpE, atpF, atpG, atpH, atpI, avtA, azaA, azaB, azl, bacA, baeR, baeS, barA, basR, basS, bax, bcp, bcr, betA, betB, betI, betT, bfd, bfm, bfr, bglA, bglB, bglF, bglG, bglJ, bglT, bglX, bioA, bioB, bioC, bioD, bioF, bioH, bioP, bipA, birA, bisC, bisZ, blc, bolA, bRNQ, brnR, bmS bmT, btuB, btuc, btuD, btuE, btuR, bymA, cadA, cadB, cadC, cafA, caiA, caiB, caiC, caiD, caiE, caiF, caiT, calA, caiC, calD, can, carA, carB, cbl, cbpA, cbt, cca, ccmA, ccmB, ccmC, ccmD, ccmE, ccmF, ccmG, ccmH, cdd, cde, cdh, cdsA, cdsS, cedA, celA, celB, celC, celD, celF, cfa, cfcA, chaA, chaB, chaC, cheA, cheB, cheR, cheW, cheY, cheZ, chpA, chpB, chpR, chpS, cirA, citA, citB, cld, cipA, cIpB, cIpP, clpX, cls, cmk, cmlA, cmr, cmtA, cmtB, coaA, cobS, cobT, cobU, codA, codB, cof, cog, corA, cpdA, cpdB, cpsA, cpsB, cpsC, cpsD, cpsE, cpsF, cpsG, cpxA, cpxB, cpxP, cpxR, crcA, crcB, creA, creB, creC, creD, crg, crl, crp, crr, csdA, csgA, csgB, csgD, csgE, csgF, csgG, csiA, csiB, csiC, csiD, csiE, csiF, cspA, cspB, cspC, cspD, cspE, cspG, csrA, csrB, cstA, cstC, cup, cutA, cutC, cutE, cutF, cvaA(ColV), cvaB(ColV), cvaC(Co-IV), cvi (ColV), cvpA, cxm, cyaA, cybB, cybC, cycA, cydA, cydB, cydC, cydD, cynR, cynS, cynT, cynX, cyoA, cyoB, cyoC, cyoD, cyoE, cysA, cysB, cysC, cysD, cysE, cysG, cysH, cysI, cysJ, cysK, cysM, cysN, cysP, cysQ, cysS, cysT, cysU, cysW, cysX, cysZ, cytR, dacA, dacB, dacC, dacD, dadA, dadB, dadQ, dadX, dam, dapA, dapB, dapD, dapE, dapF, dbpA, dcd, dcm, dcp, dcrB, dctA, dctB, dcuA, dcuB, dcuC, ddlA, ddlB, ddpA, ddpB, ddpC, ddpD, ddpF, ddpX, deaD, dedA, dedD, def, degP, degQ, degS, del, deoA, deoB, deoC, deoD, deoR, dfp, dgd, dgkA, dgkR, dgoA, dgoD, dgoK, dgoR, dgoT, dgsA, dgt, dicA, dicB, dicC, dicF, dinB, dinD, dinF, dinG, dinI, dinY, dipZ, djlA, dksA, dld, dmsA, dmsB, dmsC, dnaA, dnaB, dnaC, dnaE, dnaG, dnaI, dnaJ, dnaK, dnaL, dnaN, dnaQ, dnaT, dnaX, dppA, dppB, dppC, dppD, dppF, dppG, dps, dsbA, dsbB, dsbC, dsbG, dsdA, dsdC, dsdX, dsrA, dsrB, dut, dvl, dxs, ebgA, ebgB, ebgc, ebgR, ecfa, eco, ecpD, eda, edd, efp, enirA, emrB, emrD, emrE, endA, eno, entA, entB, entC, entD, entE, entF, envN envP, envQ, envR, envT, envY, envZ, epd, EppA, minigene, EppB, minigene, EppC, minigene, EppD, minigene, EppE, minigene, EppG, minigene, EppH, minigene, era, esp, evgA, evgs, exbB, exbC, exbD, expA, exuR, exuT, fabA, fabB, fabD, fabF, fabG, fabH, fabI, fabZ, fadA, fadB, fadD, fadE, fadH, fadL, fadR, farR, fatA, fbaA, fbaB, fbp, fcl, fcsA, fdhD, fdhE, fdhF, fdnG, fdnH, fdnI, fdoG, fdoH, fdoI, fdrA, fdx, feaB, feaR, fecA, fecB, fecC, fecD, fecE, fecI, fecR, feoA, feoB, fepA, fepB, fepC, fepD, fepE, fepG, fes, fexB, ffh, ffs, fhlA, fhlB, fhuA, fhuB, fhuD, fhuE, fhuF, fic, fimA, fimB, fimC, fimD, fimE, fimF, fimG, fimH, fimI, fipB, fipC, fis, fiu, fixA, fixB, fixC, fixX, fklB, fkpA, fldA, flgA, flgB, flgC, flgD, flgE, flgF, flgG, flgH, flgI, flgJ, flgK, flgL, flgM, flgN, flhA, flhB, flhc, flhD, fliA, fliC, fliD, fliE, fliF, fliG, fliH, fliI, fliJ, fliK, fliL, fliM, fliN, fliO, fliP, fliQ, fliR, fliS, fliT, fliy, fliZ, flk, flu, fmt, fnr, focA, focB, folA, folC, folD, folE, folK, folP, folX, fpr, frdA, frdB, frdc, frdD, frr, fruA, fruB, fruK, fruR, fsr, ftn, ftsA, ftsE, ftsI, ftsJ, ftsK, ftsL, ftsN, ftsQ, ftsW, ftsX, ftsY, ftsZ, fucA, fucI, fucK, fucO, fucP, fucR, fumA, fumB, fumC, fur, fusA, fusB, gabC gabD, gabP, gabT, gadA, gadB, gadR, galE, galF, galK, galM, galP, gaiR, galS, galT, galU, gapA, gapc, garA, garB, gatA, gatB, gatc, gatD, gatR, gatY, gatz, gcd, gcl, gcpE, gcvA, gcvH, gcvP, gcvR, gcvT, gdhA, gef, ggt, gidA, gidB, gip, glcB, glcC, glcD, glcE, glcG, gldA, glf, glgA, glgB, glgC, glgP, glgS, glgX, glk, glmM, glmS, glmU, glmX, glnA, glnB, glnD, glnE, glnG, glnH, glnK, glhL, glnP, glnQ, glnR, glnS, glnT, glnU, glnV, glnW, glnX, gloA, glpA, glpB, glpC, glpD, gipE, gipF, gipG, glpK, glpQ, gipR, glpT, glpX, gltA, gltB, gltD, glte, gltF, gltH, gltJ, gltK, gltL, gltM, gltP, gltR, gltS, gltT, gltU, gltv, gltW, gltX, glyA, glyQ, glyS, glyT, glyU, glyv, glyW, glyX, glyY, gmd, gmk, gmm, gnd, gntK, gntP, gntR, gntS, gntT, gntU, gntV, goaG, gor, gph, gpmA, gpp, gprA, gprB, gpsA, gpt, greA, greB, groL, groS, grpE, grxA, grxB, grxC, gshA, gshB, gsk, gsp, gsp*, gst, guaA, guaB, guac, gurB, gurC, gutM, gutQ, gyrA, gyrB, hcaB, hcaC, hcaD, hcaE, hcaF, hcaR, hcaT, hdeA, hdeB, hdeD, hdhA, helD, hemA, hemB, hemC, hemD, hemE, hemF, hemG, hemH, hemK, hemL, hemM, hemX, hemY, hepA, het, hflB, hflc, hflK, hflx, hfq, hha, hipA, hipB, hisA, hisB, hisC, hisD, hisF, hisG, hisH, hisI, hisJ, hisM, hisP, hisQ, hisR, hisS, hipA, hlyE, hmp, hns, holA, holB, holC, holD, holE, hopB, hopC, hopD, hpt, hrpA, hrpB, hrsA, hscA, hscB, hsdM, hsdR, hsdS, hslC, hslD, hslE-H, hslJ, hslK, hslL-N, hslO-R, hslU, hslV, hslW, htgA, htpG, htpX, htrB, htrc, htrE, htrL, hupA, hupB, hyaA, hyaB, hyaC, hyaD, hyaE, hyaF, hybA, hybB, hybC, hybD, hybE, hybF, hybG, hycA, hycB, hycC, hycD, hycE, hycF, hycG, hcH, hycI, hydA, hydG, hydH, hydN, hyfA, hyfB, hyfC, hyfD, hyfE, hyfF, hyfG, hyfH, hyfI, hyfJ, hyfR, hypA, hypB, hypc, hypD, hypE, hypF, iadA, iap, ibpA, ibpB, icd, iclR, ihfA, ihfB, ileR, ileS, ileT, ileU, ileV, ileX, ileY, ilvA, ilvB, ilvC, ilvD, ilvE, ilvF, ilvG, ilvH, ilvI, ilvJ ilvM, ilvN, ilvR, ilvU, ilvY, imp, inaA, inaR, infA, infB, infC, inm, insA(IS1), intA, isb(IS1), isfA, ispA, ispB, KanR, katE, katG, kba, kbl, kch, kdgK, kdgR, kdgT, kdpA, kdpB, kdpC, kdpD, kdpE, kdpF, kdsA, kdsB, kdtA, kdtB, kefB, kefC, kgtp, ksgA, ksgB, ksgC, ksgD, lacA, lacI, lacY, lacZ, lamB, lar, ldcC, ldhA, lepA, lepB, leuA, leuB, leuC, leuD, leuJ, leuO, leuP, leuQ, leuR, leuS, leuT, leuU, leuV, leuW, leuX, leuY, leuZ, lev, lexA, lgt, lhr, ligA, ligT, linB, lipA, lipB, lit, livF, livG, livH, livJ, livK, livM, lldD, lldP, lldR, lolA, lon, lpcA, lpcB, lpd, lplA, lpp, lpxA, lpxB, lpxC, lpxD, lpxK, lrb, lrhA, lrp, lrs lspA, lysA, lysC, lysP, lysQ, lysR, lysS, lysT, lysU, lysV, lysW, lysX, lysY, lysZ, lytA, lytB, lyx, maa, mac, mae, mafA, mafB, malE, malF, malG, malI, malK, malM, malP, malQ, malS, malT, malX, malY, malZ, manA, manC, manX, manY, manZ, map, marA, marB, marR, mbrB, mcrA, mcrB, mcrC, mcrD, mdaB, mdh, mdoB, mdoG, mdoH, meb, melA, melB, melC, menA, menB, menC, menD, menE, menF, mepA, mesJ, metA, metB, metC, metD, metE, metF, metG, metH, metJ, metK, metL, metR, metT, metU, metV, metW, metY, metZ, mfd, mglA, mglB, mglC, mglR, mgsA, mgtA, mhpA, mhpB, mhpC, mhpD, mhpE, mhpF, mhpR, miaA, miaD, micF, minC, minD, minE, mioC, mltA, mltB, mltC, mltD, mmrA(rhlB), mng, mntA, moaA, moaB, moaC, moaD, moaE, mobA, mobB, moc, modA, modB, modC, modE, modF, moeA, moeB, mog, molR, motA, motB, mpl, mppA, mprA, mraA, mraY, mrcA, mrcB, mrdA, mrdB, mreB, mreC, mreD, mrp, mrr, msbA, msbB, mscL, msrA, msyB, mtg, mtgA, mtlA, mtlD, mtlR, mtr, mttA, mttB, mttC, mukB, mukE, mukF, mul, murA, murB, murC, murD, murE, murF, murG, murH, murI, mutG(putative), mutH, mutL, mutM, mutS, mutT, mutY, nac, nadA, nadB, nadC, nadE, nagA, nagB, nagC, nagD, nagE, nalB, nalD, nanA, nanE, nanK, nanR, nanT, napA, napB, napC, napD, napF, napG, napH, narG, narH, narI, narJ, narK, narL, narP, narQ, narU, narV, narW, narX, narY, narZ, ndh, ndk, neaB, nei, nemA, nfi, nfnA, nfnB, nfo, nfrA, nfrB, nfrD, nfsA, nhaA, nhaB, nhaR, nikA, nikB, nikC, nikD, nikE, nirB, nirC, nirD, nlpA, nlpB, nlpC, nlpD, mnpC(qsr'), non, npr, nrdA, nrdB, nrdD, nrdE, nrdF, nrdG, nrfA, nrfB, nrfC, nrfD, nrfE, nrfF, nrfG, nth, ntpA, nuoA, nuoB, nuoC, nuoE, nuoF, nuoG, nuoH, nuoI, nuoJ, nuoK, nuoL, nuoM, nuoN, nupC, nupG, nusA, nusB, nusG, nuvA, nuvC, ogrK, ogt, ompA, ompC, ompF, ompG, ompR, ompT, ompX, oppA, oppB, oppC, oppD, oppE, oppF, opr, ops, oraA, ordL, orf-23(purB, reg)orf195(nikA-reg), om, osmB, osmC, osmE, osmY, otsA, otsB, oxyR, oxyS, pabA, pabB, pabC, pac, pal, panB, panC, panD, panF, parC, parE, pat, pbpG, pck, pcm, pcnB, pdhR, pdxA, pdxB, pdxH, pdxJ, pdxK, pdxL, pdxY, pepA, pepD, pepE, pepN, pepP, pepQ, pepT, pfkA, pfkB, pflA, pflB, pflC, pflD, pfs, pgi, pgk, pgl, pgm, pgpA, pgpB, pgsA, pheA, pheP, pheS, pheT, pheU, pheV, phnC, phnD, phnE, phnF, phnG, phnH, phnI, phnJ, phnK, phnL, phnM, phnN, phnO, phnP, phoA, phoB, phoE, phoH, phoP, phoQ, phoR, phoU, phrB, phxB, pin, pioO, pit, pldA, pldB, plsB, plsC, plsX, pmbA, pncA, pncB, pnp, pntA, pntB, pnuC, poaR, polA, polB, popD, potA, potB, potC, potD, potE, potF, potG, potH, potI, poxA, poxB, ppa, ppc, pphA, pphB, ppiA, ppiB, ppiC, ppk, pppA, pps, ppx, pqiA, pqiB, pqqL, pqqM, prc, prfA, prfB, prfC, priA, priB, priC, prlC, prlZ, prmA, prmB, proA, proB, proC, proK, proL, proM, prop, proQ, proS, proT, proV, proW, proX, prpA, prpC, prpR, prr, prs, psd, psiF, pspA, pspB, pspC, pspE, pspF, pssA, pssR, pstA, pstB, pstC, pstS, psu, pta, pth, ptrA, ptrB, ptsG, ptsH, ptsI, ptsN, ptsP, purA, purB, purC, purD, purE, purF, purH, purK, purL, purM, purN, purP, purR, purT, purU, pus, putA, putP, pykA, pykF, pyrB, pyrC, pyrD, pyrE, pyrF, pyrG, pyrH, pyrI, qmeC, qmeD, qmeE, qor, queA, racC, racR, radA, radC, ranA, rarD, ras, rbfA, rbn, rbsA, rbsB, rbsC, rbsD, rbsK, rbsR, rcsA, rcsB, rcsC, rcsF, rdgA, rdgB, recA, recB, recC, recD, recE, recF, recG, recJ, recN, recO, recQ, recR, recT, relA, relB, relE, relF, relX, rep, rer, rfaB, rfaC, rfaD, rfaF, rfaG, rfaH, rfaI, rfaJ, rfaK, rfaL, rfap, rfaQ, rfaS, rfay, rfaZ, rfbA, rfbB, rfbC, rfbD, rfbX, rfc, rfe, rffA, rffC, rffD, rffE, rffG, rffI, rffM, rffT, rhaA, rhaB, rhaD, rhaR, rhaS, rhaT, rhlB, rhlE, rho, ribA, ribB, ribC, ribD, ribE, ribF, ridA, ridB, rimB, rimC, rimD, rimE, rimG, rimH, rimI, rimJ, rimK, rimL, rimM, rit, rlpA, rlpB, rluA, rluC, rluD, rmf, rna, rnb, rnc, rnd, rne, rnhA, rnhB, rnk, rnpA, rnpB, rnr, rnt, rob, rorB, rpe, rph, rpiA, rpiB, rpiR, rplA, rplB, rplC, rplD, rplE, rplF, rplI, rplJ, rplK, rplL, rplM, rplN, rplO, rplP, rplQ, rplR, rplS, rplT, rplU, rplV, rplW, rplX, rplY, rpmA, rpmB, rpmC, rpmD, rpmE, rpmF, rpmG, rpmH, rpmI, rpmJ, rpoA, rpoB, rpoC, rpoD, rpoE, rpoH, rpoN, rpoS, rpoZ, rpsA, rpsB, rpsC, rpsD, rpsE, rpsF, rpsG, rpsH, rpsI, rpsJ, rpsK, rpsL, rpsM, rpsN, rpsO, rpsP, rpsQ, rpsR, rpsS, rpsT, rpsU, rrfA, rrfB, rrfC, rrfD, rrfE, rrff, rrfG, rrfH, rrlA, rrlB, rrlC, rrlD, rrlE, rrlG, rrlH, rrmA, rrsA, rrsB, rrsC, rrsD, rrsE, rrsG, rrsH, rsd, rseA, rseB, rseC, rspA, rspB, rssA, rssB, rsuA, rtcA, rtcB, rtcR, rtn, rus(qsr'), ruvA, ruvB, ruvC, sad, sanA, sapA, sapB, sapC, sapD, sapF, sbaA, sbcB, sbcC, sbcD, sbmA, sbmC(gyrI), sbp, sdaA, sdaB, sdaC, sdhA, sdhB, sdhC, sdhD, sdiA, sds, secA, secB, secD, secE, secF, secG, secY, selA, selB, selC, selD, semA, seqA, serA, serB, serC, serR serS, serT, serU, serV, serW, serX, sfa, sfcA, sfiC, sfsA, sfsB, shiA, sipC, sipD, sir, sixA, sloB, slp, slr, slt, slyD, slyx, smp, smtA, sodA, sodB, sodC, sohA, sohB, solA, soxR, soxS, speA, speB, speC, speD, speE, speF, speG, spf, spoT, sppA, spr, srlA, srlB, srlD, srlE, srlR, srlB, srmA, ssaE, ssaG, ssaH, ssb, sseA, sseB, sspA, sspB, ssrA, ssrS, ssyA, ssyD stfZ, stkA, stkB, stkC, stkD, stpA, strC, strM, stsA, sucA, sucB, sucC, sucD, sufL, sugE, suhA, suhB, sulA, supQ, surA, surE, syd, tabC, tag, talA, talB, tanA, tanB, tap, tar, tas, tauA, tauB, tauC, tauD, tbpA, tdcA, tdcB, tdcC, tdcD, tdcE, tdcF, tdcG, tdcR, tdh, tdi tdk, tehA, tehB, tesA, tesB, tgt, thdA, thdC, thdD, thiB, thiC, thiD, thiE, thiF, thiG, thiH, thiI, thiJ, thiK, thiL, thiM, thrA, thrB, thrC, thrS, thrT, thrU, thrV, thrW, thyA, tig, tktA, tktB, tldD, tlnA, tmk, tnaA, tnaB, tnaC, tnm, tol-orf1, tol-orf2, tolA, tolB, tolC, tolD, tolE, tolI, tolJ, tolM, tolQ, tolR, tonB, topA, topB, torA, tor C, torD, tor R, tor S, torT, tpiA, tpr, tpx, treA, treB, treC, treF, treR, trg, trkA, trkD, trkG, trkH, trmA, trmB, trmC, trmD, tmmE, trmF, trmH, trmU, tmA, trpA, trpB, trpC, trpD, trpE, trpR, trpS, trpT, truA, truB, trxA, trxB, trxc, tsaA, tsf, tsmA, tsr, tsx, ttdA, ttdB, ttk, tufA, tuffB, tus, tynA, tyrA, tyrB, tyrp, tyrR, tyrS, tyrT, tyrU, tyrv, ubiA, ubiB, ubiC, ubiD, ubiE, ubiF, ubiG, ubiH, ubiX, ucpA, udk, udp, ugpA, ugpB, ugpC, ugpE, ugpQ, uhpA, uhpB, uhpC, uhpT, uidA, uidB, uidR, umuC, umuD, ung, upp, uppS, ups, uraA, usg-1, usbA, uspA, uup, uvh, uvrA, uvrB, uvrC, uvrD, uvs, uxaA, uxaB, uxaC, uxuA, uxuB, uxuR, valS, valT, valU, valV, valW, valX, valY, valZ, vsr, wrbA, xapA, xapB, xapR, xasA, xerC, xerD, xni, xseA, xseB, xthA, xylA, xylB, xylE, xylF, xylG, xylH, xylR, yccA, yhhP, yihG, yjaB, f147, yjaD, yohF, yqiE, yrfE, zipA, zntA, znuA, znuB, znuC, zur, and zwf.

Non-limiting examples of mouse genes include: Ilr1, Ilr2, Gas10, Tnp1, Inhbb, Inha, Creb1, Mpmv34, Acrd, Acrg, Il110, Otf1, Rab11b-r, Ab11, ald, Amh-rs1, Bcl2B, Cchlla3, Ccnb1-rs2, Gpcr16, Htr5b, Idd5, Igfbp2, Igfbp5, 118rb, Kras2-rs1, Mov7, Mpmv6, Mpmv16, Mpmv22, Mpmv25, Mpmv29, Mpmv42, Mtv7, Mtv27, Mtv39, Oprk1, Otf-rs1, Otf8, Otf11-rs1, Ptgs2, Ren1, Ren2, Ril3, Sxv, Taz4-rs1, Tgfb2, Wnt6, Xmmv6, Xmmv9, Xmmv36, Xmmv61, Xmmv74, Xmv21, Xmv32, Xmv41, I12ra, Ab1, Mpmv3, Rap1a-ps2, anx, Mpmv43, Ryr3, Ras12-4, Adra2b, Avp, Glvr1, Il1a, Il1b, Mpmv28, Oxt, Pcsk2, a, Xmv10, Tcf4, Acra, Acra4, Ak1, Bdnf, bs, Cyct, Cyp24, Dbh, Fshb, Gcg, Gdf5, Gnas, Gpcr8, Grin1, Hcs4, Hior2, Hsp84-2, Idd12, Ilrn, Jund2, Kras3, Mc3r, Mpmv14, Mtv40, Mxi1-rs1, Otf3-rs2, Ptgs1, Ptpra, Rapsn, Src, Svp1, Svp3, Tcf3b, Wt1, Xmmv71, Xmv48, Ccna, Fgf2, Fth-rs1, Csfm, Mov10, Egf, Acrb2, Cap1, Crh, Fim3, Fps11, Glut2, Gpcr2, Gria2, Hsd3b-1, Hsd3b-2, Hsd3b-3, Hsd3b-4, Hsp86-ps2, Idd3, 112, 117, Mpvmv9, Mpmv20, Mtv4.8, Ngfb, Npra, Nras, Nras, Ntrk, Otf3-rs3, Otf3-rs4, Rap1a, Tshb, Xmmv22, Xmmv65, Mos, Ras12-7, Lyr, Ifa, Ifb, Jun, azh, db, Ipp, Mp1, Do1, Ak2, Ccnb1-rs4, Cdc211, Cga, Fgr, Foc1, Fps12, Gabrr1, Gabrr2, Gdf6, Glut1, Gnb1, Gpcr14, Grb2-ps, Grik3, Grik5, Hsp86-1ps4, Htr1da, Htr1db, Idd9, Ifa1, Ifa2, Ifa3, Ifa4, Ifa5, Ifa6, Ifa7, Ifa8, Ifa9, Ifa10, Lap18, Lmyc1, Mpmv19, Mpmv44, Mtv13, Mtv14, Mtv17, Nppb, Otf6, Otf7, Ri12, Ski, Tnfr2, Wnt4, Xmmv8, Xmmv23, Xmmv62, Xmv1, Xmv2, Xmv8, Xmv9, Xmv14, Xmv44, Xpa, Tec, Fgf5, Nos1, Tcf1, Epo, Gnb2, Flt1, Flt3, Ache, Adra2c, Adrbk2, Afp, Alb1, Ccnb1-rs1, Clock, Cyp3, Cyp3a11, Cyp3a13, Drd1b, Drd5, Fgfr3, Flk1, Gc, Gnrhr, Gpcr1, Hcs5, Hnf1, Htr5a, I15r, I16, Kit, Ltrm3, Mgsa, Mpmv7, Mpmv13, Mpmv23, Mtv32, Mtv41, Pdgfa, Pdgfra, Por, Txk, Xmmv3, Xmmv5, Xmmv52, Xmv17, Xmv28, Xmv34, Xmv38, Xmv45, Zp3, Trh, Raf1, Fth-rs2, NtB, Kras2, Pthlh, Mov1, Alox5, Braf2, Cftr, Egr4, Fps110, Fgf6, GdB, Ghrfr, Glut3, Grin2a, Hior3, Hoxa10, hop, Ica1, I15r, Int41, Itpr1, Krag, Mad, Met, Mi, Mtv8, Mtv23, Mtv29, Mtv33, Mtv34, Nkna, Npy, ob, Otf3-rs5, Tgfa, Tnfr1, Wnt2, Wnt5B, Wnt7A, Xmmv27, Xmv24, Xmv61, Fosb, Ryr1, Ngfa, Ufo, Xrcc1, Abpa, Abpga, Gabra4, Gas2, Acra7, Ccnb1-rs7, Egfbp3, Xmv30, Zp2, Fes, Pcsk3, Calc, Ccnb1-rs10, Pth, Ad, Bcl3, Cea, Cea2, Cea3, Cea4, Cea5, Cea6, Cebp, Dm9, Dm15, Drd4, Egfbp1, Egfbp2, Ercc2, Fgf3, Fgfr2, Gabra5, Gabrb3, Gtx, Hcs1, Igf1r, Igf2, I14r, Ins2, Int40, Lhb, Mpmv1, Mtv1, Mtv35, Ngfg, Ntf5, Otf2, 2, Pkcc, Ras14, Rras, Ryr, Svp2, Tcf3g, Tgfb1, tub, Xmmv31, Xmmv35, Xmmv73, Xmv33, Xmv53, Taz83, Adrb3, Junb, Jund1, Me1, Gpcr19-rs2, Agt, Cadp, Ccnb1-rs9, E, Fgfr1, Gas6, Gnb-rs1, Hcs2, Insr, Maf, Mov34, Mpmv21, Mpmv41, Mtv21, Mtnr1a, Plat, Ras15-2, Ras16, Sntb2, Xmmv29, Xmv12, Xmv26, Xmv62, Epor, Gpcr13, Otf11, Pthr, Acra3, Acra5, Acrb4, Camk1, Cdc25Mm, Crbp, Crbp2, Csk, Cyp11a, Cyp19, Drd2, Ets1, Fli1, Gnai2, Gnat1, Gpcr6, Gria4, Hgf1, Hior1, Hpx, Hsp86-1ps3, Hst2, Idd2, I11bc, Lag-rs1, Lap18-rs1, M11, Mpmv27, Penk, Pgr, Ras12-2, Tp11, Trf, Xmmv2, Xmmv67, Xmv15, Xmv16, Xmv25, Xmv60, Mgf, Amh, Braf, Cdc2a, Dmd1, Estr, Fps13, Fps14, Fps15, Gli, Gpcr17, Grik2, Ifgr, Igf1, Mpmv5, Mpmv12, Mpmv40, Myb, Oprm, Pg, Pmch, Ros1, Xmv31, Xmv51, Xmv54, Camk2b, Egfr, Int6, Lif, Mtv44, Ews, Csfgm, Flt4, I13, I14, I15, Irf1, Gria1, Glut4, Crhr, Csfg, Mov9, Xmv20, Acrb, Mpmv4, Mpmv15, Ngfr, Nos2, Rara, Taz4, Tcf2, Xmv42, Mtv3, Adra1, Crko, df, Erbb2, Gabra1, Gabra6, Gabrg2, Gh, Glra1, Grb2, Hnf1b, Hsp86-ps1, Idd4, Igfbp1, Igfbp3, I113, Int4, Mpmv2, Mpmv8, Mpmv18, Mtv45, nu, Pkca, Rab1, Re1, Shbg, Tcf7, Thra, Tnz1, Trp53, Wnt3, Wnt3A, Xmv4, Xmv5, Xmv47, Xmv49, Xmv63, Akt, Amh-rs4, Ccs1, Fps16, Fos, Gdf7, Hcs3, Hsp70-2, Hsp84-3, Hsp86-1, hyt, Ltrm1, Max, Mpmv11, Mpmv24, Mtv9, Mtv30, Pomc1, Tcf3a, Tda2, Tgfb3, Tpo, Tshr, Xmmv21, Xmmv25, Xmmv34, Xmmv50, Gli3, Xmv55, Ryr2, Inhba, Gas1, Pcsk1, Amh-rs2, Ccnb1-rs6, Ccnb1-rs13, Crhpb, Dat1, Drd1a, Fgfr4, Fps17, Fim1, Gpcr15, Gpcr18, Hbvi, Hilda, Htr1a, Idd11, I19, Ltrm4, Mak, mes, P11, P12, Pr1, Ra1, Rasa, Srd5a1, Tpbp, Xmv13, Xmv27, Rarb, Rb3, Htr2, Rb1, Acra2, Camkg, Cch11a2, Ccnb1-rs5, Ccnb1-rs12, Gnrh, Mtv11, Nras-ps, Otf3-rs6, Plau, Ptprg, Trp53-ps, Wnt5A, Xmv19, Ghr, II 7r, Lifr, Mlvi2, Prlr, Myc, Rill, cog, Amh-rs7, I12rb, Pdgfb, Acr, CP2, Rarg, Sp1-1, Wnt1, Afr1, Atf4, Bzrp, Ccnb1-rs11, Cyp11b, I13rb1, I13rb2, Ins3, Itga, Mlvi1, Mlvi3, Mtv36, Pdgfec, Svp5, Tef, Trhr, Wnt7B, Xmmv55, Xmmv72, Xmv37, Tnp2, Ets2, Casr, Chuck-rs1, din, Drd3, Erg, G22p1, Gap43, Gas4, Grik1, Htrlf, Ifgt, Int53, Ltrm2, Mpmv17, Mtv6, Mtvr1, Pit1, Xmv3, Xmv35, Xmv50, Igf2r, Mas, Tcd3, Glp1r, Idd1, Tla, Aeg1, Ccnb1-rs3, Cdc2b, Csi, Cyp21, Cyp2'-ps1, Fps18, Gna-rs1, Gpcr19-rs1, Grr1, Grr2, Hom1, Hsc70t, Hsp70, Hsp70-1, Hsp70-3, Hsp84-1, Hst1, Hst4, Hst5, Hst6, Hye, Int3, Itpr3, Lap18-rs2, Otf3, Ptprs, Rab 11b, Ras12-1, Ras12-3, Ras13, Rrs, Rxrb, Tas, Tcd1, Tcd2, Tera1, Tla-rs, Tnfa, Tnfb, Tpx1, Tpx2, Xmmv15, Xmv36, Xmv57, Csfmr, Pdgfrb, Adrb2, Apc, Camk2a, Camk4, Dcc, Fgfi, Gna1, Gpcr7, Gr11, Grp, Hsp74, Mcc, Mtv2, Mtv38, Ptpn2, Tpl2, Xmv22, Xmv23, Xmv29, Fth, Csfgmra, Mxi1, Adra2a, Adrb1, Adrbk1, Chuck, Cyp17, Gna14, Gnb-ps1, Hcs6, Htr7, Ide, Ins1, Lpc1, Pomc2, Seao, Tlx1, Xmmv42, Xmv18, Tcfe3, Araf, Avpr2, mdx, Ar, Zfx, Otf9, Ccg1, Ccnb1-rs8, Fps19, Gabra3, Glra2, Glra4, Gria3, Grpr, Hsp74-ps1, Hst3, Htr1c, I12rg, Mov14, Mov15, Mtv28, Otf3-rs8, Sts, Sxa, Sxr, Xta, Tdy, Hya, Zfy1, Zfy2, Mov15, Mov24, Mtv31, Mtv42, Sdma, Spy, Sts, Sxa, Sxr, XmmvY, Xmv7, Xmv11, and Xmv40.

Non-limiting examples of *Phaseolus vulgaris* genes include: Acc, ace, Adk, Am, Amv-1, Amv-2, Ane, aph, Arc, Are, arg, Ar1 (Arc), asp, B, bc-u, bc-1.sup.1, bc-1.sup.2, bc-2.sup.1, bc-2.sup.2, bc-3, Bcm, Beg, Bip, blu, Bpm, Bsm, By-1, By-2, C, C/c, c.sup.cr, C.sup.cir, C.sup.ma (M, R.sup.ma), C.sup.r, C.sup.res, C.sup.rho, C.sup.st, [C.sup.st R Acc] (Aeq), c.sup.u (inh, i.sub.e), [c.sup.u Prp.sup.i] (Prp, c.sup.ui, Nud), [c.sup.uprp.sup.st] (prp.sup.st), [C Prp] (Prp), c.sup.v, [C R] (R), [C r] (r), Ca, Cam, Cav, cc, ch1, cl, cm1, Co-1 (A), Co-2 (Are), Co-3 (Mexique 1), Co-3.sup.2, Co-4 (Mexique 2), Co-5 (Mexique 3), Co-6, Co-7, cr-1 cr-2, cry, cs, Ct, ctv-1 ctv-2, cyv (by-3), D (Can, Ins), Da, Db, def, dgs (g1, 1e), dia, Diap-1, Diap-2, diff, dis, D1-1 Di-2 (DL.sub.1 DL.sub.2), do, ds (te), dt-1.sup.a dt-2.sup.a, dt-i.sup.b dt-2.sup.b, dw-1 dw-2, Ea Eb, ers (restr), ers-2, Est-1, Est-2, exp, F, Fa, fast, Fb Fc, fa fb fc, Fcr, Fcr-2, fd, Fe-1 Fe-2, Fin (in), Fop-1, Fop-2, Fr, Fr-2, G (Flav, Ca, Och), Ga, gas, glb, Gpi-c1, Gr, Hb1 (L.sub.HB-1), Hbnc (SC.sub.HB-1), Hbp (PD.sub.HB-1), hmb, Hss, Hsw, Ht-1Ht-2 (L-1 L-2), I, Ia Ib, ian-1 ian-2 (ia), lbd, ico, Igr (Ih), ilo, ip, iter, iv, iw, J (Sh), Ke, L, la, Lan, Ld, Lds (Ds), Lec, Li (L), lo, Ir-1, lr-2, mar, Me, MeI (Me), MeI-2 (Me-2), mel-3 (me-3), Mf, mi, mia, Mic (Mip), miv, Mrf, Mrf.sup.2, mrf, ms-1, Mue, mu mutator, Nag, Nd-1 Nd-2 (D-1 D-2), nie, nnd (sym-1), nnd-2, No, nts (nod), Nudus, ol, P, p.sup.gri (Gri, v.sup.Pal), pa, pc, pg (pa.sub.1), Pha, Pmv, ppd (neu), Pr, prc (pc), Prx, punc, ram, Rbcs (rbcS), rf-1, rf-2, rf-3, rfi (i), Rfs (m), Rk, rk, rk.sup.d (lin), rn-1 rn-2 (r r), rnd, Ro, Sal, sb, sb.sup.ms, sb-2, sb-3, si1, Skdh, s1, Smv, St, Sur, sw-1 sw-2, T, t (z-1), Th-1 Th-2, Tm, To, Tor (T), Tr, tri, trv, Ts, tw, uni, Uni-2, uni.sup.nde, uni.sup-.nie, Ur-1, Ur-2, Ur-2.sup.2, Ur-3 (Ur-3, Ur-4), Ur-3.sup.2, Ur-4, (Up-2, Ur-C), Ur-5, (B-190), Ur-6 (Ur.sub.a, Ur-G), Ur-7 (R.sub.B11), Ur-8 (Up-1), Ur-9 (Ur.sub.p), us, V (Bi), v.sup.lae (Cor), v, var, vi (vir.sub.f), wb, Wmv, X.sup.su, y, and Z.

Non-limiting examples of *Saccharomyces cerevisiae* genes include: PRE3, PUP1, PUP3, PRE2, PRE10, PRE1, PRE8, SCL1, PUP2, PRE5, PRE7, PRE4, RPT2, RPT3, RPN3, RPN11, RPN12, RPT6, RPN1, RPN2, RPT1, RPT5, RPT4, SKI6, RRP4, DIS3, TSC10, RAT1, GND1, EXO70, ERG10, ACC1, RPP0, ACT1, ARP100, ARP3, PAN1, ARP2, ARP4, ARP9, SPE2, CYR1, ALA1, TPS1, TUB1, ABF1, DED81, NIP1, YHC1, SNU71, ATM1, MAK5, ROK1, DED1, SPB4, AUR1, PSE1, ALG1, TUB2, BPL1, MSL5, ERG24, ERG26, ERG25, CMD1, HCA4, SHE9, SHE10, CAK1, PIS1, CHO1, CDS1, ESR1, NUD1, CDC47, CDC13, CDC37, CDC1, CDC4, CDC20, CDC6, CDC46, CDC3, KAR1, BBP1, HRP1, CCT2, CCT3, HSP10, SMC1, SMC2, CHC1, CFT2, CLP1, COP1, SEC26, SEC27, RET2, SEC21, COF1, CCT4, CCT1, CCT6, SEC24, SEC7, PCF11, RNA15, RNA14, FIP1, YSH1, TFB4, TSM1, APC2, APC5, SEC31, TAF47, TAP42, MPP10, CDC53, CKS1, CDC28, KIN28, CNS1, ERG11, DBP10, DBP8, PRO3, DYS1, ALR1, TID3, DNA2, SSL2, RAD3, RFA3, RFA2, RFA1, RFC4, RFC5, RFC3, RFC2, RFC1, TOP2, RAP1, RPC25, PRI2, PRI1, POL1, POL12, HUS2, CDC2, POL2, DPB2, RPB10, RPA135, RPA190, RPA43, RPB8, RP026, RPB5, RPC40, RPC19, SRB7, SRB4, RGR1, RPB11, SRB6, RPB2, RPB7, RPO21, RET1, RP031, RPC31, RPC34, RPC53, RPC82, RPB12, RPB3, DPM1, DIP2, RNT1, CDC8, CDC14, DUT1, UBA2, UBA1, UBC9, CDC34, ENP1, ERD2, SSS1, SEC61, SEC63, SEC62, GNA1, GPI8, DAM1, DUO1, IRR1, PRP3, TIM9, HSH49, SUP35, EXM2, MEX67, ERG9, ERG20, FAS2, FAS1, NOP1, FAD1, AOS1, FBA1, NCB2, BRN1, TUB4, GDI1, GOG5, SRM1, CDC25, SPT16, YIF2, BET4, CDC43, MRS6, BET2, PRO1, GLN1, GLN4, GRS1, YIP1, FOL2, GPA1, CDC42, SAR1, YPT1, SEC4, GSP1, TEM1, RHO1, CDC24, RNA1, GUK1, VMA16, PMA1, HKR1, SIS1, MGE1, HSP60, HSF1, HAS1, MOT3, HTS1, ESA1, HSL7, HOM6, RIB7, SLY1, CSL4, PUR5, CSE1, IPP1, MDM1, USO1, SOF1, MAK11, LAS1, TEL2, DPB11, SGD1, FAL1, MTR3, MTR4, SPP2, SIK1, RRP7, POP4, RRP1, POP3, BFR2, CDC5, NRD1, MET30, MCM6, RRP46, SAS10, SCC2, ECO1, PRP43, BET3, BET5, STN1, NFS1, IDI1, SRP1, KAP95, CBF2, SKP1, CEP3, CTF13, ERG7, KRS1, PSA1, PMI40, ALG2, SSF1, MED7, RSC4, CDC54, MCM2, AFG2, ERG12, MVD1, CDC48, MHP1, ERV1, SSC1, TIM44, TIM17, TIM23, TOM22, TOM40, MAS1, MCD1, MMC1, STU1, JAC1, ABD1, CEG1, PAB1, MTR2, SEC16, ROT1, INO1, MLC1, MYO2, GPI2, SPT14, NAT2, NMT1, TRM1, NCP1, NBP1, ACF2, SPP41, NUT2, LCP5, PRP19, NMD3, RFT1, NNF1, NDC1, CRM1, KAR2, NIP29, NAB2, NIC96, NUP145, NUP49, NUP57, NUP159, NSP1, NUP82, CDC39, NPL4, POP7, NTF2, MAK16, NPL3, NOP2, NOP4, NHP2, NOP10, GAR1, NBP35, WBP1, STT3, SWP1, OST2, OST1, ORC1, ORC6, ORC5, ORC4, ORC3, RRR1, SAT2, PWP2, PEX3, TOR2, PIK1, SEC14, STT4, MSS4, PCM1, GPM1, SEC53, ERG8, YPD1, PAP1, NAB3, RRN7, SEN1, CFT1, PRP11, PRP21, PRP39, PRP24, PRP9, SLU7, PRP28, PRP31, IFH1, PTA1, SUB2, FMI1, MAS2, ESS1, PFY1, POL30, POP1, PDI1, RAM2, CDC7, SMP3, CDC15, YTH1, QR12, YAE1, SFI1, SEC1, BET1, SEC6, SEC13, SEC2, SEC8, CBF5, CDC19, YRB1, RHC18, DBF4, SDS22, MCM3, CEF1, ALG11, GAA1, MOB1, NIP7, TIP20, SEC5, SEC10, GPI10, RRP3, CDC45, DIB1, MIF2, HOP2, PBN1, NOP5, RPP1, POP5, POP8, POP6, ERO1, MPT1, DNA43, ESP1, SMC3, LST8, STS1, RPM2, RNR1, RNR2, RNR4, RPS20, RPL25, RPL3, RPL30, RPL32, RPL37A, RPL43A, RPL5, RPL10, RPS3, CET1, YRA1, SNM1, GLE1, DBP5, DRS1, DBP6, BRR2, RRN3, RRN6, RRN11, MED6, PRP16, RPR2, DIM1, RRP43, RRP42, RRP45, SEC20, BOS1, CDC12, GLC7, PKC1, IPL1, SGV1, NRK1, RAD53, LCB2, LCB1, MPS1, SES1, SPC3, SEC11, R101, ARP7, NEO1, YJU2, POB3, ARH1, IQG1, HRT1, HYM1, MAK21, FUN20, FUN9, NBN1, STB5, YIF1, SMX4, YKT6, SFT1, SMD1, PRP6, LSM2, NUF1, SPC97, SPC42, SPC98, CDC31, SPC19, SPC25, SPC34, SPC24, NUF2, PRP40, MCD4, ERG1, SMC4, CSE4, KRR1, SME1, TRA1, RLP7, SCH9, SMD3, SNP2, SSF2, SPC72, CDC27, CDC23, CDC16, APC1, APC11, APC4, ARC19, RPN6, RPN5, RSC6, RSC8, STH1, SFH1, TIM12, TIM22, TIM10, SQT1, SLS1, JSN1, STU2, SCD5, SSU72, ASM4, SED5, UFE1, SYF1, SYF2, CCT5, THF1, TOA2, TOA1, SUA7, TAF90, TAF61, TAF25, TAF60, TAF17, TAF145, TAF19, TAF40, TAF67, TFA2, TFA1, FCP1, TFG1, TFG2, TFB1, CCL1, SSL1, TFB3, TFB2, PZF1, BRF1, TFC5, TFC4, TFC3, TFC7, TFC6, TFC1, SPT15, THI80, THS1, SPT6, SPT5, ROX3, REB1, MCM1, MED4, MOT1, MED8, EFB1, YEF3, SUI1, CDC95, TIF11, SUI3, GCD11, SUI2, GCD6, GCD7, GCD2, GCD1, RPG1, GCD10, PRT1, TIF34, CDC33, TIF5, SUP45, GCD14, TIM54, SEC17, TPT1, TRL1, CCA1, SEN54, SEN2, SEN15, SEN34, WRS1, SLN1, TYS1, SNU56, PRP42, CUS1, PRP4, PRP8, SNU114, USS1, UFD1, SMT3, RSP5, QR11, ALG7, UGP1, VTI1, VAS1, SEC18, CTR86, and ZPR1.

2. Viruses

The microorganisms provided herein include viruses. Such viruses typically have one or more of the microorganism characteristics provided herein. For example, viruses provided herein can have attenuated pathogenicity, reduced toxicity, preferential accumulation in immunoprivileged cells and tissues, such as tumor, ability to activate an immune response against tumor cells, immunogenic, replication competent, and are able to express exogenous proteins, and combinations thereof. In some embodiments, the viruses have an ability to activate an immune response against tumor cells without aggressively killing the tumor cells.

The viruses provided herein can be cytoplasmic viruses, such as poxviruses, or can be nuclear viruses such as adenoviruses. The viruses provided herein can have as part of their life cycle lysis of the host cell's plasma membrane. Alternatively, the viruses provided herein can have as part of their life cycle exit of the host cell by non-lytic pathways such as budding or exocytosis. The viruses provided herein can cause a host organism to develop an immune response to virus-infected tumor cells as a result of lysis or apoptosis induced as part of the viral life cycle. The viruses provided herein also can be genetically engineered to cause a host organism to develop an immune response to virus-infected tumor cells as a result of lysis or apoptosis, regardless of whether or not lysis or apoptosis is induced as part of the viral life cycle. In some embodiments, the viruses provided herein can cause the host organism to mount an immune response against tumor cells without lysing or causing cell death of the tumor cells.

One skilled in the art can select from any of a variety of viruses, according to a variety of factors, including, but not limited to, the intended use of the virus (e.g., exogenous protein production, antibody production or tumor therapy), the host organism, and the type of tumor.

a. Cytoplasmic Viruses

The viruses provided herein can be cytoplasmic viruses, where the life cycle of the virus does not require entry of viral nucleic acid molecules in to the nucleus of the host cell. A variety of cytoplasmic viruses are known, including, but not limited to, pox viruses, African swine flu family viruses, and various RNA viruses such as picorna viruses, calici viruses, toga viruses, corona viruses and rhabdo viruses. In some embodiments, viral nucleic acid molecules do not enter the host cell nucleus throughout the viral life cycle. In other embodiments, the viral life cycle can be performed without use of host cell nuclear proteins. In other embodiments, the virulence or pathogenicity of the virus can be modulated by modulating the activity of one or more viral proteins involved in viral replication.

i. Poxviruses

In one embodiment, the virus provided herein is selected from the pox virus family. Pox viruses include Chordopoxyirinae such as orthopoxvirus, parapoxvirus, avipoxvirus, capripoxvirus, leporipoxvirus, suipoxvirus, molluscipoxvirus and yatapoxvirus, as well as Entomopoxyirinae such as entomopoxvirus A, entomopoxvirus B, and entomopoxvirus A. Chordopoxyirinae are vertebrate poxviruses and have similar antigenicities, morphologies and host ranges; thus, any of a variety of such poxviruses can be used herein. One skilled in the art can select a particular genera or individual chordopoxyirinae according to the known properties of the genera or individual virus, and according to the selected characteristics of the virus (e.g., pathogenicity, ability to elicit and immune response, preferential tumor localization), the intended use of the virus, the tumor type and the host organism. Exemplary chordopoxyirinae genera are orthopoxvirus and avipoxvirus.

Avipoxviruses are known to infect a variety of different birds and have been administered to humans. Exemplary avipoxviruses include canarypox, fowlpox, juncopox, mynahpox, pigeonpox, psittacinepox, quailpox, peacockpox, penguinpox, sparrowpox, starlingpox, and turkeypox viruses.

Orthopoxviruses are known to infect a variety of different mammals including rodents, domesticated animals, primates and humans. Several orthopoxviruses have a broad host range, while others have narrower host range. Exemplary orthopoxviruses include buffalopox, camelpox, cowpox, ectromelia, monkeypox, raccoon pox, skunk pox, tatera pox, uasin gishu, vaccinia, variola and volepox viruses. In some embodiments, the orthopoxvirus selected can be an orthopoxvirus known to infect humans, such as cowpox, monkeypox, vaccinia or variola virus. Optionally, the orthopoxvirus known to infect humans can be selected from the group of orthopoxviruses with a broad host range, such as cowpox, monkeypox, or vaccinia virus.

a. Vaccinia Virus

One exemplary orthopoxvirus is vaccinia virus. A variety of vaccinia virus strains are available, including Western Reserve (WR), Copenhagen, Tashkent, Tian Tan, Lister, Wyeth, IHD-J, and IHD-W, Brighton, Ankara, MVA, Dairen I, L-IPV, LC16M8, LC16MO, LIVP, WR 65-16, Connaught, New York City Board of Health. Exemplary vaccinia viruses are Lister or LIVP vaccinia viruses. Any known vaccinia virus, or modifications thereof that correspond to those provided herein or known to those of skill in the art to reduce toxicity of a vaccinia virus. Generally, however, the mutation will be a multiple mutant and the virus will be further selected to reduce toxicity.

The linear dsDNA viral genome of vaccinia virus is approximately 200 kb in size, encoding a total of approximately 200 potential genes. Viral gene expression can be divided into three stages. In the early stage, gene expression is mainly for viral replication, and for defense against the host's immune system. In the intermediate stage, genes not available for expression in the early stage can be expressed, including late stage transactivators. In the late stage, active transcription is mainly for viral structural components for building mature viruses.

Vaccinia virus possesses a variety of features for use in cancer gene therapy and vaccination. It has a broad host and cell type range. Vaccinia is a cytoplasmic virus, thus, it does not insert its genome into the host genome during its life cycle. Unlike many other viruses that require the host's transcription machinery, vaccinia virus can support its own gene expression in the host cell cytoplasm using enzymes encoded in the viral genome. The vaccinia virus genome has a large carrying capacity for foreign genes, where up to 25 kb of exogenous DNA fragments (approximately 12% of the vaccinia genome size) can be inserted. The genomes of several of the vaccinia strains have been completely sequenced, and many essential and nonessential genes identified. Due to high sequence homology among different strains, genomic information from one vaccinia strain can be used for designing and generating modified viruses in other strains. Finally, the techniques for production of modified vaccinia strains by genetic engineering are well established (Moss, Curr. Opin. Genet. Dev. 3 (1993), 86-90; Broder and Earl, Mol. Biotechnol. 13 (1999), 223-245; Timiryasova et al., Biotechniques 31 (2001), 534-540).

Historically, vaccinia virus was used to immunize against smallpox infection. More recently, modified vaccinia viruses are being developed as vaccines to combat a variety of diseases. Attenuated vaccinia virus can trigger a cell-mediated immune response. Strategies such as prime/boost vaccination, vaccination with nonreplicating vaccinia virus or a combination of these strategies, have shown promising results for the development of safe and effective vaccination protocols. Mutant vaccinia viruses from previous studies exhibit a variety of shortcomings, including a lack of efficient delivery of the viral vehicle to the desired tissue only (e.g., specific accumulation in a tumors), a lack of safety because of possible serious complications (e.g., in young children, eczema vaccinatum and encephalitis, and in adults disseminated or progressive vaccinia may result if the individual is severely immunodeficient).

b. Modified Vaccinia Viruses

Provided herein are vaccinia viruses with insertions, mutations or deletions, as described more generally elsewhere herein. The vaccinia viruses are modified or selected to have low toxicity and to accumulate in the target tissue. Exemplary of such viruses are those from the LIVP strain.

Exemplary insertions, mutations or deletions are those that result in an attenuated vaccinia virus relative to the wild type strain. For example, vaccinia virus insertions, mutations or deletions can decrease pathogenicity of the vaccinia virus, for example, by reducing the toxicity, reducing the infectivity, reducing the ability to replicate, or reducing the number of non-tumor organs or tissues to which the vaccinia virus can accumulate. Other exemplary insertions, mutations or deletions include, but are not limited to, those that increase antigenicity of the microorganism, those that permit detection or imaging, those that increase toxicity of the microorganism (optionally, controlled by an inducible promoter). For example, modifications can be made in genes that are involved in nucleotide metabolism, host interactions and virus formation. Any of a variety of insertions, mutations or deletions of the vaccinia virus known in the art can be used herein, including insertions, mutations or deletions of: the thymidine kinase (TK) gene, the hemagglutinin (HA) gene, the VGF gene (as taught in U.S. Pat. Pub. No. 20030031681); a hemorrhagic region or an A type inclusion body region (as taught in U.S. Pat. No. 6,596,279); Hind III F, F13L, or Hind III M (as taught in U.S. Pat. No. 6,548,068); A33R, A34R, A36R or B5R genes (see, e.g., Katz et al., J. Virology 77:12266-12275 (2003)); SalF7L (see, e.g., Moore et al., EMBO J. 1992 11:1973-1980); NIL (see, e.g., Kotwal et al., Virology 1989 171:579-587); M1 lambda (see, e.g., Child et al., Virology. 1990 174:625-629); HR, HindIII-MK, HindIII-MKF, HindIII-CNM, RR, or BamF (see, e.g., Lee et al., J. Virol. 1992 66:2617-2630); or C21L (see, e.g., Isaacs et al., Proc Natl Acad Sci USA. 1992 89:628-632).

c. The F3 Gene

In addition to the mutations known in the art, the vaccinia viruses provided herein can have an insertion, mutation or deletion of the F3 gene (SEQ ID No: 1; an exemplary F3 gene is provided in GenBank Accession No. M57977, which contains the nucleotide and predicted amino acid sequences for LIVP strain F3; see also Mikryukov et al., Biotekhnologiya 4:442-449 (1988)). For example, the F3 gene has been modified at the unique single NotI restriction site located within the F3 gene at position 35 or at position 1475 inside of the HindIII-F fragment of vaccinia virus DNA strain LIVP (Mikryukov et al., Biotekhnologiya 4 (1988), 442-449) by insertion of a foreign DNA sequence into the NotI digested virus DNA. As provided herein, an insertion of a nucleic acid molecule, such as one containing lacZ, into the NotI site of the F3 gene of the LIVP strain (nucleotides 1473-1480 in M57977, or nucleotides 33-40 of SEQ ID NO: 1) can result in decreased accumulation of vaccinia viruses in non-tumorous organs of nude mice, including brain and heart, relative to wild type vaccinia virus. Thus for use in the methods provided herein, vaccinia viruses can contain an insertion, mutation or deletion of the F3 gene or a mutation of a corresponding locus. For example, as provided herein, F3-interrupted modified LIVP vaccinia virus can selectively replicate in tumor cells in vivo. Therefore, modified vaccinia viruses (e.g., modified strain LIVP) with the interrupted F3 gene can be used in the methods provided herein, such as methods of tumor-directed gene therapy and for detection of tumors and metastases.

Thus, provided herein are vaccinia viruses having a modification of the F3 gene. For example, the vaccinia viruses provided herein can contain an insertion of foreign DNA into the F3 gene. An exemplary insertion of foreign DNA is an insertion at a site equivalent to the NotI site of the F3 gene in vaccinia strain LIVP, or at position 35 of SEQ ID NO:1. An F3-modified vaccinia virus provided herein can colonize in tumors specifically, and therefore, can be used for tumor-specific therapeutic gene delivery. A GenBank data analysis with BLAST (Basic Local Alignment Search Tool) on nucleotide sequences of different strains of vaccinia virus was performed. Based on this analysis, it was found that in vaccinia virus strain Copenhagen (Goebel et al., Virology 179 (1990), 247-266) the NotI restriction site is located between two open reading frames (ORF) encoding F14L and F15L genes. Therefore, insertion of foreign genes into NotI site of the VV genome strain Copenhagen will not interrupt any vital genes. In VV strain LIVP, the NotI restriction site is located in the ORF encoding the F3 gene with unknown function (Mikryukov et al., Biotekhnologiya 4 (1988), 442-449). Thus, the insertion of foreign genes into the NotI site of the F3 gene interrupted the F3 gene. The ability to modify the F3 gene suggests that it may have a nonessential role for virus replication. Although the F3 gene is likely nonessential for virus replication, the results of the animal experiments suggest that interruption of the F3 gene is correlated with decreased viral virulence, the inability to replicate in brain or ovary, and the ability to replicate preferentially in tumor tissue.

The F3 gene is conserved in a variety of different vaccinia virus strains, including WR (nucleotides 42238-42387 of GenBank Accession No. AY243312.1, Ankara (nucleotides 37155-37304 of GenBank Accession No. U94848.1), Tian Tan (nucleotides 41808-41954 of GenBank Accession No. AF095689), Acambis 3000 (nucleotides 31365-31514 of GenBank Accession No. AY603355.1) and Copenhagen (nucleotides 45368-45517 of GenBank Accession No. M35027.1) strains. The F3 gene also is conserved in the larger family of poxviruses, particularly among orthopoxviruses such as cowpox (nucleotides 58498-58647 of GenBank Accession No. X94355.2), rabbitpox (nucleotides 46969-47118 of GenBank Accession No. AY484669.1), camelpox (nucleotides 43331-43480 of GenBank Accession No. AY009089.1), ectromelia (nucleotides 51008-51157 of GenBank Accession No. AF012825.2), monkeypox (nucleotides 42515-42660 of GenBank Accession No. AF380138.1), and variola viruses (nucleotides 33100-33249 of GenBank Accession No. X69198.1). Accordingly, also provided are modifications of the equivalent of the F3 gene in poxviruses, such as orthopoxviruses including a variety of vaccinia virus strains. One skilled in the art can identify the location of the equivalent F3 gene in a variety of poxviruses, orthopoxviruses and vaccinia viruses. For example, an equivalent of the F3 gene in poxviruses, orthopoxviruses and vaccinia viruses can include a gene that contains at least 80%, at least 85%, at least 90%, at least 92%, at least 94%, at least 95%, at least 96%, at least 97%, at least 98%, or at least 99% identity with the nucleotide sequence of the F3 gene in SEQ ID NO:1. In another example, an equivalent of the F3 gene in poxviruses, orthopoxviruses and vaccinia viruses can include a gene that contains at least 80%, at least 85%, at least 90%, at least 92%, at least 94%, at least 95%, at least 96%, at least 97%, at least 98%, or at least 99% identity with the amino acid sequence of F3 in SEQ ID NO:2. In another example, the equivalent to the F3 gene in LIVP can be determined by its structural location in the viral genome: the F3 gene is located on the HindIII-F fragment of vaccinia virus between open reading frames F14L and F15L as defined by Goebel et al., Virology (1990) 179:247-266, and in the opposite orientation of ORFs F14L and F15L; one skilled in the art can readily identify the gene located in the structurally equivalent region in a large variety of related viruses, such as a large variety of pox viruses.

Comparative protein sequence analysis revealed some insight into protein function. The closest match with the protein encoded by the F3 gene (strain LIVP) is a prolyl 4-hydroxylase alpha subunit precursor (4-PH alpha) from the nematode *Caenorhabditis elegans* (Veijola et al., J. Biol. Chem. 269 (1994), 26746-26753). This alpha subunit forms an active alpha-beta dimer with the human protein disulfide isomerase beta subunit. Prolyl 4-hydroxylase (EC 1.14.11.2) catalyzes the formation of 4-hydroxyproline in collagen. The vertebrate enzyme is an alpha 2-beta 2 tetramer, the beta subunit of which is identical to the protein disulfide-isomerase (PDI). The importance of this protein for vaccinia viral replication is unknown, but a deficiency of this protein can result in retargeting vaccinia virus to tumor tissue.

d. Multiple Modifications

The vaccinia viruses provided herein also can contain two or more insertions, mutations or deletions. Thus, included are vaccinia viruses containing two or more insertions, mutations or deletions of the loci provided herein or other loci known in the art. In one embodiment, a vaccinia virus contains an insertion, mutation or deletion in the F3 gene, and one or more additional insertions, mutations or deletions. In one embodiment of the modified vaccinia virus, at least the F3 gene has been modified by insertion of a foreign nucleotide sequence. Modifications such as modification of the F3 gene will typically result in at least partial inactivation of the gene or gene product. In one example, the F3 gene and the TK gene have been modified by insertion of a foreign nucleotide sequence. In another example, the F3 gene and the HA gene have been modified by insertion of a foreign nucleotide sequence. In another example, the F3 gene and both the TK and HA genes have been modified by insertion of a foreign nucleotide sequence. In another example, the HA gene and the TK gene have been modified by insertion of a foreign nucleotide sequence. Accordingly, the present compositions and methods include a modified vaccinia virus wherein two or more of (a) the F3 gene, (b) the TK gene, and (c) the HA gene have been modified. In one embodiment, at least two of the F3 gene, TK gene and HA gene have been inactivated, for example by insertion, deletion and/or replacement of nucleotide(s) within the coding region, or regulatory sequences of two or more of these genes have been inactivated by insertion, deletion or mutation.

e. The Lister Strain

In another embodiment, the viruses and methods provided herein can be based on modifications to the Lister strain of vaccinia virus. Lister (also referred to as Elstree) vaccinia virus is available from any of a variety of sources. For example, the Elstree vaccinia virus is available at the ATCC under Accession Number VR-1549. The Lister vaccinia strain has high transduction efficiency in tumor cells with high levels of gene expression.

In one embodiment, the Lister strain can be an attenuated Lister strain, such as the LIVP (Lister virus from the Institute of Viral Preparations, Moscow, Russia) strain, which was produced by further attenuation of the Lister strain. The LIVP strain was used for vaccination throughout the world, particularly in India and Russia, and is widely available.

The LIVP strain has a reduced pathogenicity while maintaining a high transduction efficiency. For example, as provided herein, F3-interrupted modified LIVP vaccinia virus can selectively replicate in tumor cells in vivo. In one embodiment, provided herein are modified LIVP viruses, including viruses having a modified TK gene, viruses having a modified HA gene, viruses having a modified F3 gene, and viruses having two or more of: modified HA gene, modified TK gene, and modified F3 gene.

ii. Other Cytoplasmic Viruses

Also provided herein are cytoplasmic viruses that are not poxviruses. Cytoplasmic viruses can replicate without introducing viral nucleic acid molecules into the nucleus of the host cell. A variety of such cytoplasmic viruses are known in the art, and include African swine flu family viruses and various RNA viruses such as arenaviruses, picornaviruses, caliciviruses, togaviruses, coronaviruses, paramyxoviruses, flaviviruses, reoviruses, and rhaboviruses. Exemplary togaviruses include Sindbis viruses. Exemplary arenaviruses include lymphocytic choriomeningitis virus. Exemplary rhaboviruses include vesicular stomatitis viruses. Exemplary paramyxo viruses include Newcastle Disease viruses and measles viruses. Exemplary picornaviruses include polio viruses, bovine enteroviruses and rhinoviruses. Exemplary flaviviruses include Yellow fever virus; attenuated Yellow fever viruses are known in the art, as exemplified in Barrett et al., Biologicals 25:17-25 (1997), and McAllister et al., J. Virol. 74:9197-9205 (2000).

Also provided herein are modifications of the viruses provided above to enhance one or more characteristics relative to the wild type virus. Such characteristics can include, but are not limited to, attenuated pathogenicity, reduced toxicity, preferential accumulation in tumor, increased ability to activate an immune response against tumor cells, increased immunogenicity, increased or decreased replication competence, and are able to express exogenous proteins, and combinations thereof. In some embodiments, the modified viruses have an ability to activate an immune response against tumor cells without aggressively killing the tumor cells. In other embodiments, the viruses can be modified to express one or more detectable genes, including genes that can be used for imaging. In other embodiments, the viruses can be modified to express one or more genes for harvesting the gene products and/or for harvesting antibodies against the gene products.

b. Adenovirus, Herpes, Retroviruses

Further provided herein are viruses that include in their life cycle entry of a nucleic acid molecule into the nucleus of the host cell. A variety of such viruses are known in the art, and include herpesviruses, papovaviruses, retroviruses, adenoviruses, parvoviruses and orthomyxoviruses. Exemplary herpesviruses include herpes simplex type 1 viruses, cytomegaloviruses, and Epstein-Barr viruses. Exemplary papovaviruses include human papillomavirus and SV40 viruses. Exemplary retroviruses include lentiviruses. Exemplary orthomyxoviruses include influenza viruses. Exemplary parvoviruses include adeno associated viruses.

Also provided herein are modifications of the viruses provided above to enhance one or more characteristics relative to the wild type virus. Such characteristics can include, but are not limited to, attenuated pathogenicity, reduced toxicity, preferential accumulation in tumor, increased ability to activate an immune response against tumor cells, increased immunogenicity, increased or decreased replication competence, and are able to express exogenous proteins, and combinations thereof. In some embodiments, the modified viruses have an ability to activate an immune response against tumor cells without aggressively killing the tumor cells. In other embodiments, the viruses can be modified to express one or more detectable genes, including genes that can be used for imaging. In other embodiments, the viruses can be modified to express one or more genes for harvesting the gene products and/or for harvesting antibodies against the gene products.

3. Bacteria

Bacteria can also be used in the methods provided herein. Any of a variety of bacteria possessing the desired characteristics can be used. In one embodiment, aerobic bacteria can be used. In another embodiment, anaerobic bacteria can be used. In another embodiment, extracellular bacteria can be used. In another embodiment, intracellular bacteria can be used.

In some embodiments, the bacteria provided herein can be extracellular bacteria. A variety of extracellular bacteria are known in the art and include *vibrio, lactobacillus, streptococcus, escherichia*. Exemplary bacteria include *Vibrio cholerae, Streptococcus pyogenes*, and *Escherichia coli*. In other embodiments, the bacteria provided herein can be intracellular bacteria. A variety of intracellular bacteria are known in the art and include *listeria, salmonella, clostridium*, and *bifodobacterium*. Exemplary intracellular bacteria include *Listeria monocytogenes, Salmonella typhimurium, Clostridium histolyticus, Clostridium butyricum, Bifodobacterium longum*, and *Bifodobacterium adolescentis*. Additional bacteria include plant bacteria such as *Clavibacter michiganensis* subsp. *michiganensis, Agrobacterium tumefaciens, Erwinia herbicola, Azorhizobium caulinodans, Xanthomonas campestris* pv. *vesicatoria*, and *Xanthomonas campestris* pv. *campestris*.

A further example of a bacteria provided herein are magnetic bacteria. Such bacteria allow tumor detection through the accumulation of iron-based contrast agents. Magnetic bacteria can be isolated from fresh and marine sediments. Magnetic bacteria can produce magnetic particles (Fe3O4) (Blakemore, Annu. Rev. Microbiol. 36 (1982), 217-238). To do so, the magnetic bacteria have efficient iron uptake systems, which allow them to utilize both insoluble and soluble forms of iron. Magnetospirillum magnetic AMB-1 is an example of such magnetic bacteria that has been isolated and cultured for magnetic particle production (Yang et al., Enzyme Microb. Technol. 29 (2001), 13-19). As provided herein, these magnetic bacteria (naturally occurring or genetically modified), when injected intravenously, can selectively accumulate in tumor. Accordingly, these bacteria can be used for accumulating iron-based contrast agents in the tumors, which in turn allows tumor detection by MRI. Similarly, other naturally isolated metal accumulating strains of bacteria can be used for tumor targeting, absorption of metals from contrast agents, and tumor imaging.

Also provided herein are modifications of bacteria to enhance one or more characteristics relative to the wild type bacteria. Such characteristics can include, but are not limited to, attenuated pathogenicity, reduced toxicity, preferential accumulation in tumor, increased ability to activate an immune response against tumor cells, increased immunogenicity, increased or decreased replication competence, and are able to express exogenous proteins, and combinations thereof. In some embodiments, the modified bacteria have an ability to activate an immune response against tumor cells without aggressively killing the tumor cells. In other embodiments, the bacteria can be modified to express one or more detectable genes, including genes that can be used for imaging. In other embodiments, the bacteria can be modified to express one or more genes for harvesting the gene products and/or for harvesting antibodies against the gene products.

a. Aerobic Bacteria

Previous studies have postulated that anaerobic bacteria are preferred for administration to tumors (Lemmon et al., 1997 Gene Therapy 4:791-796). As provided herein, it has been determined that aerobic bacteria can survive and grow in tumors. Accordingly, a bacteria used in the methods provided herein can include a bacteria that can survive and grow in an oxygenated environment. In some embodiments, the bacteria must be in an oxygenated environment in order to survive and grow. A variety of aerobic bacteria are known in the art, including lactobacilli, *salmonella*, streptococci, staphylococci, *vibrio, listeria*, and *escherichia*. Exemplary bacteria include *Vibrio cholerae, Listeria monocytogenes, Salmonella typhimurium, Streptococcus pyogenes, Escherichia coli, Lactobacillus bulgaricus, Lactobacillus casei, Lacto bacillus acidophilus, Lactobacillus brevis, Lactobacillus paracasei, Lactobacillus plantarum, Lactobacillus rhamnosus, Lactobacillus salivarius, Lactobacillus sporogenes, Lactobacillus lactis, Lactobacillus fermentum, Streptococcus thermophilus, Bacillus subtilis, Bacillus megaterium, Bacillus polymyxa, Myobacterium smegmatis, Mycobacterium vaccae, Mycobacterium microti, Mycobacterium habana, Enterococcus faecalis, Pseudomonas fluorescens*, and *Pseudomonas putida*.

b. Anaerobic Bacteria

A bacteria used in the methods provided herein can include a bacteria that does not require oxygen to survive and grow. In some embodiments, the bacteria must be in an oxygen-free environment in order to survive and grow. A variety of aerobic bacteria are known in the art, including *clostridium, bifodobacterium*. Exemplary bacteria include *Clostridium histolyticus, Clostridium butyricum, Clostridium novyi, Clostridium sordellii, Clostridium absonum, Clostridium bifermentans, Clostridium difficile, Clostridium histolyticum, Clostridium perfringens, Clostridium beijerinckii, Clostridium sporogenes, Staphylococcus aureus, Staphylococcus epidermidis, Bifidobacterium longum, Bifidobacterium adolescentis, Bifidobacterium bifidum, Bifidobacterium infantis, Bifidobacterium laterosporus, Bifidobacterium animalis, Actinomyces israelii, Eubacterium lentum, Peptostreptococcus anaerobis, Peptococcus prevotti*, and *Acidaminococcus fermentans*.

4. Eukaryotic Cells

Also encompassed within the microorganisms provided herein and the methods of making and using such microorganisms are eukaryotic cells, including cells from multicellular eukaryotes, including mammals such as primates, where exemplary cells are human cells. Typically the cells are isolated cells. For example, eukaryotic cells can be tumor cells, including mammalian tumor cells such as primate tumor cells, where exemplary primate tumor cells are human tumor cells such as human breast cancer cells. In another example, eukaryotic cells can include fibrosarcoma cells such as human fibrosarcoma cells. Exemplary human fibrosarcoma cells include HT1080 (ATCC Accession Nos. CCL-121, CRL-12011 or CRL-12012). In another example, eukaryotic cells can include stem cells, including mammalian stem cells such as primate stem cells, where exemplary primate stem cells are human stem cells.

Also provided herein are modifications of eukaryotic cells to enhance one or more characteristics relative to the wild type cells. Such characteristics can include, but are not limited to, attenuated pathogenicity, reduced toxicity, preferential accumulation in tumor, increased ability to activate an immune response against tumor cells, increased immunogenicity, increased or decreased replication competence, and are able to express exogenous proteins, and combinations thereof. In some embodiments, the modified eukaryotic cells have an ability to activate an immune response against tumor cells without aggressively killing the tumor cells. In other embodiments, the eukaryotic cells can be modified to express one or more detectable genes, including genes that can be used for imaging. In other embodiments, the eukaryotic cells can be modified to express one or more genes for harvesting the gene products and/or for harvesting antibodies against the gene products.

C. METHODS FOR MAKING A MODIFIED MICROORGANISM

The microorganisms provided herein can be formed by standard methodologies well known in the art for modifying microorganisms such as viruses, bacteria and eukaryotic cells. Briefly, the methods include introducing into microorganisms one or more genetic modification, followed by screening the microorganisms for properties reflective of the modification or for other desired properties.

1. Genetic Modifications

Standard techniques in molecular biology can be used to generate the modified microorganisms provided herein. Such techniques include various nucleic acid manipulation techniques, nucleic acid transfer protocols, nucleic acid amplification protocols, and other molecular biology techniques known in the art. For example, point mutations can be introduced into a gene of interest through the use of oligonucleotide mediated site-directed mutagenesis. Alternatively, homologous recombination can be used to introduce a mutation or exogenous sequence into a target sequence of interest. Nucleic acid transfer protocols include calcium chloride transformation/transfection, electroporation, liposome mediated nucleic acid transfer, N-[1-(2,3-Dioloyloxy)propyl]-N, N,N-trimethylammonium methylsulfate meditated transformation, and others. In an alternative mutagenesis protocol, point mutations in a particular gene can also be selected for using a positive selection pressure. See, e.g., Current Techniques in Molecular Biology, (Ed. Ausubel, et al.). Nucleic acid amplification protocols include but are not limited to the polymerase chain reaction (PCR). Use of nucleic acid tools such as plasmids, vectors, promoters and other regulating sequences, are well known in the art for a large variety of viruses and cellular organisms. Further a large variety of nucleic acid tools are available from many different sources including ATCC, and various commercial sources. One skilled in the art will be readily able to select the appropriate tools and methods for genetic modifications of any particular virus or cellular organism according to the knowledge in the art and design choice.

Any of a variety of modifications can be readily accomplished using standard molecular biological methods known in the art. The modifications will typically be one or more truncations, deletions, mutations or insertions of the microorganismal genome. In one embodiment, the modification can be specifically directed to a particular sequence. The modifications can be directed to any of a variety of regions of the microorganismal genome, including, but not limited to, a regulatory sequence, to a gene-encoding sequence, or to a sequence without a known role. Any of a variety of regions of microorganismal genomes that are available for modification are readily known in the art for many microorganisms, including the microorganisms specifically listed herein. As a non-limiting example, the loci of a variety of vaccinia genes provided herein elsewhere exemplify the number of different regions that can be targeted for modification in the microorganisms provided herein. In another embodiment, the modification can be fully or partially random, whereupon selection of any particular modified microorganism can be determined according to the desired properties of the modified the microorganism.

In some embodiments, the microorganism can be modified to express an exogenous gene. Exemplary exogenous gene products include proteins and RNA molecules. The modified microorganisms can express a detectable gene product, a therapeutic gene product, a gene product for manufacturing or harvesting, or an antigenic gene product for antibody harvesting. The characteristics of such gene products are described herein elsewhere. In some embodiments of modifying an organism to express an exogenous gene, the modification can also contain one or more regulatory sequences to regulate expression of the exogenous gene. As is known in the art, regulatory sequences can permit constitutive expression of the exogenous gene or can permit inducible expression of the exogenous gene. Further, the regulatory sequence can permit control of the level of expression of the exogenous gene. In some examples, inducible expression can be under the control of cellular or other factors present in a tumor cell or present in a microorganism-infected tumor cell. In other examples, inducible expression can be under the control of an administerable substance, including IPTG, RU486 or other known induction compounds. Any of a variety of regulatory sequences are available to one skilled in the art according to known factors and design preferences. In some embodiments, such as gene product manufacture and harvesting, the regulatory sequence can result in constitutive, high levels of gene expression. In some embodiments, such as anti-(gene product) antibody harvesting, the regulatory sequence can result in constitutive, lower levels of gene expression. In tumor therapy embodiments, a therapeutic protein can be under the control of an internally inducible promoter or an externally inducible promoter.

In other embodiments, organ or tissue-specific expression can be controlled by regulatory sequences. In order to achieve expression only in the target organ, for example, a tumor to be treated, the foreign nucleotide sequence can be linked to a tissue specific promoter and used for gene therapy. Such promoters are well known to those skilled in the art (see e.g., Zimmermann et al., (1994) Neuron 12, 11-24; Vidal et al.; (1990) EMBO J. 9, 833-840; Mayford et al., (1995), Cell 81, 891-904; Pinkert et al., (1987) Genes & Dev. 1, 268-76).

In some embodiments, the microorganisms can be modified to express two or more proteins, where any combination of the two or more proteins can be one or more detectable gene products, therapeutic gene products, gene products for manufacturing or harvesting, or antigenic gene products for antibody harvesting. In one embodiment, a microorganism can be modified to express a detectable protein and a therapeutic protein. In another embodiment, a microorganism can be modified to express two or more gene products for detection or two or more therapeutic gene products. For example, one or more proteins involved in biosynthesis of a luciferase substrate can be expressed along with luciferase. When two or more exogenous genes are introduced, the genes can be regulated under the same or different regulatory sequences, and the genes can be inserted in the same or different regions of the microorganismal genome, in a single or a plurality of genetic manipulation steps. In some embodiments, one gene, such as a gene encoding a detectable gene product, can be under the control of a constitutive promoter, while a second gene, such as a gene encoding a therapeutic gene product, can be under the control of an inducible promoter. Methods for inserting two or more genes in to a microorganism are known in the art and can be readily performed for a wide variety of microorganisms using a wide variety of exogenous genes, regulatory sequences, and/or other nucleic acid sequences.

In an example of performing microorganismal modification methods, vaccinia virus strain LIVP was modified to contain insertions of exogenous DNA in three different locations of the viral genome. Using general methods known in the art, known molecular biology tools, and sequences known in the art or disclosed herein can be used to create modified vaccinia virus strains, including viruses containing insertions in the F3 gene, TK gene and/or HA gene. See, e.g., Mikryukov, et al., Biotekhnologya 4 (1998), 442-449; Goebel et al., Virology 179 (1990), 247-266; Antoine et al., Virology 244 (1998), 365-396; Mayr et al., Zentbl. Bakteriol. Hyg. Abt 1 Orig. B 167 (1978), 375-390; Ando and Matumoto, Jpn. J. Microbial. 14 (1979), 181-186; Sugimoto et al., Microbial. Immuol. 29 (1985), 421-428; Takahashi-Nishimaki et al., J. Gen. Virol. 68 (1987), 2705-2710). These methods include, for example, in vitro recombination techniques, synthetic methods and in vivo recombination methods as described, for example, in Sambrook et al., Molecular Cloning: A Laboratory Manual, 2nd edition, Cold Spring Harbor Laboratory Press, cold Spring Harbor N.Y. (1989), and in the Examples disclosed herein. The person skilled in the art can isolate the gene encoding the gene product of F3 (or a related gene product) from any vaccinia strain using, for example, the nucleotide sequence of the F3 gene of SEQ ID NO:1 or SEQ ID NOS: 10, 12, 14, 16, 18, 20, 22, 24, 26, 28, or 32, or a fragment thereof as a probe for screening a library.

Methods of producing recombinant microorganisms are known in the art. Provided herein for exemplary purposes are methods of producing a recombinant vaccinia virus. A recombinant vaccinia virus with an insertion in the F3 gene (NotI site of LIVP) can be prepared by the following steps: (a) generating (i) a vaccinia shuttle plasmid containing the modified F3 gene inserted at restriction site X and (ii) a dephosphorylated wt VV (VGL) DNA digested at restriction site X; (b) transfecting host cells infected with PUV-inactivated helper VV (VGL) with a mixture of the constructs of (i) and (ii) of step a; and (c) isolating the recombinant vaccinia viruses from the transfectants. One skilled in the art knows how to perform such methods, for example by following the instructions given in Example 1 and the legend to FIG. 1; see also Timiryasova et al., Biotechniques 31 (2001), 534-540. In one embodiment, restriction site X is a unique restriction site. A variety of suitable host cells also are known to the person skilled in the art and include many mammalian, avian and insect cells and tissues which are susceptible for vaccinia virus infection, including chicken embryo, rabbit, hamster and monkey kidney cells, for example, HeLa cells, $RK_{13}$, CV-1, Vero, BSC40 and BSC-1 monkey kidney cells.

2. Screening for Above Characteristics

Modified microorganisms can be screened for any desired characteristics, including the characteristics described herein such as attenuated pathogenicity, reduced toxicity, preferential accumulation in tumor, increased ability to activate an immune response against tumor cells, increased immunogenicity, increased or decreased replication competence, and are able to express exogenous proteins, and combinations thereof. For example, the modified microorganisms can be screened for the ability to activate an immune response against tumor cells without aggressively killing the tumor cells. In another example, the microorganisms can be screened for expression of one or more detectable genes, including genes that can be used for imaging, or for expression of one or more genes for manufacture or harvest of the gene products and/or for harvest of antibodies against the gene products.

Any of a variety of known methods for screening for such characteristics can be performed, as demonstrated in the Examples provided herein. One Exemplary method for screening for desired characteristics includes, but is not limited to, monitoring growth, replication and/or gene expression (including expression of an exogenous gene) in cell culture or other in vitro medium. The cell culture can be from any organism, and from any tissue source, and can include tumorous tissues. Other exemplary methods for screening for desired characteristics include, but are not limited to, administering a microorganism to animal, including non-human animals such as a mouse, monkey or ape, and optionally also including humans, and monitoring the microorganism, the tumor, and or the animal; monitoring can be performed by in vivo imaging of the microorganism and/or the tumor (e.g., low light imaging of microorganismal gene expression or ultrasonic tumor imaging), external monitoring of the tumor (e.g., external measurement of tumor size), monitoring the animal (e.g., monitoring animal weight, blood panel, antibody titer, spleen size, or liver size). Other exemplary methods for screening for desired characteristics include, but are not limited to, harvesting a non-human animal for the effects and location of the microorganism and expression by the microorganism, including methods such as harvesting a variety of organs including a tumor to determine presence of the microorganism and/or gene expression by the microorganism in the organs or tumor, harvesting of organs associated with an immune response or microorganismal clearance such as the spleen or liver, harvesting the tumor to determine tumor size and viability of tumor cells, harvesting antibodies or antibody producing cells. Such screening and monitoring methods can be used in any of a variety of combinations, as is known in art. In one embodiment, a microorganism can be screened by administering the microorganism to an animal such as a non-human animal or a human, followed by monitoring by in vivo imaging. In another embodiment, a microorganism can be screened by administering the microorganism to an animal such as a non-human animal, monitoring by in vivo imaging, and then harvesting the animal. Thus, provided herein are methods for screening a microorganism for desired characteristics by administering the microorganism to an animal such as an animal with a tumor, and monitoring the animal, tumor (if present), and/or microorganism in the animal for one or more characteristics. Also provided herein are methods for screening a microorganism for desired characteristics by administering the microorganism to a non-human animal such as a non-human animal with a tumor, harvesting the animal, and assaying the animal's organs, antibody titer, and/or tumor (if present) for one or more characteristics.

Provided herein are methods for screening a microorganism for attenuated pathogenicity or reduced toxicity, where the pathogenicity or toxicity can be determined by a variety of techniques, including, but not limited to, assessing the health state of the subject, measuring the body weight of a subject, blood or urine analysis of a subject, and monitoring tissue distribution of the microorganism within the subject; such techniques can be performed on a living subject in vivo, or can be performed post mortem. Methods also can include the ability of the microorganisms to lyse cells or cause cell death, which can be determined in vivo or in vitro.

When a subject drops below a threshold body weight, the microorganism can be considered pathogenic to the subject. Exemplary thresholds can be a drop of about 5% or more, a drop of about 10% or more, or a drop of about 15% or more in body weight relative to a reference. A body weight reference can be selected from any of a variety of references used in the art; for example, a body weight reference can be the weight of the subject prior to administration of the microorganism, the body weight reference can be a control subject having the same condition as the test subject (e.g., normal or tumor-injected), where the change in weight of the control is compared to the change in weight of the test subject for the time period after administration of the microorganism.

Blood or urine analysis of the subject can indicate level of immune response, level of toxins in the subject, or other levels of stress to cells, tissues or organs of the subject such as kidneys, pancreas, liver and spleen. Levels increased above established threshold levels can indicate pathogenicity of the microorganism to the subject. Threshold levels of components of blood or urine for indicating microorganismal pathogenicity are well known in the art, and any such thresholds can be selected herein according to the desired tolerance of pathogenicity or toxicity of the microorganism.

Tissue distribution of a microorganism in a subject can indicate pathogenicity or toxicity of the microorganism. In one embodiment, tissue distribution of a microorganism that is not pathogenic or toxic can be mostly in tumor relative to other tissues or organs. Microorganisms located mostly in tumor can accumulate, for example, at least about 2-fold greater, at least about 5-fold greater, at least about 10-fold greater, at least about 100-fold greater, at least about 1,000-fold greater, at least about 10,000-fold greater, at least about 100,000-fold greater, or at least about 1,000,000-fold greater, than the microorganisms that accumulate in any other particular organ or tissue.

Provided herein are methods for screening a microorganism for tissue distribution or accumulation, where the tissue distribution can be determined by a variety of techniques, including, but not limited to, harvesting a non-human subject, in vivo imaging a detectable gene product in subject. Harvesting can be accomplished by euthanizing the non-human subject, and determining the accumulation of microorganisms in tumor and, optionally, the accumulation in one or more additional tissues or organs. The accumulation can be determined by any of a variety of methods, including, but not limited to, detecting gene products such as detectable gene products (e.g., gfp or beta galactosidase), histological or microscopic evaluation of tissue, organ or tumor samples, or measuring the number of plaque or colony forming units present in a tissue, organ or tumor sample. In one embodiment, the desired amount of tissue distribution of a microorganism can be mostly in tumor relative to other tissues or organs. Microorganisms located mostly in tumor can accumulate, for example, at least about 2-fold greater, at least about 5-fold greater, at least about 10-fold greater, at least about 100-fold greater, at least about 1,000-fold greater, at least about 10,000-fold greater, at least about 100,000-fold greater, or at least about 1,000,000-fold greater, than the microorganisms that accumulate in any other particular organ or tissue.

Also provided herein are methods of screening for microorganisms that can elicit an immune response, where the immune response can be against the tumor cells or against the microorganisms. A variety of methods for measuring the ability to elicit an immune response are known in the art, and include measuring an overall increase in immune activity in a subject, measuring an increase in anti-microorganism or anti-tumor antibodies in a subject, testing the ability of a microorganism-treated (typically a non-human) subject to prevent later infection/tumor formation or to rapidly eliminate microorganisms or tumor cells. Methods also can include the ability of the microorganisms to lyse cells or cause cell death, which can be determined in vivo or in vitro.

Also provided herein are methods for determining increased or decreased replication competence, by monitoring the speed of replication of the microorganisms. Such measurements can be performed in vivo or in vitro. For example, the speed of replication in a cell culture can be used to determine replication competence of a microorganism. In another example, the speed of replication in a tissue, organ or tumor in a subject can be used to measure replication competence. In some embodiments, decreased replication competence in non-tumor tissues and organs can be the characteristic to be selected in a screen. In other embodiments, increased replication competence in tumors can be the characteristic to be selected in a screen.

Also provided herein are methods for determining the ability of a microorganism to express genes, such as exogenous genes. Such methods can be performed in vivo or in vitro. For example, the microorganisms can be screened on selective plates for the ability to express a gene that permits survival of the microorganism or permits the microorganism to provide a detectable signal, such as turning X-gal blue. Such methods also can be performed in vivo, where expression can be determined, for example, by harvesting tissues, organs or tumors a non-human subject or by in vivo imaging of a subject.

Also provided herein are methods for determining the ability of a microorganism to express genes toward which the subject can develop antibodies, including exogenous genes toward which the subject can develop antibodies. Such methods can be performed in vivo using any of a variety of non-human subjects. For example, gene expression can be determined, for example, by bleeding a non-human subject to which a microorganism has been administered, and assaying the blood (or serum) for the presence of antibodies against the microorganism-expressed gene, or by any other method generally used for polyclonal antibody harvesting, such as production bleeds and terminal bleeds.

Also provided herein are methods for screening a microorganism that has two or more characteristics provided herein, including screening for attenuated pathogenicity, reduced toxicity, preferential accumulation in tumor, increased ability to activate an immune response against tumor cells, increased immunogenicity, increased or decreased replication competence, ability to express exogenous proteins, and ability to elicit antibody production against a microorganismally expressed gene product. A single monitoring technique, such as in vivo imaging, can be used to verify two or more characteristics, or a variety of different monitoring techniques can be used, as can be determined by one skilled in the art according to the selected characteristics and according to the monitoring techniques used.

D. THERAPEUTIC METHODS

Provided herein are therapeutic methods, including methods of treating or preventing immunoprivileged cells or tissue, including cancerous cells, tumor and metastasis. The methods provided herein include administering a microorganism to a subject containing a tumor and/or metastases. The methods provided herein do not require the microorganism to kill tumor cells or decrease the tumor size. Instead, the methods provided herein include administering to a subject a microorganism that can cause or enhance an anti-tumor immune response in the subject. In some embodiments, the microorganisms provided herein can be administered to a subject without causing microorganism-induced disease in the subject. In some embodiments, the microorganisms can accumulate in tumors or metastases. In some embodiments, the microorganisms can elicit an anti-tumor immune response in the subject, where typically the microorganism-mediated anti-tumor immune response can develop over several days, such as a week or more, 10 days or more, two weeks or more, or a month or more, as a result of little or no microorganism-cause tumor cell death. In some exemplary methods, the microorganism can be present in the tumor, and can cause an anti-tumor immune response without the microorganism itself causing enough tumor cell death to prevent tumor growth.

In some embodiments, provided herein are methods for eliciting or enhancing antibody production against a selected antigen or a selected antigen type in a subject, where the methods include administering to a subject a microorganism that can accumulate in a tumor and/or metastasis, and can cause release of a selected antigen or selected antigen type from the tumor, resulting in antibody production against the selected antigen or selected antigen type. The administered microorganisms can posses one or more characteristics including attenuated pathogenicity, low toxicity, preferential accumulation in tumor, ability to activate an immune response against tumor cells, immunogenicity, replication competence, ability to express exogenous genes, and ability to elicit antibody production against a microorganismally expressed gene product.

Any of a variety of antigens can be targeted in the methods provided herein, including a selected antigen such as an exogenous gene product expressed by the microorganism, or a selected antigen type such as one or more tumor antigens release from the tumor as a result of microorganism infection of the tumor (e.g., by lysis, apoptosis, secretion or other mechanism of causing antigen release from the tumor). In at least some embodiments, it can be desirable to maintain release of the selected antigen or selected antigen type over a series of days, for example, at least a week, at least ten days, at least two weeks or at least a month.

Also provided herein are methods for providing a sustained antigen release within a subject, where the methods include administering to a subject a microorganism that can accumulate in a tumor and/or metastasis, and can cause sustained release of an antigen, resulting in antibody production against the antigen. The sustained release of antigen can last for several days, for example, at least a week, at least ten days, at least two weeks or at least a month. The administered microorganisms can posses one or more characteristics including attenuated pathogenicity, low toxicity, preferential accumulation in tumor, ability to activate an immune response against tumor cells, immunogenicity, replication competence, ability to express exogenous genes, and ability to elicit antibody production against a microorganismally expressed gene product. The sustained release of antigen can result in an immune response by the microorganism-infected host, in which the host can develop antibodies against the antigen, and/or the host can mount an immune response against cells expressing the antigen, including an immune response against tumor cells. Thus, the sustained release of antigen can result in immunization against tumor cells. In some embodiments, the microorganism-mediated sustained antigen release-induced immune response against tumor cells can result in complete removal or killing of all tumor cells.

Also provided herein are methods for inhibiting tumor growth in a subject, where the methods include administering to a subject a microorganism that can accumulate in a tumor and/or metastasis, and can cause or enhance an anti-tumor immune response. The anti-tumor immune response induced as a result of tumor or metastases-accumulated microorganisms can result in inhibition of tumor growth. The administered microorganisms can posses one or more characteristics including attenuated pathogenicity, low toxicity, preferential accumulation in tumor, ability to activate an immune response against tumor cells, immunogenicity, replication competence, ability to express exogenous genes, and ability to elicit antibody production against a microorganismally expressed gene product.

Also provided herein are methods for inhibiting growth or formation of a metastasis in a subject, where the methods include administering to a subject a microorganism that can accumulate in a tumor and/or metastasis, and can cause or enhance an anti-tumor immune response. The anti-tumor immune response induced as a result of tumor or metastasis-accumulated microorganisms can result in inhibition of metastasis growth or formation. The administered microorganisms can posses one or more characteristics including attenuated pathogenicity, low toxicity, preferential accumulation in tumor, ability to activate an immune response against tumor cells, immunogenicity, replication competence, ability to express exogenous genes, and ability to elicit antibody production against a microorganismally expressed gene product.

Also provided herein are methods for decreasing the size of a tumor and/or metastasis in a subject, where the methods include administering to a subject a microorganism that can accumulate in a tumor and/or metastasis, and can cause or enhance an anti-tumor immune response. The anti-tumor immune response induced as a result of tumor or metastasis-accumulated microorganisms can result in a decrease in the size of the tumor and/or metastasis. The administered microorganisms can posses one or more characteristics including attenuated pathogenicity, low toxicity, preferential accumulation in tumor, ability to activate an immune response against tumor cells, immunogenicity, replication competence, ability to express exogenous genes, and ability to elicit antibody production against a microorganismally expressed gene product.

Also provided herein are methods for eliminating a tumor and/or metastasis from a subject, where the methods include administering to a subject a microorganism that can accumulate in a tumor and/or metastasis, and can cause or enhance an anti-tumor immune response. The anti-tumor immune response induced as a result of tumor or metastasis-accumulated microorganisms can result in elimination of the tumor and/or metastasis from the subject. The administered microorganisms can posses one or more characteristics including attenuated pathogenicity, low toxicity, preferential accumulation in tumor, ability to activate an immune response against tumor cells, immunogenicity, replication competence, ability to express exogenous genes, and ability to elicit antibody production against a microorganismally expressed gene product.

Methods of reducing inhibiting tumor growth, inhibiting metastasis growth and/or formation, decreasing the size of a tumor or metastasis, eliminating a tumor or metastasis, or other tumor therapeutic methods provided herein include causing or enhancing an anti-tumor immune response in the host. The immune response of the host, being anti-tumor in nature, can be mounted against tumors and/or metastases in which microorganisms have accumulated, and can also be mounted against tumors and/or metastases in which microorganisms have not accumulated, including tumors and/or metastases that form after administration of the microorganisms to the subject. Accordingly, a tumor and/or metastasis whose growth or formation is inhibited, or whose size is decreased, or that is eliminated, can be a tumor and/or metastasis in which the microorganisms have accumulated, or also can be a tumor and/or metastasis in which the microorganisms have not accumulated. Accordingly, provided herein are methods of reducing inhibiting tumor growth, inhibiting metastasis growth and/or formation, decreasing the size of a tumor or metastasis, eliminating a tumor or metastasis, or other tumor therapeutic methods, where the method includes administering to a subject a microorganism, where the microorganism accumulates in at least one tumor or metastasis and causes or enhances an anti-tumor immune response in the subject, and the immune response also is mounted against a tumor and/or metastasis in which the microorganism cell did not accumulate. In another embodiment, methods are provided for inhibiting or preventing recurrence of a neoplastic disease or inhibiting or preventing new tumor growth, where the methods include administering to a subject a microorganism that can accumulate in a tumor and/or metastasis, and can cause or enhance an anti-tumor immune response, and the anti-tumor immune response can inhibit or prevent recurrence of a neoplastic disease or inhibit or prevent new tumor growth.

The tumor or neoplastic disease therapeutic methods provided herein, such as methods of reducing inhibiting tumor growth, inhibiting metastasis growth and/or formation, decreasing the size of a tumor or metastasis, eliminating a tumor or metastasis, or other tumor therapeutic methods, also can include administering to a subject a microorganism that can cause tumor cell lysis or tumor cell death. Such a microorganism can be the same microorganism as the microorganism that can cause or enhance an anti-tumor immune response in the subject. Microorganisms, such as the microorganisms provided herein, can cause cell lysis or tumor cell death as a result of expression of an endogenous gene or as a result of an exogenous gene. Endogenous or exogenous genes can cause tumor cell lysis or inhibit cell growth as a result of direct or indirect actions, as is known in the art, including lytic channel formation or activation of an apoptotic pathway. Gene products, such as exogenous gene products can function to activate a prodrug to an active, cytotoxic form, resulting in cell death where such genes are expressed.

Such methods of antigen production or tumor and/or metastasis treatment can include administration of a modified microorganism described herein or a microorganism having modifications with a functional equivalence to the vaccinia virus provided herein containing a modification of the F3 gene and the TK gene and/or the HA gene, for therapy, such as for gene therapy, for cancer gene therapy, or for vaccine therapy. Such a microorganism can be used to stimulate humoral and/or cellular immune response, induce strong cytotoxic T lymphocytes responses in subjects who may benefit from such responses. For example, the microorganism can provide prophylactic and therapeutic effects against a tumor infected by the microorganism or other infectious diseases, by rejection of cells from tumors or lesions using microorganisms that express immunoreactive antigens (Earl et al. (1986), Science 234, 728-831; Lathe et al. (1987), Nature (London) 326, 878-880), cellular tumor-associated antigens (Bernards et al., (1987), Proc. Natl. Acad. Sci. USA 84, 6854-6858; Estin et al. (1988), Proc. Natl. Acad. Sci. USA 85, 1052-1056; Kantor et al. (1992), J. Natl. Cancer Inst. 84, 1084-1091; Roth et al. (1996), Proc. Natl. Acad. Sci. USA 93, 4781-4786) and/or cytokines (e.g., IL-2, IL-12), costimulatory molecules (B7-1, B7-2) (Rao et al. (1996), J. Immunol. 156, 3357-3365; Chamberlain et al. (1996), Cancer Res. 56, 2832-2836; Oertli et al. (1996), J. Gen. Virol. 77, 3121-3125; Qin and Chatteijee (1996), Human Gene Ther. 7, 1853-1860; McAneny et al. (1996), Ann. Surg. Oncol. 3, 495-500), or other therapeutic proteins.

Provided herein, solid tumors can be treated with microorganisms, such as vaccinia viruses, resulting in an enormous tumor-specific microorganism replication, which can lead to tumor protein antigen and viral protein production in the tumors. As provided herein, vaccinia virus administration to mice resulted in lysis of the infected tumor cells and a resultant release of tumor-cell-specific antigens. Continuous leakage of these antigens into the body led to a very high level of antibody titer (in approximately 7-14 days) against tumor proteins, viral proteins, and the virus encoded engineered proteins in the mice. The newly synthesized antitumor antibodies and the enhanced macrophage, neutrophils count were continuously delivered via the vasculature to the tumor and thereby provided for the recruitment of an activated immune system against the tumor. The activated immune system then eliminated the foreign compounds of the tumor including the viral particles. This interconnected release of foreign antigens boosted antibody production and continuous response of the antibodies against the tumor proteins to function like an autoimmunizing vaccination system initiated by vaccinia viral infection and replication, followed by cell lysis, protein leakage and enhanced antibody production. Thus, the present methods can provide a complete process that can be applied to all tumor systems with immunoprivileged tumor sites as site of privileged viral, bacterial, and mammalian cell growth, which can lead to tumor elimination by the host's own immune system.

In other embodiments, methods are provided for immunizing a subject, where the methods include administering to the subject a microorganism that expresses one or more antigens against which antigens the subject will develop an immune response. The immunizing antigens can be endogenous to the microorganism, such as vaccinia antigens on a vaccinia virus used to immunize against smallpox, or the immunizing antigens can be exogenous antigens expressed by the microorganism, such as influenza or HIV antigens expressed on a viral capsid or bacterial cell surface. Thus, the microorganisms provided herein, including the modified vaccinia viruses can be used as vaccines.

1. Administration

In performing the methods provided herein, a microorganism can be administered to a subject, including a subject having a tumor or having neoplastic cells, or a subject to be immunized. An administered microorganism can be a microorganism provided herein or any other microorganism known for administration to a subject, for example, any known microorganism known for therapeutic administration to a subject, including antigenic microorganisms such as any microorganism known to be used for vaccination. In some embodiments, the microorganism administered is a microorganism containing a characteristic such as attenuated pathogenicity, low toxicity, preferential accumulation in tumor, ability to activate an immune response against tumor cells, high immunogenicity, replication competence, and ability to express exogenous proteins, and combinations thereof.

a. Steps Prior to Administering the Microorganism

In some embodiments, one or more steps can be performed prior to administration of the microorganism to the subject. Any of a variety of preceding steps can be performed, including, but not limited to diagnosing the subject with a condition appropriate for microorganismal administration, determining the immunocompetence of the subject, immunizing the subject, treating the subject with a chemotherapeutic agent, treating the subject with radiation, or surgically treating the subject.

For embodiments that include administering a microorganism to a tumor-bearing subject for therapeutic purposes, the subject has typically been previously diagnosed with a neoplastic condition. Diagnostic methods also can include determining the type of neoplastic condition, determining the stage of the neoplastic conditions, determining the size of one or more tumors in the subject, determining the presence or absence of metastatic or neoplastic cells in the lymph nodes of the subject, or determining the presence of metastases of the subject. Some embodiments of therapeutic methods for administering a microorganism to a subject can include a step of determination of the size of the primary tumor or the stage of the neoplastic disease, and if the size of the primary tumor is equal to or above a threshold volume, or if the stage of the neoplastic disease is at or above a threshold stage, a microorganism is administered to the subject. In a similar embodiment, if the size of the primary tumor is below a threshold volume, or if the stage of the neoplastic disease is at or below a threshold stage, the microorganism is not yet administered to the subject; such methods can include monitoring the subject until the tumor size or neoplastic disease stage reaches a threshold amount, and then administering the microorganism to the subject. Threshold sizes can vary according to several factors, including rate of growth of the tumor, ability of the microorganism to infect a tumor, and immunocompetence of the subject. Generally the threshold size will be a size sufficient for a microorganism to accumulate and replicate in or near the tumor without being completely removed by the host's immune system, and will typically also be a size sufficient to sustain a microorganismal infection for a time long enough for the host to mount an immune response against the tumor cells, typically about one week or more, about ten days or more, or about two weeks or more. Exemplary threshold tumor sizes for viruses such as vaccinia viruses are at least about 100 mm$^3$, at least about 200 mm$^3$, at least about 300 mm$^3$, at least about 400 mm$^3$, at least about 500 mm$^3$, at least about 750 mm$^3$, at least about 1000 mm$^3$, or at least about 1500 mm$^3$. Threshold neoplastic disease stages also can vary according to several factors, including specific requirement for staging a particular neoplastic disease, aggressiveness of growth of the neoplastic disease, ability of the microorganism to infect a tumor or metastasis, and immunocompetence of the subject. Generally the threshold stage will be a stage sufficient for a microorganism to accumulate and replicate in a tumor or metastasis without being completely removed by the host's immune system, and will typically also be a size sufficient to sustain a microorganismal infection for a time long enough for the host to mount an immune response against the neoplastic cells, typically about one week or more, about ten days or more, or about two weeks or more. Exemplary threshold stages are any stage beyond the lowest stage (e.g., Stage I or equivalent), or any stage where the primary tumor is larger than a threshold size, or any stage where metastatic cells are detected.

In other embodiments, prior to administering to the subject a microorganism, the immunocompetence of the subject can be determined. The methods of administering a microorganism to a subject provided herein can include causing or enhancing an immune response in a subject. Accordingly, prior to administering a microorganism to a subject, the ability of a subject to mount an immune response can be determined. Any of a variety of tests of immunocompetence known in the art can be performed in the methods provided herein. Exemplary immunocompetence tests can examine ABO hemagglutination titers (IgM), leukocyte adhesion deficiency (LAD), granulocyte function (NBT), T and B cell quantitation, tetanus antibody titers, salivary IgA, skin test, tonsil test, complement C3 levels, and factor B levels, and lymphocyte count. One skilled in the art can determine the desirability to administer a microorganism to a subject according to the level of immunocompetence of the subject, according to the immunogenicity of the microorganism, and, optionally, according to the immunogenicity of the neoplastic disease to be treated. Typically, a subject can be considered immunocompetent if the skilled artisan can determine that the subject is sufficiently competent to mount an immune response against the microorganism.

In some embodiments, the subject can be immunized prior to administering to the subject a microorganism according to the methods provided herein. Immunization can serve to increase the ability of a subject to mount an immune response against the microorganism, or increase the speed at which the subject can mount an immune response against a microorganism. Immunization also can serve to decrease the risk to the subject of pathogenicity of the microorganism. In some embodiments, the immunization can be performed with an immunization microorganism that is similar to the therapeutic microorganism to be administered. For example, the immunization microorganism can be a replication-incompetent variant of the therapeutic microorganism. In other embodiments, the immunization material can be digests of the therapeutic microorganism to be administered. Any of a variety of methods for immunizing a subject against a known microorganism are known in the art and can be used herein. In one example, vaccinia viruses treated with, for example, 1 microgram of psoralen and ultraviolet light at 365 nm for 4 minutes, can be rendered replication incompetent. In another embodiment, the microorganism can be selected as the same or similar to a microorganism against which the subject has been previously immunized, e.g., in a childhood vaccination.

In another embodiment, the subject can have administered thereto a microorganism without any previous steps of cancer treatment such as chemotherapy, radiation therapy or surgical removal of a tumor and/or metastases. The methods provided herein take advantage of the ability of the microorganisms to enter or localize near a tumor, where the tumor cells can be protected from the subject's immune system; the microorganisms can then proliferate in such an immunoprotected region and can also cause the release, typically a sustained release, of tumor antigens from the tumor to a location in which the subject's immune system can recognize the tumor antigens and mount an immune response. In such methods, existence of a tumor of sufficient size or sufficiently developed immunoprotected state can be advantageous for successful administration of the microorganism to the tumor, and for sufficient tumor antigen production. If a tumor is surgically removed, the microorganisms may not be able to localize to other neoplastic cells (e.g., small metastases) because such cells may not yet have matured sufficiently to create an immunoprotective environment in which the microorganisms can survive and proliferate, or even if the microorganisms can localize to neoplastic cells, the number of cells or size of the mass may be too small for the microorganisms to cause a sustained release of tumor antigens in order for the host to mount an anti-tumor immune response. Thus, for example, provided herein are methods of treating a tumor or neoplastic disease in which microorganisms are administered to a subject with a tumor or neoplastic disease without removing the primary tumor, or to a subject with a tumor or neoplastic disease in which at least some tumors or neoplastic cells are intentionally permitted to remain in the subject. In other typical cancer treatment methods such as chemotherapy or radiation therapy, such methods typically have a side effect of weakening the subject's immune system. This treatment of a subject by chemotherapy or radiation therapy can reduce the subject's ability to mount an anti-tumor immune response.

Thus, for example, provided herein are methods of treating a tumor or neoplastic disease in which microorganisms are administered to a subject with a tumor or neoplastic disease without treating the subject with an immune system-weakening therapy, such as chemotherapy or radiation therapy.

In an alternative embodiment, prior to administration of a microorganism to the subject, the subject can be treated in one or more cancer treatment steps that do not remove the primary tumor or that do not weaken the immune system of the subject. A variety of more sophisticated cancer treatment methods are being developed in which the tumor can be treated without surgical removal or immune-system weakening therapy. Exemplary methods include administering a compound that decreases the rate of proliferation of the tumor or neoplastic cells without weakening the immune system (e.g., by administering tumor suppressor compounds or by administering tumor cell-specific compounds) or administering an angiogenesis-inhibiting compound. Thus, combined methods that include administering a microorganism to a subject can further improve cancer therapy. Thus, provided herein are methods of administering a microorganism to a subject, along with prior to or subsequent to, for example, administering a compound that slows tumor growth without weakening the subject's immune system or a compound that inhibits vascularization of the tumor.

b. Mode of Administration

Any mode of administration of a microorganism to a subject can be used, provided the mode of administration permits the microorganism to enter a tumor or metastasis. Modes of administration can include, but are not limited to, intravenous, intraperitoneal, subcutaneous, intramuscular, topical, intratumor, multipuncture (e.g., as used with smallpox vaccines), inhalation, intranasal, oral, intracavity (e.g., administering to the bladder via a catheter, administering to the gut by suppository or enema), aural, or ocular administration. One skilled in the art can select any mode of administration compatible with the subject and the microorganism, and that also is likely to result in the microorganism reaching tumors and/or metastases. The route of administration can be selected by one skilled in the art according to any of a variety of factors, including the nature of the disease, the kind of tumor, and the particular microorganism contained in the pharmaceutical composition. Administration to the target site can be performed, for example, by ballistic delivery, as a colloidal dispersion system, or systemic administration can be performed by injection into an artery.

c. Dosage

The dosage regimen can be any of a variety of methods and amounts, and can be determined by one skilled in the art according to known clinical factors. As is known in the medical arts, dosages for any one patient can depend on many factors, including the subject's species, size, body surface area, age, sex, immunocompetence, and general health, the particular microorganism to be administered, duration and route of administration, the kind and stage of the disease, for example, tumor size, and other compounds such as drugs being administered concurrently. In addition to the above factors, such levels can be affected by the infectivity of the microorganism, and the nature of the microorganism, as can be determined by one skilled in the art. At least some of the viruses used the in the methods provided herein can be more infectious than the bacteria used herein. Thus, in some embodiments of the present methods, virus can be administered at lower levels than bacteria. In the present methods, appropriate minimum dosage levels of microorganisms can be levels sufficient for the microorganism to survive, grow and replicate in a tumor or metastasis. Exemplary minimum levels for administering a virus to a 65 kg human can include at least about $5\times10^5$ plaque forming units (pfu), at least about $1\times10^6$ pfu, at least about $5\times10^6$ pfu, at least about $1\times10^7$ pfu, or at least about $1\times10^8$ pfu. Exemplary minimum levels for administering a bacterium to a 65 kg human can include at least about $5\times10^6$ colony forming units (cfu), at least about $1\times10^7$ cfu, at least about $5\times10^7$ cfu, at least about $1\times10^8$ cfu, or at least about $1\times10^9$ cfu. In the present methods, appropriate maximum dosage levels of microorganisms can be levels that are not toxic to the host, levels that do not cause splenomegaly of 3× or more, levels that do not result in colonies or plaques in normal tissues or organs after about 1 day or after about 3 days or after about 7 days. Exemplary maximum levels for administering a virus to a 65 kg human can include no more than about $5\times10^{10}$ pfu, no more than about $1\times10^{10}$ pfu, no more than about $5\times10^9$ pfu, no more than about $1\times10^9$ pfu, or no more than about $1\times10^8$ pfu. Exemplary maximum levels for administering a bacterium to a 65 kg human can include no more than about $5\times10^{11}$ pfu, no more than about $1\times10^{11}$ pfu, no more than about $5\times10^{10}$ pfu, no more than about $1\times10^{10}$ pfu, or no more than about $1\times10^9$ pfu.

d. Number of Administrations

The methods provided herein can include a single administration of a microorganism to a subject or multiple administrations of a microorganism to a subject. In some embodiments, a single administration is sufficient to establish a microorganism in a tumor, where the microorganism can proliferate and can cause or enhance an anti-tumor response in the subject; such methods do not require additional administrations of a microorganism in order to cause or enhance an anti-tumor response in a subject, which can result, for example in inhibition of tumor growth, inhibition of metastasis growth or formation, reduction in tumor or metastasis size, elimination of a tumor or metastasis, inhibition or prevention of recurrence of a neoplastic disease or new tumor formation, or other cancer therapeutic effects. In other embodiments, a microorganism can be administered on different occasions, separated in time typically by at least one day. Separate administrations can increase the likelihood of delivering a microorganism to a tumor or metastasis, where a previous administration may have been ineffective in delivering a microorganism to a tumor or metastasis. Separate administrations can increase the locations on a tumor or metastasis where microorganism proliferation can occur or can otherwise increase the titer of microorganism accumulated in the tumor, which can increase the scale of release of antigens or other compounds from the tumor in eliciting or enhancing a host's anti-tumor immune response, and also can, optionally, increase the level of microorganism-based tumor lysis or tumor cell death. Separate administrations of a microorganism can further extend a subject's immune response against microorganismal antigens, which can extend the host's immune response to tumors or metastases in which microorganisms have accumulated, and can increase the likelihood of a host mounting an anti-tumor immune response.

When separate administrations are performed, each administration can be a dosage amount that is the same or different relative to other administration dosage amounts. In one embodiment, all administration dosage amounts are the same. In other embodiments, a first dosage amount can be a larger dosage amount than one or more subsequent dosage amounts, for example, at least 10× larger, at least 100× larger, or at least 1000× larger than subsequent dosage amounts. In one example of a method of separate administrations in which the first dosage amount is greater than one or more subsequent dosage amounts, all subsequent dosage amounts can be the same, smaller amount relative to the first administration.

Separate administrations can include any number of two or more administrations, including two, three, four, five or six administrations. One skilled in the art can readily determine the number of administrations to perform or the desirability of performing one or more additional administrations according to methods known in the art for monitoring therapeutic methods and other monitoring methods provided herein. Accordingly, the methods provided herein include methods of providing to the subject one or more administrations of a microorganism, where the number of administrations can be determined by monitoring the subject, and, based on the results of the monitoring, determining whether or not to provide one or more additional administrations. Deciding on whether or not to provide one or more additional administrations can be based on a variety of monitoring results, including, but not limited to, indication of tumor growth or inhibition of tumor growth, appearance of new metastases or inhibition of metastasis, the subject's anti-microorganism antibody titer, the subject's anti-tumor antibody titer, the overall health of the subject, the weight of the subject, the presence of microorganism solely in tumor and/or metastases, the presence of microorganism in normal tissues or organs.

The time period between administrations can be any of a variety of time periods. The time period between administrations can be a function of any of a variety of factors, including monitoring steps, as described in relation to the number of administrations, the time period for a subject to mount an immune response, the time period for a subject to clear microorganism from normal tissue, or the time period for microorganismal proliferation in the tumor or metastasis. In one example, the time period can be a function of the time period for a subject to mount an immune response; for example, the time period can be more than the time period for a subject to mount an immune response, such as more than about one week, more than about ten days, more than about two weeks, or more than about a month; in another example, the time period can be less than the time period for a subject to mount an immune response, such as less than about one week, less than about ten days, less than about two weeks, or less than about a month. In another example, the time period can be a function of the time period for a subject to clear microorganism from normal tissue; for example, the time period can be more than the time period for a subject to clear microorganism from normal tissue, such as more than about a day, more than about two days, more than about three days, more than about five days, or more than about a week. In another example, the time period can be a function of the time period for microorganismal proliferation in the tumor or metastasis; for example, the time period can be more than the amount of time for a detectable signal to arise in a tumor or metastasis after administration of a microorganism expressing a detectable marker, such as about 3 days, about 5 days, about a week, about ten days, about two weeks, or about a month.

e. Co-Administrations

Also provided are methods in which an additional therapeutic substance, such as a different therapeutic microorganism or a therapeutic compound is administered. These can be administered simultaneously, sequentially or intermittently with the first microorganism. The additional therapeutic substance can interact with the microorganism or a gene product thereof, or the additional therapeutic substance can act independently of the microorganism.

i. Administration of a Plurality of Microorganisms

Methods are provided for administering to a subject two or more microorganisms. Administration can be effected simultaneously, sequentially or intermittently. The plurality of microorganisms can be administered as a single composition or as two or more compositions. The two or more microorganisms can include at least two bacteria, at least two viruses, at least two eukaryotic cells, or two or more selected from among bacteria, viruses and eukaryotic cells. The plurality of microorganisms can be provided as combinations of compositions containing and/or as kits that include the microorganisms packaged for administration and optionally including instructions therefore. The compositions can contain the microorganisms formulated for single dosage administration (i.e., for direct administration) and can require dilution or other additions.

In one embodiment, at least one of the microorganisms is a modified microorganism such as those provided herein, having a characteristic such as low pathogenicity, low toxicity, preferential accumulation in tumor, ability to activate an immune response against tumor cells, immunogenic, replication competent, ability to express exogenous proteins, and combinations thereof. The microorganisms can be administered at approximately the same time, or can be administered at different times. The microorganisms can be administered in the same composition or in the same administration method, or can be administered in separate composition or by different administration methods.

In one example, a bacteria and a virus can be administered to a subject. The bacteria and virus can be administered at the same time, or at different times. For example, the virus can be administered prior to administering the bacteria, or the bacteria can be administered prior to administering the virus; typically the virus is administered prior to administering the bacteria. As provided herein, administering to a subject a virus prior to administering to the subject a bacterium can increase the amount of bacteria that can accumulate and/or proliferate in a tumor, relative to methods in which bacteria alone are administered.

Accordingly, the methods provided herein that include administration of virus prior to administration of bacteria permit the administration of a lower dosage amount of bacteria than would otherwise be administered in a method in which bacteria alone are administered or a method in which bacteria are administered at the same time as or prior to administration of a virus. For example, in some embodiments, a bacterium to be administered can have one or more properties that limit the ability of the bacterium to be used, such properties can include, but are not limited to toxicity, low tumor specificity of accumulation, and limited proliferation capacity. A bacterium to be administered that has one or more limiting properties can require administration in lower dosage amounts, or can require assistance in tumor-specific accumulation and/or proliferation. Provided herein are methods of administering such a bacterium with limiting properties, where prior to administering the bacterium, a virus is administered such that the limited bacterium can be administered in smaller quantities, can accumulate in tumor with increased specificity, and/or can have an increased ability to proliferate in a tumor.

The time period between administrations can be any time period that achieves the desired effects, as can be determined by one skilled in the art. Selection of a time period between administrations of different microorganisms can be determined according to parameters similar to those for selecting the time period between administrations of the same microorganism, including results from monitoring steps, the time period for a subject to mount an immune response, the time period for a subject to clear microorganism from normal tissue, or the time period for microorganismal proliferation in the tumor or metastasis. In one example, the time period can be a function of the time period for a subject to mount an immune response; for example, the time period can be more than the time period for a subject to mount an immune response, such as more than about one week, more than about ten days, more than about two weeks, or more than about a month; in another example, the time period can be less than the time period for a subject to mount an immune response, such as less than about one week, less than about ten days, less than about two weeks, or less than about a month. In another example, the time period can be a function of the time period for a subject to clear microorganism from normal tissue; for example, the time period can be more than the time period for a subject to clear microorganism from normal tissue, such as more than about a day, more than about two days, more than about three days, more than about five days, or more than about a week. In another example, the time period can be a function of the time period for microorganismal proliferation in the tumor or metastasis; for example, the time period can be more than the amount of time for a detectable signal to arise in a tumor or metastasis after administration of a microorganism expressing a detectable marker, such as about 3 days, about 5 days, about a week, about ten days, about two weeks, or about a month. In one example a virus can be first administered, and a bacteria can be administered about 5 days after administration of the virus. In another example, a virus can be first administered, and a bacterium can be administered upon detection of a virally-encoded detectable gene product in the tumor of the subject, optionally when the virally-encoded detectable gene product is detected only in the tumor of the subject.

ii. Therapeutic Compounds

The methods can include administering one or more therapeutic compounds to the subject in addition to administering a microorganism or plurality thereof to a subject. Therapeutic compounds can act independently, or in conjunction with the microorganism, for tumor therapeutic effects. Therapeutic compounds that can act independently include any of a variety of known chemotherapeutic compounds that can inhibit tumor growth, inhibit metastasis growth and/or formation, decrease the size of a tumor or metastasis, eliminate a tumor or metastasis, without reducing the ability of a microorganism to accumulate in a tumor, replicate in the tumor, and cause or enhance an anti-tumor immune response in the subject.

Therapeutic compounds that act in conjunction with the microorganisms include, for example, compounds that alter the expression of the microorganism or compounds that can interact with a microorganism-expressed gene, or compounds that can inhibit microorganismal proliferation, including compounds toxic to the microorganism. Therapeutic compounds that can act in conjunction with the microorganism include, for example, therapeutic compounds that increase the proliferation, toxicity, tumor cell killing, or immune response eliciting properties of a microorganism, and also can include, for example, therapeutic compounds that decrease the proliferation, toxicity, or cell killing properties of a microorganism. Thus, provided herein are methods of administering to a subject one or more therapeutic compounds that can act in conjunction with the microorganism to increase the proliferation, toxicity, tumor cell killing, or immune response eliciting properties of a microorganism. Also provided herein are methods of administering to a subject one or more therapeutic compounds that can act in conjunction with the microorganism to decrease the proliferation, toxicity, or cell killing properties of a microorganism.

In one embodiment, therapeutic compounds that can act in conjunction with the microorganism to increase the proliferation, toxicity, tumor cell killing, or immune response eliciting properties of a microorganism are compounds that can alter gene expression, where the altered gene expression can result in an increased killing of tumor cells or an increased anti-tumor immune response in the subject. A gene expression-altering compound can, for example, cause an increase or decrease in expression of one or more microorganismal genes, including endogenous microorganismal genes and/or exogenous microorganismal genes. For example, a gene expression-altering compound can induce or increase transcription of a gene in a microorganism such as an exogenous gene that can cause cell lysis or cell death, that can provoke an immune response, that can catalyze conversion of a prodrug-like compound, or that can inhibit expression of a tumor cell gene. Any of a wide variety of compounds that can alter gene expression are known in the art, including IPTG and RU486. Exemplary genes whose expression can be up-regulated include proteins and RNA molecules, including toxins, enzymes that can convert a prodrug to an anti-tumor drug, cytokines, transcription regulating proteins, siRNA, and ribozymes. In another example, a gene expression-altering compound can inhibit or decrease transcription of a gene in a microorganism such as an exogenous gene that can reduce microorganismal toxicity or reduces microorganismal proliferation. Any of a variety of compounds that can reduce or inhibit gene expression can be used in the methods provided herein, including siRNA compounds, transcriptional inhibitors or inhibitors of transcriptional activators. Exemplary genes whose expression can be down-regulated include proteins and RNA molecules, including microorganismal proteins or RNA that suppress lysis, nucleotide synthesis or proliferation, and cellular proteins or RNA molecules that suppress cell death, immunoreactivity, lysis, or microorganismal replication.

In another embodiment, therapeutic compounds that can act in conjunction with the microorganism to increase the proliferation, toxicity, tumor cell killing, or immune response eliciting properties of a microorganism are compounds that can interact with a microorganism-expressed gene product, and such interaction can result in an increased killing of tumor cells or an increased anti-tumor immune response in the subject. A therapeutic compound that can interact with a microorganism-expressed gene product can include, for example a prodrug or other compound that has little or no toxicity or other biological activity in its subject-administered form, but after interaction with a microorganism-expressed gene product, the compound can develop a property that results in tumor cell death, including but not limited to, cytotoxicity, ability to induce apoptosis, or ability to trigger an immune response. A variety of prodrug-like substances are known in the art and an exemplary set of such compounds are disclosed elsewhere herein, where such compounds can include gancyclovir, 5-fluorouracil, 6-methylpurine deoxyriboside, cephalosporin-doxorubicin, 4-[(2-chloroethyl)(2-mesuloxyethyl)amino]benzoyl-L-glutamic acid, acetominophen, indole-3-acetic acid, CB1954, 7-ethyl-10-[4-(1-piperidino)-1-piperidino]carbonyloxycamptothecin, bis-(2-chloroethyl)amino-4-hydroxyphenylaminomethanone 28, 1-chloromethyl-5-hydroxy-1,2-dihyro-3H-benz[e]indole, epirubicin-glucuronide, 5'-deoxy-5-fluorouridine, cytosine arabinoside, and linamarin.

In another embodiment, therapeutic compounds that can act in conjunction with the microorganism to decrease the proliferation, toxicity, or cell killing properties of a microorganism are compounds that can inhibit microorganismal replication, inhibit microorganismal toxins, or cause microorganismal death. A therapeutic compound that can inhibit microorganismal replication, inhibit microorganismal toxins, or cause microorganismal death can generally include a compound that can block one or more steps in the microorganismal life cycle, including, but not limited to, compounds that can inhibit microorganismal DNA replication, microorganismal RNA transcription, viral coat protein assembly, outer membrane or polysaccharide assembly. Any of a variety of compounds that can block one or more steps in a microorganismal life cycle are known in the art, including any known antibiotic, microorganismal DNA polymerase inhibitors, microorganismal RNA polymerase inhibitors, inhibitors of proteins that regulate microorganismal DNA replication or RNA transcription. In one example, when a microorganism is a bacteria, a compound can be an antibiotic. In another example, a microorganism can contain a gene encoding a microorganismal life cycle protein, such as DNA polymerase or RNA polymerase that can be inhibited by a compound that is, optionally, non-toxic to the host organism.

f. State of Subject

In another embodiment, the methods provided herein for administering a microorganism to a subject can be performed on a subject in any of a variety of states, including an anesthetized subject, an alert subject, a subject with elevated body temperature, a subject with reduced body temperature, or other state of the subject that is known to affect the accumulation of microorganism in the tumor. As provided herein, it has been determined that a subject that is anesthetized can have a decreased rate of accumulation of a microorganism in a tumor relative to a subject that is not anesthetized. Further provided herein, it has been determined that a subject with decreased body temperature can have a decreased rate of accumulation of a microorganism in a tumor relative to a subject with a normal body temperature. Accordingly, provided herein are methods of administering a microorganism to a subject, where the methods can include administering a microorganism to a subject where the subject is not under anesthesia, such as general anesthesia; for example, the subject can be under local anesthesia, or can be unanesthetized. Also provided herein are methods of administering a microorganism to a subject, where the methods can include administering a microorganism to a subject with altered body temperature, where the alteration of the body temperature can influence the ability of the microorganism to accumulate in a tumor; typically, a decrease in body temperature can decrease the ability of a microorganism to accumulate in a tumor. Thus, in one exemplary embodiment, a method is provided for administering a microorganism to a subject, where the method includes elevating the body temperature of the subject to a temperature above normal, and administering a microorganism to the subject, where the microorganism can accumulate in the tumor more readily in the subject with higher body temperature relative to the ability of the microorganism to accumulate in a tumor of a subject with a normal body temperature.

2. Monitoring

The methods provided herein can further include one or more steps of monitoring the subject, monitoring the tumor, and/or monitoring the microorganism administered to the subject. Any of a variety of monitoring steps can be included in the methods provided herein, including, but not limited to, monitoring tumor size, monitoring anti-(tumor antigen) antibody titer, monitoring the presence and/or size of metastases, monitoring the subject's lymph nodes, monitoring the subject's weight or other health indicators including blood or urine markers, monitoring anti-(microorganismal antigen) antibody titer, monitoring microorganismal expression of a detectable gene product, and directly monitoring microorganismal titer in a tumor, tissue or organ of a subject.

The purpose of the monitoring can be simply for assessing the health state of the subject or the progress of therapeutic treatment of the subject, or can be for determining whether or not further administration of the same or a different microorganism is warranted, or for determining when or whether or not to administer a compound to the subject where the compound can act to increase the efficacy of the therapeutic method, or the compound can act to decrease the pathogenicity of the microorganism administered to the subject.

a. Monitoring Microorganismal Gene Expression

In some embodiments, the methods provided herein can include monitoring one or more microorganismally expressed genes. Microorganisms, such as those provided herein or otherwise known in the art, can express one or more detectable gene products, including but not limited to, detectable proteins.

As provided herein, measurement of a detectable gene product expressed in a microorganism can provide an accurate determination of the level of microorganism present in the subject. As further provided herein, measurement of the location of the detectable gene product, for example, by imaging methods including tomographic methods, can determine the localization of the microorganism in the subject. Accordingly, the methods provided herein that include monitoring a detectable microorganismal gene product can be used to determine the presence or absence of the microorganism in one or more organs or tissues of a subject, and/or the presence or absence of the microorganism in a tumor or metastases of a subject. Further, the methods provided herein that include monitoring a detectable microorganismal gene product can be used to determine the titer of microorganism present in one or more organs, tissues, tumors or metastases. Methods that include monitoring the localization and/or titer of microorganisms in a subject can be used for determining the pathogenicity of a microorganism; since microorganismal infection, and particularly the level of infection, of normal tissues and organs can indicate the pathogenicity of the probe, methods of monitoring the localization and/or amount of microorganisms in a subject can be used to determine the pathogenicity of a microorganism. Since methods provided herein can be used to monitor the amount of microorganisms at any particular location in a subject, the methods that include monitoring the localization and/or titer of microorganisms in a subject can be performed at multiple time points, and, accordingly can determine the rate of microorganismal replication in a subject, including the rate of microorganismal replication in one or more organs or tissues of a subject; accordingly, the methods of monitoring a microorganismal gene product can be used for determining the replication competence of a microorganism. The methods provided herein also can be used to quantitate the amount of microorganism present in a variety of organs or tissues, and tumors or metastases, and can thereby indicate the degree of preferential accumulation of the microorganism in a subject; accordingly, the microorganismal gene product monitoring methods provided herein can be used in methods of determining the ability of a microorganism to accumulate in tumor or metastases in preference to normal tissues or organs. Since the microorganisms used in the methods provided herein can accumulate in an entire tumor or can accumulate at multiple sites in a tumor, and can also accumulate in metastases, the methods provided herein for monitoring a microorganismal gene product can be used to determine the size of a tumor or the number of metastases are present in a subject. Monitoring such presence of microorganismal gene product in tumor or metastasis over a range of time can be used to assess changes in the tumor or metastasis, including growth or shrinking of a tumor, or development of new metastases or disappearance of metastases, and also can be used to determine the rate of growth or shrinking of a tumor, or development of new metastases or disappearance of metastases, or the change in the rate of growth or shrinking of a tumor, or development of new metastases or disappearance of metastases. Accordingly, the methods of monitoring a microorganismal gene product can be used for monitoring a neoplastic disease in a subject, or for determining the efficacy of treatment of a neoplastic disease, by determining rate of growth or shrinking of a tumor, or development of new metastases or disappearance of metastases, or the change in the rate of growth or shrinking of a tumor, or development of new metastases or disappearance of metastases.

Any of a variety of detectable proteins can be detected in the monitoring methods provided herein; an exemplary, non-limiting list of such detectable proteins includes any of a variety of fluorescence proteins (e.g., green fluorescence proteins), any of a variety of luciferases, transferrin or other iron binding proteins; or receptors, binding proteins, and antibodies, where a compound that specifically binds the receptor, binding protein or antibody can be a detectable agent or can be labeled with a detectable substance (e.g., a radionuclide or imaging agent).

b. Monitoring Tumor Size

Also provided herein are methods of monitoring tumor and/or metastasis size and location. Tumor and/or metastasis size can be monitored by any of a variety of methods known in the art, including external assessment methods or tomographic or magnetic imaging methods. In addition to the methods known in the art, methods provided herein, for example, monitoring microorganismal gene expression, can be used for monitoring tumor and/or metastasis size.

Monitoring size over several time points can provide information regarding the increase or decrease in size of a tumor or metastasis, and can also provide information regarding the presence of additional tumors and/or metastases in the subject. Monitoring tumor size over several time points can provide information regarding the development of a neoplastic disease in a subject, including the efficacy of treatment of a neoplastic disease in a subject.

c. Monitoring Antibody Titer

The methods provided herein also can include monitoring the antibody titer in a subject, including antibodies produced in response to administration of a microorganism to a subject. The microorganisms administered in the methods provided herein can elicit an immune response to endogenous microorganismal antigens. The microorganisms administered in the methods provided herein also can elicit an immune response to exogenous genes expressed by a microorganism. The microorganisms administered in the methods provided herein also can elicit an immune response to tumor antigens. Monitoring antibody titer against microorganismal antigens, microorganismally expressed exogenous gene products, or tumor antigens can be used in methods of monitoring the toxicity of a microorganism, monitoring the efficacy of treatment methods, or monitoring the level of gene product or antibodies for production and/or harvesting.

In one embodiment, monitoring antibody titer can be used to monitor the toxicity of a microorganism. Antibody titer against a microorganism can vary over the time period after administration of the microorganism to the subject, where at some particular time points, a low anti-(microorganismal antigen) antibody titer can indicate a higher toxicity, while at other time points a high anti-(microorganismal antigen) antibody titer can indicate a higher toxicity. The microorganisms used in the methods provided herein can be immunogenic, and can, therefore, elicit an immune response soon after administering the microorganism to the subject. Generally, a microorganism against which a subject's immune system can quickly mount a strong immune response can be a microorganism that has low toxicity when the subject's immune system can remove the microorganism from all normal organs or tissues. Thus, in some embodiments, a high antibody titer against microorganismal antigens soon after administering the microorganism to a subject can indicate low toxicity of a microorganism. In contrast, a microorganism that is not highly immunogenic may infect a host organism without eliciting a strong immune response, which can result in a higher toxicity of the microorganism to the host. Accordingly, in some embodiments, a high antibody titer against microorganismal antigens soon after administering the microorganism to a subject can indicate low toxicity of a microorganism.

In other embodiments, monitoring antibody titer can be used to monitor the efficacy of treatment methods. In the methods provided herein, antibody titer, such as anti-(tumor antigen) antibody titer, can indicate the efficacy of a therapeutic method such as a therapeutic method to treat neoplastic disease. Therapeutic methods provided herein can include causing or enhancing an immune response against a tumor and/or metastasis. Thus, by monitoring the anti-(tumor antigen) antibody titer, it is possible to monitor the efficacy of a therapeutic method in causing or enhancing an immune response against a tumor and/or metastasis. The therapeutic methods provided herein also can include administering to a subject a microorganism that can accumulate in a tumor and can cause or enhance an anti-tumor immune response. Accordingly, it is possible to monitor the ability of a host to mount an immune response against microorganisms accumulated in a tumor or metastasis, which can indicate that a subject has also mounted an anti-tumor immune response, or can indicate that a subject is likely to mount an anti-tumor immune response, or can indicate that a subject is capable of mounting an anti-tumor immune response.

In other embodiments, monitoring antibody titer can be used for monitoring the level of gene product or antibodies for production and/or harvesting. As provided herein, methods can be used for producing proteins, RNA molecules or other compounds by expressing an exogenous gene in a microorganism that has accumulated in a tumor. Further provided herein are methods for producing antibodies against a protein, RNA molecule or other compound produced by exogenous gene expression of a microorganism that has accumulated in a tumor. Monitoring antibody titer against the protein, RNA molecule or other compound can indicate the level of production of the protein, RNA molecule or other compound by the tumor-accumulated microorganism, and also can directly indicate the level of antibodies specific for such a protein, RNA molecule or other compound.

d. Monitoring General Health Diagnostics

The methods provided herein also can include methods of monitoring the health of a subject. Some of the methods provided herein are therapeutic methods, including neoplastic disease therapeutic methods. Monitoring the health of a subject can be used to determine the efficacy of the therapeutic method, as is known in the art. The methods provided herein also can include a step of administering to a subject a microorganism. Monitoring the health of a subject can be used to determine the pathogenicity of a microorganism administered to a subject. Any of a variety of health diagnostic methods for monitoring disease such as neoplastic disease, infectious disease, or immune-related disease can be monitored, as is known in the art. For example, the weight, blood pressure, pulse, breathing, color, temperature or other observable state of a subject can indicate the health of a subject. In addition, the presence or absence or level of one or more components in a sample from a subject can indicate the health of a subject. Typical samples can include blood and urine samples, where the presence or absence or level of one or more components can be determined by performing, for example, a blood panel or a urine panel diagnostic test. Exemplary components indicative of a subject's health include, but are not limited to, white blood cell count, hematocrit, c-reactive protein concentration.

e. Monitoring Coordinated with Treatment

Also provided herein are methods of monitoring a therapy, where therapeutic decisions can be based on the results of the monitoring. Therapeutic methods provided herein can include administering to a subject a microorganism, where the microorganism can preferentially accumulate in a tumor and/or metastasis, and where the microorganism can cause or enhance an anti-tumor immune response. Such therapeutic methods can include a variety of steps including multiple administrations of a particular microorganism, administration of a second microorganism, or administration of a therapeutic compound. Determination of the amount, timing or type of microorganism or compound to administer to the subject can be based on one or more results from monitoring the subject. For example, the antibody titer in a subject can be used to determine whether or not it is desirable to administer a microorganism or compound, the quantity of microorganism or compound to administer, and the type of microorganism or compound to administer, where, for example, a low antibody titer can indicate the desirability of administering additional microorganism, a different microorganism, or a therapeutic compound such as a compound that induces microorganismal gene expression. In another example, the overall health state of a subject can be used to determine whether or not it is desirable to administer a microorganism or compound, the quantity of microorganism or compound to administer, and the type of microorganism or compound to administer, where, for example, determining that the subject is healthy can indicate the desirability of administering additional microorganism, a different microorganism, or a therapeutic compound such as a compound that induces microorganismal gene expression. In another example, monitoring a detectable microorganismally expressed gene product can be used to determine whether or not it is desirable to administer a microorganism or compound, the quantity of microorganism or compound to administer, and the type of microorganism or compound to administer. Such monitoring methods can be used to determine whether or not the therapeutic method is effective, whether or not the therapeutic method is pathogenic to the subject, whether or not the microorganism has accumulated in a tumor or metastasis, and whether or not the microorganism has accumulated in normal tissues or organs. Based on such determinations, the desirability and form of further therapeutic methods can be derived.

In one embodiment, determination of whether or not a therapeutic method is effective can be used to derive further therapeutic methods. Any of a variety of methods of monitoring can be used to determine whether or not a therapeutic method is effective, as provided herein or otherwise known in the art. If monitoring methods indicate that the therapeutic method is effective, a decision can be made to maintain the current course of therapy, which can include further administrations of a microorganism or compound, or a decision can be made that no further administrations are required. If monitoring methods indicate that the therapeutic method is ineffective, the monitoring results can indicate whether or not a course of treatment should be discontinued (e.g., when a microorganism is pathogenic to the subject), or changed (e.g., when a microorganism accumulates in a tumor without harming the host organism, but without eliciting an anti-tumor immune response), or increased in frequency or amount (e.g., when little or no microorganism accumulates in tumor).

In one example, monitoring can indicate that a microorganism is pathogenic to a subject. In such instances, a decision can be made to terminate administration of the microorganism to the subject, to administer lower levels of the microorganism to the subject, to administer a different microorganism to a subject, or to administer to a subject a compound that reduces the pathogenicity of the microorganism. In one example, administration of a microorganism that is determined to be pathogenic can be terminated. In another example, the dosage amount of a microorganism that is determined to be pathogenic can be decreased for subsequent administration; in one version of such an example, the subject can be pre-treated with another microorganism that can increase the ability of the pathogenic microorganism to accumulate in tumor, prior to re-administering the pathogenic microorganism to the subject. In another example, a subject can have administered thereto a bacteria or virus that is pathogenic to the subject; administration of such a pathogenic microorganism can be accompanied by administration of, for example an antibiotic, anti-microorganismal compound, pathogenicity attenuating compound (e.g., a compound that down-regulates the expression of a lytic or apoptotic gene product), or other compound that can decrease the proliferation, toxicity, or cell killing properties of a microorganism, as described herein elsewhere. In one variation of such an example, the localization of the microorganism can be monitored, and, upon determination that the microorganism is accumulated in tumor and/or metastases but not in normal tissues or organs, administration of the antibiotic, anti-microorganismal compound or pathogenicity attenuating compound can be terminated, and the pathogenic activity of the microorganism can be activated or increased, but limited to the tumor and/or metastasis. In another variation of such an example, after terminating administration of an antibiotic, anti-microorganismal compound or pathogenicity attenuating compound, the presence of the microorganism and/or pathogenicity of the microorganism can be further monitored, and administration of such a compound can be reinitiated if the microorganism is determined to pose a threat to the host by, for example, spreading to normal organs or tissues, releasing a toxin into the vasculature, or otherwise having pathogenic effects reaching beyond the tumor or metastasis.

In another example, monitoring can determine whether or not a microorganism has accumulated in a tumor or metastasis of a subject. Upon such a determination, a decision can be made to further administer additional microorganism, a different microorganism or a compound to the subject. In one example, monitoring the presence of a virus in a tumor or metastasis can be used in deciding to administer to the subject a bacterium, where, for example, the quantity of bacteria administered can be reduced according to the presence and/or quantity of virus in a tumor or metastasis. In a similar example, monitoring the presence of a virus in a tumor or metastasis can be used in deciding when to administer to the subject a bacterium, where, for example, the bacteria can be administered upon detecting to the presence and/or a selected quantity of virus in a tumor or metastasis. In another example, monitoring the presence of a microorganism in a tumor can be used in deciding to administer to the subject a compound, where the compound can increase the pathogenicity, proliferation, or immunogenicity of a microorganism or the compound can otherwise act in conjunction with the microorganism to increase the proliferation, toxicity, tumor cell killing, or immune response eliciting properties of a microorganism; in one variation of such an example, the microorganism can, for example have little or no lytic or cell killing capability in the absence of such a compound; in a further variation of such an example, monitoring of the presence of the microorganism in a tumor or metastasis can be coupled with monitoring the absence of the microorganism in normal tissues or organs, where the compound is administered if the microorganism is present in tumor or metastasis and not at all present or substantially not present in normal organs or tissues; in a further variation of such an example, the amount of microorganism in a tumor or metastasis can be monitored, where the compound is administered if the microorganism is present in tumor or metastasis at sufficient levels.

E. METHODS OF PRODUCING GENE PRODUCTS AND ANTIBODIES

Provided herein are microorganisms, and methods for making and using such microorganisms for production products of exogenous genes and/or for production of antibodies specific for exogenous gene products. The methods provided herein result in efficient recombinant production of biologically active proteins. In EP A1 1 281 772, it is disclosed that when vaccinia virus (LIVP strain) carrying the light emitting fusion gene construct rVV-ruc-gfp (RVGL9) was injected intravenously into nude mice, the virus particles were found to be cleared from all internal organs within 4 days, as determined by extinction of light emission. In contrast, when the fate of the injected vaccinia virus was similarly followed in nude mice bearing tumors grown from subcutaneously implanted C6 rat glioma cells, virus particles were found to be retained over time in the tumor tissues, resulting in lasting light emission. The presence and amplification of the virus-encoded fusion proteins in the same tumor were monitored in live animals by observing GFP fluorescence under a stereomicroscope and by detecting luciferase-catalyzed light emission under a low-light video-imaging camera. Tumor-specific light emission was detected 4 days after viral injection in nude mice carrying subcutaneous C6 glioma implants. Tumor accumulation of rVV-ruc-gfp (RVGL9) virus particles was also seen in nude mice carrying subcutaneous tumors developed from implanted PC-3 human prostate cells, and in mice with orthotopically implanted MCF-7 human breast tumors. Further, intracranial C6 rat glioma cell implants in immunocompetent rats and MB-49 human bladder tumor cell implants in C57 mice were also targeted by the vaccinia virus. In addition to primary breast tumors, small metastatic tumors were also detected externally in the contralateral breast region, as well as in nodules on the exposed lung surface, suggesting metastasis to the contralateral breast and lung. In summary it was shown that light-emitting cells or microorganisms, for example, vaccinia virus can be used to detect and treat metastatic tumors.

Similar results were obtained with light-emitting bacteria (Salmonella, Vibrio, Listeria, E. coli) which were injected intravenously into mice and which could be visualized in whole animals under a low light imager immediately. No light emission was detected twenty four hours after bacterial injection in both athymic (nu/nu) mice and immunocompetent C57 mice as a result of clearing by the immune system. In nude mice bearing tumors developed from implanted C6 glioma cells, light emission was abolished from the animal entirely twenty four hours after delivery of bacteria, similar to mice without tumors. However, forty eight hours post-injection, a strong, rapidly increasing light emission originated only from the tumor regions was observed. This observation indicated a continuous bacterial replication in the tumor tissue. The extent of light emission was dependent on the bacterial strain used. The homing-in process together with the sustained light emission was also demonstrated in nude mice carrying prostate, bladder, and breast tumors. In addition to primary tumors, metastatic tumors could also be visualized as exemplified in the breast tumor model. Tumor-specific light emission was also observed in immunocompetent C57 mice, with bladder tumors as well as in Lewis rats with brain glioma implants. Once in the tumor, the light-emitting bacteria were not observed to be released into the circulation and to re-colonize subsequently implanted tumors in the same animal. Further, mammalian cells expressing the Ruc-GFP fusion protein, upon injection into the bloodstream, were also found to home in to, and propagate in, glioma tumors. These findings opened the way for designing multifunctional viral vectors useful for the detection of tumors based on signals such as light emission, for suppression of tumor development and angiogenesis signaled by, for example, light extinction and the development of bacterial and mammalian cell-based tumor targeting systems in combination with therapeutic gene constructs for the treatment of cancer. These systems have the following advantages: (a) They target the tumor specifically without affecting normal tissue; (b) the expression and secretion of the therapeutic gene constructs can be, optionally, under the control of an inducible promoter enabling secretion to be switched on or off; and (c) the location of the delivery system inside the tumor can be verified by direct visualization before activating gene expression and protein delivery.

As provided herein, the system described above based on the accumulation of bacteria, viruses and eukaryotic cells in tumors can be used for simple, quick, and inexpensive production of proteins and other biological compounds originating from cloned nucleotide sequences. This system also is useful for the concomitant overproduction of polypeptides, RNA or other biological compounds (in tumor tissue) and antibodies against those compounds (in the serum) in the same animal. As provided herein, after intravenous injection, a microorganism such as vaccinia virus can enter the tumor of an animal and, due to the immunoprivileged state of the tumor, can replicate preferentially in the tumor tissues and thereby can overproduce the inserted gene encoded protein in the tumors. After harvesting the tumor tissues, the localized and overexpressed protein can be isolated by a simple procedure from tumor homogenates. In addition, based on the findings that only 0.2 to 0.3% of the desired proteins produced in the tumor were found in the blood stream of the same animal, a simultaneous vaccination of the mouse and efficient antibody production against the overproduced protein was achieved. Thus, serum from the same mouse (or any other animal) can be harvested and used as mouse-derived antibodies against the proteins or other products overproduced in the tumor.

Thus, provided herein are methods of producing gene products and or antibodies in a non-human subject, by administering to a subject containing a tumor, a microorganism, where the microorganism expresses a selected protein or RNA to be produced, a protein or RNA whose expression can result in the formation of a compound to be produced, or a selected protein or RNA against which an antibody is to be produced. The methods provided herein can further include administering to a subject containing a tumor, a microorganism expressing an exogenous gene encoding a selected protein or RNA to be produced, a protein or RNA whose expression can result in the formation of a compound to be produced, or a selected protein or RNA against which an antibody is to be produced. The methods provided herein can further include administering to a subject containing a tumor, a microorganism expressing a gene encoding a selected protein or RNA to be produced, a protein or RNA whose expression can result in the formation of a compound to be produced, or a selected protein or RNA against which an antibody is to be produced, where such gene expression can be regulated, for example, by a transcriptional activator or inducer, or a transcriptional suppressor. The methods provided herein for producing a protein, RNA, compound or antibody can further include monitoring the localization and/or level of the microorganism in the subject by detecting a detectable protein, where the detectable protein can indicate the expression of the selected gene, or can indicate the readiness of the microorganism to be induced to express the selected gene or for suppression of expression to be terminated or suspended. Also provided herein are methods of producing gene products and or antibodies in a non-human subject, by administering to a subject containing a tumor, a microorganism, where the microorganism expresses a selected protein or RNA to be produced, a protein or RNA whose expression can result in the formation of a compound to be produced, or a selected protein or RNA against which an antibody is to be produced, where the subject to which the microorganism is administered is not a transgenic animal. Also provided herein are methods of producing gene products and or antibodies in a non-human subject, by administering to a subject containing a tumor, a microorganism, where the microorganism expresses a selected protein to be produced, where the tumor within the subject is selected according to its ability to post-translationally process the selected protein.

The advantages of the system, include:

(a) No production of a transgenic animal carrying the novel polypeptide-encoding cassette is required;

(b) the tumor system is more efficient than tissue culture;

(c) proteins interfering with animal development and other toxic proteins can be overproduced in tumors without negative effects to the host animal;

(d) the system is fast: within 4 to 6 weeks from cDNA cloning to protein and antisera purification;

(e) the system is relatively inexpensive and can be scaled up easily;

(f) correct protein folding and modifications can be achieved;

(g) high antigenicity can be achieved, which is beneficial for better antibody production; and (h) species-specific-cell-based production of proteins in animals such as mice, with tumors as fermentors can be achieved.

Figure 2:
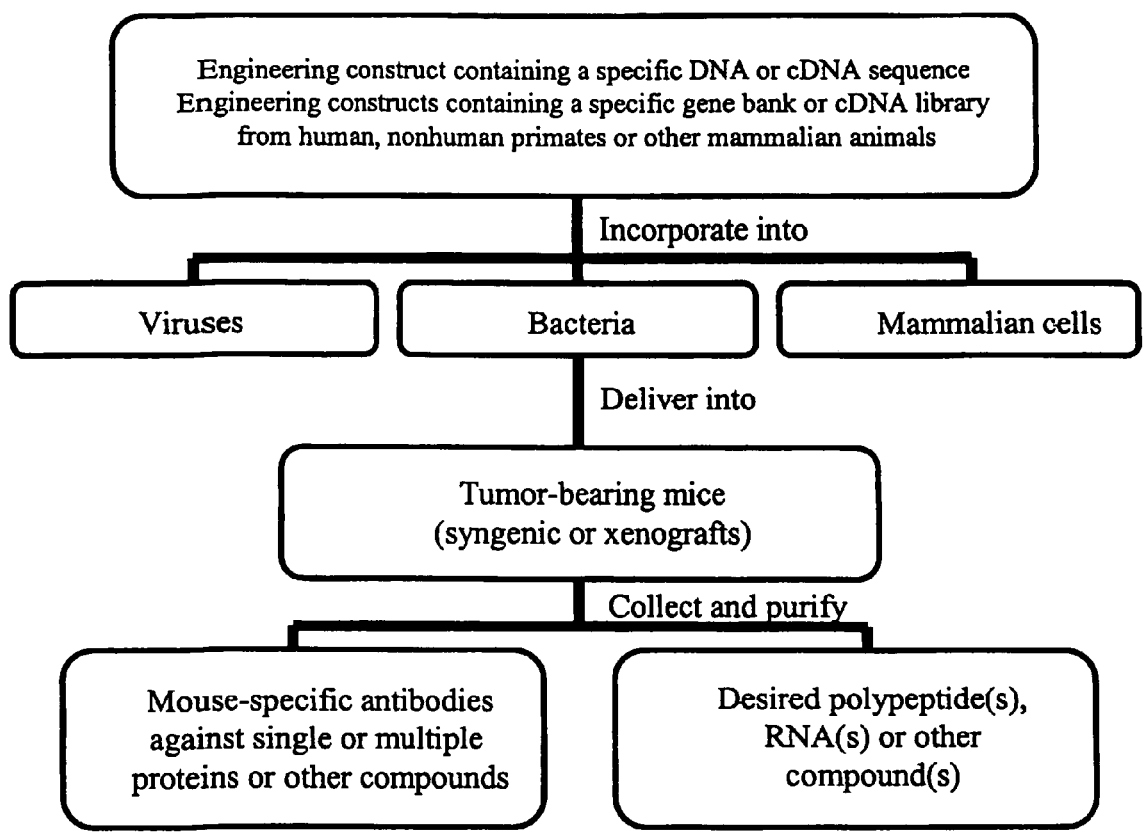
FIG. 2 sets forth a flow chart for a method for producing products, such as nucleic acid molecules, proteins and metabolic compounds or other cellular products in tumors.

Depiction of an exemplary method for production of gene products and/or antibodies against gene products is provided in FIG. 2.

In one embodiment, methods are provided for producing a desired polypeptide, RNA or compound, the method including the following steps: (a) injecting a microorganism containing a nucleotide sequence encoding the desired polypeptide or RNA into an animal bearing a tumor; (b) harvesting the tumor tissue from the animal; and (c) isolating the desired polypeptide, RNA or compound from the tumor tissue.

Steps of an exemplary method can be summarized as follows (shown for a particular embodiment, i.e. vaccinia virus additionally containing a gene encoding a light-emitting protein):

(1) Insertion of the desired DNA or cDNA into the vaccinia virus genome;

(2) modification of the vaccinia virus genome with light-emitting protein construct as expression marker;

(3) recombination and virus assembly in cell culture;

(4) screening of individual viral particles carrying inserts followed by large scale virus production and concentration;

(5) administration of the viral particles into mice or other animals bearing tumors of human, non-human primate or other mammalian origins;

(6) verification of viral replication and protein overproduction in animals based on light emission;

(7) harvest of tumor tissues and, optionally, the blood (separately); and (8) purification of overexpressed proteins from tumors and, optionally, antisera from blood using conventional methods.

Any microorganism can be used in the methods provided herein, provided that they replicate in the animal, are not pathogenic for the animal, for example, are attenuated, and are recognized by the immune system of the animal. In some embodiments, such microorganisms also can express exogenous genes. Suitable microorganisms and cells are, for example, disclosed in EP A1 1 281 772 and EP A1 1 281 767. The person skilled in the art also knows how to generate animals carrying the desired tumor (see, e.g., EP A1 1 281 767 or EP A1 1 281 777).

Also provided is a method for simultaneously producing a desired polypeptide, RNA or compound and an antibody directed to the polypeptide, RNA or compound, the method having the following steps: (a) administering a microorganism containing a nucleotide sequence encoding the desired polypeptide or RNA into an animal bearing a tumor; (b) harvesting the tumor tissue from the animal; (c) isolating the desired polypeptide, RNA or compound from the tumor tissue; and (d) isolating the antibody directed to the polypeptide, RNA or compound from the serum obtained from the animal. This approach can be used for generating polypeptides and/or antibodies against the polypeptides which are toxic or unstable, or which require species specific cellular environment for correct folding or modifications.

In another embodiment, the microorganism can further contain a nucleotide sequence encoding a detectable protein, such as a luminescent or fluorescent protein, or a protein capable of inducing a detectable signal.

Typically in methods for transfecting the microorganisms or cells with nucleotide sequences encoding the desired polypeptide or RNA and, optionally, a nucleotide sequence encoding a detectable protein such as a luminescent or fluorescent protein, or a protein capable of inducing a detectable signal, the nucleotide sequences are present in a vector or an expression vector. A person skilled in the art is familiar with a variety of expression vectors, which can be selected according to the microorganism used to infect the tumor, the cell type of the tumor, the organism to be infected, and other factors known in the art. In some embodiments, the microorganism can be a virus, including the viruses disclosed herein. Thus, the nucleotide sequences can be contained in a recombinant virus containing appropriate expression cassettes.

Suitable viruses for use herein, include, but are not limited to, baculovirus, vaccinia, Sindbis virus, Sendai virus, adenovirus, an AAV virus or a parvovirus, such as MVM or H-1. The vector can also be a retrovirus, such as MoMULV, MoMuLV, HaMuSV, MuMTV, RSV or GaLV. For expression in mammalian cells, a suitable promoter is, for example, human cytomegalovirus immediate early promoter (pCMV). Furthermore, tissue and/or organ specific promoters can be used. For example, the nucleotide sequences can be operatively linked with a promoter allowing high expression. Such promoters can include, for example, inducible promoters; a variety of such promoters are known to persons skilled in the art.

For generating protein or RNA-encoding nucleotide sequences and for constructing expression vectors or viruses that contain the nucleotide sequences, it is possible to use general methods known in the art. These methods include, for example, in vitro recombination techniques, synthetic methods and in vivo recombination methods as known in the art, and exemplified in Sambrook et al., Molecular Cloning, A Laboratory Manual, 2nd edition (1989) Cold Spring Harbor Laboratory Press, Cold Spring Harbor, N.Y. Methods of transfecting cells, of phenotypically selecting transfectants cells, of phenotypically selecting transfectants and of expressing the nucleotide sequences by using vectors containing protein or RNA-encoding DNA are known in the art.

In some embodiments, the protein or RNA to be produced in the tumor can be linked to an inducible promoter, such as a promoter that can be induced by a substance endogenous to the subject, or by a substance that can be administered to a subject. Accordingly, provided herein are methods of producing a protein or RNA in a tumor, where the production can be induced by administration of a substance to a subject, and, optionally, harvesting the tumor and isolating the protein or RNA from the tumor. Such induction methods can be coupled with methods of monitoring a microorganism in a subject. For example, a microorganism can be monitored by detecting a detectable protein. In methods that include monitoring, detection of a desired localization and/or level of microorganism in the subject can be coordinated with induction of microorganismal gene expression. For example, when a microorganismally expressed detectable protein is detected in tumor, but not appreciably in normal organs or tissues, an inducer can be administered to the subject. In another example, when a microorganismally expressed detectable protein is detected in tumor, and also in normal organs or tissues, administration of an inducer can be suspended or postponed until the detectable protein is no longer detected in normal organs or tissues. In another example, when a microorganismally expressed detectable protein is detected at sufficient levels in tumor, an inducer can be administered to the subject. In another example, when a microorganismally expressed detectable protein is not detected at sufficient levels in tumor administration of an inducer can be suspended or postponed until the detectable protein is detected at sufficient levels in the tumor.

Also provided herein are methods of producing a protein or RNA in a tumor, by administering a microorganism encoding the protein or RNA, and a suppressor of gene expression. The suppressor of gene expression can be administered for a pre-defined period of time, or until the microorganism accumulated in tumor but not in normal organs or tissues, or until sufficient levels of the microorganism have accumulated in the tumor, at which point administration of the suppressor can be terminated or suspended, which can result in expression of the protein or RNA. As will be recognized by one skilled in the art, methods similar to those provided herein in regard to monitoring a detectable protein and administering an inducer, can also apply for terminating or suspending administration of a suppressor.

In one embodiment, the microorganism is a bacterium, for example, an attenuated bacterium, such as those provided herein. Exemplary bacteria include attenuated *Salmonella typhimurium*, attenuated *Vibrio cholerae*, attenuated *Listeria monocytogenes* or *E. coli*. Alternatively, viruses such as vaccinia virus, AAV, a retrovirus can be used in the methods provided herein. In exemplary methods, the virus is vaccinia virus. Other cells that can be used in the present methods include mammalian cells, such as fibroma cells, including human cells such as human fibroma cells.

Any of a variety of animals, including laboratory or livestock animals can be used, including for example, mice, rats and other rodents, rabbits, guinea pigs, pigs, sheep, goats, cows and horses. Exemplary animals are mice. The tumor can be generated by implanting tumor cells into the animal. Generally, for the production of a desired polypeptide, RNA, or compound, any solid tumor type can be used, such as a fast growing tumor type. Exemplary fast growing tumor types include C6 rat glioma and HCT116 human colon carcinoma. Generally, for the production of a desired antibody, a relatively slow growing tumor type can be used. Exemplary slow growing tumor types include HT1080 human fibrosarcoma and GI-101A human breast carcinoma. For T-independent antibody production, nu-/nu-mice bearing allogenic tumor or xenografts can be used; while for T-dependent antibody production, immunocompetent mice with syngenic tumors can be used. In some embodiments, such as where the compound to be produced is a protein, the microorganism selected can be a microorganism that uses the translational components (e.g., proteins, vesicles, substrates) of the tumor cells, such as, for example, a virus that uses the translational components of a tumor cell. In such instances, the tumor cell type can be selected according to the desired post-translational processing to be performed on the protein, including proteolysis, glycosylation, lipidylation, disulfide formation, and any refolding or multimer assembly that can require cellular components for completing. In some examples, the tumor cell type selected can be the same species as the protein to be expressed, thus resulting in species-specific post-translational processing of the protein; an exemplary tumor cell type-expressed protein species is human.

1. Production of Recombinant Proteins and RNA Molecules

The tumor tissue can be surgically removed from the animal. After homogenization of the tumor tissue, the desired polypeptide, RNA or other biological compound can be purified according to established methods. For example, in the case of a recombinant polypeptide, the polypeptide might contain a bindable tag such as a his-tag, and can be purified, for example, via column chromatography. The time necessary for accumulation of sufficient amounts of the polypeptide or RNA in the tumor of the animal depends on many factors, for example, the kind of animal or the kind of tumor, and can be determined by the skilled person by routine experimentation. In general, expression of the desired polypeptide can be detected two days after virus injection. The expression peaks approximately two weeks after injection, and lasts up to two months. In some embodiments, the amount of desired polypeptide or RNA in the tumor can be determined by monitoring a microorganismally expressed detectable substance, where the concentration of the detectable substance can reflect the amount of desired polypeptide or RNA in the tumor.

In another embodiment, the desired polypeptide, RNA or other compound can be manufactured in the subject, and provide a beneficial effect to the subject. In one example, a microorganism can encode a protein or RNA, or a protein that manufactures a compound that is not manufactured by the subject. In one example, a microorganism can encode a peptide hormone or cytokine, such as insulin, which can be released into the vasculature of a subject lacking the ability to produce insulin or requiring increased insulin concentrations in the vasculature. In another example, blood clotting factors can be manufactured in a subject with blood clotting deficiency, such as a hemophiliac. In some embodiments, the protein or RNA to be produced in the tumor can be linked to an inducible promoter, such as a promoter that can be induced by increased glucose concentrations. In such instances, the manufacture of the protein or RNA can be controlled in response to one or more substances in the subject or by one or more substances that can be administered to a subject, such as a compound that can induce transcription, for example, RU486. Thus, in some embodiments, the methods provided herein can include administering to a subject having a tumor, a microorganism that can express one or more genes encoding a beneficial gene product or a gene product that can manufacture a beneficial compound.

2. Production of Antibodies

Also provided are methods for producing a desired antibody, the method comprising the following steps: (a) administering a microorganism containing a nucleotide sequence encoding an antigen into an animal bearing a tumor; and (b) isolating the antibody directed to the antigen from the serum obtained from the animal. The antibodies directed to the antigen can be isolated and purified according to well known methods. Antibodies that are directed against specific contaminating antigens (e.g., bacteria antigens) can be removed by adsorption, and the antibodies directed against the target antigen can be separated from contaminating antibodies by affinity purification, for example, by immuno affinity chromatography using the recombinant antigen as the ligand of the column, by methods known in the art. Antibodies can be collected from the animal in a single harvest, or can be collected over time by collection bleeds, as is known in the art.

F. PHARMACEUTICAL COMPOSITIONS, COMBINATIONS AND KITS

Provided herein are pharmaceutical compositions, combinations and kits containing a microorganism provided herein and one or more components. Pharmaceutical compositions can include a microorganism and a pharmaceutical carrier. Combinations can include two or more microorganisms, a microorganism and a detectable compound, a microorganism and a microorganism expression modulating compound, a microorganism and a therapeutic compound. Kits can include the pharmaceutical compositions and/or combinations provided herein, and one or more components such as instructions for use, a device for detecting a microorganism in a subject, a device for administering a compound to a subject, and a device for administering a compound to a subject.

1. Pharmaceutical Compositions

Also provided herein are pharmaceutical compositions containing a modified microorganism and a suitable pharmaceutical carrier. Examples of suitable pharmaceutical carriers are known in the art and include phosphate buffered saline solutions, water, emulsions, such as oil/water emulsions, various types of wetting agents, sterile solutions, etc. Such carriers can be formulated by conventional methods and can be administered to the subject at a suitable dose. Colloidal dispersion systems that can be used for delivery of microorganisms include macromolecule complexes, nanocapsules, microspheres, beads and lipid-based systems including oil-in-water emulsions (mixed), micelles, liposomes and lipoplexes. An exemplary colloidal system is a liposome. Organ-specific or cell-specific liposomes can be used in order to achieve delivery only to the desired tissue. The targeting of liposomes can be carried out by the person skilled in the art by applying commonly known methods. This targeting includes passive targeting (utilizing the natural tendency of the liposomes to distribute to cells of the RES in organs which contain sinusoidal capillaries) or active targeting (for example by coupling the liposome to a specific ligand, for example, an antibody, a receptor, sugar, glycolipid, protein etc., by well known methods). In the present methods, monoclonal antibodies can be used to target liposomes to specific tissues, for example, tumor tissue, via specific cell-surface ligands.

2. Host Cells

Also provided herein are host cells that contain a microorganism provided herein such as a modified vaccinia virus. These host cells can include any of a variety of mammalian, avian and insect cells and tissues that are susceptible to microorganisms, such as vaccinia virus infection, including chicken embryo, rabbit, hamster and monkey kidney cells, for example, CV-1, BSC40, Vero, BSC40 and BSC-1, and human HeLa cells. Methods of transforming these host cells, of phenotypically selecting transformants etc., are known in the art.

3. Combinations

Combinations can include a microorganism and one or more components. Any combination herein also can, in place of a microorganism, contain a pharmaceutical composition and/or a host cell containing a microorganism and one or more components.

Exemplary combinations can contain two or more microorganisms, a microorganism and a detectable compound, a microorganism and a microorganism expression modulating compound, or a microorganism and a therapeutic compound. Combinations that contain two or more microorganisms can contain, for example, two or more microorganisms that can both be administered to a subject in performing the methods provided herein, including sequentially administering the tow microorganisms. In one example, a combination can contain a virus and a bacterium, where, for example, the virus can first be administered to the subject, and the bacterium can be subsequently administered to the subject.

Combinations provided herein can contain a microorganism and a detectable compound. A detectable compound can include a ligand or substrate or other compound that can interact with and/or bind specifically to a microorganismally expressed protein or RNA molecule, and can provide a detectable signal, such as a signal detectable by tomographic, spectroscopic or magnetic resonance techniques. Exemplary detectable compounds can be, or can contain, an imaging agent such as a magnetic resonance, ultrasound or tomographic imaging agent, including a radionuclide. The detectable compound can include any of a variety of compounds as provided elsewhere herein or are otherwise known in the art. Typically, the detectable compound included with a microorganism in the combinations provided herein will be a compound that is a substrate, a ligand, or can otherwise specifically interact with, a protein or RNA encoded by the microorganism; in some examples, the protein or RNA is an exogenous protein or RNA. Exemplary microorganisms/detectable compounds include a microorganism encoding luciferase/luciferin, β-galactosidase/(4,7,10-tri(acetic acid)-

1-(2-β-galactopyranosylethoxy)-1,4,7,10-tetraazacyclododecane) gadolinium (Egad), and other combinations known in the art.

Combinations provided herein can contain a microorganism and a microorganism gene expression modulating compound. Compounds that modulate gene expression are known in the art, and include, but are not limited to, transcriptional activators, inducers, transcriptional suppressors, RNA polymerase inhibitors, and RNA binding compounds such as siRNA or ribozymes. Any of a variety of gene expression modulating compounds known in the art can be included in the combinations provided herein. Typically, the gene expression modulating compound included with a microorganism in the combinations provided herein will be a compound that can bind, inhibit, or react with one or more compounds active in gene expression such as a transcription factor or RNA, of the microorganism of the combination. An exemplary microorganism/expression modulator can be a microorganism encoding a chimeric transcription factor complex having a mutant human progesterone receptor fused to a yeast GAL4 DNA-binding domain an activation domain of the herpes simplex virus protein VP16 and also containing a synthetic promoter containing a series of GAL4 recognition sequences upstream of the adenovirus major late E1B TATA box, where the compound can be RU486 (see, e.g., Yu et al., Mol Genet Genomics 2002 268:169-178). A variety of other microorganism/expression modulator combinations known in the art also can be included in the combinations provided herein.

Combinations provided herein can contain a microorganism and a therapeutic compound. Therapeutic compounds can include compounds that are substrates for microorganismally expressed enzymes, compound that can kill or inhibit microorganism growth or toxicity, or other therapeutic compounds provided herein or known in the art to act in concert with a microorganism. Typically, the therapeutic compound included with a microorganism in the combinations provided herein will be a compound that can act in concert with a microorganism, such as a substrate of an enzyme encoded by the microorganism, or an antimicroorganismal agent known to be effective against the microorganism of the combination. Exemplary microorganism/therapeutic compound combinations can include a microorganism encoding Herpes simplex virus thymidine kinase/gancyclovir, and *streptococcus pyogenes*/penicillin. Any of a variety of known combinations provided herein or otherwise known in the art can be included in the combinations provided herein.

4. Kits

Kits are packaged in combinations that optionally include other reagents or devices, or instructions for use. Any kit provided herein also can, in place of a microorganism, contain a pharmaceutical composition, a host cell containing a microorganism, and/or a combination, and one or more components.

Exemplary kits can include the microorganisms provided herein, and can optionally include one or more components such as instructions for use, a device for detecting a microorganism in a subject, a device for administering a compound to a subject, and a device for administering a compound to a subject.

In one example, a kit can contain instructions. Instructions typically include a tangible expression describing the microorganism and, optionally, other components included in the kit, and methods for administration, including methods for determining the proper state of the subject, the proper dosage amount, and the proper administration method, for administering the microorganism. Instructions can also include guidance for monitoring the subject over the duration of the treatment time.

In another example, a kit can contain a device for detecting a microorganism in a subject. Devices for detecting a microorganism in a subject can include a low light imaging device for detecting light, for example emitted from luciferase, or fluoresced from green fluorescence protein, a magnetic resonance measuring device such as an MRI or NMR device, a tomographic scanner, such as a PET, CT, CAT, SPECT or other related scanner, an ultrasound device, or other device that can be used to detect a protein expressed by the microorganism within the subject. Typically, the device of the kit will be able to detect one or more proteins expressed by the microorganism of the kit. Any of a variety of kits containing microorganisms and detection devices can be included in the kits provided herein, for example, a microorganism expressing luciferase and a low light imager, or a microorganism expressing green fluorescence protein and a low light imager.

Kits provided herein also can include a device for administering a microorganism to a subject. Any of a variety of devices known in the art for administering medications or vaccines can be included in the kits provided herein. Exemplary devices include a hypodermic needle, an intravenous needle, a catheter, a needle-less injection device, an inhaler, and a liquid dispenser such as an eyedropper. Typically, the device for administering a microorganism of the kit will be compatible with the microorganism of the kit; for example, a needle-less injection device such as a high pressure injection device can be included in kits with microorganisms not damaged by high pressure injection, but is typically not included in kits with microorganisms damaged by high pressure injection.

Kits provided herein also can include a device for administering a compound to a subject. Any of a variety of devices known in the art for administering medications to a subject can be included in the kits provided herein. Exemplary devices include a hypodermic needle, an intravenous needle, a catheter, a needle-less injection an inhaler, and a liquid dispenser. Typically the device for administering the compound of the kit will be compatible with the desired method of administration of the compound. For example, a compound to be delivered subcutaneously can be included in a kit with a hypodermic needle and syringe.

G. EXAMPLES

The following examples are included for illustrative purposes only and are not intended to limit the scope of the invention.

Example 1

Generation of Recombinant Viruses

A Wild type vaccinia virus (VV) strain LIVP (the well known viral strain, originally derived by attenuation of the strain Lister from the ATCC under Accession Number VR-1549, from the Institute of Viral Preparations, Moscow, Russia; see, Al'tshtein et al., (1983) Dokl. Akad. Nauk USSR 285:696-699) designed as VGL was used as a parental virus for the construction of recombinant viruses designated RVGLX herein. All vaccinia viruses were purified using sucrose gradient (Yoklik). VVs were propagated and titers were determined by plaque assays using CV-1 cells (ATCC No. CCL-70). Methods for constructing recombinant vaccinia viruses are known to those of skill in the art (see, e.g., Chakrabarti et al., (1985 Mol. Cell. Biol. 5:3403 and U.S. Pat. No. 4,722,848)). Table 1 summarizes the recombinant VV strains described in this Example.

Inactivation of VV by PUV Treatment

LIVP VV ($3\times10^8$ pfu/ml) was incubated with 1 µg/ml psoralen (Calbiochem, La Jolla, Calif.), suspended in Hank's buffer at room temperature for 10 min, and then irradiated for 5 min in Stratalinker 1800 UV crosslinking unit (Stratagene, La Jolla Calif.) equipped with five 365 nm long wave UV bulb to produce PUV-VV.

RVGL8: LacZ Insertion into F3 of LIVP

Construction of recombinant vaccinia virus RVGL8 containing a lacZ gene inserted the NotI site was prepared as described in Timiryasova et al. (2001), BioTechniques 31, 534-540. Briefly it was prepared as follows. The BamHI/SmaI fragment (3293 bp) of pSC65 (see, Chakrabarti et al. (1997), BioTechniques 23, 1094-1097; see, also Current Protocols in Molecular Biology, Green Publishing and Wiley-Interscience Supplement 15:16.17.2 (1992); see also SEQ ID NO: 5 herein and SEQ ID NO: 57 in PCT International application No. WO 99/32646) containing the lacZ gene under the control of the vaccinia p7.5 promoter and strong synthetic vaccinia pE/L promoter was isolated by digestion with restriction enzymes, blunted with Klenow enzyme, and cloned into SmaI site of pNT8 plasmid (Timiryasova et al. (2001), BioTechniques 31: 534-540) to produce pNZ2a shuttle plasmid.

To construct pNT8, the NotI region of the wild type VV strain LIVP was amplified using the following primers:

Forward: 5'-GGGAATTCTTATACATCCTGTTCTATC-3' (SEQ ID NO: 3); Reverse: 5'-CCAAGCTTATGAGGAG-TATTGCGGGGCTAC-3' (SED ID NO: 4) with the VV as a template. The resulting 972 bp fragment contained flanking EcoRI and HindIII sites at the 5' and 3' ends, respectively. The PCR product was cleaved with EcoRI and HindIII and inserted in pUC28 (Benes et al., (1993) Gene 130: 151. Plasmid pUC28 is prepared from pUC18 (available from the ATCC under Accession Number 37253 by introducing a synthetic oligo adaptor using primers:

pUC28 I: 5'AATTCAGATCTCCATGGATCGATGAGCT 3' (SEQ ID NO: 6); pUC28 II: 3'GTCTAGAGGTACCTAGC-TAC 5' (SEQ ID NO: 7) into the EcoRI and SstI sites of pUC18. This introduces BglII, ClaI, and NcoI sites into the polylinker of pUC18.

Plasmid pNZ2 contains cDNA encoding the *E. coli* lacZ gene under the control of the vaccinia virus early/late promoter p7.5 and a synthetic early/late vaccinia pE/L promoter derived from the plasmid pSC65 (see, Chakrabarti et al. (1997), BioTechniques 23, 1094 1097; see, also Current Protocols in Molecular Biology, Green Publishing and Wiley-Interscience Supplement 15:16.17.2 (1992); see also SEQ ID NO: 5 herein and SEQ ID NO: 57 in PCT International application No. WO 99/32646). Plasmid pNZ2 provides for homologous recombination of lacZ into the NotI site of the VGL virus (ATCC VR-1549), to produce the recombinant vaccinia virus designated RVGL8. The complex of wild type vaccinia virus DNA digested with NotI and not digested plasmid DNA pNZ2 was transfected for in vivo recombination into PUV VV infected cells to produce RVGL8 (see FIG. 1). RVGL8 and the other recombinant vaccinia viruses described herein are listed in Table 1, below.

Mutant Virus Formation/Transfection

CV-1 African green monkey kidney fibroblasts (ATCC No. CCL-70) grown on 60 mm dishes (Corning, Corning, N.Y., USA) were infected with PUV-VV (strain LIVP treated with psoralen and UV; see, e.g., Tsung et al. (1996), J. Virol. 70, 165-171; Timiryasova et al. (2001), BioTechniques 31, 534-540; Timiryasova et al. (2001), J. Gene 3 Med. 3, 468-477) at multiplicity of infection (MOI) of 1.

Two hours post-infection, the cells were transfected with a mixture of NotI-digested viral DNA (4 µg) and intact plasmid DNA (4 µg). Lipid-mediated transfection of cells was carried out using 5 µl of GenePORTER reagent (Gene Therapy Systems, San Diego, Calif., USA) per µg of the DNA according to manufacturers' instructions. Cells were incubated in transfection mixture for 4 h and then supplemented with a medium containing 20% of fetal bovine serum. Cytopathic effects were monitored daily by light microscopy. Cells were incubated for 5-7 days until formation of the virus plaques and complete cytopathic effect. Then, infected cells were harvested, resuspended in 0.5 ml of medium, and frozen and thawed three times to release the virus. Single virus plaques were selected for the preparation of small and large recombinant virus stocks and analyzed for the insertion and expression of the genes.

Confirm Mutant

Viral DNA was analyzed by Southern blots. Briefly, to isolate viral DNA, confluent monolayers of CV-1 cells, grown on 10 cm plates, were infected with the wild type VV (strain LIVP) or VV of the virus stock obtained from a single recombinant plaque. When the cytopathic effect was complete, cells were harvested and the pellet was resuspended in 3 ml of 10 mM Tris-HCl, pH 9.0. Viral particles were lysed, treated with proteinase K, and the virus DNA was isolated by phenol/chloroform extraction, followed by ethanol precipitation. The DNA was resuspended in 100 µl of sterile water. The viral DNA samples were digested by NotI overnight at 37° C., followed by phenol-chloroform treatment, precipitated and 10 µg of DNA samples were separated through a 0.8% agarose gel. The DNA was transferred to a positively charged nylon membrane (Roche Diagnostics Corporation, Indianapolis, Ind., USA) and fixed to the membrane using a GS Gene Linker (Bio-Rad Laboratories, Hercules, Calif., USA). The DIG-labeling of DNA was performed using a nonradioactive DNA labeling and detection kit (Roche Diagnostics Corporation) and incubating for 60 min at 37° C. The membrane was hybridized with a denatured DIG-labeled 3357 bp NotI-NotI DNA fragment of the plasmid pNZ2 encoding the lacZ gene. Hybridization conditions and blot development were performed as suggested by the manufacturer.

The predicted size of the band is 3357 bp. The hybridization of NotI digested viral DNAs with a 3357 bp DNA probe confirmed the integration of the lacZ gene into NotI site of virus genome.

Construction of RVGL2 and RVGL23 Viruses with a Single TK Gene Mutation

Vaccinia virus LIVP was used for the construction of recombinant virus RVGL2. Vaccinia virus Western Reserve (WR) was used for the construction of recombinant virus RVGL23. The cDNA of *Renilla* luciferase and *Aequorea* GFP fusion (ruc-gfp; 1788 bp; see, Wang et al., (1996) Bioluminescence Chemiluminescence 9:419-422; Wang et al., (2002) Mol. Genet. Genomics 268:160-168; Wang et al. (1997) pp 419-422 in Bioluminescence and Chemiluminescence: molecular reporting with photons, Hastings et al., eds., Wiley, Chicheser UK; see, also U.S. Pat. No. 5,976,796; see also SEQ ID NO: 8 herein, which sets forth a sequence for a ruc-gfp construct) was excised from plasmid pcDNA-ruc-gfp (RG), which is described in Wang et al., (1996) Bioluminescence Chemiluminescence 9:419-422 and Wang et al., (2002) Mol. Genet. Genomics 268:160-168 and briefly below, by restriction endonuclease PmeI and inserted into the SmaI site of pSC65 plasmid (see SEQ ID NO: 5; see, also herein and SEQ ID NO: 57 in PCT International application No. WO 99/32646), resulting in pSC65-RG-1 plasmid DNA.

Briefly to prepare pcDNA-ruc-gfp, the EcoRI-NotI fragment encoding the modified *Renilla* luciferase-ending DNA (see, Wang et al. (1997) pp 419-422 in Bioluminescence and Chemiluminescence: molecular reporting with photons, Hastings et al., eds., Wiley, Chichester UK) was cloned into the pcDNA3.1 vector (Invitrogen, Carlsbad, Calif.), placing expression of the *Renilla* luciferase under control of the CMV promoter. The stop codon at the end of the *Renilla* luciferase ORF was removed, and the resulting plasmid digested with NotI. The NotI fragment containing the ORF encoding humanized *Aequorea* GFP (Zolotukhin et al., (1996) J. Virol. 70:4646-4654) was excised from the pTR-β-actin plasmid and inserted into the NotI site of the plasmid encoding the *Renilla* luciferase. The resulting plasmid was designated pcDNA-ruc- the ruc-gfp.

New plasmid pSC65-RG-1 containing ruc-gfp fusion under the control of the vaccinia PE/L promoter and *E. coli* β-galactosidase under control of p7.5 promoter of VV was used for the construction of a single TK gene interrupted virus RVGL2 of strain LIVP and RVGL23 of strain WR. CV-1 cells were infected with wt LIVP or wt WR virus at MOI of 0.1, and two hours later, pSC65-RG-1 plasmid DNA was transfected using FuGene6 transfection reagent (Roche). After 24 h of incubation, cells were three times frozen and thawed to release the virus. Recombinant viruses were screened on CV-cells in the presence of substrate 5-bromo-4-chloro-3-indolyl-p-D-galactopyranoside (X-gal, Stratagene, Cedar Creek, Tex., USA). After four cycles of virus purification, all virus plaques were positive for β-galactosidase expression. The expression of the ruc-gfp fusion protein was confirmed by luminescence assay and fluorescence microscopy, respectively. Schematic maps of the viruses are set forth in FIG. 1.

Construction of RVGL5 and RVGL9 Viruses with Single Gene Mutations

Recombinant vaccinia virus RVGL5 contains the lacZ gene under the control of the vaccinia late p11 promoter inserted into the HA gene of vaccinia genome (Timiryasova et al. (1993) Mol Biol 27:392-402; see, also, Timiryasova et al., (1992) Oncol. Res 11:133-144.). Recombinant vaccinia virus RVGL9 contains a fusion of the *Renilla* luciferase gene (ruc) and cDNA of green fluorescence protein (GFP) under the control of a synthetic early/late vaccinia promoter (PE/L) inserted into the F3 gene of the VV genome (Timiryasova et al., (2000)) pp. 457-459 in Proceedings of the 11th International Symposium on Bioluminescence and Chemiluminescence, Case et al., eds). RVGP5 and RVGLP9. were constructed as described for RVGLP2 and RVGLP23.

Construction of RVGL20 Virus with Double TK and F3 Gene Mutations

The cDNA of human transferrin receptor (hTR) (2800 bp) with polyA sequence was isolated from pCDTR1 plasmid (ATCC Accession No. 59324 and 59325) by BamHI, treated with Klenow and inserted into SalI site of pSC65 plasmid (SEQ ID NO: 5 herein and SEQ ID NO: 57 in PCT International application No. WO 99/32646), resulting in pSC-TfR and pSC-rTfR. Plasmid pSC-rTfR contains cDNA hTR in an orientation opposite to the vaccinia PE/L promoter and *E. coli* β-galactosidase under control of the early/late vaccinia p7.5 promoter flanked by vaccinia sequences for insertion into vaccinia TK gene. pSC-rTfR was used for the construction of RVGL20 virus. RVGL9, a recombinant virus with single deletion carrying ruc-gfp fusion in the F3 gene locus, which contains a unique NotI site in the LIVP strain (see above, see, also, Timiryasova et al., (2000) pp. 457-459 in *Proceedings of the 11th International Symposium on Bioluminescence and Chemiluminescence*, Case et al., eds), was used as a parental virus for the creation of RVGL20 virus by homologous recombination as described above. A schematic of RVGL20 virus is set forth in FIG. 1.

Construction of RVGL21 Virus with Triple TK, F3 and HA Gene Mutations

The cDNA of the β-glucuronidase (gus) of *E. coli* (1879 bp) was released from pLacGus plasmid (Invitrogen; see SEQ ID NO: 9 herein) with XbaI (blunt ended with Klenow fragment) and HindIII, and cloned into pSC11 plasmid pSC65 (Chakrabarti et al.(1985) Mol. Cell. Biol. 5:3403-3409; SEQ ID NO: 5 herein and SEQ ID NO: 57 in PCT International application No. WO 99/32646) digested with XhoI (treated with Klenow) and HindIII under the control of a vaccinia p11 late promoter, resulting in a plasmid pSC-GUS. The SmaI-HindIII fragment from pSC-GUS plasmid was inserted into pVY6 plasmid, a vector for inserting antigen genes into the hemagglutinin gene of vaccinia (see, e.g., Flexner et al., (1988) Nature 355:259-262; Flexner et al., (1988) Virology 166: 339-349; see also U.S. Pat. No. 5,718,902) digested with SmaI and BamHI, resulting in pVY-GUS plasmid. The resulting plasmid, designated pVY-GUS plasmid, contains the cDNA encoding gus under the control of the vaccinia late promoter p11 flanked by vaccinia sequences for insertion into the hemagglutinin (HA) gene. Recombinant virus RVGL20 with double deletions was used as the parental virus for the construction of RVGL21 virus. CV-1 cells were infected with RVGL20 virus at MOI of 0.1. Two hours after infection, cells were transected with pVY-GUS plasmid DNA using FuGene6 transfection reagent (Roche). Recombinant-virus plaques were selected in CV-1 cells by color screening upon addition of β-glucuronidase substrate 5-bromo-4-chloro-3-indolyl-β-D-glucuronicacid (X-GlcA) (Research Products Int. Co., Mt. Prospect, Ill., USA) into agar medium. After eight cycles of purification in agar medium in the presence of X-GlcA pure recombinant virus RVGL21 was selected. RVGL21 virus has interruptions of TK, F3 and HA genes and is presented schematically in FIG. 1.

In Vitro Virus Growth

CV-1, C6 (ATCC No. CCL-107), B16-F10 (ATCC No. CRL-6475), and GI-101A (Rumbaugh-Goodwin Institute for Cancer Research Inc. Plantation, Fla.; U.S. Pat. No. 5,693,533) cells were seeded in 24-well plates at the density of $1 \times 10^5$, $2 \times 10^5$, $4 \times 10^5$ and $2 \times 10^5$ cells/well, respectively. The next day, the cells were simultaneously infected with 0.001 or 0.01 PFU/cell of a wild type LIVP and its mutants. The virus suspension was added to cell monolayer (0.15 ml/well) and incubated at 37° C. for 1 h with brief agitation every 10 min. Then, the virus was removed, appropriate complete growth medium was added (1 ml/well), and the cells were then incubated at 37° C. for 24, 48, 72 and 96 h after virus infection. To establish resting cell culture, a confluent monolayer of CV-1 cells was incubated for 6 days in DMEM with 5% FBS at 37° C. These resting cells were infected and harvested at the same time points after infection as described above. Virus from the infected cells was released by one cycle of freezing and thawing. Viral titers were determined in duplicates by plaque assay on CV-1 cells and expressed as PFU/ml.

TABLE 1

List of recombinant vaccinia viruses (VV)

| Designation | Prior Designation | Description | Insertion Locus/loci | Reference |
|---|---|---|---|---|
| VGL | wt VV | strain LIVP VV | No Insertions | Publicly available |
| RVGL1 | recVV2 | (p7.5) Luc-(p11) LacZ of LIVP VV | HindIII-N-Interrupted | Timiryasova T M, Kopylova-Sviridova T N, Fodor I. Mol. Biol. (Russian) 27: 392-401 (1993); Timiryasova T M, Li J, Chen B. Chong D. Langridge W H R, Gridley D S, Fodor I. Oncol. Res. 11: 133-144 (1999) |
| RVGL5 | recVV8 | (p11) LacZ of LIVP VV | HA-Interrupted | Timiryasova T M, Kopylova-Sviridova T N, Fodor I. Mol. Biol. (Russian) 27: 392-401 (1993) |
| RVGL7 | rVV-EGFP or rVV-GFP | (PE/L) EGFP-(p7.5) LacZ of LIVP VV | TK-Interrupted | Umphress S, Timiryasova T., Arakawa T, Hilliker S, Fodor I, Langridge W. Transgenics 4: 19-33 (2003) |
| RVGL8 | rVV-Not-LacZ or rVV-Not-LZ | (p7.5) LacZ of LIVP VV | NotI (F3)-Interrupted | Timiryasova T M, Chen B, Fodor N, Fodor I. BioTechniques 31: 534-540 (2001) |
| RVGL9 | rVV-RG or rVV-ruc-gfp | (PE/L) Ruc-GFP of LIVP VV | NotI (F3)-Interrupted | Timiryasova T M, Yu Ya, Shabahang S, Fodor I, Szalay A A. Proceedings of the 11$^{th}$ International Symposium on Bioluminescence & Chemiluminescence pp. 457-460 (2000) |
| RVGL12 | | Same as RVGL7, except that HSV TK is inserted in place of gfp | | |
| RVGL19 | | (PE/L) Trf-(p7.5) LacZ in Tk locus (PE/L) Ruc-GFP in F3 locus of LIVP VV | TK- and NotI (F3)-Interrupted | Herein |
| RVGL20 | | (PE/L) rTrf-(p7.5) LacZ in TK locus (PE/L) Ruc-GFP in F3 locus of LIVP V | Tk- and NotI (F3)-Interrupted | Herein |
| RVGL21 | | (PE/L) rTrf-(p7.5) LacZ in TK locus, (p11) LacZ in HA locus, (PE/L) Ruc-GFP in F3 locus of LIVP VV | Tk-, HA-interrupted and NotI (F3)-Interrupted | Herein |
| RVGL23 | | (PE/L) rTrf-(p7.5) LacZ in TK locus of WR VV | Tk-Interrupted | Herein |

Example 2

In Vitro Analysis of Virus Levels

LacZ

Analysis of lacZ expression induced by recombinant vaccinia virus was performed as described previously (Timiryasova et al. (2001), BioTechniques 31, 534-540). Briefly, CV-1 cells grown 6-well plates (Corning, Corning, N.Y., USA) were infected with ten-fold dilutions of the virus stock. The virus was allowed to absorb for 1 h at 37° C. with occasional rocking. Then, the virus inoculum was replaced with a complete medium containing 1% of agar, and the incubation was carried out for 48 h. To visualize the virus plaques, 300 μg of X-Gal (Molecular Probes, Eugene, Oreg., USA) per ml and 0.1% of neutral red (Sigma, St. Louis, Mo., USA) were added to the second agar overlay, and plaques were counted and isolated after 12 h incubation at 37° C. Levels of vaccinia virus in cells in vitro could also be determined by measuring the plaque forming units (PFU) in the cells.

In Vitro Infectivity of VV's Measured by Plaque Forming Units

The ability of wt LIVP virus and its mutants to infect and replicate was analyzed in dividing and resting CV-1 cells as well as in three tumor cell lines (C6, GI-101A, B16-F10). The results demonstrate that vaccinia mutants can efficiently infect and replicate in dividing CV-1 cells at an MOI of 0.001. A significant yield of vaccinia virus was obtained from dividing CV-1 cells. The yield of wt VV and its mutants in dividing CV-1 cells was about 10 times higher than in resting CV-1 cells. There was no significant difference in viral recovery between vaccinia mutants and wt virus in vitro studies. The interruption of TK, F3 and HA genes made no difference to VV mutants replication in the dividing CV-1 cells. Three tumor cells were tested. The relative sensitivities to cytopathic effects at MOI of 0.001 were follows: CV-1 (dividing, highest), CV-1 (resting), C6, GI-101A, B16-F10 (lowest). Mouse B16-F10 melanoma cells were not sensitive to virus infection at MOI of 0.001. Very low viral titer was recovered from melanoma cells infected at MOI of 0.01. Also observed was that wt WR strain was able to infect melanoma cells in vitro more efficiently compared to LIVP strain and virus recovery was higher compared to LIVP strain.

Example 3

Animal Models and Assays

Animal Models

Athymic nude mice (nu/nu) and C57BL/6 mice (Harlan Animal Res., Inc., Wilmington, Mass.) at 6-8 weeks of age were used for animal studies. Mice in groups of five or four were infected i.v. with $10^7$ PFU of VV in a volume of 0.1 ml i.v. Mice were imaged by low-light imager and fluorescence imager for ruc and for gfp expression, respectively. The study was approved prior to initiation by the Animal Research Committee of LAB Research International Inc. (San Diego, Calif., USA). All animal care was performed under the direction of a licensed veterinarian of LAB Research International Inc. (San Diego, Calif., USA).

Glioma Model

To establish subcutaneous glioma tumor, rat glioma C6 cells (ATCC No. CCL-107) were collected by trypsinization, and $5\times10^5$ cells/0.1 ml/mouse were injected subcutaneously (s.c.) into right hind leg of 6-8 week old male athymic mice. On day 7 after C6 cell implantation when median tumor size was about 150 $mm^3$, viruses at the dose of $10^7$ PFU/0.1 ml/mouse were injected intravenously (i.v.). Mice were sacrificed 14 days after virus injection. In the kinetic studies using of RVGL9 virus, mice were sacrificed at 20 min, 1 h, 4 h, 18 h, 36 h, 3 d, 5 d, 7 d and 14 days after virus injection.

Breast Tumor Model

To develop sub cutaneous (s.c). breast tumor, human breast cancer GI-101 A cells (Rumbaugh-Goodwin Institute for Cancer Research Inc. Plantation, Fla.; U.S. Pat. No. 5,693, 533) at the dose of $5\times10^6$ cells/0.1 ml/mouse were injected s.c. into the right hind leg of 6-8 week old female athymic mice. On day 30 after GI-101A cell implantation, when median tumor size was about 500 $mm^3$, viruses at the dose of $10^7$ PFU/mouse were injected i.v. Mice were sacrificed on day 14 after virus injection. Mice for survival experiments and breast tumor therapy studies were kept for long time periods (more than 100 days after virus injection). Mice that developed tumor with the size about 4000 $mm^3$, and/or lost 50% of body weight were sacrificed.

Melanomal Model

For a melanoma model, mouse melanoma B16-F10 cells (ATCC No. CRL-6475) at the dose of $2\times10^5$ cells/0.04 ml/mouse were injected into the foot pad of 6-8 week old male C57BL/6 mice. When the tumor was established (median size of tumor about 100 $mm^3$), on day 18 after cell implantation, viruses at the dose of $10^7$/mouse were injected i.v. Mice were sacrificed 10 days after virus injection.

Vaccinia Virus in Animal Models

Vaccinia Virus Recovery from Tumor and Organs of Nude Mice

From sacrificed animals blood was collected, and organs (lung, liver, spleen, kidneys, testes, ovaries, bladder, brain, heart) and tumors were harvested and homogenized in PBS containing a mixture of protease inhibitors. Scissors and forceps were changed after each organ dissection or incision to avoid cross-contamination of the tissues. Samples were frozen and thawed, centrifuged at 1,000 g for 5 min. Viral titer was determined in the supernatant diluted in serum-free medium on CV-1 cells by plaque assay and staining them with 1% (wt/vol) crystal violet solution after 48 h incubation. Each sample was assayed in duplicate and viral titer was expressed as mean PFU/g of tissue.

Assay Measurements

Survival studies were performed on 6-week old nude mice bearing s.c. human breast tumor. Mice were injected i.v. with $10^7$ of vaccinia viruses and followed for survival. Individual body weight was measured twice a week. Gain/loss of body weight after virus infection was calculated as the percentage: body weight (g)–tumor weight (g) on day of virus injection/ body weight (g)–tumor weight (g) on day of monitoringx 100%. Spleens were excised from euthanized animals and weighed. The RSW was calculated as follows: RSW=weight of spleen (g)x$10^4$/animal body weight (g)–tumor weight (g). Mice were euthanized when the mean tumor volume reached 3000 $mm^3$ or developed the signs of disease. Rapid $CO_2$ euthanasia was humanely performed in compliance with the *NIH Guide for the Care and Use of Laboratory Animals*.

Reporter Genes Assays

LacZ

*E. coli* β-galactosidase activity in tissue samples and in the serum of the mice was determined using chemiluminescent Galacto-Light Plus™ Assay system (Applied Biosystems, Bedford, Mass., USA) according to the instructions of the kit manufacturer. Briefly, 1-20 μl of the sample was transferred into the tube with 200 μl of 1:100 diluted Reaction Buffer Diluent and incubated at RT for 30 min. A 300 μl aliquot of accelerator (-II) was added into the tube with the sample, mixed quickly and the signal was read using luminometer. β-galactosidase activity was expressed as relative light units (RLU) per g of tissue. Purified *E. coli* β-galactosidase (Sigma) was used as a positive control and to generate a standard curve.

Luciferase

*Renilla* luciferase activity was measured in the supernatant of the tissue samples after they had been homogenized using a Turner TD 20e luminometer (Turner Designs, Sunnyvale, Calif., USA) as described previously (Yu and Szalay, 2002) with some modifications. In brief, 201 of the samples was added into 500 μl of luciferase assay buffer (0.5 M NaCl, 1 mM EDTA, 0.1 M potassium phosphate pH 7.4) containing a substrate coelenterazine. Luciferase activity was measured during 10-s interval and expressed as RLU per g of tissue.

Assay Results

Presence of RVGL9 Over Time

A vaccinia virus RVGL9 with a single F3 gene mutation and carrying ruc-gfp was used to assess the pattern of vector tissue distribution following i.v. administration into immunocompromised athymic mice bearing s.c. glioma tumors. The tissue distribution data using this recombinant virus showed virus distribution and tumor targeting by this VV strain. Kinetics studies were performed by noninvasive imaging of virus replication in the mice based on ruc and gfp expression. Four to five animals per group bearing s.c. rat glioma C6 tumor were injected with $10^7$ of RVGL9 virus via the tail vein. The animals were sacrificed at 20 min, 1, 4, 18 and 36 hours, 3, 5, and 14 days after virus injection. No viable viral particles were recovered from brain, bladder or testes at any time point after i.v. injection of virus. Some viral particles were recovered from spleen, heart and lung at early time points after virus injection. After 18 h post-infection, the titer of RVGL9 virus in these organs decreased. No virus was recovered in the heart tissue after 18 h; around 156.5 and 44 PFU/g tissue was recovered from spleen and lung, respectively, on day 14 as compared to 3221.0 and 3521.9 PFU/g tissue at 20 min after virus injection, respectively. The pattern of virus recovery from liver and kidneys was different from the pattern in the spleen, heart, or lung. No virus in the kidneys and 174.9 PFU/g tissue of virus was recovered from liver at an early time after virus injection. On day 5 after virus injection, the titer of virus in these organs increased and went down on day 14 post virus injection. In tumor tissue virus was detected starting 18 h after virus administration ($1.6 \times 10^3$ PFU/g tissue), and dramatically increased over the time of observation ($1.8 \times 10^8$ PFU/g tissue on day 7). Virus in the tumor tissue was detectable for more then 60 days after a single i.v. virus injection. The results demonstrate tumor-specific replication of these vaccinia mutants. A correlation was observed between the virus recovery and the transgene expression in tumors and in organs. Based on the data of RVGL9 virus kinetics, day 10 or day 14 was used for tissue distribution studies of different vaccinia mutants in melanoma and glioma and breast tumor models, respectively.

Presence of Various VV in Mice Bearing a Glioma Tumor

To examine tissue distribution of vaccinia virus in immunodeficient mice bearing an s.c. glioma tumor, viruses were injected i.v. at a dose of $1 \times 10^7$ PFU/0.1 ml/mouse on day 7 after C6 rat glioma cell implantation. Fourteen days after virus injection, mice were sacrificed and virus titer was determined in different tissues. Mice injected with wt WR virus were sick and dying due to viral pathogenicity. Hence, WR-injected mice were sacrificed on day 7 after virus injection. Wild type LIVP virus was recovered from all analyzed tissues as well as from brain. The amount of recovered virus particles from the mice injected with wt LIVP was much lower than wt WR strain of VV. The results are presented in Table 1A.

TABLE 1A

Viral recovery from nude mice tissues in glioma model.[a]

| | LIVP Wt | RVGL2 TK- | RVGL5 HA- | RVGL9 F3- | RVGL20 TK-, F3- | RVGL21 TK-, F3-, HA- | WR[b] Wt | RVGL23 TK-, WR |
|---|---|---|---|---|---|---|---|---|
| Brain | $1.2 \times 10^3$ | $1.4 \times 10^3$ | 0 | 0 | 0 | 0 | $1.4 \times 10^7$ | $1.9 \times 10^6$ |
| Kidneys | $6.1 \times 10^2$ | $6.7 \times 10^2$ | $1.6 \times 10^2$ | 34.6 | 33.3 | 36.6 | $5.4 \times 10^6$ | $7.9 \times 10^2$ |
| Lung | $2.9 \times 10^3$ | 0 | $1.6 \times 10^2$ | $1.4 \times 10^4$ | $6.7 \times 10^3$ | $2.4 \times 10^3$ | $1.9 \times 10^6$ | $2.1 \times 10^3$ |
| Spleen | $1.9 \times 10^2$ | 0 | $1.8 \times 10^2$ | $1.0 \times 10^3$ | $1.0 \times 10^2$ | $1.7 \times 10^2$ | $1.6 \times 10^6$ | $1.8 \times 10^3$ |
| Testes | $5.8 \times 10^4$ | 64.3 | $6.4 \times 10^2$ | $7.5 \times 10^2$ | 0 | 0 | $9.8 \times 10^4$ | $1.7 \times 10^3$ |
| Bladder | $6.4 \times 10^3$ | 0 | 0 | $2.9 \times 10^3$ | 0 | 0 | $2.8 \times 10^5$ | $1.2 \times 10^3$ |
| Liver | $3.4 \times 10^4$ | 63.6 | $4.2 \times 10^2$ | 33.6 | 96.6 | 30.8 | $7.1 \times 10^3$ | $5.6 \times 10^3$ |
| Heart | $6.0 \times 10^3$ | 0 | 0 | 0 | 0 | 0 | $1.4 \times 10^5$ | 0 |
| Serum[c] | 0 | 0 | 0 | 0 | 0 | 0 | $6.0 \times 10^2$ | 0 |
| Tumor | $5.4 \times 10^7$ | $1.5 \times 10^7$ | $3.8 \times 10^7$ | $2.9 \times 10^7$ | $3.9 \times 10^7$ | $1.9 \times 10^7$ | $1.9 \times 10^8$ | $3.7 \times 10^7$ |

The results demonstrate that 10000-fold more virus was recovered in the brain of mice injected with WR strain versus wt LIVP strain. Wild type WR strain virus was recovered from the serum (600 PFU/20 μl) of mice on day 7 after virus injection. No virus was recovered in the serum of the mice injected with LIVP mutants on day 14. The level of wt LIVP in serum was not tested on day 7. About $1.9 \times 10^6$ PFU/g tissue of TK-mutant of WR strain (RVGL23) was found in the brain tissue compared to $1.4 \times 10^3$ PFU/g tissue for mice injected with the TK-mutant of LIVP strain (RVGL2).

All other mutants of VV strain LIVP were found mostly in tumor only and no virus was recovered from brain tissue of mice injected with a double or triple mutant (Table 1A). Three times as many virus particles were recovered from the tumors of mice injected with WR compared to wt LIVP. The mean of viral recovery in tumor tissue of the mutants of LIVP strain was similar to the wt LIVP and equivalent to TK-mutant of WR strain.

Presence of Various VV in Mice Bearing a Breast Tumor

Data for tissue distribution in immunocompromised mice bearing s.c. GI-101A human breast are presented in Table 1B:

TABLE 1B

Viral recovery from nude mice tissues in breast cancer model.

|  | LIVP Wt | RVGL2 TK- | RVGL5 HA- | RVGL9 F3- | RVGL20 TK-, F3- | RVGL21 TK-, F3-, HA- | WR[b] Wt | RVGL23 TK-, WR |
|---|---|---|---|---|---|---|---|---|
| Brain | 0 | 0 | 0 | 0 | 0 | 0 | $7.2 \times 10^6$ | $1.6 \times 10^4$ |
| Kidneys | $3.6 \times 10^3$ | 38.3 | 27 | $3.3 \times 10^2$ | 25.8 | 0 | $3.2 \times 10^7$ | $2.8 \times 10^5$ |
| Lung | $8.6 \times 10^3$ | $5.5 \times 10^2$ | 29.1 | $1.6 \times 10^3$ | $1.6 \times 10^3$ | $1.0 \times 10^3$ | $2.1 \times 10^6$ | $3.7 \times 10^3$ |
| Spleen | $5.5 \times 10^3$ | 99.5 | 0 | $1.8 \times 10^2$ | 0 | 0 | $1.6 \times 10^6$ | $1.8 \times 10^3$ |
| Ovaries | $1.6 \times 10^3$ | 0 | 0 | 0 | 0 | 0 | $8.0 \times 10^7$ | $2.7 \times 10^7$ |
| Bladder | $3.9 \times 10^3$ | 0 | 0 | 0 | 0 | 0 | $2.8 \times 10^4$ | $1.2 \times 10^3$ |
| Liver | $1.2 \times 10^4$ | 0 | $1.7 \times 10^2$ | $5.2 \times 10^2$ | $1.7 \times 10^2$ | $1.0 \times 10^2$ | $4.0 \times 10^5$ | $4.8 \times 10^5$ |
| Heart | $1.4 \times 10^2$ | 0 | 0 | 58.2 | $4.6 \times 10^2$ | 0 | $6.3 \times 10^4$ | $2.2 \times 10^3$ |
| Serum[c] | 0 | 0 | 0 | 0 | 0 | 0 | $2.4 \times 10^3$ | 0 |
| Tumor | $8.6 \times 10^8$ | $1.0 \times 10^9$ | $2.5 \times 10^8$ | $1.1 \times 10^9$ | $5.6 \times 10^8$ | $1.0 \times 10^9$ | $2.9 \times 10^9$ | $6.6 \times 10^8$ |

About 10-fold more viral particles were recovered from breast tumor tissue compared to glioma tumor tissue. No virus particles were recovered from the brain tissue of mice injected with either wt LIVP or its mutants. $7.2 \times 10^6$ and $1.6 \times 10^4$ PFU/g was recovered from brain tissue of mice injected with wt WR and TK-virus of WR strain VV, respectively (Table 1B). During the dissection of organs from euthanized mice, it was found that the ovaries from the mice being injected with wt WR and TK- of WR virus were drastically enlarged as compared to all other groups of mice. The analysis of viral recovery from ovaries demonstrated high titer of wt WR and TK-WR strain in ovaries, for example, $8.0 \times 10^7$ and $2.7 \times 10^7$ PFU/g, respectively. About $1.6 \times 10^3$ PFU/g was recovered from the ovaries of the mice injected with wt LIVP virus, however no virus particles at all were recovered from either ovaries or from brain of mice injected with the mutants derived from LIVP strain (Table 1B).

Presence of Various VV in Mice Bearing a Melanoma Tumor

The tissue distribution of VV in the immunocompetent mice bearing melanoma tumors on foot pads also were studied. BL/6 mice on day 17 after B16F10 melanoma cell implantation were i.v. injected with the viruses at the dose of $10^7$ PFU/mouse via the tail vein. All groups of mice were sacrificed on day 10 after virus injection due to huge tumor size in the PBS-injected control group. The results are set forth in Table 1C:

No virus was recovered from kidneys, lung, spleen, brain, testes, bladder, liver, heart, and serum of the immunocompetent mice injected with the viruses. Virus was only recovered from the tumor tissue. About 10-fold virus particles were recovered from the tumors of mice injected with wt LIVP, TK-LIVP, wt WR, and TK-WR compared to other groups.

Example 4

Reduction of Human Breast Tumor Implanted in Nude Mice by Recombinant Vaccinia Viruses RVGL7, RVGL9 and RVGL21

RVGL7 and RVGL9

FIG. 1 shows a schematic representation of the recombinant vaccinia viruses used for these experiments. RVGL7 was prepared as described for the preparation of RVGL9. RVGL7 contains nucleic acid encoding EGFP and lacZ, and includes pE/L and p7.5 regulator regions inserted into the TK gene.

Luminescence and Fluorescence Images of Tumors in a Nude Mouse

Human breast GI-101A cancer cells ($5 \times 10^6$ cells/mouse) were subcutaneously implanted into the right thigh of the mice. Thirty days after cell implantation RVGL9, the NotI (F3)-interrupted virus expressing a fusion of *Renilla* luciferase and green fluorescence protein (RVGL9=rVV-RG=rVVruc-gfp) was injected intravenously via tail vein at a dose of $1 \times 10^7$ PFU/mouse. A fluorescence image of GFP and low-light image of luciferase expression were taken nine days after virus injection, i.e. 39 days post cell implantation showing dissemination of the virus.

TABLE 1C

Viral recovery from C57BL/6 mice tissues in melanoma model.

|  | LIVP Wt | RVGL2 TK- | RVGL5 HA- | RVGL9 F3- | RVGL20 TK-, F3- | RVGL21 TK-, F3-, HA- | WR[b] Wt | RVGL23 TK-, WR |
|---|---|---|---|---|---|---|---|---|
| Tumor | $5.4 \times 10^6$ | $3.9 \times 10^6$ | $3.7 \times 10^5$ | $9.5 \times 10^5$ | $2.5 \times 10^5$ | $2.4 \times 10^5$ | $9.9 \times 10^6$ | $2.2 \times 10^6$ |
| Tissues[e] | 0 | 0 | 0 | 0 | 0 | 0 | 0 | 0 |

[a]Mean of viral recovery PFU/g of tissue for 3–5 mice/group.
[b]Mice were sacrificed on day 7 after virus injection.
[c]PFU/20 µl of serum
[d]Mice were sacrificed on day 9 after virus injection.
[e]No virus was recovered in all tested tissue.

Reduction of Human Breast Tumor Implanted into Nude Mice by Vaccinia Viruses RVGL7 or RVGL9

Human breast GI-101A cancer cells ($5 \times 10^6$ cells/mouse) were subcutaneously implanted into the right thigh of the mice. Mice were injected i.v. with RVGL7=rVV-GFT=TK- or RVGL9-rVV-ruc-gfp=NotI (3)-interrupted viruses ($1 \times 10^7$ PFU/mouse in 0.1 ml) and PBS control on day 30 after cell implantation. Images were taken on day 65 after GI-101A cell implantation and 35 days after virus or PBS injection. The results demonstrate drastic reduction of tumor volume in the mice injected with TK- or NotI (F3)-interrupted vaccinia viruses compared with the tumor in the mice injected with PBS.

GFP in Human Breast Tumor after Viral Administration

Human breast GI-101A cancer cells ($5 \times 10^6$ cells/mouse) were subcutaneously implanted into the right thigh of the mice. Mice were injected i.v. with RVGL7=rVV-GFP=TK- or RVGL9=rVV-RG-rVV-ruc-gfp-NotI (F3)-interrupted viruses ($1 \times 10^7$ PFU/mouse in 0.1 ml) on day 30 after cell implantation. The data demonstrate GFP expression in tumor area in the mice injected with TK or NotI (F3)-interrupted vaccinia viruses. No GFP signals were observed in other parts of the mice bodies. The results also showed that expression of GFP can be visualized as early as 48 h after virus injection through the tail vein. On day 16 after virus injection very strong signals of GFP which correspond to a tumor volume of about 1300-1620 $mm^3$ for TK- or NotI (F3)-interrupted virus, respectively were observed. Reduced GFP signals were observed on day 25 (1218-1277 $mm^3$ for TK- or NotI (F3)-interrupted virus, respectively) and 32 (514-887 $mm^3$ for TK- or NotI (F3)-interrupted virus, respectively) due to reduction of tumor volume.

Time course of Breast Tumor Volume over Time

G1-101A breast cancer cells were implanted subcutaneously into the right thigh of 4-5-week old female athymic (nu/nu) mice in the dose of $5 \times 10^6$ cells/mouse. Thirty days after tumor implantation, when the tumor reached about 500 $mm^3$ in volume, a single dose ($1 \times 10^7$ PFU/mouse in 0.1 ml) of RVGL7=rVV-GFP=TK- or RVGL9=rVV-RG=rVV-ruc-gfp=NotI (F3)-interrupted vaccinia viruses or PBS control was injected intravenously (via tail vein). Tumor dimensions were measured with vernier caliper twice a week and volumes were calculated as $(L \times H \times W)/2$, where L, H and W represent the length, width, and height of the tumor, respectively and expressed in $mm^3$. The data demonstrate significant (60-80% on day 65) tumor reduction in the mice injected with TK-, NotI (F3)-interrupted vaccinia viruses. In contrast, tumors grew very rapidly in the mice injected with PBS.

Monitoring of Tumor Regression by Light Extinction.

Subcutaneous GI-101A breast tumor reduction occurred in 100% of immunocompromised mice treated with a single i.v. injection of wt LIVP, single F3-, single TK-, and double F3-, TK-, mutants of LIVP strain. Some degree of toxicity was seen in the mice treated with the above viruses. RVGL21 virus with the triple deletions TK, F3 and HA genes which showed no toxicity in nude mice; hence this virus was used for long-term studies. The difference in antitumor activity and survival between high and low doses of treatment using the triple mutant RVGL21 virus was not significant. GFP expression in tumor area in the mice injected with RVGL21 was monitored. No GFP signals were observed in other parts of the mice bodies. Expression of GFP can be visualized as early as 48 h after virus injection through the tail vein. On day 16 after virus injection we observed very strong signals of GFP, which corresponded to tumor volume of about 1300-1620 $mm^3$ and reduced GFP signals on days 25 (1218-1277 $mm^3$) and 32 (514-887 $mm^3$) due to reduction of tumor volume. Tumor volume reduction also was apparent by visual inspection of the mice.

Example 5

Reduction of Vaccinia Virus Toxicity and Virulence

Reduction of Vaccinia Virus Pathogenicity by Monitoring Mouse Body Weight and Survival The percentage of body weight change in athymic and immunocompetent mice bearing different s.c. tumors after i.v. administration of the viruses was examined. Injection of wt LIVP and wt WR and some mutants at the dose of $10^7$ pfu/mouse via the tail vein led to a progressive vaccinia virus infection within a two week observation period. At one week after challenge, the mice showed typical blister formation on the tail and footpad. Later, weight loss, sometimes accompanied by swelling of the mouth region, in several cases led to death of the mice. In the case of wt WR strain of VV, mice started to die on day 7 after i.v. injection of virus. While mice receiving the recombinant LIVP viruses gained weight or remained the same weight over the same time period.

Body Weight in Glioma Model Nude Mice

Rat glioma C6 cells at the dose of $5 \times 10^5/0.1$ ml/mouse were implanted s.c. into the right thigh of nude mice (5-6 old male mice) on day 0. Vaccinia viruses were injected i.v. (via tail vein) at the dose of $1 \times 10^7$ PFU/0.1 ml/mouse on day 7. Animals were weighed twice a week. Gain/loss of body weight on day 14 post infection was calculated as the percentage: body weight–tumor weight on day of virus injection (g)/body weight-tumor weight on day 14 (g) $\times$ 100%. Injection of VGL (wild type vaccinia virus, strain LIVP) and RVGL5 (HindIII-N-interrupted) causes toxicity in nude mice: mice continue to lose the weight. Recombinant vaccinia viruses RVGL5 (HA-interrupted), RVGL7 (TK-interrupted), RVGL8 (NotI(F3)-interrupted), RVGL19 (double, TK- and NotI (F3)-interrupted) were less toxic in nude mice: after losing some body weight, 10 days post-infection, mice started to gain the body weight.

Nude mice with glioma that were injected with wild type WR strain of VV lost 31.9% of body weight on day 7 after virus injection. Mice injected with TK-virus of WR strain lost 22.4% of body weight on day 14 after virus injection compared to 1.5% in the group of mice injected with TK-virus of LIVP strain of VV. All mice injected with wild type LIVP strain survived for at least 14 days (the duration of the experiment). Mice without tumor injected with VGL (wt VV, strain LIVP) lost 11.23% of body weight. Mice bearing tumor injected with VGL (wt VV) or with RVGL1 (HindIII-N-interrupted) lost 15.79% and 10.18% of body weight, respectively. Mice in the wt LIVP group lost 15.8% of body weight versus 9.4% in the PBS injected group. Tumor-bearing mice injected with RVGL2 (TK-), RVGL5 (HA-), RVGL7 (TK-), RVGL8 (F3-), RVGL9 (F3-), RVGL20 (TK-, F3-), RVGL21 (TK-, F3-, HA-) on day 14 after virus injection lost only 1.5%, 0.4%, 2.1%, 5.0%, 7.3%, 2.4%, and 3.2% of body weight, respectively. Tumor-bearing mice injected with virus carrying double gene interruption, RVGL19 (TK- and F3-) demonstrated 0.73% gain of body weight compared to the body weight on day 0. Based on the results of body weight, a single interruption of HA, TK, F3 (NotI site) and double interruption of TK, F3 (NotI site) genes in vaccinia virus genome reduces virulence and toxicity of the vaccinia virus strain LIVP.

Injection of wt VV strain WR, however, was extremely toxic to nude mice, which died on day 7 after virus injection. Wild type and mutant VVs of strain LIVP were less toxic in nude mice. Although nude mice injected with various LIVP strains lost some body weight, after day 10-post infection mice started to gain the body weight.

Body Weight in Breast Tumor Model Athymic Mice

The body weight change of athymic mice with s.c. GI-101A human breast tumor after i.v. injection of vaccinia viruses was monitored. Mice injected with wt WR strain lost 25.6% of body weight and died due to virus toxicity. Although mice injected with wt LIVP virus survived for longer time, mice lost 26.4% of body weight. Mice injected with TK-WR strain lost 17.8% of body weight, while mice injected with TK-LIVP virus gained 1.9% of body weight. All mice injected with other mutants of LIVP strain were stable; no virus related toxicity was observed in these mice.

Body Weight in Melanoma Model Immunocompetent Mice

The toxicity of the vaccinia viruses in immunocompetent C57BL/6 mice bearing mouse B16-F10 melanoma on their foot pad was studied. Although mice in all groups survived during the experiment, wt WR strain was more toxic in immunocompetent mice compared to wt LIVP and recombinant strains. Mice injected with wt WR strain lost about 11.4% of body weight on day 10 after i.v. injection of virus, while mice injected with wt LIVP strain and its double (RVGL20) and triple (RVGL21) mutants lost only 2.2%, 1.3%, and 0.6% of body weight, respectively, versus to 7.1% of body weight lost in PBS injected mice. Mice administered i.v. with RVGL2 (TK-), RVGL5 (HA-), RVGL9 (F3-), and RVGL23 (TK-WR strain) continued to gain weight over this same period.

Long-Term Survival after Viral Infection for Breast Tumor-Bearing Mice

To examine the effect of different mutations on long-term survival, mice bearing s.c. GI-101A human breast tumor received doses of $10^7$ virus i.v., and were observed for survival after viral infection. The results showed that there are differences in survival depending upon the virus injected. Injection of the nude mice bearing s.c. breast tumor with wt WR strain (i.v., $1 \times 10^7$/mouse) resulted in 100% mortality: four mice of five died on day 9 and one mouse died on day 11 after virus injection. Mice injected with strain LIVP survived for 35 days. Mice injected with a single mutated virus RVGL9 (F3-) developed the toxicity and 25% of mice died on day 34 after virus injection, however the deletion of F3 gene in LIVP strain prolonged the survival of mice up to 57 days. Mice injected with double mutant virus RVGL20 (F3-, TK-) began to die on day 34 after virus injection, but survived longer than F3-injected mice. The RVGL20 virus injected mice reached 50% survival point on day 65 and showed significantly longer survival time up to 116 days. The single mutant TK-virus of LIVP virus was less pathogenic than the single mutant F3- or double mutant F3-, TK-viruses; all mice were alive on day 80 after injection with TK-virus and 14.3% of the mice survived 130 days. All mice injected with the triple mutant TK-, F3-, and HA-virus (RVGL21) survived 130 days (duration of the experiment) and continued to live without any signs of virus toxicity compared to other groups of mice.

Splenomegaly in Various Mice
Immunocompetent C57BL/6 Mice

Several groups of the animals demonstrated enlargement of the spleen; therefore the relative spleen weight (RSW) was calculated. The results are shown in Table 2 as follows:

TABLE 2

Relative spleen weight (RSW) in mice with or without tumors.

| Groups | Glioma model nu/nu mice | Breast cancer model nu/nu mice | Melanoma model C57BL/6 mice |
|---|---|---|---|
| No tumor, PBS | 43.6 ± 4.1$^a$ | 50.5 ± 11.2$^d$ | 30.1 ± 2.8$^g$ |
| No tumor, LIVP | 67.2 ± 11.9 | 48.0 ± 13.1 | 68.1 ± 9.4 |
| Tumor, PBS | 92.4 ± 7.4$^b$ | 84.1 ± 14.6$^e$ | 106.0 ± 46.1$^h$ |
| LIVP | 98.2 ± 28.2$^c$ | 108.4 ± 39.4$^f$ | 148.4 ± 44.8$^i$ |
| RVGL2 | 96.0 ± 34.9 | 112.7 ± 15.6 | 51.9 ± 6.6 |
| RVGL5 | 143.8 ± 20.5 | 169.6 ± 31.7 | 61.6 ± 2.9 |
| RVGL9 | 73.9 ± 10.5 | 151.8 ± 27.9 | 63.3 ± 34.9 |
| RVGL20 | 84.9 ± 6.6 | 159.9 ± 22.7 | 106.7 ± 36.0 |
| RVGL21 | 114.4 ± 12.5 | 117.7 ± 15.3 | 63.0 ± 24.6 |
| WR | 37.3 ± 3.5 | 57.9 ± 10.9 | 70.5 ± 1.8 |
| RVGL23 | 46.9 ± 15.7 | 73.1 ± 19.3 | 97.0 ± 43.9 |

Mean ± SD for n = 4-8 mice/group.
RSW = weight of spleen (g) × $10^4$/(animal body weight (g) − tumor weight (g)).
$^a$p ≤ 02.02 vs. all groups, except no tumor LIVP, WR, RVGL23
$^b$p ≤ 0.039 vs. no tumor PBS, no tumor LIVP, RVGL5, WR, RVGL23
$^c$p ≤ 0.046 vs. all groups, except PBS, RVGL2, RVGL20, RVGL21
$^d$p ≤ 0.006 vs. all groups except no tumor LIVP, PBS, WR, RVGL23
$^e$p ≤ 0.048 vs. all groups, except no tumor PBS, LIVP, RVGL2, WR, RVGL23
$^f$p ≤ 0.045 vs. all groups, except PBS, RVGL2, RVGL21
$^g$p ≤ 0.035 vs. PBS, LIVP, RVGL20, WR, RVGL23
$^h$p ≤ 0.049 vs. all other groups, except no tumor LIVP, RVGL20, WR, RVGL23
$^i$p ≤ 0.049 vs. all other groups.

As shown in the Table 2 above, some degree of splenomegaly was observed in mice. For immunocompetent C57BL/6 mice, a statistically significant difference (p<0.035) was found in tumorous mice injected with PBS, LIVP, RVGL20, WR and RVG123 compared to non-tumorous mice. In mice injected with wt VV strain LIVP spleen was enlarged greatly (p<0.049) versus all other groups. In contrast, the smallest spleens were found in the mice without tumor.

Nude Mice with a Glioma Tumor

In nude mice with or without s.c. glioma tumor, mice injected with wt WR or TK- of WR virus had the lowest RSW 37.3 or 46.9, respectively, which was similar to the RSW from the mice without tumor and injected with PBS (43.6). The largest RSW 143.8 and 114.4 was observed in RVGL5 (HA-) and RVGL21 (TK-, F3-, HA-) groups, respectively. No statistically significant difference was found among the groups of mice injected with wt LIVP, RVGL2, RVGL9, RVGL20 versus the PBS injected group.

Nude Mice with Breast Tumor

The results of RSW in the immunocompromised mice bearing s.c human breast tumor indicate that all mice injected with wt LIVP and its mutants have an enlarged spleen compared to the mice injected with wt WR or TK-WR viruses (p<0.045). The largest spleen was found in the mice injected with single HA-, single F3-, double F3-, TK-mutants of LIVP strain.

Other Results Using RVGL21 for Injection

Two mice, #437 and #458, survived more then 190 days after RVGL21 injection ($10^7$ and $4 \times 10^5$, respectively, i.v.) without any signs of diseases or virus related toxicities.

On day 30 after GI-101A cell implantation (tumor volume=594.9 mm$^3$), $10^7$ of RVGL21 was injected i.v. into mouse #437. On day 101 after virus injection (s.c. tumor size=220.4 mm³), metastasis (hard tissue) in chest area under the skin was observed. The size of the tumor was 1223.6 mm³, which disappeared by day 148. The s.c. tumor did not disappear, it started to grow back, but the mouse remained metastasis-free.

Mouse #458 had a first s.c. tumor (GI-101A) on the right hind quarter. When the first tumor started to shrink (day 29 after RVGL21 virus injection, tumor size=1924.3 mm³), a second syngeneic tumor was implanted s.c. on the left hind quarter. The second tumor grew slowly, reached the size of 1205.7 mm³ and started to shrink. The mouse was free of the first tumor on day 127 post virus injection; the size of the second tumor was 439.6 mm³. The tumor continued to shrink and the cells died. The body gradually absorbed remaining tumor tissues that were contributed by the host (such as the tumor vascular skeleton that was coming from the host). Since these remains are not considered foreign, the immune system doesn't destroy them. The tumor cells, on the other hand, were long gone and cleared by the immune system and the virus. Reduction of the second syngeneic tumor demonstrates that this mouse developed antibodies against the tumor cells. The antibodies resulted in the reduction of the second syngeneic tumor.

Example 6

Use of a Microorganism or Cell to Induce Autoimmunization of an Organism Against a Tumor This example shows that the method provided herein and in priority application EP 03 018 478.2 relating to "The production of a polypeptide, RNA or other compound in a tumor tissue" also can be used for the production of antibodies against the tumor tissue. These antibodies provide for autoimmunization of the organism bearing the tumor. Furthermore, these antibodies can be isolated and used for the treatment of tumors in other organisms.

Methods and uses of microorganisms, including cells, which can contain DNA encoding a desired polypeptide or RNA, to induce autoimmunization of an organism against a tumor are provided. Also provided are methods for the production of antibodies against a tumor by: (a) injecting a microorganism, such as a virus or cell, optionally containing a DNA sequence encoding a desired polypeptide or RNA, into an organism bearing a tumor and (b) isolating antibodies against the tumor.

This Example further demonstrates that administration of microorganisms, such as the triple mutant vaccinia virus strain provided herein, which accumulate in tumors, causing them to release tumor antigens for a sufficient time to permit production of antibodies by the host. This is exemplified by showing a reduction and elimination of xenogeneic GI-101A solid breast carcinoma tumors and their metastases in nu-/nu-mice (T cell deficient mice).

Step#1: Female nu-/nu-mice of 5 weeks age were chosen, and the GI-101A cells grown in RPMI1640 medium, supplemented with estrogen and progesterone. The confluence was reached, cells were harvested, washed with phosphate buffered saline. Cells (5×10⁶ cells per mouse) were then injected subcutaneously into mice. The tumor growth was carefully monitored every two days.

Step#2: At two stages of tumor growth (at tumor size of 400-600 mm³, and at tumor size of ~1700 mm³), purified vaccinia viral particles (RVGL12) were delivered to each tumorous mice by intravenous injection through tail vein. The colony purified virus was amplified in CV-1 cell line and the intracellular viral particles were purified by centrifugation in sucrose gradient. Two concentrations of virus (10⁶ pfu/100 μl and 10⁷ pfu/100 μl resuspended in PBS solution) were injected. The viral replication was monitored externally by visualization of virus-mediated green fluorescence protein expression. The tumor development was monitored by tumor volume determination with a digital caliper.

Vaccinia viruses RVGL12+GCV(gancyclovir), and RVGL12 (RVGL12 is the same as RVGL7, except that the nucleic acid encoding gfp is replaced by herpes simplex virus thymidine kinase (HSV TK; see, SEQ ID NOS: 35 and 36) were injected 67 days after GI-101A cellular implantation. A second administration referred to as RVGL12a, was injected 30 days after cellular implantation.

Step#3: After viral administration, it was determined that first the tumors continued to grow to a size of ~900 mm³ (from 400-600 mm³ at the time of viral injection), and to a size of ~2400 mm³ (from 1700 mm³). Then the growth rate leveled off for approximately 6-8 days.

Step#4: Approximately 14 days after viral injection, the tumor volume started to decline rapidly. Forty days after viral application, all the treated animals showed more than 60% tumor regression. Sixty-five days after viral treatment and many of the animals had complete regression of tumors.

Step#5: Some of the animals were completely tumor-free for several weeks and their body weight returned to normal. RVGL-12+GCV treatment resulted in 86.3% reduction of tumor size (Day 52 after viral injection) from their peak volumes on Day 13, RVGL-12 treatment resulted in 84.5% reduction of tumor size (Day 52) from their peak volumes (Day 13). RVGL-12a treatment resulted in 98.3% reduction of tumor size (Day 89) from their peak volumes (Day 12). After PBS+GCV control treatment, the average volume of tumors were increased by 91.8% in 38 days Step#6: The level of immune activation was determined. Sera were obtained from the animals with regressing tumors and the immune titer determined against a foreign protein (e.g. green fluorescent protein), vaccinia viral proteins, and GI-101A cancer cell proteins were determined. The following antisera obtained from the following sources were used to analyze the following listed samples.

Samples:

1). Mouse cell lysate (control);

2). Purified and denatured vaccinia viral particles;

3). GI-101A tumor cell lysate;

4). Purified green fluorescent protein;

5). Purified luciferase protein;

6). Purified beta-galactosidase protein.

Antisera:

a). Antiserum from nontumorous mouse;

b). Antiserum from GI-101A tumorous mouse;

c). Antiserum from GI-101A tumorous mouse 14 days after vaccinia i.v. injection;

d). Antiserum from GI-101A tumorous mouse 65 days after vaccinia i.v. injection;

e). Antiserum from tumor-free mouse (after elimination of GI-101A tumor) 80 days after vaccinia i.v. injection.

The results showed that there was enormous tumor-specific vaccinia virus replication in the tumors, which led to tumor protein antigen and viral protein production in the tumors. In addition, the vaccinia virus did lyse the infected tumor cells thereby releasing tumor-cell-specific antigens. The continuous leakage of these antigens into the body led to a very high level of antibody titer (in approximately 7-14 days) against foreign cell proteins (tumor proteins), viral proteins, and the virus encoded engineered proteins in the mouse body. The newly synthesized antitumor antibodies and the enhanced macrophages, neutrophils counts were continuously delivered via the vasculature into the tumor and thereby providing for the recruitment of an activated immune system in the inside of the tumor. The active immune system then eliminated the tumor including the viral particles. This interconnected release of foreign antigens boosted antibody production and continuous return of the antibodies against the tumor-contained proteins function as an autoimmunization vaccination system, initiated by vaccinia viral replication, followed by cell lyses, protein leakage and enhanced antibody production.

samples were collected. Various organs and tumors also were taken from animals for virus titer and β-galactosidase analysis.

The β-galactosidase analysis was performed using the Galacto-Light Plus system (Applied Biosystems), a chemiluminescent reporter gene assay system for the detection of β-galactosidase, according to the manufacturer's instructions.

β-galactosidase Expression Measurements

In non-tumorous mice as well as in tumorous mice injected with wild type vaccinia virus (without reporter genes and without β-galactosidase gene) no β-galactosidase expression was detected in organs, blood and tumor samples. By contrast, in the tumors of mice infected with β-galactosidase expressing virus, high levels of β-galactosidase was expressed. β-galactosidase also was detected in blood samples as shown in Table 3, but no virus was recovered from blood samples.

TABLE 3

Production of β galactosidase by vaccinia virus in tumor and blood from tumor bearing mice (day 14 after virus injection)

| Group | Virus Injected | β-gal in tumor μg/mg of total protein | β-gal in serum μg/ml of total protein | Est. total β-gal/tumor (μg) | Est. total β-gal/5 ml blood (μg) |
|---|---|---|---|---|---|
| 3 | RVGL1 | 1.59 ± 0.41 | $1.38 \times 10^{-2} \pm 1.09 \times 10^{-2}$ | 489.84 | 4.00 |
| 4 | RVGL5 | 1.51 ± 0.37 | $1.16 \times 10^{-2} \pm 1.08 \times 10^{-2}$ | 330.21 | 3.62 |
| 5 | RVGL7 | 1.35 ± 0.59 | $0.95 \times 10^{-2} \pm 1.47 \times 10^{-2}$ | 616.60 | 1.83 |
| 6 | RVGL8 | 1.81 ± 0.42 | $0.86 \times 10^{-2} \pm 0.33 \times 10^{-2}$ | 962.36 | 2.38 |
| 7 | RVGL19 | 1.30 ± 0.44 | $0.26 \times 10^{-2} \pm 0.16 \times 10^{-2}$ | 463.75 | 0.60 |

Example 7

Production of β-Galactosidase and Anti β-Galactosidase Via Vaccinia Virus Delivered lacZ in Tumor Bearing Mice Thirty five athymic nu/nu mice (5 weeks old, 25 g, male) were used to demonstrate the biodistribution and tumor targeting of vaccinia virus (strain LIVP) with different deletions in the genome. Mice were divided into 7 groups with 5 in each group as presented in Table 1

| Group | No. mice | Tumor implanted | Virus Injected | Insertion locus |
|---|---|---|---|---|
| 1 | 5 | None | VGL | wtLIVP |
| 2 | 5 | C6, s.c. 5 × 10⁵ cells | VGL | wtLIVP |
| 3 | 5 | C6, s.c. 5 × 10⁵ cells | RVGL1 | N-luc, lacZ |
| 4 | 5 | C6, s.c. 5 × 10⁵ cells | RVGL5 | HA-lacZ |
| 5 | 5 | C6, s.c. 5 × 10⁵ cells | RVGL7 | TK-egfp, lacZ |
| 6 | 5 | C6, s.c. 5 × 10⁵ cells | RVGL8 | NotI-lacZ |
| 7 | 5 | C6, s.c. 5 × 10⁵ cells | RVGL19 | TK-rTrf, lacZ, NotI-RG |

C6 gliomas were subcutaneously developed in Groups 2 to 7. Five days after tumor cell implantation ($5 \times 10^5$ cells/mouse), each animal was treated with 0.1 ml of virus at a multiplicity of infection (MOI) of $1 \times 10^7$ via tail vein injection. Two weeks after virus injection, all mice were sacrificed and blood Anti-β-Galactosidase Antibody Production To determine whether the amount of β-galactosidase presented in mouse blood was sufficient to elicit antibody production, sera taken from two mice (mouse #116 from Group 5, and #119 from Group 6) were collected and tested for primary antibodies against β-galactosidase in Western analysis. β-galactosidase from E. coli (Roche, 567 779) was used as the antigen standard, and the mouse monoclonal anti β-galactosidase from E. coli (Sigma, G6282) was used as the antibody positive control. As additional sources of β-galactosidase, total protein was obtained from CV-1 cells 24 hours after infection with RVGL7 at MOI of 1 pfu/cell, and the tumor protein sample from mouse designated #143 (treated with RVGL7) was obtained.

The protein samples were prepared in triplicate, each set including a galactosidase antigen control, a cell lysate from RVGL7 infected CV-1 cells, and tumor lysate from mouse #143. All protein samples were separated by electrophoresis using a 10% polyacrylamide gel, and transferred to NitroBind nitrocellulose membrane (MSI) using a BioRad semidry blotting system. Immunoblotting was performed with either 1:3000 mouse monoclonal anti β-galactosidase, or 1:3000 mouse serum taken from either mouse #116 or #119, and 1:3000 Goat AntiMouse IgG-HRP (BioRad). An Amplified Opti-4CN Detection Kit (BioRad) was used for detection.

The results showed that sera taken from mouse #116 and #119 exhibited similar levels of antibody when compared to a commercial mouse anti-p-galactosidase standard, and demonstrated that the tumor bearing mice #116 and #119 produced antibodies against β-galactosidase.

Example 8

Mammalian Cells for Tumor Therapy

As shown herein, certain bacteria, viruses, and mammalian cells (BVMC), when administered systemically, again enter and selectively replicate in tumors Hence, systemically injected mammalian cells and certain bacterial (anaerobic bacteria, such as *Salmonella, Clostridium* sp., *Vibrio, E. Coli*) cells gain entry into solid tumors and replicate in tumor-bearing organisms. Genetically-labeled cells can be used for tumor detection and therapy. In addition to gene expression in tumors through BVMC targeting, tumor-specific gene expression can be achieved by linking transgenes to tissue/tumor-specific promoters. To obtain tumor specific gene expression, a variety of systemic targeting schemes can be employed. These strategies include the use of tissue/tumor-specific promoters that allow the activation of gene expression only in specific organs, such as prostate-specific promoter-directed viral gene expression; the use of extracellular matrix (i.e. collagen)-targeted viral vectors; and the use of antibody-directed viral vectors. Conditionally-replicating viruses have also been explored as tumor-specific delivery vehicles for marker genes or therapeutic genes, such as oncolytic adenovirus vector particles, replication-selective HSV, vaccinia viruses and other such viruses.

When light-emitting protein encoded BVMC are injected systemically into rodents, tumor-specific marker gene expression is achieved and is detected in real time based on light emission. Consequently, the locations of primary tumors and previously unknown metastases in animals are revealed in vivo. Hence diagnosis can be coupled to therapy and to monitoring of therapy. The impaired lymphatic system in tumors may be responsible for the lack of clearance of bacteria from tumors by the host immunosurveillance after escaping the vascular system.

Example 9

Tumor Development is Inhibited Following *S. pyogenes* Administration

This example and following examples demonstrate the use of bacterial cells to colonize tumors, use of reporter in the cells to quantitate colonization; use of the colonized attenuated bacterial cells for tumor inhibition. Co-administration or sequential administration of bacteria and viruses. Administration of virus before bacteria increase tumor colonization by the bacteria. Administer bacteria that expresses an enzyme that will activate a prodrug, thereby targeting colonized cells.

Bacterial Strains

*Streptococcus pyogenes* M-type 1 T-type 1 (ATCC catalog no. 700294) was transformed with pDC123-luxF plasmid) that contains the bacterial luciferase expression cassette (Lamberton G R, Pereau M J, Illes K, Kelly I L, Chrisler J, Childers B J, Oberg K C, Szalay A A. 2002. *Construction and characterization of a bioluminescent Streptococcus pyogenes*. Proceedings of the 12th International Symposium on Bioluminescence and Chemiluminescence, Case J F, Herring P J, Robison B H, Haddock S H D, Kricka L J, Stanley PE (eds). Chichester: Wiley, pp 85-88. Luciferase can be detected in the presence of exogenous decanal.

Transformed *S. pyogenes* were grown overnight in BH1 media in the presence of 20 μg/ml of chloramphenicol at 37° C. After overnight growth, the bacteria were counted at $OD_{600}$ and bacteria were resuspended in BH1 media at the indicated density for injection.

Tumor Development and Bacterial Injection

Twenty 5-week old mice were injected subcutaneously in the right lateral thigh. Each mouse was injected with $5\times10^5$ C6 glioma cells transformed with pLEIN-derived retrovirus (Clontech; see also WO 03/14380). The subcutaneous tumors were developed for 7 days after implantation before bacterial injection.

For bacterial injection, the tumor-bearing mice were anesthetized with isofluorane. The suspensions were injected intravenously with a 1-cc insulin syringe equipped with a 29½-gauge needle through a surgically exposed femoral vein. After the injections, the incisions were sutured.

Tumor growth was monitored twice a week following bacterial injection using a digital caliper. In addition, fluorescence imaging and photographic images of the animals were taken at the end time points. The presence of luminescent bacteria was analyzed by intravenously injecting the animals with 30 μl of decanal. Analysis of whole animals for bacterial luciferase activity, followed methods similar to Yu et al. (2004) *Nature Biotechnology* 22(3): 313-20. Briefly, anesthetized animals were placed inside the dark box for photon counting (ARGUS 100 low light Imager, Hamamatsu). Photon collection was for 1 minute from ventral and dorsal sides of the animal and the images were recorded with Image Pro Plus 3.1 software (Media Cybernetics) and/or Lighttools® macroimaging system. A light image also was recorded. The luminescent images were superimposed on the light image to localize the luminescent activity on the animal. Total intensity of photon emission in localized regions, e.g. in the tumor region, also was recorded. *S. pyogenes* was isolated from removed tumors and ground tissue was plated on LB-chloramphenicol (20 μg/ml) plates. Luminescent bacteria were counted in the presence of decanal vapor.

Results

Four groups of mice were tested. Each group contained five mice.

| Group | S. Pyogenes |
| --- | --- |
| 1 | None |
| 2 | $1 \times 10^6$ |
| 3 | $1 \times 10^7$ |
| 4 | $5 \times 10^7$ |

Tumor volume was measured after 7 days of tumor development and the injection of *S. pyogenes*, through 21 days post-tumor development.

The control group of mice with no *S. pyogenes* had continuous and accelerating tumor growth over the 2-week period. The mice injected with *S. pyogenes* had slower tumor growth. Groups 3 and 4 had the slowest tumor growth rates. Both groups maintained a slower linear rate throughout the monitoring period, whereas the control group, not injected with bacteria, exhibited tumor growth that accelerated at later time periods.

At all time points following bacterial injection, tumor volumes were smaller in Groups 3 and 4 mice than in the control mice (Group 1). At day 21, the average tumor volume of the control group was approximately 2.5-3 fold greater than the average tumor volumes in Groups 3 and 4. Group 2, injected with the lowest titer of bacteria, also had a reduced tumor volume from the control group at the later time points, although the tumor volume was larger than Groups 3 and 4.

Bacterial colonization and tumor inhibition also is assayed in a fibrosarcoma model. HT1080 fibrosarcoma cells transformed with the pLEIN retrovirus are injected subcutaneously into the right lateral thigh of five week old nude male mice $5 \times 10^5$ cells/mouse). *S. pyogenes* transformed with pDC123-luxF is injected into the femoral vein of the animals after 8 or 14 days of tumor growth (5 animals on each day). A group of 5 animals are not injected as serve as a control group. Tumor growth and luciferase activity is monitored at subsequent time points. *S. pyogenes* is isolated from tumors and cultured on BH1+chloramphenicol (20 µg/ml) plates. Luminescent bacterial colonies are counted in the presence of decanal vapor.

Example 10

Vibrio Cholera Localization to Tumors

Plasmids and Bacterial Strains

Attenuated *Vibrio Cholerae*, strain Bengal 2 serotype 0139, M1010 DattRS1, was transformed with pLITE201 which contains the luxCDABE cassette (Voisey et al. (1998) *Biotechniques* 24:56-58). The transformed strain is a light emitting strain due to the expression of the luciferase genes.

Tumor Development and Bacterial Injection

Groups of nude mice (n>20) were implanted with C6 glioma tumors (500 mm$^3$) as described in the Examples herein. $1 \times 10^8$ transformed bacteria (*V. Cholerae*) were suspended in 100 µl of phosphate buffered saline (PBS). The bacterial suspension was injected into the right hind leg of each mouse. The animals were then monitored after injection under a low light imager as described in Example 3.

In a separate experiment, for comparison, groups of nude mice (n>20) were implanted with C6 glioma tumors (500 mm$^3$) as described in the Examples herein. These mice were injected with $1 \times 10^8$ pfu/mouse of rVV-RUC-GFP (RVGL9) virus (see Example 1).

Results

Titer and Luciferase Activity

Mice from each of the two injected groups were sacrificed at time points after injection. Tumors were excised and homogenized. Bacterial and viral titers and luciferase activities were measured as described in the Examples herein.

Both bacterial and viral titer increased following injection. The increase in bacterial growth over time was proportional to luciferase levels in the tumors. A log-log plot of bacterial titer versus luciferase activity in tumors in the mice injected with *V. cholera* demonstrated a linear relationship between bacterial titer and luciferase activity. The groups of mice injected with rVV-RUC-GFP virus, also demonstrated a linear relationship between virus titer and luciferase activity.

| | Time after *V. Cholera*/pLITE injection | | | |
|---|---|---|---|---|
| | 4 hrs | 8 hrs | 16 hrs | 32 hrs |
| Bacterial Titer (cfu/tumor) | $3.79 \times 10^4 \pm 2.93$ | $3.14 \times 10^6 \pm 2.45$ | $1.08 \times 10^8 \pm 1.3$ | $5.97 \times 10^8 \pm 4.26$ |
| | Time after rVV-ruc-gfp virus injection | | | |
| | 36 hrs | Day 3 | Day 5 | Day 7 |
| Viral Titer (pfu/tumor) | $3.26 \times 10^6 \pm 3.86$ | $7.22 \times 10^7 \pm 3.67$ | $1.17 \times 10^8 \pm 0.76$ | $3.77 \times 10^8 \pm 1.95$ |

The experiments demonstrated a linear relationship between titer and luciferase activity. Thus, luciferase activity of the injected bacteria and/or virus can be used a correlative measurement of titer.

Localization

Localization of *V. cholera* was performed as detailed in the Examples herein for virus. Briefly, organs and blood samples were isolated from animals euthanized with $CO_2$ gas. The organs were ground and plated on agar plates with chloramphenicol drug selection for analysis of bacterial titer.

Bacterial titer was assayed in tumor, liver, testes, spleen, kidney, lung, heart, bladder and brain of the injected mice. Samples were taken from mice sacrificed at zero, and subsequent times up to 150 hours following *V. cholera* injection.

At the time point immediately following injection (t=0), *V. cholera* was present in all samples, with the highest levels in the liver and spleen. By 50 hours post-injection, titer of *V. cholera* in all tissues had reduced with the exception of tumor tissue. In contrast, *V. cholera* titer had increased about 4 orders of magnitude as compared to time zero. This level increased slightly and then stayed constant throughout the remainder of the experiment. By 150 hours post-infection, titer in all samples except tumor had decreased. For example, the titer in liver had decreased by approximately 5 orders of magnitude from the time zero point. At the 150 hour point, the *V. cholera* titer in the tumor tissue was about 6 orders of magnitude greater than any other tissue sample.

Example 11

Co-Administration and Sequential Administration of Bacteria and Virus

*V. Cholera*/pLITE (see Example 10) and vaccinia virus RVGL2 (see Example 1) were administered together or sequentially. Groups of nude mice with C6 glioma tumors were injected with bacteria and/or virus as shown in the Table below. Three male mice were injected per group. Bacteria and/or virus were injected on day 11 and day 16 following tumor implantation. Tumor growth, luciferase and GFP activity were monitored as described in the Examples herein.

| Group | Day 11 injection | Day 16 injection |
|---|---|---|
| 1 | $1 \times 10^7$ VV-TK$^-$-gfp-lacZ | $1 \times 10^7$ *V. Cholera*/pLITE |
| 2 | None | $1 \times 10^7$ *V. Cholera*/pLITE |
| 3 | $1 \times 10^7$ *V. Cholera*/pLITE | $1 \times 10^7$ VV-TK$^-$-gfp-lacZ |
| 4 | None | $1 \times 10^7$ VV-TK$^-$-gfp-lacZ |
| 5 | None | $1 \times 10^7$ VV-TK$^-$-gfp-lacZ and $1 \times 10^7$ *V. Cholera*/pLITE |

Results

On day 21 (21 days post tumor implantation) animals were sacrificed. Tumors were excised from each animal and ground. Viral titer was assayed on Groups 3, 4 and 5. Bacterial titer was assessed on Groups 1, 2 and 5. Titers (colony forming units and plaque forming units) were performed as previously described in the Examples.

A comparison of the bacterial titer in tumors Groups 1, 2 and 5 demonstrated that bacterial titer was highest in Group 1 that had been injected first with vaccinia virus at day 11, and followed by *V. cholera* injection on day 16. Co-injection of bacteria and virus at day 16 (Group 5) gave an intermediate bacterial titer. Group 2, injected only with *V. cholera* at day 16, had a lower bacterial titer in the tumor tissue than either of groups 1 or 5. Thus, tumors were more susceptible to bacterial colonization when first colonized by VV-TK$^-$-gfp-lacZ virus.

A comparison of the viral titer in Groups 3, 4 and 5 demonstrated that Group 4, with only virus injection at day 16, had the highest viral titer followed by Groups 5 and 3. The viral titer of Group 5 was slightly higher than Group 3, but not apparently significantly different. One mouse in Group 4 had a viral titer that was an extreme outlier in comparison to the viral titer of the other 2 mice in Group 4. When the numbers were reassessed without this mouse, the general trend remained the same. The average viral titer in Group 4 was much closer to the viral titers of Groups 3 and 5. The data from the three groups in this analysis was not significantly different. Thus, pre-administration of bacteria followed by administration of virus did not significantly change the viral colonization of the tumor as compared with viral administration alone.

Example 12

Tumor Inhibition by Administering PNP-expressing bacteria and prodrug Plasmids pSOD-DeoD contains the bacterial purine nucleoside phosphorylase gene (PNP) (Sorcher et al. (1994) Gene Ther. 1(4):223-238), under the control of the constitutive SOD (superoxide dismutase) promoter. Plasmid pSOD-DeoD-lux, contains the luxCDABE expression cassette (Voisey et al. (1998) *Biotechniques* 24:56-58) inserted into pSOD-DeoD.

PNP converts the non-toxic prodrug 6-methylpurine deoxyribose (6-MPDR) to 6-methyl purine which inhibits DNA replication, transcription and translation (Sorcher et al. (1994) *Gene Ther.* 1(4):223-238).

Tumor Growth Inhibition

Nude mice were injected with pLEIN retrovirus transformed C6 glioma cells. The pLEIN retrovirus expresses EGFP under the control of the viral promoter LTR (Clontech; see also WO 03/14380). *E. coli* DH5a expressing the bacterial purine nucleoside phosphorylase gene was injected at day 8 following tumor implantation with or without prodrug (6-methylpurine deoxyribose (6-MPDR)). Tumor volume was monitored at subsequent time points (as performed in previous examples).

| Group | Administered |
|-------|--------------|
| 1 | *E. coli*/PNP + prodrug |
| 2 | *E. coli*/PNP |
| 3 | *E. coli* control + prodrug |

Groups 2 and 3 exhibited equal tumor growth over time points from 8 to 21 days post tumor implantation. Group 1, which received both the *E. coli* expressing PNP and the prodrug exhibited ~20% reduction in tumor size as compared to the control Groups 2 and 3 at the end time points.

To further test bacterial colonization and prodrug effects on tumor growth, a human breast cancer model, GI-101A adenocarcinoma in nude mice, was chosen. GI-101A was derived from GI-101. GI-101 originated from a local first recurrence of an infiltrating duct adenocarcinoma (stage IIIa, T3N2MX) in a 57 year old female patient by researchers at Rumbaugh-Goodwin Institute for Cancer Research. In the subcutaneous xenograft nude mice model, the tumor consistently metastasizes to the lungs. The GI-101A is a slower growing tumor model as compared to the C6 glioma tumor model.

Fifteen 4 week old female nude mice are each injected subcutaneously in the right lateral thigh with GI-101A cells. Thirty days after tumor development, bacteria are injected. *Escherichia coli* DH5a is transformed with pSOD-DeoD or pSOD-DeoD-lux. The bacteria are grown overnight in LB media in the presence of 20 µg/ml of chloramphenicol at 37° C. After overnight growth, the bacteria are counted at $OD_{600}$ and bacteria resuspended in BH1 media at the indicated density. The suspensions are injected intravenously with a 1-cc insulin syringe equipped with a 29½-gauge needle into the animal through a surgically exposed vein or as otherwise indicated. After the injections, the incisions are sutured.

Prodrug is administered to groups of mice every four days following injection of bacteria. Tumor growth is monitored twice per week using a digital caliper. Luciferase imaging is performed as described in the Examples herein. At the end point, the animal are sacrificed and organs are assayed as described in Example 9. Histological analyses are performed to determine the degree of tumor necrosis due to bacterial colonization and/or drug treatment.

Since modifications will be apparent to those of skill in this art, it is intended that this invention be limited only by the scope of the appended claims.

The invention claimed is:

1. A combination, comprising:
   a recombinant vaccinia virus, wherein:
      the recombinant vaccinia virus contains a modified thymidine kinase (TK) gene, a modified hemagglutinin (HA) gene, and an insertion, deletion or replacement in the locus or gene designated F3, whereby the vaccinia virus is TK-, HA- and F3-;
      the vaccinia virus is a Lister strain; and
      each gene or locus is inactivated; and
   an anti-cancer therapeutic compound, wherein:
      the virus and anti-cancer therapeutic compound are formulated separately or are formulated together for administration of each for anti-cancer therapy.

2. The combination of claim 1, wherein each of the TK gene, HA gene and F3 gene is inactivated by insertion or deletion of nucleic acid.

3. The combination of claim 1, wherein heterologous nucleic acid is inserted into the TK and HA genes to inactivate them, and heterologous nucleic acid is inserted into the F3 locus.

4. The combination of claim 1, wherein the vaccinia virus is an LIVP strain.

5. The combination of claim 3, wherein the vaccinia virus is a LIVP strain.

6. The combination of claim 1, wherein the virus is formulated as a pharmaceutical composition.

7. The combination of claim 2, wherein there is an insertion in the F3 locus at the NotI site within the F3 gene or at a corresponding locus.

8. The combination of claim 7, wherein:
   the virus is an LIVP strain; and
   the insertion in the F3 locus is at position 1475 inside of the HindIII-F fragment.

9. The combination of claim 1, wherein at least one of the TK, HA gene and F3 locus comprises an insertion of heterologous nucleic acid that encodes a protein.

10. The combination of claim 9, wherein the heterologous nucleic acid comprises a regulatory sequence operatively linked to the nucleic acid encoding the protein.

11. The combination of claim 10, wherein the regulatory sequence comprises the vaccinia virus early/late promoter p7.5 or an early/late vaccinia pE/L promoter.

12. The combination of claim 9, wherein the virus or encoded protein is immunogenic when expressed in a human.

13. The combination of claim 9, wherein the heterologous nucleic acid encodes a detectable protein or a protein capable of inducing a detectable signal.

14. The combination of claim 1, wherein the anti-cancer compound is a chemotherapeutic compound.

15. The combination of claim 1, wherein the anti-cancer compound is selected from among alkylating agents, antimetabolites, platinum coordination complexes, anthracenediones, substituted ureas, methylhydrazine derivatives, adrenocortical suppressants and anti-cancer polysaccharides.

16. The combination of claim 1, wherein the anti-cancer compound is selected from among gancyclovir, 5-fluorouracil, 6-methylpurine deoxyriboside, cephalosporin-doxorubicin, 4-[(2-chloroethyl)(2-mesuloxyethyl)-amino]benzoyl-L-glutamic acid, indole-3-acetic acid, CB1954, 7-ethyl-10-[4-(1-piperidino)-1-piperidino]carbonyloxycamptothecin, bis-(2-chloro-ethyl)amino-4-hydroxyphenylaminomethanone 28, 1-chloromethyl-5-hydroxy-1,2-dihydro-3H-benz[e]indole, epirubicin-glucoronide, 5'-deoxy-5-fluorouridine, cytosine arabinoside, and linamarin.

17. A kit, comprising:
   a composition containing an anti-cancer compound: and
   a composition containing a recombinant vaccinia virus, wherein:
      the vaccinia virus is a Lister strain; and
      the virus contains a modified thymidine kinase (TK) gene, a modified hemagglutinin (HA) gene, and an insertion, deletion or replacement in the locus or gene designated F3, whereby the vaccinia virus is TK-, HA- and F3-.

18. The combination of claim 1, wherein the anti-cancer compound and virus are formulated as a single composition.

19. The combination of claim 4, wherein the anti-cancer compound is selected from among alkylating agents, antimetabolites, platinum coordination complexes, anthracenediones, substituted ureas, methylhydrazine derivatives, adrenocortical suppressants and anti-cancer polysaccharides.

20. The combination of claim 4, wherein the anti-cancer compound is selected from among gancyclovir, 5-fluorouracil, 6-methylpurine deoxyriboside, cephalosporin-doxorubicin, 4-[(2-chloroethyl)(2-mesuloxyethyl)-amino]benzoyl-L-glutamic acid, indole-3-acetic acid, CB1954, 7-ethyl-10-[4-(1-piperidino)-1-piperidino]carbonyloxycamptothecin, bis-(2-chloro-ethyl)amino-4-hydroxyphenylaminomethanone 28, 1-chloromethyl-5-hydroxy-1,2-dihydro-3H-benz[e]indole, epirubicin-glucuronide, 5'-deoxy-5-fluorouridine, cytosine arabinoside and linamarin.

21. A kit, comprising:
   a combination of claim 1 packaged as a kit; and
   optionally instructions for administration thereof for treatment of cancer.

22. The kit of claim 17, wherein the vaccinia virus has an insertion at the NotI site in the F3 locus.

* * * * *

UNITED STATES PATENT AND TRADEMARK OFFICE
CERTIFICATE OF CORRECTION

PATENT NO. : 7,662,398 B2
APPLICATION NO. : 11/529662
DATED : February 16, 2010
INVENTOR(S) : Aladar A. Szalay et al.

It is certified that error appears in the above-identified patent and that said Letters Patent is hereby corrected as shown below:

IN THE TITLE PAGES:

Please remove "Item (30) Foreign Application Priority Data:
Jun. 18, 2003 (EP)................03013826
Aug. 14, 2003 (EP)...............03018478
Oct. 22, 2003 (EP)................03024283"

IN THE CLAIMS:

Column 312, line 6 to Column 312, line 15 should read
16. The combination of claim 1, wherein the anti-cancer compound is selected from among gancyclovir, 5-fluorouracil, 6-methylpurine deoxyriboside, cephalosporin-doxorubicin, 4-[(2-chloroethyl)(2-mesyloxyethyl)amino]benzoyl-L-glutamic acid, indole-3-acetic acid, CB1954, 7-ethyl-10-[4-(1-piperidino)-1-piperidino]carbonyloxycamptothecin, bis-(2-chloro-ethyl)amino-4-hydroxyphenylamino-methanone 28, 1-chloromethyl-5-hydroxy-1,2-dihydro-3H-benz[e]indole, epirubicin-glucuronide, 5'-deoxy-5-fluorouridine, cytosine arabinoside, and linamarin.

Column 312, line 33 to Column 312, line 42 should read
20. The combination of claim 4, wherein the anti-cancer compound is selected from among gancyclovir, 5-fluorouracil, 6-methylpurine deoxyriboside, cephalosporin-doxorubicin, 4-[(2-chloroethyl)(2-mesyloxyethyl)amino]benzoyl-L-glutamic acid, indole-3-acetic acid, CB1954, 7-ethyl-10-[4-(1-piperidino)-1-piperidino]carbonyloxycamptothecin, bis-(2-chloro-ethyl)amino-4-hydroxyphenylamino methanone 28, 1-chloromethyl-5-hydroxy-1,2-dihydro-3H-benz[e]indole, epirubicin-glucuronide, 5'-deoxy-5-fluorouridine, cytosine arabinoside and linamarin.

Signed and Sealed this

Fourth Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,662,398 B2  
APPLICATION NO. : 11/529662  
DATED : February 16, 2010  
INVENTOR(S) : Aladar A. Szalay et al.

Page 1 of 1

It is certified that error appears in the above-identified patent and that said Letters Patent is hereby corrected as shown below:

IN THE SPECIFICATION:

At column 28, line 18, please replace "pseudomonas A endotoxin" with --Pseudomonas exotoxin--

Signed and Sealed this  
Tenth Day of December, 2013

Margaret A. Focarino  
*Commissioner for Patents of the United States Patent and Trademark Office*

SEQUENCE LISTING

<160> NUMBER OF SEQ ID NOS: 36

<210> SEQ ID NO 1
<211> LENGTH: 148
<212> TYPE: DNA
<213> ORGANISM: Artificial Sequence
<220> FEATURE:
<223> OTHER INFORMATION: LIVP F3

<400> SEQUENCE: 1

```
aatatagcaa cagtagttct tgctcctcct tgattctagc atcctcttca ttattttctt    60
ctacgtacat aaacatgtcc aatacgttag acaacacacc gacgatggcg gccgctacag   120
acacgaatat gactaaaccg atgaccat                                      148
```

```
<210> SEQ ID NO 2
<211> LENGTH: 49
<212> TYPE: PRT
<213> ORGANISM: Artificial Sequence
<220> FEATURE:
<223> OTHER INFORMATION: Translation LIVP F3

<400> SEQUENCE: 2
```

Met Val Ile Gly Leu Val Ile Phe Val Ser Val Ala Ala Ile Val
1               5                   10                  15

Gly Val Leu Ser Asn Val Leu Asp Met Phe Met Tyr Val Glu Glu Asn
            20                  25                  30

Asn Glu Glu Asp Ala Arg Ile Lys Glu Glu Gln Glu Leu Leu Leu Leu
        35                  40                  45

Tyr

```
<210> SEQ ID NO 3
<211> LENGTH: 27
<212> TYPE: DNA
<213> ORGANISM: Artificial Sequence
<220> FEATURE:
<223> OTHER INFORMATION: Forward primer

<400> SEQUENCE: 3
gggaattctt atacatcctg ttctatc                                        27

<210> SEQ ID NO 4
<211> LENGTH: 30
<212> TYPE: DNA
<213> ORGANISM: Artificial Sequence
<220> FEATURE:
<223> OTHER INFORMATION: Reverse primer

<400> SEQUENCE: 4
ccaagcttat gaggagtatt gcggggctac                                     30

<210> SEQ ID NO 5
<211> LENGTH: 7252
<212> TYPE: DNA
<213> ORGANISM: Artificial Sequence
<220> FEATURE:
<223> OTHER INFORMATION: psc65
<300> PUBLICATION INFORMATION:
<308> DATABASE ACCESSION NUMBER: GenBank No. AX003206
<309> DATABASE ENTRY DATE: 2000-08-24

<400> SEQUENCE: 5
agcttttgcg atcaataaat ggatcacaac cagtatctct taacgatgtt cttcgcagat    60
gatgattcat tttttaagta tttggctagt caagatgatg aaatcttcat tatctgatat   120
attgcaaatc actcaatatc tagactttct gttattatta ttgatccaat caaaaaataa   180
attagaagcc gtgggtcatt gttatgaatc tctttcagag gaatacagac aattgacaaa   240
attcacagac tttcaagatt ttaaaaaact gtttaacaag gtccctattg ttacagatgg   300
aagggtcaaa cttaatataag gatatttgtt cgactttgtg attagtttga tgcgattcaa   360
aaaagaatcc tctctagcta ccaccgcaat agatcctgtt agatacatag atcctcgtcg   420
caatatcgca ttttctaacg tgatggatat attaaagtcg aataaagtga acaataatta   480
```

-continued

```
attctttatt gtcatcatga acggcggaca tattcagttg ataatcggcc ccatgttttc    540
aggtaaaagt acagaattaa ttagacgagt tagacgttat caaatagctc aatataaatg    600
cgtgactata aaatattcta acgataatag atacggaacg ggactatgga cgcatgataa    660
gaataatttt gaagcattgg aagcaactaa actatgtgat ctcttggaat caattacaga    720
tttctccgtg ataggtatcg atgaaggaca gttctttcca gacattgttg aattagatcg    780
ataaaaatta attaattacc cgggtaccag gcctagatct gtcgacttcg agcttattta    840
tattccaaaa aaaaaaaata aaatttcaat ttttaagctt tcactaattc caaacccacc    900
cgcttttat agtaagtttt tcacccataa ataataaata caataattaa tttctcgtaa    960
aagtagaaaa tatattctaa tttattgcac ggtaaggaag tagatcataa ctcgagcatg   1020
ggagatcccg tcgttttaca acgtcgtgac tgggaaaacc ctggcgttac ccaacttaat   1080
cgccttgcag cacatccccc tttcgccagc tggcgtaata gcgaagaggc ccgcaccgat   1140
cgcccttccc aacagttgcg cagcctgaat ggcgaatggc gctttgcctg gtttccggca   1200
ccagaagcgg tgccggaaag ctggctgagt gcgatcttc ctgaggccga tactgtcgtc   1260
gtcccctcaa actggcagat gcacggttac gatgcgccca tctacaccaa cgtaacctat   1320
cccattacgg tcaatccgcc gtttgttccc acggagaatc cgacgggttg ttactcgctc   1380
acatttaatg ttgatgaaag ctggctacag gaaggccaga cgcgaattat ttttgatggc   1440
gttaactcgg cgtttcatct gtggtgcaac gggcgctggg tcggttacgg ccaggacagt   1500
cgtttgccgt ctgaatttga cctgagcgca tttttacgcg ccggagaaaa ccgcctcgcg   1560
gtgatggtgc tgcgttggag tgacggcagt tatctggaag atcaggatat gtggcggatg   1620
agcggcattt ccgtgacgt ctcgttgctg cataaaccga ctacacaaat cagcgatttc    1680
catgttgcca ctcgctttaa tgatgatttc agccgcgctg tactggaggc tgaagttcag   1740
atgtgcggca gttgcgtga ctacctacgg gtaacagttt ctttatggca gggtgaaacg   1800
caggtcgcca gcggcaccgc gcctttcggc ggtgaaatta tcgatgagcg tggtggttat   1860
gccgatcgcg tcacactacg tctcaacgtc gaaaacccga actgtggag cgccgaaatc   1920
ccgaatctct atcgtgcggt ggttgaactg cacaccgccg acggcacgct gattgaagca   1980
gaagcctgcg atgtcggttt ccgcgaggtg cggattgaaa atggtctgct gctgctgaac   2040
ggcaagccgt tgctgattcg aggcgttaac cgtcacgagc atcatcctct gcatggtcag   2100
gtcatggatg agcagacgat ggtgcaggat atcctgctga tgaagcagaa caactttaac   2160
gccgtgcgct gttcgcatta tccgaaccat ccgctgtggt acacgctgtg cgaccgctac   2220
ggcctgtatg tggtggatga agccaatatt gaaacccacg gcatggtgcc aatgaatcgt   2280
ctgaccgatg atccgcgctg gctaccggcg atgagcgaac gcgtaacgcg aatggtgcag   2340
cgcgatcgta atcacccgag tgtgatcatc tggtcgctgg gaatgaatc aggccacggc   2400
gctaatcacg acgcgctgta tcgctggatc aaatctgtcg atccttcccg cccggtgcag   2460
tatgaaggcg gcggagccga caccacggcc accgatatta tttgcccgat gtacgcgcgc   2520
gtggatgaag accagcccct cccggctgtg ccgaaatggt ccatcaaaaa atggcttcg   2580
ctacctggag agacgcgccc gctgatcctt tgcgaatacg cccacgcgat gggtaacagt   2640
cttggcggtt tcgctaaata ctggcaggcg tttcgtcagt atccccgttt acagggcggc   2700
ttcgtctggg actgggtgga tcagtcgctg attaaatatg atgaaaacgg caacccgtgg   2760
tcggcttacg gcggtgattt tggcgatacg ccgaacgatc gccagttctg tatgaacggt   2820
```

```
ctggtctttg ccgaccgcac gccgcatcca gcgctgacgg aagcaaaaca ccagcagcag    2880 ttttccagt tccgtttatc cgggcaaacc atcgaagtga ccagcgaata cctgttccgt    2940
catagcgata acgagctcct gcactggatg gtggcgctgg atggtaagcc gctggcaagc    3000
ggtgaagtgc ctctggatgt cgctccacaa ggtaaacagt tgattgaact gcctgaacta    3060
ccgcagccgg agagcgccgg gcaactctgg ctcacagtac gcgtagtgca accgaacgcg    3120
accgcatggt cagaagccgg gcacatcagc gcctggcagc agtggcgtct ggcggaaaac    3180
ctcagtgtga cgctccccgc cgcgtcccac gccatcccgc atctgaccac cagcgaaatg    3240 gattttgca tcgagctggg taataagcgt tggcaattta accgccagtc aggctttctt    3300
tcacagatgt ggattggcga taaaaaacaa ctgctgacgc cgctgcgcga tcagttcacc    3360
cgtgcaccgc tggataacga cattggcgta agtgaagcga cccgcattga ccctaacgcc    3420
tgggtcgaac gctggaaggc ggcgggccat taccaggccg aagcagcgtt gttgcagtgc    3480
acggcagata cacttgctga tgcggtgctg attacgaccg ctcacgcgtg gcagcatcag    3540
gggaaaacct tatttatcag ccggaaaacc taccggattg atggtagtgg tcaaatggcg    3600
attaccgttg atgttgaagt ggcgagcgat acaccgcatc cggcgcggat tggcctgaac    3660
tgccagctgg cgcaggtagc agagcgggta aactggctcg gattagggcc gcaagaaaac    3720
tatcccgacc gccttactgc cgcctgtttt gaccgctggg atctgccatt gtcagacatg    3780 tatacccgt acgtcttccc gagcgaaaac ggtctgcgct gcgggacgcg cgaattgaat    3840
tatggcccac accagtggcg cggcgacttc cagttcaaca tcagccgcta cagtcaacag    3900
caactgatgg aaaccagcca tcgccatctg ctgcacgcgg aagaaggcac atggctgaat    3960
atcgacggtt ccatatggg gattggtggc gacgactcct ggagcccgtc agtatcggcg    4020
gaattcagct gagcgccggt cgctaccatt accagttggt ctggtgtcaa aataataat    4080 aaccgggcag gggggatcct tctgtgagcg tatgcaaac gaaggaaaaa tagttatagt    4140
agccgcactc gatgggacat ttcaacgtaa accgtttaat aatatttga atcttattcc    4200 attatctgaa atggtggtaa aactaactgc tgtgtgtatg aaatgcttta aggaggcttc    4260
cttttctaaa cgattgggtg aggaaaccga gatagaaata ataggaggta atgatatgta    4320
tcaatcggtg tgtagaaagt gttacatcga ctcataatat tatattttt atctaaaaaa    4380 ctaaaaataa acattgatta aattttaata taatacttaa aaatggatgt tgtgtcgtta    4440
gataaaccgt ttatgtattt tgaggaaatt gataatgagt tagattacga accagaaagt    4500
gcaaatgagg tcgcaaaaaa actgccgtat caaggacagt taaaactatt actaggagaa    4560 ttatttttc ttagtaagtt acagcgacac ggtatattag atggtgccac cgtagtgtat    4620
ataggatctg ctcccggtac acatatacgt tatttgagag atcatttcta aatttagga    4680 gtgatcatca aatggatgct aattgacggc cgccatcatg atcctatttt aaatggattg    4740
cgtgatgtga ctctagtgac tcggttcgtt gatgaggaat atctacgatc catcaaaaaa    4800
caactgcatc cttctaagat tattttaatt tctgatgtga gatccaaacg aggaggaaat    4860
gaacctagta cggcggattt actaagtaat tacgctctac aaaatgtcat gattagtatt    4920
ttaaaccccg tggcgtctag tcttaaatgg agatgcccgt ttccagatca atggatcaag    4980 gactttata tcccacacgg taataaaatg ttacaacctt ttgctccttc atattcagct    5040
gaaatgagat tattaagtat ttataccggt gagaacatga gactgactcg ggccgcgttg    5100
ctggcgtttt tccataggct ccgccccct gacgagcatc acaaaaatcg acgctcaagt    5160
cagaggtggc gaaacccgac aggactataa agataccagg cgtttccccc tggaagctcc    5220
```

-continued

```
ctcgtgcgct ctcctgttcc gaccctgccg cttaccggat acctgtccgc ctttctccct    5280
tcgggaagcg tggcgctttc tcaatgctca cgctgtaggt atctcagttc ggtgtaggtc    5340
gttcgctcca agctgggctg tgtgcacgaa ccccccgttc agcccgaccg ctgcgcctta    5400
tccggtaact atcgtcttga gtccaacccg gtaagacacg acttatcgcc actggcagca    5460
gccactggta acaggattag cagagcgagg tatgtaggcg gtgctacaga gttcttgaag    5520
tggtggccta actacggcta cactagaagg acagtatttg gtatctgcgc tctgctgaag    5580
ccagttacct tcggaaaaag agttggtagc tcttgatccg gcaaacaaac caccgctggt    5640
agcggtggtt ttttgtttg caagcagcag attacgcgca gaaaaaagg atctcaagaa    5700 gatcctttga tcttttctac ggggtctgac gctcagtgga acgaaaactc acgttaaggg    5760
attttggtca tgagattatc aaaaaggatc ttcacctaga tccttttaaa ttaaaaatga    5820
agttttaaat caatctaaag tatatatgag taaacttggt ctgacagtta ccaatgctta    5880
atcagtgagg cacctatctc agcgatctgt ctatttcgtt catccatagt tgcctgactc    5940
cccgtcgtgt agataactac gatacgggag ggcttaccat ctggccccag tgctgcaatg    6000
ataccgcgag acccacgctc accggctcca gatttatcag caataaacca gccagccgga    6060
agggccgagc gcagaagtgg tcctgcaact ttatccgcct ccatccagtc tattaattgt    6120
tgccgggaag ctagagtaag tagttcgcca gttaatagtt tgcgcaacgt tgttgccatt    6180
gctgcaggca tcgtggtgtc acgctcgtcg tttggtatgg cttcattcag ctccggttcc    6240
caacgatcaa ggcgagttac atgatccccc atgttgtgca aaaaagcggt tagctccttc    6300
ggtcctccga tcgttgtcag aagtaagttg gccgcagtgt tatcactcat ggttatggca    6360
gcactgcata attctcttac tgtcatgcca tccgtaagat gcttttctgt gactggtgag    6420
tactcaacca agtcattctg agaatagtgt atgcggcgac cgagttgctc ttgcccggcg    6480
tcaacacggg ataataccgc gccacatagc agaactttaa aagtgctcat cattggaaaa    6540
cgttcttcgg ggcgaaaact ctcaaggatc ttaccgctgt tgagatccag ttcgatgtaa    6600
cccactcgtg cacccaactg atcttcagca tcttttactt tcaccagcgt ttctgggtga    6660
gcaaaaacag gaaggcaaaa tgccgcaaaa aagggaataa gggcgacacg gaaatgttga    6720
atactcatac tcttcctttt tcaatattat tgaagcattt atcagggtta ttgtctcatg    6780
agcggataca tatttgaatg tatttagaaa aataaacaaa taggggttcc gcgcacattt    6840
ccccgaaaag tgccacctga cgtctaagaa accattatta tcatgacatt aacctataaa    6900
aataggcgta tcacgaggcc ctttcgtctt cgaataaata cctgtgacgg aagatcactt    6960
cgcagaataa ataaatcctg gtgtccctgt tgataccggg aagccctggg ccaacttttg    7020
gcgaaaatga ccgttgatc ggcacgtaag aggttccaac tttcaccata atgaaataag    7080
atcactaccg ggcgtatttt ttgagttatc gagattttca ggagctaagg aagctaaaat    7140
ggagaaaaaa atcactggat ataccaccgt tgatatatcc caatggcatc gtaaagaaca    7200
ttttgaggca tttcagtcag ttgctcaatg tacctataac cagaccgttc ag          7252
```

<210> SEQ ID NO 6
<211> LENGTH: 28
<212> TYPE: DNA
<213> ORGANISM: Artificial Sequence
<220> FEATURE:
<223> OTHER INFORMATION: Primer pUC28 I

<400> SEQUENCE: 6
aattcagatc tccatggatc gatgagct                                        28

<210> SEQ ID NO 7
<211> LENGTH: 20
<212> TYPE: DNA
<213> ORGANISM: Artificial Sequence
<220> FEATURE:
<223> OTHER INFORMATION: Primer pUC28 II

<400> SEQUENCE: 7
catcgatcca tggagatctg                                                 20

<210> SEQ ID NO 8
<211> LENGTH: 1665
<212> TYPE: DNA
<213> ORGANISM: Artificial Sequence
<220> FEATURE:
<223> OTHER INFORMATION: Renilla luciferase-Aequeora GFP fusion gene

<400> SEQUENCE: 8
atgacttcga aagtttatga tccagaacaa aggaaacgga tgataactgg tccgcagtgg     60
tgggccagat gtaaacaaat gaatgttctt gattcattta ttaattatta tgattcagaa    120
aaacatgcag aaaatgctgt tatttttta catggtaacg cggcctcttc ttatttatgg    180
cgacatgttg tgccacatat tgagccagta gcgcggtgta ttataccaga tcttattggt    240
atgggcaaat caggcaaatc tggtaatggt tcttataggt tacttgatca ttacaaatat    300
cttactgcat ggtttgaact tcttaattta ccaaagaaga tcattttgt cggccatgat    360
tggggtgctt gtttggcatt tcattatagc tatgagcatc aagataagat caaagcaata    420
gttcacgctg aaagtgtagt agatgtgatt gaatcatggg atgaatggcc tgatattgaa    480
gaagatattg cgttgatcaa atctgaagaa ggagaaaaaa tggttttgga gaataacttc    540
ttcgtggaaa ccatgttgcc atcaaaaatc atgagaaagt tagaaccaga gaatttgca    600
gcatatcttg aaccattcaa agacaaaggt gaagttcgtc gtccaacatt atcatggcct    660
cgtgaaatcc cgttagtaaa aggtggtaaa cctgacgttg tacaaattgt taggaattat    720
aatgcttatc tacgtgcaag tgatgattta ccaaaaatgt ttattgaatc ggatccagga    780
ttcttttcca atgctattgt tgaaggcgcc aagaagtttc ctaatactga atttgtcaaa    840
gtaaaaggtc ttcattttc gcaagaagat gcacctgatg aaatgggaaa atatatcaaa    900
tcgttcgttg agcgagttct caaaaatgaa caagcggccg caccgcatat gagtaaagga    960
gaagaactttt tcactggagt tgtcccaatt cttgttgaat tagatggtga tgttaatggg   1020
cacaaatttt ctgtcagtgg agagggtgaa ggtgatgcaa catacggaaa acttacccctt   1080
aaatttattt gcactactgg aaaactacct gttccatggc caacacttgt cactactttc   1140
tcttatggtg ttcaatgctt ttcaagatac ccagatcata tgaaacagca tgacttttc   1200
aagagtgcca tgcccgaagg ttatgtacag gaaagaacta tatttttcaa agatgacggg   1260
aactacaaga cacgtgctga agtcaagttt gaaggtgata cccttgttaa tagaatcgag   1320
ttaaaggta ttgattttaa agaagatgga acattcttg acacaaaatt ggaatacaac   1380
tataactcac acaatgtata tcatcatggca gacaaacaaa agaatggaat caaagttaac   1440
ttcaaaatta gacacaacat tgaagatgga agcgttcaac tagcagacca ttatcaacaa   1500
aatactccaa ttggcgatgg ccctgtcctt ttaccagaca accattacct gtccacacaa   1560
tctgcccttt cgaaagatcc caacgaaaag agagaccaca tggtccttct tgagtttgta   1620
acagctgctg ggattacaca tggcatggat gaactataca aataa                   1665

-continued

```
<210> SEQ ID NO 9
<211> LENGTH: 11096
<212> TYPE: DNA
<213> ORGANISM: Artificial Sequence
<220> FEATURE:
<223> OTHER INFORMATION: pLacGus Plasmid

<400> SEQUENCE: 9
aagcttgcat gcctgcagca attcccgagg ctgtagccga cgatggtgcg ccaggagagt      60
tgttgattca ttgtttgcct ccctgctgcg gtttttcacc gaagttcatg ccagtccagc     120 gttttttgcag cagaaaagcc gccgacttcg gtttgcggtc gcgagtgaag atccctttct   180
tgttaccgcc aacgcgcaat atgccttgcg aggtcgcaaa atcggcgaaa ttccatacct    240
gttcaccgac gacggcgctg acgcgatcaa agacgcggtg atacatatcc agccatgcac    300
actgatactc ttcactccac atgtcggtgt acattgagtg cagcccggct aacgtatcca    360
cgccgtattc ggtgatgata tcggctgat gcagtttctc ctgccaggcc agaagttctt     420
tttccagtac cttctctgcc gtttccaaat cgccgctttg gacataccat ccgtaataac    480
ggttcaggca cagcacatca aagagatcgc tgatggtatc ggtgtgagcg tcgcagaaca    540
ttacattgac gcaggtgatc ggacgcgtcg ggtcgagttt acgcgttgct tccgccagtg    600
gcgcgaaata ttcccgtgca ccttgcggac gggtatccgg ttcgttggca atactccaca    660
tcaccacgct tgggtggttt ttgtcacgcg ctatcagctc tttaatcgcc tgtaagtgcg    720
cttgctgagt ttccccgttg actgcctctt cgctgtacag ttctttcggc ttgttgcccg    780
cttcgaaacc aatgcctaaa gagaggttaa agccgacagc agcagtttca tcaatcacca    840
cgatgccatg ttcatctgcc cagtcgagca tctcttcagc gtaagggtaa tgcgaggtac    900
ggtaggagtt ggccccaatc cagtccatta tgcgtggtc gtgcaccatc agcacgttat     960
cgaatccttt gccacgcaag tccgcatctt catgacgacc aaagccagta aagtagaacg   1020
gtttgtggtt aatcaggaac tgttcgccct tcactgccac tgaccggatg ccgacgcgaa   1080
gcgggtagat atcacactct gtctggcttt tggctgtgac gcacagttca tagagataac   1140
cttcacccgg ttgccagagg tgcggattca ccacttgcaa agtcccgcta gtgccttgtc   1200
cagttgcaac cacctgttga tccgcatcac gcagttcaac gctgacatca ccattggcca   1260
ccacctgcca gtcaacagac gcgtggttac agtcttgcgc gacatgcgtc accacggtga   1320
tatcgtccac ccaggtgttc ggcgtggtgt agagcattac gctgcgatgg attccggcat   1380
agttaaagaa atcatggaag taagactgct ttttcttgcc gttttcgtcg gtaatcacca   1440
ttcccggcgg gatagtctgc cagttcagtt cgttgttcac acaaacggtg atacgtacac   1500
ttttcccggc aataacatac ggcgtgacat cggcttcaaa tggcgtatag ccgccctgat   1560
gctccatcac ttcctgatta ttgacccaca ctttgccgta atgagtgacc gcatcgaaac   1620
gcagcacgat acgctggcct gcccaacctt tcggtataaa gacttcgcgc tgataccaga   1680
cgttgcccgc ataattacga atatctgcat cggcgaactg atcgttaaaa ctgcctggca   1740
cagcaattgc ccggctttct tgtaacgcgc tttcccacca acgctgatca attccacagt   1800
tttcgcgatc cagactgaat gcccacaggc cgtcgagttt ttgatttca cgggttgggg    1860 tttctacagg acgtaacatt ctagacatta tagttttttc tccttgacgt taaagtatag   1920
aggtatatta acaattttttt gttgatactt ttattacatt tgaataagaa gtaatacaaa   1980
ccgaaaatgt tgaaagtatt agttaaagtg gttatgcagt ttttgcattt atatatctgt   2040
```

```
taatagatca aaaatcatcg gttcgctgat taattacccc agaaataagg ctaaaaaact   2100
aatcgcatta tcatccctcg agctatcacc gcaagggata aatatctaac accgtgcgtg   2160
ttgactattt tacctctggc ggtgataatg ctcgaggtaa gattagatat ggatatgtat   2220
atggatatgt atatggtggt aatgccatgt aaatgatta ttaaacttct ttgcgtccat    2280
ccaaaaaaaa agtaagaatt tttgaaaatt caatataaat gacagctcag ttacaaagtg   2340
aaagtacttc taaaattgtt ttggttacag gtggtgctgg atacattggt tcacacactg   2400
tggtagagct aattgagaat ggatatgact gtgttgttgc tgataacctg tcgaatagat   2460
cgacctgaag tctaggtccc tatttatttt tttatagtta tgttagtatt aagaacgtta   2520
tttatatttc aaattttct tttttttctg tacagacgcg tgtacgaatt tcgacctcga    2580
ccggccggtt ttacaaatca gtaagcaggt cagtgcgtac gccatggccg gagtggctca   2640
cagtcggtgg tccggcagta caatggattt ccttacgcga aatacgggca gacatggcct   2700
gcccggttat tattattttt gacaccagac caactggtaa tggtagcgac cggcgctcag   2760
ctggaattcc gccgatactg acgggctcca ggagtcgtcg ccaccaatcc ccatatggaa   2820
accgtcgata ttcagccatg tgccttcttc cgcgtgcagc agatggcgat ggctggtttc   2880
catcagttgc tgttgactgt agcggctgat gttgaactgg aagtcgccgc gccactggtg   2940
tgggccataa ttcaattcgc gcgtcccgca gcgcagaccg ttttcgctcg gaagacgta    3000 cggggtatac atgtctgaca atggcagatc ccagcggtca aaacaggcgg cagtaaggcg   3060
gtcgggatag ttttcttgcg gccctaatcc gagccagttt accccgctctg ctacctgcgc  3120 cagctggcag ttcaggccaa tccgcgccgg atgcggtgta tcgctcgcca cttcaacatc   3180
aacggtaatc gccatttgac cactaccatc aatccggtag ttttccggc tgataaataa    3240 ggttttcccc tgatgctgcc acgcgtgagc ggtcgtaatc agcaccgcat cagcaagtgt   3300
atctgccgtg cactgcaaca acgctgcttc ggcctggtaa tggcccgccg ccttccagcg   3360
ttcgacccag gcgttagggt caatgcgggt cgcttcactt acgccaatgt cgttatccag   3420
cggtgcacgg gtgaactgat cgcgcagcgg cgtcagcagt tgttttttat cgccaatcca   3480
catctgtgaa agaaagcctg actggcggtt aaattgccaa cgcttattac ccagctcgat   3540
gcaaaaatcc atttcgctgg tggtcagatg cgggatggcg tgggacgcgg cggggagcgt   3600
cacactgagg ttttccgcca gacgccactg ctgccaggcg ctgatgtgcc cggcttctga   3660
ccatgcggtc gcgttcggtt gcactacgcg tactgtgagc cagagttgcc cggcgctctc   3720
cggctgcggt agttcaggca gttcaatcaa ctgtttacct tgtggagcga catccagagg   3780
cacttcaccg cttgccagcg gcttaccatc cagcgccacc atccagtgca ggagctcgtt   3840
atcgctatga cggaacaggt attcgctggt cacttcgatg gtttgccgg ataaacggaa    3900 ctggaaaaac tgctgctggt gttttgcttc cgtcagcgct ggatgcggcg tgcggtcggc   3960
aaagaccaga ccgttcatac agaactggcg atcgttcggc gtatcgccaa aatcaccgcc   4020
gtaagccgac cacgggttgc cgttttcatc atatttaatc agcgactgat ccacccagtc   4080
ccagacgaag ccgccctgta aacggggata ctgacgaaac gcctgccagt atttagcgaa   4140
accgccaaga ctgttaccca tcgcgtgggc gtattcgcaa aggatcagcg ggcgcgtctc   4200
tccaggtagc gaaagccatt ttttgatgga ccatttcggc acagccggga agggctggtc   4260
ttcatccacg cgcgcgtaca tcgggcaaat aatatcggtg gccgtggtgt cggctccgcc   4320
gccttcatac tgcaccgggc gggaaggatc gacagatttg atccagcgat acagcgcgtc   4380
gtgattagcg ccgtggcctg attcattccc cagcgaccag atgatcacac tcgggtgatt   4440
```

```
acgatcgcgc tgcaccattc gcgttacgcg ttcgctcatc gccggtagcc agcgcggatc    4500
atcggtcaga cgattcattg gcaccatgcc gtgggtttca atattggctt catccaccac    4560
atacaggccg tagcggtcgc acagcgtgta ccacagcgga tggttcggat aatgcgaaca    4620
gcgcacggcg ttaaagttgt tctgcttcat cagcaggata tcctgcacca tcgtctgctc    4680
atccatgacc tgaccatgca gaggatgatg ctcgtgacgg ttaacgcctc gaatcagcaa    4740
cggcttgccg ttcagcagca gcagaccatt ttcaatccgc acctgcgga aaccgacatc     4800 gcaggcttct gcttcaatca gcgtgccgtc ggcggtgtgc agttcaacca ccgcacgata    4860
gagattcggg atttcggcgc tccacagttt cgggttttcg acgttcagac gtagtgtgac    4920
gcgatcggca taaccaccac gctcatcgat aatttcaccg ccgaaaggcg cggtgccgct    4980
ggcgacctgc gtttcacccct gccataaaga aactgttacc cgtaggtagt cacgcaactc   5040
gccgcacatc tgaacttcag cctccagtac agcgcggctg aaatcatcat taaagcgagt    5100
ggcaacatgg aaatcgctga tttgtgtagt cggtttatgc agcaacgaga cgtcacggaa    5160
aatgccgctc atccgccaca tatcctgatc ttccagataa ctgccgtcac tccagcgcag    5220
caccatcacc gcgaggcggt tttctccggc gcgtaaaaat gcgctcaggt caaattcaga    5280
cggcaaacga ctgtcctggc cgtaaccgac ccagcgcccg ttgcaccaca gatgaaacgc    5340
cgagttaacg ccatcaaaaa taattcgcgt ctggccttcc tgtagccagc tttcatcaac    5400
attaaatgtg agcgagtaac aacccgtcgg attctccgtg ggaacaaacg gcggattgac    5460
cgtaatggga taggtcacgt tggtgtagat gggcgcatcg taaccgtgca tctgccagtt    5520 tgagggacg acgacagtat cggcctcagg aagatcgcac tccagccagc tttccggcac     5580
cgcttctggt gccggaaacc aggcaaagcg ccattcgcca ttcaggctgc gcaactgttg    5640
ggaagggcga tcggtgcggg cctcttcgct attacgccag ctggcgaaag ggggatgtgc    5700
tgcaaggcga ttaagtcggg aaacctgtcg tgccagctgc attaatgaat cggccaacgc    5760
gcggggagag gcggtttgcg tattgggcgc cagggtggtt tttcttttca ccagtgagac    5820
gggcaacagc caagctccgg atccgggctt ggccaagctt ggaattccgc acttttcggc    5880
caatggtctt ggtaattcct ttgcgctaga attgaactca ggtacaatca cttcttctga    5940
atgagattta gtcattatag ttttttctcc ttgacgttaa agtatagagg tatattaaca    6000
attttttgtt gatacttttta ttacatttga ataagaagta atacaaaccg aaaatgttga    6060
aagtattagt taaagtggtt atgcagtttt tgcatttata tatctgttaa tagatcaaaa    6120
atcatcgctt cgctgattaa ttaccccaga aataaggcta aaaaactaat cgcattatca    6180
tcccctcgac gtactgtaca tataaccact ggttttatat acagcagtac tgtacatata    6240
accactggtt ttatatacag cagtcgacgt actgtacata taaccactgg ttttatatac    6300
agcagtactg gacatataac cactggtttt atatacagca gtcgaggtaa gattagatat    6360
ggatatgtat atggatatgt atatggtggt aatgccatgt aatatgatta ttaaacttct    6420
ttgcgtccat ccaaaaaaaa agtaagaatt tttgaaaatt caatataaat gacagctcag    6480
ttacaaagtg aaagtacttc taaaattgtt ttggttacag gtggtgctgg atacattggt    6540
tcacacactg tggtagagct aattgagaat ggatatgact gtgttgttgc tgataacctg    6600
tcgaattcca agctcggatc cccgagctcg gatccccta agaaaccatt attatcatga    6660
cattaaccta taaaaatagg cgtatcacga ggccctttcg tctcgcgcgt ttcggtgatg    6720
acggtgaaaa cctctgacac atgcagctcc cggagacggt cacagcttgt ctgtaagcgg    6780
```

```
atgccgggag cagacaagcc cgtcagggcg cgtcagcggg tgttggcggg tgtcggggct   6840
ggcttaacta tgcggcatca gagcagattg tactgagagt gcaccataac gcatttaagc   6900
ataaacacgc actatgccgt tcttctcatg tatatatata tacaggcaac acgcagatat   6960
aggtgcgacg tgaacagtga gctgtatgtg cgcagctcgc gttgcatttt cggaagcgct   7020
cgttttcgga aacgctttga agttcctatt ccgaagttcc tattctctag ctagaaagta   7080
taggaacttc agagcgcttt tgaaaaccaa aagcgctctg aagacgcact ttcaaaaaac   7140
caaaaacgca ccggactgta acgagctact aaaatattgc gaataccgct tccacaaaca   7200
ttgctcaaaa gtatctcttt gctatatatc tctgtgctat atccctatat aacctaccca   7260
tccacctttc gctccttgaa cttgcatcta aactcgacct ctacatttt tatgtttatc   7320 tctagtatta ctctttagac aaaaaaattg tagtaagaac tattcataga gtgaatcgaa   7380
aacaatacga aaatgtaaac atttcctata cgtagtatat agagacaaaa tagaagaaac   7440
cgttcataat tttctgacca atgaagaatc atcaacgcta tcactttctg ttcacaaagt   7500
atgcgcaatc cacatcggta tagaatataa tcggggatgc ctttatcttg aaaaaatgca   7560
cccgcagctt cgctagtaat cagtaaacgc gggaagtgga gtcaggcttt ttttatggaa   7620
gagaaaatag acaccaaagt agccttcttc taaccttaac ggacctacag tgcaaaaagt   7680
tatcaagaga ctgcattata gagcgcacaa aggagaaaaa aagtaatcta agatgctttg   7740
ttagaaaaat agcgctctcg ggatgcattt ttgtagaaca aaaagaagt atagattctt    7800 tgttggtaaa atagcgctct cgcgttgcat ttctgttctg taaaaatgca gctcagattc   7860
tttgtttgaa aaattagcgc tctcgcgttg cattttgtt ttacaaaaat gaagcacaga   7920
ttcttcgttg gtaaaatagc gctttcgcgt tgcatttctg ttctgtaaaa atgcagctca   7980
gattctttgt ttgaaaaatt agcgctctcg cgttgcattt ttgttctaca aaatgaagca   8040
cagatgcttc gttgcttccg tgtggaagaa cgattacaac aggtgttgtc ctctgaggac   8100
ataaaataca caccgagatt catcaactca ttgctggagt tagcatatct acaattcaga   8160
agaactcgtc aagaaggcga tagaaggcga tgcgctgcga atcgggagcg gcgataccgt   8220
aaagcacgag gaagcggtca gcccattcgc cgccaagctc ttcagcaata tcacgggtag   8280
ccaacgctat gtcctgatag cggtccgcca cacccagccg gccacagtcg atgaatccag   8340
aaaagcggcc attttccacc atgatattcg gcaagcaggc atcgccatgg gtcacgacga   8400
gatcctcgcc gtcgggcatg ctcgccttga gcctggcgaa cagttcggct ggcgcgagcc   8460
cctgatgctc ttcgtccaga tcatcctgat cgacaagacc ggcttccatc cgagtacgtg   8520
ctcgctcgat gcgatgtttc gcttggtggt cgaatgggca ggtagccgga tcaagcgtat   8580
gcagccgccg cattgcatca gccatgatgg atactttctc ggcaggagca aggtgagatg   8640
acaggagatc ctgccccggc acttcgccca atagcagcca gtcccttccc gcttcagtga   8700
caacgtcgag cacagctgcg caaggaacgc ccgtcgtggc cagccacgat agccgcgctg   8760
cctcgtcttg cagttcattc agggcaccgg acaggtcggt cttgacaaaa agaaccgggc   8820
gcccctgcgc tgacagccgg aacacggcgg catcagagca gccgattgtc tgttgtgccc   8880
agtcatagcc gaatagcctc tccacccaag cggccggaga acctgcgtgc aatccatctt   8940
gttcaatcat gcgaaacgat cctcatcctg tctcttgatc agagcttgat ccctgcgcc    9000 atcagatcct ggcggcaag aaagccatcc agtttacttt gcagggcttc ccaaccttac    9060
cagagggcgc cccagctggc aattccggtt cgcttgctgt ccataaaacc gcccagtcta   9120
gctatcgcca tgtaagccca ctgcaagcta cctgctttct ctttgcgctt gcgttttccc   9180
```

| | |
|---|---|
| ttgtccagat agcccagtag ctgacattca tccggggtca gcaccgtttc tgcggactgg | 9240 |
| ctttctacgt gaaaaggatc taggtgaaga tccttttga taatctcatg accaaaatcc | 9300 |
| cttaacgtga gttttcgttc cactgagcgt cagaccccgt agaaaagatc aaggatctt | 9360 |
| cttgagatcc ttttttctg cgcgtaatct gctgcttgca acaaaaaaa ccaccgctac | 9420 |
| cagcggtggt ttgtttgccg gatcaagagc taccaactct ttttccgaag gtaactggct | 9480 |
| tcagcagagc gcagatacca aatactgttc ttctagtgta gccgtagtta ggccaccact | 9540 |
| tcaagaactc tgtagcaccg cctacatacc tcgctctgct aatcctgtta ccagtggctg | 9600 |
| ctgccagtgg cgataagtcg tgtcttaccg ggttggactc aagacgatag ttaccggata | 9660 |
| aggcgcagcg gtcgggctga acggggggtt cgtgcacaca gcccagcttg gagcgaacga | 9720 |
| cctacaccga actgagatac ctacagcgtg agctatgaga aagcgccacg cttcccgaag | 9780 |
| ggagaaaggc ggacaggtat ccggtaagcg gcagggtcgg aacaggagag cgcacgaggg | 9840 |
| agcttccagg gggaaacgcc tggtatcttt atagtcctgt cgggtttcgc cacctctgac | 9900 |
| ttgagcgtcg atttttgtga tgctcgtcag ggggcggag cctatggaaa aacgccagca | 9960 |
| acgcggcctt tttacggttc ctggccttt gctggccttt tgctcacatg atataattca | 10020 |
| attgaagctc taatttgtga gtttagtata catgcattta cttataatac agttttttag | 10080 |
| ttttgctggc cgcatcttct caaatatgct tcccagcctg cttttctgta acgttcaccc | 10140 |
| tctaccttag catcccttcc ctttgcaaat agtcctcttc aacaataat aatgtcagat | 10200 |
| cctgtagaga ccacatcatc cacgttcta tactgttgac ccaatgcgtc tcccttgtca | 10260 |
| tctaaaccca caccgggtgt cataatcaac caatcgtaac cttcatctct tccacccatg | 10320 |
| tctctttgag caataaagcc gataacaaaa tctttgtcgc tcttcgcaat gtcaacagta | 10380 |
| cccttagtat attctccagt agatagggag cccttgcatg acaattctgc taacatcaaa | 10440 |
| aggcctctag gttcctttgt tacttcttct gccgcctgct tcaaaccgct aacaatacct | 10500 |
| gggcccacca caccgtgtgc attcgtaatg tctgcccatt ctgctattct gtatacaccc | 10560 |
| gcagagtact gcaatttgac tgtattacca atgtcagcaa attttctgtc ttcgaagagt | 10620 |
| aaaaaattgt acttggcgga taatgccttt agcggcttaa ctgtgccctc catggaaaaa | 10680 |
| tcagtcaaga tatccacatg tgttttagt aaacaaattt gggacctaa tgcttcaact | 10740 |
| aactccagta attccttggt ggtacgaaca tccaatgaag cacacaagtt tgtttgcttt | 10800 |
| tcgtgcatga tattaaatag cttggcagca acaggactag gatgagtagc agcacgttcc | 10860 |
| ttatatgtag ctttcgacat gatttatctt cgtttcctgc aggttttgt tctgtgcagt | 10920 |
| tgggttaaga atactgggca atttcatgtt tcttcaacac tacatatgcg tatatatacc | 10980 |
| aatctaagtc tgtgctcctt ccttcgttct tccttctgtt cggagattac cgaatcaaaa | 11040 |
| aaatttcaag gaaaccgaaa tcaaaaaaaa gaataaaaaa aaatgatga attgaa | 11096 |

```
<210> SEQ ID NO 10
<211> LENGTH: 150
<212> TYPE: DNA
<213> ORGANISM: Vaccinia Virus/LIVP
<300> PUBLICATION INFORMATION:
<308> DATABASE ACCESSION NUMBER: GenBank No. M57977
<309> DATABASE ENTRY DATE: 2000-04-14

<400> SEQUENCE: 10
```

| | |
|---|---|
| atggtcatcg gttagtcat attcgtgtct gtggcggccg ccatcgtcgg tgtgttgtct | 60 |
| aacgtattgg acatgcttat gtacgtagaa gaaaataatg aagaggatgc tagaatcaag | 120 |

```
gaggagcaag aactactgtt gctatattga                                        150

<210> SEQ ID NO 11
<211> LENGTH: 49
<212> TYPE: PRT
<213> ORGANISM: Vaccinia Virus/LIVP
<300> PUBLICATION INFORMATION:
<308> DATABASE ACCESSION NUMBER: GenBank No. AAA48282
<309> DATABASE ENTRY DATE: 2000-04-14

<400> SEQUENCE: 11

Met Val Ile Gly Leu Val Ile Phe Val Ser Val Ala Ala Ala Ile Val
1               5                   10                  15

Gly Val Leu Ser Asn Val Leu Asp Met Leu Met Tyr Val Glu Glu Asn
            20                  25                  30

Asn Glu Glu Asp Ala Arg Ile Lys Glu Glu Gln Glu Leu Leu Leu Leu
        35                  40                  45

Tyr

<210> SEQ ID NO 12
<211> LENGTH: 150
<212> TYPE: DNA
<213> ORGANISM: Vaccinia Virus/WR
<300> PUBLICATION INFORMATION:
<308> DATABASE ACCESSION NUMBER: GenBank No. AY243312
<309> DATABASE ENTRY DATE: 2003-04-10

<400> SEQUENCE: 12
tcaatatagc aacagtagtt cttgctcctc cttgattcta gcatcctctt cattattttc     60
ttctacgtac ataagcatgt ccaatacgtt agacaacaca ccgacgatgg cggccgccac    120
agacacgaat atgactagac cgatgaccat                                      150

<210> SEQ ID NO 13
<211> LENGTH: 49
<212> TYPE: PRT
<213> ORGANISM: Vaccinia Virus/WR

<400> SEQUENCE: 13

Met Val Ile Gly Leu Val Ile Phe Val Ser Val Ala Ala Ala Ile Val
1               5                   10                  15

Gly Val Leu Ser Asn Val Leu Asp Met Leu Met Tyr Val Glu Glu Asn
            20                  25                  30

Asn Glu Glu Asp Ala Arg Ile Lys Glu Glu Gln Glu Leu Leu Leu Leu
        35                  40                  45

Tyr

<210> SEQ ID NO 14
<211> LENGTH: 150
<212> TYPE: DNA
<213> ORGANISM: Vaccinia Virus/Ankara
<300> PUBLICATION INFORMATION:
<308> DATABASE ACCESSION NUMBER: GenBank No. U94848.1
<309> DATABASE ENTRY DATE: 2003-04-14

<400> SEQUENCE: 14
tcaatatagc aacagtagtt cttgctcctc cttgattcta gcatcctctt cattattttc     60
ttctacgtac ataaacatgt ccaatacgtt agacaacaca ccgacgatgg cggccgccac    120
agacacgaat atgactaaac cgatgaccat                                      150
```

<210> SEQ ID NO 15
<211> LENGTH: 49
<212> TYPE: PRT
<213> ORGANISM: Vaccinia Virus/Ankara

<400> SEQUENCE: 15

Met Val Ile Gly Leu Val Ile Phe Val Ser Val Ala Ala Ala Ile Val
1               5                   10                  15

Gly Val Leu Ser Asn Val Leu Asp Met Phe Met Tyr Val Glu Glu Asn
            20                  25                  30

Asn Glu Glu Asp Ala Arg Ile Lys Glu Glu Gln Glu Leu Leu Leu Leu
        35                  40                  45

Tyr

<210> SEQ ID NO 16
<211> LENGTH: 146
<212> TYPE: DNA
<213> ORGANISM: Vaccinia Virus/Tian Tan
<300> PUBLICATION INFORMATION:
<308> DATABASE ACCESSION NUMBER: GenBank No. AF095689
<309> DATABASE ENTRY DATE: 2000-02-14

<400> SEQUENCE: 16
caatatagca acagtagttc ttgctcctcc ttgattctag catcctcttc attattttct       60
tctacgtaca taaacatgtc caatacgtta gacaacacac cgacgatggc cgccacagac      120
acgaatatga ctagaccgat gaccat                                           146

<210> SEQ ID NO 17
<211> LENGTH: 48
<212> TYPE: PRT
<213> ORGANISM: Vaccinia Virus/Tian Tan

<400> SEQUENCE: 17

Met Val Ile Gly Leu Val Ile Phe Val Ser Val Ala Ala Ile Val Gly
1               5                   10                  15

Val Leu Ser Asn Val Leu Asp Met Phe Met Tyr Val Glu Glu Asn Asn
            20                  25                  30

Glu Glu Asp Ala Arg Ile Lys Glu Glu Gln Glu Leu Leu Leu Leu Tyr
        35                  40                  45

<210> SEQ ID NO 18
<211> LENGTH: 150
<212> TYPE: DNA
<213> ORGANISM: Vaccinia Virus/Acambis 3000 MVA
<300> PUBLICATION INFORMATION:
<308> DATABASE ACCESSION NUMBER: GenBank No. AY603355
<309> DATABASE ENTRY DATE: 2004-05-15

<400> SEQUENCE: 18
tcaatatagc aacagtagtt cttgctcctc cttgattcta gcatcctctt cattattttc       60
ttctacgtac ataaacatgt ccaatacgtt agacaacaca ccgacgatgg cggccgccac      120
agacacgaat atgactaaac cgatgaccat                                        150

<210> SEQ ID NO 19
<211> LENGTH: 49
<212> TYPE: PRT
<213> ORGANISM: Vaccinia Virus/Acambis 3000 MVA

<400> SEQUENCE: 19

Met Val Ile Gly Leu Val Ile Phe Val Ser Val Ala Ala Ala Ile Val
1               5                   10                  15

```
Gly Val Leu Ser Asn Val Leu Asp Met Phe Met Tyr Val Glu Glu Asn
            20                  25                  30

Asn Glu Glu Asp Ala Arg Ile Lys Glu Glu Gln Glu Leu Leu Leu Leu
        35                  40                  45

Tyr

<210> SEQ ID NO 20
<211> LENGTH: 150
<212> TYPE: DNA
<213> ORGANISM: Vaccinia Virus/Copenhagen
<300> PUBLICATION INFORMATION:
<308> DATABASE ACCESSION NUMBER: GenBank No. M35027.1
<309> DATABASE ENTRY DATE: 1993-08-03

<400> SEQUENCE: 20
tcaatatagc aacagtagtt cttgctcctc cttgattcta gcatcctctt cattattttc      60
ttctacgtac ataaacatgt ccaatacgtt agacaacaca ccgacgatgg cggccgccac     120
agacacgaat atgactagac cgatgaccat                                      150

<210> SEQ ID NO 21
<211> LENGTH: 49
<212> TYPE: PRT
<213> ORGANISM: Vaccinia Virus/Copenhagen

<400> SEQUENCE: 21

Met Val Ile Gly Leu Val Ile Phe Val Ser Val Ala Ala Ala Ile Val
1               5                   10                  15

Gly Val Leu Ser Asn Val Leu Asp Met Phe Met Tyr Val Glu Glu Asn
            20                  25                  30

Asn Glu Glu Asp Ala Arg Ile Lys Glu Glu Gln Glu Leu Leu Leu Leu
        35                  40                  45

Tyr

<210> SEQ ID NO 22
<211> LENGTH: 150
<212> TYPE: DNA
<213> ORGANISM: Cowpox Virus
<300> PUBLICATION INFORMATION:
<308> DATABASE ACCESSION NUMBER: GenBank No. X94355.2
<309> DATABASE ENTRY DATE: 2003-05-09

<400> SEQUENCE: 22
tcaatatagc aacagtagtt cttgctcctc cttgattcta gcatcctctt cattattttc      60
ttctacgtac ataagcatgt ccaatacgtt agacaacaca ccgacgatgg cggccgccac     120
agacacgaat atgactagac cgatgaccat                                      150

<210> SEQ ID NO 23
<211> LENGTH: 49
<212> TYPE: PRT
<213> ORGANISM: Cowpox Virus

<400> SEQUENCE: 23

Met Val Ile Gly Leu Val Ile Phe Val Ser Val Ala Ala Ala Ile Val
1               5                   10                  15

Gly Val Leu Ser Asn Val Leu Asp Met Leu Met Tyr Val Glu Glu Asn
            20                  25                  30

Asn Glu Glu Asp Ala Arg Ile Lys Glu Glu Gln Glu Leu Leu Leu Leu
        35                  40                  45
```

Tyr

<210> SEQ ID NO 24
<211> LENGTH: 150
<212> TYPE: DNA
<213> ORGANISM: Rabbitpox Virus
<300> PUBLICATION INFORMATION:
<308> DATABASE ACCESSION NUMBER: GenBank No. AY484669
<309> DATABASE ENTRY DATE: 2004-03-30

<400> SEQUENCE: 24
tcaatatagc aacagtagtt cttgctcctc cttgattcta gcatcctctt cattattttc    60
ttctacgtac ataagcatgt ccaatacgtt agacaacaca ccgacgatgg cggccgccac   120
agacacgaat atgactagac cgatgaccat                                    150

<210> SEQ ID NO 25
<211> LENGTH: 49
<212> TYPE: PRT
<213> ORGANISM: Rabbitpox Virus

<400> SEQUENCE: 25

Met Val Ile Gly Leu Val Ile Phe Val Ser Val Ala Ala Ala Ile Val
1               5                   10                  15

Gly Val Leu Ser Asn Val Leu Asp Met Leu Met Tyr Val Glu Glu Asn
            20                  25                  30

Asn Glu Glu Asp Ala Arg Ile Lys Glu Glu Gln Glu Leu Leu Leu Leu
        35                  40                  45

Tyr

<210> SEQ ID NO 26
<211> LENGTH: 150
<212> TYPE: DNA
<213> ORGANISM: Camelpox Virus/CMS
<300> PUBLICATION INFORMATION:
<308> DATABASE ACCESSION NUMBER: GenBank No. AY009089
<309> DATABASE ENTRY DATE: 2002-07-30

<400> SEQUENCE: 26
tcaatatagc aacagtagtt cttgctcctc cttaattcta gcatcttctt cattattttc    60
ttctacatac ataagcatgt ccaatacgtt agacaacaca ccgacgatgg cggccgccac   120
agacacgaat atgactagac cgatgaccat                                    150

<210> SEQ ID NO 27
<211> LENGTH: 49
<212> TYPE: PRT
<213> ORGANISM: Camelpox Virus/CMS

<400> SEQUENCE: 27

Met Val Ile Gly Leu Val Ile Phe Val Ser Val Ala Ala Ala Ile Val
1               5                   10                  15

Gly Val Leu Ser Asn Val Leu Asp Met Leu Met Tyr Val Glu Glu Asn
            20                  25                  30

Asn Glu Glu Asp Ala Arg Ile Lys Glu Glu Gln Glu Leu Leu Leu Leu
        35                  40                  45

Tyr

<210> SEQ ID NO 28
<211> LENGTH: 150
<212> TYPE: DNA
<213> ORGANISM: Ectromelia Virus/Moscow -continued <300> PUBLICATION INFORMATION:
<308> DATABASE ACCESSION NUMBER: GenBank No. AF012825
<309> DATABASE ENTRY DATE: 2002-08-06

<400> SEQUENCE: 28
tcaatatagc aacaacagtt cttgctcctc cttgattcta gcatcctctt cattattttc    60
ttctacgtac ataagcatgt ccaatacgtt agacaacaca ccgacaatgg cggccgccac   120
agacacgaat atgactagac cgaggaccat                                    150

<210> SEQ ID NO 29
<211> LENGTH: 49
<212> TYPE: PRT
<213> ORGANISM: Ectromelia Virus/Moscow

<400> SEQUENCE: 29

Met Val Leu Gly Leu Val Ile Phe Val Ser Val Ala Ala Ala Ile Val
1               5                   10                  15

Gly Val Leu Ser Asn Val Leu Asp Met Leu Met Tyr Val Glu Glu Asn
            20                  25                  30

Asn Glu Glu Asp Ala Arg Ile Lys Glu Glu Gln Glu Leu Leu Leu Leu
        35                  40                  45

Tyr

<210> SEQ ID NO 30
<211> LENGTH: 146
<212> TYPE: DNA
<213> ORGANISM: Monkeypox Virus/Zaire
<300> PUBLICATION INFORMATION:
<308> DATABASE ACCESSION NUMBER: GenBank No. AF380138
<309> DATABASE ENTRY DATE: 2001-12-13

<400> SEQUENCE: 30
tatagcaaca gtaattcttg ctcctccttg attttagcat cctcttcatt attttcttct    60
acgtacataa gcatgtccaa tacgttagac aacaccga cgatggtggc cgccacagac    120
acgaatatga ctagaccgat gaccat                                       146

<210> SEQ ID NO 31
<211> LENGTH: 48
<212> TYPE: PRT
<213> ORGANISM: Monkeypox Virus/Zaire

<400> SEQUENCE: 31

Met Val Ile Gly Leu Val Ile Phe Val Ser Val Ala Ala Thr Ile Val
1               5                   10                  15

Gly Val Leu Ser Asn Val Leu Asp Met Leu Met Tyr Val Glu Glu Asn
            20                  25                  30

Asn Glu Glu Asp Ala Lys Ile Lys Glu Glu Gln Glu Leu Leu Leu Leu
        35                  40                  45

<210> SEQ ID NO 32
<211> LENGTH: 150
<212> TYPE: DNA
<213> ORGANISM: Variola Virus
<300> PUBLICATION INFORMATION:
<308> DATABASE ACCESSION NUMBER: GenBank No. X69198.1
<309> DATABASE ENTRY DATE: 1996-12-13

<400> SEQUENCE: 32
tcaatatagc aacagtagtt cttgctcctc cttaattcta gcatcttctt cattattttc    60
ttctacatac ataagcatct ccaatacgtt agacagcaca ccgatgatgg cggccgccac   120
agacacgaat atgactagac tgatgaccat                                         150

<210> SEQ ID NO 33
<211> LENGTH: 49
<212> TYPE: PRT
<213> ORGANISM: Variola Virus

<400> SEQUENCE: 33

Met Val Ile Ser Leu Val Ile Phe Val Ser Val Ala Ala Ala Ile Ile
 1               5                  10                  15

Gly Val Leu Ser Asn Val Leu Glu Met Leu Met Tyr Val Glu Glu Asn
            20                  25                  30

Asn Glu Glu Asp Ala Arg Ile Lys Glu Glu Gln Glu Leu Leu Leu Leu
        35                  40                  45

Tyr

<210> SEQ ID NO 34
<211> LENGTH: 186854
<212> TYPE: DNA
<213> ORGANISM: Artificial Sequence
<220> FEATURE:
<223> OTHER INFORMATION: LIVP Complete Genome

<400> SEQUENCE: 34
ttccactatc tgtggtacga acggtttcat cttctttgat gccatcaccc agatgttcta      60
taaacttggt atcctcgtcc gatttcatat cctttgccaa ccaatacata tagctaaact     120
caggcatatg ttccacacat cctgaacaat gaaattctcc agaagatgtt acaatgtcta     180
gatttggaca tttggtttca accgcgttaa catatgagtg aacacaccca tacatgaaag     240
cgatgagaaa taggattctc atcttgccaa aatatcacta gaaaaatttt atttatcaat     300
tttaaaggta taaaaaatac ttattgttgc tcgaatattt tgtatttgat ggtatacgga     360
agattagaaa tgtaggtatt atcatcaact gattctatgg ttttatgtat tctatcatgt     420
ttcactattg cgttggaaat aatatcatat gcttccacat atattttatt ttgttttaac     480
tcataatact cacgtaattc tggattattg gcatatctat gaataatttt agctccatga     540
tcagtaaata ttaatgagaa catagtatta ccacctacca ttatttttt catctcattc      600 aattcttaat tgcaaagatc tatataatca ttatagcgtt gacttatgga ctctggaatc     660
ttagacgatg tacagtcatc tataatcatg gcatatttaa tacattgttt tatagcatag     720
tcgttatcta cgatgttaga tatttctctc aatgaatcaa tcacacaatc taatgtaggt     780
ttatgacata atagcatttt cagcagttca atgttttag attcgttgat ggcaatggct     840
atacatgtat atccgttatt tgatctaatg ttgacatctg aaccggattc tagcagtaaa     900
gatactagag attgtttatt atatctaaca gccttgtgaa gaagtgtttc tcctcgtttg     960
tcaatcatgt taatgtcttt aagataaggt aggcaaatgt ttatagtact aagaattggg    1020
caagcataag acatgtcaca aagaccctt tttgtatgta taagtgtaaa aattataaca     1080
tccatagttg gatttacata ggtgtccaat cgggatctct ccatcatcga gataattgat    1140
ggcatctccc ttcctttttt agtagatatt tcatcgtgta agaatcaata ttaatatttc    1200
taaagtatcc gtgtatagcc tctttatta ccacagctcc atattccact agagggatat    1260
cgccgaatgt catatactca attagtatat gttggaggac atccgagttc attgtttca     1320 atatcaaaga gatggtttcc ttatcatttc tccatagtgg tacaaatacta cacattattc    1380 cgtgcggctt tccatttcc aaaaacaatt tgaccaaatc taaatctaca tctttattgt     1440

```
atctataatc actatttaga taatcagcca taattcctcg agtgcaacat gttagatcgt   1500
ctatatatga ataagcagtg ttatctattc ctttcattaa caatttaacg atgtctatat   1560
ctatatgaga tgacttaata taatattgaa gagctgtaca atagttttta tctataaaag   1620
acggcttgat tccgtgatta attagacatt taacaacttc cggacgcaca tatgctctcg   1680
tatccgactc tgaatacaga tgagagatga tatacagatg caatacggta ccgcaatttc   1740
gtagttgata atcatcatac gcgtatcagt actcgtcctc ataaagaaca ctgcagccat   1800
tttctatgaa caaatcaata attttagaaa caggatcatt gtcattacat aattttctat   1860
aactgaacga tggttttcac atttaacact caagtcaaat ccatgttcta ccaacacctt   1920
tatcaagtca acgtctacat ttttggattt catatagctg aatatattaa agttatttat   1980
gttgctaaat ccagtggctt ctagtagagc catcgctata tccttattaa ctttaacatg   2040
tctactattt gtgtattctt ctaatggggt aagctgtctc caattttgc gtaatggatt    2100 agtgccactg tctagtagta gtttgacgac ctcgacatta ttacaatgct cattaaaaag   2160
gtatgcgtgt aaagcattat tcttgaattg gttcctggta tcattaggat ctctgtcttt   2220
caacatctgt ttaagttcat caagagccac ctcctcattt tccaaatagt caaacatttt   2280
gactgaatga gctactgtga actctataca cccacacaac taatgtcatt aaatatcatg   2340
tcaaaaactt gtacaattat taataaaaat aatttagtgt ttaaatttta ccagttccag   2400
attttacacc tccgttaata cctccattaa ccccactgga cgatcctcct ccccacattc   2460
caccgccacc agatgtataa gttttagatc ctttattact accatcatgt ccatggataa   2520
agacactcca catgccgcca ctacccccctt tagaagacat attaataaga cttaaggaca   2580
agtttaacaa taaaattaat cacgagtacc ctactaccaa cctacactat tatatgatta   2640
tagtttctat tttacagta ccttgactaa agtttctagt cacaagagca atactaccaa    2700
cctacactat tatatgatta tagtttctat tttatagga acgcgtacga gaaaatcaaa   2760
tgtctaattt ctaacggtag tgttgataaa cgattgttat ccgcggatac ctcctctatc   2820
atgtcgtcta ttttcttact ttgttctatt aacttattag cattatatat tatttgatta   2880
taaaacttat attgcttatt agcccaatct gtaaatatcg gattattaac atatcgtttc   2940
tttgtaggtt tatttaacat gtacatcact gtaagcatgt ccttaccatt tattttaatt   3000
tgacgcatat ccgcaatttc ttttttcgcag tcggttataa attctatata tgatggatac   3060
atgctacatg tgtacttata atcgactaat atgaagtact tgatacatat tttcagtaac   3120
gattttatat taccacctat gaataagtac ctgtgatcgt ctaggtaatc aactgttttc   3180
ttaatacatt cgatggttgg taatttactc agaataattt ccaatatctt aatatataat   3240
tctgctattt ctgggatata tttatctgcc agtataacac aaatagtaat acatgtaaac   3300
ccatattttg ttattatatt aatgtctgcg ccattatcta ttaaccattc tactaggctg   3360
acactatgcg actcaataca atgataaagt atactacatc catgtttatc tattttgttt   3420
atatcatcaa tatacggctt acaaagtttt agtatcgata acacatccaa ctcacgcata   3480
gagaaggtag ggaataatgg cataatattt attaggttat catcattgtc attatctaca   3540
actaagtttc catttttta aatatactcg acaactttag gatctctatt gccaaatttt   3600
tgaaaatatt tatttatatg cttaaatcta tataatgtag ctccttcatc aatcatacat   3660
ttaataacat tgatgtatac tgtatgataa gatacatatt ctaacaatag atcttgtata   3720
gaatctgtat atctttaag aattgtggat attaggatat tattacataa actattacac    3780
```

```
aattctaaaa tataaaacgt atcacggtcg aataatagtt gatcaactat ataattatcg    3840
attttgtgat ttttcttcct aaactgttta cgtaaatagt tagatagaat attcattagt    3900
tcatgaccac tatagttact atcgaataac gcgtcaaata tttcccgttt aatatcgcat    3960
ttgtcaagat aataatagag tgtggtatgt tcacgataag tataataacg catctctttt    4020
tcgtgtgaaa ttaaatagtt tattacgtcc aaagatgtag cataaccatc ttgtgaccta    4080
gtaataatat aataatagag aactgtttta cccattctat catcataatc agtggtgtag    4140
tcgtaatcgt aatcgtctaa ttcatcatcc caattataat attcaccagc acgtctaatc    4200
tgttctattt tgatcttgta tccatactgt atgttgctac atgtaggtat tcctttatcc    4260
aataatagtt taaacacatc tacattggga tttgatgttg tagcgtattt ttctacaata    4320
ttaataccat ttttgatact atttatttct atacctttcg aaattagtaa tttcaataag    4380
tctatattga tgttatcaga acatagatat tcgaatatat caaaatcatt gatatttta    4440
tagtcgactg acgacaataa caaaatcaca acatcgtttt tgatattatt attttcttg    4500
gtaacgtatg cctttaatgg agtttcacca tcatactcat ataatggatt tgcaccactt    4560
tctatcaatg attgtgcact gctggcatcg atgttaaatg ttttacaact atcatagagt    4620
atcttatcgt taaccatgat tggttgttga tgctatcgca ttttttggtt tctttcattt    4680
cagttatgta tggatttagc acgtttggga agcatgagct catatgattt cagtactgta    4740
gtgtcagtac tattagtttc aataagatca atctctagat ctatagaatc aaaacacgat    4800
aggtcagaag ataatgaata tctgtaggct tcttgttgta ctgtaacttc tggttttgtt    4860
agatggttgc atcgtgcttt aacgtcaatg gtacaaattt tatcctcgct ttgtgtatca    4920
tattcgtccc tactataaaa ttgtatattc agattatcat gcgatgtgta tacgctaacg    4980
gtatcaataa acggagcaca ccatttagtc ataaccgtaa tccaaaaatt tttaaagtat    5040
atcttaacga aagaagttgt gtcattgtct acggtgtatg gtactagatc ctcataagtg    5100
tatatatcta gagtaatgtt taatttatta aatggttgat aatatggatc ctcgtgacaa    5160
tttccgaaga tggaaataag acataaacac gcaataaatc taattgcgga catggttact    5220
ccttaaaaaa atacgaataa tcaccttggc tatttagtaa gtgtcattta acactatact    5280
catattaatc catggactca taatctctat acgggattaa cggatgttct atatacgggg    5340
atgagtagtt ctcttctta actttatact ttttactaat catatttaga ctgatgtatg    5400
ggtaatagtg tttgaagagc tcgttctcat catcagaata aatcaatatc tctgttttt    5460
tgttatacag atgtattaca gcctcatata ttacgtaata gaacgtgtca tctaccttat    5520
taactttcac cgcatagttg tttgcaaata cggttaatcc tttgacctcg tcgatttccg    5580
accaatctgg gcgtataatg aatctaaact ttaattgctt gtaatcattc gaaataattt    5640
ttagtttgca tccgtagtta tcccctttat gtaactgtaa atttctcaac gcgatatctc    5700
cattaataat gatgtcgaat tcgtgctgta tacccatact gaatggatga acgaataccg    5760
acggcgttaa tagtaattta cttttttcatc tttacatatt gggtactagt tttactatca    5820
taagtttata aattccacaa gctactatgg aataagccaa ccatcttagt ataccacaca    5880
tgtcttaaag tttattaatt aattacatgt tgttttatat atatcgctac gaatttaaag    5940
agaaattagt ttaggaagaa aaattatcta tctacatcat cacgtctctg tattctacga    6000
tagagtgcta ctttaagatg cgacagatcc gtgtcatcaa atatatactc cattaaaatg    6060
attattccgg cagcgaactt gatattggat atatcacaac ctttgttaat atctacgaca    6120
atagacagca gtcccatggt tccataaaca gtgagtttat ctttctttga agagatattt    6180
```

```
tgtagagatc ttataaaact gtcgaatgac atcgcattta tatctttagc taaatcgtat    6240
atgttaccat cgtaatatct aaccgcgtct atcttaaacg tttccatcgc tttaaagacg    6300
tttccgatag atggtctcat ttcatcagtc atactgagcc aacaaatata atcgtgtata    6360
acatctttga tagaatcaga ctctaaagaa aacgaatcgg ctttattata cgcattcatg    6420
ataaacttaa tgaaaatgt ttttcgttgt ttaagttgga tgaatagtat gtcttaataa     6480
ttgttattat ttcattaatt aatatttagt aacgagtaca ctctataaaa acgagaatga    6540
cataactaat cataactagt tatcaaagtg tctaggacgc gtaattttca tatggtatag    6600
atcctgtaag cattgtctgt attctggagc tattttctct atcgcattag tgagttcaga    6660
atatgttata aatttaaatc gaataacgaa cataacttta gtaaagtcgt ctatattaac    6720
tcttttattt tctagccatc gtaataccat gtttaagata gtatattctc tagttactac    6780
gatctcatcg ttgtctagaa tatcacatac tgaatctaca tccaatttta gaaattggtc    6840
tgtgttacat atctcttcta tattattgtt gatgtattgt cgtagaaaac tattacgtag    6900
accatttcct ttataaaacg aatatatagt actccaatta tctttaccga tatatttgca    6960
cacataatcc attctctcaa tcactacatc tttaagattt tcgttgttaa gatatttggc    7020
taaactatat aattctatta gatcatcaac agaatcagta tatttttc tagatccaaa      7080 gacgaactct ttggcgtcct ctataatatt cccagaaaag atattttcgt gttttagttt    7140
atcgagatct gatctgttca tatacgccat gattgtacgg tacgttatga taaccgcata    7200
aaataaaaat ccattttcat ttttaaccaa tactattcat aattgagatt gatgtaatac    7260
tttgttactt tgaacgtaaa gacagtacac ggatccgtat ctccaacaag cacgtagtaa    7320
tcaaatttgg tgttgttaaa cttcgcaata ttcatcaatt tagatagaaa cttatactca    7380
tcatctgttt taggaatcca tgtattatta ccactttcca acttatcatt atcccaggct    7440
atgtttcgtc catcatcgtt gcgcagagtg aataattctt ttgtattcgg tagttcaaat    7500
atatgatcca tgcatagatc ggcaaagcta ttgtagatgt gattttttcct aaatctaata   7560 taaaactcgt ttactagcaa acactttcct gattatcga ccaagacaca tatggtttct     7620
aaatctatca agtggtgggg atccatagtt atgacgcagt aacatatatt attacattct    7680
tgactgtcgc taatatctaa atatttattg ttatcgtatt ggattctgca tatagatggc    7740
ttgtatgtca aagatataga acacataacc aatttatagt cgcgctttac attctcgaat    7800
ctaaagttaa gagatttaga aaacattata tcctcggatg atgttatcac tgtttctgga    7860
gtaggatata ttaaagtctt tacagatttc gtccgattca aataaatcac taaataatat    7920
cccacattat catctgttag agtagtatca ttaaatctat tatattttat gaaagatata    7980
tcactgctca cctctatatt tcgtacattt ttaaactgtt tgtataatat ctctctgata    8040
caatcagata tatctattgt gtcggtagac gataccgtta catttgaatt aatggtgttc    8100 catttttacaa cttttaacaa gttgaccaat tcatttctaa tagtatcaaa ctctccatga   8160
ttaaatattt taatagtatc catttttatat cactacggac acaaagtagc tgacataaac   8220
cattgtataa tttttatgtt ttatgtttat tagcgtacac attttggaag ttccggcttc    8280
catgtatttc ctggagagca agtagatgat gaggaaccag atagtttata tccgtacttg    8340
cacttaaagt ctacattgtc gttgtatgag tatgatcttt taaacccgct agacaagtat    8400
ccgtttgata ttgtaggatg tggacattta acaatctgac acgtgggtgg atcggaccat    8460
tctcctcctg aacacaggac actagagtta ccaatcaacg aatatccact attgcaacta    8520
```

```
taagttacaa cgctcccatc ggtataaaaa tcctcgtatc cgttatgtct tccgttggat    8580
atagatggag gggattggca tttaacagat tcacaaatag gtgcctcggg attccatacc    8640
atagatccag tagatcctaa ttcacaatac gatttagatt caccgatcaa ctgatatccg    8700
ctattacaag agtacgttat actagagcca aagtctactc caccaatatc aagttggcca    8760
ttatcgatat ctcgaggcga tgggcatctc cgtttaatac attgattaaa gagtgtccat    8820
ccagtacctg tacatttagc atatataggt cccatttttt gctttctgta tccaggtaga    8880
catagatatt ctatagtgtc tcctatgttg taattagcat tagcatcagt ctccacacta    8940
ttcttaaatt tcatattaat gggtcgtgac ggaatagtaa agcatgatag aacgcatcct    9000
attcccaaca atgtcaggaa cgtcacgctc tccaccttca tatttattta tccgtaaaaa    9060
tgttatcctg gacatcgtac aaataataaa aagcccatat atgttcgcta ttgtagaaat    9120
tgtttttcac agttgctcaa aaacgatggc agtgacttat gagttacgtt acactttgga    9180
gtctcatctt tagtaaacat atcataatat tcgatattac gagttgacat atcgaacaaa    9240
ttccaagtat ttgattttgg ataatattcg tattttgcat ctgctataat taagatataa    9300
tcaccgcaag aacacacgaa catctttcct acatggttaa agtacatgta caattctatc    9360
catttgtctt ccttaactat atatttgtat agataattac gagtctcgtg agtaattcca    9420
gtaattacat agatgtcgcc gtcgtactct acagcataaa ctatactatg atgtctaggc    9480
atgggagact ttttatcca acgattttta gtgaaacatt ccacatcgtt taatactaca     9540
tatttctcat acgtggtata aactccaccc attacatata tatcatcgtt tacgaatacc    9600
gacgcgcctg aatatctagg agtaattaag tttggaagtc ttatccatt cgaagtgccg     9660 tgtttcaaat attctgccac acccgttgaa atagaaaatt ctaatcctcc tattacatat    9720
aactttccat cgttaacaca agtactaact tctgatttta acgacgacat attagtaacc    9780
gttttccatt ttttcgtttt aagatctacc cgcgatacgg aataaacatg tctattgtta    9840
atcatgccgc caataatgta tagacaatta tgtaaaacat ttgcattata gaattgtcta    9900
tctgtattac cgactatcgt ccaatattct gttctaggag agtaatgggt tattgtggat    9960
atataatcag agttttttaat gactactata ttatgtttta taccatttcg tgtcactggc   10020
tttgtagatt tggatatagt taatcccaac aatgatatag cattgcgcat agtattagtc   10080
ataaacttgg gatgtaaaat gttgatgata tctacatcgt ttggattttt atgtatccac   10140
tttaataata tcatagctgt aacatcctca tgatttacgt taacgtcttc gtgggataag   10200
atagttgtca gttcatcctt tgataatttt ccaaattctg gatcggatgt caccgcagta   10260
atattgttga ttatttctga catcgacgca ttatatagtt ttttaattcc atatcttta    10320 gaaaagttaa acatccttat acaatttgtg aaattaaat tatgaatcat agttttaca     10380 catagatcta ctacaggcgg aacatcaatt attatggcag caactagtat catttctaca   10440
ttgtttatgg tgatgtttat cttcttccag cgcatatagt ctaatagcga ttcaaacgcg   10500
tgatagttta taccattcaa tataatcgct tcatcctttta gatggtgatc ctgaatgcgt   10560
ttaaaaaaat tatacggaga cgccgtaata atttccttat tcacttgtat aatttcccca   10620
ttgatagaaa atattacgct ttccattctt aaagtactat aagtaattat agtataatgt   10680
aaacgtttat atattcaata ttttataaa atcattttg acattaattc cttttttaaat   10740 ttccgtctat catctataga aacgtattct atgaatttat aaaatgcttt tacgtgtcct   10800
atcgtaggcg atagaaccgc taaaaagcct atcgaatttc tacaaaagaa tctgttatat   10860
ggtataggga gagtataaaa cattaaatgt ccgtacttat taaagtattc agtagccaat   10920
```

```
cctaactctt tcgaatactt attaatggct cttgttctgt acgaatctat tttttttgaac    10980
aacggaccta gtggtatatc ttgttctatg tatctaaaat aatgtctgac tagatccgtt    11040
agtttaatat ccgcagtcat cttgtctaga atggcaaatc taactgcggg tttaggcttt    11100
agtttagttt ctatatctac atctatgtct ttatctaaca ccaaaaatat aatagctaat    11160
attttattac aatcatccgg atattcttct acgatctcac taactaatgt ttctttggtt    11220
atactagtat agtcactatc ggacaaataa agaaaatcag atgatcgatg aataatacat    11280
ttaaattcat catctgtaag attttttgaga tgtctcatta gaatattatt agggttagta    11340
ctcattatca ttcggcagct attacttatt ttattatttt tcaccatata gatcaatcat    11400
tagatcatca aaatatgttt caatcatcct aaagagtatg gtaaatgact cttcccatct    11460
aatttctgaa cgttcaccaa tgtctctagc cactttggca ctaatagcga tcattcgctt    11520
agcgtcttct atattattaa ctggttgatt caatctatct agcaatggac cgtcggacag    11580
cgtcattctc atgttcttaa tcaatgtaca tacatcgccg tcatctacca attcatccaa    11640
caacataagc ttttttaaaat catcattata ataggtttga tcgttgtcat ttctccaaag    11700
aatatatcta ataagtagag tcctcatgct tagttaacaa ctattttta tgttaaatca    11760
attagtacac cgctatgttt aatacttatt catatttag ttttttaggat tgagaatcaa    11820
tacaaaaatt aatgcatcat taattttaga aatacttagt ttccacgtag tcaatgaaac    11880
atttgaactc atcgtacagg acgttctcgt acaggacgta actataaacc ggtttatatt    11940
tgttcaagat agatacaaat ccgataactt tttttacgaa ttctacggga tccactttaa    12000
aagtgtcata ccgggttctt tttatttttt taaacagatc aatggtgtga tgttgattag    12060
gtcttttacg aatttgatat agaatagcgt ttacatatcc tccataatgg tcaatcgcca    12120
tttgttcgta tgtcataaat tctttaatta tatgacactg tgtattattt agttcatcct    12180
tgttcattgt taggaatcta tccaaaatgg caattatact agaactatag gtgcgttgta    12240
tacacatatt gatgtgtctg tttatacaat caatgctact accttcgggt aaaattgtag    12300
catcatatac catttctagt actttaggtt cattattatc cattgcagag gacgtcatga    12360
tcgaatcata aaaaaatata ttatttttat gttattttgt taaaaataat catcgaatac    12420
ttcgtaagat actccttcat gaacataatc agttacaaaa cgtttatatg aagtaaagta    12480
tctacgattt ttacaaaagt ccggatgcat aagtacaaag tacgcgataa acggaataat    12540
aatagattta tctagtctat cttttttctat agctttcata gttagataca tggtctcaga    12600
agtaggatta tgtaacatca gcttcgataa aatgactggg ttatttagtc ttacacattc    12660
gctcatacat gtatgaccgt taactacaga gtctacacta aaatgattga acaatagata    12720
gtctaccatt gtttcgtatt cagatagtac agcgtagtac atggcatctt cacaaattat    12780
atcattgtct aatagatatt tgacgcatct tatggatccc acttcaacag ccatcttaaa    12840
atcggtagaa tcatattgct ttcctttatc attaataatt tctagaacat catctctatc    12900
ataaaagata caaatattaa ctgtttgatc cgtaataaca ttgctagtcg atagcaattt    12960
gttaataaga tgcgctgggc tcaatgtctt aataagaagt gtaagaggac tatctccgaa    13020
tttgttttgt ttattaacat ccgttgatgg aagtaaaaga tctataatgt ctacattctt    13080
gactgtttta gagcatacaa tatggagagg tgtatttcca tcatgatctg gttttgaggg    13140
actaattcct agtttcatca tccatgagat tgtagaagct tttggattgt ctgacataag    13200
atgtctatga atatgatttt tgccaaattt atccactatc ctggcttcga atccgatgga    13260
```

```
cattattttt ttaaacactc tttctgaagg atctgtacac gccaacaacg gaccacatcc   13320
ttcttcatca accgagttgt taatcttggc tccatactgt accaataaat ttattctctc   13380
tatgacttca tcatctgttc ccgagagata atatagaggc gttttatgct gtttatcaca   13440
cgcgtttgga tctgcgccgt gcgtcagcag catcgcgact attctattat tattaatttt   13500
agaagctata tgcaatggat aatttccatc atcatccgtc tcatttggag agtatcctct   13560
atgaagaagt tcttcgacaa atcgttcatc tagtcccttta attccacaat acgcatgtag   13620
aatgtgataa ttatttccag aaggttcgat agcttgtagc atattcctaa atacatctaa   13680
atttttacta ttatatttgg cataaagaga tagataatac tcggccgaca taatgttgtc   13740
cattgtagta taaaaattaa tatttctatt tctgtatatt tgcaacaatt tactctctat   13800
aacaaatatc ataacttagt tcttttatgt caagaaggca ctggtttagt tcatctataa   13860
atgtcacgcc ataactacca cgcatgccat actcagaatt atgataaaga tatttatcct   13920
tggggtgtag gtaatgggga ttaatctttg ttggatcagt ctctaagtta acacatgtca   13980
cacatgatcc atttatagtt atatcacacg atgatgattt atgaattgat tccggaagat   14040
cgctatcgta ttttgtggtt ccacaattca tttccataca tgttattgtc acactaatat   14100
tatgatgaac tttatctagc cgctgagtgg taaacaacag aacagatagt ttattatctt   14160
taccaacacc ctcagccgct gccacaaatc tctgatccgt atccatgatg gtcatgttta   14220
tttctagtcc gtatccagtc aacactatgt tagcatttct gtcgatatag ctttcactca   14280
tatgacactc accaataata gtagaattaa tgtcgtaatt tacaccaata gtgagttcgg   14340
cggcaaagta ccaataccgg taatcttgtc gaggaggaca tatagtattc ttgtattcta   14400
ccgaataccc gagagatgcg atacaaaaga gcaagactaa tttgtaaacc atcttactca   14460
aaatatgtaa caatagtacg atgcaatgag taagacaata ggaaatctat cttatataca   14520
cataattatt ctatcaatttt taccaattag ttagtgtaat gttaacaaaa atgtgggaga   14580
atctaattag tttttctttta cacaattgac gtacatgagt ctgagttcct tgttttttgct   14640 aattatttca tccaatttat tattcttgac gatatcgaga tcttttgtat aggagtcaaa   14700
cttgtattca acatgctttt ctataatcat tttagctatt tcggcatcat ccaatagtac   14760
attttccaga ttagcagaat agatattaat gtcgtatttg aacagagcct gtaacatctc   14820 aatgtctttta ttatctatag ccaatttaat gtccggaatg aagagaaggg aattattggt   14880
gtttgtcgac gtcatatagt cgagcaagag aatcatcata tccacgtgtc cattttttat   14940
agtgatgtga atacaactaa ggagaatagc cagatcaaaa gtagatggta tctctgaaag   15000
aaagtaggaa acaatactta catcattaag catgacggca tgataaaatg aagttttcca   15060
tccagttttc ccatagaaca tcagtctcca attttttctta acaaacagtt ttaccgtttg   15120
catgttacca ctatcaaccg cataatacaa tgcggtgttt cccttgtcat caaattgtga   15180
atcatccagt ccactgaata gcaaaatctt tactattttg gtatcttcca atgtggctgc   15240
ctgatgtaat ggaaattcat tctctagaag attttttcaat gctccagcgt tcaacaacgt   15300
acatactaga cgcacgttat tatcagctat tgcataatac aaggcactat gtccatggac   15360
atccgcctta aatgtatctt tactagagag aaagcttttc agctgcttag acttccaagt   15420
attaattcgt gacagatcca tgtctgaaac gagacgctaa ttagtgtata ttttttcatt   15480
ttttataatt ttgtcatatt gcaccagaat taataatatc tttaatagat ctgattagta   15540
gatacatggc tatcgcaaaa caacatatac acatttaata aaaataatat ttattaagaa   15600
aattcagatt tcacgtaccc atcaatataa ataaaataat gattccttac accgtaccca   15660
```

-continued

```
tattaaggag attccacctt acccataaac aatataaatc cagtaatatc atgtctgatg    15720
atgaacacaa atggtgtatt aaattccagt ttttcaggag atgatctcgc cgtagctacc    15780
ataatagtag atgcctctgc tacagttcct tgttcgtcga catctatctt tgcattctga    15840
aacattttat aaatatataa tgggtcccta gtcatatgtt taaacgacgc attatctgga    15900
ttaaacatac taggagccat catttcggct atcgacttaa tatccctctt attttcgata    15960
gaaaatttag ggagtttaag attgtacact ttattcccta attgagacga ccaatagtct    16020
aattttgcag ccgtgataga atctgtgaaa tgggtcatat tatcacctat tgccaggtac    16080
atactaatat tagcatcctt atacggaagg cgtaccatgt catattcttt gtcatcgatt    16140
gtgattgtat ttccttgcaa tttagtaact acgttcatca tgggaaccgt tttcgtaccg    16200
tacttattag taaaactagc attgcgtgtt ttagtgatat caaacggata ttgccatata    16260
cctttaaaat atatagtatt aatgattgcc catagagtat tattgtcgag catattagaa    16320
tctactacat tagacatacc ggatctacgt tctactatag aattaatttt attaaccgca    16380
tctcgtctaa agtttaatct atataggccg aatctatgat attgttgata atacgacggt    16440
ttaatgcaca cagtattatc tacgaaactt tgataagtta gatcagtgta cgtatattta    16500
gatgttttca gcttagctaa tcctgatatt aattctgtaa atgctggacc cagatctctt    16560
tttctcaaat ccatagtctt caataattct attctagtat tacctgatgc aggcaatagc    16620
gacataaaca tagaaaacga ataaccaaac ggtgagaaga caatattatc atcttgaata    16680
tttttatacg ctactatacc ggcattggta aatccttgta gacgataggc ggacgctgaa    16740
cacgctaacg atagtatcaa taacgcaatc atgattttat ggtattaata attaaccttg    16800
tttttatgtt cggtataaaa aaattattga tgtctcacaca tccttttgta attgacatct    16860
atatatcctt ttgtataatc aactctaatc actttaactt ttacagtttt ccctaccagt    16920
ttatccctat attcaacata tctatccata tgcatcttaa cactctctgc caagatagct    16980
tcagagtgag gatagtcaaa aagataaata tatagagcat aatcattctc gtatactctg    17040 cccctttatta catcacccgc attgggcaac gaataacaaa atgcaagcat cttgttaacg    17100
ggctcgtaaa ttgggataaa aattatgttt ttattgtctt atatctattt tattcaagag    17160
aatattcagg aatttctttt tccggttgta tctcgtcgca gtatatatca tttgtacatt    17220
gtttcatatt ttttaatagt ttacacccttt tagtaggact agtatcgtac aattcatagc    17280
tgtattttga attccaatca cgcataaaaa tatcttccaa ttgttgacga agacctaatc    17340
catcatccgg tgtaatatta atagatgctc cacatgtatc cgtaaagtaa tttcctgtcc    17400
aatttgaggt acctatatag gccgttttat cggttaccat atatttggca tggtttaccc    17460
tagaatacgg aatgggagga tcagcatctg gtacaataaa tagctttact tctatattta    17520 tgttttaga tttagcata gcgatagatc ttaaaaagtt tctcatgata aacgaagatc    17580
gttgccagca actaatcaat agcttaacgg atacttgtct gtctatagcg gatcttctta    17640
attcatcttc tatataaggc caaaacaaaa ttttacccgc cttcgaataa ataataggga    17700
taaagttcat aacagataca taaacgaatt tactcgcatt tctaatacat gacaataaag    17760
cggttaaatc attggttctt tccatagtac atagttgttg cggtgcagaa gcaataaata    17820
cagagtgtgg aacgccgctt acgttaatac taagaggatg atctgtatta taatacgacg    17880
gataaaagtt tttccaatta tatggtagat tgttaactcc aagataccag tatacctcaa    17940
aaatttgagt gagatccgct gccaagttcc tattattgaa gatcgcaata cccaattcct    18000
```

```
tgacctgagt tagtgatctc caatccatgt tagcgcttcc taaataaata tgtgtattat    18060
cagatatcca aaattttgta tgaagaactc ctcctaggat atttgtaata tctatgtatc    18120
gtacttcaac tccggccatt tgtagtcttt caacatcctt taatggtttg ttagatttat    18180
taacggctac tctaactcgt actcctcttt tgggtaattg tacaatctcg tttaatatta    18240
tcgtgccgaa attcgtaccc acttcatccg ataaactcca ataaaagat gatatatcta     18300
gtgttttgt ggtattggat agaatttccc tccacatgtt aaatgtagac aaatatactt     18360
tatcaaattg catacctata ggaatagttt ctgtaatcac tgcgattgta ttatccggat    18420
tcattttatt tgttaaaaga ataatcctat atcacttcac tctattaaaa atccaagttt    18480
ctatttcttt catgactgat tttttaactt catccgtttc cttatgaaga tgatgtttgg    18540
caccttcata aattttttatt tctctattac aatttgcatg ttgcatgaaa taatatgcac   18600
ctaaaacatc gctaatctta ttgtttgttc cctggagtat gagagtcggg ggggtgttaa    18660
tcttggaaat tattttttcta accttgttgg tagccttcaa gacctgacta gcaaatccag   18720
ccttaatttt ttcatgattg actaatgggt cgtattggta tttataaact ttatccatat    18780
ctctagatac tgattctgga catagctttc cgactggcgc atttggtgtg atggttccca    18840
taagtttggc agctagcaga ttcagtcttg aaacagcatc tgcattaact agaggagaca    18900
ttagaatcat tgctgtaaac aagtttggat tatcgtaaga ggctagctcc catgaatga    18960
cccaataagt agatttaata gttaccacgt gctgtaccaa agtcatcaat catcattttt    19020
tcaccattac ttcttccatg tccaatatga tcatgtgaga atactaaaat tcctaacgat    19080
gatatgtttt cagctagttc gtcataacgt ccagaatgtt taccagctcc atgacttatg    19140
aatactaatg ccttaggata tgtaataggt ttccaatatt tacaatatat gtaatcattg    19200
tccagattga acatacagtt tgcactcatg attcacgtta tataactatc aatattaaca    19260
gttcgtttga tgatcatatt attttttatgt tttattgata attgtaaaaa catacaatta   19320
aatcaatata gaggaaggag acggctactg tcttttgtaa gatagtcatg gcgactaaat    19380
tagattatga ggatgctgtt ttttactttg tggatgatga taaaatatgt agtcgcgact    19440
ccatcatcga tctaatagat gaatatatta cgtggagaaa tcatgtttata gtgtttaaca   19500
aagatattac cagttgtgga agactgtaca aggaattgat gaagttcgat gatgtcgcta    19560
tacggtacta tggtattgat aaaattaatg agattgtcga agctatgagc gaaggagacc    19620
actacatcaa ttttacaaaa gtccatgatc aggaaagttt attcgctacc ataggaatat    19680
gtgctaaaat cactgaacat tggggataca aaaagatttc agaatctaga ttccaatcat    19740
tgggaaacat tacagatttg atgaccgacg ataatataaa catcttgata cttttttctag   19800
aaaaaaaatt gaattgatga tataggggtc ttcataacgc ataattatta cgttagcatt    19860
ctatatccgt gttaaaaaaa attatcctat catgtatttg agagttttat atgtagcaaa    19920
catgatagct gtgatgccaa taagctttag atattcacgc gtgctagtgt tagggatggt    19980
attatctggt ggtgaaatgt ccgttatata atctacaaaa caatcatcgc atatagtatg    20040
cgatagtaga gtaaacattt ttatagtttt tactggattc atacatcgtc tacccaattc    20100
ggttataaat gaaattgtcg ccaatcttac acccaacccc ttgttatcca ttagcatagt    20160
attaacttcg ttatttatgt cataaactgt aaatgatttt gtagatgcca tatcatacat    20220
gatattcatg tccctattat aatcattact aactttatca caatatatgt tgataatatc    20280
tatatatgat ctagtctttg tgggcaactg tctatacaag tcgtctaaac gttgtttact    20340
catatagtat cgaacagcca tcattacatg gtcccgttcc gttgatagat aatcgagtat    20400
```

```
gttagtggac ttgtcaaatc tatataccat attttctgga agtggatata catagtcgtg   20460
atcaacatta ttgctagcct catcttctat atcctgtact ataccattat ctatatcatc   20520
tacataatct atgatattat tacacataaa catcgacaac atactattgt ttattatcta   20580
agtcctgttg atccaaaccc ttgatctcct ctatttgtac tatctagaga ttgtacttct   20640
tccagttctg gataatatat acgttgatag attagctgag ctattctatc tccagtattt   20700
acattaaacg tacattttcc attattaata agaatgactc ctatgttttcc cctataatct   20760 tcgtctatta caccacctcc tatatcaatg ccttttagtg acagaccaga cctaggagct   20820
attctaccat agcagaactt aggcatggac atactaatat ctgtcttaat taactgtctt   20880
tctcctggag ggatagtata atcgtaagcg ctatacaaat catatccggc agcacccggc   20940
gattgcctag taggagattt agctctgtta gtttccttaa caaatctaac tggtgagtta   21000
atattcatgt tgaacataaa actaatattt tatttcaaaa ttatttacca tcccatatat   21060
tccatgaata agtgtgatga ttgtacactt ctatagtatc tatatacgat ccacgataaa   21120
atcctcctat caatagcagt ttattatcca ctatgatcaa ttctggatta tccctcggat   21180
aaataggatc atctatcaga gtccatgtat tgctggattc acaataaaat tccgcatttc   21240
taccaaccaa gaataacctt ctaccgaaca ctaacgcgca tgatttataa tgaggataat   21300
aagtggatgg tccaaactgc cactgatcat gattgggtag caaatattct gtagttgtat   21360
cagtttcaga atgtcctccc attacgtata taacattgtt tatggatgcc actgctggat   21420
tacatctagg tttcagaaga ctcggcatat taacccaagc agcatccccg tggaaccaac   21480
gctcaacaga tgtgggattt ggtagacctc ctactacgta taatttattg ttagcgggta   21540
tcccgctagc atacagtctg gggctattca tcggaggaat tggaatccaa ttgtttgata   21600
tataatttac cgctatagca ttgttatgta tttcattgtt catccatcca ccgatgagat   21660
atactacttc tccaacatga gtacttgtac acatatggaa tatatctata atttgatcca   21720
tgttcatagg atactctatg aatggatact tgtatgattt gcgtggttgt ttatcacaat   21780
gaaatatttt ggtacagtct agtatccatt ttacattatt tatacctctg ggagaaagat   21840
aatttgacct gattacattt ttgataagga gtagcagatt tcctaattta tttcttcgct   21900
ttatatacca cttaatgaca aaatcaacta cataatcctc atctggaaca tttagttcat   21960
cgctttctag aataagtttc atagatagat aatcaaaatt gtctatgatg tcatcttcca   22020
gttccaaaaa gtgtttggca ataaagtttt tagtatgaca taagagattg gatagtccgt   22080
attctatacc catcatgtaa cactcgacac aatattcctt tctaaaatct cgtaagataa   22140
agtttataca agtgtagatg ataaattcta cagaggttaa tatagaagca cgtaataaat   22200
tgacgacgtt atgactatct atatatacct ttccagtata cgagtaaata actatagaag   22260
ttaaactgtg aatgtcaagg tctagacaaa ccctcgtaac tggatcttta tttttcgtgt   22320 attttttgacg taaatgtgtg cgaaagtaag gagataactt tttcaatatc gtagaattga   22380
ctattatatt gcctcctatg gcatcaataa ttgttttgaa tttcttagtc atagacaatg   22440
ctaatatatt cttacagtac acagtattga caaatatcgg catttatgtt tctttaaaag   22500
tcaacatcta gagaaaaatg attatctttt tgagacataa ctcccatttt ttggtattca   22560
cccacacgtt tttcgaaaaa attagttttt ccttccaatg atatattttc catgaaatca   22620
aacggattgg taacattata aattttttta aatcccaatt cagaaatcaa tctatccgcg   22680
acgaattcta tatatgtttt catcatttca caattcattc ctataagttt aactggaaga   22740
```

```
gccgcagtaa gaaattcttg ttcaatggat actgcatctg ttataataga tctaacggtt    22800
tcttcactcg gtggatgcaa taaatgttta aacatcaaac atgcgaaatc gcagtgcaga    22860
ccctcgtctc tactaattag ttcgttggaa aacgtgagtc cgggcattag gccacgcttt    22920
ttaagccaaa atatggaagc gaatgatccg gaaaagaaga ttccttctac tgcagcaaag    22980
gcaataagtc tctctccata accggcgctg tcatgtatcc acttttgagc ccaatcggcc    23040 ttcttttta cacaaggcat cgtttctatg gcattaaaga gatagttttt ttcattacta    23100
tctttaacat aagtatcgat caaaagacta tacatttccg aatgaatgtt ttcaatggcc    23160
atctgaaatc cgtagaaaca tctagcctcg gtaatctgta cttctgtaca aaatcgttcc    23220
gccaaatttt cattcactat tccgtcactg gctgcaaaaa acgccaatac atgttttata    23280
aaatattttt cgtctggtgt tagtttattc caatcattga tatctttaga tatatctact    23340
tcttccactg tccaaaatga tgcctctgcc ttttatatca tgttccagat gtcatgatat    23400
tggattggga aaataacaaa tctatttgga tttggtgcaa ggatgggttc cataactaaa    23460
ttaacaataa caataaattt ttttcagtt atctatatgc ctgtacttgg attttttgta    23520
catcgatatc gccgcaatca ctacaataat tacaagtatt attgatagca ttgttattag    23580
tactatcata attaaattat ctacattcat gggtgctgaa taatcgttat tatcatcatt    23640
atcattttgt aattgtgaca tcatactaga taaatcgttt gcgagattgt tgtgggaagc    23700
gggcatggag gatgcattat cattattatt taacgccttc catttggatt cacaaatgtt    23760
acgcacattc aacattttat ggaaactata attttgtgaa aacaaataac aagaaaactc    23820
gtcatcgttc aaattttaa cgatagtaaa ccgattaaac gtcgagctaa tttctaacgc    23880
tagcgactct gttggatatg ggtttccaga tatatatctt ttcagttccc ctacgtatct    23940
ataatcatct gtaggaaatg gaagatattt ccatttatct actgttccta atatcatatg    24000
tggtggtgta gtagaaccat taagcgcgaa agatgttatt tcgcatcgta ttttaacttc    24060
gcaataattt ctggttagat aacgcactct accagtcaag tcaatgatat tagcctttac    24120
agatatattc atagtagtcg taacgatgac tccatctttt agatgcgata ctcctttgta    24180
tgtaccagaa tcttcgtacc tcaaactcga tatatttaaa caagttaatg agatattaac    24240
gcgttttatg aatgatgata tataaccaga agttttatcc tcggtggcta gcgctataac    24300
cttatcatta taataccaac tagtgtgatt aatatgtgac acgtcagtgt gggtacaaat    24360
atgtacatta tcgtctacgt cgtattcgat acatccgcat acagccaaca aatataaaat    24420
gacaaatact ctaacgccgt tcgtacccat cttgatgcgg tttaataaat gttttgattt    24480
caatttattg taaaaaaaga ttcggtttta tactgttcga tattctcatt gcttatattt    24540
tcatctatca tctccacaca gtcaaatccg tggttagcat gcacctcatc aaccggtaaa    24600
agactatcgg actcttctat cattataact ctagaatatt taatttggtc attattaatc    24660
aagtcaatta tcttattttt aacaaacgtg agtattttac tcattttta taaaaacttt    24720 tagaaatata cagactctat cgtgtgtcta tatcttcttt ttatatccaa tgtatttatg    24780 tctgatttt cttcatttat catatataat ggtccaaatt ctacacgtgc ttcggattca    24840
tccagatcat taaggttctt ataattgtaa catccttctc ttccctcttc tacatcttcc    24900
ttcttattct tattccttagc gtcacagaat ctaccacagc aggatcccat gacgagcgtc    24960
atattaaact aatccatttt caattataat atatgattag taatgaccat taaaataaaa    25020
aatattcttc ataaccggca agaaagtgaa aagttcacat tgaaactatg tcagtagtat    25080
acatcatgaa atgatgatat atatatactc tattttggtg gaggattata tgatataatt    25140
```

```
cgtggataat catttttaag acacatttct ttattcgtaa atcttttcac gttaaatgag   25200
tgtccatatt ttgcaatttc ttcatatgat ggcggtgtac gtggacgagg ctgctcctgt   25260
tcttgttgtg gtcgccgact gtcgtgtctg cgtttagatc cctccattat cgcgattgcg   25320
tagatggagt actattttat accttgtaat taaatttttt tattaattaa acgtataaaa   25380
acgttccgta tctgtattta agagccagat ttcgtctaat agaacaaata gctacagtaa   25440
aaataactag aataattgct acacccacta gaaaccacgg atcgtaatac ggcaatcggt   25500
tttcgataat aggtggaacg tatattttat ttaaggactt aacaattgtc tgtaaaccac   25560
aatttgcttc cgcggatcct gtattaacta tctgtaaaag catatgttga ccgggcggag   25620
ccgaacattc tccgatatct aatttctgta tatctataat attattaacc tccgcatacg   25680
cattacagtt cttttctagc ttggataccg cactaggtac atcgtctaga tctattccta   25740
tttcctcagc gatagctctt ctatcctttt ccggaagcaa tgaaatcact tcaataaatg   25800
attcaaccat gagtgtgaaa ctaagtcgag aattactcat gcatttgtta gttattcgga   25860
gcgcgcaatt tttaaactgt cctataacct ctcctatatg aatagcacaa gtgacattag   25920
tagggataga atgttgagct aatttttgta ataactatc tataaaaaga ttatacaaag   25980
ttttaaactc tttagtttcc gccatttatc cagtctgaga aaatgtctct cataataaat   26040
ttttccaaga aactaattgg gtgaagaatg gaaacctta atctatattt atcacagtct   26100
gttttggtac acatgatgaa ttcttccaat gccgtactaa attcgatatc ttttcgatt   26160
tctggatatg ttttaataa agtatgaaca aagaaatgga atcgtaata ccagttatgt   26220
ttaactttga aattgttttt tattttcttg ttaatgattc cagccacttg ggaaaagtca   26280
aagtcgttta atgccgattt aatacgttca ttaaaaacaa acttttatc ctttagatga   26340
attattattg gttcattgga atcaaaaagt aagatattat cgggtttaag atctgcgtgt   26400
aaaaagttgt cgcaacaggg tagttcgtag attttaatgt ataacagagc catctgtaaa   26460
aagataaact ttatgtattg taccaaagat ttaaatccta atttgatagc taactcggta   26520
tctactttat ctgccgaata cagtgctagg ggaaaaatta taatgtttcc tctttcatat   26580
tcgtagttag ttctcttttc atgttcgaaa aagtgaaaca tgcggttaaa atagtttata   26640
acattaatat tactgttaat aactgccgga taaaagtggg atagtaattt cacgaatttg   26700
atactgtcct ttctctcgtt aaacgccttt aaaaaaactt tagaagaata tctcaatgag   26760
agttcctgac catccatagt ttgtatcaat aatagcaaca tatgaagaac acgtttatac   26820
agagtatgta aaaatgttaa tttatagttt aatcccatgg cccacgcaca cacgattaat   26880
ttttttcat ctcccttag attgttgtat agaaatttgg gtactgtgaa ctccgccgta   26940
gtttccatgg gactatataa ttttgtggcc tcgaatacaa attttactac atagttatct   27000
atcttaaaga ctataccata tcctcctgta gatatgtgat aaaaatcgtc gtttatagga   27060
taaaatcgtt tatccttttg ttggaaaaag gatgaattaa tgtaatcatt ctcttctatc   27120
tttagtagtg tttccttatt aaaattctta aaataattta acaatctaac tgacggagcc   27180
caattttggt gtaaatctaa ttgggacatt atattgttaa aatacaaaca gtctcctaat   27240
ataacagtat ctgataatct atggggagac atccattgat attcagggga tgaatcattg   27300
gcaacaccca tttattgtac aaaaagcccc aatttacaaa cgaaagtcca ggtttgatag   27360
agacaaacaa ttaactattt tgtctctgtt tttaacacct ccacagtttt taatttcttt   27420
agtaatgaaa ttattcacaa tatcagtatc ttctttatct accagagatt ttactaactt   27480
```

```
gataaccttg gctgtctcat tcaatagggt agtaatattt gtatgtgtga tattgatatc   27540
tttttgaatt gtttctttta gaagtgattc tttgatggtg ccagcatacg aattacaata   27600
atgcagaaac tcggttaaca tgcaggaatt atagtaagcc aattccaatt gttgcctgtg   27660
ttgtattaga gtgtcaatat gagcaatggt gtccttgcgt ttctctgata gaatgcgagc   27720
agcgattttg gcgttatcat ttgacgatat ttctggaatg acgaatcctg tttctactaa   27780 cttttttggta ggacaaagtg aaacaatcaa gaagatagct ctcctcccta tttgtggaag   27840
aaattgaact cctctagatg atctactgac gatagtatct ccttgacaga tattggaccg   27900
aattacagaa gtacctggaa tgtaaagccc tgaaacccccc tcatttttta agcagattgt   27960
tgccgtaaat cctgcactat gcccaagata gagagctcct ttggtgaatc catctctatg   28020
tttcagttta accaagaaac agtcagctgg tctaaaattt ccatctctat ctaatacagc   28080
atctaacttg atgtcaggaa ctatgaccgg tttaatgtta tatgtaacat tgagtaaatc   28140
cttaagttca taatcatcac tgtcatcagt tatgtacgat ccaaacaatg tttctaccgg   28200
catagtggat acgaagatgc tatccatcag aatgtttccc tgattagtat tttctatata   28260
gctattcttc tttaaacgat tttccaaatc agtaactatg ttcattttttt taggagtagg   28320 acgcctagcc agtatggaag aggatttttct agatcctctc ttcaacatct ttgatctcga   28380
tggaatgcaa aacccccatag tgaaacaacc aacgataaaa ataatattgt ttttcacttt   28440
ttataatttt accatctgac tcatggattc attaatatct ttataagagc tactaacgta   28500 taattccttta taactgaact gagatatata caccggatct atggtttcca taattgagta   28560
aatgaatgct cggcaataac taatggcaaa tgtatagaac aacgaaatta tactagagtt   28620
gttaaagtta atattttcta tgagctgttc caataaatta tttgttgtga ctgcgttcaa   28680
gtcataaatc atcttgatac tatccagtaa accgttttta agttctggaa tattatcatc   28740
ccattgtaaa gcccctaatt cgactatcga atatcctgct ctgatagcag tttcaatatc   28800
gacggacgtc aatactgtaa taaaggtggt agtattgtca tcatcgtgat aaactacggg   28860
aatatggtcg ttagtaggta cggtaacttt acacaacgcg atatataact ttccttttgt   28920
accattttta acgtagttgg gacgtcctgc agggtattgt tttgaagaaa tgatatcgag   28980
aacagatttg atacgatatt tgttggattc ctgattattc actataatat aatctagaca   29040
gatagatgat tcgataaata gagaaggtat atcgttggta ggataataca tccccattcc   29100
agtattctcg gatactctat tgatgacact agttaagaac atgtcttcta ttctagaaaa   29160
cgaaaacatc ctacatggac tcattaaaac ttctaacgct cctgattgtg tctcgaatgc   29220
ctcgtacaag gatttcaagg atgccataga ttctttgacc aacgatttag aattgcgttt   29280
agcatctgat tttttttatta aatcgaatgg tcggctctct ggtttgctac cccaatgata   29340
acaatagtct tgtaaagata aaccgcaaga aaatttatac gcatccatcc aaataaccct   29400
agcaccatcg gatgatatta atgtattatt atagattttc catccacaat tattgggcca   29460
gtatactgtt agcaacggta tatcgaatag attactcatg taacctacta gaatgatagt   29520
tcgtgtacta gtcataatat cttttaatcca atctaaaaaa tttaaaatta gattttttac   29580
actgttaaag ttaacaaaag tattacccgg gtacgtggat atcatatatg gcattggtcc   29640
attatcagta atagctccat aaactgatac ggcgatggtt tttatatgtg tttgatctaa   29700
cgaggaagaa attcgcgccc acaattcatc tctagatatg tatttaatat caaacggtaa   29760
cacatcaatt tcgggacgcg tatatgtttc taaatttttta atccaaatat aatgatgacc   29820
tatatgccct attatcatac tgtcaactat agtacaccta gggaacttac gatacatctg   29880
```

-continued

```
tttcctataa tcgttaaatt ttacaaatct ataacatgct aaaccttttg acgacagcca    29940
ttcattaatt tctgatatgg aatctgtatt ctcgataccg tatcgttcta aagccagtgc    30000
tatatctccc tgttcgtggg aacgcttccg tataatatcg atcaacggat aatctgaagt    30060
ttttggagaa taatatgact catgatctat ttcgtccata aacaatctag acataggaat    30120
tggaggcgat gatcttaatt ttgtgcaatg agtcgtcaat cctataactt ctaatcttgt    30180
aatattcatc atcgacataa tactatctat gttatcatcg tatattagta taccatgacc    30240
ttcttcattt cgtgccaaaa tgatatacag tcttaaatag ttacgcaata tctcaatagt    30300
ttcataattg ttagctgttt tcatcaaggt ttgtatcctg tttaacatga tggcgttcta    30360
taacgtctct attttctatt tttaattttt taaatttta acgatttact gtggctagat     30420
acccaatctc tctcaaatat ttttttagcc tcgcttacaa gctgtttatc tatactatta    30480
aaactgacga atccgtgatt ttggtaatgg gttccgtcga aatttgccga agtgatatga    30540
acatattcgt cgtcgactat caacaatttt gtattattct gaatagtgaa aaccttcaca    30600
gatagatcat tttgaacaca caacgcatct agacttttgg cggttgccat agaatatacg    30660
tcgttcttat cccaattacc aactagaagt ctgatcttaa ctcctctatt aatggctgct    30720
tctataatgg agttgtaaat gtcgggccaa tagtagctat taccgtcgac acgtgtagtg    30780
ggaactatgg ccaaatgttc aatatctata ctagtcttag ctgacctgag tttatcaata    30840
actacatcgg tatctagatc tctagaatat cccaataggt gttccggaga atcagtaaag    30900
aacactccac ctataggatt cttaatatga tacgcagtgc taactggcaa acaacaagcc    30960
gcagagcata aattcaacca tgaattttt gcgctattaa aggctttaaa agtatcaaat     31020
cttctacgaa gatctgtggc cagcggggga taatcagaat atacacctaa cgttttaatc    31080
gtatgtatag atcctccagt aaatgacgcg tttcctacat aacatctttc atcatctgac    31140
acccaaaaac aaccgagtag tagtcccaca ttatttttt tatctatatt aacgttata     31200 aaatttatat ccgggcagtg actttgtagc tctcccagat ttcttttccc tcgttcatct    31260
agcaaaacta ttatttttaat ccctttttca gatgcctctt ttagttttatc aaaataagc   31320 gctcccctag tcgtactcag aggattacaa caaaagatg ctatgtatat atatttctta    31380
gctagagtga taatttcgtt aaaacattca aatgttgtta aatgatcgga tctaaaatcc    31440
atattttctg gtagtgtttc taccagccta cattttgctc ccgcaggtac cgatgcaaat    31500
ggccacattt agttaacata aaaacttata catcctgttc tatcaacgat tctagaatat    31560
catcggctat atcgctaaaa ttttcatcaa agtcgacatc acaacctaac tcagtcaata    31620
tattaagaag ttccatgatg tcatcttcgt ctatttctat atccgtatcc attgtagatt    31680
gttgaccgat tatcgagttt aaatcattac taatactcaa tccttcagaa tacaatctgt    31740
gtttcattgt aaatttatag gcggtgtatt taagttggta gattttcaat tatgtattaa    31800
tatagcaaca gtagttcttg ctcctccttg attctagcat cctcttcatt attttcttct    31860
acgtacataa acatgtccaa tacgttagac aacacaccga cgatggcggc cgctacagac    31920
acgaatatga ctaaaccgat gaccattta aaaccctct ctagctttca cttaaactgt     31980
atcgatcatt ctttagcac atgtataata taaaaacatt attctatttc gaatttaggc    32040
ttccaaaaat ttttcatccg taaaccgata ataatatata tagacttgtt aatagtcgga   32100
ataaatagat taatgcttaa actatcatca tctccacgat tagagataca atatttacat    32160
tctttttgct gtttcgaaac tttatcaata cacgttaata caaacccagg aaggagatat    32220
```

```
tgaaactgag gctgttgaaa atgaaacggt gaatacaata attcagataa tgtaaaatca    32280
tgattccgta ttctgatgat attagaactg ctaatggatg tcgatggtat gtatctagga    32340
gtatctattt taacaaagca tcgatttgct aatatacaat tatccttttg attaattgtt    32400
attttattca tattcttaaa aggtttcata tttatcaatt cttctacatt aaaaatttcc    32460 attttttaatt tatgtagccc cgcaatactc ctcattacgt ttcattttttt gtctataata   32520 tccatttttgt tcatctcggt acatagatta tccaattgag aagcgcattt agtagttttg    32580 tacatttttaa gtttattgac gaatcgtcga aaactagtta tagttaacat tttattattt    32640
gataccctga tattaatacc cctgccgtta ctattattta taactgatgt aatccacgta    32700
acattggaat taactatcga tagtaatgca tcgacgcttc caaaattgtc tattataaac    32760
tcaccgataa tttttttatt gcatgttttc atattcatta ggattatcaa atctttaatc    32820
ttattacgat tgtatgcgtt gatattacaa gacgtcattc taaagacgg aggatctcca     32880 tcaaatgcca gacaatcacg tacaaagtac atggaaatag gttttgttct attgcgcatc    32940
atagatttat atagaacacc cgtagaaata ctaatttgtt ttactctata aaatactaat    33000
gcatctattt catcgttttg tataacgtct ttccaagtgt caaattccaa attttttca     33060 ttgatagtac caaattcttc tatctcttta actacttgca tagataggta attacagtga    33120
tgcctacatg ccgttttttg aaactgaata gatgcgtcta gaagcgatgc tacgctagtc    33180
acaatcacca ctttcatatt tagaatatat atatgtaaaa atatagtaga atttcatttt    33240 gttttttttct atgctataaa tgaattctca ttttgcatct gctcatactc cgttttatat    33300
taataccaaa gaaggaagat atctggttct aaaagccgtt aaagtatgcg atgttagaac    33360
tgtagaatgc gaaggaagta aagcttcctg cgtactcaaa gtagataaac cctcatcgcc    33420
cgcgtgtgag agaagaccct tcgtccccgtc cagatgcgag agaatgaata accctggaaa    33480
acaagttccg tttatgagga cggacatgct acaaaatatg ttcgcggcta atcgcgataa    33540
tgtagcttct agactttttgt cctaaaatac tattatatcc ttttcgatat taataaatcc    33600
gtgtcgtcca ggttttttat ctctttcagt atgtgaatag ataggtattt tatctctatt    33660
catcatcgaa tttaagagat ccgataaaca ttgtttgtat tctccagatg tcagcatctg    33720
atacaacaat atatgtgcac ataaacctct ggcacttatt tcatgtacct tcccttatc     33780 actaaggaga atagtatttg agaaatatgt atacatgata ttatcatgaa ttagatatac    33840
agaatttgta acactctcga aatcacacga tgtgtcggcg ttaagatcta atatatcact    33900
cgataacaca ttttcatcta gatacactag acatttttta aagctaaaat agtctttagt    33960
agtaacagta actatgcgat tattttcatc gatgatacat ttcatcggca tattattacg    34020
cttaccatca aagactatac catgtgtata tctaacgtat tctagcatgg ttgccatacg    34080
cgcattaaac ttttcaggat ctttggatag atcttccaat ctatctattt gagaaaacat    34140
ttttatcatg ttcaatagtt gaaacgtcgg atccactata tagatattat ctataaagat    34200
tttaggaact acgttcatgg tatcctggcg aatattaaaa ctatcaatga tatgattatc    34260
gttttcatct tttatcacca tatagtttct aagatatggg atttactta atataatatt     34320 atttcccgtg ataaattta ttagaaaggc caaatctata agaaaagtcc tagaattagt     34380
ctgaagaata tctatatcgc cgtatagtat atttggatta attagatata gagaatatga    34440
tccgtaacat atacaacttt tattatggcg tctaagatat tcttccatca acttattaac    34500 attttttgact agggaagata cattatgacg tcccattact tttgccttgt ctattactgc    34560
gacgttcata gaatttagca tatctcttgc caattcttcc attgatgtta cattataaga    34620
```

```
aattttagat gaaattacat ttggagcttt aatagtaaga actcctaata tgtccgtgta   34680
tgtggtcact aatacagatt gtagttctat aatcgtaaat aatttaccta tattatatgt   34740
ttgagtctgt ttagaaaagt agctaagtat acgatctttt atttctgatg cagatgtatt   34800
aacatcggaa aaaatctttt ttttattctt ttttactaaa gatacaaata tgtctttgtt   34860
aaaaacagtt atttttctgaa tatttctagc ttgtaatttt aacatatgat attcgttcac   34920
actaggtact ctgcctaaat aggtttctat aatctttaat gtaatattag gaaaagtatt   34980
ctgatcagga ttcctattca ttttgaggat ttaaaactct gattattgtc taatatggtc   35040
tctacgcaaa cttttcaca gagcgataga gtttttgata actcgttttt cttaagaaat   35100
ataaaactac tgtctccaga gctcgctcta tcttttattt tatctaattc gatacaaact   35160
cctgatactg gttcagaaag taattcatta attttcagtc ctttatagaa gatatttaat   35220
atagataata caaatcttc agttttgat atcgatctga ttgatcctag aactagatat   35280
attaataacg tgctcattag gcagtttatg gcagcttgat aattagatat agtatattcc   35340
agttcatatt tattagatac cgcattgccc agattttgat attctatgaa ttcctctgaa   35400
aataaatcca aaataactag acattctatt ttttgtggat tagtgtactc tcttccctct   35460
atcatgttca ctactggtgt ccacgatgat aaatatctag agggaatata atatagtcca   35520
taggatgcca atctagcaat gtcgaataac tgtaatttta ttcttcgctc ttcattatga   35580
attgattctt gaggtataaa cctaacacaa attatattat tagactttc gtatgtaatg   35640 tctttcatgt tataagtttt taatcctgga atagaatcta ttttaatgag ctttttaaac   35700
gcagagttct ccaacgagtc aaagcataat actctgttgt ttttcttata tacgatgtta   35760
cgattttctt ctttgaatgg aataggtttt tgaattagtt tataattaca acataataga   35820
taaggaagtg tgcaaatagt acgcggaaaa aacataatag ctcccctgtt ttcatccatg   35880
gttttaagta aatgatcact ggcttcttta gtcaatggat attcgaacat taaccgtttc   35940
atcatcattg gacagaatcc atatttctta atgtaaagag tgatcaaatc attgtgttta   36000
ttgtaccatc ttgttgtaaa tgtgtattcg gttatcggat ctgctccttt ttctattaaa   36060
gtatcgatgt caatctcgtc taagaattca actatatcga catatttcat ttgtatacac   36120
ataaccatta ctaacgtaga atgtatagga agagatgtaa cgggaacagg gtttgttgat   36180
tcgcaaacta ttctaataca taattcttct gttaatacgt cttgcacgta atctattata   36240
gatgccaaga tatctatata attattttgt aagatgatgt taactatgtg atctatataa   36300
gtagtgtaat aattcatgta ttttgatata tgttccaact ctgtctttgt gatgtctagt   36360
ttcgtaatat ctatagcatc ctcaaaaaat atattcgcat atattcccaa gtcttcagtt   36420
ctatcttcta aaaaatcttc aacgtatgga atataataat ctattttacc tcttctgata   36480
tcattaatga tatagttttt gacactatct tctgtcaatt gattcttatt cactatatct   36540
aagaaacgga tagcgtccct aggacgaact actgccatta atatctctat tatagcttct   36600
ggacataatt catctattat accagaatta atgggaacta ttccgtatct atctaacata   36660
gttttaagaa agtcagaatc taagacttga tgttcatata ttggttcata catgaaatga   36720
tctctattga tgatagtgac tatttcattc tctgaaaatt ggtaactcat tctatatatg   36780
ctttccttgt tgatgaagga tagaatatac tcaatagaat ttgtaccaac aaactgttct   36840
cttatgaatc gtatatcatc atctgaaata atcatgtaag gcatacattt aacaattaga   36900
gacttgtctc ctgttatcaa tatactattc ttgtgataat ttatgtgtga ggcaaatttg   36960
```

```
tccacgttct ttaattttgt tatagtagat atcaaatcca atggagctac agttcttggc    37020
ttaaacagat atagtttttc tggaacaaat tctacaacat tattataaag gactttgggt    37080
aaataagtgg gatgaaatcc tattttaatt aatgcgatag ccttgtcctc gtgcagatat    37140
ccaaacgctt ttgtgatagt atggcattca ttgtctagaa acgctctacg aatatctgtg    37200
acagatatca tctttagaga atatactagt cgcgttaata gtactacaat ttgtattttt    37260
taatctatct caataaaaaa attaatatgt atgattcaat gtataactaa actactaact    37320
gttattgata actagaatca gaatctaatg atgacgtacc caagaagttt atctactgcc    37380
aatttagctg cattattttt agcatctcgt ttagattttc catctgcctt atcgaatact    37440
cttccgtcga tatctacaca ggcataaaat gtaggagagt tactaggccc aactgattca    37500
atacgaaaag accaatctct cttagttatt ggcagtact cattaataac ggtgacaggg    37560
ttagcatctt tccaatcaat aattttttta gccggaataa catcatcaaa agacttatga    37620
tcctctctca ttgattttc gcgggataca tcatctatta tgacgtcagc cataacatca    37680
gcatccggct tatccgcctc cgttgtcata aaccaacgag gaggaatatc gtcggagctg    37740
tacaccatag cactacgttg aagatcgtac agagctttat taacttctcg cttctccata    37800
ttaagttgtc tagttagttg tgcagcagta gctccttcga ttccaatggt tttaatagcc    37860
tcacacacaa tctctgcgtt agaacgttcg tcgatataga ttttagacat ttttagagag    37920
aactaacaca accagcaata aaactgaacc tactttatca ttttttttatt catcatcctc    37980 tggtggttcg tcgttcctat caaatgtagc tctgattaac ccgtcatcta taggtgatgc    38040
tggttctgga gattctggag gagatggatt attatctgga agaatctctg ttatttcctt    38100
gttttcatgt atcgattgcg ttgtaacatt aagattgcga aatgctctaa atttgggagg    38160
cttaaagtgt tgtttgcaat ctctacacgc gtgtctaact agtggaggtt cgtcagctgc    38220
tctagtttga atcatcatcg gcgtagtatt cctacttta cagttaggac acggtgtatt    38280
gtatttctcg tcgagaacgt taaaataatc gttgtaactc atcccttta ttttatctat    38340 attgtattct actcctttct taatgcattt tataccgaat aagagatagc gaaggaattc    38400
tttttcggtg ccgctagtac ccttaatcat atcacatagt gttttatatt ccaaatttgt    38460
ggcaatagac ggtttatttc tatacgatag tttgttctg gaatcctttg agtattctat    38520
accaatatta ttctttgatt cgaatttagt ttcttcgata ttagattttg tattacctat    38580
attcttgatg tagtactttg atgattttc catggcccat tctattaagt cttccaagtt    38640
ggcatcatcc acatattgtg atagtaattc tcggatatca gtagcggcta ccgccattga    38700
tgtttgttca ttggatgagt aactactaat gtatacattt tccatttata acacttatgt    38760
attaactttg ttcatttata ttttttcatt attatgttga tattaacaaa agtgaatata    38820
tatatatgtt aataattgta ttgtggttat acggctacaa ttttataatg agtgaaagtc    38880
agtgtccgat gatcaatgac gatagcttta ctctgaaaag aaagtatcaa atcgatagtc    38940
cggagtcaac aataaaaatg gataagaaga ggataaagtt tcagaataga gccaaaatgg    39000
taaaagaaat aaatcagaca ataagagcag cacaaactca ttacgagaca ttgaaactag    39060
gatacataaa atttaagaga atgattagga ctactactct agaagatata gcaccatcta    39120
ttccaaataa tcagaaaact tataaactat tctcggacat ttcagccatc ggcaaagcat    39180
cacagaatcc gagtaagatg gtatatgctc tgctgcttta catgtttccc aatttgtttg    39240
gagatgatca tagattcatt cgttatagaa tgcatccaat gagtaaaatc aaacacaaga    39300
tcttctctcc tttcaaactt aatcttatta gaatattagt ggaagaaaga ttctataata    39360
```

```
atgaatgcag atctaataaa tggaaaataa ttggaacaca agttgataaa atgttgatag    39420
ctgaatctga taaatataca atagatgcaa ggtataacct aaaacccatg tatagaatca    39480
agggagaatc tgaagaagat accctcttca tcaaacagat ggtagaacaa tgtgtgacat    39540
cccaggaatt ggtggaaaaa gtgttgaaga tactgtttag agatttgttc aagagtggag    39600
aatacaaagc gtacagatac gatgatgatg tagaaaatgg atttattgga ttggatacac    39660
taaaattaaa cattgttcat gatatagttg aaccatgtat gcctgttcgt aggccagtgg    39720
ctaagatact gtgtaaagaa atggtaaata atactttga gaatccgcta catattattg    39780
gtaagaatct tcaagagtgc attgactttg ttagtgaata ggcatttcat ctttctccaa    39840
tactaattca aattgttaaa ttaataatgg atagtataaa tagtaaaaat aattattaga    39900
ataagagtgt agtatcatag ataactctct tctataaaaa tggattttat tcgtagaaag    39960
tatcttatat acacagtaga aaataatata gattttttaa aggatgatac attaagtaaa    40020
gtaaacaatt ttaccctcaa tcatgtacta gctctcaagt atctagttag caattttcct    40080
caacacgtta ttactaagga tgtattagct aataccaatt ttttgttttt catacatatg    40140
gtacgatgtt gtaaagtgta cgaagcggtt ttacgacacg catttgatgc acccacgttg    40200
tacgttaaag cattgactaa gaattattta tcgtttagta acgcaataca atcgtacaag    40260
gaaaccgtgc ataaactaac acaagatgaa aaattttag aggttgccga atacatggac    40320
gaattaggag aacttatagg cgtaaattat gacttagttc ttaatccatt atttcacgga    40380
ggggaaccca tcaaagatat ggaaatcatt tttttaaaac tgtttaagaa aacagacttc    40440
aaagttgtta aaaaattaag tgttataaga ttacttattt gggcatacct aagcaagaaa    40500
gatacaggca tagagtttgc ggataatgat agacaagata tatatactct atttcaacaa    40560
actggtagaa tcgtccatag caatctaaca gaaacgttta gagattatat ctttcccgga    40620
gataagacta gctattgggt gtggttaaac gaaagtatag ctaatgatgc ggatatcgtt    40680
cttaatagac ccgccattac catgtatgat aaaattctta gttatatata ctctgagata    40740
aaacaaggac gcgttaataa aaacatgctt aagttagttt atatctttga gcctgaaaaa    40800
gatatcagag aacttctgct agaaatcata tatgatattc ctggagatat cctatctatt    40860
attgatgcaa aaaacgacga ttggaaaaaa tattttatta gtttttataa agctaattt    40920 attaacggta atacatttat tagtgataga acgtttaacg aggacttatt cagagttgtt    40980
gttcaaatag atcccgaata tttcgataat gaacgaatta tgtctttatt ctctacgagt    41040
gctgcggaca ttaaacgatt tgatgagtta gatattaata acagttatat atctaatata    41100
atttatgagg tgaacgatat cacattagat acaatggatg atatgaagaa gtgtcaaatc    41160
tttaacgagg atacgtcgta ttatgttaag gaatacaata catacctgtt tttgcacgag    41220
tcggatccca tggtcataga gaacggaata ctaaagaaac tgtcatctat aaaatccaag    41280
agtagacggc tgaacttgtt tagcaaaaac attttaaaat attatttaga cggacaattg    41340
gctcgtctag gtcttgtgtt agatgattat aaaggagact tgttagttaa aatgataaac    41400
catcttaagt ctgtggagga tgtatccgca ttcgttcgat tttctacaga taaaaaccct    41460
agtattcttc catcgctaat caaaactatt ttagctagtt ataatatttc catcatcgtc    41520
ttatttcaaa ggttttttgag agataatcta tatcatgtag aagaattctt ggataaaagc    41580
atccatctaa ccaagacgga taagaaatat atacttcaat tgataagaca cggtagatca    41640
tagaacagac caaatatatt attaataatt tgtatataca tagatataat tatcacacat    41700
```

```
ttttgataaa tgggaactgc tgcaacaatt cagactccca ccaaattaat gaataaagaa    41760
aatgcagaaa tgattttgga aaaaattgtt gatcatatag ttatgtatat tagtgacgaa    41820
tcaagtgatt cagaaaataa tcctgaatat attgattttc gtaacagata cgaagactat    41880
agatctctca ttataaaaag tgatcacgag tttgtaaagc tatgtaaaaa tcatgcggag    41940
aaaagttctc cagaaacgca acaaatgatt atcaaacaca tatacgaaca atatcttatt    42000
ccagtatctg aagtactatt aaaacctata atgtccatgg gtgacataat tacatataac    42060
ggatgtaaag acaatgaatg gatgctagaa caactctcta ccctaaactt taacaatctc    42120
cgcacatgga actcatgtag cataggcaat gtaacgcgtc tgttttatac atttttagt    42180 tatctgatga aagataaact aaatatataa gtataatccc attctaatac tttaacctga    42240
tgtattagca tcttattaga atattaacct aactaaaaga cataacataa aaactcatta    42300
catagttgat aaaaagcggt aggatataaa tattatggct gccaccgttc cgcgttttga    42360
cgacgtgtac aaaaatgcac aaagaagaat tctagatcaa gaaacatttt ttagtagagg    42420
tctaagtaga ccgttaatga aaacacata tctatttgat aattacgcgt atggatggat    42480
accagaaact gcaatttgga gtagtagata cgcaaactta gatgcaagtg actattatcc    42540
catttcgttg ggattactta aaaagttcga gtttctcatg tctctatata aaggtcctat    42600
tccagtatac gaagaaaaag taaatactga attcattgct aatggatctt ctctccggtag   42660 atacgtatca tatcttagaa agttttctgc tcttccaaca aacgagttta ttagtttttt    42720
gttactgact tccattccaa tctataatat cttgttctgg tttaaaaata ctcagtttga    42780
tattactaaa cacacattat tcagatacgt ctatacagat aatgccaaac acctggcgtt    42840
ggctaggtat atgtatcaaa caggagacta taagcctttg tttagtcgtc tcaaagagaa    42900
ttatatattt accggtcccg ttccaatatg tatcaaagat atagatcacc ctaatcttag    42960
tagagcaaga agtccatccg attatgagac attagctaat attagtacta tattgtactt    43020
taccaagtat gatccggtat taatgttttt attgttttac gtacctgggt attcaattac    43080
tacaaaaatt actccagccg tagaatatct aatggataaa ctgaatctaa caaagagcga    43140
cgtacaactg ttgtaaatta ttttatgctt cgtaaaatgt aggttttgaa ccaaacattc    43200
tttcaaagaa tgagatgcat aaaactttat tatccaatag attgactatt tcggacgtca    43260
atcgttaaaa gtaaacttcg taaaatattc tttgatcact gccgagttta aaacttctat    43320
cgataattgt ttcatatgtt ttaatattta caagtttttt ggtccatggt ccattaggac    43380
aaatatatgc aaaataatat cgttctccaa gttctatagt ctctggatta ttttattat    43440 attcagtaac caaatacata ttagggttat ctgcggattt ataatttgag tgatgcattc    43500
gactcaacat aaataattct agaggagacg atctactatc aaattcggat cgtaaatctg    43560
tttctaaaga acggagaata tctatacata cctgattaga attcatccgt ccttcagaca    43620
acatctcaga cagtctggtt ttgtacatct taatcatatt cttatgaaac ttggaaacat    43680
ctcttctagt ttcactagta cctttattaa ttctctcagg tacagatttt gaattcgacg    43740
atgctgagta tttcatcgtt gtatatttct tcttcgattg cataatcaga ttcttatata    43800
ccgcctcaaa ctctatttta aaattattaa acaatactct attattaatc agtcgttcta    43860
actctttcgc tatttctata gacttatcta catcttgact gtctatctct gtaaacacgg    43920
agtcggtatc tccatacacg ctacgaaaac gaaatctgta atctataggc aacgatgttt    43980
tcacaatcgg attaatatct ctatcgtcca tataaaatgg attacttaat ggattggcaa    44040
accgtaacat accgttagat aactctgctc catttagtac cgattctaga tacaagatca    44100
```

```
ttctacgtcc tatggatgtg caactcttag ccgaagcgta tgagtataga gcactatttc  44160
taaatcccat cagaccatat actgagttgg ctactatctt gtacgtatat tgcatggaat  44220
catagatggc cttttcagtt gaactggtag cctgttttag catctttta tatctggctc    44280
tctctgccaa aaatgttctt aatagtctag gaatggttcc ttctatcgat ctatcgaaaa  44340
ttgctatttc agagatgagg ttcggtagtc taggttcaca atgaaccgta atatatctag  44400
gaggtggata tttctgaagc aatagctgat tatttatttc ttcttccaat ctattggtac  44460
taacaacgac accgactaat gtttccggag atagatttcc aaagatacac acattaggat  44520
acagactgtt ataatcaaag attaatacat tattactaaa cattttttgt tttggagcaa  44580
ataccttacc gccttcataa ggaaactttt gttttgtttc tgatctaact aagatagttt  44640
tagtttccaa caatagcttt aacagtggac ccttgatgac tgtactcgct ctatattcga  44700
ataccatgga ttgaggaagc acatatgttg acgcacccgc gtctgttttt gtttctactc  44760
cataatactc ccacaaatac tgacacaaac aagcatcatg aatacagtat ctagccatat  44820
ctaaagctat gtttagatta taatccttat acatctgagc taaatcaacg tcatcctttc  44880
cgaaagataa tttatatgta tcattaggta aagtaggaca taatagtacg actttaaatc  44940
cattttccca aatatcttta cgaattactt tacatataat atcctcatca acagtcacat  45000
aattacctgt ggttaaaacc tttgcaaatg cagcggcttt gcctttcgcg tctgtagtat  45060
cgtcaccgat gaacgtcatt tctctaactc ctctatttaa tacttaccc atgcaactga    45120
acgcgttctt ggatatagaa tccaatttgt acgaatccaa ttttttcaaat ttttgaatga  45180
atgaatatag atcgaaaaat atagttccat tattgttatt aacgtgaaac gtagtattgg  45240
ccatgccgcc tactcccta tgactagact gatttctctc ataaatacag agatgtacag    45300
cttccttttt gtccggagat ctaaagataa ttttctctcc tgttaataac tctagacgat  45360
tagtaatata tctcagatca aagttatgtc cgttaaaggt aacgacgtag tcgaacgtta  45420
gttccaacaa ttgtttagct attcgtaaca aaactatttc agaacataga actagttctc  45480
gttcgtaatc catttccatt agtgactgta tcctcaaaca tcctctatcg acggcttctt  45540
gtatttcctg ttccgttaac atctcttcat taatgagcgt aaacaataat cgtttaccac  45600
ttaaatcgat ataacagtaa cttgtatgcg agattgggtt aataaataca gaaggaaact  45660
tcttatcgaa gtgacactct atatctagaa ataagtacga tcttgggata tcgaatctag  45720
gtatttttt agcgaaacag ttacgtggat cgtcacaatg ataacatcca ttgttaatct    45780
ttgtcaaata ttgctcgtcc aacgagtaac atccgtctgg agatatcccg ttagaaatat  45840
aaaaccaact aatattgaga aattcatcca tggtggcatt ttgtatgctg cgtttctttg  45900
gctcttctat caaccacata tctgcgacgg agcattttct atctttaata tctagattat  45960
aacttattgt ctcgtcaatg tctatagttc tcatctttcc caacggcctc gcattaaatg  46020
gaggaggaga caatgactga tatatttcgt ccgtcactac gtaataaaag taatgaggaa  46080
atcgtataaa tacggtctca ccatttcgac atctggattt cagatataaa aatctgttt    46140
caccgtgact ttcaaaccaa ttaatgcacc gaacatccat ttatagaatt tagaaatata  46200
ttttcattta aatgaatccc aaacattggg gaagagccgt atggaccatt atttttatag  46260
tactttcgca agcgggttta gacggcaaca tagaagcgtg taaacgaaaa ctatatacta  46320
tagttagcac tcttccatgt cctgcatgta gacggcacgc gactatcgct atagaggaca  46380
ataatgtcat gtctagcgat gatctgaatt atatttatta ttttttcatc agattattta  46440
```

```
acaatttggc atctgatccc aaatacgcga tcgatgtgac aaaggttaac cctttataaa    46500
cttaacccat tataaaactt atgattagtc acaactgaaa taaccgcgtg attatttttt    46560
ggtataattc tacacggcat ggtttctgtg actatgaatt caaccccgt tacattagtg     46620 aaatctttaa caaacagcaa gggttcgtca aagacataaa actcattgtt tacaatcgaa    46680
atagaccccc tatcacactt aaaataaaaa atatccttat cctttaccac caaataaaat    46740
tctgattggt caatgtgaat gtattcactt aacagttcca caaatttatt tattaactcc    46800
gaggcacata catcgtcggt atttttatg gcaaacttta ctcttccagc atccgtttct     46860
aaaaaaatat taacgagttc catttatatc atccaatatt attgaaatga cgttgatgga    46920
cagatgatac aaataagaag gtacggtacc tttgtccacc atctcctcca attcatgctc    46980 tatttgtca ttaactttaa tgtatgaaaa cagtacgcca catgcttcca tgacagtgtg     47040
taacactttg gatacaaaat gtttgacatt agtataattg ttcaagactg tcaatctata    47100
atagatagta gctataatat attctatgat ggtattgaag aagatgacaa ccttggcata    47160
ttgatcattt aacacagaca tggtatcaac agatagcttg aatgaaagag aatcagtaat    47220
tggaataagc gtcttctcga tagagtgtcc gtataccaac atgtctgata ttttgatgta    47280
ttccattaaa ttatttagtt ttttcttttt attctcgtta aacagcattt ctgtcaacgg    47340
accccaacat cgttgaccga ttaagttttg attgattttt ccgtgtaagg cgtatctagt    47400
cagatcgtat agcctatcca ataatccatc atctgtgcgt agatcacatc gtacactttt    47460
taattctcta tagaagagcg acagacatct ggagcaatta cagacagcaa tttctttatt    47520
ctctacagat gtaagatact tgaagacatt cctatgatga tgcagaattt tggataacac    47580
ggtattgatg gtatctgtta ccataattcc tttgatggct gatagtgtca gagcacaaga    47640
tttccaatct ttgacaattt ttagcaccat tatctttgtt ttgatatcta tatcagacag    47700
catggtgcgt ctgacaacac agggattaag acggaaagat gaaatgattc tctcaacatc    47760
ttcaatagat accttgctat tttttctggc attatctata tgtgcgagaa tatcctctag    47820
agaatcagta tccttttga tgatagtgga tctcaatgac atgggacgtt taaaccttct     47880
tattctatca ccagattgca tggtgatttg tcttctttct tttatcataa tgtaatctct    47940
aaattcatcg gcaaattgtc tatatctaaa atcataatat gagatgttta cctctacaaa    48000
tatctgttcg tccaatgtta gagtatttac atcagttttg tattccaaat taaacatggc    48060
aacggattta attttatatt cctctattaa gtcctcgtcg ataataacag aatgtagata    48120
atcatttaat ccatcgtaca tggttggaag atgcttgttg acaaaatctt taattgtctt    48180
gatgaaggtg ggactatatc taacatcttg attaataaaa tttataacat tgtccatagg    48240
atactttgta actagtttta tacacatctc ttcatcggta agtttagaca gaatatcgtg    48300
aacaggtggt atattatatt catcagatat acgaagaaca atgtccaaat ctatattgtt    48360
taatatatta tatagatgta gcgtagctcc tacaggaata tctttaacta agtcaatgat    48420
ttcatcaacc gttagatcta tttaaagtt aatcatatag gcattgattt ttaaaaggta     48480
tgtagccttg actacattct cattaattaa ccattccaag tcactgtgtg taagaagatt    48540
atattctatc ataagcttga ctacatttgg tcccgatacc attaaagaat tcttatgata    48600
taaggaaaca gcttttaggt actcatctac tctacaagaa ttttggagag ccttaacgat    48660
atcagtgacg tttattattt caggaggaaa aaacctaaca ttgagaatat cggaattaat    48720
agcttccaga tacagtgatt ttggcaatag tccgtgtaat ccataatcca gtaacacgag    48780
ctggtgcttg ctagacacct tttcaatgtt taattttttt gaaataagct tgataaagc     48840
```

```
cttcctcgca aattccggat acatgaacat gtcggcgaca tgattaagta ttgtttttc    48900
attattttct caataccca atagatgata gaatatcacc caatgcgtcc atgttgtcta    48960
tttccaacag gtcgctatat ccaccaatag aagttttcc aaaaaagatt ctaggaacag    49020
ttctaccacc agtaatttgt tcaaaatagt cacgcaattc attttcgggt ttaaattctt   49080
taatatcgac aatttcatac gctcctcttt tgaaactaaa cttatttaga atatccagtg   49140
catttctaca aaaggacat gtatacttga caaaaattgt cactttgtta ttggccaacc    49200
tttgttgtac aaattcctcg gccatttaa tatttaagtg atataaaact atctcgactt    49260
atttaactct ttagtcgaga tatatggacg cagatagcta tatgatagcc aactacagaa   49320
ggcaaacgct ataaaaaaca taattacgac gagcatattt ataaatattt ttattcagca   49380
ttacttgata tagtaatatt aggcacagtc aaacattcaa ccactctcga tacattaact   49440
ctctcatttt ctttaacaaa ttctgcaata tcttcgtaaa aagattcttg aaactttta   49500
gaatatctat cgactctaga tgaaatagcg ttcgtcaaca tactatgttt tgtatacata   49560
aaggcgccca ttttaacagt ttctagtgac aaaatgctag cgatcctagg atcctttaga   49620
atcacataga ttgacgattc gtctctctta gtaactctag taaaataatc atacaatcta   49680
gtacgcgaaa taatattatc cttgacttga ggagatctaa acaatctagt tttgagaaca   49740
tcgataagtt catcgggaat gacatacata ctatctttaa tagaactctt ttcatccagt   49800
tgaatggatt cgtccttaac caactgatta atgagatctt ctattttatc attttccaga   49860
tgatatgtat gtccattaaa gttaaattgt gtagcgcttc ttttttagtct agcagccaat   49920
actttaacat cactaatatc gatatacaaa ggagatgatt tatctatggt attaagaatt   49980
cgttttcga catccgtcaa aaccaattcc tttttgcctg tatcatccag ttttccatcc     50040
tttgtaaaga aattattttc tactagacta ttaataagac tgataaggat tcctccataa    50100
ttgcacaatc caaactttt cacaaaacta gactttacaa gatctacagg aatgcgtact    50160
tcaggtttt tagcttgtga ttttttcttt tgcggacatt tcttgtgac caactcatct     50220
accatttcat tgattttagc agtgaaataa gctttcaatg cacgggcact gatactattg    50280
aaaacgagtt gatcttcaaa ttccgccatt taagttcacc aaacaacttt taaatacaaa    50340
tatatcaata gtagtagaat aagaactata aaaaaaataa taattaacca ataccaaccc    50400
caacaaccgg tattattagt tgatgtgact gttttctcat cacttagaac agatttaaca    50460
atttctataa agtctgtcaa atcatcttcc ggagacccca taaatacacc aaatatagcg    50520
gcgtacaact tatccattta tacattgaat attggctttt ctttatcgct atcttcatca    50580
tattcatcat caatatcaac aagtcccaga ttacgagcca gatcttcttc tacattttca    50640
gtcattgata cacgttcact atctccagag agtccgataa cgttagccac cacttctcta    50700
tcaatgatta gttcttgag cgcgaaagta atttttgttt ccgttccgga tctatagaag     50760
acgataggtg tgataattgc cttggccaat tgtctttctc ttttactgag tgattctagt    50820
tcaccttcta tagatctgag aatggatgat tctccagtcg aaacatattc taccatggat    50880
ccgtttaatt tgttgatgaa gatggattca tccttaaatg ttttctctgt aatagtttcc    50940
accgaaagac tatgcaaaga atttggaatg cgttccttgt gcttaatgtt tccatagacg    51000
gcttctagaa gttgatacaa cataggacta gccgcggtaa ctttttatttt tagaaagtat    51060
ccatcgcttc tatcttgttt agatttattt ttataaagtt tagtctctcc ttccaacata    51120
ataaaagtgg aagtcatttg actagataaa ctatcagtaa gttttataga gatagacgaa    51180
```

```
caattagcgt attgagaagc atttagtgta acgtattcga tacattttgc attagattta   51240
ctaatcgatt ttgcatactc tataacaccc gcacaagtct gtagagaatc gctagatgca   51300
gtaggtcttg gtgaagtttc aactctcttc ttgattacct tactcatgat taaacctaaa   51360
taattgtact ttgtaatata atgatatata ttttcacttt atctcatttg agaataaaaa   51420
tgttttttgtt taaccactgc atgatgtaca gatttcggaa tcgcaaacca ccagtggttt   51480
tattttatcc ttgtccaatg tgaattgaat gggagcggat gcgggtttcg tacgtagata   51540
gtacattccc gtttttagac cgagactcca tccgtaaaaa tgcatactcg ttagtttgga   51600
ataactcgga tctgctatat ggatattcat agattgactt tgatcgatga aggctcccct   51660
gtctgcagcc atttttatga tcgtcttttg tggaatttcc caaatagttt tataaactcg   51720
cttaatatct tctggaaggt ttgtattctg aatggatcca ccatctgcca taatcctatt   51780
cttgatctca tcattccata attttctctc ggttaaaact ctaaggagat gcggattaac   51840
tacttgaaat tctccagaca atactctccg agtgtaaata ttactggtat acggttccac   51900
cgactcatta tttcccaaaa tttgagcagt tgatgcagtc ggcataggtg ccaccaataa   51960
actatttcta agaccgtatg ttctgatttt atcttttaga ggttcccaat tccaaagatc   52020
cgacggtaca acattccaaa gatcatattg tagaataccg ttactggcgt acgatcctac   52080
atatgtatcg tatggtcctt ccttctcagc tagttcacaa ctcgcctcta atgcaccgta   52140
ataaatggtt tcgaagatct tcttatttag atcttgtgct tccaggctat caaatggata   52200
atttaagaga ataaacgcgt ccgctaatcc ttgaacacca ataccgatag gtctatgtct   52260
cttattagag atttcagctt ctggaatagg ataataatta atatctataa ttttattgag   52320
atttctgaca attactttga ccacatcctt cagtttgaga aaatcaaatc gcccatctat   52380
tacaaacatg ttcaaggcaa cagatgccag attacaaacg gctacctcat tagcatccgc   52440
atattgtatt atctcagtgc aaagattact acacttgata gttcctaaat tttgttgatt   52500
actcttttg ttacacgcat ccttataaag aatgaatgga gtaccagttt caatctgaga   52560
ttctataatc gctttccaga cgactcgagc ctttattata gatttgtatc tcctttctct   52620
ttcgtatagt gtatacaatc gttcgaactc gtctccccaa acattgtcca atccaggaca   52680
ttcatccgga cacatcaacg accactctcc gtcatccttc actcgtttca taaagagatc   52740
aggaatccaa agagctataa atagatctct ggttctatgt tcctcgtttc ctgtattctt   52800
tttaagatcg aggaacgcca taatatcaga atgccacggt tccaagtata tggccataac   52860
tccaggccgt ttgtttcctc cctgatctat gtatctagcg gtgttattat aaactctcaa   52920
cattggaata ataccgtttg atataccatt ggtaccggag atatagcttc cactggcacg   52980
aatattacta attgatagac ctattccccc tgccatttta gagattaatg cgcatcgttt   53040
taacgtgtca tagatacccct ctatgctatc atcgatcatg ttaagtagaa aacagctaga   53100
catttggtga cgactagttc ccgcattaaa taaggtagga gaagcgtgcg taaaccattt   53160
ttcagaaagt agattgtacg tctcaatagc tgagtctata tcccattgat gaattcctac   53220
tgcgacacgc attaacatgt gctgaggtct ttcaacgatc ttgttgttta ttttcaacaa   53280
gtaggatttt tccaaagttt taaaccaaa atagttgtat gaaaagtctc gttcgtaaat   53340
aataaccgag ttgagtttat ccttatattt gttaactata tccatggtga tacttgaaat   53400
aatcggagaa tgtttcccat ttttaggatt aacatagttg aataaatcct ccatcacttc   53460
actaaatagt tttttttgttt ccttgtgtag atttgatacg gctattctgg cggctagaat   53520
ggcataatcc ggatgttgtg tagtacaagt ggctgctatt tcggctgcca gagtgtccaa   53580
```

```
ttctaccgtt gttactccat tatatattcc ttgaataacc ttcatagcta ttttaatagg    53640
atctatatga tccgtgttta agccataaca taattttcta atacgagacg tgattttatc    53700
aaacatgaca ttttccttgt atccatttcg tttaatgaca aacattttg ttggtgtaat     53760 aaaaaaatta tttaactttt cattaatagg gatttgacgt atgtagcgta caaaatgatc    53820
gttcctggta tatagataaa gagtcctata tatttgaaaa tcgttacggc tcgattaaac    53880
tttaatgatt gcatagtgaa tatatcatta ggatttaact ccttgactat catggcggcg    53940
ccagaaatta ccatcaaaag cattaataca gttatgccga tcgcagttaa aacggttata   54000
gcatccacca tttatatcta aaaattagat caaagaatat gtgacaaagt cctagttgta    54060
tactgagaat tgacgaaaca atgtttctta catattttt tcttattagt aactgactta     54120
atagtaggaa ctggaaagct agacttgatt attctataag tatagatacc cttccagata    54180
atgttctctt tgataaaagt tccagaaaat gtagaatttt ttaaaaagtt atcttttgct    54240
attaccaaga ttgtgtttag acgcttatta ttaatatgag tgatgaaatc cacaccgcct    54300
ctagatatcg cctttatttc cacattagat ggtaaatcca atagtgaaac tatctttta    54360 ggaatgtatg gactcgcgtt tagaggagtg aacgtcttgg gcgtcggaaa ggatgattcg    54420
tcaaacgaat aaacaatttc acaaatggat gttaatgtat tagtaggaaa ttttttgacg    54480
ctagtggaat tgaagattct aatggatgat gttctaccta tttcatccga taacatgtta    54540
atttccgaca ccaacggttt taatatttcg atgatatacg gtagtctctc tttcggactt    54600
atatagctta ttccacaata cgagtcatta tatactccaa aaaacaaaat aactagtata    54660
aaatctgtat cgaatgggaa aaacgaaatt atcgacatag gtatagaatc cggaacattg    54720
aacgtattaa tacttaattc ttttttctgtg gtaagtaccg ataggttatt gacattgtat    54780
ggttttaaat attctataac ttgagacttg atagatatta gtgatgaatt gaaaattatt    54840
tttatcacca cgtgtgtttc aggatcatcg tcgacgcccg tcaaccaacc gaatggagta    54900
aaataaatat cattaatata tgctctagat attagtattt ttattaatcc tttgattatc    54960
atcttctcgt aggcgaatga ttccatgatc aagagtgatt tgagaacatc ctccggagta    55020
ttaatgggct tagtaaacag tccatcgttg caataataaa agttatccaa gttaaaggat    55080
attatgcatt cgtttaaaga tatcacctca tctgacggag acaattttt ggtaggtttt      55140 agagactttg aagctacttg tttaacaaag ttattcatcg tcgtctacta ttctatttaa    55200
ttttgtagta aatttatcac atatcacatt aattgacttt ttggtccatt tttccatacg    55260
tttatattct tttaatcctg cgttatccgt ttccgttata tccagggata gatcttgcaa    55320
gttaaataga atgctcttaa ataatgtcat tttcttatcc gctaaaaatt taagaatgt      55380 ataaaccttt ttcagagatt tgaaactctt aggtggtgtc ctagtacaca atatcataaa    55440
caaactaata aacattccac attcagattc aacagctga ttaacttcca cattaataca     55500
gcctattttc gctccaaatg tacattcgaa aaatctgaat aaaacatcga tgtcacaatt    55560
tgtattatcc aatacagaat gtttgtgatt cgtgttaaaa ccatcggaga aggaatagaa    55620
ataaaaatta ttatagtggt ggaattcagt tggaatattg cctccggagt cataaaagga    55680
tactaaacat tgttttttat cataaattac acatttccaa tgagacaaat aacaaaatcc    55740
aaacattaca aatctagagg tagaacttt aattttgtct ttaagtatat acgataagat     55800
atgtttattc ataaacgcgt caaatttttc atgaatcgct aaggagttta agaatctcat    55860
gtcaaattgt cctatataat ccacttcgga tccataagca aactgagaga ctaagttctt    55920
```

```
aatacttcga ttgctcatcc aggctcctct ctcaggctct attttcatct tgacgacctt    55980
tggattttca ccagtatgta ttcctttacg tgataaatca tcgattttca aatccatttg    56040
tgagaagtct atcgccttag atacttttc ccgtagtcga ggtttaaaaa aatacgctaa     56100
cggtatacta gtaggtaact caaagacatc atatatagaa tggtaacgcg tctttaactc    56160
gtcggttaac tctttctttt gatcgagttc gtcgctacta ttgggtctgc tcaggtgccc    56220
cgactctact agttccaaca tcataccgat aggaatacaa gacactttgc cagcggttgt    56280
agatttatca tatttctcca ctacatatcc gttacaattt gttaaaaatt tagatacatc    56340
tatattgcta cataatccag ctagtgaata tatatgacat aataaattgg taaatcctag    56400
ttctggtatt ttactaatta ctaaatctgt atatctttcc atttatcatg gaaaagaatt    56460
taccagatat cttcttttt ccaaactgcg ttaatgtatt ctcttacaaa tattcacaag     56520
atgaattcag taatatgagt aaaacggaac gtgatagttt ctcattggcc gtgtttccag    56580
ttataaaaca tagatggcat aacgcacacg ttgtaaaaca taaggaata tacaaagtta     56640 gtacagaagc acgtggaaaa aaagtatctc ctccatcact aggaaaaccc gcacacataa    56700
acctaaccgc gaagcaatat atatacagtg aacacacaat aagctttgaa tgttatagtt    56760
ttctaaaatg tataacaaat acagaaatca attcgttcga tgagtatata ttaagaggac    56820
tattagaagc tggtaatagt ttacagatat tttccaattc cgtaggtaaa cgaacagata    56880
ctataggtgt actagggaat aagtatccat ttagcaaaat tccattggcc tcattaactc    56940
ctaaagcaca acgagagata ttttcagcgt ggatttctca tagacctgta gttttaactg    57000
gaggaactgg agtgggtaag acgtcacagg tacccaagtt attgctttgg tttaattatt    57060
tatttggtgg attctctact ctagataaaa tcactgactt tcacgaaaga ccagtcattc    57120
tatctcttcc taggatagct ttagttagat tgcatagcaa taccatttta aaatcattgg    57180
gatttaaggt actagatgga tctcctattt ctttacggta cggatctata ccggaagaat    57240
taataaacaa acaaccaaaa aaatatggaa ttgtattttc tacccataag ttatctctaa    57300
caaaactatt tagttatggc actcttatta tagacgaagt tcatgagcat gatcaaaatag   57360 gagatattat tatagcagta gcgagaaagc atcatacgaa aatagattct atgtttttaa    57420
tgactgccac gttagaggat gacagggaac ggctaaaagt atttttacct aatcccgcat    57480
ttatacatat tcctggagat acactgttta aaattagcga ggtatttatt cataataaga    57540
taaatccatc ttccagaatg gcatacatag aagaagaaaa gagaaattta gttactgcta    57600
tacagatgta tactcctcct gatggatcat ccggtatagt ctttgtggca tccgttgcac    57660
agtgtcacga atataatca tatttagaaa aaagattacc gtatgatatg tatattattc     57720
atggtaaggt cttagatata gacgaaatat tagaaaaagt gtattcatca cctaatgtat    57780
cgataattat ttctactcct tatttggaat ccagcgttac tatacgcaat gttacacaca    57840
tttatgatat gggtagagtt tttgtccccg ctccttttgg aggatcgcaa caatttattt    57900
ctaaatctat gagagatcaa cgaaaaggaa gagtaggaag agttaatcct ggtacatacg    57960
tctatttcta tgatctgtct tatatgaagt ctatacagcg aatagattca gaatttctac    58020
ataattatat attgtacgct aataagttta atctaacact ccccgaagat tgtttataa     58080 tccctacaaa tttggatatt ctatggcgta caaaggaata tatagactcg ttcgatatta    58140
gtacagaaac atggaataaa ttattatcca attattatat gaagatgata gagtatgcta    58200
aactttatgt actaagtcct attctcgctg aggagttgga taactttgag aggacgggag    58260
aattaactag tattgtacga gaagccattt tatctctaaa tttacaaatt aagattttaa    58320
```

```
attttaaaca taaagatgat gatacgtata tacacttttg taaaatatta ttcggtgtct   58380
ataacggaac aaacgctact atatattatc atagacctct aacgggatat atgaatatga   58440
tttcagatac tatatttgtt cctgtagata taaactaaaa atcaaactct aatgaccaca   58500
tcttttttta gagatgaaaa attttccaca tctccttttg tagacacgac taaacatttt   58560
gcagaaaaaa gtttattagt gtttagataa tcgtatactt catcagtgta gatagtaaat   58620
gtgaacagat aaaaggtatt cttgctcaat agattggtaa attccataga atatattaat   58680
cctttcttct tgagatccca catcatttca accagagacg ttttatccaa tgatttacct   58740
cgtactatac cacatacaaa actagatttt gcagtgacgt cgtacctggt attcctacca   58800
aacaaaattt tacttttagt tcttttagaa aattctaagg tagaatctct atttgccaat   58860
atgtcatcta tggaattacc actagcaaaa aatgatagaa atatatattg atacatcgca   58920
gctggttttg atctactata ctttaaaaac gaatcagatt ccataattgc ctgtatatca   58980
tcagctgaaa aactatgttt tacacgtatt ccttcggcat ttctttttaa tgatatatct   59040
tgtttagaca atgataaagt tatcatgtcc atgagagacg cgtctccgta tcgtataaat   59100
atttcattag atgttagacg cttcattagg ggtatacttc tataaggttt cttaatcagt   59160
ccatcattgg ttgcgtcaag aactactatc ggatgttgtt gggtatctct agtgttacac   59220
atggccttac taaagtttgg gtaaataact atgatatctc tattaattat agatgcatat   59280
atttcattcg tcaaggatat tagtatcgac ttgctatcgt cattaatacg tgtaatgtaa   59340
tcatataaat catgcgatag ccaaggaaaa tttaaataga tgttcatcat ataatcgtcg   59400
ctataattca tattaatacg ttgacattga ctaatttgta atatagcctc gccacgaaga   59460
aagctctcgt attcagtttc atcgataaag gataccgtta aatataactg gttgccgata   59520
gtctcatagt ctattaagtg gtaagtttcg tacaaataca gaatccctaa aatattatct   59580
aatgttggat taatctttac cataactgta taaaatggag acggagtcat aactatttta   59640
ccgtttgtac ttactggaat agatgaagga ataatctccg gacatgctgg taaagaccca   59700
aatgtctgtt tgaagaaatc caatgttcca ggtcctaatc tcttaacaaa aattacgata   59760
ttcgatcccg atatccttta cattctattt accagcatat cacgaactat attaagatta   59820
tctatcatgt ctattctccc accgttatat aaatcgcctc cgctaagaaa cgttagtata   59880
tccatacaat ggaatacttc atttctaaaa tagtattcgt tttctaattc tttaatgtga   59940
aatcgtatac tagaaaggga aaaattatct ttgagttttc cgttagaaaa gaaccacgaa   60000
actaatgttc tgattgcgtc cgattccgtt gctgaattaa tggatttaca ccaaaaactc   60060
atataacttc tagatgtaga agcattcgct aaaaaattag tagaatcaaa ggatataagt   60120
agatgttcca acaagtgagc aattcccaag atttcatcta tatcattctc gaatccgaaa   60180
ttagaaattc ccaagtagat atcctttttc atccgatcgt tgatgaaaat acgaacttta   60240
ttcggtaaga caatcattta ctaaggagta aaataggaag taatgttcgt atgtcgttat   60300
catcgtataa attaaaggtg tgttttttac cattaagtga cattataatt ttaccaatat   60360
tggaattata atataggtgt atttgcgcac tcgcgacggt tgatgcatcg gtaaatatag   60420
ctgtatctaa tgttctagtc ggtatttcat catttcgctg tctaataata gcgttttctc   60480
tatctgtttc cattacagct gcctgaagtt tattggtcgg ataatatgta aaataataag   60540
aaatacatac gaataacaaa ataaaataa gatataataa agatgccatt tagagatcta   60600
attttgttta acttgtccaa attcctactt acagaagatg aggaatcgtt ggagatagtg   60660
```

```
tcttccttat gtagaggatt tgaaatatct tataatgact tgataactta ctttccagat    60720
aggaaatacc ataaatatat ttataaagta tttgaacatg tagatttatc ggaggaatta    60780
agtatggaat tccatgatac aactctgaga gatttagtct atcttagatt gtacaagtat    60840
tccaagtgta tacggccgtg ttataaatta ggagataatc taaaaggcat agttgttata    60900
aaggacagga atatttatat tagggaagca aatgatgact tgatagaata tctcctcaag    60960
gaatacactc ctcagattta tacatattct aatgagcgcg tccccataac tggttcaaaa    61020
ttaattcttt gtggattttc tcaagttaca tttatggcgt atacaacgtc gcatataaca    61080
acaaataaaa aggtagatgt tctcgtttcc aaaaaatgta tagatgaact agtcgatcca    61140
ataaattatc aaatacttca aaatttattt gataaaggaa gcggaacaat aaacaaaata    61200
ctcaggaaga tattttattc ggtaacaggt ggccaaactc cataggtagc ttttctatt    61260 tcggatttta gaatttccaa attcaccagc gatttatcgg ttttggtgaa atccaaggat    61320
ttattaatgt ccacaaatgc catttgtttt gtctgtggat tgtatttgaa aatggaaacg    61380
atgtagttag atagatgcgc tgcgaagttt cctattaggg ttccgcgctt cacgtcaccc    61440
agcatacttg aatcaccatc ctttaaaaaa aatgataaga tatcaacatg gagtatatca    61500
tactcggatt ttaattcttc tactgcatca ctgacatttt cacaaatact acaatacggt    61560
ttaccgaaaa taatcagtac gttcttcatt tatgggtatc aaaaacttaa aatcgttact    61620
gctggaaaat aaatcactga cgatattaga tgataattta tacaaagtat acaatggaat    61680
atttgtggat acaatgagta tttatatagc cgtcgccaat tgtgtcagaa acttagaaga    61740
gttaactacg gtattcataa aatacgtaaa cggatgggta aaaaagggag ggcatgtaac    61800 ccttttttatc gatagaggaa gtataaaaat taaacaagac gttagagaca agagacgtaa    61860
atattctaaa ttaaccaagg acagaaaaat gttagaatta gaaaagtgta catccgaaat    61920
acaaaatgtt accggattta tggaagaaga aataaaggca gaaatgcaat taaaaatcga    61980
taaactcaca tttcaaatat atttatctga ttctgataac ataaaaatat cattgaatga    62040
gatactaaca catttcaaca ataatgagaa tgttacatta ttttattgtg atgaacgaga    62100
cgcagaattc gttatgtgtc tcgaggctaa aacacatttc tctaccacag gagaatggcc    62160
gttgataata agtaccgatc aggatactat gctatttgca tctgctgata atcatcctaa    62220
gatgataaaa aacttaactc aactgtttaa atttgttccc tcggcagagg ataactattt    62280
agcaaaatta acggcgttag tgaatggatg tgatttcttt cctggactct atggggcatc    62340
tataacaccc accaacttaa acaaaataca attgtttagt gattttacaa tcgataatat    62400
agtcactagt ttggcaatta aaaattatta tagaaagact aactctaccg tagacgtgcg    62460
taatattgtt acgtttataa acgattacgc taatttagac gatgtctact cgtatattcc    62520
tccttgtcaa tgcactgttc aagaattatt atttttccgca ttagatgaaa atggaatga    62580 atttaaatca tcttatttag aaagcgtgcc gttaccctgc caattaatgt acgcgttaga    62640
accacgcaag gagattgatg tttcagaagt taaaacttta tcatcttata tagatttcga    62700
aaatactaaa tcagatatcg atgttataaa atctatatcc tcgatcttcg gatattctaa    62760
cgaaaactgt aacacgatag tattcggcat ctataaggat aatttactac tgagtataaa    62820
taattcattt tactttaacg atagtctgtt aataaccaat actaaaagtg ataatataat    62880
aaatataggt tactagatta aaaatggtgt tccaactcgt gtgctctaca tgcggtaaag    62940
atatttctca cgaacgatat aaattgatta tacgaaaaaa atcattaaag gatgtactcg    63000
tcagtgtaaa gaacgaatgt tgtaggttaa aattatctac acaaatagaa cctcaacgta    63060
```

```
acttaacagt gcaacctcta ttggatataa actaatatgg atccggttaa ttttatcaag    63120
acatatgcgc ctagaggttc tattatttt attaattata ccatgtcatt aacaagtcat    63180
ttgaatccat cgatagaaaa acatgtgggt atttattatg gtacgttatt atcggaacac    63240
ttggtagttg aatctaccta tagaaaagga gttcgaatag tcccattgga tagttttttt    63300
gaaggatatc ttagtgcaaa agtatacatg ttagagaata ttcaagttat gaaaatagca    63360
gctgatacgt cattaacttt attgggtatt ccgtatggat ttggtcataa tagaatgtat    63420
tgttttaaat tggtagctga ctgttataaa aatgccggta ttgatacatc gtctaaacga    63480
atattgggca aagatatttt tctgagccaa aacttcacag acgataatag atggataaag    63540
atatatgatt ctaataattt aacattttgg caaattgatt accttaaagg gtgagttaat    63600
atgcataact actcctccgt tgttttttcc ctcgttcttt ttcttaacgt tgtttgccat    63660
cactctcata atgtaaagat attctaaaat ggtaaacttt tgcatatcgg acgcagaaat    63720
tggtataaat gttgtaattg tattatttcc cgtcaatgga ctagtcacag ctccatcagt    63780
tttatatcct ttagagtatt tctcactcgt gtctaacatt ctagagcatt ccatgatctg    63840
tttatcgttg atattggccg gaaagataga tttttatt tttattatat tactattggc    63900
aattgtagat ataacttctg gtaaatattt ttctacctt tcaatctctt ctattttcaa    63960
gccggctata tattctgcta tattgttgct agtatcaata cctttctgg ctaagaagtc    64020 atatgtggta ttcactatat cagttttaac tggtagttcc attagccttt ccacttctgc    64080
agaataatca gaaattggtt ctttaccaga aaatccagct actataatag gctcaccgat    64140
gatcattggc aaaatcctat attgtaccag attaatgaga gcatatttca tttccaataa    64200
ttctgctagt tcttgagaca ttgatttatt tgatgaatct agttggttct ctagatactc    64260
taccatttct gccgcataca ataacttgtt agataaaatc agggttatca aagtgtttag    64320
cgtggctaga ataagtgggct tgcatgtatt aaagaatgcg gtagtatgag taaaccgttt    64380
taacgaatta tatagtctcc agaaatctgt ggcgttacat acatgagccg aatgacatcg    64440
aagattgtcc aatattttta atagctgctc tttgtccatt atttctatat ttgactcgca    64500
acaattgtag ataccattaa tcaccgattc cttttttcgat gccggacaat agcacaattg    64560
tttagctttg gactctatgt attcagaatt aatagatata tctctcaata cagattgcac    64620
tatacatttt gaaactatgt caaaaattgt agaacgacgc tgttctgcag ccatttaact    64680
ttaaataatt tacaaaaatt taaatgagc atccgtataa aaatcgataa actgcgccaa    64740
attgtggcat attttcaga gttcagtgaa gaagtatcta taaatgtaga ctcgacggat    64800
gagttaatgt atatttttgc cgccttggg ggatctgtaa acatttgggc cattatacct    64860
ctcagtgcat cagtgtttta ccgaggagcc gaaaatattg tgtttaatct tcctgtgtcc    64920
aaggtaaaat cgtgtttgtg tagttttcac aatgatgcca tcatagatat agaacctgat    64980
ctggaaaata atctagtaaa actttctagt tatcatgtag taagtgtcga ttgtaacaag    65040
gaactgatgc ctattaggac agatactact atttgtctaa gtagagatca aaagaaatct    65100
tacgtgttta attttcacaa gtatgaagaa aaatgttgtg gtagaaccgt cattcattaa    65160
gtgacattat aattttacca atattggaat tataatatag gtgtatttgc gcacttgcga    65220
cggttgatgc atcggtaaat atagctgtat ctaatgttct agtcggtatt tcatcatttc    65280
gctgtctaat aatagcgttt tctctatctg tttccattac agctgcctga agtttattgg    65340
tcggataata tgtaaaataa taagaaatac atacgaataa caaaaataaa ataagatata    65400
```

```
ataaagatgc catttagaga tctaattttg tttaacttgt ccaaattcct acttacagaa    65460
gatgaggaat cgttggagat agtgtcttcc ttatgtagag gatttgaaat atcttataat    65520
gacttgataa cttactttcc agataggaaa taccataaat atatttataa agtatttgaa    65580
catgtagatt tatcggagga attaagtatg gaattccatg atacaactct gagagattta    65640
gtctatctta gattgtacaa gtattccaag tgtatacggc cgtgttataa attaggagat    65700
aatctaaaag gcatagttgt tataaaggac aggaatattt atattaggga agcaaatgat    65760
gacttgatag aatatctcct caaggaatac actcctcaga tttatacata ttctaatgag    65820
cgcgtcccca taactggttc aaaattaatt ctttgtggat tttctcaagt tacatttatg    65880
gcgtatacaa cgtcgcatat aacaacaaat aaaaaggtag atgttctcgt ttccaaaaaa    65940
tgtatagatg aactagtcga tccaataaat tatcaaatac ttcaaaattt atttgataaa    66000
ggaagcggaa caataaacaa aatactcagg aagatatttt attcggtaac aggtggccaa    66060
actccatagg tagcttttc tatttcggat tttagaattt ccaaattcac cagcgattta    66120
tcggttttgg tgaaatccaa ggatttatta atgtccacaa atgccatttg ttttgtctgt    66180
ggattgtatt tgaaaatgga aacgatgtag ttagatagat gcgctgcgaa gtttcctatt    66240
agggttccgc gcttcacgtc acccagcata cttgaatcac catcctttaa aaaaaatgat    66300
aagatatcaa catggagtat atcatactcg gattttaatt cttctactgc atcactgaca    66360
ttttcacaaa tactacaata cggtttaccg aaaataatca gtacgttctt catttatggg    66420
tatcaaaaac ttaaaatcgt tactgctgga aaataaatca ctgacgatat tagatgataa    66480
tttatacaaa gtatacaatg gaatatttgt ggatacaatg agtatttata tagccgtcgc    66540
caattgtgtc agaaacttag aagagttaac tacggtattc ataaaatacg taaacggatg    66600
ggtaaaaaag ggagggcatg taacccttt tatcgataga ggaagtataa aaattaaaca    66660
agacgttaga gacaagagac gtaaatattc taaattaacc aaggacagaa aaatgctaga    66720
attagaaaag tgtacatccg aaatacaaaa tgttaccgga tttatggaag aagaaataaa    66780
ggcagaaatg caattaaaaa tcgataaact cacatttcaa atatatttat ctgattctga    66840
taacataaaa atatcattga atgagatact aacacatttc aacaataatg agaatgttac    66900
attattttat tgtgatgaac gagacgcaga attcgttatg tgtctcgagg ctaaaacaca    66960
tttctctacc acaggagaat ggccgttgat aataagtacc gatcaggata ctatgctatt    67020
tgcatctgct gataatcatc ctaagatgat aaaaaactta actcaactgt ttaaatatgt    67080
tccatctgca gaggataact atttagcaaa attaacggcg ttagtgaatg gatgtgattt    67140
ctttcctgga ctctatgggg catctataac acccaccaac ttaaacaaaa tacaattgtt    67200
tagtgatttt acaatcgata atatagtcac tagtttggca attaaaaatt attatagaaa    67260
gactaactct accgtagacg tgcgtaatat tgttacgttt ataacgatt acgctaattt    67320 agacgatgtc tactcgtatg ttcctccttg tcaatgcact gttcaagaat ttatatttc    67380 cgcattagat gaaaaatgga atgaatttaa atcatcttat ttagagaccg tgccgttacc    67440
ctgtcaatta atgtacgcgt tagaaccacg taaggagatt gatgtttcag aagttaaaac    67500
tttatcatct tatatagatt tcgaaaatac taaatcagat atcgatgtta taaaatctat    67560
atcctcgatc ttcggatatt ctaacgaaaa ctgtaacacg atagtattcg gcatctataa    67620
ggataattta ctactgagta taaataattc attttacttt aacgatagtc tgttaataac    67680
caatactaaa agtgataata taataaatat aggttactag attaaaaatg gtgttccaac    67740
tcgtgtgctc tacatgcggt aaagatattt ctcacgaacg atataaattg attatacgaa    67800
```

```
aaaaatcatt aaaggatgta ctcgtcagtg taaagaacga atgttgtagg ttaaaattat    67860
ctacacaaat agaacctcaa cgtaacttaa cagtgcaacc tctattggat ataaactaat    67920
atggatccgg ttaattttat caagacatat gcgcctagag gttctattat ttttattaat    67980
tataccatgt cattaacaag tcatttgaat ccatcgatag aaaaacatgt gggtatttat    68040
tatggtacgt tattatcgga acacttggta gttgaatcta cctatagaaa aggagttcga    68100
atagtcccat tggatagttt ttttgaagga tatcttagtg caaaagtata catgttagag    68160
aatattcaag ttatgaaaat agcagctgat acgtcattaa ctttattggg tattccgtat    68220
ggatttggtc ataatagaat gtattgtttt aaattggtag ctgactgtta taaaaatgcc    68280
ggtattgata catcgtctaa acgaatattg ggcaaagata ttttctgag ccaaaacttc     68340 acagacgata atagatggat aaagatatat gattctaata atttaacatt ttggcaaatt    68400
gattacctta aagggtgagt taatatgcat aactactcct ccgttgtttt ttccctcgtt    68460 cttttttctta acgttgtttg ccatcactct cataatgtaa agatattcta aaatggtaaa    68520
cttttgcata tcggacgcag aaattggtat aaatgttgta attgtattat ttccatatta    68580
ttatgaagac tcctggtaat actgatggcg ttttccaggg aatattctat gactgaatgt    68640
tctcaagaac tacaaaagtt ttcttcaaa atagctatct cgtctctcaa caaactacga    68700
ggattcaaaa agagagtcaa tgttttgaa actagaatcg taatggataa tgacgataac    68760
attttaggaa tgttgttttc ggatagagtt caatccttta agatcaacat ctttatggcg    68820
tttttagatt aatactttca atgagataaa tatgggtggc ggagtaagtg ttgagctccc    68880
taaacgggat ccgcacccgg gagtaccac tgatgagatg ttattaaacg tggataaaat    68940
gcatgacgtg atagctcccg ctaagctttt agaatatgtg catataggac cactagcaaa    69000
agataaagag gataaagtaa agaaaagata tccagagttt agattagtca acacaggacc    69060
cggtggtctt tcggcattgt taagacaatc gtaatggga accgcaccca attgctgtcg    69120 cactttaat cgtactcatt attggaagaa ggatggaaag atatcagata agtatgaaga    69180
gggtgcagta ttagaatcgt gttggccaga cgttcacgac actggaaaat gcatgttga    69240 tttattcgac tggtgtcagg gggatacgtt cgatagaaac atatgccatc agtggatcgg    69300
ttcagccttt aataggagta atagaactgt agagggtcaa caatcgttaa taaatctgta    69360
taataagatg caaacattat gtagtaaaga tgctagtgta ccaatatgcg aatcatttt     69420 gcattattta cgcgcacaca atacagaaga tagcaaagag atgatcgatt atattctaag    69480
acaacagtct gcggacttta aacagaaata tatgagatgt agttatccca ctagagataa    69540
gttagaagag tcattaaaat atgcggaacc tcgagaatgt tgggatccag agtgttcgaa    69600
tgccaatgtt aatttcttac taacacgtaa ttataataat ttaggacttt gcaatattgt    69660
acgatgtaat accagcgtga acaacttaca gatggataaa acttcctcat taagattgtc    69720
atgtggatta agcaatagtg atagattttc tactgttccc gtcaatagag caaaagtagt    69780
tcaacataat attaaacact cgttcgacct aaaattgcat ttgatcagtt tattatctct    69840
cttggtaata tggatactaa ttgtagctat ttaaatgggt gccgcggcaa gcatacagac    69900
gacggtgaat acactcagcg aacgtatctc gtctaaatta gaacaagaag cgaacgctag    69960
tgctcaaaca aaatgtgata tagaaatcgg aaatttttat atccgacaaa accatggatg    70020
taacctcact gttaaaaata tgtgctctgc ggacgcggat gctcagttgg atgctgtgtt    70080
atcagccgct acagaaacat atagtggatt aacaccggaa caaaaagcat acgtgccagc    70140
```

```
tatgtttact gctgcgttaa acattcagac gagtgtaaac actgttgtta gagattttga    70200
aaattatgtg aaacagactt gtaattctag cgcggtcgtc gataacaaat taaagataca    70260
aaacgtaatc atagatgaat gttacggagc cccaggatct ccaacaaatt tggaatttat    70320
taatacagga tctagcaaag gaaattgtgc cattaaagcg ttgatgcaat tgacgactaa    70380
ggccactact caaatagcac ctagacaagt tgctggtaca ggagttcagt tttatatgat    70440
tgttatcggt gttataatat tggcagcgtt gtttatgtac tatgccaagc gtatgttgtt    70500
cacatccacc aatgataaaa tcaaacttat tttagccaat aaggaaaacg tccattggac    70560
tacttacatg gacacattct ttagaacttc tccgatggtt attgctacca cggatatgca    70620
aaactgaaaa tatattgata atattttaat agattaacat ggaagttatc gctgatcgtc    70680
tagacgatat agtgaaacaa aatatagcgg atgaaaaatt tgtagatttt gttatacacg    70740
gtctagagca tcaatgtcct gctatacttc gaccattaat taggttgttt attgatatac    70800
tattatttgt tatagtaatt tatattttta cggtacgtct agtaagtaga aattatcaaa    70860
tgttgttggt ggtgctagtc atcacattaa ctatttttta ttactttata ctataatagt    70920
actagactga cttctaacaa acatctcacc tgccataaat aaatgcttga tattaaagtc    70980
ttctatttct aacactattc catctgtgga aaataatact ctgacattat cgctaattga    71040
cacatcggtg agtgatatgc ctataaagta ataatcttct tgggcacat ataccagtgt    71100 accaggttct aacaacctat ttactggtgc tcctgtagca tactttttct ttaccttgag    71160
aatatccatc gtttgcttgg tcaatagcga tatgtgattt tttatcaacc actcaaaaaa    71220
gtaattggag tgttcatatc ctctacgggc tattgtctca tggccgtgta tgaaatttaa    71280
gtaacacgac tgtggtagat tgttctata gagccgattg ccgcaaatag atagaactac    71340
caatatgtct gtacaaatgt taaacattaa ttgattaaca gaaaaaacaa tgttcgttct    71400
gggaatagaa accagatcaa aacaaaattc gttagaatat atgccacgtt tatacatgga    71460
atataaaata actacagttt gaaaaataac agtatcattt aaacatttaa cttgcggggt    71520
taatctcaca actttactgt ttttgaactg ttcaaaatat agcatcgatc cgtgagaaat    71580
acgtttagcc gcctttaata gaggaaatcc caccgccttt ctggatctca ccaacgacga    71640
tagttctgac cagcaactca tttcttcatc atccacctgt tttaacatat aataggcagg    71700
agatagatat ccgtcattgc aatattcctt ctcgtaggca cacaatctaa tattgataaa    71760
atctccattc tcttctctgc atttattatc ttgtctcggt ggctgattag gctgtggtct    71820
tggtttaggc cttggtctat cgttgttgaa tctatttttgg tcattaaatc tttcatttct    71880
tcctggtata tttctatcac ctcgtttggt tggattttg tctatattat cgtttgtaac    71940
atcggtacgg gtattcattt atcacaaaaa aaacttctct aaatgagtct actgctagaa    72000
aacctcatcg aagaagatac catatttttt gcaggaagta tatctgagta tgatgattta    72060
caaatggtta ttgccggcgc aaaatccaaa tttccaagat ctatgctttc tattttaat    72120 atagtaccta gaacgatgtc aaaatatgag ttggagttga ttcataacga aaatatcaca    72180
ggagcaatgt ttaccacaat gtataatata agaaacaatt tgggtctagg agatgataaa    72240
ctaactattg aagccattga aaactatttc ttggatccta acaatgaagt tatgcctctt    72300
attattaata atacgatat gactgccgtc attcctaaaa aaagtggtag gagaaagaat    72360
aagaacatgg ttatcttccg tcaaggatca tcacctatct tgtgcatttt cgaaactcgt    72420
aaaaagatta atatttataa agaaaatatg gaatccgcgt cgactgagta tacacctatc    72480
ggagacaaca aggctttgat atctaaatat gcgggaatta atgtcctgaa tgtgtattct    72540
```

```
ccttccacat ccataagatt gaatgccatt tacggattca ccaataaaaa taaactagag    72600
aaacttagta ctaataagga actagaatcg tatagttcta gccctcttca agaacccatt    72660
aggttaaatg attttctggg actattggaa tgtgttaaaa agaatattcc tctaacagat    72720
attccgacaa aggattgatt actataaatg gagaatgttc ctaatgtata ctttaatcct    72780
gtgtttatag agcccacgtt taaacattct ttattaagtg tttataaaca cagattaata    72840
gttttatttg aagtattcgt tgtattcatt ctaatatatg tatttttag atctgaatta    72900 aatatgttct tcatgcctaa acgaaaaata cccgatccta ttgatagatt acgacgtgct    72960
aatctagcgt gtgaagacga taaattaatg atctatggat taccatggat gacaactcaa    73020
acatctgcgt tatcaataaa tagtaaaccg atagtgtata aagattgtgc aaagcttttg    73080
cgatcaataa atggatcaca accagtatct cttaacgatg ttcttcgcag atgatgattc    73140
attttttaag tatttggcta gtcaagatga tgaatcttca ttatctgata tattgcaaat    73200
cactcaatat ctagactttc tgttattatt attgatccaa tcaaaaaata aattagaagc    73260
tgtgggtcat tgttatgaat ctcttcaga ggaatacaga caattgacaa aattcacaga    73320
ctttcaagat tttaaaaaac tgtttaacaa ggtccctatt gttacagatg aagggtcaa    73380 acttaataaa ggatatttgt tcgactttgt gattagtttg atgcgattca aaaagaatc    73440 ctctctagct accaccgcaa tagatcctgt tagatacata gatcctcgtc gtgatatcgc    73500
attttctaac gtgatggata tattaaagtc gaataaagtg aacaataatt aattctttat    73560
tgtcatcatg aacggcggac atattcagtt gataatcggc cccatgtttt caggtaaaag    73620
tacagaatta attagacgag ttagacgtta tcaaatagct caatataaat gcgtgactat    73680
aaaatattct aacgataata gatacggaac gggactatgg acgcatgata agaataattt    73740
tgaagcattg gaagcaacta aactatgtga tgtcttggaa tcaattacag atttctccgt    73800
gataggtatc gatgaaggac agttcttcc agacattgtt taattctgtg agcgtatggc    73860
aaacgaagga aaaatagtta tagtagccgc actcgatggg acatttcaac gtaaaccgtt    73920
taataatatt ttgaatctta ttccattatc tgaaatggtg gtaaaactaa ctgctgtgtg    73980
tatgaaatgc tttaaggagg cttccttttc taaacgattg ggtgaggaaa ccgagataga    74040
gataatagga ggtaatgata tgtatcaatc ggtgtgtaga aagtgttacg tcggctcata    74100
atattatatt ttttatctaa aaaactaaaa ataaacattg attaaatttt aatataatac    74160
ttaaaaatgg atgttgtgtc gttagataaa ccgtttatgt attttgagga aattgataat    74220
gagttagatt acgaaccaga aagtgcaaat gaggtcgcaa aaaaactgcc gtatcaagga    74280
cagttaaaac tattactagg agaattattt tttcttagta agttacagcg acacggtata    74340
ttagatggtg ccaccgtagt gtatatagga tcggctcctg gtacacatat acgttatttg    74400
agagatcatt tctataattt aggagtgatc atcaaatgga tgctaattga cggccgccat    74460
catgatccta tttaaatgg attgcgtgat gtaactctag tgactcggtt cgttgatgag    74520
gaatatctac gatccatcaa aaaacaactg catccttcta agattatttt aatttctgat    74580
gtaagatcca aacgaggagg aaatgaacct agtacggcgg atttactaag taattacgct    74640
ctacaaaatg tcatgattag tatttaaac cccgtggcat ctagtcttaa atggagatgc    74700
ccgtttccag atcaatggat caaggacttt tatatcccac acggtaataa aatgttacaa    74760
ccttttgctc cttcatattc agctgaaatg agattattaa gtatttatac cggtgagaac    74820
atgagactga ctcgagttac caaattagac gctgtaaatt atgaaaaaaa gatgtactac    74880
```

```
cttaataaga tcgtccgtaa caaagtagtt gttaactttg attatcctaa tcaggaatat    74940
gactattttc acatgtactt tatgctgagg accgtgtact gcaataaaac atttcctact    75000
actaaagcaa aggtactatt tctacaacaa tctatatttc gtttcttaaa tattccaaca    75060
acatcaactg aaaaagttag tcatgaacca atacaacgta aaatatctag caaaaattct    75120
atgtctaaaa acagaaatag caagagatcc gtacgcggta ataaatagaa acgtactact    75180
gagatatact accgatatag agtataatga tttagttact ttaataaccg ttagacataa    75240
aattgattct atgaaaactg tgtttcaggt atttaacgaa tcatccataa attatactcc    75300
ggttgatgat gattatggag aaccaatcat tataacatcg tatcttcaaa aaggtcataa    75360
caagtttcct gtaaattttc tatacataga tgtggtaata tctgacttat ttcctagctt    75420
tgttagacta gatactacag aaactaatat agttaatagt gtactacaaa caggcgatgg    75480
taaaaagact cttcgtcttc ccaaaatgtt agagacggaa atagttgtca agattctcta    75540
tcgccctaat ataccattaa aaattgttag attttccgc aataacatgg taactggagt     75600
agagatagcc gatagatctg ttatttcagt cgctgattaa tcaattagta gagatgagat    75660
aagaacatta taataatcaa taatatatct tatatcttat atcttatatc ttatatcttg    75720
tttagaaaaa tgctaatatt aaaatagcta acgctagtaa tccaatcgga agccatttga    75780
tatctataat agggtatcta atttcctgat ttaaatagcg gacagctata ttctcggtag    75840
ctactcgttt ggaatcacaa acattattta catctaattt actatctgta atggaaacgt    75900
ttcccaatga aatggtacaa tccgatacat tgcattttgt tatattttt tttaaagagg     75960
ctggtaacaa cgcatcgctt cgtttacatg gctcgtacca acaataatag ggtaatcttg    76020
tatctattcc tatccgtact atgctttat caggataaat acatttacat cgtatatcgt     76080
ctttgttagc atcacagaat gcataaattt gttcgtccgt catgataaaa atttaaagtg    76140
taaatataac tattatttt atagttgtaa taaaaaggga aatttgattg tatactttcg     76200
gttctttaaa agaaactgac ttgataaaaa tggctgtaat ctctaaggtt acgtatagtc    76260
tatatgatca aaaagagatt aatgctacag atattatcat tagtcatgtt aaaaatgacg    76320
acgatatcgg taccgttaaa gatggtagac taggtgctat ggatggggca ttatgtaaga    76380
cttgtgggaa aacggaattg gaatgtttcg gtcactgggg taaagtaagt atttataaaa    76440
ctcatatagt taagcctgaa tttatttcag aaattattcg tttactgaat catatatgta    76500
ttcactgcgg attattgcgt tcacgagaac cgtattccga cgatattaac ctaaaagagt    76560
tatcgggaca cgctcttagg agattaaagg ataaatatt atccaagaaa aagtcatgtt     76620
ggaacagtga atgtatgcaa ccgtatcaaa aaattacttt ttcaaagaaa aaggtttgtt    76680
tcgtcaacaa gttggatgat attaacgttc ctaattctct catctatcaa aagttaatt     76740
ctattcatga aaagttttgg ccattattag aaattcatca atatccagct aacttatttt    76800
atacagacta ctttcccatc cctccgttga ttattagacc ggctattagt ttttggatag    76860
atagtatacc caaagagacc aatgaattaa cttacttatt aggtatgatc gttaagaatt    76920
gtaacttgaa tgctgatgaa caggttatcc agaaggcggt aatagaatac gatgatatta    76980
aaattatttc taataacact accagtatca atttatcata tattcatccc ggcaaaaata    77040
atatgattag aagttatatc gtcgcccgac gaaaagatca gaccgctaga tctgtaattg    77100
gtcccagtac atctatcacc gttaatgagg taggaatgcc cgcatatatt agaaatacac    77160
ttacagaaaa gatatttgtt aatgccttta cagtggataa agttaaacaa ctattagcgt    77220
caaaccaagt taaattttac tttaataaac gattaaacca attaacaaga atacgccaag    77280
```

```
gaaagtttat taaaaataaa atacatttat tgcctggtga ttgggtagaa gtagctgttc    77340
aagaatatac aagtattatt tttggaagac agccgtctct acatagatac aacgtcatcg    77400
cttcatctat cagagctacc gaaggagata ctatcaaaat atctcccgga attgccaact    77460
ctcaaaatgc tgatttcgac ggggatgagg aatggatgat attagaacaa atcctaaag     77520 ctgtaattga acaaagtatt cttatgtatc cgacgacgtt actcaaacac gatattcatg    77580
gagcccccgt ttatggatct attcaagatg aaatcgtagc agcgtattca ttgtttagga    77640
tacaagatct tgtttagat gaagtattga acatcttggg gaaatatgga agagagttcg     77700
atcctaaagg taaatgtaaa ttcagcggta agatatcta acttacttg ataggtgaaa      77760 agattaatta tccgggtctc ttaaaggatg gtgaaattat tgcaaacgac gtagatagta    77820
attttgttgt ggctatgagg catctgtcat tggctggact cttatccgat cataagtcga    77880
acgtggaagg tatcaacttt attatcaagt catcttatgt ttttaagaga tatctatcta    77940
tttacggttt tggggtgaca ttcaaagatc tgagaccaaa ttcgacgttc actaataaat    78000
tggaggccat caacgtagaa aaaatagaac ttatcaaaga agcatacgcc aaatatctca    78060
acgatgtaag agacgggaaa atagttccat tatctaaagc tttagaggcg gactatgtgg    78120
aatccatgtt atccaacttg acaaatctta atatccgaga gatagaagaa catatgagac    78180
aaacgctgat agatgatcca gataataacc tcctgaaaat ggccaaagcg ggttataaag    78240
taaatcccac agaactaatg tatattctag gtacgtatgg acaacaaagg attgatggtg    78300
aaccagcaga gactcgagta ttgggtagag ttttaccta ctatcttcca gactctaagg     78360
atccagaagg aagaggttat attcttaatt ctttaacaaa aggattaacg ggttctcaat    78420 attactttc gatgctggtt gcaagatctc aatctactga tatcgtctgt gaaacatcac     78480
gtaccggaac actggctaga aaaatcatta aaaagatgga ggatatggtg gtcgacggat    78540
acggacaagt agttataggt aatacgctca tcaagtacgc cgccaattat accaaaattc    78600
taggctcagt atgtaaacct gtagatctta tctatccaga tgagtccatg acttggtatt    78660
tggaaattag tgctctgtgg aataaaataa acagggatt cgttactct cagaaacaga     78720 aacttgcaaa gaagacattg gcgccgttta atttcctagt attcgtcaaa cccaccactg    78780
aggataatgc tattaaggtt aaggatctgt acgatatgat tcataacgtc attgatgatg    78840
tgagagagaa atacttcttt acggtatcta atatagattt tatggagtat atattcttga    78900
cgcatcttaa tccttctaga attagaatta caaaagaaac ggctatcact atctttgaaa    78960
agttctatga aaaactcaat tatactctag gtggtggaac tcctattgga attatttctg    79020
cacaggtatt gtctgagaag tttacacaac aagcccctgtc cagttttcac actactgaaa   79080
aaagtggtgc cgtcaaacaa aaacttggtt tcaacgagtt taataacttg actaatttga    79140
gtaagaataa gaccgaaatt atcactctgg tatccgatga tatctctaaa cttcaatctg    79200
ttaagattaa tttcgaattt gtatgtttgg gagaattaaa tccaaacatc actcttcgaa    79260
aagaaacaga taggtatgta gtagatataa tagtcaatag attatacatc aagagagcag    79320
aaataaccga attagtcgtc gaatatatga ttgaacgatt catctccttt agcgtcattg    79380
taaaggaatg gggtatggag acattcattg aggacgagga taatattaga tttactgtct    79440
acctaaattt cgttgaaccg gaagaattga atcttagtaa gtttatgatg gttcttccgg    79500
gggcagccaa caagggaaag attagtaaat tcaagattcc tatctctgac tatacgggat    79560
atgacgactt caatcaaaca aaaaagctca ataagatgac tgtagaactc atgaatctaa    79620
```

```
aagaattggg ttctttcgat ttggaaaacg tcaacgtgta tcctggagta tggaatacat    79680
acgatatctt cggtatcgag gccgctcgtg aatacttgtg cgaagccatg ttaaacacct    79740
atggagaagg gttcgattat ctgtatcagc cttgtgatct tctcgctagt ttactatgtg    79800
ctagttacga accagaatca gtgaataaat tcaagttcgg cgcagctagt actcttaaga    79860
gagctacgtt cggagacaat aaagcattgt taaacgcggc tcttcataaa aagtcagaac    79920
ctattaacga taatagtagc tgccactttt ttagcaaggt ccctaatata ggaactggat    79980
attacaaata ctttatcgac ttgggtcttc tcatgagaat ggaaggaaa ctatctgata    80040 agatatcttc tcaaaagatc aaggaaatgg aagaaacaga agacttttaa ttcttatcaa    80100
taacatattt ttctatgatc tgtcttttaa acgatggatt ttccacaaat gcgcctctca    80160
agtccctcat agaatgatac acgtataaaa aatatagcat aggcaatgac tccttatttt    80220
tagacattag atatgccaaa atcatagccc cgcttctatt tactcccgca gcacaatgaa    80280
ccaacacggg ctcgtttcgt tgatcacatt tagataaaaa ggcggttacg tcgtcaaaat    80340
atttactaat atcggtagtt gtatcatcta ccaacggtat atgaataata ttaatattag    80400
agttaggtaa tgtatattta tccatcgtca aatttaaaac atatttgaac ttaacttcag    80460
atgatggtgc atccatagca tttttataat ttcccaaata cacattattg gttacccttg    80520
tcattatagt gggagatttg gctctgtgca tatctccagt tgaacgtagt agtaagtatt    80580
tatacaaact tttcttatcc atttataacg tacaaatgga taaaactact ttatcggtaa    80640
acgcgtgtaa tttagaatac gttagagaaa aggctatagt aggcgtacaa gcagccaaaa    80700
catcaacact tatattcttt gttattatat tggcaattag tgcgctatta ctctggtttc    80760
agacgtctga taatccagtc tttaatgaat taacgagata tatgcgaatt aaaaatacgg    80820
ttaacgattg gaaatcatta acggatagca aaacaaaatt agaaagtgat agaggtagac    80880
ttctagccgc tggtaaggat gatatattcg acttcaaatg tgtggatttc ggcgcctatt    80940
ttatagctat gcgattggat aagaaaacat atctgccgca agctattagg cgaggtactg    81000
gagacgcgtg gatggttaaa aaggcggcaa aggtcgatcc atctgctcaa caattttgtc    81060
agtatttgat aaaacacaag tctaataatg ttattacttg tggtaatgag atgttaaatg    81120
aattaggtta tagcggttat tttatgtcac cgcattggtg ttccgatttt agtaatatgg    81180
aatagtgtta gataaatgcg gtaacgaatg ttcctgtaag gaaccataac agcttagatt    81240
taacgttaaa gatgagcata acataataa acaaaattac aatcaaactt ataacattaa    81300
tatcaaacaa tccaaaaaat gaaatcagtg gagtagtaaa cgcgtacata actcctggat    81360
aacgtttagc agctgccgtt cctattctag accaaaaatt cggtttcatg ttttcgaaac    81420
ggtattctgc aacaagtcga ggatcgtgtt ctacatattt ggcggcatta tccagtatct    81480
gcctattgat cttcatttcg ttttcaattc tggctatttc aaaataaaat cccgatgata    81540
gacctccaga ctttataatt tcatctacga tgttcagcgc cgtagtaact ctaataatat    81600
aggctgataa gctaacatca taccctcctg tatatgtgaa tatggcatga ttttttgtcca    81660 ttacaagctc ggttttaact ttattgcctg taataatttc tctcatctgt aggatatcta    81720 ttttttttgtc atgcattgcc ttcaagacgg gacgaagaaa cgtaatatcc tcaataacgt    81780
tatcgttttc tacaataact acatattcta cctttttatt ttctaactcg gtaaaaaat    81840 tagaatccca tagggctaaa tgtctagcga tatttctttt cgtttcctct gtacacatag    81900
tgttacaaaa ccctgaaaag aagtgagtat acttgtcatc atttctaatg tttcctccag    81960
tccactgtat aaacgcataa tccttgtaat gatctggatc atccttgact accacaacat    82020
```

```
ttcttttttc tggcataact tcgttgtcct ttacatcatc gaacttctga tcattaatat  82080
gctcatgaac attaggaaat gtttctgatg gaggtctatc aataactggc acaacaataa  82140
caggagtttt caccgccgcc atttagttat tgaaattaat catatacaac tctttaatac  82200
gagttatatt ttcgtctatc cattgtttca cattgacata tttcgacaaa agatataaa   82260
atgcgtattc caatgcttct ctgtttaatg aattactaaa atatacaaac acgtcactgt  82320
ctggcaataa atgatatctt agaatattgt aacaatgtaa ggaaccataa cagtttagat  82380
ttaacgttaa agatgagcat aaacataata aacaaaatta caatcaaacc tataacatta  82440
atatcaaaca atccaaaaaa tgaaatcagt ggagtagtaa acgcgtacat aactcctgga  82500
taacgtttag cagctgccgt tcctattcta gaccaaaaat ttggtttcat gttttcgaaa  82560
cggtattctg caacaagtcg gggatcgtgt tctacatatt tggcggcatt atccagtatc  82620
tgcctattga tcttcatttc gttttcgatt ctggctattt caaaataaaa tcccgatgat  82680
agacctccag actttataat ttcatctacg atgttcagcg ccgtagtaac tctaataata  82740
taggctgata agctaacatc ataccctcct gtatatgtga atatggcatg attttgtcc   82800
attacaagct cggttttaac tttattgcct gtaataattt ctctcatctg taggatatct  82860
attttttgt catgcattgc cttcaagacg ggacgaagaa acgtaatatc ctcaataacg   82920
ttatcgtttt ctacaataac tacatattct accttttat tttctaactc ggtaaaaaa    82980
ttagaatccc ataggctaa atgtctagcg atatttcttt tcgtttcctc tgtacacata   83040
gtgttacaaa accctgaaaa gaagtgagta tacttgtcat catttctaat gtttcctcca  83100
gtccactgta taaacgcata atccttgtaa tgatctggat catccttgac taccacaaca  83160
tttcttttt ctggcataac ttcgttgtcc tttacatcat cgaacttctg atcattaata   83220
tgctcatgaa cattaggaaa tgtttctgat ggaggtctat caataactgg cacaacaata  83280
acaggagttt tcaccgccgc catttagtta ttgaaattaa tcatatacaa ctctttaata  83340
cgagttatat tttcgtctat ccattgtttc acatttacat atttcgacaa aagatataa   83400
aatgcgtatt ccaatgcttc tctgtttaat gaattactaa aatatacaaa cacgtcactg  83460
tctggcaata aatgatatct tagaatattg taacaattta ttttgtattg cacatgttcg  83520
tgatctatga gttcttcttc gaatggcata ggatctccga atctgaaaac gtataaatag  83580
gagttagaat aataatattt gagagtattg gtaatatata aactctttag cggtataatt  83640
agtttttttc tctcaatttc tattttaga tgtgatggaa aaatgactaa ttttgtagca   83700
ttagtatcat gaactctaat caaaatctta atatcttcgt cacacgttag ctctttgaag  83760
ttttaagag atgcatcagt tggttctaca gatggagtag gtgcaacaat tttttgttct   83820
acacatgtat gtactggagc cattgtttta actataatgg tgcttgtatc gaaaaacttt  83880
aatgcagata gcggaagctc ttcgccgcga ctttctacgt cgtaatggg ttctaacgcc    83940
gatctctgaa tggatactag ttttctaagt tctaatgtga ttctctgaaa atgtaaatcc  84000
aattcctccg gcattataga tgtgtataca tcggtaaata aaactatagt atccaacgat  84060
cccttctcgc aaattctagt cttaaccaaa aaatcgtata taaccacgga gatggcgtat  84120
ttaagagtgg attcttctac cgttttgttc ttggatgtca tataggaaac tataaagtcc  84180
gcactactgt taagaatgat tactaacgca actatatagt ttaaattaag cattttggaa  84240
acataaaata actctgtaga cgatacttga ctttcgaata agtttgcaga caaacgaaga  84300
aagaacagac ctctcttaat ttcagaagaa aactttttt cgtattcctg acgtctagag   84360
```

```
tttatatcaa taagaaagtt aagaattagt cggttaatgt tgtatttcat tacccaagtt   84420
tgagatttca taatattatc aaaagacatg ataatattaa agataaagcg ctgactatga   84480
acgaaatagc tatatggttc gctcaagaat atagtcttgt taaacgtgga aacgataact   84540
gtatttttaa tcacgtcagc ggcatctaaa ttaaatatag gtatatttat tccacacact   84600
ctacaatatg ccacaccatc ttcataataa ataaattcgt tagcaaaatt attaatttta   84660
gtgaaatagt tagcgtcaac tttcatagct tccttcaatc taatttgatg ctcacacggt   84720
gcgaattcca ctctaacatc ccttttccat gcctcaggtt catcgatctc tataatatct   84780
agttttttgc gtttcacaaa cacaggctcg tctctcgcga tgagatctgt atagtaacta   84840
tgtaaatgat aactagatag aaagatgtag ctatatagat gacgatcctt taagagaggt   84900
ataataactt taccccaatc agatagactg ttgttatggt cttcggaaaa agaattttta   84960
taaatttttc cagtattttc caaatatacg tacttaacat ctaaaaaatc cttaatgata   85020
ataggaatgg ataatccgtc tatttttataa agaaatacat atcgcacatt atactttttt   85080
ttggaaatgg gaataccgat gtgtctacat aaatatgcaa agtctaaata ttttttagag   85140
aatcttagtt ggtccaaatt cttttccaag tacggtaata gatttttcat attgaacggt   85200
atcttcttaa tctctggttc tagttccgca ttaaatgatg aaactaagtc actattttta   85260
taactaacga ttcatcacc tctaacatca tcatttacca gaatactgat cttcttttgt   85320
cgtaaataca tgtctaatgt gttaaaaaaa agatcataca agttatacgt catttcatct   85380
gtggtattct tgtcattgaa ggataaactc gtactaatct cttctttaac agcctgttca   85440
aatttatatc ctatatacga aaaaatagca accagtgttt gatcatccgc gtcaatattc   85500
tgttctatcg tagtgtataa caatcgtata tcttcttctg tgatagtcga tacgttataa   85560
aggttgataa cgaaaatatt tttatttcgt gaaataaagt catcgtagga ttttggactt   85620
atattcgcgt ctagtagata tgcttttatt tttggaatga tctcaattag aatagtctct   85680
ttagagtcca tttaaagtta caaacaacta ggaaattggt ttatgatgta taattttttt   85740 agttttata gattctttat tctatactta aaaaatgaaa ataaatacaa aggttcttga   85800
gggttgtgtt aaattgaaag cgagaaataa tcataaatta tttcattatc gcgatatccg   85860
ttaagtttgt atcgtaatgg cgtggtcaat tacgaataaa gcggatacta gtagcttcac   85920
aaagatggct gaaatcagag ctcatctaaa aaatagcgct gaaaataaag ataaaaacga   85980
ggatattttc ccggaagatg taataattcc atctactaag cccaaaacca aacgagccac   86040
tactcctcgt aaaccagcgg ctactaaaag atcaaccaaa aaggaggaag tggaagaaga   86100
agtagttata gaggaatatc atcaaacaac tgaaaaaaat tctccatctc ctggagtcag   86160
cgacattgta gaaagcgtgg ccgctgtaga gctcgatgat agcgacgggg atgatgaacc   86220
tatggtacaa gttgaagctg gtaaagtaaa tcatagtgct agaagcgatc tctctgacct   86280
aaaggtggct accgacaata tcgttaaaga tcttaagaaa attattacta gaatctctgc   86340
agtatcgacg gttctagagg atgttcaagc agctggtatc tctagacaat ttacttctat   86400
gactaaagct attacaacac tatctgatct agtcaccgag ggaaaatcta agttgttcg   86460 taaaaaagtt aaaacttgta agaagtaaat gcgtgcactt ttttataaag atggtaaact   86520
ctttaccgat aataatttt taatcctgt atcagacgat aatccagcgt atgaggtttt   86580
gcaacatgtt aaaattccta ctcatttaac agatgtagta gtatatgaac aaacgtggga   86640
ggaggcgtta actagattaa ttttttgtggg aagcgattca aaaggacgta gacaatactt   86700
ttacggaaaa atgcatgtac agaatcgcaa cgctaaaaga gatcgtatt ttgttagagt   86760
```

```
atataacgtt atgaaacgaa ttaattgttt tataaacaaa aatataaaga aatcgtccac  86820
agattccaat tatcagttgg cggttttat gttaatggaa actatgtttt ttattagatt   86880
tggtaaaatg aaatatctta aggagaatga aacagtaggg ttattaacac taaaaaataa  86940
acacatagaa ataagtcccg atgaaatagt tatcaagttt gtaggaaagg acaaagtttc  87000
acatgaattt gttgttcata agtctaatag actatataaa ccgctattga aactgacgga  87060
tgattctagt cccgaagaat ttctgttcaa caaactaagt gaacgaaagg tatacgaatg  87120
tatcaaacag tttggtatta gaatcaagga tctccgaacg tatggagtca attatacgtt  87180
tttatataat ttttggacaa atgtaaagtc catatctcct cttccgtcac caaaaaagtt  87240
aatagcgtta actatcaaac aaactgctga agtggtaggt catactccat caatttcaaa  87300
aagagcttat atggcaacga ctattttaga aatggtaaag gataaaaatt ttttagatgt  87360
agtatctaaa actacgttcg atgaattcct atctatagtc gtagatcacg ttaaatcatc  87420
tacggatgga tgatatagat ctttacacaa ataattacaa gaccgataaa tggaaatgga  87480
taagcgtatg aaatctctcg caatgacagc tttcttcgga gagctaagca cattagatat  87540
tatggcattg ataatgtcta tatttaaacg ccatccaaac aataccattt tttcagtgga  87600
taaggatggt cagtttatga ttgatttcga atacgataat tataaggctt ctcaatattt  87660
ggatctgacc ctcactccga tatctggaga tgaatgcaag actcacgcat cgagtatagc  87720
cgaacaattg gcgtgtgtgg atattattaa agaggatatt agcgaatata tcaaaactac  87780
tccccgtctt aaacgattta taaaaaaata ccgcaataga tcagatactc gcatcagtcg  87840
agatacagaa aagcttaaaa tagctctagc taaaggcata gattacgaat atataaaaga  87900
cgcttgttaa taagtaaatg aaaaaaaact agtcgtttat aataaaacac gatatggatg  87960
ccaacgtagt atcatcttct actattgcga cgtatataga cgctttagcg aagaatgctt  88020
cagaattaga acagaggtct accgcatacg aaataaataa tgaattggaa ctagtattta  88080
ttaagccgcc attgattact ttgacaaatg tagtgaatat ctctacgatt caggaatcgt  88140
ttattcgatt taccgttact aataaggaag gtgttaaaat tagaactaag attccattat  88200
ctaaggtaca tggtctagat gtaaaaaatg tacagttagt agatgctata gataacatag  88260
tttgggaaaa gaaatcatta gtgacggaaa atcgtcttca caaagaatgc ttgttgagac  88320
tatcgacaga ggaacgtcat atatttttgg attacaagaa atatggatcc tctatccgac  88380
tagaattagt caatcttatt caagcaaaaa caaaaaactt tacgatagac tttaagctaa  88440
aatattttct aggatccggt gcccaatcta aaagttcttt gttgcacgct attaatcatc  88500
caaagtcaag gcctaataca tctctggaaa tagaattcac acctagagac aatgaaacag  88560
ttccatatga tgaactaata aaggaattga cgactctctc gcgtcatata tttatggctt  88620
ctccagagaa tgtaattctt tctccgccta ttaacgcgcc tataaaaacc tttatgttgc  88680
ctaaacaaga tatagtaggt ttggatctgg aaaatctata tgccgtaact aagactgacg  88740
gcattcctat aactatcaga gttacatcaa acggggttgta ttgttatttt acacatcttg  88800
gttatattat tagatatcct gttaagagaa taatagattc cgaagtagta gtctttggtg  88860
aggcagttaa ggataagaac tggaccgtat atctccattaa gctaatagag cccgtgaatg  88920
ctatcagtga tagactagaa gaaagtaagt atgttgaatc taaactagtg gatatttgtg  88980
atcggatagt attcaagtca aagaaatacg aaggtccgtt tactacaact agtgaagtcg  89040
tcgatatgtt atctacatat ttaccaaagc aaccagaagg tgttattctg ttctattcaa  89100
```

```
agggacctaa atctaacatt gattttaaaa ttaaaaagga aaatactata gaccaaactg   89160
caaatgtagt atttaggtac atgtccagtg aaccaattat ctttggagaa tcgtctatct   89220
ttgtagagta taagaaattt agcaacgata aaggctttcc taaagaatat ggttctggta   89280
agattgtgtt atataacggc gttaattatc taaataatat ctattgtttg gaatatatta   89340
atacacataa tgaagtgggt attaagtccg tggttgtacc tattaagttt atagcagaat   89400
tcttagttaa tggagaaata cttaaaccta gaattgataa aaccatgaaa tatattaact   89460
cagaagatta ttatggaaat caacataata tcatagtcga acatttaaga gatcaaagca   89520
tcaaaatagg agatatcttt aacgaggata aactatcgga tgtgggacat caatacgcca   89580
ataatgataa atttagatta aatccagaag ttagttattt tacgaataaa cgaactagag   89640
gaccgttggg aattttatca aactacgtca agactcttct tatttctatg tattgttcca   89700
aaacattttt agacgattcc aacaaacgaa aggtattggc gattgatttt ggaaacggtg   89760
ctgacctgga aaaatacttt tatggagaga ttgcgttatt ggtagcgacg gatccggatg   89820
ctgatgctat agctagagga aatgaaagat acaacaaatt aaactctgga attaaaacca   89880
agtactacaa atttgactac attcaggaaa ctattcgatc cgatacattt gtctctagtg   89940
tcagagaagt attctatttt ggaaagttta atatcatcga ctggcagttt gctatccatt   90000
attcttttca tccgagacat tatgctaccg tcatgaataa cttatccgaa ctaactgctt   90060
ctggaggcaa ggtattaatc actaccatgg acggagacaa attatcaaaa ttaacagata   90120
aaaagacttt tataattcat aagaatttac ctagtagcga aaactatatg tctgtagaaa   90180
aaatagctga tgatagaata gtggtatata atccatcaac aatgtctact ccaatgactg   90240
aatacattat caaaaagaac gatatagtca gagtgtttaa cgaatacgga tttgttcttg   90300
tagataacgt tgatttcgct acaattatag aacgaagtaa aaagtttatt aatggcgcat   90360
ctacaatgga agatagaccg tctacaaaaa acttttttcga actaaataga ggagccatta   90420
aatgtgaagg tttagatgtc gaagacttac ttagttacta tgttgtttat gtcttttcta   90480
agcggtaaat aataatatgg tatgggttct gatatccccg ttctaaatgc attaaataat   90540
tccaatagag cgattttttgt tcctatagga ccttccaact gtggatactc tgtattgtta   90600
atagatatat taatacttttt gtcgggtaac agaggttcta cgtcttctaa aaataaaagt   90660
tttataacat ctggcctgtt cataaataaa aacttggcga ttctatatat actcttatta   90720
tcaaatctag ccattgtctt atagatgtga gctactgtag gtgtaccatt tgattttctt   90780
tctaatacta tatatttctc tcgaagaagt tcttgcacat catctgggaa taaaatacta   90840
ctgttgagta aatcagttat ttttttttata tcgatattga tggacatttt tatagttaag   90900
gataataagt atcccaaagt cgataacgac gataacgaag tatttatact tttaggaaat   90960
cacaatgact ttatcagatt aaaattaaca aaattaaagg agcatgtatt tttttctgaa   91020
tatattgtga ctccagatac atatggatct ttatgcgtcg aattaaatgg gtctagtttt   91080
cagcacggtg gtagatatat agaggtggag gaatttatag atgctggaag acaagttaga   91140
tggtgttcta catccaatca tatatctaaa gatatacccg aagatatgca cactgataaa   91200
tttgtcattt atgatatata cactttttgac gctttcaaga ataaacgatt ggtattcgta   91260
caggtacctc cgtcgttagg agatgatagt catttgacta atccgttatt gtctccgtat   91320
tatcgtaatt cagtagccag acaaatggtc aataatatga ttttttaatca agattcattt   91380 ttaaatatatt tattagaaca tctgattaga agccactata gagtttctaa acatataaca   91440
atagttagat acaaggatac cgaagaatta aatctaacga gaatatgtta taatagagat   91500
```

```
aagtttaagg cgtttgtatt cgcttggttt aacggcgttt cggaaaatga aaaggtacta    91560
gatacgtata aaaaggtatc taatttgata taatgaattc agtgactgta tcacacgcgc    91620
catatactat tacttatcac gatgattggg aaccagtaat gagtcaattg gtagagtttt    91680
ataacgaagt agccagttgg ctgctacgag acgagacgtc gcctattcct gataagttct    91740
ttatacagtt gaaacaaccg cttagaaata acgagtatg tgtgtgcggt atagatccgt     91800
atccgaaaga tggaactggt gtaccgttcg aatcaccaaa ttttacaaaa aaatcaatta    91860
aggagatagc ttcatctata tctagattaa ccggagtaat tgattataaa ggttataacc    91920
ttaatataat agacggggtt atacctggaa attattactt aagttgtaaa ttaggagaaa    91980
caaaaagtca cgcgatctac tgggataaga tttccaagtt actgctgcag catataacta    92040
aacacgttag tgttctttat tgtttgggta aaacagattt ctcgaatata cgggcaaagt    92100
tagaatcccc ggtaactacc atagtcggat atcatccagc ggctagagac cgccaattcg    92160
agaaagatag atcatttgaa attatcaacg ttttactgga attagacaac aaggcaccta    92220
taaattgggc tcaagggttt atttattaat gctttagtga aattttaact tgtgttctaa    92280
atggatgcgg ctattagagg taatgatgtt atctttgttc ttaagactat aggtgtcccg    92340
tcagcgtgca gacaaaatga agatccaaga tttgtagaag catttaaatg cgacgagtta    92400
gaaagatata ttgagaataa tccagaatgt acactattcg aaagtcttag ggatgaggaa    92460
gcatactcta tagtcagaat tttcatggat gtagatttag acgcgtgtct agacgaaata    92520
gattatttaa cggctattca agattttatt atcgaggtgt caaactgtgt agctagattc    92580
gcgtttacag aatgcggtgc cattcatgaa aatgtaataa aatccatgag atctaatttt    92640
tcattgacta agtctacaaa tagagataaa acaagttttc atattatctt tttagacacg    92700
tataccacta tggatacatt gatagctatg aaacgaacac tattagaatt aagtagatca    92760
tctgaaaatc cactaacaag atcgatagac actgccgtat ataggagaaa aacaactctt    92820
cgggttgtag gtactaggaa aaatccaaat tgcgacacta ttcatgtaat gcaaccaccg    92880
catgataata tagaagatta cctattcact tacgtggata tgaacaacaa tagttattac    92940
ttttctctac aacaacgatt ggaggattta gttcctgata agttatggga accagggttt    93000
atttcattcg aagacgctat aaaaagagtt tcaaaaatat tcattaattc tataataaac    93060
tttaatgatc tcgatgaaaa taattttaca acggtaccac tggtcataga ttacgtaaca    93120
ccttgtgcat tatgtaaaaa acgatcgcat aaacatccgc atcaactatc gttggaaaat    93180
ggtgctatta gaatttacaa aactggtaat ccacatagtt gtaaagttaa aattgttccg    93240
ttggatggta taaactgtt taatattgca caaagaattt tagacactaa ctctgtttta    93300
ttaaccgaac gaggagacca tatagtttgg attaataatt catggaaatt taacagcgaa    93360
gaacccttga taacaaaact aattttgtca ataagacatc aactacctaa ggaatattca    93420
agcgaattac tctgtccgag gaaacgaaag actgtagaag ctaacatacg agacatgtta    93480
gtagattcag tggagaccga tacctatccg gataaacttc cgtttaaaaa tggtgtattg    93540
gacctggtag acggaatgtt ttactctgga gatgatgcta aaaaatatac gtgtactgta    93600
tcaaccggat ttaaatttga cgatacaaag ttcgtcgaag acagtccaga aatggaagag    93660
ttaatgaata tcattaacga tatccaacca ttaacggatg aaaataagaa aaatagagag    93720
ctatatgaaa aaacattatc tagttgttta tgcggtgcta ccaaaggatg tttaacattc    93780
ttttttggag aaactgcaac tggaaagtcg acaaccaaac gtttgttaaa gtctgctatc    93840
```

```
ggtgacctgt tgttgagac gggtcaaaca attttaacag atgtattgga taaaggacct    93900
aatccattta tcgctaacat gcatttgaaa agatctgtat tctgtagcga actacctgat    93960
tttgcatgta gtgggtcaaa gaaaatcaga tctgataata ttaaaaagtt gacagaacct    94020
tgtgtcattg gaagaccgtg tttctccaat aaaattaata atagaaacca tgcgacaatc    94080
attatcgata ctaattacaa acctgttttt gataggatag ataacgcatt aatgagaaga    94140
attgccgtcg tgcgattcag aacacacttt tctcaacctt ctggtagaga ggctgctgaa    94200
aataatgacg cgtacgataa agtcaaacta ttagacgagg ggttagatgg taaaatacaa    94260
aataatagat atagattcgc atttctatac ttgttggtga atggtacag aaaatatcat     94320
gttcctatta tgaaactata tcctacaccc gaagagattc ctgactttgc attctatctc    94380
aaaataggta ctctgttggt atctagctct gtaaagcata ttccattaat gacggacctc    94440
tccaaaaagg gatatatatt gtacgataat gtggtcactc ttccgttgac tactttccaa    94500
cagaaaatat ccaagtattt taattctaga ctatttggac acgatataga gagcttcatc    94560
aatagacata agaaatttgc caatgttagt gatgaatatc tgcaatatat attcatagag    94620
gatatttcat ctccgtaaat atatgctcat atatttatag aagatatcac atatctaaat    94680
gaataccgga atcatagatt tatttgataa tcatgttgat agtataccaa ctatattacc    94740
tcatcagtta gctactctag attatctagt tagaactatc atagatgaga acagaagcgt    94800
gttattgttc catattatgg gatcaggtaa acaataatc gctttgttgt tcgccttggt     94860
agcttccaga tttaaaaagg tttacattct agtgccgaac atcaacatct taaaaatttt    94920
caattataat atgggtgtag ctatgaactt gtttaatgac gaattcatag ctgagaatat    94980
ctttattcat tccacaacaa gttttttattc tcttaattat aacgataacg tcattaatta    95040
taacggatta tctcgctaca ataactctat ttttatcgtt gatgaggcac ataatatctt    95100
tgggaataat actggagaac ttatgaccgt gataaaaaat aaaaacaaga ttccttttt     95160
actattgtct ggatctccca ttactaacac acctaatact ctgggtcata ttatagattt    95220
aatgtccgaa gagacgatag attttggtga aattattagt cgtggtaaga aagtaattca    95280
gacacttctt aacgaacgcg gtgtgaatgt acttaaggat ttgcttaaag gaagaatatc    95340
atattacgaa atgcctgata aagatctacc aacgataaga tatcacggac gtaagtttct    95400
agatactaga gtagtatatt gtcacatgtc taaacttcaa gagagagatt atatgattac    95460
tagacgacag ctatgttatc atgaaatgtt tgataaaaat atgtataacg tgtcaatggc    95520
agtattggga caacttaatc tgatgaataa tttagatact ttatttcagg aacaggataa    95580
ggaattgtac ccaaatctga aaataaataa tggcgtgtta tacggagaag aattggtaac    95640
gttaaacatt agttccaaat ttaaatactt tattaatcgg atacagacac tcaacggaaa    95700
acattttata tacttttcta attctacata tggcggattg gtaattaaat atatcatgct    95760
cagtaatgga tattctgaat ataatggttc tcagggaact aatccacata tgataaacg     95820
caaaccaaaa acatttgcta tcgttactag taaaatgaaa tcgtctttag aggatctatt    95880
agatgtgtat aattctcctg aaaacgatga tggtagtcaa ttgatgtttt tgttttcatc    95940
aaacattatg tccgaatcct atactctaaa agaggtaagg catatttggt ttatgactat    96000
cccagatact ttttctcaat acaaccaaat tcttggacga tctattagaa aattctctta    96060
cgccgatatt tctgaaccag ttaatgtata tcttttagcc gccgtatatt ccgatttcaa    96120
tgacgaagtg acgtcattaa acgattacac acaggatgaa ttaattaatg tttttaccatt    96180
tgacatcaaa aagctgttgt atctaaaatt taagacgaaa gaaacgaata gaatatactc    96240
```

```
tattcttcaa gagatgtctg aaacgtattc tcttccacca catccatcaa ttgtaaaagt    96300
tttattggga gaattggtca gacaattttt ttataataat tctcgtatta agtataacga    96360
taccaagtta cttaaaatgg ttacatcagt tataaaaaat aaagaagacg ctaggaatta    96420
catagatgat attgtaaacg gtcacttctt tgtatcgaat aaagtatttg ataaatctct    96480
tttatacaaa tacgaaaacg atattattac agtaccgttt agactttcct acgaaccatt    96540
tgtttgggga gttaactttc gtaaagaata taacgtggta tcttctccat aaaactgatg    96600
agatatataa agaaataaat gtcgagcttt gttaccaatg gatacctttc cgttacattg    96660
gaacctcatg agctgacgtt agacataaaa actaatatta ggaatgccgt atataagacg    96720
tatctccata gagaaattag tggtaaaatg gccaagaaaa tagaaattcg tgaagacgtg    96780
gaattacctc tcggcgaaat agttaataat tctgtagtta taaacgttcc gtgtgtaata    96840
acctacgcgt attatcacgt tggggatata gtcagaggaa cattaaacat cgaagatgaa    96900
tcaaatgtaa ctattcaatg tggagattta atctgtaaac taagtagaga ttcgggtact    96960
gtatcattta gcgattcaaa gtactgcttt tttcgaaatg gtaatgcgta tgacaatggc    97020
agcgaagtca ctgccgttct aatggaggct caacaaggta tcgaatctag ttttgttttt    97080
ctcgcgaata tcgtcgactc ataaaaaaga gaatagcggt aagtataaac acgaatacta    97140
tggcaataat tgcgaatgtt ttattctctt cgatatattt ttgataatat gaaaaacatg    97200
tctctctcaa atcggacaac catctcataa aatagttctc gcgcgctgga gaggtagttg    97260
ccgctcgtat aatctctcca gaataatata cttgcgtgtc gtcgttcaat ttatacggat    97320
ttctatagtt ctctgttata taatgcggtt tgccctcatg attagacgac gacaatagtg    97380
ttctaaattt agatagttga tcagaatgaa tgtttattgg cgttggaaaa attatccata    97440
cagcgtctgc agagtggttg atagttgttc ctagatatgt aaaataatcc aacttactag    97500
gcagcaaatt gtctagataa aatactgaat caaacggtgc agacgtattg gcggatctaa    97560
tggaatccaa ttgattaact atcttttgaa aatatacatt tttatgatcc aatacttgta    97620
agaatataga aataatgata agtccatcat cgtgtttttt tgcctcttca taagaactat    97680 atttttctt attccaatga acaagattaa tctctccaga gtatttgtac acatctatca    97740
agtgattgga tccataatcg tcttcctttc cccaatatat atgtagtgat gataacacat    97800
attcattggg gagaaaccct ccacttatat atcctccttt aaaattaatc cttactagtt    97860
ttccagtgtt ctggatagtg gttggtttcg actcattata atgtatgtct aacggcttca    97920
atcgcgcgtt agaaattgct tttttagttt ctatattaat aggagatagt tgttgcggca    97980
tagtaaaaat gaaatgataa ctgtttaaaa atagctctta gtatgggaat tacaatggat    98040
gaggaagtga tatttgaaac tcctagagaa ttaatatcta ttaaacgaat aaaagatatt    98100
ccaagatcaa aagacacgca tgtgtttgct gcgtgtataa caagtgacgg atatccgtta    98160
ataggagcta gaagaacttc attcgcgttc caggcgatat tatctcaaca aaattcagat    98220
tctatcttta gagtatccac taaactatta cggtttatgt actacaatga actaagagaa    98280
atctttagac ggttgagaaa aggttctatc aacaatatcg atcctcactt tgaagagtta    98340
atattattgg gtggtaaact agataaaaag gaatctatta aagattgttt aagaagagaa    98400
ttaaaagagg aaagtgatga acgtataaca gtaaaagaat ttggaaatgt aattctaaaa    98460
cttacaacac gggataaatt attaataaa gtatatataa gttattgcat ggcgtgtttt    98520
attaatcaat cgttggagga tttatcgcat actagtattt acaatgtaga aattagaaag    98580
```

```
attaaatcat taaatgattg tattaacgac gataaatacg aatatctgtc ttatatttat   98640
aatatgctag ttaatagtaa atgaactttt acagatctag tataattagt cagattatta   98700
agtataatag acgactagct aagtctatta tttgcgagga tgactctcaa attattacac   98760
tcacggcatt cgttaaccaa tgcctatggt gtcataaacg agtatccgtg tccgctattt   98820
tattaactac tgataacaaa atattagtat gtaacagacg agatagtttt ctctattctg   98880
aaataattag aactagaaac atgtttagaa agaaacgatt atttctgaat tattccaatt   98940
atttgaacaa acaggaaaga agtatactat cgtcattttt ttctctagat ccagctacta   99000
ctgataatga tagaatagac gctatttatc cgggtggcat acccaaaagg ggtgagaatg   99060
ttccagagtg tttatccagg gaaattaaag aagaagttaa tatagacaat tcttttgtat   99120
tcatagacac tcggtttttt attcatggca tcatagaaga taccattatt aataaatttt   99180
ttgaggtaat cttctttgtc ggaagaatat ctctaacgag tgatcaaatc attgatacat   99240
ttaaaagtaa tcatgaaatc aaggatctaa tattttttaga tccgaattca ggtaatggac   99300
tccaatacga aattgcaaaa tatgctctag atactgcaaa acttaaatgt tacggccata   99360
gaggatgtta ttatgaatca ttaaaaaaat taactgagga tgattgatta aaaaatataa   99420
attaatttac catcgtgtat ttttataacg ggattgtccg gcatatcatg tagatagtta   99480
ccgtctacat cgtatactcg accatctacg cctttaaatc ctctatttat tgacattaat   99540
ctattagaat tggaatacca aatattagta ccctcaatta gtttattggt aatatttttt   99600
ttagacgata gatcgatggc tcttgaaacc aaggttttcc aaccggactc attgtcgatc   99660
ggtgagaagt cttttcatt agcatgaatc cattctaatg atgtatgttt aaacactcta   99720
aacaattgga caaattcttt tgatttgctt tgaatgattt caaataggtc ttcgtctaca   99780
gtaggcatac cattagataa tctagccatt ataaagtgca cgtttacata tctacgttct   99840
ggaggagtaa gaacgtgact attgagacga atggctcttc ctactatctg acgaagagac   99900
gcctcgttcc atgtcatatc taaaatgaag atatcattaa ttgagaaaaa actaataccc   99960
tcgcctccac tagaagagaa tacgcatgtt ttaatgcatt ctccgttagt gtttgattct  100020
tggttaaact cagccaccgc cttgattcta gtatcttttg ttctagatga gaactctata  100080
ttagagatac caaagacttt gaaatatagt aataagattt ctattcctga ctgattaaca  100140
aatggttcaa agactagaca tttaccatgg gatgctaata ttcccaaaca tacatctata  100200
aatttgacgc ttttctcttt taattcagta aatagagaga tatcagccgc actagcatcc  100260
cctttcaata gttctccctt tttaaaggta tctaatgcgg atttagaaaa ctctctatct  100320
cttaatgaat ttttaaaatc attatatagt gttgctatct cttgcgcgta ttcgcccgga  100380
tcacgatttt gtctttcagg aaagctatcg aacgtaaacg tagtagccat acgtctcaga  100440
attctaaatg atgatatacc tgttttttatt tcagcgagtt tagccttttg ataaatttct  100500
tcttgctttt tcgacatatt aacgtatcgc attaatactg ttttcttagc gaatgatgca  100560
gacccttcta cgtcatcaaa aatagaaaac tcgttattaa ctatatacga acatagtcct  100620
cctagtttgg agactaattc ttttcatcg actagacgtt tattctcaaa tagtgattgg  100680
tgttgtaagg atcctggtcg tagtaagtta accaacatgg tgaattcttg cacactattg  100740
acgataggtg tagccgataa acaaatcatc ttatggtttt ttaacgcaat ggtcttagat  100800
aaaaaattat atactgaacg agtaggacgg atcttaccat cttctttgat taatgattta  100860
gaaatgaagt tatgacattc atcaatgatg acgcatattc tactcttgga attaatagtt  100920
ttgatattag taaaaaattt atttctaaaa ttttgatcat cgtaattaat aaaaatacaa  100980
```

```
tccttcgtta tctctggagc gtatctgagt atagtgttca tccaaggatc ttctatcaaa   101040 gccttttca ccaataagat aatagcccaa ttcgtataaa tatccttaag atgtttgaga    101100
atatatacag tagtcattgt tttaccgaca cccgtttcat ggaacaataa aagagaatgc   101160
atactgtcta atcctaagaa aactcttgct acaaaatgtt gataatcctt gaggcgtact   101220
acgtccgacc ccatcatttc aacgggcata ttagtagttc tgcgtaaggc ataatcgata   101280
taggccgcgt gtgatttact catttatgag tgataagtaa taactatgtt ttaaaaatca   101340
cagcagtagt ttaactagtc ttctctgatg tttgttttcg atactttttg aatcagaagt   101400
catactagaa taaagcaacg agtgaacgta atagagagct tcgtatactc tattcgaaaa   101460
ctctaagaac ttattaatga attccgtatc cactggattg tttaaaatac taaattgaac   101520
actgttcaca tccttccaag aagaagactt agtgacggac ttaacatgag acataaataa   101580
atccaaattt tttttacaaa catcactagc caccataatg gcgctatctt tcaaccagct   101640
atcgcttacg cattttagca gtctaacatt tttaaagaga ctacaatata ttctcatagt   101700
atcgattaca cctctaccga ataaagttgg aagtttaata atacaatatt tttcgtttac   101760
aaaatcaaat aatggtcgaa acacgtcgaa ggttaacatc ttataatcgc taatgtatag   101820
attgttttca gtgagatgat tattagattt aatagcatct cgttcacgtt tgaacagttt   101880
attgcgtgcg ctgaggtcgg caactacggc gtccgcttta gtactcctcc cataatactt   101940
tacgctatta atcttaaaa tttcatagac tttatctaga tcgctttctg gtaacatgat    102000
atcatgtgta aaaagtttta acatgtcggt cggcattcta tttagatcat taactctaga   102060
aatctgaaga aagtaattag ctccgtattc cagactaggt aatgggcttt tacctagaga   102120
cagattaagt tctggcaatg tttcataaaa tggaagaagg acatgcgttc cctcccggat   102180 atttttaca atttcatcca tttacaactc tatagtttgt tttcattatt attagttatt    102240
atctcccata atcttggtaa tacttacccc ttgatcgtaa gataccttat acaggtcatt   102300
acatacaact accaattgtt tttgtacata atagattgga tggttgacat ccatggtgga   102360
ataaactact cgaacagata gtttatcttt cccctagat acattagccg taatagttgt    102420
cggcctaaag aatatctttg gtgtaaagtt aaaagttagg gttcttgttc cattattgct   102480
ttttgtcagt agttcattat aaattctcga gatgggtccg ttctctgaat atagaacatc   102540
atttccaaat ctaacttcta gtctagaaat aatatcggtc ttattcttaa aatctattcc   102600
cttgatgaag ggatcgttaa tgaacaaatc cttggccttt gattcggctg atctattatc   102660
tccgttatag acgttacgtt gactagtcca aagacttaca ggaatagatg tatcgatgat   102720
gttgatacta tgtgatatgt gagcaaagat tgttctctta gtggcatcac tatatgttcc   102780
agtaatggcg gaaaactttt tagaaatgtt atatataaaa gaattttttc gtgttccaaa   102840
cattagcaga ttagtatgaa gataaacact catattatca ggaacattat caattttac    102900 atacacatca gcatcttgaa tagaaacgat accatcttct ggaacctcta cgatctcggc   102960
agactccgga taaccagtcg gtgggccatc gctaacaata actagatcat ccaacaatct   103020
actcacatat gcatctatat aatcttttc atcttgtgag taccctggat acgaaataaa    103080
tttattatcc gtatttccat aataaggttt agtataaaca gagagagatg ttgccgcatg   103140
aacttcagtt acagtcgccg ttggttggtt tatttgacct attactctcc taggtttctc   103200
tataaacgat ggtttaattt gtacattctt aaccatatat ccaataaagc tcaattcagg   103260
aacataaaca aattctttgt tgaacgtttc aaagtcgaac gaagagtcac gaataacgat   103320
```

```
atcggatact ggattgaagg ttaccgttac ggtaattttt gaatcggata gtttaagact    103380
gctgaatgta tcttccacat caaacggagt tttaatataa acgtatactg tagatggttc    103440
tttaatagtg tcattaggag ttaggccaat agaaatatca ttaagttcac tagaatatcc    103500
agagtgtttc aaagcaattg tattattgat acaattatta tataattctt cgccctcaat    103560
ttcccaaata acaccgttac acgaagagat agatacgtga ttaatacatt tatatccaac    103620
atatggtacg taactgaatc ttcccatacc tttaacttct ggaagttcca aactcagaac    103680
caaatgatta agcgcagtaa tatactgatc cctaatttcg aagctagcga tagcctgatt    103740
gtctggacca tcgtttgtca taactccgga tagagaaata tattgcggca tatataaagt    103800
tggaatttga ctatcgactg cgaagacatt agaccgttta atagagtcat ccccaccgat    103860
caaagaatta atgatagtat tattcatttt ctatttaaaa tggaaaaagc ttacaataaa    103920
ctccgtagag aaatatctat aatttgtgag ttttccttaa agtaacagct tccgtaaacg    103980
ccgtctttat ctcttagtag gtttattgta tttatgacct tttccttatc ttcatagaat    104040
actaaaggca acaaagaaat ttttggttct tctctaagag ctacgtgaga cttaaccata    104100
gaagccaacg aatccctaca tattttagaa cagaaatacc ctacttcacc acccttgtat    104160
gtctcaatac taataggtct aaaaaccaaa tcttgattac aaaaccaaca cttatcaatt    104220
acactatttg tcttaataga cacatctgcc atagatttat aatactttgg tagtatacaa    104280
gcgagtgctt cttctttagc gggcttaaag actgctttag gtgctgaaat aaccacatct    104340
ggaaggctta ctcgcttagc catttaatta cggaactatt tttttatact tctaatgagc    104400
aagtagaaaa cctctcatct acaaaaacgt actcgtgtcc ataatcctct accatagtta    104460
cacgtttttt agatctcata tgtgctaaaa agttttccca tactaattgg ttactattat    104520
ttttcgtata attttttaaca gtttgaggtt ttagattttt agttacagaa gtgatatcga    104580
atattttatc caaaagaat gaataattaa ttgtcttaga aggagtgttt tcttggcaaa    104640
agaataccaa gtgcttaaat atttctacta cttcattaat ctttttctgta ctcagattca    104700
gtttctcatc ttttacttga ttgattattt caaagactaa cttataatcc tttttattta    104760
ttctctcgtt agccttaaga aaactagata caaaatttgc atctacatca tccgtggata    104820
tttgattttt ttccatgata tccaagagtt ccgagataat ttctccagaa cattgatgag    104880
acaataatct ccgcaataca tttctcaaat gaataagttt attagacacg tggaagtttg    104940
actttttttg tacctttgta catttttgaa ataccgactc gcaaaaaata caatattcat    105000
atccttgttc agatactata ccgttatgtc tacaaccgct acataatcgt agattcatgt    105060
taacactcta cgtatctcgt cgtccaatat tttatataaa acatttttat ttctagacgt    105120
tgccagaaaa tcctgtaata ttttttagttt tttgggctgt gaataaagta tcgccctaat    105180
attgttaccg tcttccgcca atatagtagt taaattatcc gcacatgcag aagaacaccg    105240
cttaggcgga ttcagtacaa tgttatattt ttcgtaccaa ctcatttaaa tatcataatc    105300
taaaatagtt ctgtaatatg tctagcgcta atatattgat cataatcctg tgcataaatt    105360
aagatacaac aatgtctcga aatcatcgac atggcttctt ccatagttag aagatcgtcg    105420
tcaaagttag caacgtgatt catcaacatt tgctgttttg aggcagcaaa tactgaaccg    105480
tcgccattca accattcata aaaaccatcg tctgaatcca ttgataattt cttgtactgg    105540
tttttgagag ctcgcatcaa tctagcattt ctagctcccg gattgaaaac agaaagagga    105600
tcgtacatcc agggtccatt ttctgtaaat agaatcgtat aatgtcccctt caagaagata    105660
tcagacgatc cacaatcaaa gaattggtct ccgagtttgt aacaaactgc ggactttaac    105720
```

```
ctatacatga taccgtttag cataatttct ggtgatacgt caatcggagt atcatctatt    105780
agagatctaa agccggtgta acattctcca ccaaacatat tcttattctg acgtcgttct    105840
acataaaaca tcattgctcc attaacgata acaggggaat gaacagcact acccatcaca    105900
ttagttccca atggatcaat gtgtgtaact ccagaacatc ttccatagcc tatgttagga    105960
ggagcgaaca ccactcttcc actattgcca tcgaatgcca tagaataaat atccttggaa    106020
ttgatagaaa tcggactgtc ggatgttgtg atcatcttca taggattaac aactatgtat    106080
ggtgccgcct gaagtttcat atcgtaactg atgccgttta taggtctagc cacagaaacc    106140
aacgtaggtc taaatccaac tatagacaaa atagaagcca atatctgttc ctcatctgtc    106200
ataacttgag agcatccagt atgaataatc ttcattagat ggggatctac cgcatcatca    106260
tcgttacaat aaaaaattcc cattctaatg ttcataattg cttttctaat catggtatgc    106320
atgtttgctc tctgaatctc tgtggaaatt agatctgata cacctgtaat cactatcgga    106380
ttatcctccg taagacgatt aaccaacaac atataattat aagactttac ttttctaaat    106440
tcataaagtt gctggattag ctataggtg tctccatgta catacgcgtt ctcgagcgca    106500
ggaagtttaa taccgaatag tgccatcaga ataggatgaa tatagtaatt agtttctggt    106560
tttctataaa taaagacaa atcttgtgaa ctagacatat cggtaaaatg catggattgg    106620
aatcgtgtag tcgacagaag aatatgatga ttagatggag agtatatttt atctaactct    106680
ttgagttggt caccgattct aggactagct cgagaatgaa taagtactaa aggatgagta    106740
catttcacag aaacactagc attgttcaat gtgctcttta catgggtaag gagttgaaat    106800
agctcgtttc tatttgttct gacaatattt agtttattca taatgttaag catatcctga    106860
atagtaaagt tagatgtgtc atacttgtta gtagttagat atttagcaat tgcattccca    106920
tcatttctca atctcgtact ccaatcatgt gtagatgcta cttcgtcgat ggaaaccata    106980
caatcctttt tgataggctg ttgagattga tcatttcctg cacgtttagg tttggtacgt    107040
tgatttctag cccctgcgga tataaagtca tcgtctacaa tttgggacaa tgaattgcat    107100
acactacaag acaaagattt atcagaagtg tgaatatgat cttcatctac caagaaaga    107160 gtttgattag tataactaga ttttagtcct gcgttagatg ttaaaaaaac atcgctattg    107220
accacggctt ccattattta tattcgtagt ttttactcga aagcgtgatt ttaatatcca    107280
atcttattac ttttggaatc gttcaaaacc tttgactagt tgtagaattt gatctattgc    107340
cctacgcgta tactcccttg catcatatac gttcgtcacc agatcgtttg tttcggcctg    107400
aagttggtgc atatctcttt caacattcga catgagatcc ttaagggcca tatcgtctag    107460
attttgttga gatgctgctc ctggatttgg attttgttgt gctgttgtac atactgtacc    107520
accagtaggt gtaggagtac atacagtggc cacaatagga ggttgagaaa gtgtaaccgt    107580
tggagtagta caagaaatac ttccatccga ttgttgtgta catgtagttg ttggtaacgt    107640
ctgagaaggt tgggtagatg gcggcgtcgt cgttttttga tctttattaa atttagagat    107700
aatatcctga acagcattgc tcggcgtcaa cgctggaagg agtgaactcg ccggcgcatc    107760
agtatcttca gacagccaat caaaaagatt agacatatca gatgatgtat tagtttgttg    107820
tcgtggtttt ggtgtaggag cagtactact aggtagaaga ataggagccg atgtagcgt    107880 tggaaccggc tgtggagtta tatgaatagt tggttgtagc ggttggatag gctgtctgct    107940
ggcggccatc atattatctc tagctagttg ttctcgcaac tgtctttgat aatacgactc    108000
ttgagacttt agtcctattt caatcgcttc atccttttc gtatccggat ccttttcttc    108060
```

```
agaataatag attgacgact ttggtgtaga ggattctgcc agcctctgtg agaacttgtt  108120
aaagaagtcc atttaaggct ttaaaattga attgcgatta taagattaaa tggcagacac  108180
agacgatatt atcgactatg aatccgatga tctcaccgaa tacgaggatg atgaagaaga  108240
ggaagaagat ggagagtcac tagaaactag tgatatagat cccaaatctt cttataagat  108300
tgtagaatca gcatccactc atatagaaga tgcgcattcc aatcttaaac atataggaa   108360
tcatatatct gctcttaaac gacgctatac tagacgtata agtctatttg aaatagcggg  108420
tataatagca gaaagctata acttgcttca acgaggaaga ttacctctag tttcagaatt  108480
ttctgacgaa acgatgaagc aaaatatgct acatgtaatt atacaagaga tagaggaggg  108540
ttcttgtcct atagtcatcg aaaagaacgg agaattgttg tcggtaaacg attttgacaa  108600
agatggtcta aaattccatc tagactatat tatcaaaatt tggaaacttc aaaaacgata  108660
ttagaattta tacgaatatc gttctctaaa tgtcacaatc aagtctcgca tgttcagcaa  108720
tttattgtcg tactttatat cgtgttcatt aacgatatct tgcaaaatag taatgattct  108780
atcttccttc gatagatatt cttcagagat tattgtctta tattctttct tgttatcaga  108840
tatgaatttg ataagacttt gaacattatt gatacccgtc tgtttaattt tttctacaga  108900
tattttagtt ttggcagatt ctatcgtatc tgtcaataga catccaacat cgacattcga  108960
cgtcaattgt ctataaatca acgtataaat tttagaaata acattagcga attgttgtgc  109020
gttgatgtcg ttattctgaa acagtatgat tttaggtagc attttcttaa caaagagaac  109080
gtatttattg ttactcagtt gaacagatga tatatccaga ttactaacgc atctgattcc  109140
gtataccaaa ctttcagaag aaatggtata caattgtttg tattcattca atgtctcttt  109200
ttcagaaatt agtttagagt cgaatactgc aataattttc aagagatagt tttcatcaga  109260
taagatttta tttagtgtag atatgataaa actattgttt tgttggagaa cttgatacgc  109320
cgcgttctct gtagtcgacg ctctcaaatg ggaaacaatc tccattattt ttttggaatc  109380
ggatactata tcttcggtat cttgacgcag tctagtatac atagagttaa gagagattag  109440
agtttgtaca ttaagcaaca tgtctctaaa tgtggctaca aacttttcct ttttcacatc  109500
atctagttta ttatataccg atttcacaac ggcaccagat ttaaggaacc agaatgaaaa  109560
actctgataa ctacaatatt tcatcatagt tacgatttta tcatcttcta tagttggtgt  109620
aatagcgcat accttttct ccaagactgg aaccaacgtc ataaaatgt ttaaatcaaa   109680
atccatatca acatctgatg cgctaagacc agtctcgcgt tcaagattat ctttactaat  109740
ggtgacgaac tcatcgtata aaactctaag tttgtccatt atttatttac agatttagtt  109800
gtttaattta tttgtgctct tccagagttg ggatagtatt tttctaacgt cggtattata  109860
ttattaggat ctacgttcat atgtatcata atattaatca tccacgtttt gataaatcta  109920
tctttagctt ctgaaataac gtatttaaac aaaggagaaa aatatttagc tacggcatca  109980
gacgcaataa cattttttgt aaatgtaacg tatttagacg acagatcttc gttaaaaagt  110040
tttccatcta tgtagaatcc atcggttgtt aacaccattc ccgcgtcaga ttgaatagga  110100
gtttgaatag tttgttttgg aaatagatcc ttcaataact tatagttggg tgggaaaaaa  110160
tcgattttat cactagactc tttctttttt actatcatta cctcatgaac tatttcttga  110220
atgagtatat gtattttctt tcctatatcg gacgcgttca ttggaaaata taccatgtcg  110280
ttaactataa gaatattttt atcctcgttt acaaactgaa taatatcaga tgtagttcgt  110340
aaacgaacta tatcatcacc agcacaacat ctaactatat gatatccact agtttccttt  110400
agccgtttat tatcttgttc catattagca gtcattccat catttaagaa ggcgtcaaag  110460
```

```
ataataggga gaaatgacat tttggattct gttacgactt taccaaaatt aaggatatac   110520
ggacttacta tcttttttctc aacgtcaatt tgatgaacac acgatgaaaa tgtgcttcta   110580
tgagattgat catgtagaaa acaacaaggg atacaatatt tccgcatatc atgaaatata   110640
ttaagaaatc ccaccttatt atatttcccc aaaggatcca tgcacgtaaa cattatgccg   110700
ttatcattaa taaagacttc tttctcatcg gatctgtaaa agttgttact gattttttttc  110760 attccaggat ctagataatt aataatgatg ggttttctat tcttattctt tgtattttgg   110820
catatcctag accagtaaac agtttccact ttggtaaaat cagcagactt ttgaacgcta   110880
ttaaacatgg cattaatggc aataactaaa aatgtaaaat atttttctat gttaggaata   110940 tggttttttca ctttaataga tatatggttt ttggccaaaa tgatagatat ttttttatcc  111000
gaggatagta aaatattatt agtcgccgtc tctataaaaa tgaagctagt ctcgatatcc   111060
aattttattc tagaattgat aggagtcgcc aaatgtacct tatacgttat atctcccttg   111120
atgcgttcca tttgtgtatc tatatcggac acaagatctg taaatagttt tacgttatta   111180
atcatcacgg tatcgccgtc gctagataac gctaatgtac catccaagtc ccaaatggag   111240
agatttaact gttcatcgtt tagaataaaa tgattaccgg tcatattaat aaagtgttca   111300
tcgtatctag ataacaacga cttataatta atgtccaagt cttgaactcg ctgaatgatc   111360
ttttttaacc cagttagttt tagattggta cgaaatatat tgttaaactt tgattctaca   111420
gtaatgtcca aatctagttg tggaaatact tccatcaaca ttgtttcaaa cttgataata   111480
ttattatcta catcttcgta cgatccaaat tccggaatag atgtatcgca cgctctggcc   111540
acccagataa ccaaaaagtc acacgctcca ggatatacat tgtataaaaa gctatcgttt   111600
tttagtaggg ttttttttctg cgtgtatacg aagggattaa aaatagtatt atcaacgtaa   111660
ctatattcca aattattctt atgagaatag ataataatat cgtccttaat atctaacaaa   111720
tttcctaaat atcccttttaa ttgagtcatt cgaagcgtca atagaatatg tctcttaact   111780
atttccggct gttgtatatt taaatgactt cgtaaaaaat aatatatggg cgacttctca   111840
tctatgtaat catatggagt gagatatagg gctcgttcta cctcctgccc cttacccacc   111900
tgtaatacca attgcggact tactatatat cgcatattta tatcgtgggg taaagtgaaa   111960
atctactacc gatgatgtaa gtcttacaat gttcgaacca gtaccagatc ttaatttgga   112020
ggcctccgta gaactagggg aggtaaatat agatcaaaca acacctatga taaaggagaa   112080
tagcggtttt atatcccgca gtagacgtct attcgcccat agatctaagg atgatgagag   112140
aaaactagca ctacgattct ttttacaaag acttttatttt ttagatcata gagagattca   112200
ttatttgttc agatgcgttg acgctgtaaa agacgtcact attaccaaaa aaataacat    112260 tatcgtggcg ccttatatag cacttttaac tatcgcatca aaaggatgca aacttacaga   112320
aacaatgatt gaagcattct ttccagaact atataatgaa catagtaaga aatttaaatt   112380
caactctcaa gtatccatca tccaagaaaa actcggatac cagtttggaa actatcacgt   112440
ttatgatttt gaaccgtatt actctacagt agctctggct attcgagatg aacattcatc   112500 tggcatttttt aatatccgtc aagagagtta tctggtaagt tcattatctg aaataacata   112560
tagattttat ctaattaatc taaaatctga tcttgttcaa tggagtgcta gtacgggcgc   112620
tgtaattaat caaatggtaa atactgtatt gattacagtg tatgaaaagt tacaactggt   112680
catagaaaat gattcacaat ttacatgttc attggctgtg gaatcaaaac ttccaataaa   112740
attacttaaa gatagaaatg aattatttac aaaattcatt aacgagttaa aaaagaccag   112800
```

```
ttcattcaag ataagcaaac gcgataagga tacgctacta aaatatttta cttaggactg  112860
gagttagaat ttatagacga ctcatttcgt ttatcattgt tactattatt actattacta  112920
tcattattag tgttggcatt attagtattc ttcttgtcat cttgttcaga aatatacagc  112980
aatgctatac ctaatactaa atacattatc atgctcgcaa tggctctaac aacaacgaac  113040
caaaatgaat ttggtcgtag cttttgttca caaaaataca taagaaatg tctacataaa  113100
tctatggcgc cattggctac ttgaaatagc gccagtcctc ctacagattt taatatagct  113160
gtataacatg acatttattc atcatcaaaa gagacagagt caccatctgt catatttaga  113220
ttttttttca tgtgttcaaa gtatcctcta ctcatttcat tataatagtt tatcatactt  113280
agaattttag gacggatcaa tgagtaagac ttgactagat cgtcagtagt aatttgtgca  113340
tcgtctattc tgcatccgct tcgtcgaata atgtatagca tcgctttgag attctccata  113400
gctatcaagt ctttatacaa tgacatggaa atatctgtga atactttata cttctccaac  113460
atcgatgcct taacatcatc gcctacttta gcattgaaaa tacgttctat tgtgtagatg  113520
gatgtagcaa gatttttaaa caacaatgcc atcttacacg atgattgcct caagtctcca  113580
atcgtttgtt tagaacgatt agctacagag tccaatgctt ggctgactag catattatta  113640
tctttagaaa ttgtattctt caatgaggcg tttatcatat ctgtgatttc gttagtcata  113700
ttacagtctg actgggttgt aatgttatcc aacatatcac ctatggatac ggtacacgta  113760
ccagcatttg taataatcct atctaagatg ttgtatggca ttgcgcagaa aatatcttct  113820
cctgtaatat ctccactctc gataaatcta ctcagattat tcttaaatgc cttattctct  113880
ggagaaaaga tatcagtgtc catcatttca ttaatagtat acgcagaaaa gataccacga  113940
gtatcaattc tatccaagat acttatcggt tccgagtcac agataatggt ttcctctcct  114000
tcgggagatc ctgcatagaa atatctagga caatagtttc tatactgtct gtaactctga  114060
taatctctaa agtcactaac tgataccatg aaattgagaa gatcaaacgc tgaagtaatt  114120
aattttctg cctcgttttt actacaacta gttttcatca atgtagtgac gatgtattgt  114180
ttagttactt ttggtctaat actgatgata gagatattat tgcttcccat aatggatctt  114240
ctagtagtca ccttaaagcc cattgatgcg aatagcagat agataaagtc ttggtatgac  114300
tcctttctaa tatagtacgg actaccttg tcacccaact ttatacccac ataagccata  114360
acaacctctt taatagccgt ttcatgaggt ttatcagcca tgagcctgag tagttggaag  114420
aatctcatga atcccgtctc agaaagtcct atatgcatga tagatttatc tttcctggga  114480
aactctcgta tagtcataga tgaaatactc tttaaagttt ctgaaataag attagtaaca  114540
gtcttacctc cgactactct aggtaacaaa caaactctaa taggtgtttt ctctgcggag  114600
ataatatcag aaaggataga gcaataagta gtattattgt gattataaag accgaataca  114660
taacaggtag aatttataaa catcatgtcc tgaaggtttt tagacttgta ttcctcgtaa  114720
tccataccgt cccaaaacat ggatttggta actttgatag ccgtagatct ttgttccttc  114780
gccaacaggt taaagaaatt aataaagaat ttgttgtttc tatttatgtc cacaaattgc  114840
acgtttggaa gcgccacggt tacattcact gcagcatttt gaggatcgcg agtatgaagt  114900
acgatgttat tgtttactgg tatatctgga aagaaatcta ccagtctagg aataagagat  114960
tgatatcgca tagaaatagt aaagtttata atctcatcat cgaagagcat tttgttacca  115020
ttgtaataaa tatccactct gtcatatgta taaatgaagt actgttcaaa catgatgaga  115080
tgtttatatg ttggcatagt agtgagatcg acgtttggta atggcaatgt attaagatta  115140
actccataat gtctagcagc atctgcgatg ttataagcgt cgtcaaagcg gggtcgatct  115200
```

```
tgtattgtta tatattgtct aacacctata agattatcaa atcttgtct gcttaataca   115260 ccgttaacaa ttttttgcctt gaattctttt attggtgcat taataacatc cttatagagg  115320
atgttaaaca aataagtgtt atcaaagtta agatctggat atttcttttc tgctagaaca   115380
tccattgagt cggagccatc tggtttaata taaccaccga taaatctagc tctgtattct   115440
gtatccgtca atctaatatt aagaaggtgt tgagtgaaag gtggaagatc gtaaaagctg   115500
tgagtattaa tgataggatt agtttccgaa ctaatgttaa ttggggtatt aataatatct   115560
atatttccag cgttaagtgt aacattaaac agttttaatt cacgtgacgt ggtatcaatt   115620
aaataattaa tgcccaattt ggatatagca gcctgaagct catcttgttt agttacggat   115680
cctaatgagt tattaagcaa tatatcgaac ggatgaacga aggttgtttt aagttggtca   115740
catactttgt aatctagaca tagatgcgga agaacggtag aaactatacg aaataaatat   115800
tcagagtcct ctaattgatc aagagtaact attgacttaa taggcatcat ttatttagta   115860
ttaaatgacg accgtaccag tgacggatat acaaaacgat ttaattacag agttttcaga   115920 agataaattat ccatctaaca aaaattatga ataactctt cgtcaaatgt ctattctaac   115980
tcacgttaac aacgtggtag atagagaaca taatgccgcc gtagtgtcat ctccagagga   116040
aatatcctca caacttaatg aagatctatt tccagatgat gattcaccgg ccactattat   116100
cgaacgagta caacctcata ctactattat tgacgatact ccacctccta cgtttcgtag   116160
agagttatta atatcggaac aacgtcaaca acgagaaaaa agatttaata ttacagtatc   116220
gaaaaatgct gaagcaataa tggaatctag atctatgata acttctatgc caacacaaac   116280
accatccttg ggagtagttt atgataaaga taaagaatt cagatgttag aggatgaagt   116340
ggttaatctt agaaatcaac gatctaatac aaaatcatct gataatttag ataattttac   116400
caaaatacta tttggtaaga ctccgtacaa atcaacagaa gttaataagc gtatagccat   116460
cgttaattat gcaaatttga acgggtcccc cttatcagtc gaggacttgg atgtttgttc   116520
ggaggatgaa atagatagaa tctataaaac gattaaacaa tatcacgaaa gtagaaaacg   116580
aaaaattatc gtcactaacg tgattattat tgtcataaac attatcgagc aggcattgct   116640
aaaactcgga tttgaagaaa tcaaaggact gagtaccgat atcacttcag aaattatcga   116700
tgtggagatc ggagatgact gcgatgctgt agcatctaaa ctaggaatcg gtaacagtcc   116760
ggttcttaat attgtattgt ttatactcaa gatattcgtt aaacgaatta aaattattta   116820
atttaataca ttcccatatc cagacaacaa tcgtctggat taatctgttc ctgtcgtctc   116880
ataccggacg acatattaat cttttattta gtgggcatct ttttagatgg tttcttttc   116940 ccagcattaa ctgagtcgat acctagaaga tcgtgattga tctctccgac cattccacga   117000
acttctaatt ggccgtctct gacggtacca taaactattt taccagcatt agtaacagct   117060
tggacaatct gaccatccat cgcattgtac gatgtagtag taactgttgt tctacgtcta   117120
ggagcaccag aagtattttt ggagcccttg gatgttgatg tagaagaaga cgaggatttt   117180
gattttggtt tacatgtaat acattttgaa ctctttgatt ttgtatcaca tgcgccggca   117240
gtcacatctg tttgagaatt aagattattg ttgcctcctt tgacggctgc atctccaccg   117300 attgcgcta gtagattttt aagctgtggt gtaatcttat taactgtttc gataatca   117360 tcgtaactgc ttctaacggc taaattttt ttatccgcca tttagaagct aaaaatattt   117420
ttatttatgc agaagattta actagattat acaatgaact aatatgatcc ttttccagat   117480
tatttacaaa cttggtattt tttggttctg gaggaggcga atttaaattc ggacttggat   117540
```

```
tcggattttg taagttcttg atcttattat acatcgagta taggatggcg acagtaactg  117600
ctacacaaat accgatcaaa agaagaatac caatcattta ttgacaataa cttcactatt  117660
gatcaagtat gcaatatatc atcttttcac taaataagta gtaataatga ttcaacaatg  117720
tcgagatata tggacgataa taatttagtt catggaaata tcgctatgat tggtgtgaat  117780
gactccgcta actctgtggg gtgcgcagtg ctttccccac atagaataaa ttagcattcc  117840
gactgtgata ataataccaa gtataaacgc cataatactc aatactttcc atgtacgagt  117900
gggactggta gacttactaa agtcaataaa ggcgaagata cacgaaagaa tcaaaagaat  117960
gattccagcg attagcacgc cggaaaaata atttccaatc ataagcatca tgtccattta  118020
actaataaaa attttaaatc gccgaatgaa caaagtggaa tataaaccat ataaaaacaa  118080
tagtttgtac tgcaaaaata atatctattt ttgttttcga agatatggta aaattaaata  118140
gtagtacaca gcatgttata actaacagca gcaacggctc gtaattactt atcatttact  118200
agacgaaaag gtggtgggat attttcttgc tcaaataata cgaatatatc acccatccat  118260
tttatgcgat gtttatatac tctaatcttt aatagatcta tagacgacgg gtttaccaac  118320
aatatagatt ttatcgattc atctaattta aacccttcct taaacgtgaa tgatctatta  118380
tctggcataa cgatgacccct acctgatgaa tcggacaatg tactgggcca tgtagaataa  118440
attatcaacg aattatcgtc tacgaacatt tatatcattt gttttaattt taggacgcga  118500
ataaatggat ataaaataga aaataacaga tattcaaacc agtgttatgg ccgcgcccaa  118560
ccaggtaggc agttttattt tatcttttac tacaggttct cctggatgta cgtcaccaac  118620
ggcggacgta gttctagtac aattagacgt aagttccgct tgggaatttt ttaacgctaa  118680
agagttaacg ttaatcgtgc acccaacgta tttacatcta gttcgttgaa catcttgatt  118740
ataatataac cattttctat ctctagattc gtcagtgcac tcatgtaacc aacatacccct  118800
aggtcctaaa tatttatctc cggaattaga ttttggataa ttcgcgcacc aacaatttct  118860
atttccttta tgatcgttac aaaagacgta taatgccgta tccccaaaag taaaataatc  118920
aggacgaata attctaataa actcagaaca atatctcgca tccatatgtt tggagcaaat  118980
atcggaataa gtagacatag ccggtttccg ttttgcacgt aaccattcta aacaattggg  119040
gtttccagga tcgtttctac aaaatccagt catgaaatcg tcacaatgtt ctgtcttgta  119100
attattatta aatattttg gacagtgttt ggtatttgtc ttagaacaac attttgccac  119160
gctatcacta tcgcccagga gataatcctt ttttataaaa tgacatcgtt gcccggatgc  119220
tatataatca gtagcgtgtt ttaaatcctt aatatattca ggagttacct cgttctgata  119280
atagattaat gatccaggac gaaatttgaa agaactacat ggttctccat gaattaatac  119340
atattgttta gcaaattcag gaactataaa actactacaa tgatctatcg acataccatc  119400
tatcaaacaa aacttgggtt taatttctcc cggagatgtt tcataatagt acgtataact  119460
ttcttctgca aacttaacag ctctattata ttcaggataa ttaaaaccta attccatata  119520
tttgtctcgt atatctgcta ttcctggtgc tatttttgatt ctattaagag taacagctgc  119580
ccccattctt aataatcgtc agtatttaaa ctgttaaatg ttggtatatc aacatctacc  119640
ttatttcccg cagtataagg tttgttgcag gtatactgtt caggaatggt tacatttata  119700
cttcttctat agtcctgtct ttcgatgttc atcacatatg caaagaacag aataaacaaa  119760
ataatgtaag aaataatatt aaatatctgt gaattcgtaa atacattgat tgccataata  119820
attacagcag ctacaataca cacaatagac attcccacag tgttgccatt acctccacga  119880
tacatttgag ttactaagca ataggtaata actaagctag taagaggcaa tagaaaagat  119940
```

```
gagataaata tcatcaatat agagattaga ggagggctat atagagccaa gacgaacaaa 120000
atcaaaccga gtaacgttct aacatcatta tttttgaaga ttcccaaata atcattcatt 120060
cctccataat cgttttgcat cataccctcca tctttaggca taaacgattg ctgctgttcc 120120
tctgtaaata aatctttatc aagcactcca gcacccgcag agaagtcgtc aagcatattg 120180
taatatctta ataactcat ttatatatta aaaaatgtca ctattaaaga tggagtataa 120240
tctttatgcc gaactaaaaa aaatgacttg tggtcaaccc ctaagtcttt ttaacgaaga 120300
cggggatttc gtagaagttg aaccgggatc atcctttaag tttctgatac ctaagggatt 120360
ttacgcctct ccttccgtaa agacgagtct agtattcgag acattaacaa cgaccgataa 120420
taaaatcact agtatcaatc caacaaatgc gccaaagtta tatcctcttc aacgcaaagt 120480
cgtatctgaa gtagtttcta atatgaggaa aatgatcgaa tcaaaacgtc ctctatacat 120540
tactcttcac ttggcgtgtg gatttggtaa gactattacc acgtgttatc ttatggctac 120600
acacggtaga aaaaccgtca tttgcgtacc caataaaatg ttaatacatc aatggaagac 120660
acaggtagag gcagtcggat tggaacataa gatatccata gatggagtaa gtagtctatt 120720
aaaggaacta aagactcaaa gtccggatgt attaatagta gtcagtagac atctgacaaa 120780
cgatgccttt tgtaaatata tcaataagca ttatgatttg ttcatcttgg atgaatcaca 120840
tacgtataat ctgatgaaca atacagcagt tacaagattt ttagcgtatt atcctccgat 120900
gatgtgttat ttttttaactg ctacacctag accatctaac cgaatttatt gtaacagtat 120960
tattaatatt gccaagttat ccaatctaaa aaaaactatc tatgcagtag atagttttttt 121020 tgagccatat tccacagata atattagaca tatggtaaaa cgactagatg gaccatctaa 121080
taaatatcat atatataccg agaagttatt atctgtagac gagcctagaa atcaacttat 121140
tcttgatacc ctggtagaag aattcaagtc aggaactatt aatcgcattt tagttattac 121200
taaactacgt gaacatatgg tattattcta caaacgatta ttagattttt tcggaccaga 121260
ggttgtattt ataggagacg cccaaaatag acgtactcca gatatggtca aatcaatcaa 121320
ggaactaaat agatttatat tcgtatccac cttattttat tccggtactg gtttagatat 121380
tcctagtttg gattcgttgt tcatttgctc ggcagtaatc aacaatatgc aaatagagca 121440
attactaggg agggtatgtc gagaaacaga actattagat aggacggtat atgtatttcc 121500
taacacatcc atcaaagaaa taaagtacat gataggaaat ttcatgcaac gaattattag 121560
tctgtctgta gataaactag gatttaaaca aaaaagttat cggaaacatc aagaatccga 121620
tcccacttct gcatgtacaa catcatccag agaagaacgt gtattaaata gaatatttaa 121680
ctcgcaaaat cgttaagaag tttaagcgac gatccgcatg ctgcgcaggc cagtgtatta 121740
cccctcatag tattaatata atccaatgat acttttgtga tgtcggaaat cttaaccaat 121800
ttagactgac aggcagaaca cgtcatgcaa tcatcatcgt catcgataac tgtagtcttg 121860
ggcttctttt tgcgactctt cattccggaa cgcacattgg tgctatccat ttaggtagta 121920
aaaaataagt cagaatatgc cctataacac gatcgtgcaa aacctggtat atcgtctcta 121980
tctttatcac aatatagtgt atcgacattt ttattattat tgacctcgtt tatccttggaa 122040 catggaatgg gaacattttt gttatcaacg gccatctttg ccttaattcc agatgttgta 122100
aaattataac taaacagtct atcatcgaca caaatgaaat tcttgtttag acgtttgtag 122160
tttacgtatg cggctcgttc gcgtctcatt ttttcagata ttgcaggtac tataatatta 122220
aaaataagaa tgaaataaca taggattaaa aataaagtta tcatgacttc tagcgctgat 122280
```

```
ttaactaact taaaagaatt acttagtctg tacaaaagtt tgagattttc agattctgcg  122340
gctatagaaa agtataattc tttggtagaa tggggaacat ctacttactg gaaaataggc  122400
gtgcaaaagg tagctaatgt cgagacgtca atatctgatt attatgatga ggtaaaaaat  122460
aaaccgttta atattgatcc gggctattac attttcttac cggtatattt tgggagcgtc  122520
tttatttatt cgaagggtaa aaatatggta gaacttggat ctggaaactc ttttcaaata  122580
ccagatgata tgcgaagtgc gtgtaacaaa gtattagaca gcgataacgg aatagacttt  122640
ctgagatttg ttttgttaaa caatagatgg ataatggaag atgctatatc aaaatatcag  122700
tctccagtta atatatttaa actagctagt gagtacggat taaacatacc caaatattta  122760
gaaattgaaa tagaggaaga cacattattt gacgacgagt tatactctat tatagaacgc  122820
tctttcgatg ataaatttcc aaaaatatcc atatcgtata ttaagttggg agaacttaga  122880
cggcaagttg tagactttt caaattctca ttcatgtata ttgagtccat caaggtagat  122940
cgtataggag ataatatttt tattcctagc gttataacaa aatcaggaaa aaagatatta  123000
gtaaaagatg tagaccattt aatacgatcc aaggttagag aacatacatt tgtaaaagta  123060
aaaaagaaaa acacattttc cattttatac gactatgatg gaaacggaac agaaactaga  123120
ggagaagtaa taaaacgaat tatagacact ataggacgag actattatgt taacggaaag  123180
tatttctcta aggttggtag tgcaggctta aagcaattga ctaataaatt agatattaat  123240
gagtgcgcaa ctgtcgatga gttagttgat gagattaata aatccggaac tgtaaaacga  123300
aaaataaaaa accaatcagc atttgattta agcagagaat gtttgggata tccagaagcg  123360
gattttataa cgttagttaa taacatgcgg ttcaaaatag aaaattgtaa ggttgtaaat  123420
ttcaatattg aaaatactaa ttgtttaaat aacccgagta ttgaaactat atatggaaac  123480
tttaaccagt tcgtctcaat ctttaatgtc gtcaccgatg tcaaaaaaag attattcgag  123540
tgaaataata tgcgcctttg ataggtgc aaaaaatcct gccagaactg ttttagaagt  123600
caaggataac tccgttaggg tattggatat atcaaaatta gactggagtt ctgattggga  123660
aaggcgcata gctaaagatt tgtcacaata tgaatacact acagttcttc tagaacgtca  123720
gcctagaagg tcgccgtatg ttaaatttat ctattttatt aaaggctttt tatatcatac  123780
atcggctgcc aaagttattt gcgtctcgcc tgtcatgtct ggtaattcat atagagatcg  123840
aaaaaagaga tcggtcgaag catttcttga ttggatggac acattcggat tgcgagactc  123900
cgttccggat agacgcaaat tagacgatgt agcggatagt ttcaatttgg ctatgagata  123960
cgtattagat aaatggaata ctaattatac accttataat aggtgtaaat ctagaaatta  124020
cataaaaaaa atgtaataac gttagtaacg ccattatgga taatctattt acctttctac  124080
atgaaataga agatagatat gccagaacta tttttaactt tcatctaata agttgcgatg  124140
aaataggaga tatatatggt cttatgaaag aacgcatttc ctcagaggat atgtttgata  124200
atatagtgta taataaagat atacatcctg ccattaagaa actagtgtat tgcgacatcc  124260
aacttactaa acacattatt aatcagaata cgtatccggt atttaacgat tcttcacaag  124320
tgaaatgttg tcattatttc gacataaact cagataatag caatattagc tctcgtacag  124380
tagagatatt tgagagggaa aagtcatctc ttgtatcata tattaaaact accaataaga  124440
agagaaaggt caattacggc gaaataaaga aaactgttca tggaggcact aatgcaaatt  124500
acttttccgg taaaaagtct gacgagtatc tgagtactac agttagatcc aacattaatc  124560
aaccttggat caaaaccatc tctaagagga tgagagttga tatcattaat cactctatag  124620
taacgcgtgg aaaaagctct atattacaaa ctatagaaat tattttttact aatagaacat  124680
```

```
gtgtgaaaat attcaaggat tctactatgc acattattct atccaaggac aaggatgaaa    124740 agggtgtat acacatgatt gacaaattat tctatgtcta ttataattta tttctgttgt    124800
tcgaagatat catccaaaac gagtacttta aagaagtagc taatgttgta aaccacgtac    124860
tcacggctac ggcattagat gagaaattat tcctaattaa gaaaatggct gaacacgatg    124920
tttatggagt tagcaatttc aaaataggga tgtttaacct gacatttatt aagtcgttgg    124980
atcataccgt tttcccctct ctgttagatg aggatagcaa aataaagttt tttaagggga    125040
aaaagctcaa tattgtagca ttacgatctc tggaggattg tataaattac gtgactaaat    125100
ccgagaatat gatagaaatg atgaaggaaa gatcgactat tttaaatagc atagatatag    125160
aaacggaatc ggtagatcgt ctaaaagaat tgcttctaaa atgaaaaaaa acactaattc    125220
agaaatggat caacgactag ggtataagtt tttggtgcct gatcctaaag ccggagtttt    125280
ttatagaccg ttacatttcc aatatgtatc gtattctaat tttatattgc atcgattgca    125340
tgaaatcttg accgtcaagc ggccactctt atcgtttaag aataatacag aacgaattat    125400
gatagaaatt agcaatgtta aagtgactcc tccagattac tcacctataa tcgcgagtat    125460
taaaggtaag agttatgacg cattagccac gttcactgta aatatcttta aagaggtaat    125520
gaccaaagag ggtatatcca tcactaaaat aagtagttat gagggaaaag attctcattt    125580
gataaaaatt ccgctactaa taggatacgg gaataaaaat ccacttgata cagccaagta    125640
tcttgttcct aatgtcatag gtggagtctt tatcaataaa caatctgtcg aaaaagtagg    125700
aattaatcta gtagaaaaga ttacaacatg gccaaaattt aggttgtta agccaaactc     125760 attcactttc tcgttttcct ccgtatcccc tcctaatgta ttaccgacaa gatatcgcca    125820
ttacaagata tctctggata tatcacaatt ggaagcgttg aatatatcat cgacaaagac    125880
atttataacg gtcaatattg ttttgctgtc tcaatattta tctagagtga gtctagaatt    125940
cattagacgt agtttatcat acgatatgcc tccagaagtt gtctatctag taaacgcgat    126000
aatagatagt gctaaacgaa ttactgaatc tattactgac tttaatattg atacatacat    126060
taatgacctg gtggaagctg aacacattaa acaaaaatct cagttaacga ttaacgagtt    126120
caaatatgaa atgctgcata acttttacc tcatatgaac tatacacccg atcaactaaa     126180 gggatttat atgatatctt tactaagaaa gtttctctac tgtatcttcc acacttctag     126240
atatccagat agagattcga tggtttgtca tcgcatccta acgtacggca aatattttga    126300
gacgttggca catgatgaat tagagaatta cataggcaac atccgaaacg atatcatgaa    126360
caatcacaag aacagaggca cttacgcggt aaacattcat gtactaacaa ctcccggact    126420
taatcacgcg ttttctagct tattgagtgg aaagttcaaa aagtcagacg gtagttatcg    126480
aacacatcct cactattcat ggatgcagaa tattctatt cctaggagtg ttggattta      126540 tccggatcaa gtaaagattt caaagatgtt ttctgtcaga aaataccatc caagtcaata    126600
tctttacttt tgttcatcag acgttccgga aagaggtcct caggtaggtt tagtatctca    126660
attgtctgtc ttgagttcca ttacaaatat actaacgtct gagtatttgg atttggaaaa    126720
gaaaatttgt gagtatatca gatcatatta taaagatgat ataagttact ttgaaacagg    126780
atttccaatc actatagaaa atgctctagt cgcatctctt aatccaaaata tgatatgtga    126840 ttttgtaact gactttagac gtagaaaacg gatgggattc ttcggtaact tggaggtagg    126900 tattactttta gttagggatc acatgaatga aattcgcatt aatattggag cgggaagatt    126960
agtcagacca ttccttggttg tggataacgg agagctcatg atggatgtgt gtccggagtt    127020
```

```
agaaagcaga ttagacgaca tgacattctc tgacattcag aaagagtttc cgcatgtcat   127080
cgaaatggta gatatagaac aatttacttt tagtaacgta tgtgaatcgg ttcaaaaatt   127140
tagaatgatg tcaaaggatg aaagaaagca atacgattta tgtgactttc ctgccgaatt   127200
tagagatgga tatgtagcat cttcactagt gggaatcaat cacaattctg gacccagagc   127260
tattcttgga tgtgctcaag ctaaacaagc tatctcttgt ctgagttcgg atatacgaaa   127320
taaaatagac aatggaattc atttgatgta tccagagagg ccaatcgtga ttagtaaggc   127380
tttagaaact tcaaagattg cggctaattg cttcggccaa catgttacta tagcattaat   127440
gtcgtacaaa ggtatcaatc aagaggatgg aattatcatc aaaaaacaat ttattcagag   127500
aggcggtctc gatattgtta cagccaagaa acatcaagta gaaattccat tggaaaactt   127560
taataacaaa gaaagagata ggtctaacgc ctattcaaaa ttagaaagta atggattagt   127620
tagactgaat gctttcttgg aatccggaga cgctatggca cgaaatatct catcaagaac   127680
tcttgaagat gattttgcta gagataatca gattagcttc gatgtttccg agaaatatac   127740
cgatatgtac aaatctcgcg ttgaacgagt acaagtagaa cttactgaca aagttaaggt   127800
acgagtatta accatgaaag aaagaagacc cattctagga gacaaattta ccactagaac   127860
gagtcaaaag ggaacagtcg cgtatgtcgc ggatgaaacg gaacttccat acgacgaaaa   127920
tggtatcaca ccagatgtca ttattaattc tacatccatc ttctctagaa aaactatatc   127980
tatgttgata gaagttattt taacagccgc atattctgct aagccgtaca caataagggg   128040
agaaaaccga cctgtctgtt ttcctagtag taacgaaaca tccatcgata catatatgca   128100
attcgctaaa caatgttatg agcattcaaa tccgaaattg tccgatgaag aattatcgga   128160
taaaatcttt tgtgaaaaga ttctctatga tcctgaaacg gataagcctt atgcatccaa   128220 agtattttt ggaccaattt attacttgcg tctgaggcat ttaactcagg acaaggcaac   128280
cgttagatgt agaggtaaaa agacgaagct cattagacag gcgaatgagg gacgaaaacg   128340
tggaggaggt atcaagttcg gagaaatgga gagagactgt ttaatagcgc atggtgcagc   128400
caatactatt acagaagttt tgaaagattc ggaagaagat tatcaagatg tgtatgtttg   128460
tgaaaattgt ggagacatag cagcacaaat caagggtatt aatacatgtc ttagatgttc   128520
aaaacttaat ctctctcctc tcttaacaaa aattgatacc acgcacgtat ctaaagtatt   128580
tcttactcaa atgaacgcca gaggcgtaaa agtcaaatta gatttcgaac gaaggcctcc   128640
ttcgttttat aaaccattag ataaagttga tctcaagccg tcttttctgg tgtaatattc   128700
tagtttggta gtagatacat atcaatatca tcaaattcga gatccgaatt ataaaatggg   128760
cgtggattgt taactataga atcggacgtc tgatattcga aaatctgtgg agtttcaggt   128820
tttggtggag gtgtaactgc tacttgggat actgaagtct gatattcaga aagctgtgga   128880
tgttctggtt cggcatccac cgatggtgtc acatcactaa tcggttcggt aacgtctgtg   128940
gatggaggtg ctacttctac agaacctgta gcctcagttg tcaacggaga tacatttta   129000 atgcgagaaa atgtataatt tggtaatggt ttcttatgtg gatctgaaga agaggtaaga   129060
tatctactag aaagataccg atcacgttct agttctcttt tgtagaactt aacttttct   129120 ttctccgcat ctagttgata ttccaacctc ttcacgttac tacgttcaga ttccaattca   129180
cgttcgcatg ggttacctcc gcagttttta cgagcgattt cacgttcagc cttcatgcgt   129240 ctctcctct ctctatcgag tttatcagag cagtctttct gaaggcgatc gaactccata   129300
aatttctcca acgctttgat tgtttccata gattccgaa gttcagcttt taggactgtg   129360 attcttttc tttcgaattc acagctggat gtacaaccgt ttccattacc gccatctcta   129420
```

```
agtttcttt  ctagatcggc  aacatttcat  ccccatgcct  tttacattcc  tcgagtctac  129480
tgtcgtcgaa  atatcgttcc  agctccttt  cgacatcaat  aactttagca  cgttgtctct  129540
caagctctct  tttgtagtta  tctgattccc  tggcacgttt  aagatcttca  tgcaattgag  129600
tcagctctta  acttcctctc  ttgcttcttc  gtcatagtac  gcgcaatcac  tgtgagatcc  129660
attgttacca  cgtctacact  cggcgagctc  gcgtttaaga  gattcaattt  cccgtttgta  129720
ttggtccatg  tttccattgc  taccaccatt  agatttacag  gctgctagtt  gtcgttcgag  129780
atcagaaata  cgggttttct  tggaattgat  ttcgtcgatg  tacttggcat  cgaaacactt  129840
attaagttct  ttttccaatt  ctacgatttt  atttctttcg  cgagtcaatt  ccctcctgta  129900
gtaactatct  gttttgtcag  attcacgctc  tctacgtaga  ctttcttgca  agttactaat  129960
ttgttcccta  gcacgtccga  gtttagtttt  atatgctgaa  tagagttctg  attcatcctt  130020
tgagcagatc  tctagcgatc  gtttaagatt  cctaattcta  gtctttagcc  tatttacctc  130080
ctcagaagat  gttccgttac  cgttgcgttt  acactcgtta  agctgtctat  caagatccat  130140
gattctatct  ctaagacgtt  gcatctctct  ttccatatca  gcattgcttt  cattattacg  130200
tctgcagtca  ctcaactgtc  tttcaatatc  tgagattcta  tctctaagac  gtcgcatctc  130260
tctctgtttc  ggcattggtt  tcattattac  gtctacagtc  gttcaactgt  ctttcaagat  130320
ctgatattct  agattggagt  ctgctaatct  ctgtagcatt  tcacggcat  tcactcagtt  130380
gtctttcaag  atctgaaatt  ttagattgga  gtctgctaat  ctctgtaaga  tttcctcctc  130440
cgctctcgat  gcagtcggtc  aacttattct  ctagttctct  aatacgcgaa  cgcagtgcat  130500
caacttcttg  cgtgtcttcc  tggttgcgtg  tacattcatc  gagtctagat  tcgagatctc  130560
taacgcgtcg  tcgttcttcc  tcaagttctc  tgcgtactac  agaaagcgtg  tccttatctt  130620
gttgatattt  agcaatttct  gattctagag  tactgatttt  gcttacgtag  ttactaatat  130680
ttgtcttggc  cttatcaaga  tcctccttgt  atttgtcgca  ttccttgata  tccctacgaa  130740
gtctggacag  ttcccattcg  acattacgac  gtttatcgat  ttcagctcgg  agatcgtcat  130800
cgcgttgttt  tagccacata  cgactgagtt  caagttctcg  ttgacaagat  ccatctactt  130860
ttccattcct  aatagtatcc  agttcctttt  ctagttctga  acgcatttct  cgttccctat  130920
caagcgattc  tctcaattct  cggatagtct  tcttatcaat  ttctaataaa  tctgaaccat  130980
catctgtccc  atttgaata  tccctgtgtt  ctttgatctc  ttttgtaagt  cggtcgattc  131040
tttcggtttt  ataaacagaa  tcccttcca  aagtcctaat  cttactgagt  ttatcactaa  131100
gttctgcatt  caattcggtg  agttttctct  tggcttcttc  caactctgtt  ttaaactctc  131160
cactatttcc  gcattcttcc  tcgcatttat  ctaaccattc  aattagttta  ttaataacta  131220
gttggtaatc  agcgattcct  atagccgttc  ttgtaattgt  gggaacataa  ttaggatctt  131280
ctaatggatt  gtatggcttg  atagcatcat  ctttatcatt  attaggggga  tggacaacct  131340
taattggttg  gtcctcatct  cctccagtag  cgtgtggttc  ttcaatacca  gtgttagtaa  131400
taggcttagg  caaatgcttg  tcgtacgcgg  gcacttcctc  atccatcaag  tatttataat  131460
cgggttctac  ttcagaatat  tctttttctaa  gagacgcgac  ttcgggagtt  agtagaagaa  131520
ctctgtttct  gtatctatca  acgctggaat  caatactcaa  gttaaggata  gcgaatacct  131580
catcgtcatc  atccgtatct  tctgaaacac  catcatatga  catttcatga  agtctaacgt  131640
attgataaat  agaatcagat  ttagtattaa  acagatcctt  aacctttta  gtaaacgcat  131700
atgtatattt  tagatctcca  gatttcataa  tatgatcaca  tgcctaaat  gtcagtgctt  131760
```

```
ccatgatata atctggaaca ctaatgggtg acgaaaaaga tacagcacca tatgctacgt    131820
tgataaataa atctgaacca ctaagtagat aatgattaat gttaagaaag aggaaatatt    131880
cagtgtatag gtatgtcttg gcgtcatatc ttgtactaaa cacgctaaac agtttgttaa    131940
tgtgatcaat ttccaataga ttaattagag cagcgggaat accaacaaac atattaccac    132000
atccgtattt tctatgaata tcacatatca tgttaaaaaa tcttgataga agagcgaata    132060
tctcgtctga cttaatgagt cgtagttcag cagcaacata agtcataact gtaaatagaa    132120
catactttcc tgtagtgttg attctagact ccacatcaac accattatta aaaatagttt    132180
tatatacatc tttaatctgc tctccgttaa tcgtcgaacg ttctagtata cggaaacact    132240
ttgatttctt atctgtagtt aatgacttag tgatatcacg aagaatatta cgaattacat    132300
ttcttgtttt tcttgagaga cctgattcag aactcaactc atcgttccat agtttttcta    132360
cctcagtggc gaaatctttg gagtgcttgg tacattttc aataaggttc gtgacctcca     132420
tttattataa aaaatttatt caaaacttaa ctacaatcgg gtaattataa aatcgtagat    132480
ctcccatgtg gcggaatact accatctatc gcatgtggat ggacagtagg taatggccat    132540
gggaacagta atgtttgcat atttatcttt cttgccagta ttactgcata ttgtcccaat    132600
gtttcgatgt gatgttctaa cctatcaact gccgctgtat cacaacaata gtgtccgatg    132660
aaattaagat tatgatccaa tgtgtttaat atatgattat caagtcttat acgatccgcg    132720
tcttttttga caggatcagg ttcttctaca ggaagaagtt tcggcctctt atgatattca    132780
tgtctgggaa acgtggtct agggtgaggc tccggtatcg gagtgggttt tggattataa    132840
tcatcatcgt ctatgacatc atcttcgact tcgatattta ttttgctatc ttgatgatgt    132900
cctgtatcag ttgcattttc agcactcgac tgaatattag cgcattcatt gtctattatt    132960
accatatttc taaacccaaa atgtatgtgt tgaacatcag tactatcgtt gatgagtctt    133020
atagcatgaa ttcgcttatc gttatcgggt ttatcttctg tcaccttagc aattcctttt    133080
ttattaaact ctacataatc atatccattt ctattgtttg ttctaatata aacgagtata    133140
gcatcattgc taaattttc aatagtatca aaaacagaat atcctaaacc atataatata    133200
tattcaggaa cactcaaact aaatgtccag gattctccta aatacgtaaa ctttaatagt    133260
gcgaaatcat tcaaaaatct accacttata gatagatagt acataaatgc gtatagtagt    133320
ctacctatct ctttattatg aaaaccggca ttacgatcat atatgtcgtg atatacctgt    133380
gatccgttta cgttaaacca taaatacatg ggtgatccta taaacatgaa tttatttcta    133440
attctcagag ctatagttaa ttgaccgtgt aatatttgct tacatgcata cttgatacgc    133500
ttattaataa gattttatc attgctcgtt atttcagaat cgtatatata aggagtacca    133560
tcgtgattct taccagatat tatacaaaat actatatata aaatatattg acccacgtta    133620
gtaatcatat aaatgtttaa cgttttaaat tttgtattca atgatccatt atcatacgct    133680
atcatggtct tgtaatattc attctttaaa atataatatt gtgttagcca ttgcattgga    133740
gctcctaatg gagattttct attctcatcc attttaggat aggctttcat aaagtcccta    133800
ataacttcgt gaataatgtt tctatgtttt ctactgatgc atgtatttgc ttcgattttt    133860
ttatcccatg tttcatctat catagattta aacgcagtaa tgctcgcaac attaacatct    133920
tgaaccgttg gtacaattcc gttccataaa tttataatgt tcgccattta tataactcat    133980
tttttgaata tacttttaat taacaaaaga gttaagttac tcatatggac gccgtccagt    134040
ctgaacatca atctttttag ccagagatat catagccgct cttagagttt cagcgtgatt    134100
ttccaaccta aatagaactt catcgttgcg tttacaacac ttttctattt gttcaaactt    134160
```

```
tgttgttaca ttagtaatct ttttttccaa attagttagc cgttgtttga gagtttcctc    134220
attgtcgtct tcatcggctt taacaattgc ttcgcgttta gcctctggct ttttagcagc    134280
ctttgtagaa aaaaattcag ttgctggaat tgcaagatcg tcatctccgg ggaaaagagt    134340
tccgtccatt taaagtacag attttagaaa ctgacactct gcgttattta tatttggtac    134400
aacacatgga ttataaatat tgatgttaat aacatcagaa aatgtaaagt ctatacattg    134460
ttgcatcgtg ttaaattttc taatggatct agtattattg ggtccaactt ctgcctgaaa    134520
tccaaatatg gaagcggata caaaaccgtt tcctggataa accacacatc tccacttttg    134580
ctttacatca gaaattgtgt cgttgacatc ttgaactctc ctatctaatg ccggtgttcc    134640
acctatagat tttgaatatt cgaatgctgc atgagtagca ttaaattcct taatattgcc    134700 ataatttttca tatattgagt aaccctggat aaaaagtaaa cacaccgcag ccgtcgctac    134760
cacaataaaa aaaattgata gagagttcat ttataatcta ttagaagctg acaaaatttt    134820
tttacacgca tcagacaatg ctttaataaa tagttcaaca tctacttttg tcatatcgaa    134880
ccgatggtat gattctaacc tagaattaca tccgaaaaag ttgactatgt tcatagtcat    134940
taagtcatta acaaacaaca ttccagactc tggattataa gacgatactg tttcgtcaca    135000
attacctacc ttaatcatgt gattatgaat attggctatt agagcacctt ctaagaaatc    135060
tataatatct ttgaaacacg atttaaaatc aaaccacgaa tatacttcta cgaagaaagt    135120
tagtttaccc ataggagaaa taactataaa tggagatcta aatacaaaat ccggatctat    135180
gatagtttta acattattat attctctatt aaatacctcc acatctaaaa atgttaattt    135240
tgaaactatg tcttcgttta ttaccgtacc tgaactaaac gctataagct ctattgtttg    135300
agaactcttt aaacgatatt cttgaaatac atgtaacaaa gtttccttta actcggtcgg    135360
tttatctacc atagttacag aatttgtatc cttatctata atataataat caaaatcgta    135420
taaagttata taattatcgc gttcagattg ggatctttc aaatagacta aaaccccat     135480 ttctctagta agtatcttat gtatatgttt gtaaaatatc ttcatggtgg aatatgctc     135540 taccgcagtt agccattcct cattgacagc ggtagatgta ttagacaaaa ctattccaat    135600
gtttaacaag ggccatttta cgagattatt aaatccttgt ttgataaatg tagccaatga    135660
gggttcgagt tcaacgacga ttgaattctc ttcccgcgga tgctgcatga tgaacgacgg    135720
gatgttgttc gattgatttg gaattctttt tcgactttt gtttatatta aatattttaa     135780
aatttatagc ggatagcaat tcatgtacca cggataatgt agacgcgtat tgcgcatcga    135840
tatctttatt attagataaa tttatcaata aatgtgagaa gtttgcctcg ttaaggtctt    135900
ccatttaaat attatataaa catttgtgtt tgtaacttat tcgtctttta tggaatagtt    135960
ttttactagt aaagctgcaa ttacacactt tgtccgtaaa acataaatat aaacaccagc    136020
ttttatcaat cgttccaaaa agtcgacggc ggacattttt aacatggcat ctattttaaa    136080
tacacttagg ttttttggaaa aaacatcatt ttataattgt aacgattcaa taactaaaga    136140
aaagattaag attaaacata agggaatgtc atttgtattt tataagccaa agcattctac    136200
cgttgttaaa tacttgtctg gaggaggtat atatcatgat gatttggttg tattggggaa    136260
ggtaacaatt aataatctaa agatgatgct attttacatg gatttatcat atcatggagt    136320
gacaagtagt ggagcaattt acaaattggg atcgtctatc gatagacttt ctctaaatag    136380
gactattgtt acaaaagtta ataattatga tgatacattt tttgacgacg atgattgatc    136440
gctattgcac aatttttgttt ttgtactttc taatatagtg tttaggttct ttttcatatg    136500
```

```
agaatattga tttactaaaa tatctatgtt taacttttgt tctatgacgt ccttatcggc   136560
ggtatcggta catatacgta attcaccttc acaaaatacg gagtcttcga taataatagc   136620
caatcgatta ttggatctag ctgtctgtat catattcaac atgtttaata tatcctttcg   136680
tttccccttt acaggcatcg atcgtagcat attttccgcg tctgatatgg aaatgttaaa   136740
actacaaaaa tgcgtaatgt tagcccgtcc taatattggt acgtgtctat aagtttggca   136800
tagtagaata atagacgtgt ttaaatgcct tccaaagttt aagaattcta ttagagtatt   136860
gcattttgat agtttatcgc ctacatcatc aaaaataagt aaaaagtgtg ctgatttttt   136920
atgattttgt gcgacagcaa tacatttttc tatgttactt ttagttcgta tcagattata   136980
ttctagagat tcctgactac taacgaaatt aatatgattt ggccaaatgt atccatcata   137040
atctgggtta taaacgggtg taaacaagaa tatatgttta tattttttaa ctagtgtaga   137100
aaacagagat agtaaataga tagttttttcc agatccagat cctcctgtta aaaccattct   137160
aaacggcatt tttaataaat tttctcttga aaattgtttt tcttggaaac aattcataat   137220
tatatttaca gttactaaat taatttgata ataaatcaaa atatggaaaa ctaaggttgt   137280
tagtagggag gagaacaaag aaggcacatc gtgatataaa taacatttat tatcatgatg   137340
acaccagaaa acgacgaaga gcagacatct gtgttctccg ctactgttta cggagacaaa   137400
attcaggaaa agaataaacg caaacgcgtg attggtctat gtattagaat atctatggtt   137460
atttcactac tatctatgat taccatgtcc gcgtttctca tagtgcgcct aaatcaatgc   137520
atgtctgcta acgaggctgc tattactgac gccgctgttg ccgttgctgc tgcatcatct   137580
actcatagaa aggttgcgtc tagcactaca caatatgatc acaaagaaag ctgtaatggt   137640
ttatattacc agggttcttg ttatatatta cattcagact accagttatt ctcggatgct   137700
aaagcaaatt gcactgcgga atcatcaaca ctacccaata aatccgatgt cttgactacc   137760
tggctcattg attatgttga ggatacatgg ggatctgatg gtaatccaat tacaaaaact   137820
acatccgatt atcaagattc tgatgtatca caagaagtta gaaagtattt ttgtgttaaa   137880
acaatgaact aatatttatt tttgtacatt aataaatgaa atcgcttaat agacaaactg   137940
taagtaggtt taagaagttg tcggtgccgg ccgctataat gatgatactc tcaaccatta   138000
ttagtggcat aggaacattt ctgcattaca agaagaact gatgcctagt gcttgcgcca   138060
atggatggat acaatacgat aaacattgtt atttagatac taacattaaa atgtctacag   138120
ataatgcggt ttatcagtgt cgtaaattac gagctagatt gcctagacct gatactagac   138180
atctgagagt attgtttagt attttttata agattattg ggtaagttta aaaaagacca   138240
atgataaatg gttagatatt aataatgata agatataga tattagtaaa ttaacaaatt   138300
ttaaacaact aaacagtacg acggatgctg aagcgtgtta tatatacaag tctggaaaac   138360
tggttaaaac agtatgtaaa agtactcaat ctgtactatg tgttaaaaaa ttctacaagt   138420
gacaacaaaa aatgaattaa taataagtcg ttaacgtacg ccgccatgga cgccgcgttt   138480
gttattactc caatgggtgt gttgactata acagatacat tgtatgatga tctcgatatc   138540
tcaatcatgg actttatagg accatacatt ataggtaaca taaaaactgt ccaaatagat   138600
gtacgggata taaaatattc cgacatgcaa aaatgctact ttagctataa gggtaaaata   138660
gttcctcagg attctaatga tttggctaga ttcaacattt atagcatttg tgccgcatac   138720
agatcaaaaa ataccatcat catagcatgc gactatgata tcatgttaga tatagaagat   138780
aaacatcagc catttatct attcccatct attgatgttt taacgctac aatcatgaaa   138840 gcgtataacc tgtatacagc tggagattat catctaatca tcaatccttc agataatctg   138900
```

```
aaaatgaaat tgtcgtttaa ttcttcattc tgcatatcag acggcaatgg atggatcata   138960
attgatggga aatgcaatag taatttttta tcataaaagt tgtaaagtaa ataataaaac   139020
aataaatatt gaactagtag tacgtatatt gagcaatcag aaatgatgct ggtacctctt   139080
atcacggtga ccgtagttgc gggaacaata ttagtatgtt atatattata tatttgtagg   139140
aaaaagatac gtactgtcta taatgacaat aaaattatca tgacaaaatt aaaaagata    139200 aagagttcta attccagcaa atctagtaaa tcaactgata gcgaatcaga ctgggaggat   139260
cactgtagtg ctatggaaca aaacaatgac gtagataata tttctaggaa tgagatattg   139320
gacgatgata gcttcgctgg tagtttaata tgggataacg aatccaatgt tatggcgcct   139380
agcacagaac acatttacga tagtgttgct ggaagcacgc tgctaataaa taatgatcgt   139440
aatgaacaga ctatttatca gaacactaca gtagtaatta atgaaacgga gactgttgaa   139500
gtacttaatg aagataccaa acagaatcct aactattcat ccaatccttt cgtaaattat   139560
aataaaacca gtatttgtag caagtcaaat ccgtttatta cagaacttaa caataaattt   139620
agtgagaata atccgtttag acgagcacat agcgatgatt atcttaataa gcaagaacaa   139680
gatcatgaac acgatgatat agaatcatcg gtcgtatcat tggtgtgatt agtttccttt   139740
ttataaaatt gaagtaatat ttagtattat tgctgccgtc acgttgtaca aatggagata   139800
ttccctgtat tcggcatttc taaaattagc aattttattg ctaataatga ctgtagatat   139860
tatatagata cagaacatca aaaaattata tctgatgaga tcaatagaca gatggatgaa   139920
acggtacttc ttaccaacat cttaagcgta gaagttgtaa atgacaatga gatgtaccat   139980
cttattcctc atagattatc gacgattata ctctgtatta gttctgtcgg aggatgtgtt   140040
atctctatag ataatgacat caatggcaaa aatattctaa cctttcccat tgatcatgct   140100
gtaatcatat ccccactgag taaatgtgtc gtagttagca agggtcctac aaccatattg   140160
gttgttaaag cggatatacc tagcaaacga ttggtaacat cgtttacaaa cgacatacta   140220
tatgtaaaca atctgtcact gattaattat ttgccgttgt ctgtattcat tattagacga   140280
gtcaccgact atttggatag acacatatgc gatcagatat ttgctaataa taagtggtat   140340
tcccttataa ccatcgacga taagcaatat cctattccat caaactgtat aggtatgtcc   140400
tctgccaagt acataaattc tagcatcgag caagatactt taatccatgt ttgtaacctc   140460
gagcatccgt tcgactcagt atacaaaaaa atgcagtcgt acaattctct acctatcaag   140520
gaacaaatat tgtacggtag aattgataat ataaatatga gcattagtat ttctgtggat   140580
taatagattt ctagtatggg gatcattaat catctctaat ctctaaatac ctcataaaac   140640
gaaaaaaaag ctattatcaa atactgtacg gaatggattc attctcttct cttttttatga  140700 aactctgttg tatatctact gataaaactg gaagcaaaaa atctgataga aagaataaga   140760
ataagatcaa ggattatatg gaacacgatt attataaaat aacaatagtt cctggttcct   140820
cttccacgtc tactagctcg tggtattata cacatgccta gtaatagtct ctttgcgttg   140880
acggaaagca gactagaaat aacaggctaa aatgttcaga caccataata gttcccaacc   140940
cagataataa cagagttcca tcaacacatt cctttaaact caatcccaaa cccaaaaccg   141000
ttaaaatgta tccggccaat tgatagtaga taatgaggtg tacagcgcat gataatttac   141060
acagtaacca aaatgaaaat actttagtaa ttataagaaa tatagacggt aatgtcatca   141120
tcaacaatcc gataatatgc ctgagagtaa acattgacgg ataaaacaaa aatgctccgc   141180
ataactctat catggcaata acacaaccaa atacttgtaa gattcctaaa ttagtagaaa   141240
```

```
atacaacgaa tatcgatgta taagtgatct cgagaaataa taagaataaa gtaatgcccg  141300
taaagataaa catcaacatt gtttggtaat cattaaacca attagtatga agttgaacta  141360
atttcacagt agattttatt ccagtgttat cctcgcatgt ataagtacct ggtaagatat  141420
ctttatattc cataatcaat gagacatcac tatctgataa cgaatgaagt ctagcactag  141480
tatgccattt acttaatatt gtcgtcttgg aagttttatt ataagttaaa atatcatggt  141540
tatccaattt ccatctaata tactttgtcg gattatctat agtacacgga ataatgatgg  141600
tatcattaca tgctgtatac tctatggtct ttgtagttgt tataacaacc aacgtataga  141660
ggtatatcaa cgatattcta actcttgaca tttttttatt atttaaaatg ataccttttgt 141720 tatttatttt attctatttt gctaacggta ttgaatggca taagtttgaa acgagtgaag  141780
aaataatttc tacttactta ttagacgacg tattatacac gggtgttaat ggggcggtat  141840
acacattttc aaataataaa ctaaacaaaa ctggtttaac taataataat tatataacaa  141900
catctataaa agtagaggat gcggataagg atacattagt atgcggaacc aataacgaaa  141960
atcccaaatg ttggaaaata gacggttcag acgacccaaa acatagaggt agaggatacg  142020
ctccttatca aaatagcaaa gtaacgataa tcagtcacaa cggatgtgta ctatctgaca  142080
taaacatatc aaaagaagga attaaacgat ggagaagatt tgacggacca tgtggttatg  142140
atttattcac ggcggataac gtaattccaa aagatggttt acgaggagca ttcgtcgata  142200
aagacggtac ttatgacaaa gtttacattc ttttcactga tactatcggc tcaaagagaa  142260
ttgtcaaaat tccgtatata gcacaaatgt gcctaaacga cgaaggtggt ccatcatcat  142320
tgtctagtca tagatggtcg acgtttctca aagtcgaatt agaatgtgat atcgacggaa  142380
gaagttatag acaaattatt cattctagaa ctataaaaac agataatgat acgatactat  142440
atgtattctt cgatagtcct tattccaagt ccgcattatg tacctattct atgaatacca  142500
ttaaacaatc tttttctacg tcaaaattgg aaggatatac aaagcaattg ccgtctccag  142560
ctcctggtat atgtttacca gctggaaaag ttgttccaca taccacgttt gaagtcatag  142620
aacaatataa tgtactagat gatattataa agcctttatc taaccaacct atcttcgaag  142680
gaccgtctgg tgttaaatgg ttcgatataa aggagaagga aaatgaacat cgggaatata  142740
gaatatactt cataaaagaa aattctatat attcgttcga tacaaaatct aaacaaactc  142800
gtagctcgca agtcgatgcg cgactatttt cagtaatggt aactgcgaaa ccgttattta  142860
tagcagatat agggataggba gtaggaatgc cacaaatgaa aaaaatactt aaaatgtaat  142920
cttaatcgag tacaccacac gacaatgaac aaacataaga cagattatgc tggttatgct  142980
tgctgcgtaa tatgcggtct aattgtcgga attattttta cagcgacact attaaaagtt  143040
gtagaacgta aattagttca tacaccatta atagataaaa cgataaaaga tgcatatatt  143100
agagaagatt gtcctactga ctggataagc tataataata aatgtatcca tttatctact  143160
gatcgaaaaa cctgggagga aggacgtaat gcatgcaaag ctctaaattc aaattcggat  143220
ctaattaaga tagagactcc aaacgagtta agttttttaa gaagccttag acgaggctat  143280
tgggtaggag aatccgaaat attaaaccag acaaccccat ataatttat  agctaagaat  143340 gccacgaaga atggaactaa aaaacggaaa tatatttgta gcacaacgaa tactcccaaa  143400
ctgcattcgt gttacactat ataacaatta cactacattt ttatcatacc actacttcgg  143460
ttagatgttt tagaaaaaaa taaatatcgc cgtaccgttc ttgtttttat aaaaataaca  143520
attaacaatt atcaaatttt ttctttaata ttttacgtgg ttgaccattc ttggtggtaa  143580
aataatctct tagtgttgga atggaatgct gtttaatgtt tccacactca tcgtatattt  143640
```

```
tgacgtatgt agtcacatcg tttacgcaat agtcagactg tagttctatc atgcttccta 143700
catcagaagg aggaacagtt ttaaagtctc ttggttttaa tctattaccg ttagttttca 143760
tgaaatcctt tgttttatcc acttcacatt ttaaataaat gtccactata cattcttttg 143820
ttaattttac tagatcgtca tgggtcatag aatttatagg ttccgtagtc catggatcca 143880
aactagcaaa cttcgcgtat acggtatcgc gattagtgta tacaccaact gtatgaaaat 143940
taagaaaaca gtttaataaa tcaacagaaa tatttaatcc tccgtttgat acagatgcgc 144000
catatttatg gatttcggat tcacacgttg tttgtctgag gtgttcgtct agtgttgctt 144060
ctacgtaaac ttcgattccc atatattctt tattgtcaga atcgcatacc gatttatcat 144120
catacactgt ttgaaaacta aatggtatac acatcaaaat aataaataat aacgagtaca 144180
ttctgcaata ttgttatcgt aattggaaaa atagtgttcg agtgagttgg attatgtgag 144240
tattggattg tatattttat tttatatttt gtaataagaa taaatgctaa atgtcaagtt 144300
tattccaata gatgtcttat taaaaacata tataataaat aacaatggct gaatggcata 144360
aaattatcga ggatatctca aaaaataata agttcgagga tgccgccatc gttgattaca 144420
agactacaaa gaatgttcta gctgctattc ctaacagaac atttgccaag attaatccgg 144480
gtgaaattat tcctctcatc actaatcgta atattctaaa acctcttatt ggtcagaaat 144540
attgtattgt atatactaac tctctaatgg atgagaacac gtatgctatg gagttgctta 144600
ctgggtacgc ccctgtatct ccgatcgtta tagcgagaac tcataccgca cttatatttt 144660
tgatgggtaa gccaacaaca tccagacgtg acgtgtatag aacgtgtaga gatcacgcta 144720
cccgtgtacg tgcaactggt aattaaaata aaaagtaata ttcatatgta gtgtcaattt 144780
taaatgatga tgatgaaatg gataatatcc atattgacga tgtcaataat gccggtattg 144840
gcatacagtt catcgatttt tagatttcat tcagaggatg tggaattatg ttatgggcat 144900
ttgtattttg ataggatcta taatgtagta aatataaaat ataatccgca tattccatat 144960
agatataatt ttattaatcg cacgttaacc gtagatgaac tagacgataa tgtctttttt 145020
acacatggtt atttttaaa acacaaatat ggttcactta atcctagttt gattgtctca 145080
ttatcaggaa acttaaaata taatgatata caatgctcag taaatgtatc gtgtctcatt 145140
aaaaatttgg caacgagtac atctactata ttaacatcta aacataagac ttattctcta 145200
catcggtcca cgtgtattac tataatagga tacgattcta ttatatggta taagatata 145260
aatgacaagt ataatgacat ctatgatttt actgcaatat gtatgctaat agcgtctaca 145320
ttgatagtga ccatatacgt gtttaaaaaa ataaaaatga actcttaatt atgctatgct 145380
attagaaatg gataaaatca aaattacggt tgattcaaaa attggtaatg ttgttaccat 145440
atcgtataac ttggaaaaga taactattga tgtcacacct aaaagaaaa agaaaagga 145500
tgtattatta gcgcaatcag ttgctgtcga agaggcaaaa gatgtcaagg tagaagaaaa 145560
aaatattatc gatattgaag atgacgatga tatggatgta gaaagcgcat aatacgatct 145620
ataaaaataa gtatataaat acttttatt tactgtactc ttactgtgta gtggtgatac 145680
cctactcgat tattttttta aaaaaaaat acttattctg attcttctaa ccatttccgt 145740
gttcgttcga atgccacatc gacgtcaaag ataggggagt agttaaaatc tagttctgca 145800
ttgttggtac acaccttaaa tgtagtgttg gatatcttca acgtatagtt gttgagtagt 145860
gatggttttc taaatagaat tctcttcata tcattcttgc acgcgtacat ttttagcatc 145920
catcttggaa accttaactt tcgaggttat tggttgtgga tcttctacaa tatctatgac 145980
```

```
tctgatttct tgaacatcat ctgcactaat taacagtttt actatatacc tgcctagaaa  146040
tccggcacca ccagtaaccg cgtacacggc cattgctgcc actcataata tcagactact  146100
tattctattt tactaaataa tggctgtttg tataatagac cacgataata tcagaggagt  146160
tatttacttt gaaccagtcc atggaaaaga taaagttta ggatcagtta ttggattaaa  146220
atccggaacg tatagtttga taattcatcg ttacggagat attagtcaag gatgtgattc  146280
cataggcagt ccagaaatat ttatcggtaa catctttgta aacagatatg gtgtagcata  146340
tgtttattta gatacagatg taaatatatc tacaattatt ggaaaggcgt tatctatttc  146400
aaaaaatgat cagagattag cgtgtggagt tattggtatt tcttacataa atgaaaagat  146460
aatacatttt cttacaatta acgagaatgg cgtttgatat atcagttaat gcgtctaaaa  146520
caataaatgc attagtttac ttttctactc agcaaaataa attagtcata cgtaatgaag  146580
ttaatgatac acactacact gtcgaatttg atagggacaa agtagttgac acgtttattt  146640
catataatag acataatgac accatagaga taagaggggt gcttccagag gaaactaata  146700
ttggttgcgc ggttaatacg ccggttagta tgacttactt gtataataag tatagtttta  146760
aactgatttt agcagaatat ataagacaca gaaatactat atccggcaat atttattcgg  146820
cattgatgac actagatgat ttggctatta acagtatgg agacattgat ctattattta  146880
atgagaaact taaagtagac tccgattcgg gactatttga ctttgtcaac tttgtaaagg  146940
atatgatatg ttgtgattct agaatagtag tagctctatc tagtctagta tctaaacatt  147000
gggaattgac aaataaaaag tataggtgta tggcattagc cgaacatata tctgatagta  147060
ttccaatatc tgagctatct agactacgat acaatctatg taagtatcta cgcggacaca  147120
ctgagagcat agaggataaa tttgattatt ttgaagacga tgattcgtct acatgttctg  147180
ccgtaaccga cagggaaacg gatgtataat ttttttttata gcgtgaagga tatgataaaa  147240
aatataattg ttgtatttat cccattccaa tcaccttata tgattctgta acacaataaa  147300
ggagtcttat agatgtatag aggtcagata ctggtttgat aaactgttta ttccacataa  147360
gtatgtttga ctttatggtt agacccgcat actttaacaa atcactgaaa attggagtta  147420
ggtattgacc tctcagaatc agttgccgtt ctggaacatt aaatgtattt tttatgatat  147480
actccaacgc atttatgtgg gcatacaaca agtcattact aatggaatat tccaagagtt  147540
ttagttgtct agtatttaac aagagaagag atttcaacag actgtttatg aactcgaatg  147600
ccgcctcatt gtcgcttata ttgatgatgt cgaattctcc caatatcatc accgatgagt  147660
agctcatctt gttatcggga tccaagtttt ctaaagatgt cattaaaccc tcgatcatga  147720
atggatttat catcatcgtt tttatgttgg acatgagctt agtccgtttg tccacatcta  147780
tagaagatga tttctgaatt atttcatata tctctctctt taactccagg aacttgtcag  147840
gatggtctac tttaatatgt tctcgtctaa gagatgaaaa tctttggatg gttgcacgcg  147900
acttttctct aaaggatgac gttgcccaag atcctctctt aaatgaatcc atcttatcct  147960
tggacaagat ggacagtcta ttttccttag atggtttaat attttgtta cccatgatct  148020
ataaaggtag acctaatcgt ctcggatgac catatattta ttttcagttt tattatacgc  148080
ataaattgta aaaatatgt taggtttaca aaaatgtctc gtggggcatt aatcgttttt  148140
gaaggattgg acaaatctgg aaaaacaaca caatgtatga acatcatgga atctataccg  148200
gcaaacacga taaaatatct taactttcct cagagatcca ctgtcactgg aaaaatgata  148260
gatgactatc taactcgtaa aaaaacctat aatgatcata tagttaatct attatttgt  148320
gcaaatagat gggagtttgc atcttttata caagaacaac tagaacaggg aattacttta  148380
```

```
atagttgata gatacgcatt ttctggagta gcgtatgccg ccgctaaagg cgcgtcaatg   148440
actctcagta agagttatga atctggattg cctaaacccg acttagttat attcttggaa   148500
tctggtagca aagaaattaa tagaaacgtc ggcgaggaaa tttatgaaga tgttacattc   148560
caacaaaagg tattacaaga atataaaaaa atgattgaag aaggagatat tcattggcaa   148620
attatttctt ctgaattcga ggaagatgta aagaaggagt tgattaagaa tatagttata   148680
gaggctatac acacggttac tggaccagtg gggcaactgt ggatgtaata gtgaaattac   148740
attttttata aatagatgtt agtacagtgt tataaatgga tgaagcatat tactctggca   148800
acttggaatc agtactcgga tacgtgtccg atatgcatac cgaactcgca tcaatatctc   148860
aattagttat tgccaagata gaaactatag ataatgatat attaaacaag gacattgtaa   148920
attttatcat gtgtagatca aacttggata atccatttat ctctttccta gatactgtat   148980
atactattaa aaataactag ttataagttt gaatccgtca attttgattc caaaattgaa   149040
tggactgggg atggtctata caatatatcc cttaaaaatt atggcatcaa gacgtggcaa   149100
acaatgtata caaatgtacc agaaggaaca tacgacatat ccgcatttcc aaagaatgat   149160
ttcgtatctt tctgggttaa atttgaacaa ggcgattata aagtggaaga gtattgtacg   149220
ggactatgcg tcgaagtaaa aattggacca ccgactgtaa cattaactga atacgacgac   149280
catatcaatt tgtacatcga gcatccgtat gctactagag gtagcaaaaa gattcctatt   149340
tacaaacgcg gtgacatgtg tgatatctac ttgttgtata cggctaactt cacattcgga   149400
gattctaaag aaccagtacc atatgatatc gatgactacg attgcacgtc tacaggttgc   149460
agcatagact ttgtcacaac agaaaaagtg tgcgtgacag cacagggagc cacagaaggg   149520
tttctcgaaa aaattactcc atggagttcg aaagtatgtc tgacacctaa aaagagtgta   149580
tatacatgcg caattagatc caaagaagat gttcccaatt tcaaggacaa aatggccaga   149640
gttatcaaga gaaaatttaa tacacagtct caatcttatt taactaaatt tctcggtagc   149700
acatcaaatg atgttaccac ttttcttagc atgcttaact tgactaaaata ttcataatta   149760
ttttttatta atgatacaaa aacgaaataa aactgcatat tatacactgg ttaacgccct   149820
tataggctct aaccattttc aagatgaggt ccctgattat agtccttctg ttcccctcta   149880
tcatctactc catgtctatt agacgatgtg agaagactga agaggaaaca tggggattga   149940
aaatagggtt gtgtataatt gccaaagatt tctatcccga aagaactgat tgcagtgttc   150000
atctcccaac tgcaagtgaa ggattgataa ctgaaggcaa tggattcagg gatatacgaa   150060
acaccgataa attataaaaa aagcaatgtg tccgctgttt ccgttaataa tactattttc   150120
gtaactggcg gattattcat aaataactct aatagcacga tcgtggacat ttataaagac   150180
aaacaatggt cgattataga aatggctagg gtatatcacg gcatcgactc gacatttgga   150240
atgttatatt ttgccggagg tctatccgtt accgaacaat atggtaattt agagaaaaac   150300
aacgagatat cttgttacaa tcctagaacg aataagtggt ttgatatttc atatactatt   150360
tataagatat ccatatcatc attgtgtaaa ctaaataacg tcttctatgt atttagtaag   150420
gacattggat atgtggaaaa gtatgatggt gcatggaagt tagtacatga tcgtctcccc   150480
gctataaagg cattatcaac ttctccttat tgattgaaaa tgaaaatata aatagttttt   150540
atgtatagca gtattacccct atagttttat tgcttactac taacatggat acagatgtta   150600
caaatgtaga agatatcata aatgaaatag atagagagaa agaagaaata ctaaaaaatg   150660
tagaaattga aaataataaa aacattaaca agaatcatcc caatgaatat attagagaag   150720
```

```
cactcgttat taataccagt agtaatagtg attccattga taaagaagtt atagaatgta 150780
tcagtcacga tgtaggaata tagatcatat ctactaattt ttataatcga tacaaaacat 150840
aaaaaacaac tcgttattac atagcaggca tggaatcctt caagtattgt tttgataacg 150900
atggcaagaa atggattatc ggaaatactt tatattctgg taattcaata ctctataagg 150960
tcagaaaaaa tttcactagt tcgttctaca attacgtaat gaagatagat cacaaatcac 151020
acaagccatt gttgtctgaa atacgattct atatatctgt attggatcct ttgactatcg 151080
acaactggac acgggaacgt ggtataaagt atttggctat tccagatctg tatgaaattg 151140
gagaaaccga tgattatatg ttcttcgtta taaagaattc gggaagagta ttcgccccaa 151200
aggatactga atcagtcttc gaagcatgcg tcactatgat aaacacgtta gagtttatac 151260
actctcgagg atttacccat ggaaaaatag aaccgaggaa tatactgatt agaaataaac 151320
gtctttcact aattgactat tctagaacta acaaactata caagagtgga aactcacata 151380
tagattacaa cgaggacatg ataacttcag gaaatatcaa ttatatgtgt gtagacaatc 151440
atcttggagc aacagtttca agacgaggag atttagaaat gttgggatat tgcatgatag 151500
aatggttcgg tggcaaactt ccatggaaaa acgaaagtag tataaaagta ataaaacaaa 151560
aaaaagaata taaaaaattt atagctactt tctttgagga ctgttttcct gaaggaaatg 151620
aacctctgga attagttaga tatatagaat tagtatacac gttagattat tctcaaactc 151680
ctaattatga cagactacgt aaactgttta tacaagattg aaattatatt ctttttttta 151740
tagagtgtgg tagtgttacg gatatctaat attaatatta gactatctct atcgcgctac 151800
acgaccaata tcgattacta tggatatctt ctatgaaagg agagaatgta tttatttctc 151860
cagcgtcaat ctcgtcagta ttgacaatac tgtattatgg agctaatgga tccactgctg 151920
aacagctatc aaaatatgta gaaacggagg agaacacgga taaggttagc gctcagaata 151980
tctcattcaa atccatgaat aaagtatatg ggcgatattc tgccgtgttt aaagattcct 152040
ttttgagaaa aattggcgat aagtttcaaa ctgttgactt cactgattgt cgcactatag 152100
atgcaatcaa caagtgtgta gatatcttta ctgaggggaa aatcaatcca ctattggatg 152160
aaccattgtc tcctagcaat tagtgccgta tactttaaag caaaatggtt gacgccattc 152220
gaaaaggaat ttaccagtga ttatcccttt tacgtatctc cgacggaaat ggtagacgta 152280
agtatgatgt ctatgtacgg caaggcattt aatcacgcat ctgtaaaaga atcattcggc 152340
aacttttcaa tcatagaact gccatatgtt ggagatacta gtatgatggt cattcttcca 152400
gacaagattg atggattaga atccatagaa caaaatctaa cagatacaaa ttttaagaaa 152460
tggtgtgact ttatggatgc tatgtttata gatgttcaca ttcccaagtt taaggtaaca 152520
ggctcgtata atctggtgga tactctagta aagtcaggac tgacagaggt gttcggttca 152580
actggagatt atagcaatat gtgtaattta gatgtgagtg tcgacgctat gatccacaaa 152640
acgtatatag atgtcaatga agagtataca gaagcagctc cagcaacttc tgtactagtg 152700
gcagactgtg catcaacaat tacaaatgag ttctgtgcag atcatccgtt catctatgtg 152760
attaggcatg ttgatggaaa aattcttttc gttggtagat attgctctcc gacaactaat 152820
tgttaaccat ttttttttaa aaaaacaatg ggtgatggat acacttgatg gtataatgat 152880
gaatgaacgc gatgtttctg taagcgttgg caccggaata ctattcatgg aaatgttttt 152940
ccgttacaat aaaaatagta tcaacaatca actaatgtat gatataatta atagcgtatc 153000
tataagtgta gctaattata gatatagaag ctgcttttaa cgacgatggt atatacatcc 153060
gtagaaatat gattaacaag ttgtacggat acgcatctct aactactatt ggcacgatcg 153120
```

```
ctggaggtgt tgttattat ctgttgatgc atctagttag tttgtataaa taattatttc  153180
aatatactag ttaaaatttt aagattttaa atgtataaaa aactaataac gtttttattt  153240
gtaataggtg cattagcatc ctattcgaat aatgagtaca ctccgtttaa taaactgagt  153300
gtaaaactct atatagatgg agtagataat atagaaaatt catatactga tgataataat  153360
gaattggtgt taaattttaa agagtacaca atttctatta ttacagagtc atgcgacgtc  153420
ggatttgatt ccatagatat agatgttata aacgactata aaattattga tatgtatacc  153480
attgactcgt ctactattca acgcagaggt cacacgtgta gaatatctac caaattatca  153540
tgccattatg ataagtaccc ttatattcac aaatatgatg gtgatgagcg acaatattct  153600
attactgcag agggaaaatg ctataaagga ataaaatatg aaataagtat gatcaacgat  153660
gatactctat tgagaaaaca tactcttaaa attggatcta cttatatatt tgatcgtcat  153720
ggacatagta atacatatta ttcaaaatat gattttttaaa aatttaaaat atattatcac  153780
ttcagtgaca gtagtcaaat aacaaacaac accatgagat atattataat tctcgcagtt  153840
ttgttcatta atagtataca cgctaaaata actagttata agtttgaatc cgtcaatttt  153900
gattccaaaa ttgaatggac tggggatggt ctatacaata tatcccttaa aaattatggc  153960
atcaagacgt ggcaaacaat gtatacaaat gtaccagaag gaacatacga catatccgca  154020
tttccaaaga atgatttcgt atctttctgg gttaaatttg aacaaggcga ttataaagtg  154080
gaagagtatt gtacgggact atgcgtcgaa gtaaaaattg gaccaccgac tgtaacattg  154140
actgaatacg acgaccatat caatttgtac atcgagcatc cgtatgctac tagaggtagc  154200
aaaaagattc ctatttacaa acgcggtgac atgtgtgata tctacttgtt gtatacggct  154260
aacttcacat tcggagattc taagaaacca gtaccatatg atatcgatga ctacgattgc  154320
acgtctacag gttgcagcat agactttgtc acaacagaaa aagtgtgcgt gacagcacag  154380
ggagccacag aagggtttct cgaaaaaatt actccatgga gttcgaaagt atgtctgaca  154440
cctaaaaaga gtgtatatac atgcgcaatt agatccaaag aagatgttcc caatttcaag  154500
gacaaaatgg ccagagttat caagagaaaa tttaatacac agtctcaatc ttatttaact  154560
aaatttctcg gtagcacatc aaatgatgtt accacttttc ttagcatgct taacttgact  154620
aaatattcat aactaatttt tattaatgat acaaaaacga aataaaactg catattatac  154680
actggttaac gcccttatag gctctaacca ttttcaagat gaggtccctg attatagtcc  154740
ttctgttccc ctccatgtct attagacgat gtgagaagac tgaagaggaa acatggggat  154800
tgaaaatagg gttgtgtata attgccaaag attttttatcc cgaaagaact gattgcagtg  154860
ttcatctccc aactgcaagt gaaggattga taactgaagg caatggattc agggatatac  154920
gaaacaccga taaattataa aaaaagcaat gtgtccgctg tttccgttaa taatactatt  154980
ttcgtaactg gcggattatt cataaataac tctaatagca cgatcgtgga catttataaa  155040
gacaaacaat ggtcgattat agaaatggct agggtatatc acggcatcga ctcgacattt  155100
ggaatgttat attttgccgg aggtctatcc gttaccgaac aatatggtaa tttatagaaa  155160
aacaacgaga tatcttgtta caatcctaga acgaataagt ggtttgatat ttcatatact  155220
atttataaga tatccatatc atcattgtgt aaactaaata acgtcttcta tgtatttagt  155280
aaggacattg gatatgtgga aaagtatgat ggtgcatgga agttagtaca tgatcgtctc  155340
cccgctataa aggcattatc aacttctcct tattgattga aaatgaaaat ataaatagtt  155400
tttatgtata gcagtattac cctatagttt tattgcttac tactaacatg gatacagatg  155460
```

```
ttacaaatgt agaagatatc ataaatgaaa tagatagaga gaaagaagaa atactaaaaa   155520
atgtagaaat tgaaaataat aaaaacatta acaagaatca tcccaatgaa tatattagag   155580
aagcactcgt tattaatacc agtagtaata gtgattccat tgataaagaa gttatagaat   155640
gtatcagtca cgatgtagga atatagatca tatctactaa ttttataat cgatacaaaa    155700 cataaaaaac aactcgttat tacatagcag gcatggaatc cttcaagtat tgtttgata    155760 acgatggcaa gaaatggatt atcggaaata ctttatattc tggtaattca atactctata   155820
aggtcagaaa aaatttcact agttcgttct acaattacgt aatgaagata gatcacaaat   155880
cacacaagcc attgttgtct gaaatacgat tctatatatc tgtattggat cctttgacta   155940
tcgacaactg gacacgggaa cgtggtataa agtatttggc tattccagat ctgtatggaa   156000
ttggagaaac cgatggatta tatgttcttc gttataaaga attcgggaag agtattcgcc   156060
ccaaaggata ctgaatcagt cttcgaagca tgcgtcacta tgataaacac gttagagttt   156120
atacactctc gaggatttac ccatggaaaa atagaaccga ggaatataat attaaaactt   156180
accacgtaaa acttaaaatt taaaatgata tttcattgac agatagatca cacattatga   156240
actttcaagg acttgtgtta actgacaatt gcaaaaatca atgggtcgtt ggaccattaa   156300
taggaaaagg tggatttggt agtatttata ctactaatga caataattat gtagtaaaaa   156360
tagagcccaa agctaacgga tcattattta ccgaacaggc attttatact agagtactta   156420
aaccatccgt tatcgaagaa tggaaaaaat ctcacaatat aaagcacgta ggtcttatca   156480
cgtgcaaggc atttggtcta tacaaatcca ttaatgtgga atatcgattc ttggtaatta   156540
atagattagg tgcagatcta gatgcggtga tcagagccaa taataataga ctaccaaaaa   156600
ggtcggtgat gttgatcgga atcgaaatct taaataccat acaatttatg cacgagcaag   156660
gatattctca cggagatatt aaagcgagta atatagtctt agatcaaata gataagaata   156720
aattatatct agtggattac ggattggttt ctaaattcat gtctaatggc gaacatgttc   156780
catttataag aaatccaaat aaaatggata acggtactct agaatttaca cctatagatt   156840
cgcataaagg atacgttgta tctagacgtg gagatctaga aacacttgga tattgtatga   156900
ttagatggtt gggaggtatc ttaccatgga ctaagatatc tgaaacaaag aattgtgcat   156960
tagtaagtgc cacaaaacag aaatatgtta acaatactgc gactttgtta atgaccagtt   157020
tgcaatatgc acctagagaa ttgctgcaat atattaccat ggtaaactct ttgacatatt   157080
ttgaggaacc caattacgac aagtttcggc acatattaat gcagggtgta tattattaag   157140
tgtggtgttt ggtcgataaa aattaaaaaa taacttaatt tattattgat ctcgtgtgta   157200
caaccgaaat catggcgatg ttttacgcac acgctctcgg tgggtacgac gagaatcttc   157260
atgcctttcc tggaatatca tcgactgttg ccaatgatgt caggaaatat tctgttgtgt   157320
cagtttataa taacaagtat gacattgtaa aagacaaata tatgtggtgt tacagtcagg   157380
tgaacaagag atatattgga gcactgctgc ctatgtttga gtgcaatgaa tatctacaaa   157440
ttggaaatcc gatccatgat caagaaggaa atcaaatctc tatcatcaca tatcgccaca   157500
aaaactacta tgctctaagc ggaatcgggt acgagagtct agacttgtgt ttggaaggag   157560
tagggattca tcatcacgta cttgaaacag gaaacgctgt atatggaaaa gttcaacatg   157620
attattctac tatcaaagag aaggccaaag aaatgagtgc acttagtcca ggacctatca   157680
tcgattacca cgtctggata ggagattgta tctgtcaagt tactgctgtg gacgtacatg   157740
gaaaggaaat tatgaaaatg agattcaaaa agggtcgcgt gcttccgatc ccaaatctgg   157800
taaaagttaa acttggggag aatgatacag aaaatctttc ttctactata tcggcgacac   157860
```

```
catcgaggta accacctctc tggaagacag cgtgaataat gtactcatga aacgtttgga    157920
aactatacgc catatgtggt ctgttgtata tgatcatttt gatattgtga atggtaaaga    157980
atgctgttat gtgcatacgc atttgtctaa tcaaaatctt ataccgagta ctgtaaaaac    158040
aaatttgtac atgaagacta tgggatcatg cattcaaatg gattccatgg aagctctaga    158100
gtatcttagc gaactgaagg aatcaggtgg atggagtccc agaccagaaa tgcaggaatt    158160
tgaatatcca gatggagtgg aagacactga atcaattgag agattggtag aggagttctt    158220
caatagatca gaacttcagg ctggtgaatc agtcaaattt ggtaattcta ttaatgttaa    158280
acatacatct gtttcagcta agcaactaag aacacgtata cggcagcagc ttccttctat    158340
actctcatct tttaccaaca caaagggtgg atatttgttc attggagttg ataataatac    158400
acacaaagta tttggattca cggtgggtta cgactacctc agactgatag agaatgatat    158460
agaaaagcat atcaaaagac tttgtgttgt gtatttctgt gagaagaaag aggacatcaa    158520
gtacgcgtgt cgattcatca aggtatataa acctggggat gaggctacct cgacatacgt    158580
gtgcgctatc aaagtggaaa gatgctgttg tgctgtgttt gcagattggc cagaatcatg    158640
gtatatggat actaatggta tcaagaagta ttctccagat gaatgggtgt cacatataaa    158700
atttaattta atgtaactat agagaacaaa taataaggtt gtaatatcat atagacaata    158760
actaacaatt aattagtaac tgttatctct tttttaatta accaactaac tatataccta    158820
ttaatacatc gtaattatag ttcttaacat ctattaatca ttaattcgct tcttttaattt    158880 tttataaact aacattgtta attgaaaagg gataacatgt tacagaatat aaattatata    158940 tggattttt taaaaaggaa atacttgact ggagtatata tttatctctt cattatatag    159000
cacgcgtgtt ttccaatttt tccacatccc atataataca ggattataat ctcgttcgaa    159060
catacgagaa agtggataaa acaatagttg attttttatc taggttgcca aatttattcc    159120
atattttaga atatggggaa aatattctac atatttattc tatggatgat gctaatacga    159180
atattataat tttttttcta gatagagtat taaatattaa taagaacggg tcatttatac    159240
acaatctcgg gttatcatca tccattaata taaaagaata tgtatatcaa ttagttaata    159300
atgatcatcc agataatagg ataagactaa tgcttgaaaa tggacgtaga acaagacatt    159360
ttttgtccta tatatcagat acagttaata tctatatatg tattttaata aatcatggat    159420
tttatataga tgccgaagac agttacggtt gtacattatt acatagatgt atatatcact    159480
ataagaaatc agaatcagaa tcatacaatg aattaattaa gatattgtta aataatggat    159540
cagatgtaga taaaaagat acgtacggaa acacaccttt tatcctatta tgtaaacacg    159600
atatcaacaa cgtggaattg tttgagatat gtttagagaa tgctaatata gactctgtag    159660
actttaatag atatacacct cttcattatg tctcatgtcg taataaatat gattttgtaa    159720
agttattaat ttctaaagga gcaaatgtta atgcgcgtaa taaattcgga actactccta    159780
tttattgtgg aattatacac ggtatctcgc ttataaaact atatttggaa tcagacacag    159840
agttagaaat agataatgaa catatagttc gtcatttaat aatttttgat gctgttgaat    159900
ctttagatta tctattatcc agaggagtta ttgatattaa ctatcgtact atatacaacg    159960
aaacatctat ttacgacgct gtcagttata atgcgtataa tacgttggtc tatctattaa    160020 acaaaatgg tgattttgag acgattacta ctagtggatg tacatgtatt tcggaagcag    160080
tcgcaaacaa caacaaaata ataatggaag tactattgtc taaacgacca tctttgaaaa    160140
ttatgataca gtctatgata gcaattacta aacataaaca gcataatgca gatttattga    160200
```

```
aaatgtgtat aaaatatact gcgtgtatga ccgattatga tactcttata gatgtacagt  160260
cgctacagca atataaatgg tatattttaa gatgtttcga tgaaatagat atcatgaaga  160320
gatgttatat aaaaaataaa actgtattcc aattagtttt ttgtatcaaa gacattaata  160380
ctttaatgag atacggtaaa catccttctt tcgtgaaatg cactagtctc gacgtatacg  160440
gaagtcgtgt acgtaatatc atagcatcta ttagatatcg tcagagatta attagtctat  160500
tatccaagaa gctggatcct ggagataaat ggtcgtgttt tcctaacgaa ataaaatata  160560
aaatattgga aaactttaac gataacgaac tatccacata tctaaaaatc ttataaacat  160620
tattaaaata taaaatctaa gtaggataaa atcacactac atcattgttt cctttagtg   160680 ctcgacagtg tatactattt ttaacgctca taaataaaaa tgaaaacgat ttccgttgtt  160740
acgttgttat gcgtactacc tgctgttgtt tattcaacat gtactgtacc cactatgaat  160800
aacgctaaat taacgtctac cgaaacatcg tttaatgata accagaaagt tacgtttaca  160860
tgtgatcagg gatatcattc tttgatccaa aatgctgtct gtgaaacaga taaatggaaa  160920
tacgaaaatc catgcaaaaa aatgtgcaca gtttctgatt atgtctctga actatataat  160980
aaaccgctat acgaagtgaa ttccaccatg acactaagtt gcaacggcga aacaaaatat  161040
tttcgttgcg aagaaaaaaa tggaaatact tcttggaatg atactgttac gtgtcctaat  161100
gcggaatgtc aacctcttca attagaacac ggatcgtgtc aaccagttaa agaaaaatac  161160
tcatttgggg aatatatgac tatcaactgt gatgttggat atgaggttat tggtgcttcg  161220
tacataagtt gtacagctaa ttcttggaat gttattccat catgtcaaca aaaatgtgat  161280
atgccgtctc tatctaacgg attaattttcc ggatctacat tttctatcgg tggcgttata  161340
catcttagtt gtaaaagtgg ttttacacta acggggtctc catcatccac atgtatcgac  161400
ggtaaatgga atcccatact cccaatatgt gtacgaacta acgaaaaatt tgatccagtg  161460
gatgatggtc ccgacgatga gacagatttg agcaaactct cgaaagacgt tgtacaaat   161520 gaacaagaaa tagaatcgtt agaagcaact tatcatataa tcatagtggc gttgacaatt  161580
atgggcgtca tattttttaat ctccgttata gtattagttt gttcctgtga caaaaataat  161640
gaccaatata agttccataa attgctaccg taaatataaa tccgttaaaa taattaataa  161700
tttaataaca aacaagtatc aaaagattaa agacttatag ctagaatcaa ttgagatgtc  161760
ttcttcagtg gatgttgata tctacgatgc cgttagagca ttttttactca ggcactatta  161820 taacaagaga tttattgtgt atggaagaag taacgccata ttacataata tatacaggct  161880
atttacaaga tgcgccgtta taccgttcga tgatatagta cgtactatgc caaatgaatc  161940
acgtgttaaa caatgggtga tggatacact taatggtata atgatgaatg aacgcgatgt  162000
ttctgtaagc gttggcaccg gaatactatt catggaaatg tttttcgatt acaataaaaa  162060
tagtatcaac aatcaactaa tgtatgatat aattaatagc gtatctataa ttctagctaa  162120
tgagagatat agaagcgctt ttaacgacga tggtatatac atccgtagaa atatgattaa  162180
caagttgtac ggatacgcat ctctaactac tattggcacg atcgctggag gtgtttgtta  162240
ttatctgttg atgcatctag ttagtttgta taaataatta tttcaatata ctagttaaaa  162300
ttttaagatt ttaaatgtat aaaaaactaa taacgttttt attgtaata ggtgcattag   162360 catcctattc gaataatgag tacactccgt ttaataaact gagtgtaaaa ctctatatag  162420
atggagtaga taatatagaa aattcatata ctgatgataa taatgaattg gtgttaaatt  162480
ttaaagagta cacaatttct attattacag agtcatgcga cgtcggattt gattccatag  162540
atatagatgt tataaacgac tataaaatta ttgatatgta taccattgac tcgtctacta  162600
```

```
ttcaacgcag aggtcacacg tgtagaatat ctaccaaatt atcatgccat tatgataagt 162660
acccttatat tcacaaatat gatggtgatg agcgacaata ttctattact gcagagggaa 162720
aatgctataa aggaataaaa tatgaaataa gtatgatcaa cgatgatact ctattgagaa 162780
aacatactct taaaattgga tctacttata tatttgatcg tcatggacat agtaatacat 162840
attattcaaa atatgatttt taaaaattta aaatatatta tcacttcagt gacagtagtc 162900
aaataacaaa caacaccatg agatatatta taattctcgc agttttgttc attaatagta 162960
tacatgctaa ataactagt tataagtttg aatccgtcaa ttttgattcc aaaattgaat 163020
ggactgggga tggtctatac aatatatccc ttaaaaatta tggcatcaag acgtggcaaa 163080
caatgtatac aaatgtacca gaaggaacat acgacatatc cgcatttcca agaatgatt 163140 tcgtatcttt ctgggttaaa tttgaacaag gcgattataa agtggaagag tattgtacgg 163200
gactatgcgt cgaagtaaaa attggaccac cgactgtaac attgactgaa tacgacgacc 163260
ataaacagaa aaagtgtgcg tgacagcaca gggagccaca gaagggtttc tcgaaaaaat 163320
tactccatgg agttcgaaag tatgtctgac acctaaaaag agtgtatata catgcgcaat 163380
tagatccaaa gaagatgttc ccaatttcaa ggacaaaatg gccagagtta tcaagagaaa 163440
atttaataca cagtctcaat cttatttaac taaatttctc ggtagcacat caaatgatgt 163500
taccactttt cttagcatgc ttaacttgac taaatattca taactaattt ttattaatga 163560
tacaaaaacg aaataaaact gcatattata cactggttaa cgcccttata ggctctaacc 163620
attttcaaga tgaggtccct gattatagtc cttctgttcc cctctatcat ctactccatg 163680
tctattagac gatgtgagaa gactgaagag gaaacatggg gattgaaaat agggttgtgt 163740
ataattgcca aagatttcta tcccgaaaga actgattgca gtgttcatct cccaactgca 163800
agtgaaggat tgataactga aggcaatgga ttcagggata tacgaaacac cgataaatta 163860
taaaaaaagc aatgtgtccg ctgtttccgt taataatact attttcgtaa ctggcggatt 163920
attcataaat aactctaata gcacgatcgt ggttaacaat atggaaaaac ttgacattta 163980
taaagacaaa caatggtcga ttatagaaat gcctatggct agggtatatc acggcattga 164040
ctcgacattt ggaatgttat attttgccgg aggtctatcc gttaccgaac aatatggtaa 164100
tttagagaaa acaacgagaa tatcttgtta caatcctaga acgaataagt ggtttgatat 164160
ttcatatact atttataaga tatccatatc atcattgtgt aaactaaata acgtcttcta 164220
tgtatttagt aaggacattg gatatgtgga aaagtatgat ggtgcatgga agttagtaca 164280
tgatcgtctc cccgctataa aggcattatc aacttctcct tattgattga aaatataaat 164340 agttttatg tatagcagta ttaccctata gtttttattgc ttactactaa catggataca 164400
gatgttacaa atgtagaaga tatcataaat gaaatagata gagagaaaga agaaatacta 164460
aaaaatgtag aaattgaaaa taataaaaac attaacaaga atcatcccaa tgaatatatt 164520
agagaagcac tcgttattaa taccagtagt aatagtgatt ccattgataa agaagttata 164580
gaatgtatca gtcacgatgt aggaatatag atcatatcta ctaatttta taatcgatac 164640 aaaacataaa aaacaactcg ttattacata gcaggcatgg aatccttcaa gtattgtttt 164700
gataacgatg gcaagaaatg gattatcgga aatactttat attctggtaa ttcaatactc 164760
tataaggtca gaaaaaattt cactagttcg ttctacaatt acgtaatgaa gatagatcac 164820
aaatcacaca agccattgtt gtctgaaata cgattctata tatctgtatt ggatcctttg 164880
actatcgaca actggacacg ggaacgtggt ataaagtatt tggctattcc agatctgtat 164940
```

```
ggaattggag aaaccgatga ttatatgttc ttcgttataa agaattcggg aagagtattc   165000
gccccaaagg atactgaatc agtcttcgaa gcatgcgtca ctatgataaa cacgttagag   165060
tttatacact ctcgaggatt tacccatgga aaaatagaac cgaggaatat actgattaga   165120
aataaacgtc tttcactaat tgactattct agaactaaca aactatacaa gagtggaaac   165180
tcacatatag attacaacga ggacatgata acttcaggaa atatcaatta tatgtgtgta   165240
gacaatcatc ttggagcaac agtttcaaga cgaggagatt tagaaatgtt gggatattgc   165300
atgatagaat ggttcggtgg caaacttcca tggaaaaacg aaagtagtat aaaagtaata   165360
aaacaaaaaa aagaatataa aaaatttata gctactttct ttgaggactg ttttcctgaa   165420
ggaaatgaac ctctggaatt agttagatat atagaattag tatacacgtt agattattct   165480
caaactccta attatgacag actacgtaaa ctgtttatac aagattgaaa ttatattctt   165540 tttttttatag agtgtggtag tgttacggat atctaatatt aatattagac tatctctatc   165600
gcgctacacg accaatatcg attactatgg atatcttcta tgaaaggaga gaatgtattt   165660
atttctccag cgtcaatctc gtcagtattg acaatactgt attatggagc taatggatcc   165720
actgctgaac agctatcaaa atatgtagaa acggaggaga acacggataa ggttagcgct   165780
cagaatatct cattcaaatc catgaataaa gtatatgggc gatattctgc cgtgtttaaa   165840
gattcctttt tgagaaaaat tggcgataag tttcaaactg ttgacttcac tgattgtcgc   165900
actatagatg caatcaacaa gtgtgtagat atctttactg aggggaaaat caatccacta   165960
ttggatgaac cattgtctcc tagcaattag tgccgtatac tttaaagcaa aatggttgac   166020
gccattcgaa aaggaattta ccagtgatta tcccttttac gtatctccga cggaaatggt   166080
agacgtaagt atgatgtcta tgtacggcaa ggcatttaat cacgcatctg taaaagaatc   166140
attcggcaac ttttcaatca tagaactgcc atatgttgga gatactagta tgatggtcat   166200
tcttccagac aagattgatg gattagaatc catagaacaa aatctaacag atacaaattt   166260
taagaaatgg tgtgacttta tggatgctat gtttatagat gttcacattc ccaagtttaa   166320
ggtaacaggc tcgtataatc tggtggatac tctagtaaag tcaggactga cagaggtgtt   166380
cggttcaact ggagattata gcaatatgtg taatttagat gtgagtgtcg acgctatgat   166440
ccacaaaacg tatatagatg tcaatgaaga gtatacagaa gcagctgcag caacttctgt   166500
actagtggca gactgtgcat caacaattac aaatgagttc tgtgcagatc atccgttcat   166560
ctatgtgatt aggcatgttg atggaaaaat tcttttcgtt ggtagatatt gctctccgac   166620
aactaattgt taaccatttt ttttaaaaaa aatagaaaaa acatgtggta ttagtgcagg   166680
tcgttgttct tccaattgca attggtaaga tgacggccaa ctttagtacc cacgtctttt   166740
caccacagca ctgtggatgt gacagactga ccagtattga tgacgtcaaa caatgtttga   166800
ctgaatatat ttattggtcg tcctatgcat accgcaacag gcaatgcgct ggacaattgt   166860
attccacact cctctctttt agagatgatg cggaattagt gttcatcgac attcgcgagc   166920
tggtaaaaaa tatgccgtgg gatgatgtca agattgtac agaaatcatc cgttgttata   166980
taccggatga gcaaaaaacc atcagagaga tttcggccat catcggactt tgtgcatatg   167040
ctgctactta ctgggaggt gaagaccatc ccactagtaa cagtctgaac gcattgtttg   167100
tgatgcttga gatgctaaat tacgtggatt ataacatcat attccggcgt atgaattgat   167160
gagttgtaca tcttgacatt ttcttctt tcttctccct ttcttctctt ctcccttcct   167220
ccctcttctc ccttttcccag aaacaaactt tttacccac tataaaataa aatgagtata   167280
ctacctgtta tatttctttc tatattttt tattcttcat tcgttcagac ttttaacgcg   167340
```

```
tctgaatgta tcgacaaagg gcaatatttt gcatcattca tggagttaga aaacgagcca 167400
gtaatcttac catgtcctca aataaatacg ctatcatccg gatataatat attagatatt 167460
ttatgggaaa aacgaggagc ggataatgat agaattatac cgatagataa tggtagcaat 167520
atgctaattc tgaacccgac acaatcagac tctggtattt atatatgcat taccacgaac 167580
gaaacctact gtgacatgat gtcgttaaat ttgacaatcg tgtctgtctc agaatcaaat 167640
atagatttta tctcgtatcc acaaatagta aatgagagat ctactggcga aatggtatgt 167700
cccaatatta atgcatttat tgctagtaac gtaaacgcag atattatatg gagcggacat 167760
cgacgcctta gaaataagag acttaaacaa cggacacctg gaattattac catagaagat 167820
gttagaaaaa atgatgctgg ttattataca tgtgttttag aatatatata cggtggcaaa 167880
acatataacg taaccagaat tgtaaaatta gaggtacggg ataaaataat accttctact 167940
atgcaattac cagatggcat tgtaacttca ataggtagta atttgactat tgcatcgttg 168000
agacctccca caacggatgc agacgtcttt tggataagta atggtatgta ttacgaagaa 168060
gatgatgggg acggaaacgg tagaataagt gtagcaaata aaatctatat gaccgataag 168120
agacgtgtta ttacatcccg gttaaacatt aatcctgtca aggaagaaga tgctacaacg 168180
tttacgtgta tggcgtttac tattcctagc atcagcaaaa cagttactgt tagtataacg 168240
tgaatgtatg ttgttacatt tccatgtcaa ttgagtttat aagaattttt atacattatc 168300
ttccaacaaa caattgacga acgtattgct atgattaact cccacgatac tatgcatatt 168360
attaatcatt aacttgcaga ctatacctag tgctattttg acatactcat gttcttgtgt 168420
aattgcggta tctatattat taaagtacgt aaatctagct atagttttat tatttaattt 168480
tagataatat accgtctcct tattttttaaa aattgccaca tcctttatta aatcatgaat 168540
gggaatttct atgtcatcgt tagtatattg tgaacaacaa gagcagatat ctataggaaa 168600
gggtggaatg cgatacattg atctatgtag ttttaaaaca cacgcgaact ttgaagaatt 168660
tatataaatc attccatcga tacatccttc tatgttgaga tgtatatatc caggaattcg 168720
tttattaata tcgggaaatg tataaactaa acattgccc gaaagcggtg cctctatctg 168780
cgttatatcc gttcttaact tacaaaatgt aaccaatacc tttgcatgac ttgttttgtt 168840
cggcaacgtt agtttaaact tgacgaatgg attaattaca atagcatgat ccgcgcatct 168900
attaagtttt tttacttaa cgcccttgta tgtttttaca gagactttat ctaaatttct 168960
agtgcttgta tgtgttataa atataacggg atatagaacc gaatcaccta ccttagatac 169020
ccaattacat tttatcagat ccagataata aacaaatttt gtcgccctaa ctaattctat 169080
attgttatat atttttacaat tggttatgat atcatgtaat aacttggagt ctaacgcgca 169140
tcgtcgtacg tttatacaat tgtgatttag tgtagtatat ctacacatgt atttttccgc 169200
actatagtat tctggactag tgataaaact atcgttatat ctatcttcaa tgaactcatc 169260
gagatattgc tctctgtcat attcatacac ctgcataaac tttctagaca tcttacaatc 169320
cgtgttattt taggatcata tttacatatt tacgggtata tcaaagatgt tagattagtt 169380
aatgggaatc gtctataata atgaatatta acaattata tgaggacttt taccacaaag 169440
catcataaaa atgagtcgtc gtctgattta tgttttaaat atcaaccgca aatcaactca 169500
taaaatacaa gagaatgaaa tatatacata ttttagtcat tgcaatatag accatacttc 169560
tacagaactt gattttgtag ttaaaaacta tgatctaaac agacgacaac ctgtaactgg 169620
gtatactgca ctacactgct atttgtataa taattacttt acaaacgatg tactgaagat 169680
```

```
attattaaat catggagtgg atgtaacgat gaaaaccagt agcggacgta tgcctgttta  169740
tatattgctt actagatgtt gtaatatttc acatgatgta gtgatagata tgatagacaa  169800
agataaaaac cacttattac atagagacta ttccaaccta ttactagagt atataaaatc  169860
tcgttacatg ttattaaagg aagaggatat cgatgagaac atagtatcca ctttattaga  169920
taagggaatc gatcctaact ttaaacaaga cggatataca gcgttacatt attattattt  169980
gtgtctcgca cacgtttata aaccaggtga gtgtagaaaa ccgataacga taaaaaaggc  170040
caagcgaatt atttctttgt ttatacaaca tggagctaat ctaaacgcgt tagataattg  170100
tggtaataca ccattccatt tgtatcttag tattgaaatg tgtaataata ttcatatgac  170160
taaaatgctg ttgacttttα atccgaattt cgaaatatgt aataatcatg gattaacgcc  170220
tatactatgt tatataactt ccgactacat acaacacgat attcttgtta tgttaataca  170280
tcactatgaa acaaatgttg gagaaatgcc gatagatgag cgtcgtatga tcgtattcga  170340
gtttatcaaa acatattcta cacgtccggc agattcgata acttatttga tgaataggtt  170400
taaaaatata aatatttata cccgctatga aggaaagaca ttattacacg tagcatgtga  170460
atataataat acacacgtaa tagattatct tatacgtatc aacggagata taaatgcgtt  170520
aaccgacaat aacaaacacg ctacacaact cattatagat aacaaagaaa attccccata  170580
taccattaat tgtttactgt atatacttag atatattgta gataagaatg tgataagatc  170640
gttggtggat caacttccat ctctacctat cttcgatata aaatcatttg agaaattcat  170700
atcctactgt atacttttag atgacacatt ttacgatagg cacgttaaga atcgcgattc  170760
taaaacgtat cgatacgcat tttcaaaata catgtcgttt gataaatacg atggtataat  170820
aactaaatgt cacgacgaaa caatgttact caaactgtcc actgttctag acactacact  170880
atatgcagtt ttaagatgtc ataattcgag aaagttaaga agatacctca acgagttaaa  170940
aaaatataat aacgataagt cctttaaaat atattctaat attatgaatg agagatacct  171000
taatgtatat tataaagata tgtacgtgtc aaaggtatat gataaactat ttcctgtttt  171060
cacagataaa aattgtctac taacattact accttcagaa attatatacg aaatattata  171120
catgctgaca attaacgatc tttataatat atcgtatcca cctaccaaag tatagttgta  171180
tttttctcat gcgatgtgtg taaaaaaact gatattatat aaatatttta gtgccgtata  171240
ataaagatga cgatgaaaat gatggtacat atatatttcg tatcattatt gttattgcta  171300
ttccacagtt acgccataga catcgaaaat gaaatcacag aattcttcaa taaaatgaga  171360
gatactctac cagctaaaga ctctaaatgg ttgaatccag catgtatgtt cggaggcaca  171420
atgaatgata tagccgctct aggagagcca ttcagcgcaa agtgtcctcc tattgaagac  171480
agtcttttat cgcacagata taagactat gtggttaaat gggagaggct agaaaagaat  171540
agacggcgac aggtttctaa taaacgtgtt aaacatggtg atttatggat agccaactat  171600
acatctaaat tcagtaaccg taggtatttg tgcaccgtaa ctacaaagaa tggtgactgt  171660
gttcagggta tagttagatc tcatattaaa aaacctcctt catgcattcc aaaaacatat  171720
gaactaggta ctcatgataa gtatggcata gacttatact gtggaattct ttacgcaaaa  171780
cattataata atataacttg gtataaagat aataaggaaa ttaatatcga cgacattaag  171840
tattcacaaa cgggaaagga attaattatt cataatccag agttagaaga tagcggaaga  171900
tacgactgtt acgttcatta cgacgacgtt agaatcaaga atgatatcgt agtatcaaga  171960 tgtaaaaatac ttacggttat accgtcacaa gaccacaggt ttaaactaat actagatccg  172020
aaaatcaacg taacgatagg agaacctgcc aatataacat gcactgctgt gtcaacgtca  172080
```

```
ttattgatcg acgatgtact gattgaatgg gaaaatccat ccggatggct tataggattc  172140
gattttgatg tatactctgt tttaactagt agaggcggta tcaccgaggc gaccttgtac  172200
tttgaaaatg ttactgaaga atatataggt aatacatata aatgtcgtgg acacaactat  172260
tattttgaaa aaaccettac aactacagta gtattggagt aaatatacaa tgcatttta  172320
tatacattac tgaattatta ttactgaatt attattactg aattattatt aattatatcg  172380
tatttgtgct atagaatgga tgaagatacg cgactatcta ggtatttgta tctcaccgat  172440
agagaacata taaatgtaga ctctattaaa cagttgtgta aaatatcaga tcctaatgca  172500
tgttatagat gtggatgtac ggctttacat gagtactttt ataattatag atcagtcaac  172560
ggaaaataca agtatagata caacggttac tatcaatatt attcatctag cgattatgaa  172620
aattataatg aatattatta tgatagaact ggtatgaaca gtgagagtga taatatatca  172680
atcaaaacag aatatgaatt ctatgatgaa acacaagatc aaagtacaca actagtaggt  172740
tacgacatta aactcaaaac caatgaggat gattttatgg ctatgataga tcagtgggtg  172800
tccatgatta tatagatgaa tcaattaata aagtagtata tggaagagag tctcacgtaa  172860
gatggcggga tatatggcaa gaacataatg atggcgtata cagtatagga aaggagtgca  172920
tagataatat atacgaagac aaccataccg tagacgaatt ctacaagata gacagcgtat  172980
cagatgtaga tgacgcggaa cacatatctc cgataactaa aaaaccatag aatcagttga  173040
tgataatacc tacatttcta atcttccgta taccatcaaa tacaaaatat tcgagcaaca  173100
ataagtattt tttataccttt taaaactgat aaataaattt tttctagtga tattttggca  173160
agatgagaat cctatttctc atcgctttca tgtatgggtg tgttcactca tatgttaacg  173220
cggttgaaac caaatgtcca aatctagaca ttgtaacatc ttctggagaa tttcattgtt  173280
caggatgtgt ggaacatatg cctgagttta gctatatgta ttggttggca aaggatatga  173340
aatcggacga ggataccaag tttatagaac atctgggtga tggcatcaaa gaagatgaaa  173400
ccgttcgtac cacagatagt ggaatcgtca ctctacgtaa agtccttcat gtaaccgata  173460
ctaataaatt tgataattat aggttcactt gtgtcctcac tacgatagat ggcgtttcaa  173520
aaagaatat ttggctgaag tagtgcgtgc tactattttt atttatgata taatctaatg  173580
gaattaattt gaattgatat ttatccaata ctaaagatta tattagaatc aaattaatct  173640
tttatacgag aaaaaataac gacatacgtc gtcaacaaat taaacttttt atttattagt  173700
taactagctt atagaacttg ctcattgtta tgtttctaaa acgggtacgg catataggac  173760
aattatccga cgcaccggtt tctcttcgtg ttctatgcca tatattgatg catgttatgc  173820
aaaatatatg agtacacgaa tccaataaac caaagtatct atcgttttga gtaaacaact  173880
tcatagcaaa ttccacattc ttttttcttta cttactctat acacgtcctc gtatttattt  173940
agtattttga tgatatccaa ctcagaaatg gttgttgtat tattgggtgt ataggtatta  174000
ttagctatgt accaatttac caaccctctt aatattgatt gataatcaca tcggttatcc  174060
aatcaataac cacattaata actaaattgt agtgtatata tagaccatat atgtttctat  174120
tttttgaca gttacgtata gtttcagtaa gttttgattg ttgtattcct gtatctctag  174180
ataagttagt catatagtcc cttccggcga tacgttttt ccaagcccga aattgattag  174240
ccaaatgtgt atttattttt gtgatattga tataatattt cggataatgc atactgttag  174300
tcttatatca tttggttcat ctatgtattg taatattgtt acatgatcta tagatgatgt  174360
attgattttg gcaggatcga attccatatc cgcgactaaa cagtgaaaaa aatgtaaata  174420
```

```
cttttaaat ttaaattag taaaactttt ttttatttt tatgattcca aaaatactga    174480
atacaaagtc ctaaattata aatatggaga tcatactacc acaacttatt attatgtata    174540
caaggccggt gtaatagata gatatatata attctattac accggcagac aattaccgac    174600
cggtatttgt cgttaccaac ataccgtata atatgtaata tacaattcca taacccattg    174660
acagttgtta tacatcaaaa ttgcaattct tttgattacg atgttataag aatgtagtta    174720
attgatgtat gatgttaatg tgtcctcttt cctcttataa catcgtaatc aaaaactttt    174780
ttataatata tacctaataa tgtgtcttaa tagttctcgt gattcgtcaa acaatcattc    174840
ttataaaata taataaagca acgtaaaaac acataaaaat aagcgtaact aataagacaa    174900
tggatattta cgacgataaa ggtctacaga ctattaaact gtttaataat gaatttgatt    174960
gtataaggaa tgacatcaga gaattattta aacatgtaac tgattccgat agtatacaac    175020
ttccgatgga agacaattct gatattatag aaaatatcag aaaaatacta tatagacgat    175080
taaaaaatgt agaatgtgtt gacatcgata acacaataac ttttatgaaa tacgatccaa    175140
atgatgataa taagcgtacg tgttctaatt gggtacccct aactaataac tatatggaat    175200
attgtctagt aatatatttg gaaacaccga tatgtggagg caaaataaaa ttataccacc    175260
ctacaggaaa tataaagtcg gataaggata ttatgtttgc aaagactcta gactaagata    175320
gacagcgtat cagatgtaga tgacgcggaa cacatatctc ctataactaa tgatgtatct    175380
acacaaacat gggaaaagaa atcagagtta gatagataca tggaatcgta tcctcgtcat    175440
agatatagta aacattctgt atttaaggga ttttctgata aagttagaaa aaatgattta    175500
gacatgaatg tggtaaaaga attactttct aacggtgcat ctctaacaat caaggatagc    175560
agtaataagg atccaattgc tgtttatttt agaagaacga taatgaattt agaaatgatt    175620
gatattatta acaaacatac aactattgat gaacgaaagt atatagtaca ctcctatcta    175680
aaaaattata gaaatttcga ttatccattt ttcaggaagt tagttttgac taataaacat    175740
tgtctcaaca attattataa tataagcgac agcaaatatg gaacaccgct acatatattg    175800
gcgtctaata aaaaattaat aactcctaat tacatgaagt tattagtgta taacggaaat    175860
gatataaacg cacgaggtga agatacacaa atgcgaacca actcagaaat ggttgttgta    175920
ttattgggtg tataggtatt attagctatg taccaattta ccaaccctct taatattgat    175980
tgataatcac atcggttatc caattaataa ctaaattgta gtgtatatat agaccatata    176040
tgtttctatt tttttgacag ttacgtatag tttcagtaag tttgattgt tgtattcctg    176100
tatctctaga taagttagtc atatagtccc ttccggcgat acgttttttc caagcccgaa    176160
attgattagc caaatgtgta tttattttg tgatattgat ataatatttc ggataatgca    176220
tactgttagt cttatatcat ttggttcatc tatgtattgt aatattgtta catgatctat    176280
agatgatgta ttgattttgg caggatcgaa ttccatatcc gcgactaaac agtgaaaaaa    176340
atgtaaatac ttttaaatt ttaaattagt aaaactttt ttatttttt atgattcca    176400
aaatactgaa tacaaagtcc taaattataa atatggagat catactacca caacttatta    176460
ttatgtatac aaggccggtg taatagatag atatatataa ttctattaca ccggcagaca    176520
attaccgacc ggtatttgtc gttaccaaca taccgtataa tatgtaatat acaattccat    176580
aacccattga cagttgttat acatcaaaat tgcaattctt ttgattacga tgttataaga    176640
atgtagttaa ttgatgtatg atgttaatgt gtcctctttc ctcttataac atcgtaatca    176700
aaaactttt tataatatat acctaataat gtgtcttaat agttctcgtg attcgtcaaa    176760
caatcattct tataaaatat aataaagcaa cgtaaaaaca cataaaaata agcgtaacta    176820
```

-continued

```
ataagacaat ggatatttac gacgataaag gtctacagac tattaaactg tttaataatg 176880
aatttgattg tataaggaat gacatcagag aattatttaa acatgtaact gattccgata 176940
gtatacaact tccgatggaa gacaattctg atattataga aaatatcaga aaaatactat 177000
atagacgatt aaaaaatgta gaatgtgttg acatcgataa cacaataact tttatgaaat 177060
acgatccaaa tgatgataat aagcgtacgt gttctaattg ggtaccctta actaataact 177120
atatggaata ttgtctagta atatatttgg aaacaccgat atgtggaggc aaaataaaat 177180
tataccaccc tacaggaaat ataaagtcgg ataaggatat tatgtttgca aagactctag 177240
actttaaatc aacgaaagtg ttaactggac gtaaaacaat tgccgttcta gacatatccg 177300
tttcatataa tagatcaatg actactattc actacaacga cgacgttgat atagatatac 177360
atactgataa aaatggaaaa gagttatgtt attgttatat aacaatagat gatcattact 177420
tggttgatgt ggaaactata ggagttatag tcaatagatc tggaaaatgt ctgttagtaa 177480
ataaccatct aggtataggt atcgttaaag ataaacgtat aagcgatagt tttggagatg 177540
tatgtatgga tacaatattt gacttttctg aagcacgaga gttattttca ttaactaatg 177600
atgataacag gaatatagca tgggacactg ataaactaga cgatgataca gatatatgga 177660
ctcccgtcac agaagatgat tacaaatttc tttctagact agtattgtat gcaaaatctc 177720
aatcggatac tgtatttgac tattatgttc ttactggtga tacggaacca cccactgtat 177780
tcattttcaa ggtaactaga ttttacttta atatgccgaa ataaaaaatt tttgtataat 177840
atctagaggt agaggtattg tttagataaa tacaaataac atagatacat cgcatactta 177900
gcatttttat aaatatacat aagacataca ctttatacat ttttgtaaaa atactcataa 177960
aaaaattat aaaaattatg gcacaaccat atcttgtata ggtagtttag ttcgtcgagt 178020
gaacctataa acagataata gacaacacat aataatgcct actaatacaa gcataatacc 178080
gggagatggg atatatgacg ttgtagtgtt tgggttttct gaacgttgat agtctactaa 178140
tactacatgc tgacatctaa tgcctgtata accatgagag catctacaat acataccgtc 178200
aatatctcta gcgtggatac agtcaccgtg taaacaatat ccatctccct ctggaccgca 178260
taatctgata gctggaatat ctgttgtagc gtttgtaatt tctggcaatg tcgtttcgat 178320
agcgttacca ctatcggcga atgatctgat tatcatagca gcgaacaaca acatcagata 178380
atttatcaac atttttgatg gattctgtgt ttatgctgtt tctcagtgtg tgtttatgac 178440
aagattggga attttatatt attaattcag taatataaac taataatata ttgttaattg 178500
tgtaaataat ataaaaataa caatacaata ttgaatgtgt tgctgttaaa aatgtatgtg 178560
ttaatataat agaataaaat aaatgagtat gatcatttta gataacgatt gattttatca 178620
ttaccgcttc attcttatat tctttgctta cggaacctat atttagaaac atctactaac 178680
aattttttat gcttgcatta ttaatggtat gtaatatgat tgattgtgta cgcaatacca 178740
atttgttaag tatgaatacg gggtacaaac ataaattgaa atttaacatt atttatttat 178800
gatatatatc gttatcgtta ggtctatacc atggatatct ttaaagaact aatcttaaaa 178860
caccctgatg aaaatgtttt gatttctcca gtttccattt tatctacttt atctattcta 178920
aatcatggag cagctggttc tacagctgaa caactatcaa aatatataga gaatatgaat 178980
gagaatacac ccgatgacaa taatgatgac atggaggtag atattccgta ttgtgcgaca 179040
ctagctaccg caaataaaat atacggtagc gatagtatcg agttccacgc ctccttccta 179100
caaaaaataa aagacgattt tcaaactgta aactttaata atgctaacca aacaaaggaa 179160
```

```
ctaatcaacg aatgggttaa gacaatgaca aatggtaaaa ttaattcctt attgactagt 179220
ccgctatcca ttaatactcg tatgacagtt gttagcgccg tccattttaa agcaatgtgg 179280
aaatatccat tttctaaaca tcttacatat acagacaagt tttatatttc taagaatata 179340
gttaccagcg ttgatatgat ggtgggtacc gagaataact tgcaatatgt acatattaat 179400
gaattattcg gaggattctc tattatcgat attccatacg agggaaactc tagtatggta 179460
attatactac cggacgacat agaaggtata tataacatag aaaaaaatat aacagatgaa 179520
aaatttaaaa aatggtgtgg tatgttatct actaaaagta tagacttgta tatgccaaag 179580
tttaaagtgg aaatgacaga accgtataat ctggtaccga ttttagaaaa tttaggactt 179640
actaatatat tcggatatta tgcagatttt agcaagatgt gtaatgaaac tatcactgta 179700
gaaaaatttc tacatacgac gtttatagat gttaatgagg agtatacaga agcatcggcc 179760
gttacaggag tatttacgat taacttttcg atggtatatc gtacgaaggt ctacataaac 179820
catccattca tgtacatgat taaagacacc acaggacgta tacttttat agggaaatac 179880
tgctatccgc aataaatata acaaataga cttttataaa gagtcttcaa cgataagtat 179940
atcgacatac tacttatgct gcgaaagatt ctgaacgaga acgactatct caccctcttg 180000
gatcatatcc gcactgctaa atactaaatc tccactacac ttttatcat cttatgagga 180060
atgattgcct tcgtgaaata ggaataatta gcaccagaat agctatggat tattgtggta 180120
gagagtgcac tattctatgt cgtctactgg atgaagatgt gacgtacaaa aaaataaaac 180180
tagaaattga aacgtgtcac aacttatcaa acatataga tagacgagga aacaatgcgc 180240
tacattgtta cgtctccaat aaatgcgata cagacattaa gattgttctc tcgcggagtc 180300
gagagacttt gtagaaacaa cgaaggatta actccgctag gagtatacag taagcataga 180360
tacgtaaaat ctcagattgt gcatctactg atatccagct attcaaattc ctctaacgaa 180420
ctcaagtcga atataaatga tttcgatctg tattcggata atatcgactt acgtctgcta 180480
aaatacctaa ttgtggataa acggatacgt ccgtccaaga atacgaatta tgcaatcaat 180540
ggtctcggat tggtggatat atacgtaacg acgcctaatc cgagaccaga agtattgcta 180600
tggcttctta aatcagaatg ttacagcacc ggttacgtat ttcgtacctg tatgtacgac 180660
agtgatatgt gtaagaactc tcttcattac tatatatcgt ctcatagaga atctcaatct 180720
ctatccaagg atgtaattaa atgtttgatc gataacaatg tttccatcca tggcagagac 180780
gaaggaggat ctttacccat ccaatactac tggtctttct caaccataga tatagagatt 180840
gttaaattat tattaataaa ggatgtggac acgtgtagag tatacgacgt cagccctata 180900
ttagaggcgt attatctaaa caagcgattt agagtaaccc catataatgt agacatgaa 180960
atcgttaatc ttcttattga gagacgtcat actcttgtcg acgtaatgcg tagtattact 181020
tcgtacgatt ccagagaata taaccactac atcatcgata acattctaaa gagatttaga 181080
caacaggatg tacaagccat gttgataaac tacttacatt acggcgatat ggtcgttcga 181140
tgcatgttag ataacggaca acaactatcc tctgcacgac tactttgtta ataatcct 181200
cgtcgatgta aacgtcgtaa ggtttatcgt ggaaaatatg gacacgcggc tgtaaatcac 181260
gtatcgaaca atggccgtct atgtatgtac ggtctgatat tatcgagatt taataattgc 181320
gggtatcact gttatgaaac catactgata gatgtatttg atatactaag caagtacatg 181380
gatgatatag atatgatcga taactctact atattacgcg gtcgatgtca ataatataca 181440
atttgcaaag cggttattgg aatatggagc gagtgtcacg ctcgataatc aatacggcca 181500
tccagaaaag cagttaccaa agagaaaaca aaacgaagct agttgattta ttactgagtt 181560
```

-continued

```
accatcccac tctagagact atgattgacg catttaatag agatatacgc tatctatatc   181620
ctgaaccatt attcgcctgt atcagatacg ccttaatcct agatgatgat tttccttcta   181680
aagtaaagta tgatatcgcc ggtcgtcata aggaactaaa gcgctataga gtagacatta   181740
atagaatgaa gaatgtctac atatcaggcg tctccatgtt tgatatatta tttaaacgaa   181800
gcaaacgcca caaattgaga tacgcaaaga atccgacatc aaatggtaca aaaaagaact   181860
aacgtccatc attacagaaa ctgtaaagaa caatgagagg atcgactcca tagtggacaa   181920
cattaataca gacgataact tgatttcgaa attacccatg gagatacttt attactccat   181980
taaataattt atcatggagc gataatgtcc tgtttcattt gtttccatga catattacaa   182040
aatcgattcc gtccaagatg ataaaaacat ttaccggcat cataaacacg gagtttattt   182100
tatatgtctc gcataaacat tactaaaaaa atatattgtc gataacttga tttcgaaatt   182160
acccatggag atactttatt actccattaa ataatttatc atggagcgat aatgtcctgt   182220
ttcatttgtt tccatgacat attacaaaat cgattccgtc caagatgata aaacattta    182280
ccggcatcat aaaacacgag tttattttat atgtctcgca taaacattac taaaaaaata   182340
tattgttctg ttttttctttc acatctttaa ttatgaaaaa gtaaatcatt atgagatgga   182400
cgagattgta cgcatcgttc gcgacagtat gtggtacata cctaacgtat ttatggacga   182460
cggtaagaat gaaggtcacg tttctgtcaa caatgtctgt catatgtatt ttacgttctt   182520
tgatgtggat acatcgtctc atctgtttaa gctagttatt aaacactgcg atctgaataa   182580
acgaggtaac tctccattac attgctatac gatgaataca cgatttaatc catctgtatt   182640
aaagatattg ttacaccacg gcatgcgtaa ctttgatagc aaggatgacc actatcaatc   182700
gataacaaga tctttgatat actaacggac accattgatg actttagtaa atcatccgat   182760
ctattgctgt gttatcttag atataaattc aatgggagct taaactatta cgttctgtac   182820
aaaggatccg accctaattg cgccgacgag gatgaactca cttctcttca ttactactgt   182880
aaacacatat ccacgttcta cgaaagcaat tattacaagt taagtcacac taagatgcga   182940
gccgagaagc gattcatcta cgcgataata gattatggag caaacattaa cgcggttaca   183000
cacttacctt caacagtata ccaaacatag tcctcgtgtg gtgtatgctc ttttatctcg   183060
aggagccgat acgaggatac gtaataatct tgattgtaca cccatcatgg aacgattgtg   183120
caacaggtca tattctcata atgttactca attggcacga acaaaaggaa gaaggacaac   183180
atctacttta tctattcata aaacataatc aaggatacac tctcaatata ctacggtatc   183240
tattagatag gttcgacatt cagaaagacg aatactataa taccgccttt caaaattgta   183300
acaacaatgt tgcctcatac atcggatacg acatcaacct tccgactaaa gacggtattc   183360
gacttggtgt ttgaaaacag aaacatcata tacaaggcgg atgttgtgaa tgacatcatc   183420
caccacagac tgaaagtatc tctacctatg attaaatcgt tgttctacaa gatgtctctc   183480
cctacgacga ttactacgta aaaagatac tagcctactg cctattaagg gacgagtcat    183540
tcgcggaact acatagtaaa ttctgtttaa acgaggacta taaagtgta tttatgaaaa    183600
atatatcatt cgataagata gattccatca tcgtgacata agtcgcctca aagagattcg   183660
aatctccgac accgacctgt atacggtatc acagctatct taaagccata cattcagaca   183720
gtcacatttc atttcccatg tacgacgatc tcatagaaca gtgccatcta tcgatggagc   183780
gtaaaagtaa actcgtcgac aaagcactca ataaattaga gtctaccatc ggtcaatcta   183840
gactatcgta tttgcctccg gaaattatgc gcaatatcat ctaaacagta tgttgtacgg   183900
```

```
aaagaaccat tacaaatatt atccatgata gaaagaaaat atctatatga ttggagaagt   183960
aggaaacagg aacaagacaa cgattactac attattaaat catgaagtcc gtattatact   184020
cgtatatatt gtttctctca tgtataataa taaacggaag agatatagca ccgcatgcac   184080
catccgatgg aaagtgtaaa gacaacgaat acaaacgcca taatttgtgt ccgggaacat   184140
acgcttccag attatgcgat agcaagacta acacacgatg tacgccgtgt ggttcgggta   184200
ccttcacatc tcgcaataat catttacccg cttgtctaag ttgtaacgga agacgcgatc   184260
gtgtaacacg actcacaata gaatctgtga atgctctccc ggatattatt gtcttctcaa   184320
aggatcatcc ggatgcaagg catgtgtttc ccaaacaaaa tgtggaatag gatacggagt   184380
atccggagac gtcatctgtt ctccgtgtgg tctcggaaca tattctcaca ccgtctcttc   184440
cgcagataaa tgcgaacccg tacccagaaa tacgtttaac tatatcgatg tggaaattaa   184500
cctgtatcca gttaacgaca cgtcgtgtac tcggacgacc actaccggtc tcagcgaatc   184560
catctcaacg tcggaactaa ctattactat gaatcataaa gactgtaatc ccgtatttcg   184620
tgatggatac ttctccgttc ttaataaggt agcgacttca ggtttcttta caggagaaag   184680
gtgtgcactc tgaatttcga gattaaatgc aataacaaag attcttcctc caaacagtta   184740
acgaaagcaa agaatgatac tatcatgccg cattcggaga cagtaactct agtgggcgac   184800
atctatatac tatatagtaa taccaatact caagactacg aaactgatac aatctcttat   184860
catgtgggta atgttctcga tgtcgatagc catatgcccg gtagttgcga tatacataaa   184920
ctgatcacta attccaaacc cacccacttt ttatagtaag ttttttcaccc ataaataata   184980 aatacaataa ttaatttctc gtaaaagtag aaaatatatt ctaatttatt gcacggtaag   185040
gaagtagaat cataaagaac agtactcaat caatagcaat tatgaaacaa tatatcgtcc   185100
tggcatgcat gtgcctggcg gcagctgcta tgcctgccag tcttcagcaa tcatcctcat   185160
cctcctcctc gtgtacggaa gaagaaaaca aacatcatat gggaatcgat gttattatca   185220
aagtcacaaa gcaagaccaa acaccgacca atgataagat ttgccaatcc gtaacggaaa   185280
ttacagagtc cgagtcagat ccagatcccg aggtggaatc agaagatgat tccacatcag   185340
tcgaggatgt agatcctcct accacttatt actccatcat cggtggaggt ctgagaatga   185400
actttggatt caccaaatgt cctcagatta aatccatctc agaatccgct gatgaaaca    185460 cagtgaatgc tagattgtcc agcgtgtccc caggacaagg taaggactct cccgcgatca   185520
ctcatgaaga agctcttgct atgatcaaag actgtgaagt gtctatcgac atcagatgta   185580
gcgaagaaga gaaagacagc gacatcaaga cccatccagt actcgggtct aacatctctc   185640
ataagaaagt gagttacgaa gatatcatcg gttcaacgat cgtcgataca aaatgcgtca   185700
agaatctaga gtttagcgtt cgtatcggag acatgtgcaa ggaatcatct gaacttgagg   185760
tcaaggatgg attcaagtat gtcgacggat cggcatctga aggtgcaacc gatgatactt   185820
cactcatcga ttcaacaaaa ctcaaagcgt gtgtctgaat cgataactct attcatctga   185880
aattggatga gtagggttaa tcgaacgatt caggcacacc acgaattaaa aaagtgtacc   185940
ggacactata ttccggtttg caaaacaaaa atgttcttaa ctacattcac aaaaagttac   186000
ctctcgcgac ttcttctttt tctgtctcaa tagtgtgata cgattatgac actattccta   186060
ttcctattcc tatttccttt cagagtatca caaaaatatt aaacctcttt ctgatggtct   186120
cataaaaaaa gttttacaaa atattttta ttctctttct ctcttgatg gtctcataaa    186180 aaaagttttta caaaaatatt tttattctct ttctctcttt gatggtctca taaaaaagt   186240 tttacaaaaa tattttatt ctctttctct ctttgatggt ctcataaaaa aagttttaca   186300
```

| aaaatatttt | tattctcttt | ctctctttga | tggtctcata | aaaaaagttt | tacaaaaata | 186360 |
| tttttattct | ctttctctct | ttgatggtct | cataaaaaaa | gttttacaaa | aatatttta | 186420 |
| ttctctttct | ctctttgatg | gtctcataaa | aaaagtttta | caaaaatatt | tttattctct | 186480 |
| ttctctcttt | gatggtctca | taaaaaagt | tttacaaaaa | tatttttatt | ctctttctct | 186540 |
| ctttgatggt | ctcataaaaa | aagttttaca | aaaatatttt | tattctcttt | ctctctttga | 186600 |
| tggtctcata | aaaaagttt | tacaaaaata | tttttattct | ctttctctct | ttgatggtct | 186660 |
| cataaaaaaa | gttttacaaa | aatatttta | ttctctttct | ctctttgatg | gtctcataaa | 186720 |
| aaaagtttta | caaaaatatt | tttattctct | ttctctcttt | gatggtctca | taaaaaaagt | 186780 |
| tttacaaaaa | tatttttatt | ctctttctct | ctttgatggt | ctcataaaaa | aagttttaca | 186840 |
| aaaatatttt | tatt | | | | | 186854 |

<210> SEQ ID NO 35
<211> LENGTH: 1131
<212> TYPE: DNA
<213> ORGANISM: Human Herpesvirus-1
<300> PUBLICATION INFORMATION:
<308> DATABASE ACCESSION NUMBER: GenBank No. NC_00180
<309> DATABASE ENTRY DATE: 2004-01-13

<400> SEQUENCE: 35

| atggcttcgt | accctgcca | tcaacacgcg | tctgcgttcg | accaggctgc | gcgttctcgc | 60 |
| ggccataaca | accgacgtac | ggcgttgcgc | cctcgccggc | aacaaaaagc | cacggaagtc | 120 |
| cgcctggagc | agaaaatgcc | cacgctactg | cgggtttata | tagacggtcc | ccacgggatg | 180 |
| gggaaaacca | ccaccacgca | actgctggtg | gccctgggtt | cgcgcgacga | tatcgtctac | 240 |
| gtacccgagc | cgatgactta | ctggcgggtg | ttgggggctt | ccgagacaat | cgcgaacatc | 300 |
| tacaccacac | aacaccgcct | cgaccagggt | gagatatcgg | ccggggacgc | ggcggtggta | 360 |
| atgacaagcg | cccagataac | aatgggcatg | ccttatgccg | tgaccgacgc | cgttctggct | 420 |
| cctcatatcg | gggggaggc | tgggagctca | catgccccgc | cccggccct | cacctcatc | 480 |
| ttcgaccgcc | atccatcgc | cgccctcctg | tgctacccgg | ccgcgcgata | ccttatgggc | 540 |
| agcatgaccc | ccaggccgt | gctggcgttc | gtggccctca | tcccgccgac | cttgcccggc | 600 |
| acaaacatcg | tgttgggggc | ccttccggag | gacagacaca | tcgaccgcct | ggccaaacgc | 660 |
| cagcgccccg | cgagcggct | tgacctggct | atgctggccg | cgattcgccg | cgtttatggg | 720 |
| ctgcttgcca | atacggtgcg | gtatctgcag | ggcggcgggt | cgtggcggga | ggattgggga | 780 |
| cagctttcgg | gggcggccgt | gccgccccag | ggtgccgagc | cccagagcaa | cgcgggccca | 840 |
| cgaccccata | tcggggacac | gttatttacc | ctgtttcggg | cccccgagtt | gctggccccc | 900 |
| aacggcgacc | tgtataacgt | gtttgcctgg | gctttggacg | tcttggccaa | acgcctccgt | 960 |
| cccatgcatg | tctttatcct | ggattacgac | caatcgcccg | ccggctgccg | ggacgccctg | 1020 |
| ctgcaactta | cctccgggat | ggtccagacc | cacgtcacca | ccccaggctc | cataccgacg | 1080 |
| atctgcgacc | tggcgcgcac | gtttgcccgg | gagatggggg | aggctaactg | a | 1131 |

<210> SEQ ID NO 36
<211> LENGTH: 376
<212> TYPE: PRT
<213> ORGANISM: Human Herpesvirus-1
<300> PUBLICATION INFORMATION:
<308> DATABASE ACCESSION NUMBER: GenBank No. NP_04462
<309> DATABASE ENTRY DATE: 2004-01-13

<400> SEQUENCE: 36

Met Ala Ser Tyr Pro Cys His Gln His Ala Ser Ala Phe Asp Gln Ala
1               5                   10                  15

Ala Arg Ser Arg Gly His Asn Asn Arg Arg Thr Ala Leu Arg Pro Arg
            20                  25                  30

Arg Gln Gln Lys Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Arg Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Gly Gly Gly Ser Trp Arg
                245                 250                 255

Glu Asp Trp Gly Gln Leu Ser Gly Ala Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Pro Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375